US009273317B2

(12) United States Patent
Toyoshima et al.

(10) Patent No.: US 9,273,317 B2
(45) Date of Patent: Mar. 1, 2016

(54) METHODS AND COMPOSITIONS FOR INHIBITING THE GROWTH AND/OR PROLIFERATION OF MYC-DRIVEN TUMOR CELLS

(75) Inventors: Masafumi Toyoshima, Sendai (JP); Carla Grandori, Seattle, WA (US)

(73) Assignee: Fred Hutchinson Cancer Research Center, Seattle, WA (US)

(*) Notice: Subject to any disclaimer, the term of this patent is extended or adjusted under 35 U.S.C. 154(b) by 0 days.

(21) Appl. No.: 14/237,838

(22) PCT Filed: Aug. 9, 2012

(86) PCT No.: PCT/US2012/050186

§ 371 (c)(1), (2), (4) Date: Jun. 12, 2014

(87) PCT Pub. No.: WO2013/023084

PCT Pub. Date: Feb. 14, 2013

(65) Prior Publication Data

US 2015/0148401 A1 May 28, 2015

Related U.S. Application Data

(60) Provisional application No. 61/521,715, filed on Aug. 9, 2011.

(51) Int. Cl.

| | |
|---|---|
| ***C12N 15/11*** | (2006.01) |
| ***C07H 21/02*** | (2006.01) |
| ***C07H 21/04*** | (2006.01) |
| ***C12N 15/113*** | (2010.01) |
| ***A61K 31/00*** | (2006.01) |
| ***A61K 31/713*** | (2006.01) |

(52) U.S. Cl.

CPC ............ *C12N 15/1135* (2013.01); *A61K 31/00* (2013.01); *A61K 31/713* (2013.01); *C12N 15/1137* (2013.01); *C12N 2310/14* (2013.01)

(58) Field of Classification Search

None

See application file for complete search history.

(56) References Cited

U.S. PATENT DOCUMENTS

| | | | | |
|---|---|---|---|---|
| 7,485,297 | B2 * | 2/2009 | Wood | C07K 16/005 424/130.1 |
| 2007/0099209 | A1 | 5/2007 | Clarke et al. | |
| 2007/0105114 | A1 | 5/2007 | Li et al. | |
| 2010/0179154 | A1 | 7/2010 | Almario Garcia et al. | |
| 2013/0065939 | A1 | 3/2013 | Judge et al. | |
| 2013/0115309 | A1 | 5/2013 | Grandori et al. | |

FOREIGN PATENT DOCUMENTS

| | | | |
|---|---|---|---|
| WO | WO 2004/035076 | A1 | 4/2004 |
| WO | WO 2005/056043 | A2 | 6/2005 |
| WO | WO 2009/016286 | A2 | 2/2009 |
| WO | WO 2009/145815 | A2 | 12/2009 |
| WO | WO 2010/111712 | A2 | 9/2010 |
| WO | WO 2011/127202 | A2 | 10/2011 |
| WO | WO 2013/023084 | A2 | 2/2013 |
| WO | WO 2015/077602 | A1 | 5/2015 |

OTHER PUBLICATIONS

Moses et al (RNA (2010), 16:430-441).*

Weber et al (Int. J. Cancer: 80, 935-943, 1999).*

Wen et al (Urology 73: 1407-1411, 2009).*

Luoto et al (Cancer Res; 70(21); 8748-59, 2010).*

Kaelin et al (Nature Reviews, Cancer 5:689-698, 2005 ).*

Hewett et al (Mol. Med. 12(1-3): 8-16, 2006).*

Aarts et al. "Forced Mitotic Entry of S-Phase Cells as a Therapeutic Strategy Induced by Inhibition of WEE1", *Cancer Discovery* (2012), 2: 524-539. Published Online First Apr. 23, 2012; doi: 10.1158/2159-8290.CD-11-0320.

Agochiya et al. "Increased dosage and amplification of the focal adhesion kinase gene in human cancer cells", *Oncogene* (1999), 18(41): 5646-5653.

Arabi et al. "c-Myc associates with ribosomal DNA and activates RNA polymerase I transcription", *Nat Cell Biol* (2005), 7(3): 303-310.

Barna et al. "Suppression of Myc oncogenic activity by ribosomal protein haploinsufficiency", *Nature* (2008), 456(7224): 971-975.

Bartz et al. "Small interfering RNA screens reveal enhanced cisplatin cytotoxicity in tumor cells having both BRCA network and TP53 disruptions", *Molecular and Cellular Biology* (2006), 26(24): 9377-9386.

Behrend et al. "IC261, a specific inhibitor of the protein kinases casein kinase 1-delta and -epsilon, triggers the mitotic checkpoint and induces p53-dependent postmitotic effects", *Oncogene* (2000), 19(47): 5303-5313.

Benanti et al. "Epigenetic down-regulation of ARF expression is a selection step in immortalization of human fibroblasts by c-Myc", *Mol Cancer Res* (2007), 5(11): 1181-1189. Published Online First Nov. 2, 2007; doi: 10.1158/1541-7786.MCR-06-0372.

Benanti and Galloway. "Normal human fibroblasts are resistant to RAS-induced senescence", *Molecular and Cellular Biology* (2004), 24(7): 2842-2852.

Berns, et al. "c-myc Amplification Is a Better Prognostic Factor than HER2/neu Amplification in Primary Breast Cancer", *Cancer Res* (1992), 52(5): 1107-1113.

Biechele et al. "Transcription-Based Reporters of Wnt/β-Catenin Signaling", *Cold Spring Harb Protoc* (2009), 4(Issue 6): 1-8. doi:10.1101/pdb.prot5223.

Birmingham et al. "Statistical methods for analysis of high-throughput RNA interference screens", *Nat. Methods.* (2009), 6(8): 569-575.

Blancato et al. "Correlation of amplification and overexpression of the c-myc oncogene in high-grade breast cancer: FISH, in situ hybridisation and immunohistochemical analyses", *British Journal of Cancer* (2004), 90(8): 1612-1619.

(Continued)

*Primary Examiner* — Richard Schnizer

(74) *Attorney, Agent, or Firm* — Cooley LLP

(57) ABSTRACT

The invention generally relates to methods for identifying and using anticancer therapeutic agents and, more particularly, to methods for identifying and using inhibitors of genes for inhibiting the growth and/or proliferation of MYC-driven tumor cells relative to normal cells.

24 Claims, 28 Drawing Sheets

(56) References Cited

OTHER PUBLICATIONS

Boon et al. "N-myc enhances the expression of a large set of genes functioning in ribosome biogenesis and protein synthesis", *The EMBO Journal* (2001), 20(6):1383-1393.
Bridges et al. "MK-1775, a Novel Wee1 Kinase Inhibitor, Radiosensitizes p53-Defective Human Tumor Cells", *Clinical Cancer Research* (2011), 17(17): 5638-5648. Published Online First Jul. 28, 2011; doi: 10.1158/1078-0432.CCR-11-0650.
Brockschmidt et al. "Anti-apoptotic and growth-stimulatory functions of CK1 delta and epsilon in ductal adenocarcinoma of the pancreas are inhibited by IC261 in vitro and in vivo", *Gut* (2008), 57(6): 799-806. Epub Jan. 18, 2008.
Campaner, et al. "Cdk2 suppresses cellular senescence induced by the c-myc oncogene", *Nat Cell Biol* (2010), 12(1): 54-59 (sup pp. 51-14).
Chen, et al. "Overexpression of c-Myc were observed in 66% of Epithelial Ovarian Cancers (EOCs)", *Int J Gynecol Cancer* (2005), 15(5): 878-883.
Cheong et al. "IC261 induces cell cycle arrest and apoptosis of human cancer cells via CK1δ/ϵ and Wnt/βcatenin independent inhibition of mitotic spindle formation", *Oncogene* (2011), 30: 2558-2569.
Chiao et al. "Susceptibility to ras oncogene transformation is coregulated with signal transduction through growth factor receptors", *Oncogene* (1991), 6(5): 713-720.
Chung, et al. "MicroRNA-21 promotes the ovarian teratocarcinoma PA1 cell line by sustaining cancer stem/progenitor populations in vitro", *Stem Cell Research & Therapy* (2013), 4(88): 1-10.
Chung et al. "Median Absolute Deviation to Improve Hit Selection for Genome-Scale RNAi Screens", *Journal of Biomolecular Screening* (2008), 13(2): 149-158.
Cole et al. "RNAi screen of the protein kinome identifies checkpoint kinase 1 (CHK1) as a therapeutic target in neuroblastoma," *Proceedings of the National Academy of Sciences* (2011), 108(8): 3336-3341.
Cowling and Cole. "Turning the Tables: Myc Activates Wnt in Breast Cancer", *Cell Cycle* (2007), 6(21): 2625-2627.
Dar et al. "Aurora Kinase Inhibitors—Rising Stars in Cancer Therapeutics?", *Molecular Cancer Therapy* (2010), 9(2): 268-278. Published Online First Feb. 2, 2010; doi: 10.1158/1535-7163.MCT-09-0765.
Darcy et al. "Prognostic relevance of c-MYC gene amplification and polysomy for chromosome 8 in suboptimally-resected, advanced stage epithelial ovarian cancers: A Gynecologic Oncology Group study", *Gynecologic Oncology* (2009), 114(3): 472-479.
De Witt Hamer et al. "WEE1 Kinase Targeting Combined with DNA-Damaging Cancer Therapy Catalyzes Mitotic Catastrophe", *Clinical Cancer Research* (2011), 17: 4200-4207. Published Online First May 11, 2011.
Debnath et al. "rlk/TXK Encodes Two Forms of a Novel Cysteine String Tyrosine Kinase Activated by Src Family Kinases", *Molecular and Cellular Biology*(1999), 19(2): 1498-1507.
Doles and Hemann. "Nek4 Status Differentially Alters Sensitivity to Distinct Microtubule Poisons", *Cancer Research* (2010), 70: 1033-1041.
Dominguez-Sola et al. "Non-transcriptional control of DNA replication by c-Myc", *Nature* (2007), 448(7152): 445-451.
Egloff and Grandis. "Targeting epidermal growth factor receptor and SRC pathways in head and neck cancer", *Semin Oncol.* (2008), 35(3): 286-297.
EP Patent Application No. 11766677.6, Supplemental European Search Report, mailed Oct. 7, 2013.
EP Patent Application No. 11766677.6, EPO Communication dated Jul. 10, 2014.
EP Patent Application No. 12772551.3, EPO Communication dated Jul. 30, 2015.
Firestein, et al. "CDK8 is a colorectal cancer oncogene that regulates β-catenin activity", *Nature* (2008), 455(7212): 547-551.
Fuja et al. "Somatic Mutations and Altered Expressions of the Candidate Tumor Suppressors CSNK1ϵ, DLG1, and EDD/hHYD in Mammary Ductal Carcinoma", *Cancer Research* (2004), 64: 942-951.
Goga et al. "Inhibition of CDK1 as a potential therapy for tumors over-expressing MYC", *Nature Medicine* (2007), 13(7): 820-827.
Grandori et al. "c-Myc binds to human ribosomal DNA and stimulates transcription of rRNA genes by RNA polymerase I", *Nat. Cell. Biol.* (2005), 7(3): 311-318.
Grandori et al. "Myc-Max heterodimers activate a DEAD box gene and interact with multiple E box-related sites in vivo", *The EMBO Journal* (1996), 15(16): 4344-4357.
Grandori et al. "Werner syndrome protein limits MYC-induced cellular senescence", *Genes & Development* (2003), 17(13): 1569-1574.
Greer and Rubin. "Casein kinase 1 delta functions at the centrosome to mediate Wnt-3a-dependent neurite outgrowth", *J. Cell. Biol.* (2011), 192(6): 993-1004.
Grinshtein et al. "Small Molecule Kinase Inhibitor Screen Identifies Polo-Like Kinase 1 as a Target for Neuroblastoma Tumor-Initiating Cells", *Cancer Research*, 71: 1385-1395 (2011) Published Online First Feb. 8, 2011; doi: 10.1158/0008-5472.CAN-10-2484.
Hanks and Hunter. "The eukaryotic protein kinase superfamily: kinase (catalytic domain structure and classification", *The FASEB Journal* (1995), 9: 576-596.
Hanson et al. "Effects of c-myc Expression on Cell Cycle Progression", *Molecular and Cellular Biology* (1994), 14(9): 5748-5755.
Harsha et al. "A Compendium of Potential Biomarkers of Pancreatic Cancer", *PLOS Medicine* (2009), 6(4): e1000046, 1-6.
Hirai et al. "Small-molecule inhibition of Wee1 kinase by MK-1775 selectively sensitizes p53-deficient tumor cells to DNA-damaging agents", *Molecular Cancer Therapeutics* (2009), 8(11): 2992-3000. Published Online First Nov. 3, 2009; doi: 10.1158/1535-7163.MCT-09-0463.
Hopkins and Groom. "The druggable genome", *Nat Rev Drug Discov* (2002), 1(9): 727-730.
Japanese Patent Application No. 2013-503298, Notice of Reasons for Rejection mailed Mar. 20, 2015 (with English translation).
Jenkins et al. "Detection of c-myc oncogene amplification and chromosomal anomalies in metastatic prostatic carcinoma by fluorescence in situ hybridization", *Cancer Research* (1997), 57(3): 524-531.
Jones et al. "Core signaling pathways in human pancreatic cancers revealed by global genomic analyses", Science (2008), 321(5897): 1801-1806.
Katayama and Sen. "Aurora kinase inhibitors as anticancer molecules", *Biochim Biophys Acta.* (2010), 1799(10-12): 829-839. doi: 10.1016/j.bbagrm.2010.09.004. Epub Sep. 20, 2010.
Kikuchi et al. "Treatment options in the management of ovarian cancer", *Expert Opinion on Pharmacotherapy* (2005), 6(5): 743-754.
Kim et al. "CK1ϵ is required for breast cancers dependent on β-catenin activity", *PLoS One* (2010), 5(2): e8979, 1-10.
Kiyono et al. "Both Rb/p16$^{INK4a}$ inactivation and telomerase activity are required to immortalize human epithelial cells", *Nature* ( 1998), 396(6706): 84-88.
Kozma et al. "Investigation of c-myc oncogene amplification in colorectal cancer", *Cancer Letters* (1994), 81(2): 165-169.
Lutz et al. "Conditional expression of N-myc in human neuroblastoma cells increases expression of α-prothymosin and ornithine decarboxylase and accelerates progression into S-phase early after mitogenic stimulation of quiescent cells," *Oncogene* (1996), 13(4): 803-812.
Ma et al. "Death by releasing the breaks: CHK1 inhibitors as cancer therapeutics", *Trends Mol Med.* (2011), 17(2): 88-96. doi: 10.1016/j.molmed.2010.10.009. Epub Nov. 17, 2010.
Major, et al. "New Regulators of Wnt/β-Catenin Signaling Revealed by Integrative Molecular Screening", *Science Signaling* (2008), 1(45): ra12, 1-11.
Malynn et al. "N-myc Can Functionally Replace c-myc in Murine Development, Cellular Growth, and Differentiation", *Genes & Development* (2000), 14: 1390-1399.
Mano et al. "Tec protein-tyrosine kinase is an effector molecule of Lyn protein-tyrosine kinase", *FASEB* (1996), 10: 637-42.
Marcu et al. "myc function and regulation", *Ann. Rev. Biochem.* (1992), 61: 809-860.
Mashhoon et al. "Crystal Structure of a Conformation-Selective Casein Kinase-1 Inhibitor", *The Journal of Biological Chemistry* (2000), 275(26): 20052-20060.

(56) References Cited

OTHER PUBLICATIONS

McMahon et al. "The essential cofactor TRRAP recruits the histone acetyltransferase hGCN5 to c-Myc", *Molecular & Cellular Biology* (2000), 20(2): 556-562.
Mestdagh et al. "MYCN/c-MYC-induced microRNAs repress coding gene networks associated with poor outcome in MYCN/c-MYC-activated tumors", *Oncogene* (2010), 29(9): 1394-1404.
Mitani et al. "Analysis of c-myc DNA amplification in non-small cell lung carcinoma in comparison with small cell lung carcinoma using polymerase chain reaction", *Clin Exp Med* (2001), 1(2): 105-111.
Moniz et al. "Nek family of kinases in cell cycle, checkpoint control and cancer", *Cell Division* (2011) 6: 18, 10 pages.
Nguyen et al. "Nek4 regulates entry into replicative senescence and the response to DNA damage in human fibroblasts", *Molecular and Cellular Biology* (2012), 32: 3963-3977.
Nikiforov et al. "TRRAP-Dependent and TRRAP-Independent Transcriptional Activation by Myc Family Oncoproteins", *Molecular and Cellular Biology* (2002), 22(14): 5054-5063.
Park et al. "Neuroblastoma: Biology, Prognosis and Treatment", *Pediatric Clinics of North America* (2008), 55: 97-120.
PCT/US2011/031460, International Search Report, mailed Dec. 20, 2011.
PCT/US2011/031460, Written Opinion of the International Searching Authority, mailed Dec. 20, 2011.
PCT/US2011/031460, International Preliminary Report on Patentability, mailed Oct. 9, 2012.
PCT/US2012/050186, International Search Report, mailed Apr. 18, 2013.
PCT/US2012/050186, Written Opinion of the International Searching Authority, mailed Apr. 18, 2013.
PCT/US2012/050186, International Preliminary Report on Patentability, mailed Feb. 11, 2014.
PCT/US2014/066884, International Search Report, mailed Apr. 30, 2015.
PCT/US2014/066884, Written Opinion of the International Searching Authority, mailed Apr. 30, 2015.
Poeta et al. "TP53 Mutations and Survival in Squamous-Cell Carcinoma of the Head and Neck", *N. Engl J Med.* (2007), 357(25): 2552-2561.
Rajeshkumar et al. "MK-1775, a Potent Wee1 Inhibitor, Synergizes with Gemcitabine to Achieve Tumor Regressions, Selectively in p53-Deficient Pancreatic Cancer Xenografts", *Clinical Cancer Research* (2011), 17: 2799-2806. Published Online First Mar. 9, 2011; doi: 10.1158/1078-0432.CCR-10-2580.
Ray, et al. "MYC Can Induce DNA Breaks In Vivo and In Vitro Independent of Reactive Oxygen Species", *Cancer Research* (2006), 66(13): 6598-6605.
Regan et al. "Hsp90 inhibition increases p53 expression and destabilizes MYCN and MYC in neuroblastoma", *International Journal of Oncology* (2011), 32(1): 105-112.
Riley et al. "A Systematic Review of Molecular and Biological Tumor Markers in Neuroblastoma", *Clinical Cancer Research* (2004), 10: 4-12.
Robinson, et al. "c-Myc Accelerates S-Phase and Requires WRN to Avoid Replication Stress", PLoS One (2009), 4(6): e5951, 1-10.
Russo et al. "c-myc Down-Regulation Induces Apoptosis in Human Cancer Cell Lines Exposed to RPR-115135 ($C_{31}H_{29}N_{04}$), a Non-Peptidomimetic Farnesyltransferase Inhibitor", *Journal of Pharmacology and Experimental Therapeutics* (2002), 304(1): 37-47.
Sakanaka, "Phosphorylation and Regulation of β-Catenin by Casein Kinase Iϵ", J Biochem (2002), 132: 697-703.
Sarraf et al. "The human ovarian teratocarcinoma cell line PA-1 demonstrates a single translocation: analysis with fluorescence in situ hybridization, spectral karyotyping, and bacterial artificial chromosome microarray", *Cancer Genetics and Cytogenetics* (2005), 161(1): 63-69.
Sasaki et al. "A binding site for Gli proteins is essential for HNF-3β floor plate enhancer activity in transgenics and can respond to Shh in vitro", *Development* (1997), 124: 1313-1322.
Sato et al. "Fluorescence in situ hybridization analysis of c-myc amplification in stage $T_3N_0M_0$ prostate cancer in Japanese patients", *International Journal of Urology* (2006), 13(6): 761-766.
Schleger et al. "c-MYC Activation in Primary and Metastatic Ductal Adenocarcinoma of the Pancreas: Incidence, Mechanisms, and Clinical Significance", *Modern Pathology* (2002), 15(4): 462-469.
Soucek et al. "Modelling Myc inhibition as a cancer therapy", *Nature* (2008), 455(7213): 679-683.
Stabile et al. "c-Src Activation Mediates Erlotinib Resistance in Head and Neck Cancer by Stimulating c-Met", *Clinical Cancer Research* (2013), 19(2): 380-392. Published Online First, Dec. 4, 2012, doi: 10.1158/1078-0432.CCR-12-1555.
Tainsky et al. "PA-1, A Human Cell Model for Multistage Carcinogenesis: Oncogenes and Other Factors", *Anticancer Research* (1988), 8(5A): 899-914.
Takahashi et al. "Amplification of c-myc and cyclin D1 genes in primary and metastatic carcinomas of the liver", *Pathology International* (2007), 57(7): 437-442.
Tashiro, et al. "c-myc Over-Expression in Human Primary Ovarian Tumours: Its Relevance to Tumour Progression", *Int. J. Cancer*, 50: 828-833 (1992).
Toyoshima et al. "Functional genomics identifies therapeutic targets for MYC-driven Cancer" *PNAS*, 109(24): 9545-9550 (2012).
Trumpp et al. "c-Myc regulates mammalian body size by controlling cell number but not cell size", *Nature* (2001), 414(6865): 768-773.
U.S. Appl. No. 13/639,258, Office Action mailed Aug. 15, 2013.
U.S. Appl. No. 13/639,258, Office Action mailed Jan. 16, 2014.
U.S. Appl. No. 13/639,258, Office Action mailed Sep. 9, 2014.
U.S. Appl. No. 13/639,258, Office Action mailed Jan. 5, 2015.
U.S. Appl. No. 13/639,258, Advisory Action mailed Mar. 25, 2015.
Valsesia-Wittmann et al., "Oncogenic cooperation between H-Twist and N-Myc overrides failsafe programs in cancer cells", *Cancer Cell*, 6(6): 625-630 (2004).
Van Linden et al. "Inhibition of Wee1 Sensitizes Cancer Cells to Antimetabolite Chemotherapeutics In Vitro and In Vivo, Independent of p53 Functionality", *Molecular Cancer Therapy* (2013), 12: 2675-2684. Published Online First Oct. 11, 2013; doi: 10.1158/1535-7163.MCT-13-0424.
Walton et al. "Selective Inhibition of Casein Kinase 1E Minimally Alters Circadian Clock Period", *Journal of Pharmacology and Experimental Therapeutics* (2009), 330(2): 430-439.
Wang et al. "Improved low molecular weight Myc-Max inhibitors", *Molecular Cancer Therapy* (2007), 6(9): 2399-2408.
Wang et al. "Increased radio-resistance and accelerated B cell lymphomas in mice with Mdmx mutations that prevent modifications by DNA-damage-activated kinases", *Cancer Cell* (2009), 16(1): 33-43.
Weiss et al. "Targeted Expression of MYCN Causes Neuroblastoma in Transgenic Mice", *The EMBO Journal* (1997), 16(11):2985-2995.
Wheeler et al. "Lyn Kinase Mediates Cell Motility and Tumor Growth in EGFRvIII-Expressing Head and Neck Cancer", *Clinical Cancer Research* (2012), 18: 2850-2860. Published Online First Apr. 6, 2012; doi: 10.1158/1078-0432.CCR-11-2486.
Wu et al. "Amplification and Overexpression of the L-MYC Proto-Oncogene in Ovarian Carcinomas", *American Journal of Pathology* (2003), 162(5): 1603-1610.
Xi et al. "Src kinases mediate STAT growth pathways in squamous cell carcinoma of the head and neck", *J Biol Chem.* (2003), 278(34): 31574-31583. First Published Online May 27, 2003, doi: 10.1074/jbc.M303499200.
Xu et al. "Integrative analysis of DNA copy number and gene expression in metastatic oral squamous cell carcinoma identifies genes associated with poor survival", *Molecular Cancer* (2010), 9: 143, 12 pages.
Xu et al. "Integrative genomics in combination with RNA interference identifies prognostic and functionally relevant gene targets for oral squamous cell carcinoma", *PLOS Genetics* (2013), 9(1): e1003169. doi: 10.1371/journal.pgen.1003169.
Yang and Stockwell. "Inhibition of casein kinase 1-epsilon induces cancer-cell-selective, PERIOD2-dependent growth arrest", *Genome Biology* (2008), 9(6): R92, 1-13.

(56) References Cited

OTHER PUBLICATIONS

Zhang et al. "A Simple Statistical Parameter for Use in Evaluation and Validation of High Throughput Screening Assays", *Journal of Biomolecular Screening* (1999), 4(2): 67-73.
Zhang et al. "SRC family kinases mediate epidermal growth factor receptor ligand cleavage, proliferation, and invasion of head and neck cancer cells", *Cancer Research* (2004), 64: 6166-6173.
Zhou et al. "Overexpression of Cyclin D1 Enhances Gene Amplification", *Cancer Research* (1996), 56: 36-39.
Iba et al., "Expression of the c-myc gene as a predictor of chemotherapy response and a prognostic factor in patients with ovarian cancer", Cancer Science (2004), 95(5): 418-423.
Li et al., "Down-regulation of pescadillo inhibits proliferation and tumorigenicity of breast cancer cells", Cancer Science (2009), 100(12): 2255-2260.

* cited by examiner

FIG. 2C
shCtr
sh#1
sh#2
Dox
CSNK1e
Actin

METHODS AND COMPOSITIONS FOR INHIBITING THE GROWTH AND/OR PROLIFERATION OF MYC-DRIVEN TUMOR CELLS

CROSS-REFERENCE TO RELATED APPLICATIONS

This application claims benefit under 35 U.S.C. §119(e) of U.S. Provisional Application No. 61/521,715, filed on Aug. 9, 2011, which is incorporated by reference in its entirety.

STATEMENT OF GOVERNMENT LICENSE RIGHTS

This invention was made with U.S. Government support under grant number AG026661 awarded by the National Institutes of Health. The U.S. Government has certain rights in this invention.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is FHCR_014_01WO_ST25.txt. The text file is about 509 KB, was created on Aug. 9, 2012, and is being submitted electronically via EFS-Web.

FIELD OF THE INVENTION

The invention relates generally to methods for identifying and using anticancer therapeutic agents and, more particularly, to methods for identifying and using inhibitors of genes for inhibiting the growth and/or proliferation of MYC-driven tumor cells relative to normal cells.

BRIEF SUMMARY

Embodiments of the present invention include methods for inhibiting the growth and/or proliferation of a myc-driven cancer or tumor cell comprising the step of contacting the cancer or tumor cell with at least one inhibitor that inhibits the gene function of at least one of the genes listed in Table 1 or 2.

In certain embodiments, the myc-driven cancer cell is derived from one of the following: a neuroblastoma tumor, a metastatic neuroblastoma tumor, a medulloblastoma, a lymphoma, a rhabdomyosarcoma, a melanoma, a lung cancer, a liver cancer, a breast cancer, a colon cancer, a prostate cancer, an ovarian cancer, or Burkitt's lymphoma.

In particular embodiments, the tumor cell is contacted in vitro. In specific embodiments, the cancer cell is contacted in vivo in a mammalian subject, optionally a human patient diagnosed with a MYC-driven cancer, such as any of the aforementioned cancers/tumors.

In some embodiments, the inhibitor is a small molecule inhibitor that inhibits the function of the gene product. In certain embodiments, the inhibitor interferes with the transcription of mRNA from the gene. In particular embodiments, the inhibitor interferes with production/expression of functional gene product of the gene.

In certain embodiments, the gene is selected from the genes listed in Table 1. In specific embodiments, the gene is selected from the group consisting of ALDOA, CECR2, IGF2R, PAK6, PES1, RAD21, REV1L, SUV39H1, TIE1.

Also included are methods of treating a subject suffering from a tumor comprising myc-driven tumor cells, comprising administering to the subject an amount of a composition comprising an inhibitor that inhibits the gene function, transcription, production/expression, or activity of the gene product of at least one of the genes listed in Table 1 or 2, and is effective to inhibit the growth and/or proliferation of the tumor cells.

FIG. 3. IC261 treatment blocks MYCN amplified neuroblastoma tumor growth in vivo. a, Representative images of MYCN amplified neuroblastoma xenograft in NOD/SCID mice before and after treatment with either DMSO or IC261. Tumors were engrafted, and allowed to reach a size of about 100 $mm^3$, then IC261 (21.5 mg/kg) or DMSO was injected subcutaneously daily for 8 days. b, Quantitation of tumor size over the 8-day treatment regimen with either IC261 or DMSO control. Values represent mean tumor volume at each time point (n=5 for each group, error bars indicate SD). c, Immunohistochemical analysis of tumor sections from IC261 and DMSO treatment groups described in a and b. Representative images of H-E, TUNEL and BrdU staining for each group are shown. BrdU was administered 2 h before collection. d. Quantification of TUNEL positive cells and BrdU positive cells per field in DMSO or IC-261 treated xenograft tumors. Error bars indicate SD of means.

FIG. 4. CSNK1e expression correlates with poor prognosis and MYCN amplification in neuroblastoma. a, Kaplan-Meier survival curves of neuroblastoma patients divided on the basis of CSNK1e expression; lower solid line indicates high and upper solid line indicates low CSNK1e mRNA expression based on microarray data accessible at the Oncogenomics neuroblastoma prognosis database. b, Graphical representation of expression intensities for CSNK1e mRNA derived from microarray data of neuroblastoma tumor samples. Each bar represents one sample. The shaded horizontal line (-MYCN ampl.) indicates samples derived from MYCN amplified neuroblastoma c. Representative western blot of CSNK1e, MYCN and β-actin (loading control) protein levels in SN-N-AS (MYCN not amplified), SK-N-BE2 and IMR-32 (MYCN amplified) neuroblastoma cells. d, Representative western blot of CSNK1e, MYCN and β-actin (loading control) protein levels in HFF pB and HFF c-Myc cells. e, Representative western blot of CSNK1e, MYCN and β-actin (loading control) protein levels in Tet21N (MYCN Tet-Off) cells. f, Real time RT-PCR quantification of the relative levels of each casein kinase I isoforms normalized to glyceraldehydes-3-phosphate dehydrogenase (GAPDH) mRNA levels in neuroblastoma cell lines with or without MYCN amplification. The bars for each isoform, from left to right, refer to SK-N-AS, SH-SY-5Y, LAN-5, IMR-32, KCN. KCNR, SK-N-BE2 neuroblastoma cell lines.

Figure 5:
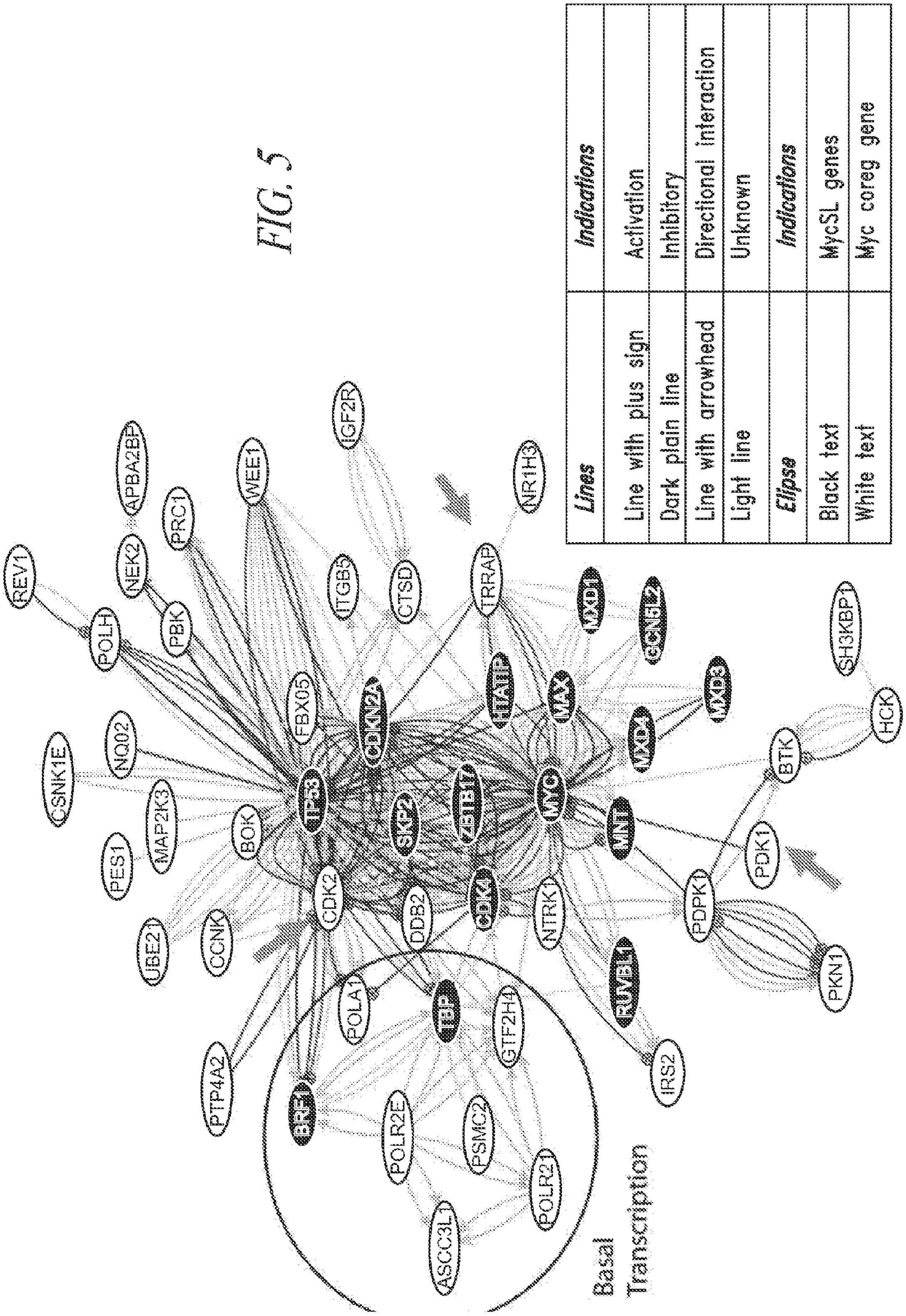

FIG. 5. Network analysis of MYC-SL “Hits” (light shading) and their connection with a pre-assembled MYC “core” pathway (dark shading). The network was built to visualize known literature connections between the “Hits” (light shading) and a pre-assembled MYC core pathway (dark shading). All connections were drawn based on Ingenuity curated database. Only the MYC-SL with known direct connections with the MYC core components are here visualized. Each line represents a single reference and the connecting lines indicate the type of interaction as indicated in the box. Arrows mark genes referred to in the text.

Figure 6:
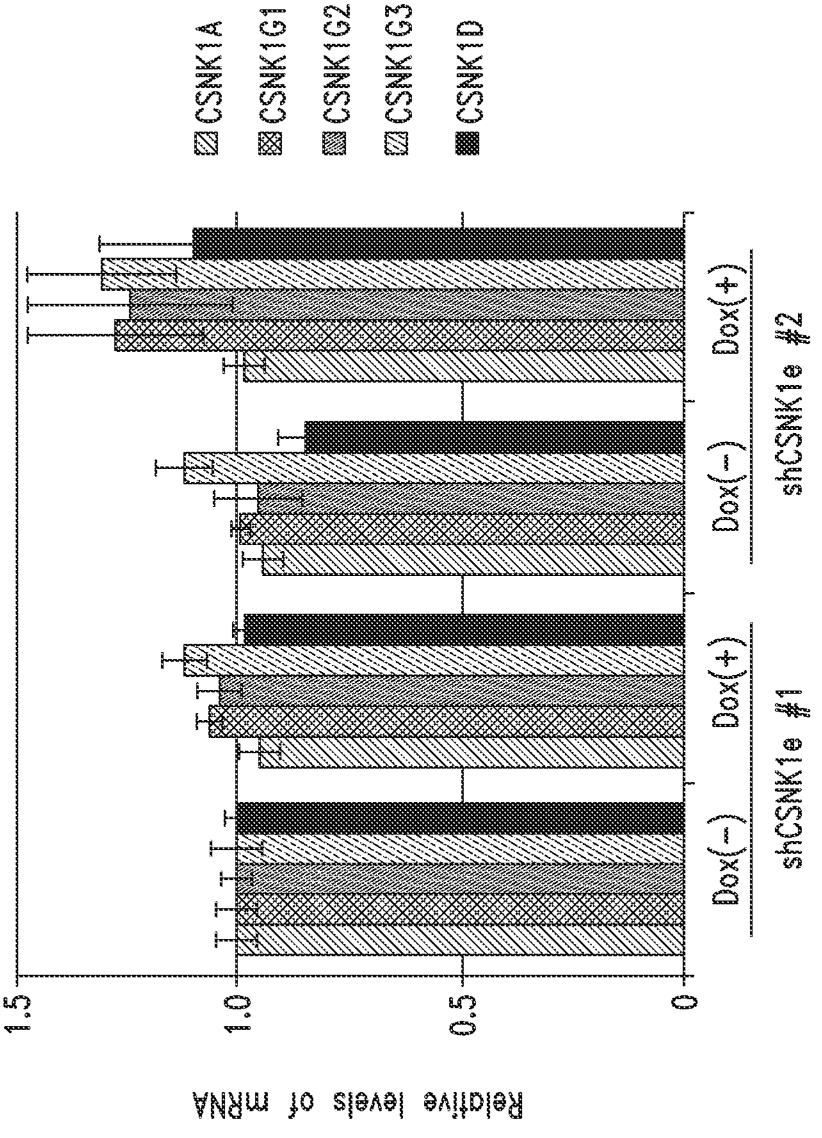

FIG. 6. Conditional knock-down of CSNK1e with lentiviral expressed short hairpins does not affect expression of other CSNK1e isoforms.

Relative mRNA expression of CSNK1 A (α), G1 (γ1), G2 (γ2), G3 (γ3) and D (δ) in SKNBE2 cells were transduced with lentiviral vectors expressing shCSNK1e#1 and #2 (see FIG. 2) and either treated or untreated with Doxycycline for 48 hrs. Relative levels of each gene were calculated using the ΔΔCT method and using GAPDH to normalize mRNA levels within each sample.

FIG. 7. Chemical inhibition of CSNK1e kinase activity shows selective toxicity to MYC overexpressing cells.

a. HFF cell lines with or without c-Myc over-expression were treated with 0-10 uM IC261 for 48 hrs. The cells were exposed to CellTiter-Glo reagent and viability was assessed by ATP-induced chemiluminescence. Values indicate mean±SD. b. Tet21N cells with or without doxycyclin treatment and IMR-32 cells (MYCN+) were treated with 0-30 uM IC261 for 48 hrs. The cells were exposed to CellTiter-Glo reagent and the viability was assessed by ATP-induced chemiluminescence. Values indicate mean±SD. c. Cell growth curves for HFF-pBabe incubated with different concentrations of IC261. d. Cell growth curves for HFF-MYC incubated with different concentrations of IC261.

Figure 8:
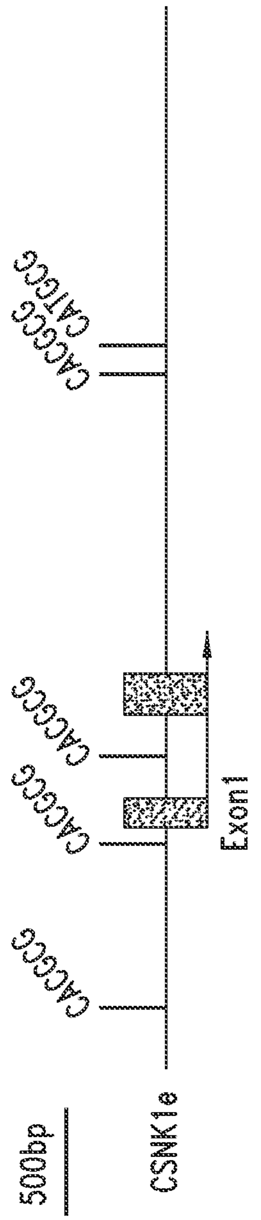

FIG. 8. The CSNK1e gene contains MYC-MAX consensus sites. The DNA sequence surrounding the transcription start site as well as the first and second intron of CSNK1e contains several MYC-MAX potential binding sites[41] both upstream and downstream from the transcription start site.

DETAILED DESCRIPTION

Embodiments of the present invention relate to the discovery of druggable gene targets in MYC-driven cancers, and related methods of inhibiting the growth and/or proliferation of myc-driven cancer cells by targeting one or more of these genes or their encoded protein(s) with inhibitory agent(s), including small molecule inhibitors of the protein(s). Also included are methods using such inhibitors to treat a subject having a MYC-driven cancer. In particular aspects, the cancer is a c-MYC-driven or a MYCN-driven cancer, such as a c-MYC-amplified or a MYCN-amplified cancer, and the gene (or its encoded protein) targeted for inhibition is described in Table 1 or 2.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles “a” and “an” are used herein to refer to one or to more than one (i.e., to at least one) of the grammatical object of the article. By way of example, “an element” means one element or more than one element.

By “about” is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words “comprise,” “comprises,” and “comprising” will be understood to imply the inclusion of a stated step or element or group of steps or elements but not the exclusion of any other step or element or group of steps or elements. By “consisting of” is meant including, and limited to, whatever follows the phrase “consisting of.” Thus, the phrase “consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

"Cancer" relates generally to a class of diseases or conditions in which a group of cells display one or more of uncontrolled growth (i.e., division beyond normal limits), invasion (i.e., intrusion on and destruction of adjacent tissues), and/or metastasis (i.e., spread to other locations in the body via lymph or blood). These malignant properties of cancers differentiate them from benign cancers, which are self-limited, and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form solid tumors, but some, e.g., leukemia, do not necessarily form tumors. For those cancers that form tumors, the terms cancer (cell) and tumor (cell) are used interchangeably.

As used herein, the terms "function" and "functional" and the like refer to a biological, enzymatic, or therapeutic function.

The term "gene" refers to a locatable region of genomic sequence, corresponding to a unit of inheritance, which is associated with regulatory regions, transcribed regions, and or other functional sequence regions. A gene optionally encodes for a protein or polypeptide that has at least one function in an organism.

The terms "modulating" and "altering" include "increasing," "enhancing" or "stimulating," as well as "inhibiting," "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., the absence of polypeptide of conjugate of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18% , 19%, 20%, 25%, 30%, 35%, 40%, 45%, 50%, 55%, 60%, 65%, 70%, 75%, 80%, 85%, 90%, 95%, or 100% decrease in the amount produced by no composition or a control composition, including all integers in between. As one non-limiting example, a control could compare the growth and/or proliferation of a MYC-driven tumor cell after being contacted with an inhibitor that inhibits the gene function of a gene listed in Table 1 or 2, relative to the growth and/or proliferation of a normal/healthy of the same or similar type, or relative to the growth and/or proliferation of a non-MYC-driven tumor of the same or similar type, after being contacted with that same inhibitor. Other examples of comparisons and "statistically significant" amounts will be apparent to persons skilled in the art from the description provided herein.

The term "MYC" refers to the Myc family of transcription factors, including c-MYC (encoded by the MYC gene) and N-MYC (or MYCN; encoded by the MYCN gene). A "MYC-driven" cancer cell or cancer cell derived therefrom includes a cancer cell that has increased expression and/or activity of at least one Myc transcription factor such as c-MYC and/or MYCN, relative to a control cell such as a normal (e.g., non-cancerous) cell of the same or corresponding cell type. As one example, a "MYC-driven" cancer cell includes a "MYC-amplified" or "MYCN-amplified" cancer cell, such as a cell that has an increase (1.5×, 2×, 3×, 4×, etc.) in the number of copies (e.g., 1, 2, 3, 4, 5, 6 copies) of a MYC and/or a MYCN gene, optionally without a proportional increase in other genes.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

A "subject," as used herein, includes any animal that has a cancer or exhibits a symptom or cancer, or is at risk for having a cancer or exhibiting a symptom of cancer, which can be treated by inhibiting the function of a gene described herein (see Table 1 and Table 2). Suitable subjects (patients) include laboratory animals (such as mouse, rat, rabbit, or guinea pig), farm animals, and domestic animals or pets (such as a cat or dog). Non-human primates and, preferably, human patients, are included. In certain aspects, prior to treatment with an inhibitor described herein, a subject is first identified as having a MYC-driven cancer or tumor, for instance, by measuring the expression levels and/or number of gene copies of a Myc transcription factor, such as MYC and/or MYCN. In some aspects, the subject is monitored before, during, and/or after treatment for the presence of a MYC-driven cancer or tumor, and the treatment is adapted accordingly.

"Substantially" or "essentially" means nearly totally or completely, for instance, 95%, 96%, 97%, 98%, 99% or greater of some given quantity.

"Treatment" or "treating," as used herein, includes any desirable effect on the symptoms or pathology of a disease or condition such as a MYC-driven cancer, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild type gene or gene product (e.g., a polypeptide) is that which is most frequently observed in a population and is thus arbitrarily designed the "normal" or "wild-type" form of the gene.

Inhibition and Treatment of MYC-Driven Cancers

Drugs directed toward oncoproteins have demonstrated therapeutic efficacy while avoiding systemic toxicities associated with standard chemotherapeutics. However, the MYC family of oncoproteins, which are broadly implicated in many human cancers, are difficult to inhibit with small molecules or antibody based therapies. To target MYC-driven cancers, we have taken the approach of identifying druggable genes that exhibit a synthetic lethal relationship with aberrant MYC expression. Using an isogenic cell model system, we identified, via high throughput siRNA screening, more than 100 druggable genes that exhibit a synthetic lethal interaction with MYC (referred to as MYC-synthetic lethal genes, MYC-SL). Among the MYC-SL genes, we focused on casein kinase 1 epsilon (CSNK1e), whose relevance in MYC-driven human cancer was demonstrated by correlation between high levels of CSNK1e expression, MYCN amplification, and poor clinical prognosis in neuroblastoma cases. The requirement of CSNK1e for growth of neuroblastomas with MYCN amplification was validated in vivo by conditional knock-down and via a small molecule inhibitor of its activity. Thus, our studies show how high throughput siRNA screening can be used to identify a network of synthetic lethal genes and potential new therapeutic targets functionally linked to a previously undruggable oncogene.

Figure 1A:
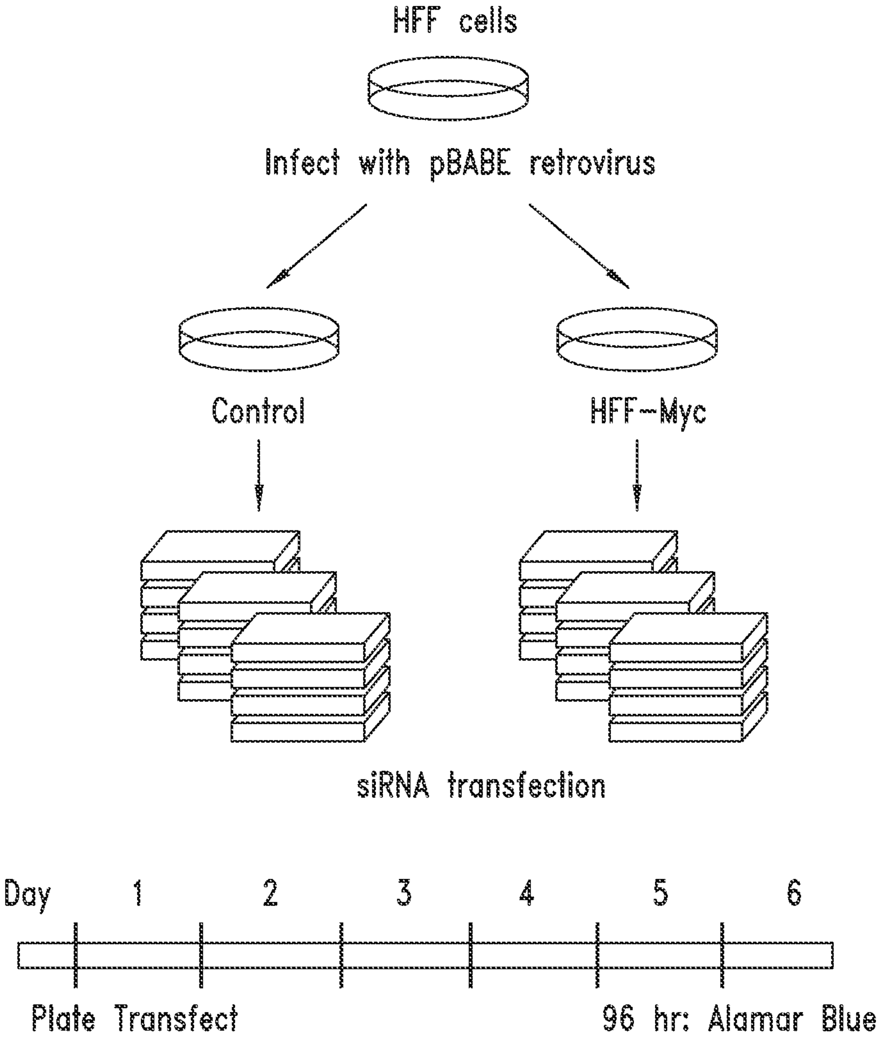
FIG. 1. Identification of synthetic lethal genes with c-MYC overexpression by high throughput siRNA screening. a, Graphical schematic of the siRNA screen. HFF expressing either c-MYC or transduced with an empty retroviral vector, pB, were plated in 384 well plates. 24 hr later they were transfected with siRNA pools (3 siRNAs/pool) targeting a total of ~3,311 genes, with one gene targeted per well. At day 5, the viability was quantified utilizing an Alamar Blue staining assay and an EnVision plate reader. b, Graphical representation of cell viability as affected by each siRNA pool in both HFF-pB or HFF-c-MYC and quantified as % relative to mock (on a log10 scale). Values represent the average viability of 3 replicates. A set of siRNAs (targeting 102 genes labeled as light shaded+) caused differential loss of viability (Z score>2) in the HFF-MYC versus control pB. An additional set of siRNAs targeting 20 genes caused selective growth advantage to HFF-MYC. c, CSNK1e, PES1 and CECR2 mRNA levels following lentiviral-mediated shRNA knock-down. Relative levels of each gene were calculated using the ΔΔCT method and using GAPDH to normalize mRNA levels within each sample. d, Viability of HFF-pBabe and HFF-Myc following stable, lentiviral based knock-down of MYC-SL genes CSNK1e, PES1 and CECR2. Values represent mean viability from 3 independent assays. e, -γ-H2AX staining following transduction of HFF-pBabe and HFF-MYC with siRNAs pools corresponding to 40 MYC-SL genes and a previously identified MYC transcriptional target, DDX18. Representative images of anti-γ-H2AX staining from the INCell automated scope (20× magnification) are shown. f, Graphical representation of the γ-H2AX staining shown in (e). Y-axis indicates the % of cells stained with anti-γ-H2AX that scored for nuclear fluorescence levels above a negative control established threshold. Quantitation was obtained by automated microscopy in 96 well format, from triplicate samples. g, Quantitative assessment of Caspase-3 and -7 cleavage following transfection of the same siRNA pools as above (measured by the CaspaseGlo kit, Promega). Horizontal dark bold line indicates the background levels in HFF c-Myc cells. Results were normalized for cell number by the Alamar Blue assay.
Figure 1B:
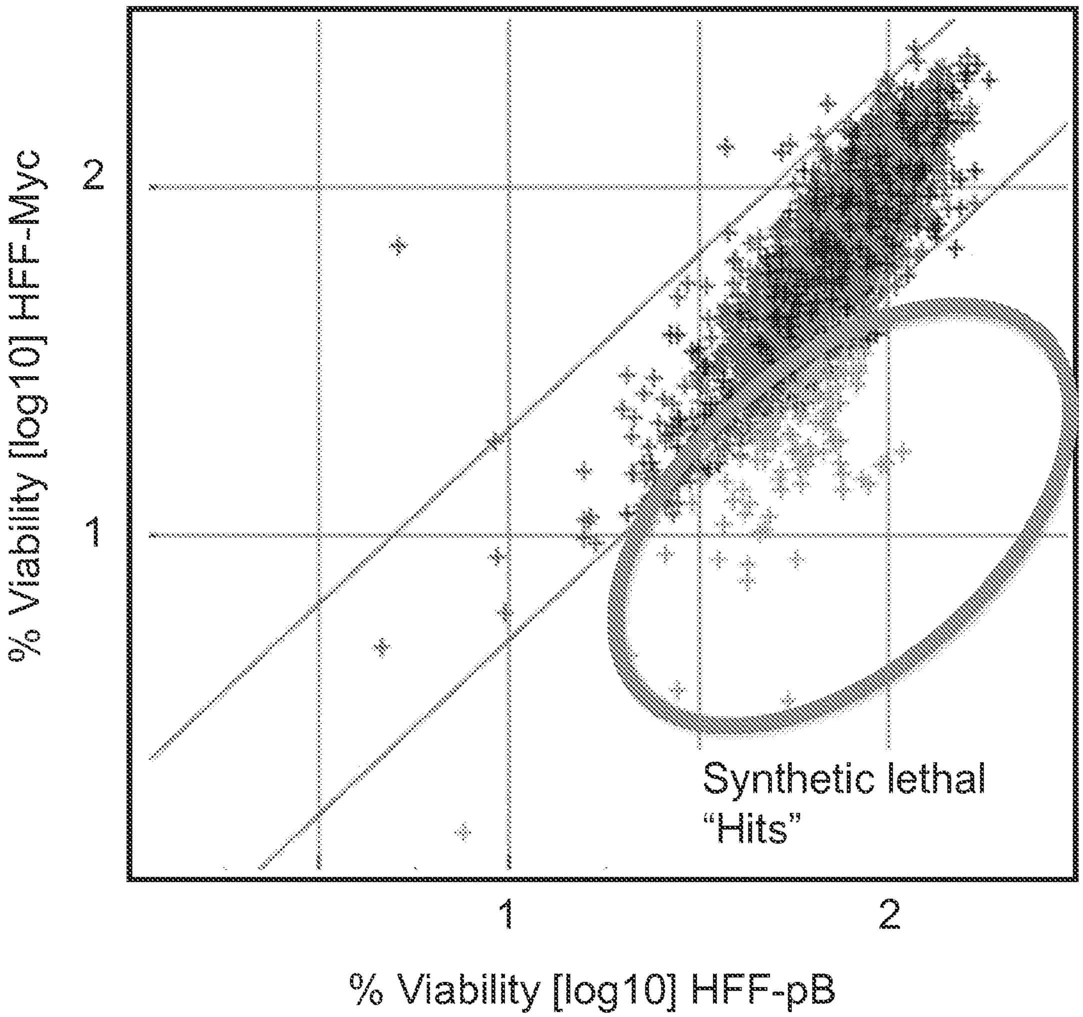

The MYC oncogene is a central driver in many human cancers, and its amplification is associated with poor prognosis in breast[1 2] prostate[3 4], colon[5] and pediatric cancers such as neuroblastoma (for review see[6]). In addition, c-MYC overexpression, together with gene amplification has been reported in over 50% of ovarian cancers[7], in ~30% of hepatocellular carcinoma[8], and in a high percentage of small-cell and non-small-cell lung cancer[9]. Such a high frequency of MYC family deregulation in human cancers suggests that a strategy to target MYC-driven cancers may be relevant for the treatment of a broad population of patients. Recently, systemic inhibition of MYC utilizing a transgenic mouse model has demonstrated the efficacy of a dominant negative MYC in mediating tumor regression[10]. However, MYC family members encode for transcription factors without obvious druggable domains[11] rendering the identification of small molecule inhibitors a challenge[12]. In addition, as MYC oncoproteins carry out essential functions in proliferative tissues[13], prolonged inhibition of MYC function could cause severe side effects. Rather than targeting MYC itself, we elected to apply a functional genomic screen to identify druggable genes that are preferentially required for survival of MYC overexpressing cells. To avoid the genetic noise inherent in cancer cells, we chose to screen an isogenic pair of primary cells, where the only perturbation was overexpression of c-MYC through a retroviral vector[14]. Human foreskin fibroblasts (HFFs) are unique in that they do not senesce in response to MYC overexpression[14] or activated Ras[15], a property that has been attributed to lack of culture stress. Furthermore, c-MYC overexpression in HFFs recapitulates both the gene expression signature and cellular phenotypes of MYC-driven cancers ([14 16 17] and CG unpublished observations).

siRNA Screening to Identify a Network of Genes Required for Survival of c-MYC Overexpressing Cells We employed a high throughput robotics-based approach for massive parallel testing of an arrayed siRNA library to accurately quantify the effects of siRNAs against ~3,300 druggable genes and 200 microRNAs on the viability of HFF-MYC (stably transduced with a retroviral vector expressing c-MYC), or a control empty vector, HFF-pB[14], see FIG. 1*a* for schematic of the experimental set-up). The siRNA library collection was selected so as to target all known human kinases, ubiquitin ligases, DNA repair proteins and a custom collection of genes involved in cancer pathways, with each target gene being interrogated by a pool of three unique siRNAs (SIGMA and Rosetta-Merck custom collection). Three technical replicates and the one gene/well approach enabled derivation of hits with statistical significance for each gene tested, similarly to what has been shown for other biological systems[18 19]. Cell viability was assessed using Alamar Blue staining, and quantified using an EnVision plate reader (Perkin-Elmer). The results of the screen revealed 148 hits comprised of 140 genes and 8 microRNAs, defined according to a Z score ≥2[20] (FIG. 1*b*). Here, we will only focus on gene hits, referred to as MYC synthetic lethal (MYC-SL) genes. To eliminate siRNAs that despite their differential toxicity exhibited substantial growth inhibition properties in normal cells, siRNAs with >50% reduced viability in HFF-pB were eliminated. This process left 102 MYC-SL gene hits for follow up (Table 2).

Network analysis identified known literature connections (based on Ingenuity curated database) between the “Hits” (light shading) and a pre-assembled MYC core pathway (dark shading) as shown in FIG. 5. About 50% of the MYC-SL hits had known functional connections with MYC and functionally related genes. For example TRRAP is a direct MYC binding partner that mediates recruitment of histone acetylase to selective MYC bound promoters[21 22]. Several MYC-SL hits were linked to the basic transcriptional machinery (see TBP node in FIG. 5) including POLR2E, POLR2I, and GTF2H4. CDK2, was also identified as MYC-SL, a finding consistent with its essential role in limiting MYC-induced senescence in a mouse model of tumorigenesis[23]. Additionally, the identification of PES1 (a gene involved in ribosomal biogenesis) among MYC-SL, is consistent with the direct stimulation of ribosomal RNA synthesis by c-MYC[16 24] and by the “addiction” to elevated ribosomal function demonstrated by the suppression of MYC oncogenicity through ribosomal protein haploinsufficiency in mice[25]. The broad spectrum of potential MYC-SL genes thus reflects known MYC functions linked to not only to chromatin modification (TRRAP, BRD4, CECR2,) and to ribosomal biogenesis (PES1), but also metabolism (AldoA, PDK1), DNA repair (DDB2, GTF2H4, NEIL1, POLH, RAD21), apoptosis (BNIP2, BOK, MCL1), and mitotic control (WEE1, NEK2) (see FIG. 5 and Table 2).

Figure 1C:
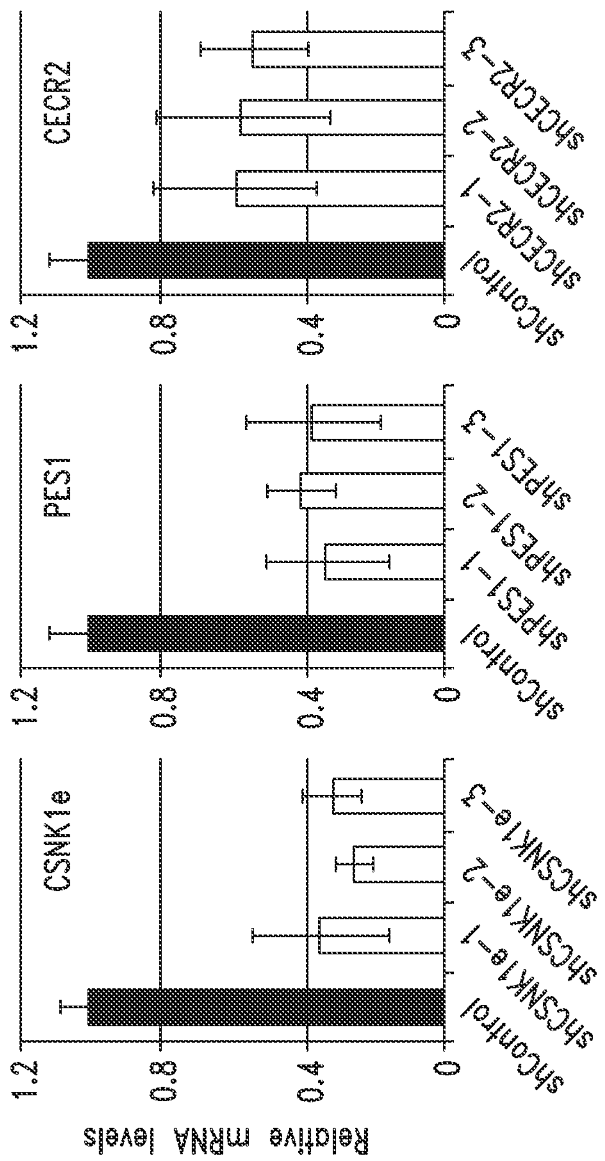
Figure 1D:
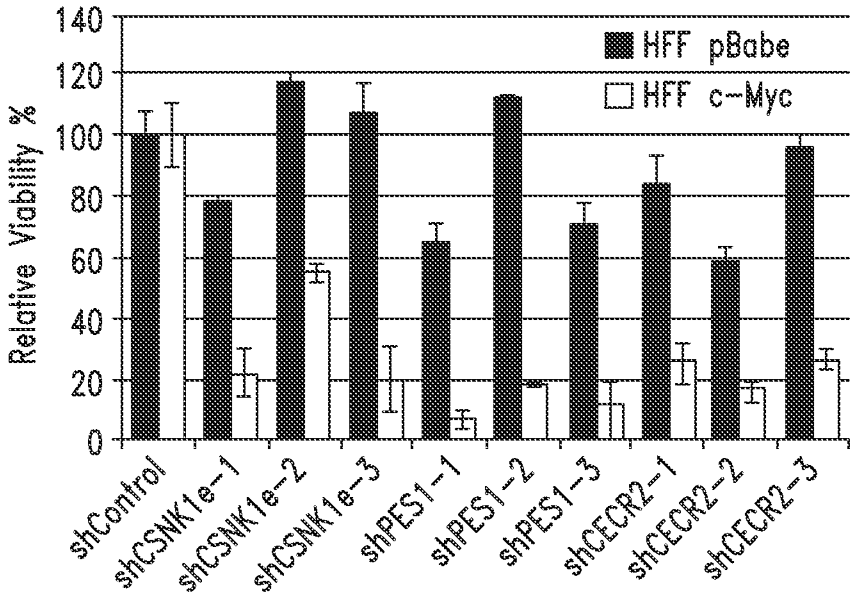
Figure 1E:
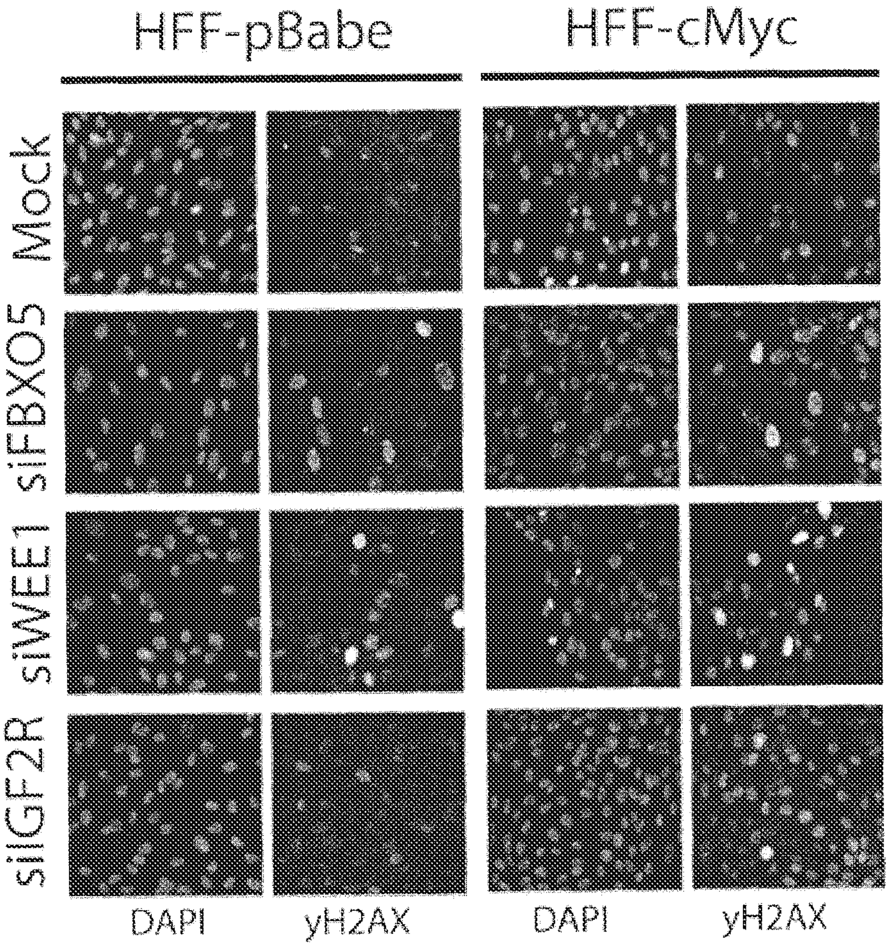
Figure 1F:
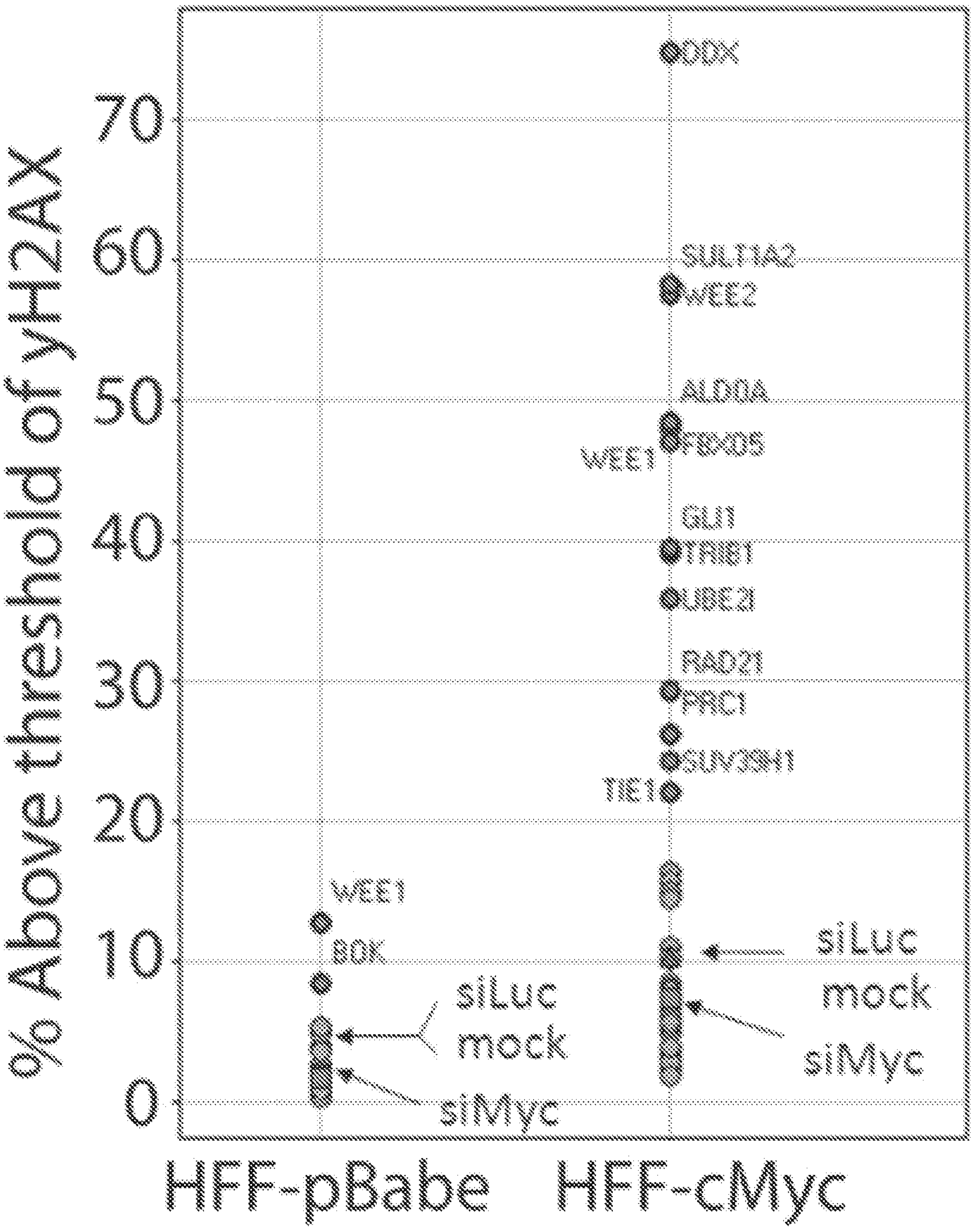

We selected 49 MYC-SL genes based upon best predicted druggability, their potential involvement in cancer pathways and their ranking in the screen in terms of differential toxicity, for follow up. Impressively, 48 out of the 49 tested genes were confirmed with more than one siRNA and in an additional matched pairs of HFFs (98% confirmation rate, see Table 1 for the list of validated and selected MYC-SL), thus highlighting the robustness of our initial screening process. Twelve MYC-SL hits, PES1, CECR2, CSNK1e, MYLK, TXK, TIE1, CDK2, PRKCL1, TRRAP, MAP3K13, NEK2 and WEE1 were assessed via stable, lentiviral-mediated shRNA knock-down, confirming their differential growth inhibition in HFF-MYC versus HFF-pB control (FIG. 1*c-d*, and data not shown). Examination of selective toxicity in HFF-MYC cells was carried out for 38 genes by assessing levels DNA damage and apoptosis. siRNA-mediated knock-down of twelve (25%) of the hits resulted in elevated γ-H2AX foci only in HFF-MYC but not HFF cells. This indicates that induction of DNA damage is a significant consequence of the MYC-synthetic lethal interaction (FIG. 1*e* for representative images and if for quantitation; summarized in Table 1). This finding is consistent with the role of MYC in promoting genomic instability[26] and replication associated damage due to an acceleration of S-phase[17 27]. Additionally, 34 of the 48 MYC-SL genes (>70%) induced caspase-3 and 7 cleavage in HFF-MYC but not in HFF-pB upon siRNA transfection (FIG. 2*g*, Table 1). Importantly, our ability to recapitulate the results from the original high-throughput screen using a combination of three knockdown protocols (siRNA pools, deconvoluted siRNA pools, and lentiviral shRNAs) as well as independent assays suggests that our screening protocol was not only comprehensive but also robust and accurate in predicting MYC-SL genes.

Casein Kinase 1 Epsilon is a MYC-SL Gene in Preclinical Models of Neuroblastoma

Figure 1G:
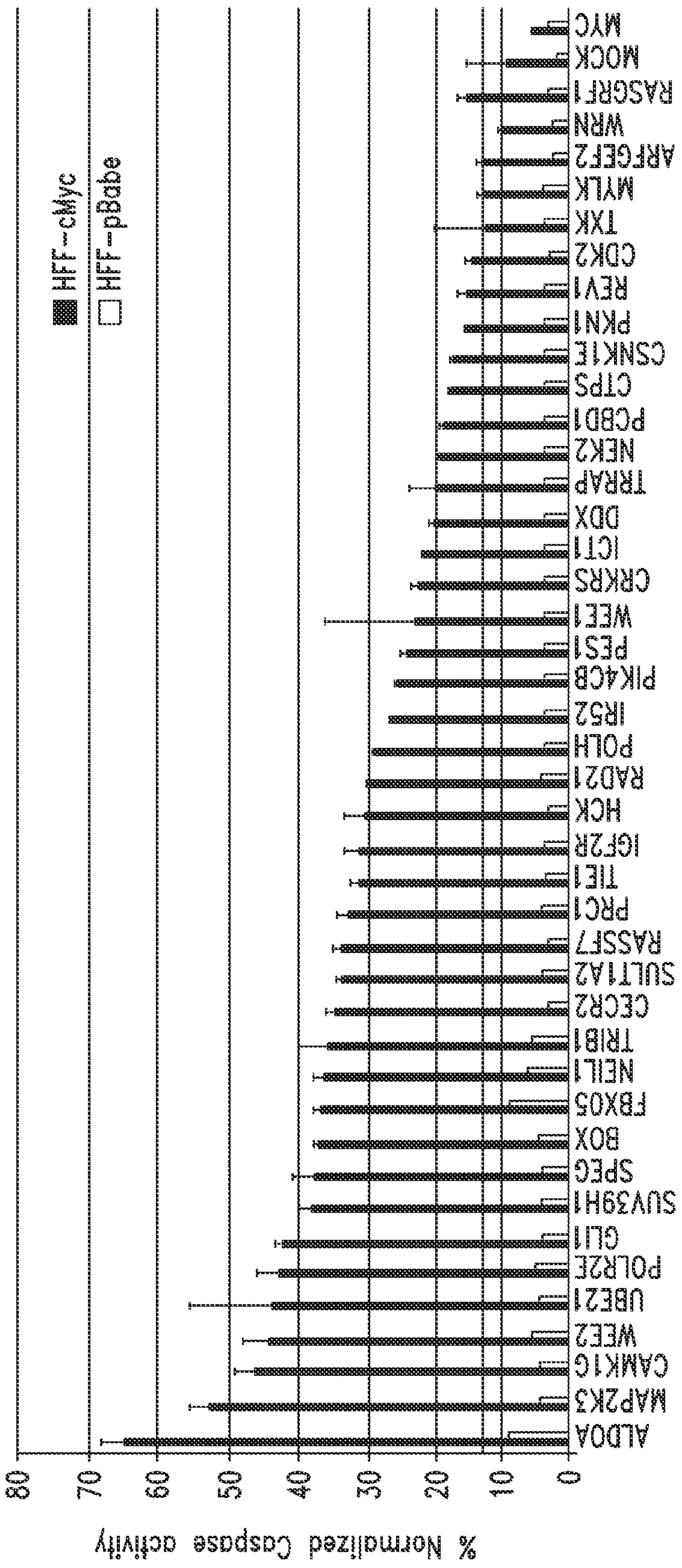
Figure 2A:
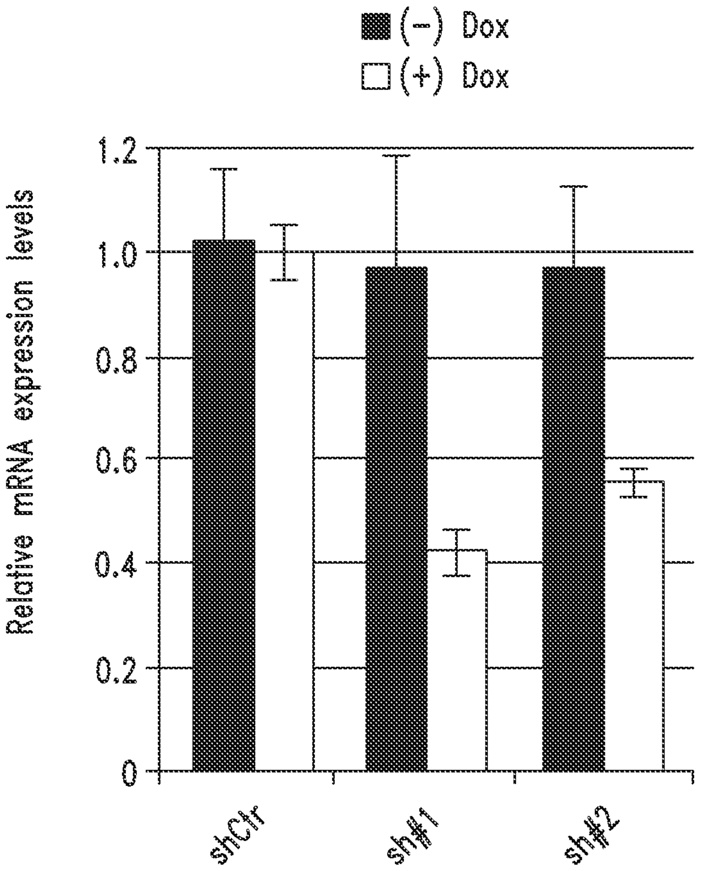
FIG. 2. The knockdown of CSNK1e in neuroblastoma cell lines impairs growth of neuroblastoma with MYCN amplification in vitro and in vivo. a, Relative levels of CSNK1e mRNA following doxycycline or DMSO treatment of neuroblastoma cells harboring shCSNK1e #1, #2 and sh control expressing lentivirus. Relative levels of each gene were calculated using the AACT method and using GAPDH to normalize mRNA levels within each sample. b, Viability assessment following growth under doxycycline containing medium for 4 days as measured by CellTiter Glo (Promega). Values represent mean viability normalized to mock treated cells. c, Representative western blot showing levels of CSNK1e protein in neuroblastoma cells transduced with doxycycline inducible shRNA lentivirus (two different sh: #1 and #2) targeting CSNK1e and non-target sequence (shControl) used in FIG. 2*a*. Cells were cultured in the presence or absence of doxycycline for 4 days. Actin is shown as a loading control. d, Xenograft tumor growth of SK-N-BE2 neuroblastoma cells transduced with doxycycline inducible shRNA for CSNK1e or shControl in NOD/SCID mice. Doxycycline exposure was started when tumors reached a size of about 100 $mm^3$ Knockdown of CSNK1e inhibited growth of established xenograft in 3 out of 4 mice compared to no doxycycline treated control (arrows).
Figure 2B:
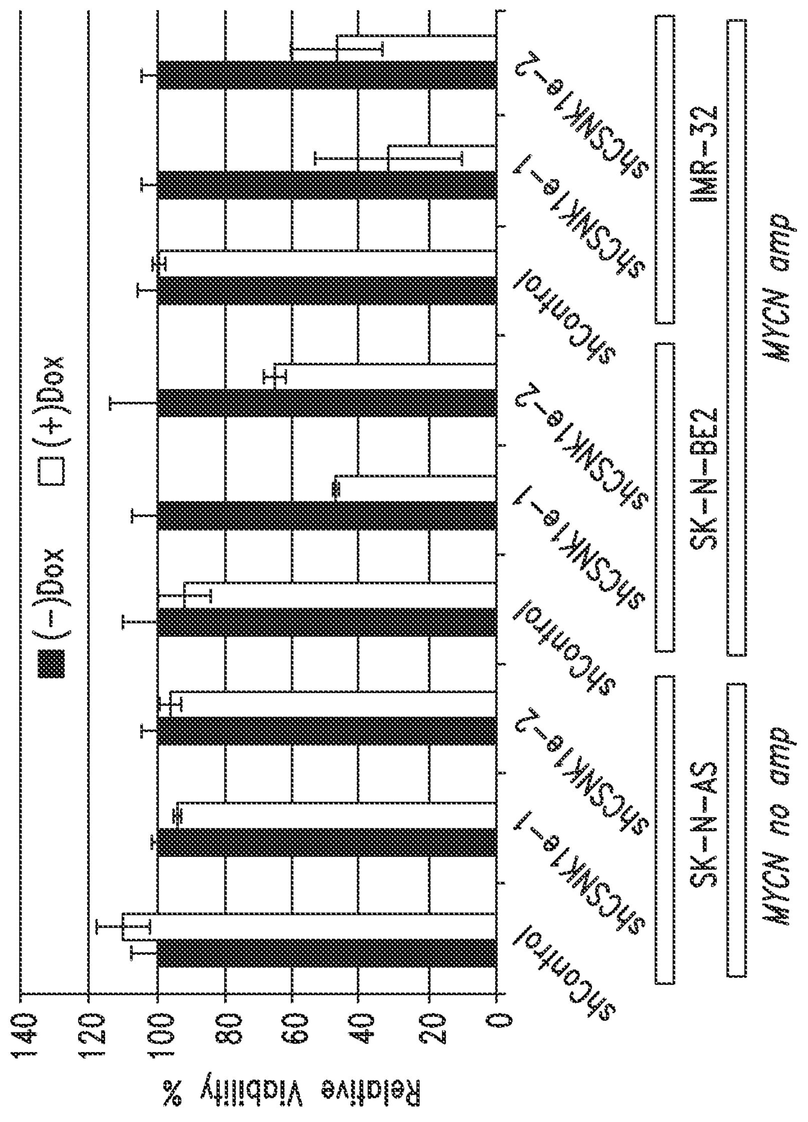
Figure 2C:
Figure 2D:
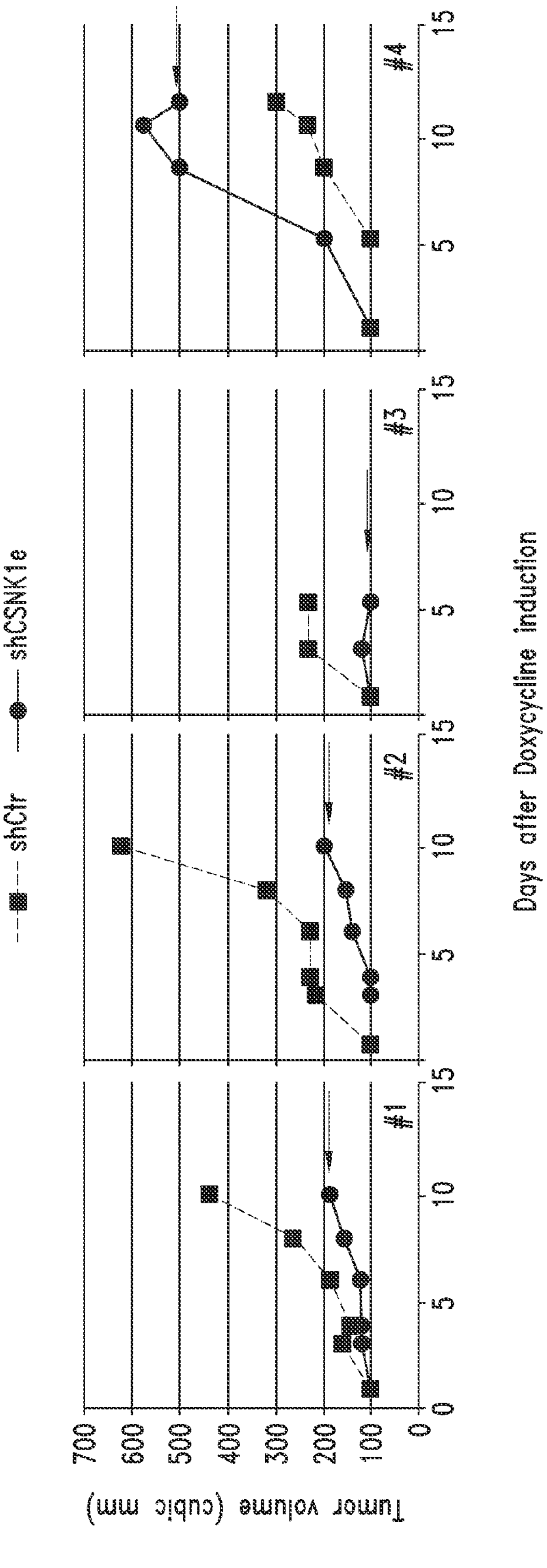

We next wished to validate the MYC-SL genes in neuroblastoma cell lines with or without MYCN amplification, as a model of MYC-driven cancer[28]. In humans, amplification of MYCN in neuroblastoma is the strongest molecular marker of poor prognosis and is utilized for treatment stratification[29]. The potential conservation of synthetic lethal interactions with both c-MYC and MYCN is supported by the fact that MYCN and c-MYC control a similar set of target genes and cellular phenotypes[30 31], and that c-MYC can replace MYCN during murine development[32]. We screened neuroblastoma cell lines with (IMR-32) or without (SK-N-AS) MYCN amplification with siRNAs targeting the selected 48 MYC-SL genes. 11 MYC-SL genes exhibited selective lethality in MYCN amplified neuroblastomas (indicated with shading in the first column of Table 1), indicating conserved synthetic lethal interaction with both MYC family members and in a cancer cell setting. We chose to focus on one of these genes, Casein kinase 1 epsilon (CSNK1e) for preclinical validation because siRNAs and stable knock-down had showed minimal toxicity to normal HFFs (FIG. 1), suggesting the possibility of a good therapeutic window. Moreover, pharmacologic inhibitors were readily available, enabling us to verify that blocking its enzymatic activity would mimic the effect of gene knock-down[33]. We first tested the differential growth inhibition in MYCN amplified neuroblastoma cells in vitro, using conditional lentiviral vectors targeting CSNK1e with two different short hairpins (sh#1, and sh#2, FIG. 2*a, b* and *c*). As there are six isoforms of CSNK1, the specificity of the lentiviral-expressed short hairpins was examined by assessing the relative levels of mRNA expression of the other isotypes. CSNK1 e-specific short hairpins reproducibly lowered the expression of the epsilon isoform, but had no effect on the mRNA expression of the other isoforms (FIG. 6). As a preclinical validation model, neuroblastoma cells were transduced in vitro with either a control sh expressing lentiviral vector or shCSNK1e #1 and injected into the flanks of immunodeficient mice. Once tumors became engrafted and had reached a minimal size of ~>100 $mm^3$, mice were exposed to doxycycline and tumor growth was measured over time. As shown in FIG. 2*d*, neuroblastoma growth was significantly impaired in 3 out of 4 treated mice, validating the MYC-synthetic lethal relationship of CSNK1e knock-down in vivo.

Figure 3A:
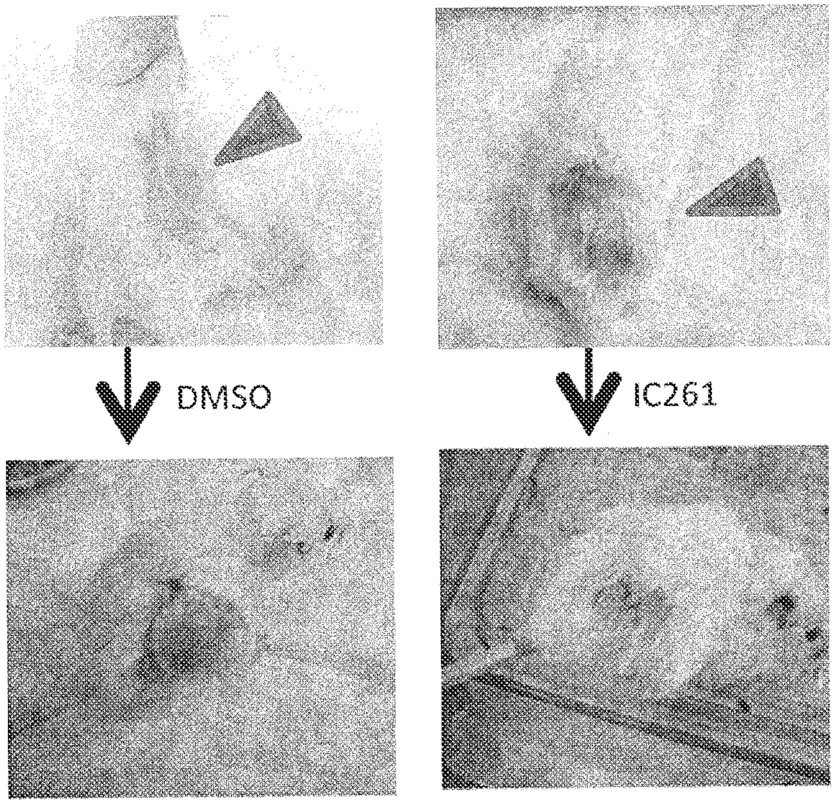
Figure 3B:
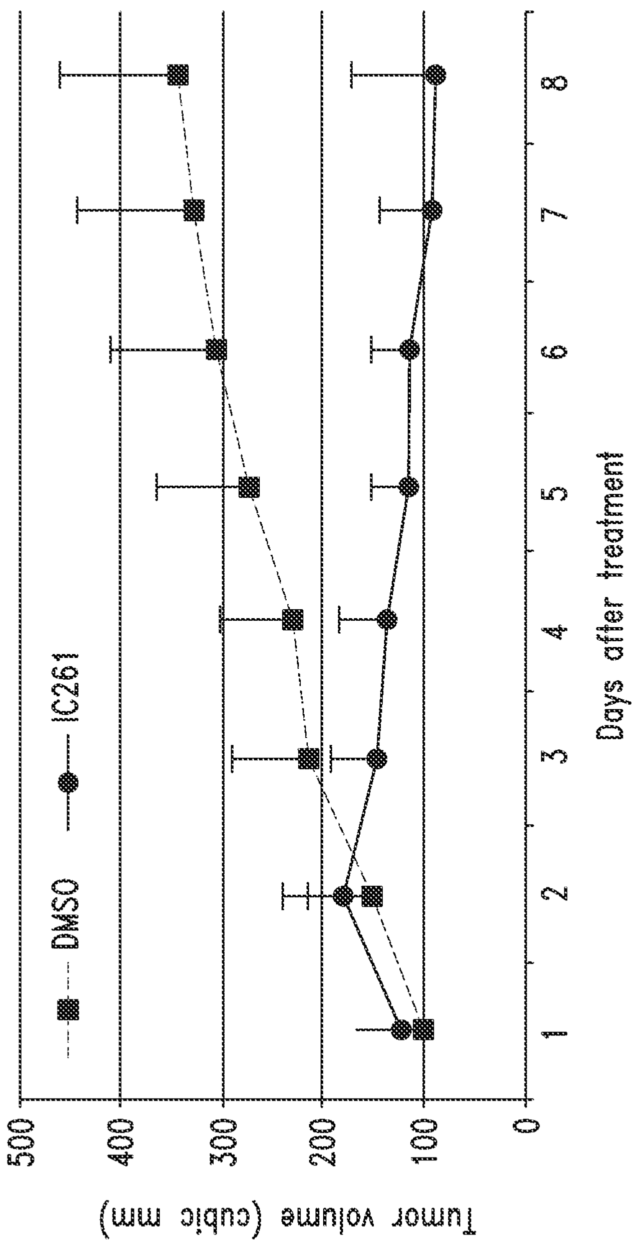
Figure 3C:
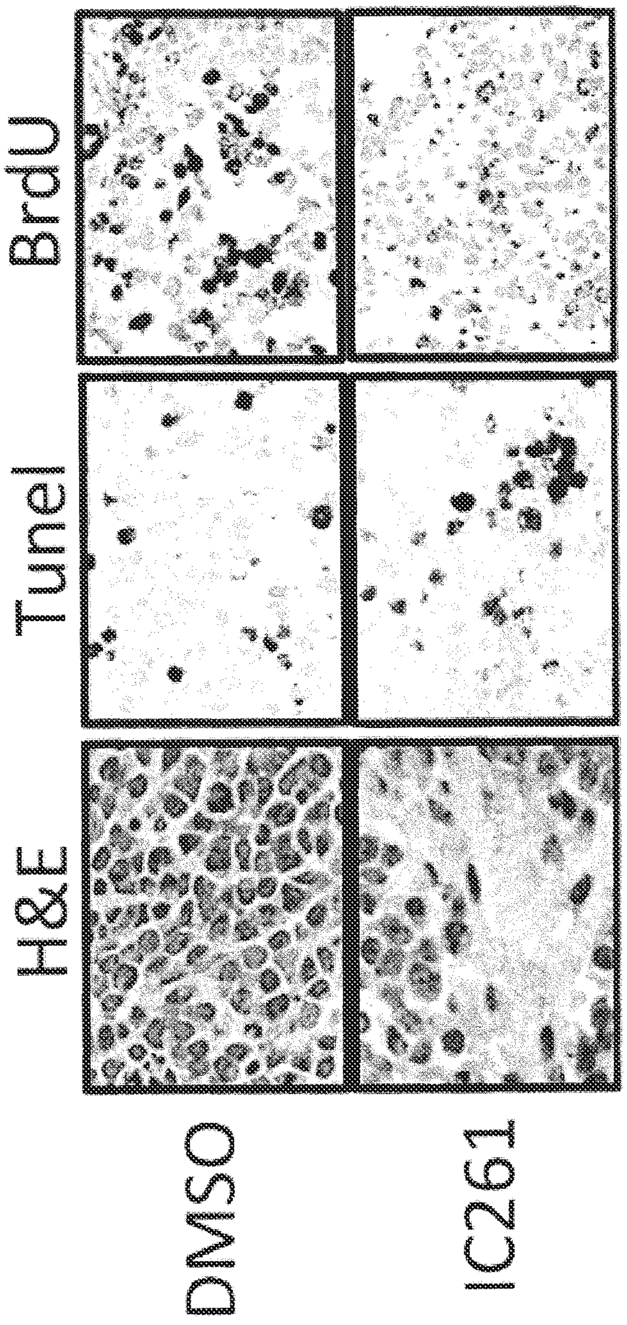
Figure 3D:
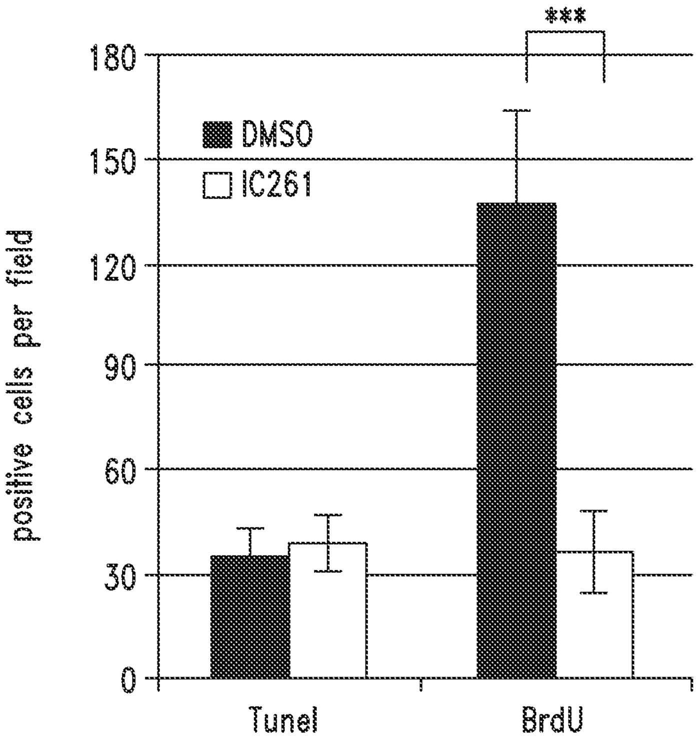
Figure 7A:
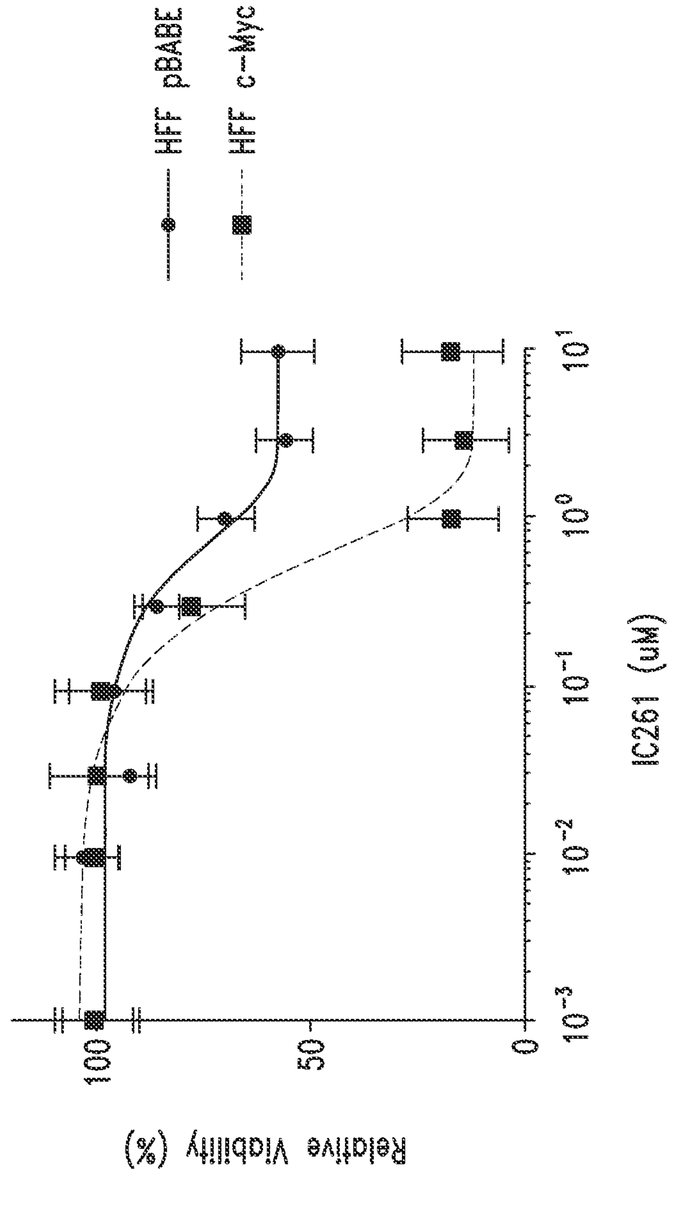
Figure 7B:
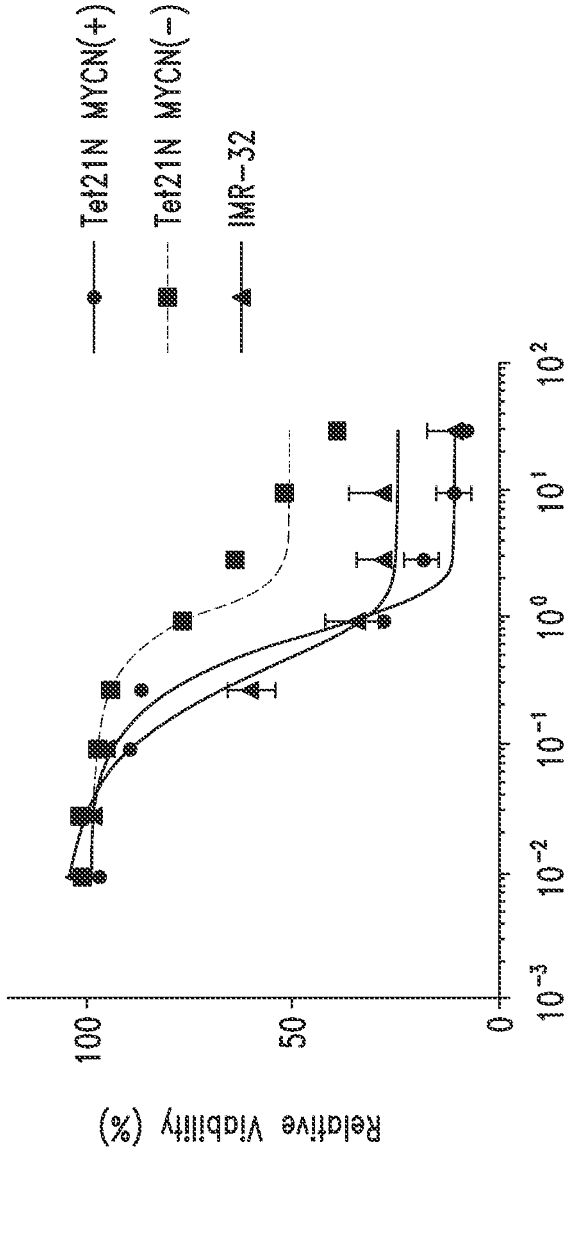
Figure 7C:
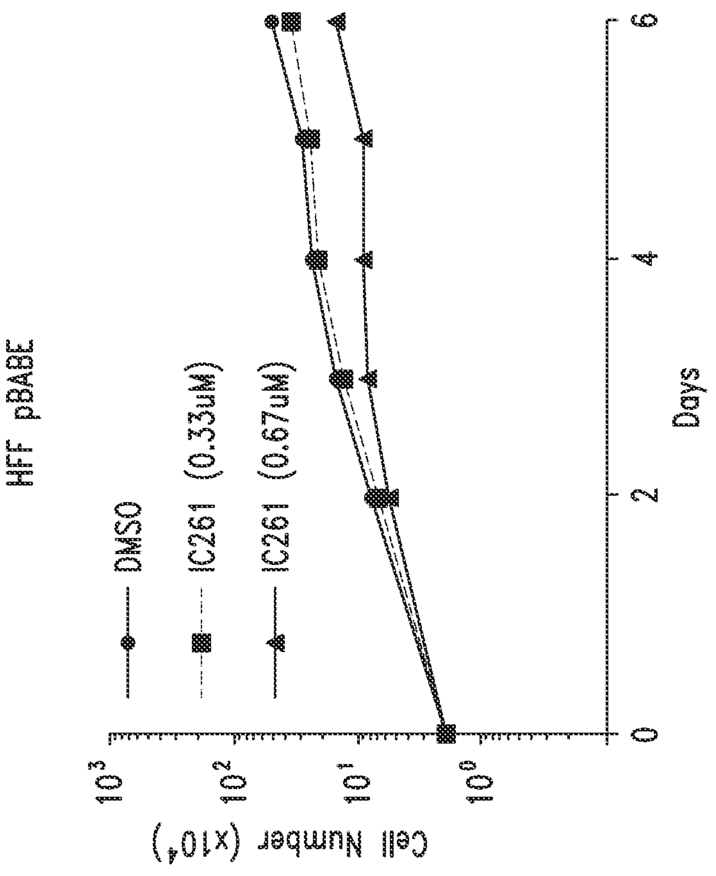
Figure 7D:
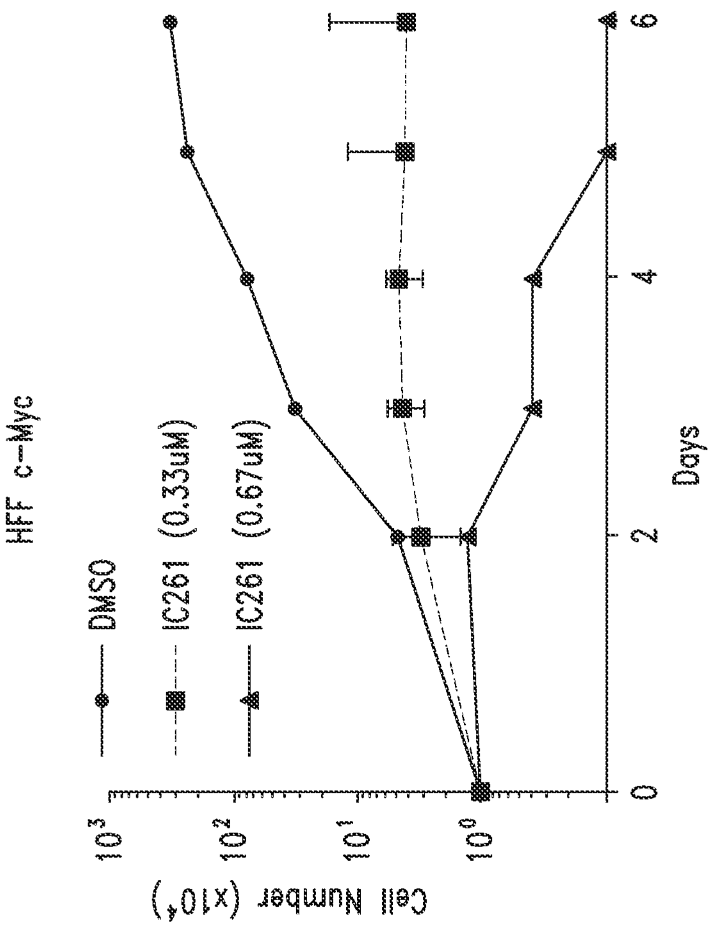

As there is strong selection to escape lentiviral-mediated silencing of genes that are necessary for cell growth, we proceeded to evaluate a small molecule inhibitor of CSNK1e enzymatic activity, IC261[33]. In vitro experiments had indicated that MYC overexpressing cells were indeed more sensitive to IC261 relative to normal or low MYC expressing cells, with >100 fold differences in IC50 (FIGS. 7*a* and 7*b*). IMR32 (MYCN+) cells were utilized as a therapeutic xenograft model as they were established in culture prior to patient chemotherapy and were highly sensitive to IC261 in vitro (FIG. 7*b*). A cohort of ten xenograft bearing mice was randomized into two groups with approximate equal tumor burden; one group was treated with daily subcutaneous injection of IC261 for 8 consecutive days, while the control group was treated with DMSO vehicle only. A photograph of a representative mouse from each group before and after treatment is shown in FIG. 3*a*. Importantly, IC261 was effective in halting tumor growth in all treated mice (FIG. 3*b*). Histopathological examination of the tumor tissue remaining after IC261 treatments, indicated a pronounced proliferative defect as indicated by the marked decrease in BrdU labeling, while very little apoptosis was detected via TUNEL staining (FIG. 3*c* and *d*). This result is consistent with the observation that CSNK1e knock-down did not induce prominent caspase-3 or 7 cleavage in HFFs (FIG. 1*g*). Taken together, the results obtained by genetic knock-down as well as via small molecule inhibitor validate CSNK1e as a potential therapeutic target for MYCN-driven neuroblastoma.

Figure 4A:
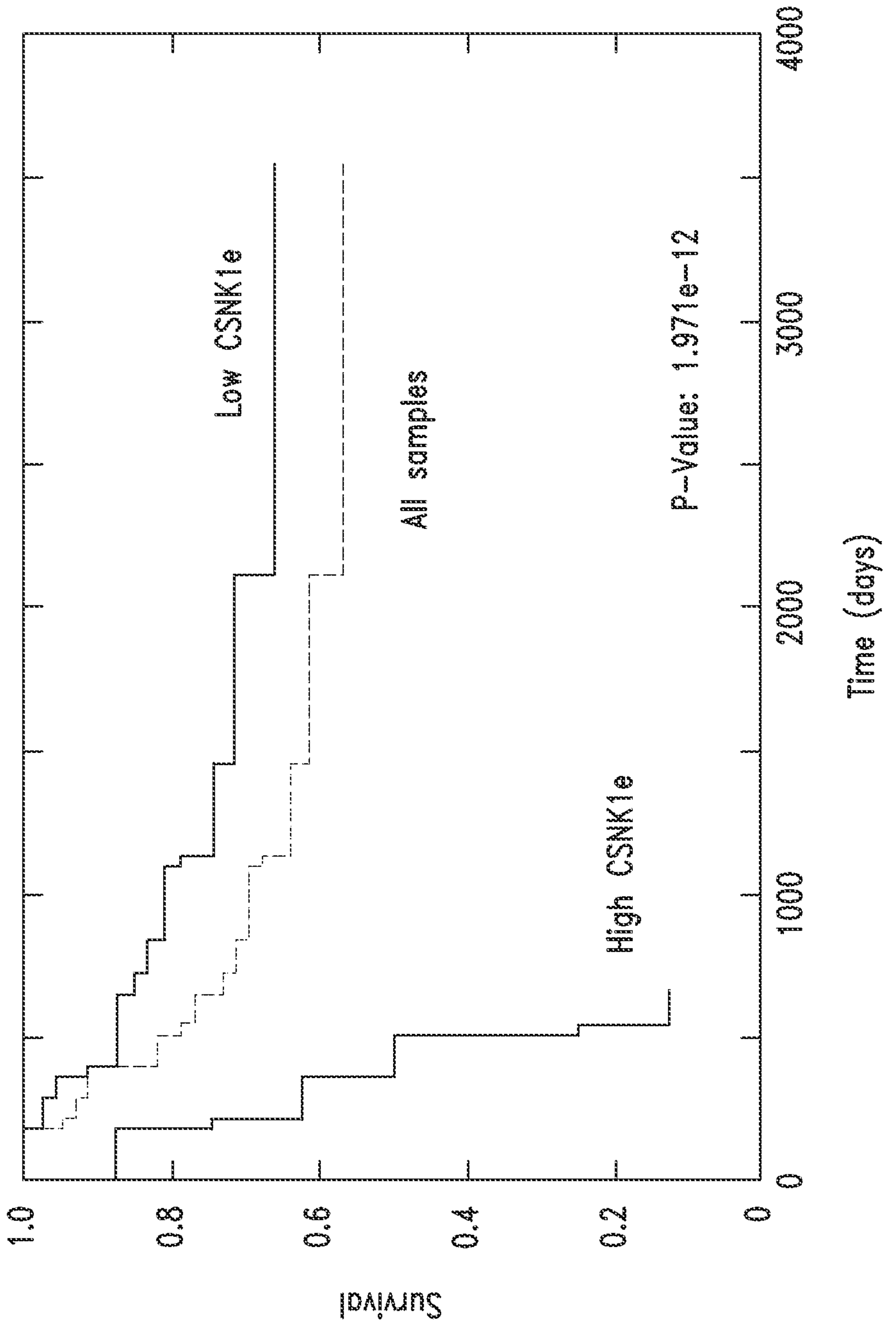
Figure 4B:
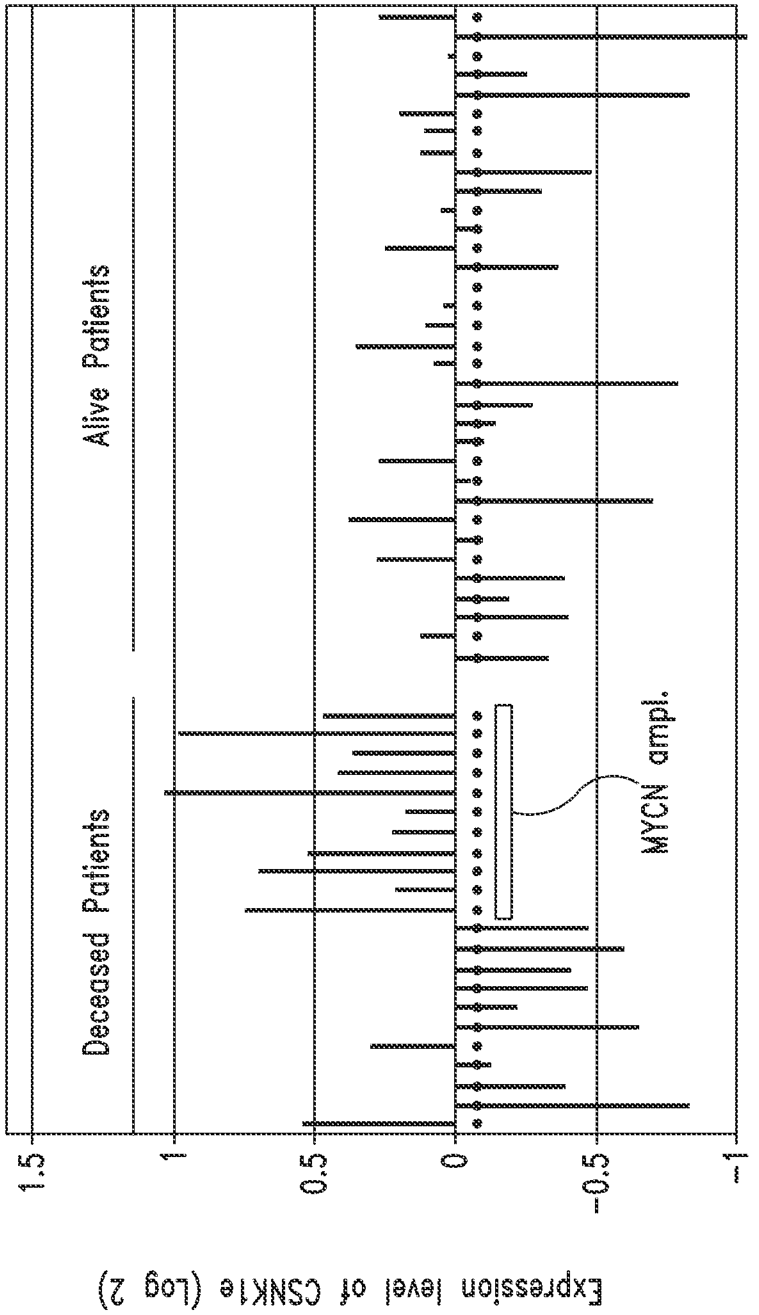
Figure 4C:
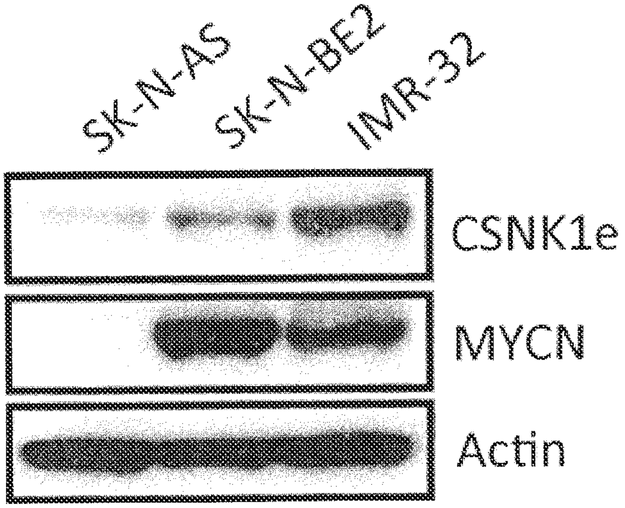
Figure 4D:
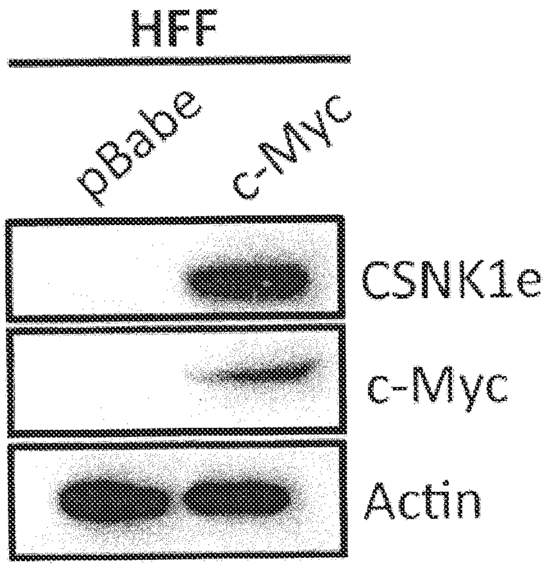
Figure 4E:
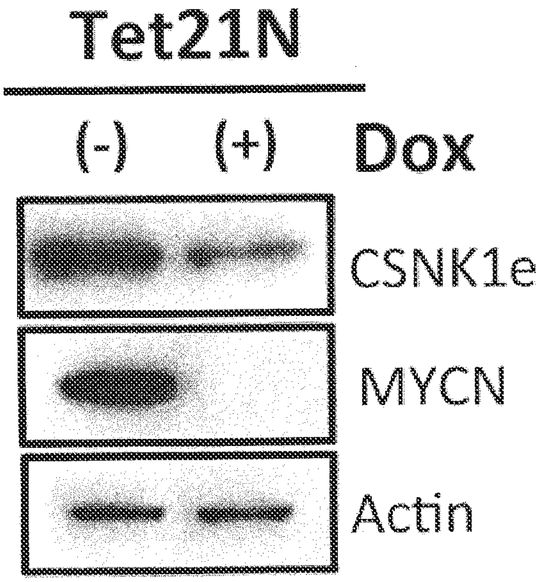
Figure 4F:
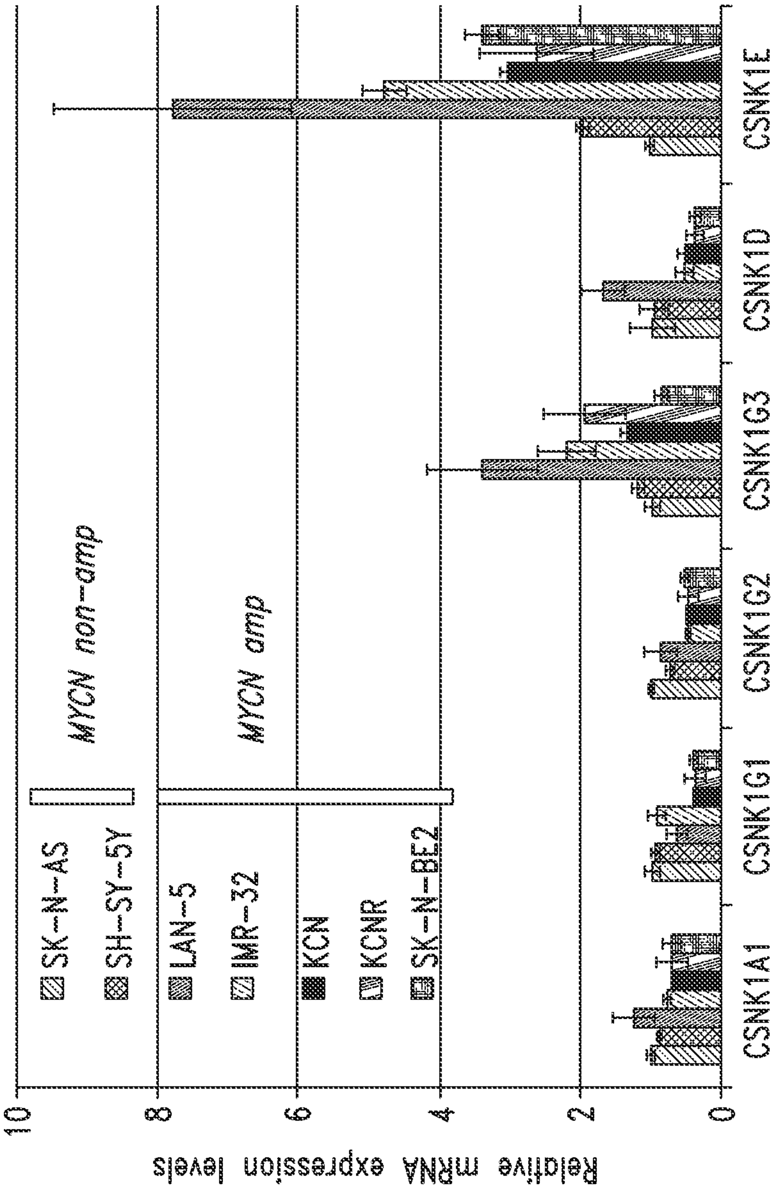

Importantly, CSNK1e expression correlates with both MYCN amplification and poor prognosis in primary neuroblastomas (FIG. 4*a* and *b*). The correlation of high CSNK1e expression in MYCN+ neuroblastoma at the protein level was confirmed in three representative cell lines (FIG. 4*c*) and at the RNA level in these and additional cell lines (FIG. 4*f*). Among the six CSNK1 isoforms, tested, epsilon, was predominantly expressed in lines with MYCN amplification[34] (FIG. 4*f*). These findings, as well as the presence of potential MYC-MAX binding sites in the promoter region of CSNK1e (FIG. 8) suggest a direct regulation of CSNK1e mRNA by c-MYC/MYCN. Consistent with this, CSNK1e is upregulated in both HFF-MYC (FIG. 4*d*) and upon induced MYCN expression in the neuroblastoma cell line Tet21N[35] (FIG. 4*e*). Together, these data support the model where MYC overexpression stimulates expression of CSNK1e, which is in turn required for its survival. In this scenario, CSNK1e represents an “induced dependency” of MYC overexpressing cells. This finding is reminiscent of a previously identified functional dependency of MYC overexpressing cell upon one of its direct transcriptional targets, the Werner syndrome gene (WRN)[36].

Identifying a means to target oncogenic transcription factors as a cancer treatment remains a challenging goal, due to the non-druggability of these proteins, and their essential cellular functions in non-cancerous tissue. Here, we have identified druggable genes that are synthetically lethal in the context of high MYC expression. These genes include those known to be involved in MYC-dependent processes, as well as genes not previously identified as part of the MYC pathway. We focused on CSNK1e, a gene with no previous functional links with MYC, which we validated as a candidate therapeutic target in neuroblastoma with MYCN amplification. The potential that CSNK1e could represent a therapeutic target in other MYC-driven cancers is likely, as its expression is not restricted to HFFs or neuroblastoma, and unpublished results indicate its synthetic lethal interaction with MYC overxpression/amplification is observed in other cancer contexts.

CSNK1e has been previously implicated in the regulation of WNT and SHH signaling. Consistent with the potential for CSNK1e to affect WNT signaling, meta-analysis of gene expression in neuroblastoma tumors indicated that both Frizzeld (FZL) and its the ligand WNT10 were found elevated in MYCN+ stage 4 neuroblastoma versus stage 4 MYCN− tumors, while DKK3, a WNT inhibitor, was found to be repressed (CG, unpublished observations). This finding supports the conclusion from studies in breast cancer where WNT signaling has been shown to be stimulated by MYC overexpression[37]. Moreover, GLI1, the well-studied mediator of SHH signaling, was among the hits in the HFF screen, while the receptor for SHH, smoothened (SMO), was also found elevated in MYCN+ neruroblastoma by meta-analysis. Thus, it is possible that CSNK1e activity might be essential for survival of cells with MYCN amplification through its activity on both developmental pathways. During the course of this work, two publications involving functional screens also identified CSNK1e as a target to block proliferation of colon cancer and breast cancer with WNT-deregulation[38 39].

In addition, a functional genomic screen carried out in human fibrosarcoma lines identified CSNK1e as a "hit" that differentially affected viability of transformed fibroblasts[40]. Together, these findings indicate the relevance of CSNK1e in other cancer contexts and it reinforces the value of functional genomics to reveal cancer therapeutic targets, which might be missed by sequencing approaches.

In summary, here we have demonstrated an efficient pipeline, which combines the power of a robust high throughput functional genomics approach with a biological controlled cell systems, to reveal candidates for therapeutic development toward un-druggable oncogenic targets. This approach can be supplemented through the use of arrayed lentiviral libraries to enable long-term knock-down. For example, the screen did not detect the dependency of MYC upon expression of the WRN gene, likely due to the high stability of the WRN protein and mRNA and the need for HFFs to undergo several cell divisions under WRN depletion prior entering cellular senescence[36]. Our study utilizing siRNAs has uncovered several genes that represent critical survival pathways for cancers with MYC overexpression/gene amplification. Many of these genes were not previously known to have an interaction with the MYC oncoprotein. Targeting these genes provides novel therapeutic opportunities for proliferative tissues. Inhibitors of the genes have valuable potential as cancer therapeutics. Additionally, the genes identified herein constitute biomarkers for MYC-driven cancers that can guide therapeutic choices or suggest drug combinations for maximum therapeutic effect.

TABLES

TABLE 1

List of MYC-synthetic lethal genes. The effect of siRNAs pools targeting these genes was confirmed through pool deconvolution and testing in independent HFF cell pairs. 48 out of 49 gene hits tested, which confirmed selective growth inhibition in an additional pair of matched HFF-c-MYC and control HFF-pB and with more than one siRNA upon deconvolution of the siRNA pool used in the screen.

| Gene Symbol | % Viability HFF-pB | % Viability HFF-MYC | % Viability PB/MYC | Apoptosis positive | H2AX positive | Functional Annotations |
|---|---|---|---|---|---|---|
| ALDOA | 59.31 | 13.85 | 4.28 | yes | yes | Aldolase A cleaves fructose-1,6-bisphosphate, glycolysis |
| ARFGEF2 | 54.66 | 3.29 | 16.62 | no | no | ADP-ribosylation factor guanine nucleotide-exchange factor 2 (brefeldin A-inhibited) |
| BOK | 74.57 | 18.12 | 4.12 | yes | no | BCL2-related ovarian killer, apoptosis in response to DNA damage via TP53 pathway |
| BTK | 57.41 | 8.38 | 6.85 | NT | NT | Bruton agammaglobulinemia tyrosine kinase pre-B cell receptor signaling and B cell development |
| CAMK1G | 64.77 | 24.63 | 2.63 | yes | no | Calcium/calmodulin-dependent protein kinase IG, highly expressed in brain |
| CAMK2D | 62.00 | 17.64 | 3.51 | NT | NT | Calcium-calmodulin-dependent protein kinase (CaM kinase) II delta |
| CDK2 | 54.01 | 19.41 | 2.78 | yes | no | Cyclin-dependent protein kinase 2 |
| CECR2* | 80.97 | 28.42 | 2.85 | yes | no | Cat eye syndrome chromosome region candidtae 2, an ATPase that interacts with SNF2L (SMARCA1) |
| CRKRS | 59.16 | 16.71 | 3.54 | yes | no | Cdc2-related kinase arginine-serine-rich, an SR domain- and proline-rich region-kinase, t phosphorylates the C-terminal domain of RNA polymerase II |

TABLE 1-continued

| | | | | | | |
|---|---|---|---|---|---|---|
| CSNK1E | 76.69 | 28.59 | 2.68 | yes | no | Casein kinase 1 epsilon, regulates Wnt receptor signaling and circadian clock |
| CTPS | 70.57 | 19.44 | 3.63 | yes | no | CTP synthetase, inhibited by cyclopentenyl cytosine, increased expression in T-ALL |
| FBXO5 | 70.44 | 25.28 | 2.79 | yes | yes | F-box containing proteins, subunit of the SCF ubiquitin ligase complex |
| GLI1 | 58.54 | 25.07 | 2.33 | yes | yes | Glioma-associated oncogene homolog 1, member of the GLI-Kruppel transcriptional activators of the SHH |
| GTF2H4 | 73.10 | 18.01 | 4.06 | NT | NT | General transcription factor IIH polypeptide 4 52 kDa, functions in transcription and nucleotide excision repair |
| HCK | 67.95 | 16.98 | 4.00 | yes | no | Hematopoietic cell kinase, a Src family tyrosine kinase involved in signaling, phagocytosis and cell shape changes |
| HECTD3 | 62.93 | 28.52 | 2.21 | NT | NT | HECT domain containing protein with similarity to human HERC1, which acts as a guanine-nucleotide exchange factor for ARF1 and Rab related proteins |
| HSD17B4 | 70.05 | 21.83 | 3.21 | NT | NT | Type IV 17 beta-hydroxysteroid dehydrogenase, a peroxisomal multifunctional enzyme involved in steroid and bile acid metabolism |
| IGF2R | 58.76 | 15.43 | 3.81 | yes | no | Insulin-like growth factor II receptor, a receptor tyrosine-kinase |
| IRS2 | 72.71 | 28.46 | 2.55 | yes | no | Insulin receptor substrate 2, mediates signal transduction for insulin, integrin, and cytokines, may be associated with type 2 diabetes and carcinoma cell invasion |
| MAP2K3 | 56.31 | 16.88 | 3.34 | yes | no | Mitogen activated protein kinase kinase 3, phosphorylates MAP kinase p38, involved in stress and inflammatory responses, senescence, apoptosis |
| MAP2K7 | 98.97 | 43.13 | 2.29 | NT | NT | Mitogen-activated protein kinase kinase 7, c-Jun N-terminal kinase kinase 2 |

TABLE 1-continued

| | | | | | | |
|---|---|---|---|---|---|---|
| MYLK | 89.77 | 13.70 | 6.55 | no | no | Myosin light polypeptide kinase, calcium and calmodulin-dependent kinase, lamellipodia protrusion/retractions |
| NEIL1 | 77.77 | 28.16 | 2.76 | yes | no | Nei endonuclease VIII-like 1, an endonuclease with DNA glycosylase and lyase activities toward mismatched or oxidized nucleotides, S phase-specific activation |
| NEK2 | 62.97 | 27.57 | 2.28 | yes | no | NIMA-related kinase 2, involved in centrosome cycle during mitosis, inhibits protein phosphatase 1 |
| PAK6 | 64.80 | 20.78 | 3.12 | NT | NT | p21(CDKN1A)-activated kinase 6, activated by MAP kinases, interacts with steroid hormone receptors and suppresses receptor-mediated transcriptional activation |
| PCBD1 | 64.08 | 23.88 | 2.68 | yes | no | Pterin 4 alpha carbinolamine dehydratase, co-activator for TCF1, altered expression is associated with hyperphenylalaninemia, vitiligo, and colorectal ca. |
| PES1 | 51.38 | 14.28 | 3.60 | yes | no | Pescadillo homolog containing BRCT domain 1, role in transformation, rRNA synthesis, neural crest migration |
| PIK4CB | 58.97 | 25.54 | 2.31 | yes | no | Phosphatidylinositol 4-kinase catalytic beta polypeptide, a wortmannin-sensitive lipid kinase |
| PKN1 | 86.39 | 32.82 | 2.63 | yes | no | Protein kinase, activated by Rac, Rho and fatty acids, stimulates phospholipase D1 and PLC activity, regulates G2-M and cytoskeletal function |

TABLE 1-continued

| | | | | | | |
|---|---|---|---|---|---|---|
| POLH | 84.32 | 28.71 | 2.94 | yes | no | DNA polymerase eta, acts in DNA damage checkpoint by regulating p53(TP53) activation; gene is mutated in xeroderma pigmentosum |
| POLR2E | 77.27 | 31.46 | 2.46 | yes | no | RNA Polymerase II DNA directed polypeptide E 25 kD, subunit of RNA polymerases I, II, III, involved in transcriptional activation |
| PRC1 | 60.94 | 15.68 | 3.89 | yes | yes | Regulator of cytokinesis 1, associates with the mitotic spindle, required for cytokinesis but not nuclear division, microtubule bundling |
| RAD21 | 62.63 | 16.73 | 3.74 | yes | yes | RAD21 homolog, sister chromatid separation, chromatid cohesion, G2-M cell cycle arrest, and cytokinesis, upregulated in prostate cancer, and breast ca. |
| RASGRF1 | 97.27 | 42.12 | 2.31 | no | no | Ras protein specific guanine nucleotide releasing factor 1, similar to the *Saccharomyces cerevisiae* CDC25 |
| RASSF7 | 109.39 | 17.15 | 6.38 | yes | no | helix-loop-helix motif, and a leucine zipper dimerization motif with four heptad repeats |
| REV1L | 76.20 | 13.26 | 5.75 | yes | no | REV1-like (yeast), a DNA template-dependent dCMP transferase, extends primer strand in mutagenic translesion DNA synthesis |
| SDC4 | 70.19 | 21.12 | 3.32 | NT | NT | Syndecan 4, regulates inositol phospholipid binding and signaling, protein kinase C activation |

TABLE 1-continued

| | | | | | | |
|---|---|---|---|---|---|---|
| SULT1A2 | 70.56 | 22.63 | 3.12 | yes | yes | Sulfotransferase cytosolic 1A phenol-preferring member 2, sulfonates para-nitrophenol; polymorphism associated with early onset breast cancer risk |
| SUV39H1 | 67.94 | 31.00 | 2.19 | yes | yes | Suppressor variegation 3-9 homolog 1, histone methyltransferase that of histone H3 on lysine 9, represses transcription by interaction with RB1 |
| TIE1 | 74.99 | 23.57 | 3.18 | yes | yes | Tyrosine kinase with immunoglobulin-like and EGF-like domains 1, a putative tyrosine kinase receptor, angiopoietin R, upregulated in invasive cancers |
| TRIB1 | 57.34 | 17.24 | 3.33 | yes | yes | Phosphoprotein regulated by mitogenic pathways, a putative kinase that interacts with and may regulate 12-lipoxygenase (ALOX12) |
| TRRAP | 81.13 | 31.33 | 2.59 | yes | no | ATM-related protein, a component of a multiprotein histone acetyltransferase complex essential for MYC and E2F transcription factor pathways |
| TXK | 96.42 | 15.71 | 6.14 | no | no | Tec-Src kinases that lack the pleckstrin domain, activates MAPK, positively regulate interferon gamma (IFNG) transcription, binds PARP1 |
| UBE2I | 52.17 | 15.08 | 3.46 | yes | yes | Ubiquitin-conjugating enzyme E2I UBC9 homolog yeast, SUMO-1 (UBL1) conjugating enzyme |
| WEE1 | 62.12 | 28.85 | 2.15 | yes | yes | WEE1 homolog, a tyrosine kinase that regulates the G2 mitotic checkpoint and nucleocytoplasmic transport |
| WEE2 | 84.88 | 29.99 | 2.83 | yes | yes | homologue of WEE1 |
| YES1 | 68.36 | 22.16 | 3.08 | NT | NT | Yamaguchi sarcoma viral oncogene homolog 1, a nonreceptor protein tyrosine kinase of the Src family, functions downstream of GM-CSF (CSF2) |

Shaded in "Gene Symbol" column: confirmed selective lethality in MYCN+ versus MYCN− neuroblastoma secondary screen
"no" in "Apoptosis positive" and "H2AX positive" columns: scored negative for either apoptosis or y-H2AX staining
"yes" in "Apoptosis positive" and "H2AX positive" columns: scored positive for either apoptosis or y-H2AX staining
*only 1 siRNA of the original pool was active, but confirmed by stable knock-down

TABLE 2

List of all gene hits here referred to as MYC-SL. 102 genes out of 148 hits remained after siRNAs with percent viability of less then <50% in control HFF-pB were eliminated. microRNAs are also not listed here. The indicated % viability is the average of 3 replicates and is expressed as percent viability relative to the median value of wells transfected with an siRNA to luciferase. Hits were determined by Z score => 2, calculated as described[20]. The last column refers to the ratio of percent viability of a given siRNA pool in HFF-pB/HFF-MYC. The nucleotide sequence for each gene is hereby incorporated by reference to the Genbank accession number, as accessed on Aug. 9, 2011 (listed in the second column).

| Gene Symbol | Accession number | Z score (>than) | % Viability HFF-pB | % Viability HFF-MYC | Ratio pBabe/Myc | SEQ ID NO: |
|---|---|---|---|---|---|---|
| ADRBK2 | NM_005160 | 2 | 66.14 | 30.55 | 2.17 | 1 |
| ALDOA | NM_000034 | 2.5 | 59.31 | 13.85 | 4.28 | 2 |
| ALPK1 | NM_025144 | 2.5 | 59.67 | 21.80 | 2.74 | 3 |
| AMID | NM_032797 | 2 | 93.61 | 47.65 | 1.96 | 4 |
| APBA2BP | NM_031231 | 2.5 | 74.31 | 25.88 | 2.87 | 5 |
| APEG1 | NM_005876 | 2.5 | 67.41 | 20.36 | 3.31 | 6 |
| ARFGEF2 | NM_006420 | 2.5 | 54.66 | 3.29 | 16.62 | 7 |
| ASCC3L1 | NM_014014 | 2.5 | 55.94 | 18.89 | 2.96 | 8 |
| ATP5D | NM_001687 | 2 | 83.38 | 35.32 | 2.36 | 9 |
| BMPR1A | NM_004329 | 2 | 61.70 | 30.02 | 2.06 | 10 |
| BNIP2 | NM_004330 | 2 | 56.13 | 26.07 | 2.15 | 11 |
| BOK | NM_032515 | 2.5 | 74.57 | 18.12 | 4.11 | 12 |
| BRD4 | NM_014299 | 2 | 60.05 | 28.99 | 2.07 | 13 |
| BTK | NM_000061 | 2.5 | 57.41 | 8.38 | 6.85 | 14 |
| C17orf49 | BC040036 | 2.5 | 83.05 | 26.24 | 3.17 | 15 |
| C1orf117 | NM_182623 | 2.5 | 75.21 | 15.91 | 4.73 | 16 |
| CAMK1G | NM_020439 | 2.5 | 64.77 | 24.63 | 2.63 | 17 |
| CAMK2D | NM_001221 | 2.5 | 62.00 | 17.64 | 3.51 | 18 |
| CAMK2G | NM_172171 | 2 | 99.46 | 38.96 | 2.55 | 19 |
| CCNK | BC015935 | 2 | 51.64 | 21.59 | 2.39 | 20 |
| CDH5 | NM_001795 | 2.5 | 60.30 | 24.99 | 2.41 | 21 |
| CDK2 | NM_001798 | 2.5 | 54.01 | 19.41 | 2.78 | 22 |
| CECR2 | AB051527 | 2 | 80.97 | 28.42 | 2.85 | 23 |
| CPS1 | NM_001875 | 2 | 58.12 | 25.10 | 2.32 | 24 |
| CRADD | NM_003805 | 2.5 | 49.68 | 21.30 | 2.33 | 25 |
| CRKRS | NM_016507 | 2.5 | 59.16 | 16.71 | 3.54 | 26 |
| CSNK1E | NM_001894 | 2 | 76.69 | 28.59 | 2.68 | 27 |
| CTPS | NM_001905 | 2.5 | 70.57 | 19.44 | 3.63 | 28 |
| CTSD | NM_001909 | 2 | 66.42 | 36.06 | 1.84 | 29 |
| CXXC1 | NM_014593 | 2.5 | 49.66 | 18.00 | 2.76 | 30 |
| DDB2 | NM_000107 | 2 | 69.50 | 27.21 | 2.55 | 31 |
| EFNA5 | NM_001962 | 2 | 65.45 | 27.30 | 2.40 | 32 |
| FBXO5 | NM_012177 | 2.5 | 70.44 | 25.28 | 2.79 | 33 |
| GLI1 | NM_005269 | 2.5 | 58.54 | 25.07 | 2.33 | 34 |
| GNRHR | NM_000406 | 2 | 66.69 | 31.96 | 2.09 | 35 |
| GRK1 | NM_002929 | 2 | 59.11 | 29.62 | 2.00 | 36 |
| GSG2 | NM_031965 | 2 | 60.67 | 28.26 | 2.15 | 37 |
| GTF2H4 | BC004935 | 2.5 | 73.10 | 18.01 | 4.06 | 38 |
| HCK | NM_002110 | 2.5 | 67.95 | 16.98 | 4.00 | 39 |
| HECTD3 | NM_024602 | 2.5 | 62.93 | 28.52 | 2.21 | 40 |
| HPS1 | NM_000195 | 2 | 66.79 | 28.63 | 2.33 | 41 |
| HSD17B4 | NM_000414 | 2.5 | 70.05 | 21.83 | 3.21 | 42 |
| ICT1 | NM_001545 | 2.5 | 50.08 | 18.64 | 2.69 | 43 |
| IGF2R | NM_000876 | 2.5 | 58.76 | 15.43 | 3.81 | 44 |
| IRS2 | NM_003749 | 2.5 | 72.71 | 28.46 | 2.55 | 45 |
| ITGB5 | NM_002213 | 2 | 53.73 | 23.28 | 2.31 | 46 |
| KIF18A | NM_031217 | 2 | 50.87 | 21.92 | 2.32 | 47 |
| LATS1 | NM_004690 | 2 | 81.03 | 40.38 | 2.01 | 48 |
| LIMK2 | NM_005569 | 2 | 75.57 | 41.03 | 1.84 | 49 |
| MAP2K3 | NM_145110 | 2.5 | 56.31 | 16.88 | 3.34 | 50 |
| MAP2K7 | NM_145185 | 2.5 | 98.97 | 43.13 | 2.29 | 51 |
| MAP3K13 | NM_004721 | 2 | 74.85 | 29.33 | 2.55 | 52 |
| MATK | NM_139355 | 2 | 90.87 | 45.88 | 1.98 | 53 |
| MCL1 | NM_021960 | 2 | 94.93 | 52.15 | 1.82 | 54 |
| MGC11266 | NM_024322 | 2 | 56.20 | 23.98 | 2.34 | 55 |
| MLCK | NM_182493 | 2.5 | 52.37 | 13.23 | 3.96 | 56 |
| MYLK | NM_053025 | 2.5 | 89.77 | 13.70 | 6.55 | 57 |
| MYO3B | NM_138995 | 2.5 | 59.84 | 15.87 | 3.77 | 58 |
| NEIL1 | NM_024608 | 2 | 77.77 | 28.16 | 2.76 | 59 |
| NEK2 | NM_002497 | 2.5 | 62.97 | 27.57 | 2.28 | 60 |
| NQO2 | NM_000904 | 2 | 69.74 | 28.61 | 2.44 | 61 |
| NR1H3 | NM_005693 | 2 | 67.14 | 30.84 | 2.18 | 62 |
| NTRK1 | NM_002529 | 2 | 58.10 | 27.85 | 2.09 | 63 |
| PAK6 | NM_020168 | 2.5 | 64.80 | 20.78 | 3.12 | 64 |
| PBK | NM_018492 | 2 | 77.68 | 33.01 | 2.35 | 65 |

TABLE 2-continued

List of all gene hits here referred to as MYC-SL. 102 genes out of 148 hits remained after siRNAs with percent viability of less then <50% in control HFF-pB were eliminated. microRNAs are also not listed here. The indicated % viability is the average of 3 replicates and is expressed as percent viability relative to the median value of wells transfected with an siRNA to luciferase. Hits were determined by Z score => 2, calculated as described[20]. The last column refers to the ratio of percent viability of a given siRNA pool in HFF-pB/HFF-MYC. The nucleotide sequence for each gene is hereby incorporated by reference to the Genbank accession number, as accessed on Aug. 9, 2011 (listed in the second column).

| Gene Symbol | Accession number | Z score (>than) | % Viability HFF-pB | % Viability HFF-MYC | Ratio pBabe/Myc | SEQ ID NO: |
|---|---|---|---|---|---|---|
| PCBD1 | NM_000281 | 2.5 | 64.08 | 23.88 | 2.68 | 66 |
| PDK1 | NM_002610 | 2 | 69.99 | 29.57 | 2.37 | 67 |
| PES1 | NM_014303 | 2.5 | 51.38 | 14.28 | 3.60 | 68 |
| PIK4CB | NM_002651 | 2.5 | 58.97 | 25.54 | 2.31 | 69 |
| PKN1 | NM_002741 | 2 | 86.39 | 32.82 | 2.63 | 70 |
| POLA | NM_016937 | 2 | 61.21 | 23.89 | 2.56 | 71 |
| POLH | NM_006502 | 2.5 | 84.32 | 28.71 | 2.94 | 72 |
| POLR2E | NM_002695 | 2.5 | 77.27 | 31.46 | 2.46 | 73 |
| POLR2I | NM_006233 | 2 | 54.05 | 26.32 | 2.05 | 74 |
| PRC1 | NM_003981 | 2.5 | 60.94 | 15.68 | 3.89 | 75 |
| PSMC2 | NM_002803 | 2 | 60.43 | 27.13 | 2.23 | 76 |
| PTP4A2 | NM_003479 | 2 | 54.60 | 29.73 | 1.84 | 77 |
| PTPN9 | NM_002833 | 2 | 80.76 | 40.14 | 2.01 | 78 |
| RAD21 | NM_006265 | 2.5 | 62.63 | 16.73 | 3.74 | 79 |
| RASGRF1 | NM_002891 | 2.5 | 97.27 | 42.12 | 2.31 | 80 |
| RASSF7 | NM_003475 | 2.5 | 109.39 | 17.15 | 6.38 | 81 |
| REV1L | NM_016316 | 2.5 | 76.20 | 13.26 | 5.75 | 82 |
| SCYL1 | NM_020680 | 2 | 64.55 | 29.37 | 2.20 | 83 |
| SDC4 | NM_002999 | 2.5 | 70.19 | 21.12 | 3.32 | 84 |
| SH3KBP1 | NM_031892 | 2 | 61.19 | 27.82 | 2.20 | 85 |
| SLC1A4 | NM_003038 | 2 | 83.39 | 36.38 | 2.29 | 86 |
| SLC25A26 | NM_173471 | 2 | 62.05 | 34.62 | 1.79 | 87 |
| SULF2 | NM_018837 | 2.5 | 69.11 | 24.20 | 2.86 | 88 |
| SULT1A2 | NM_001054 | 2.5 | 70.56 | 22.63 | 3.12 | 89 |
| SUV39H1 | NM_003173 | 2.5 | 67.94 | 31.00 | 2.19 | 90 |
| TIE1 | NM_005424 | 2.5 | 74.99 | 23.57 | 3.18 | 91 |
| TRIB1 | NM_025195 | 2.5 | 57.34 | 17.24 | 3.33 | 92 |
| TRIP13 | NM_004237 | 2 | 71.01 | 40.01 | 1.77 | 93 |
| TRRAP | NM_003496 | 2.5 | 81.13 | 31.33 | 2.59 | 94 |
| TXK | NM_003328 | 2.5 | 96.42 | 15.71 | 6.14 | 95 |
| UBE2I | NM_003345 | 2.5 | 52.17 | 15.08 | 3.46 | 96 |
| UIP1 | NM_017518 | 2 | 66.20 | 24.65 | 2.69 | 97 |
| WEE1 | NM_003390 | 2 | 62.12 | 28.85 | 2.15 | 98 |
| WEE2 | AK131218 | 2 | 84.88 | 29.99 | 2.83 | 99 |
| WNK1 | NM_018979 | 2 | 53.61 | 26.65 | 2.01 | 100 |
| YES1 | AF119914 | 2.5 | 68.36 | 22.16 | 3.08 | 101 |

REFERENCES

[1] Berns, E. M. et al., c-myc amplification is a better prognostic factor than HER2/neu amplification in primary breast cancer. *Cancer Res* 52 (5), 1107-1113 (1992).

[2] Blancato, J., Singh, B., Liu, A., Liao, D. J., & Dickson, R. B., Correlation of amplification and overexpression of the c-myc oncogene in high-grade breast cancer: FISH, in situ hybridisation and immunohistochemical analyses. *Br J Cancer* 90 (8), 1612-1619 (2004).

[3] Sato, H., Minei, S., Hachiya, T., Yoshida, T., & Takimoto, Y., Fluorescence in situ hybridization analysis of c-myc amplification in stage TNM prostate cancer in Japanese patients. *Int J Urol* 13 (6), 761-766 (2006).

[4] Jenkins, R. B., Qian, J., Lieber, M. M., & Bostwick, D. G., Detection of c-myc oncogene amplification and chromosomal anomalies in metastatic prostatic carcinoma by fluorescence in situ hybridization. *Cancer Res* 57 (3), 524-531 (1997).

[5] Kozma, L., Kiss, I., Szakall, S., & Ember, I., Investigation of c-myc oncogene amplification in colorectal cancer. *Cancer Lett* 81 (2), 165-169 (1994).

[6] Park, J., Eggert, A., Caron H., Neuroblastoma: Biology, Prognosis and Treatment. *Pediatric Clinics of North America* 55 (1), 97-120 (2008).

[7] Chen, C. H., Shen, J., Lee, W. J., & Chow, S. N., Overexpression of cyclin D1 and c-Myc gene products in human primary epithelial ovarian cancer. *Int J Gynecol Cancer* 15 (5), 878-883 (2005).

[8] Takahashi, Y. et al., Amplification of c-myc and cyclin D1 genes in primary and metastatic carcinomas of the liver. *Pathol Int* 57 (7), 437-442 (2007).

[9] Mitani, S. et al., Analysis of c-myc DNA amplification in non-small cell lung carcinoma in comparison with small cell lung carcinoma using polymerase chain reaction. *Clin Exp Med* 1 (2), 105-111 (2001).

[10] Soucek, L. et al., Modelling Myc inhibition as a cancer therapy. *Nature* 455 (7213), 679-683 (2008).

[11] Hopkins, A. L. & Groom, C. R., The druggable genome. *Nat Rev Drug Discov* 1 (9), 727-730 (2002).

[12] Wang, H. et al., Improved low molecular weight Myc-Max inhibitors. *Mol Cancer Ther* 6 (9), 2399-2408 (2007).

[13] Trumpp, A. et al., c-Myc regulates mammalian body size by controlling cell number but not cell size. *Nature* 414 (6865), 768-773 (2001).

[14] Benanti, J. A. et al., Epigenetic down-regulation of ARF expression is a selection step in immortalization of human fibroblasts by c-Myc. *Mol Cancer Res* 5 (11), 1181-1189 (2007).
[15] Benanti, J. A. & Galloway, D. A., Normal human fibroblasts are resistant to RAS-induced senescence. *Mol Cell Biol* 24 (7), 2842-2852 (2004).
[16] Grandori, C. et al., c-Myc binds to human ribosomal DNA and stimulates transcription of rRNA genes by RNA polymerase I. *Nat Cell Biol* 7 (3), 311-318 (2005).
[17] Dominguez-Sola, D. et al., Non-transcriptional control of DNA replication by c-Myc. *Nature* 448 (7152), 445-451 (2007).
[18] Bartz, S. R. et al., Small interfering RNA screens reveal enhanced cisplatin cytotoxicity in tumor cells having both BRCA network and TP53 disruptions. *Mol Cell Biol* 26 (24), 9377-9386 (2006).
[19] Major, M. B. et al., New regulators of Wnt/beta-catenin signaling revealed by integrative molecular screening. *Sci Signal* 1 (45), ra 12 (2008).
[20] Chung, N. et al., Median absolute deviation to improve hit selection for genome-scale RNAi screens. *J Biomol Screen* 13 (2), 149-158 (2008).
[21] McMahon, S. B., Wood, M. A., & Cole, M. D., The essential cofactor TRRAP recruits the histone acetyltransferase hGCN5 to c-Myc. *Molecular & Cellular Biology* 20 (2), 556-562 (2000).
[22] Nikiforov, M. A. et al., TRRAP-dependent and TRRAP-independent transcriptional activation by Myc family oncoproteins. *Mol Cell Biol* 22 (14), 5054-5063 (2002).
[23] Campaner, S. et al., Cdk2 suppresses cellular senescence induced by the c-myc oncogene. *Nat Cell Biol* 12 (1), 54-59; sup pp 51-14.
[24] Arabi, A. et al., c-Myc associates with ribosomal DNA and activates RNA polymerase I transcription. *Nat Cell Biol* 7 (3), 303-310 (2005).
[25] Barna, M. et al., Suppression of Myc oncogenic activity by ribosomal protein haploinsufficiency. *Nature* 456 (7224), 971-975 (2008).
[26] Ray, S. et al., MYC can induce DNA breaks in vivo and in vitro independent of reactive oxygen species. *Cancer Res* 66 (13), 6598-6605 (2006).
[27] Robinson, K., Asawachaicharn, N., Galloway, D. A., & Grandori, C., c-Myc accelerates S-Phase and requires WRN to avoid replication stress. *PLoS One* 4 (6), e5951 (2009).
[28] Weiss, W. A., Aldape, K., Mohapatra, G., Feuerstein, B. G., & Bishop, J. M., Targeted expression of MYCN causes neuroblastoma in transgenic mice. *Embo J* 16 (11), 2985-2995 (1997).
[29] Riley, R. D. et al., A systematic review of molecular and biological tumor markers in neuroblastoma. *Clin Cancer Res* 10 (1 Pt 1), 4-12 (2004).
[30] Boon, K. et al., N-myc enhances the expression of a large set of genes functioning in ribosome biogenesis and protein synthesis. *EMBO J* 20 (6), 1383-1393 (2001).
[31] Mestdagh, P. et al., MYCN/c-MYC-induced microRNAs repress coding gene networks associated with poor outcome in MYCN/c-MYC-activated tumors. *Oncogene* 29 (9), 1394-1404.
[32] Malynn, B. A. et al., N-myc can functionally replace c-myc in murine development, cellular growth, and differentiation. *Genes Dev* 14 (11), 1390-1399 (2000).
[33] Mashhoon, N. et al., Crystal structure of a conformation-selective casein kinase-1 inhibitor. *J Biol Chem* 275 (26), 20052-20060 (2000).
[34] Hanks, S. K. & Hunter, T., Protein kinases 6. The eukaryotic protein kinase superfamily: kinase (catalytic) domain structure and classification. *Faseb J* 9 (8), 576-596 (1995).
[35] Lutz, W. et al., Conditional expression of N-myc in human neuroblastoma cells increases expression of alpha-prothymosin and ornithine decarboxylase and accelerates progression into S-phase early after mitogenic stimulation of quiescent cells. *Oncogene* 13 (4), 803-812 (1996).
[36] Grandori, C. et al., Werner syndrome protein limits MYC-induced cellular senescence. *Genes Dev* 17 (13), 1569-1574 (2003).
[37] Cowling, V. H. & Cole, M. D., Turning the tables: Myc activates Wnt in breast cancer. *Cell Cycle* 6 (21), 2625-2627 (2007).
[38] Kim, S. Y. et al., CK1 epsilon is required for breast cancers dependent on beta-catenin activity. *PLoS One* 5 (2), e8979.
[39] Firestein, R. et al., CDK8 is a colorectal cancer oncogene that regulates beta-catenin activity. *Nature* 455 (7212), 547-551 (2008).
[40] Yang, W. S. & Stockwell, B. R., Inhibition of casein kinase 1-epsilon induces cancer-cell-selective, PERIOD2-dependent growth arrest. *Genome Biol* 9 (6), R92 (2008).
[41] Grandori, C., Mac, J., Siebelt, F., Ayer, D. E., & Eisenman, R. N., Myc-Max heterodimers activate a DEAD box gene and interact with multiple E box-related sites in vivo. *EMBO Journal* 15 (16), 4344-4357 (1996).

While certain embodiments of the invention have been illustrated and described, it will be appreciated that various changes can be made therein without departing from the spirit and scope of the invention.

The invention claimed is:

1. A method for inhibiting the growth and/or proliferation of a neuroblastoma tumor cell having increased expression of a Myc transcription factor as compared to a non-tumor cell of the same cell type, comprising the step of contacting the tumor cell with at least one inhibitor that inhibits the gene product of at least one of the following genes: PES1, TIE1, or CECR2, wherein the inhibitor interferes with production or expression of the gene product of the gene.

2. The method of claim 1, wherein the tumor cell is a metastatic neuroblastoma tumor.

3. The method of claim 1, wherein the tumor cell is contacted in vitro.

4. The method of claim 1, wherein the tumor cell is contacted in vivo in a mammalian subject.

5. A method of treating a subject suffering from a neuroblastoma tumor having increased expression of a Myc transcription factor as compared to a non-tumor cell of the same cell type, comprising administering to the subject an amount of a composition comprising an inhibitor that inhibits the gene function of at least one of the following genes: PES1, TIE1, or CECR2, and is effective to inhibit the growth and/or proliferation of the tumor, wherein the inhibitor interferes with production or expression of the gene product of the gene.

6. The method of claim 1 wherein the gene is CECR2.

7. The method of claim 1 wherein the gene is PES1.

8. The method of claim 1 wherein the gene is TIE1.

9. The method of claim 5 wherein the gene is CECR2.

10. The method of claim 5 wherein the gene is PES1.

11. The method of claim 5 wherein the gene is TIE1.

12. The method of claim 5 wherein the tumor is a metastatic neuroblastoma tumor.

13. A method for inhibiting the growth and/or proliferation of an ovarian tumor cell having increased expression of a Myc transcription factor as compared to a non-tumor cell of the same cell type, comprising the step of contacting the tumor cell with at least one inhibitor that inhibits the gene product of at least one of the following genes: PES1, TIE1, CRKRS or CECR2, wherein the inhibitor interferes with production or expression of the gene product of the gene.

14. The method of claim 13, wherein the tumor cell is contacted in vitro.

15. The method of claim 13, wherein the tumor cell is contacted in vivo in a mammalian subject.

16. The method of claim 13 wherein the gene is CRKRS.

17. The method of claim 13 wherein the gene is CECR2.

18. The method of claim 13 wherein the gene is PES1.

19. The method of claim 13 wherein the gene is TIE1.

20. A method of treating a subject suffering from an ovarian tumor having increased expression of a Myc transcription factor as compared to a non-tumor cell of the same cell type, comprising administering to the subject an amount of a composition comprising an inhibitor that inhibits the gene function of at least one of the following genes: PES1, TIE1, CRKRS or CECR2, and is effective to inhibit the growth and/or proliferation of the tumor, wherein the inhibitor interferes with production or expression of the gene product of the gene.

21. The method of claim 20 wherein the gene is CRKRS.

22. The method of claim 20 wherein the gene is CECR2.

23. The method of claim 20 wherein the gene is PES1.

24. The method of claim 20 wherein the gene is TIE1.

* * * * *

SEQUENCE LISTING

```
<160> NUMBER OF SEQ ID NOS: 101

<210> SEQ ID NO 1
<211> LENGTH: 9068
<212> TYPE: DNA
<213> ORGANISM: Homo sapiens

<400> SEQUENCE: 1

cggcgcgcgc gcggggcggg ggcgcgcgga gggggggct gccccggggc ggcccccca      60

ggtcggggcg cggcgggcgg cggcggcggg cgcgcgtccc gtccaggtcc ggagtaaccg    120

ccgccgccgc cgccaaagct cgccaacatg gcggacctgg aggctgtgct ggccgatgtc    180

agttacctga tggccatgga gaagagcaag gcgaccccgg ccgcccgcgc cagcaagagg    240
```

-continued

```
atcgtcctgc cggagcccag tatccggagt gtgatgcaga agtaccttgc agagagaaat    300
gaaataacct ttgacaagat tttcaatcag aaaattggtt tcttgctatt taaagatttt    360
tgtttgaatg aaattaatga agctgtacct caggtgaagt tttatgaaga gataaaggaa    420
tatgaaaaac ttgataatga ggaagaccgc ctttgcagaa gtcgacaaat ttatgatgcc    480
tacatcatga aggaacttct ttcctgttca catcctttct caaagcaagc tgtagaacac    540
gtacaaagtc atttatccaa gaaacaagtg acatcaactc tttttcagcc atacatagaa    600
gaaatttgtg aaagccttcg aggtgacatt tttcaaaaat ttatggaaag tgacaagttc    660
actagatttt gtcagtggaa aaacgttgaa ttaaatatcc atttgaccat gaatgagttc    720
agtgtgcata ggattattgg acgaggagga ttcggggaag tttatggttg caggaaagca    780
gacactggaa aaatgtatgc aatgaaatgc ttagataaga agaggatcaa aatgaaacaa    840
ggagaaacat tagccttaaa tgaaagaatc atgttgtctc ttgtcagcac aggagactgt    900
cctttcattg tatgtatgac ctatgccttc catacccag  ataaactctg cttcatcctg    960
gatctgatga acgggggcga tttgcactac cacctttcac aacacggtgt gttctctgag   1020
aaggagatgc ggttttatgc cactgaaatc attctgggtc tggaacacat gcacaatcgg   1080
tttgttgtct acagagattt gaagccagca aatattctct tggatgaaca tggacacgca   1140
agaatatcag atcttggtct tgcctgcgat tttccaaaa  agaagcctca tgcgagtgtt   1200
ggcacccatg ggtacatggc tcccgaggtg ctgcagaagg ggacggccta tgacagcagt   1260
gccgactggt tctccctggg ctgcatgctt ttcaaacttc tgagaggtca cagccctttc   1320
agacaacata aaaccaaaga caagcatgaa attgaccgaa tgacactcac cgtgaatgtg   1380
gaacttccag acaccttctc tcctgaactg aagtcccttt tggagggctt gcttcagcga   1440
gacgttagca agcggctggg ctgtcacgga ggcggctcac aggaagtaaa agagcacagc   1500
tttttcaaag gtgttgactg gcagcatgtc tacttacaaa agtacccacc acccttgatt   1560
cctccccggg gagaagtcaa tgctgctgat gcctttgata ttggctcatt tgatgaagag   1620
gataccaaag ggattaagct acttgattgc gaccaagaac tctacaagaa cttccctttg   1680
gtcatctctg aacgctggca gcaagaagta acggaaacag tttatgaagc agtaaatgca   1740
gacacagata aaatcgaggc caggaagaga gctaaaaata agcaacttgg ccacgaagaa   1800
gattacgctc tggggaagga ctgtattatg cacgggtaca tgctgaaact gggaaaccca   1860
tttctgactc agtggcagcg tcgctatttt tacctctttc caaatagact tgaatggaga   1920
ggagagggag agtcccggca aaatttactg acaatggaac agattctctc tgtggaagaa   1980
actcaaatta aagacaaaaa atgcattttg ttcagaataa aaggagggaa acaatttgtc   2040
ttgcaatgtg agagtgatcc agagtttgtg cagtggaaga aagagttgaa cgaaaccttc   2100
aaggaggccc agcggctatt gcgtcgtgcc ccgaagttcc tcaacaaacc tcggtcaggt   2160
actgtggagc tcccaaagcc atccctctgt cacagaaaca gcaacggcct ctagcaccca   2220
gaaacaggga gggtcctcga ggaggacaca ccagggtctc agccttttgg ggtgaacgag   2280
gatgaggcat ctgatctatt cgctaccggg actcctccag gctcccgaga ggagtcggga   2340
cccttcggct tggggtcagc tcagctccct gccttgtcac atttgtctgc attagaaact   2400
actgaagaaa taaaagttct ttttctttgc tacacacttt ggtacctatg aacctagaac   2460
ttgaagtgac tcctacttat cacgtaaatt tttatgtctg atatcaaaca catcttagac   2520
tccccagaat ggaatttaaa gatgttcagt gttgggtaac agattgccct aagcattgcc   2580
acatattctg tctagtcact gctgattttc tatgtctttg ctccatactg ctggggggatg   2640
```

-continued

```
ggagagccac agtgtgtttc ttttgtgcac ttcgcaactg acttcttgtc ctggggttaa   2700
aagttgaaga tattttctga tgatattaaa agttgaagat atttctgcac ttgggccctc   2760
ctctgggagc cgcacccaca tgactgccct gcctctgacc agtctgttcc ggggccccct   2820
cagccaggtg ggaatgacgg acacgtacta tccaagtgta tgggattaac taatcattga   2880
aggcattcat ccgtccatca ttggaaagat ttacagtgat tctgaaggac aggccgtgga   2940
gttttaggtt tcaggggcaa gagcagtttt caaaagtctt tgagtccagt gtgcacgagt   3000
cgacaagcag tacctggcat gcaggagcac tcatgggtga gtccgtctca ggtctcgaca   3060
attagcagtt gtgtgacagt cattctggtt ccttctgcct gaccctggga gacatatcag   3120
taatggatgt acaaaagcag gtctgtttta tgtcttagta taatttcaga tgaattgtat   3180
tgaaaaaatg ctgaggaatg aatgtgtcaa aatgggttaa ctgtgtatat tgactttcat   3240
gtcgtcatgc atctgtcatg aatgaatgat actttgcact gggctgtacg acagtgagga   3300
ccttagggca tgaagccttt ttcctggtcc cagcagcatc tgccctgtga agtttgtttt   3360
ctcccactgc ctccaggccc cactgatacc cccaaataga tgctgggtta tgagaaccag   3420
cgaaatcccc catgtcatca gtcttaaaaa aaaaatttta caaatccacg tatttgtccc   3480
attcttggag tagttttagt gtatgtcttt acattaacta ctaacagtat aaataacttg   3540
acatcgtaat tgtctgcatc ctgtccttga tatttttagc agttccaaat ctttgttttt   3600
gtatttgttt gctgtgttca tgggcaaagt aagtactttt taatgcagtt attttgagag   3660
tttggaagat aattaccaaa agggtccatt atttcataag agttactttg caaaaaaaaa   3720
aatgtgggtt tttttttttg tctatctcaa ctactagttg ggtttaaat taacatacat   3780
tttctactat ctgttatttc cagtgtggga ggagggatgt actacttaca tgcattctcc   3840
ttatttaaaa aggaagaata gtattcaaat tctgttgaaa cacacacaca cacacacaca   3900
cacacacaca cacactccag aagcagaaaa gccattgttc ttaaagagtg aatgtcttcc   3960
cagccctggt taattatagc tgtgactgat gccgttcccg tctgcatctc aagctcatag   4020
gttctcagca tgtgcagttg aggatgcgct gggcctcatg cctgttctag atctccagga   4080
taaagggcct gctgttgact ccaccagggt ctgggcttag cgtctaatat ctcgtaccta   4140
gggcgtgagc tgcacaaacg tgttcagaaa gattattcaa ctttcccata cttgttctaa   4200
aattgagctg atccgcatct ctttcaaaaa ctagaatttc tgctctaaga atagaacata   4260
aggctccact ccctttttaga aaagatatat gaattggaaa atgctctgaa agtccttttg   4320
cttcaaacaa aagtgtaaac ttttacactt ccccaactca catttgattt gtaatgatat   4380
ggttgagaag tacatctaga tgtcatttat taaaagtgct ttgtaagact agattgagct   4440
gtttctgagg gcggtcacca gttgtgttgg ggtctggttt gagtgccttc tgccaaaatg   4500
ttgtgatgga ggtgtttctg cgaccagaca caggataccg ctgtgtctgc acccggttgc   4560
ctgcatggcc agaggaaaag tcagttggat taaacatcat ggtatacttg gctgttgttt   4620
ttttttaatt ttttaatttt ttgggatagg gcctcgctct gtcacccagg ctggagaaca   4680
gtgggatgat catggctcac tgcagccttg aattcctagg ttcaagcaat cctcccacgt   4740
cagcctcctg agtagctagg actacaggtg catgccacct ttcctggcta atttattttt   4800
tgggtagaga tggggtcttg aactcttagg ctcaagtgat cctccttcct tggcctccca   4860
aaatgctgga attagagatg taagccacca tgcccagcca tagtacttgg atgttttaga   4920
aggttttcca agtattacat aattcctaga tgttcaccct tattacactc caactattaa   4980
```

-continued

```
aaaggtcaaa attcagccta tttttttca ttattttaga ttcctgtggt tgggatattt   5040
taacattgat gagaaaaata attgaggttg atatttttac aaaatcatgc ggtaataagt   5100
cttgatttca tgattcaaaa gaatcaataa agcctaaaaa taatagatta ctttaagctg   5160
ctatgtaaga tatatatgga ataaattaaa aacctttgtg aattcaggtt tattattttt   5220
aacctaaaac attctctttg gttcattcat cccctcatgt catgggggct cattggtttt   5280
ccttctttgt catatttaag tatgattttt caacaaaact tctagaagtc agcttattat   5340
gtcaccattc atgcaaagtg ctcatgcctc tgattggtcc attcactgac gtgacaattt   5400
caggtcctat gtttaaaaag aaggggctgg ccgggcacga tggctcacgc ctataatccc   5460
agcactttgg gaggccgaga ggggcggttc acgaggtcag gagattgaga ccatcctggt   5520
tagcagagtg aaaccccgtc tctactaaaa atacaaataa aaattagccg ggcgtggtgg   5580
cgggcgcctg tagtcccagc tacttgggag gctgaggcag gagaatggca tgaacccggg   5640
aggcagagct tgcagtgagc cgagattgcg ccactgcact ccagcctggg cgacagagcg   5700
agactctgtc tcaaaaaaaa aaaggagggg ggctaaatat ccagtgagat gcactgagga   5760
aaggaagcat tttgctgaag acagcagcag caacaaacaa tggtctgttt gttgcaaaca   5820
agatgtagct tgatttctgg tctgacatat gccatataca gatattagaa acgactgttt   5880
gaaggccaca ctggtcatct acaaagtaat gtttaccaat tgacgacagg gatttaacta   5940
gattaaaaag atcaaagtgt ggtttttctc tgctttttaa aatttcactc ggaatttgta   6000
gctgggccaa ttcaacacat tttacttttc agtggaattg atttttctaa tgtttcagaa   6060
ttttaacata tcaagaagaa aacaacgttc tcaaagtctg gcctctttag catgatgtaa   6120
acctatagaa atgctttgaa atgtgctggt gtaagataag agttatcttg tatgatttaa   6180
tcatatgcag tgttgtctca gttacgttca gggaaatgtt tctgtgtcat tcagagatgc   6240
ttgatgaatt aacacctccc accctgagtg aggggttgac ttgttgggag atgatttggg   6300
cttcactggg atctgtgaca ggtgggggct gggctgggtg tcacaaagag aatagtggta   6360
gaaatcgggc gaaggaagaa agaagttact ggtaaaaatc attacaccat aaagcaccaa   6420
ggaaataact gagttaaaat aggtgaagtt tctttttcc cccctgtaac aggagagttt   6480
tccttatgat aattattctg agacttggtc actttgtttt tgaatgtgga gctgctgaac   6540
tcattcagaa gccatttgct gcctatcagg actttctgaa gaagttcttt tgcctctgcc   6600
taccctctgg caccctccca tggaggcaca ggggacccag agctaaagca ttaccaggcc   6660
atctccaaaa caccccgtgt gtgtgtgtgt gtgtgtgtgt gtgtgtgtgt gtgtgtgtgt   6720
gcactttgca gcccccgagg tggagaggca gtgtctggat cactgtgaat gcattgcccc   6780
attggtcagt tggggacact gttacaaatc cactgaagtc ctggtaaaac tgtcaagagt   6840
aacaggcctc ttctgttcta ccctgctcac ttccacggtg agttaccagc ctgggcaaca   6900
cagcaagacc ccatctctac aaaaaaaatt tttttaagta attaaccgtt taaatttttt   6960
cctaaagatt taacatgatt tttccctcct atgtaaagtt tactggagag acttgaatta   7020
cttaaattca tgttaatatg atttttttt aatccaggtc acattttaac aaagtttatt   7080
atgaaacaaa tgaaatttga actctaaaat ggtactcctt ggcttcctca agtcacaatg   7140
aactttatat tttctttgtc cttaaggact aagatagttg ttttatttca gccgaatcac   7200
agagataacc actcctgcag gcccccacag ctggcccaaa ggggctgtct ttctgacctg   7260
gctgtgttag cactgattga gaaacgcagg ctcccaaatt ttaaattgcc tttattaaaa   7320
acacaaacta cagaaaatgg gttaagagta tacgcatttc atcaaacaca tatagggggaa   7380
```

```
aaaatccttc aatttagagt taaataactc agctttgtat agtagagtta gcgctccagt   7440
atctaacaat ctcagaatca tctctgaaaa ctggtaacta tgcttccatt tttaattttg   7500
tcctaaatat cagatgtctt tgatgtaagg gtagggaatg gagaaatatt ttcaattgtg   7560
tatttgtatt acaaagaact tgaaatttac tttcttagtt gattatatta aatgatgtat   7620
atattatatg tggtttataa gctcaacact ggccattttt ttagttttat tgttaaatgg   7680
tatttttcta tgtttaatta taatagatct ggctttttct ggatagcata aagatcactg   7740
aactatatat atataagaaa caagagttct attttagcac aaaggcattt tatattattt   7800
attgaatcca taagtttgtt ttcgtcaaaa acattccata ttatttctgc tcctttttat   7860
ttgtatagtt tgttatttaa agaaatggca gtccttcctg ttcttaatac aataaaattg   7920
aaataatgca cctagtaatg tggccgacat ctcttctcac caccatggac tgttttcaac   7980
aacagttgat cttctggtct gtgctgagag gcgcatgcat gtctttcgtc acgtcgggca   8040
gcacacctgc tgtgaaatac tgctttcatc tacctcttca gaaggcttct tgcttgttga   8100
caagtaccgc aaaggcttta ttctggactg gctatctcat aaaaggattt ctgtaagact   8160
ttgcagtgtc attccctcag aacctaggtt tgtttctaaa gccacggtat tgtccaggag   8220
cccctgtgtg tggggcaggt agctatccct cccatgtcat tagtaatcct ttaggattta   8280
aggtacaact ggacagcatc attccttccc cttattgtgc caaatcccca ccatcagcct   8340
tgccattgcc ttaagatttg attattgcac ccaattacct aaccactaaa cagaaaggcc   8400
accttcactc tttgaaaaag gcaagctgtg cttagaaaca ctgcttttaa gagtagcaca   8460
tttgagtgtg actttttccc cccttcacta tttcaaaatg gttttgaaat ggggtcttaa   8520
aggtaagcgc cctcatacat gactgaaact ttgtgagagg tcttatattt gaatggaccc   8580
ttaatgattt atgtgaaata gaatgaagtc ctgtctctgt gagagaacgt gcctcctcac   8640
tcatttgtct ctgtctgttt tcatagccat caatatagta acatatttac tatattcttg   8700
aataccottg aagaaagaaa tccgttttct attgtgcatt gctatacgaa gtgaagccag   8760
taaactagat actgtaaatc tagatattgt acctagacaa aatatcattg gttctatctc   8820
tttttgtatc tgttgtgcca gggaaggttt ataatccctt ctcagtatac actcactagt   8880
gcacgtctga aatagtatcc cacgggagat gctgctccac gtctgaggtc acctgccctg   8940
tgtggggcac accaccgtca gcaccaccgt ttttacagtt actttggagc tgctagactg   9000
gttttctgtg ttggtaaatt gcctatataa atctgaataa aaaggatctg tacaaaaaaa   9060
aaaaaaaa                                                            9068
```

<210> SEQ ID NO 2
<211> LENGTH: 2408
<212> TYPE: DNA
<213> ORGANISM: Homo sapiens

<400> SEQUENCE: 2

```
aaacaccgct ctggtcacca tggcaacagc gggatgccgc gaacggcttc tgggcggggc     60
cggtccctcg gacgattgga cctagcttgg cgcggaatcc gtgaattgcc cgcggcccga    120
gggtgcagct cccggactga ctggctctgc ccttccccat ggacgcctcc tctagcccgt    180
ggaatccaac cccggctcct gtcagcagcc ctcccctgct gctccccatc cctgccatcg    240
tcttcatcgc tgtgggcatc tatttgttgc tgctgggtct agtcctgctg actaggaact    300
gcctgctggc ccagggctgc tgcgcggacg gtagctcccc ctgcaggaag caaggttcct    360
```

-continued

```
ccgggccccc agactgctgc tggacctgtg cagaagcctg caactttcct ctgcctagcc    420

cggcccactt cctggatgct tgctgccccc agcccaccag agctgactgg gcacctcgct    480

gcccccgctg ctgcccactc tgcgactgtg cctgtacgtg ccagctcccc gactgccaga    540

gcctcaactg tctctgcttc gagatcaagc tccgatgagg acccagggcc cctgccctct    600

ggggagcggc cagcccccag ggcccatgtg ccctcctccc tgaagagcct ttccccacgc    660

cactggaacc acagatggcc tgccgagcac ccaggcctgg gaactggaag tggcagcgca    720

gggcctggct ccctgcaggg caggactctt ggccggctgg acggcagctc ctctggaggg    780

ccagaaaaga gaggggctag tgctcgggca ggtgccctgg cttcccttcc cctccacacg    840

tcaacgattc tatttgaagt tgggcagggg ggtggcgctg ctcaccacac acaagtgtta    900

taggaggagt ctggcccttg agtaccgggt acgcaggggt gcctcaacca cactccgtcc    960

acggactctc cgttatttta ggaggtccct ggccaaagat ttatttctct tgacaaccaa   1020

gggcctccgt ctggatttcc aaggaagaat ttcctctgaa gcaccggaac ttgctactac   1080

cagcaccatg ccctaccaat atccagcact gaccccggag cagaagaagg agctgtctga   1140

catcgctcac cgcatcgtgg cacctggcaa gggcatcctg gctgcagatg agtccactgg   1200

gagcattgcc aagcggctgc agtccattgg caccgagaac accgaggaga accggcgctt   1260

ctaccgccag ctgctgctga cagctgacga ccgcgtgaac ccctgcattg gggtgtcat    1320

cctcttccat gagacactct accagaaggc ggatgatggg cgtcccttcc cccaagttat   1380

caaatccaag ggcggtgttg tgggcatcaa ggtagacaag ggcgtggtcc ccctggcagg   1440

gacaaatggc gagactacca cccaagggtt ggatgggctg tctgagcgct gtgcccagta   1500

caagaaggac ggagctgact tcgccaagtg gcgttgtgtg ctgaagattg ggaacacac    1560

cccctcagcc ctcgccatca tggaaaatgc caatgttctg gcccgttatg ccagtatctg   1620

ccagcagaat ggcattgtgc ccatcgtgga gcctgagatc ctccctgatg gggaccatga   1680

cttgaagcgc tgccagtatg tgaccgagaa ggtgctggct gctgtctaca aggctctgag   1740

tgaccaccac atctacctgg aaggcacctt gctgaagccc aacatggtca ccccaggcca   1800

tgcttgcact cagaagtttt ctcatgagga gattgccatg gcgaccgtca cagcgctgcg   1860

ccgcacagtg ccccccgctg tcactgggat caccttcctg tctggaggcc agagtgagga   1920

ggaggcgtcc atcaacctca atgccattaa caagtgcccc ctgctgaagc cctgggccct   1980

gaccttctcc tacggccgag ccctgcaggc ctctgccctg aaggcctggg gcgggaagaa   2040

ggagaacctg aaggctgcgc aggaggagta tgtcaagcga gccctggcca acagccttgc   2100

ctgtcaagga aagtacactc cgagcggtca ggctggggct gctgccagcg agtccctctt   2160

cgtctctaac cacgcctatt aagcggaggt gttcccaggc tgcccccaac actccaggcc   2220

ctgcccctc ccactcttga agaggaggcc gcctcctcgg ggctccaggc tggcttgccc    2280

gcgctctttc ttccctcgtg acagtggtgt gtggtgtcgt ctgtgaatgc taagtccatc   2340

accctttccg gcacactgcc aaataaacag ctatttaagg gggagtcggc aaaaaaaaaa   2400

aaaaaaaa                                                            2408
```

<210> SEQ ID NO 3
<211> LENGTH: 5441
<212> TYPE: DNA
<213> ORGANISM: Homo sapiens

<400> SEQUENCE: 3

```
aattcctact tcctgaaact gaagccgttt atgagaaaca gtgtgtttca gagaggctgt     60
```

-continued

```
accagaatta actctgctca gagttagatt tgctggtctt aaagtacttt tcctctttaa    120
gataaaagaa gttcttctaa atcaggaatg gattgaaatc taatgaaccg aaactttggg    180
tacttcggcc ttcaaggggc tcctttattg agaatcaatg tcttctccta ggtaattgat    240
caccctagac ccagggacac ccaattcatc gtaatcatca tgaataatca aaaagtggta    300
gctgtgctac tgcaagagtg caagcaagtg ctggatcagc tcttgttgga agcgccagat    360
gtgtcggaag aggacaagag cgaggaccag cgctgcagag ctttactccc cagcgagtta    420
aggaccctga tccaggaggc aaaggaaatg aagtggccct tcgtgcctga aaagtggcag    480
tacaaacaag ccgtgggccc agaggacaaa acaaacctga aggatgtgat tggcgccggg    540
ttgcagcagt tactggcgtc cctgagggcc tccatcctcg ctcgggactg tgcggctgcg    600
gcggctattg tgttcttggt ggaccggttc ctgtatgggc tcgacgtctc tggaaaactt    660
ctgcaggtcg ccaaaggtct ccacaagttg cagccagcca cgccaattgc cccgcaggtg    720
gttattcgcc aagcccgaat ctccgtgaac tcaggaaaac ttttaaaagc agagtatatt    780
ctgagcagtc taataagcaa caatggagca acgggtacct ggctgtacag aaatgaaagt    840
gacaaggtcc tggtgcagtc ggtctgtata cagatcagag ggcagattct gcaaaagctg    900
gggatgtggt acgaagcagc agagttaata tgggcctcca ttgtaggata tttggcactt    960
cctcagccgg ataaaaaggg cctctccacg tcgctaggta tactggcaga catctttgtt   1020
tccatgagca agaacgatta tgaaaagttt aaaaacaatc cacaaattaa tttgagcctg   1080
ctgaaggagt ttgaccacca tttgctgtcc gctgcagaag cctgcaagct ggcagctgcc   1140
ttcagtgcct atacgccgct cttcgtgctc acagctgtga atatccgtgg cacgtgttta   1200
ttgtcctaca gtagttcaaa tgactgtcct ccagaattga aaaacttaca tctgtgtgaa   1260
gccaaagagg cctttgagat tggcctcctc accaagagag atgatgagcc tgttactgga   1320
aaacaggagc ttcacagctt tgtcaaagct gctttcggtc tcaccacagt gcacagaagg   1380
ctccatgggg agacagggac ggtccatgca gcaagtcagc tctgtaagga agcaatgggg   1440
aagctgtaca atttcagcac ttcctccaga agtcaggaca gagaagctct gtctcaagaa   1500
gttatgtctg tgattgccca ggtgaaggaa catttacaag ttcaaagctt ctcaaatgta   1560
gatgacagat cttatgttcc cgagagtttc gagtgcaggt tggataaact tatcttgcat   1620
gggcaagggg atttccaaaa aatccttgac acctattcac agcaccatac ttcggtgtgt   1680
gaagtatttg aaagtgattg tggaaacaac aaaaatgaac agaaagatgc aaaaacagga   1740
gtctgcatca ctgctctaaa aacagaaata aaaaacatag atactgtgag tactactcaa   1800
gaaaagccac attgtcaaag agacacagga atatcttcct ccctaatggg taagaatgtt   1860
cagagggaac tcagaagggg aggaaggaga aactggaccc attctgatgc atttcgagtc   1920
tccttggatc aagatgtgga gactgagact gagccatcgg actacagcaa tggtgaggga   1980
gctgttttca acaagtctct gagtggcagc cagacttcca gtgcttggag caacttatca   2040
gggtttagtt cctctgcaag ctgggaggaa gtgaattatc acgttgacga caggtcagcc   2100
agaaaagagc ctggcaaaga acatctggtg gacactcagt gttccactgc cttgtctgag   2160
gagctagaga atgacaggga aggcagagct atgcattcat tgcattcaca gcttcatgat   2220
ctctctcttc aggaacccaa caatgacaat ttggagcctt ctcaaaatca gccacagcaa   2280
cagatgccct tgacaccctt ctcgcctcat aataccccag gcattttctt ggcccctggt   2340
gcagggcttc tagaaggagc tccagaaggt atccaggaag tcagaaatat gggacccaga   2400
```

-continued

```
aatacttctg ctcactccag accctcatat cgttctgctt cttggtcttc tgattctggt   2460
aggcccaaga atatgggcac acatccttca gtccaaaaag aagaagcctt tgaaataatt   2520
gttgagtttc cagaaaccaa ctgcgatgtc aaagacaggc aggggaaaga gcagggagaa   2580
gaaattagtg aaagaggcgc aggccctaca tttaaagcta gtccctcctg ggttgaccca   2640
gaaggagaaa cagcagaaag cactgaagat gcacccttag actttcacag ggtcctgcac   2700
aattctctgg gaaacatttc catgctgcca tgtagctcct tcacccctaa ttggcctgtt   2760
caaaatcctg actccagaaa aagtggtggc ccagtcgcag agcagggcat cgaccctgat   2820
gcctccacag tggatgagga ggggcaactg ctcgacagca tggatgttcc ctgcacaaat   2880
gggcacggct ctcatagact gtgcattctg agacagccgc ctggtcagag ggcggagacc   2940
cccaattcct ctgtaagcgg taacatcctc ttccctgtcc tcagcgagga ctgcactacc   3000
acagaggaag gaaatcagcc tggaaacatg ctaaactgca gccagaactc cagctcatcc   3060
tcagtgtggt ggctgaaatc acctgcattt tccagtggtt cttctgaggg ggacagccct   3120
tggtcctatc tgaattccag tgggagttct tgggtttcat tgccgggaaa gatgaggaaa   3180
gagatccttg aggctcgcac cttgcaacct gatgactttg aaaagctgtt ggcaggagtg   3240
aggcatgatt ggctgtttca gagactagag aatacggggg tttttaagcc cagtcaactc   3300
caccgagcac atagtgctct tttgttaaaa tattcaaaaa aatctgaact gtggacggcc   3360
caggaaacta ttgtctattt gggggactac ttgactgtga agaaaaaagg cagacaaaga   3420
aatgcttttt gggttcatca tcttcatcaa gaagaaattc tggggaggta tgttgggaaa   3480
gactataagg agcagaaggg gctctggcac cacttcactg atgtggagcg acagatgacc   3540
gcacagcact atgtgacaga atttaacaag agactctatg aacaaaacat tcccacccag   3600
atattctaca tcccatccac aatactactg attttagagg acaagacaat aaagggatgt   3660
atcagtgtgg agccttacat actgggagaa tttgtaaaat tgtcaaataa cacgaaagtg   3720
gtgaaaacag aatacaaagc cacagaatat ggcttggcct atggccattt ttcttatgag   3780
ttttctaatc atagagatgt tgtggtcgat ttacaaggtt gggtaaccgg taatggaaaa   3840
ggactcatct acctcacaga tccccagatt cactccgttg atcagaaagt tttcactacc   3900
aattttggaa agagaggaat tttttacttc tttaataacc agcatgtgga atgtaatgaa   3960
atctgccatc gtctttcttt gactagacct tcaatggaga aaccatgcac atagaatacg   4020
gcacagtctg gtcctttggg gcttgggcag ggccgtgaca caggttctgg ccaatgattt   4080
gcaagaggaa ttgatcagta tcactttaag tcctgcattt aattggcagc acaagatcct   4140
gcagagcctc tttccctctg ccacagttat caagaatggg tcaggagacc gctgcttctg   4200
ggcataagtc ctgcaaggaa agcaacatgg aaaacagccc caactcaccc atgagggatg   4260
aaaagcactc ttgagaaagg catgtgttgt ttaagccatt gagattttag agctttttgt   4320
cactatctgt caagactgat actactgggg cttttcctat tgatttggga gttctttaca   4380
tattaaaaaa atgtgagcct ttgtgatacg aattcaattt gttttcctgt cttttgacat   4440
ttgactttgc ataaaagttt atctgtgcat aattttatat gtagttgaat tcatcaatct   4500
tttattttgt atggcttttt ggttatgtat aatacttaga tcctccttat actctgagtt   4560
tctttctttt taattctcct gtatttcctt ctagtataat taaatctgta aaaagtaaga   4620
tggaagagtg gtacagtttt ctttatccag tctgtccttg atgggcattt aggtagactg   4680
gataaagaaa atgtggtaca tatacaccat ggaacactat gtgtattaat ccactctcac   4740
actgctatga agagatacct gagactgggt aatttagaaa gaaaagaggt ttaattaact   4800
```

cacagttcca catggctggg gagacctcag gaaacttaca atcatggcag aaggcacctc 4860
ttcatagggt agcaggagag agaatgagtg ccagcagggg aaatgccaga tgcttataaa 4920
gccatcagat cttgtgagaa ttcattcact ctcacgagaa cagcatggga aaaactgcct 4980
caattacctc ctaccaggtc cttcccatga cacatgggaa ttatgggact acaattcgag 5040
atgagatttg ggtggggaca caaagccaaa ccatatcaca atgtaaccat aaaaaagaat 5100
gagatcatgt cctttgcagg gacatggata gagctggagg ccattatttt tagcaaacta 5160
atgcaagaac agaaaactaa ataccacttg ttctcactta taggtgagag ctaagtgatg 5220
agagtaggtg gacacataga gggaacaaca cacaccaggg cttatcagag ggtggacagt 5280
gggaggaggg agaggatcag gaaaaataac taatgggtac taggctgaat acctgggtga 5340
tgaagtaatt cgcacaacaa acccccatga cacaaacctg cacatgtacc cctgaactta 5400
aaataaaagt aaaaaaaaaa aaaaaaaaaa aaaaaaaaaa a 5441

<210> SEQ ID NO 4
<211> LENGTH: 3253
<212> TYPE: DNA
<213> ORGANISM: Homo sapiens

<400> SEQUENCE: 4
ggccgttcgg agaccagccc cagcgtgcca ggaccgtttc cggggcctgg ccggggcgtt 60
gccgcggggt cggggaccag cacgagtgct gagtcacgcc ccgcccggga gcgcctcggg 120
tcagtaactc gggaagacga ccaagcggga gcgggagcgg gagcgggagc cggagcgaga 180
gcgcgcgggc gcggccgaca gtgcctgatt tgagatgggg tcccaggtct cggtggaatc 240
gggagctctg cacgtggtga ttgtgggtgg gggctttggc gggatcgcag cagccagcca 300
gctgcaggcc ctgaacgtcc ccttcatgct ggtggacatg aaggactcct tccaccacaa 360
tgtggctgct ctccgagcct ccgtggagac agggttcgcc aaaaagacat tcatttctta 420
ctcggtgact ttcaaggaca acttccggca ggggctagta gtggggatag acctgaagaa 480
ccagatggtg ctgctgcagg gtggcgaggc cctgcccttc tctcatctta tcctggccac 540
gggcagcact gggcccttcc cgggcaagtt taatgaggtt tccagccagc aggccgctat 600
ccaggcctat gaggacatgg tgaggcaggt ccagcgctca cggttcatcg tggtggtggg 660
aggaggctcg gctggagtgg agatggcagc agagattaaa acagaatatc ctgagaaaga 720
ggtcactctc attcactccc aagtggccct ggctgacaag gagctcctgc cctccgtccg 780
gcaggaagtg aaggagatcc tcctccggaa gggcgtgcag ctgctgctga gtgagcgggt 840
gagcaatctg gaggagctgc ctctcaatga gtatcgagag tacatcaaag tgcagacgga 900
caaaggcaca gaggtggcca ccaacctggt gattctctgc accggcatca agatcaacag 960
ctccgcctac cgcaaagcgt ttgagagcag actagccagc agtggtgctc tgagagtgaa 1020
cgagcacctc caggtggagg gccacagcaa cgtctacgcc attggtgact gtgccgacgt 1080
gaggacgccc aagatggcct atcttgccgg cctccacgcc aacatcgccg tggccaacat 1140
cgtcaactct gtgaagcagc ggcctctcca ggcctacaag ccgggtgcac tgacgttcct 1200
cctgtccatg gggagaaatg acggtgtggg ccaaatcagt ggcttctatg tgggccggct 1260
catggttcgg ctgaccaaga gccgggacct gttcgtctct acgagctgga aaaccatgag 1320
gcagtctcca ccttgatgga gaggccaggc gggagaacta ccgcagcagg tgggcgtacg 1380
gactgcttgg cgcatggcac ccgcctggca agtgctagaa ctaatgctat tcttctggaa 1440

-continued

```
taagatgcca atgatgtggt ggctagaaat gcaacttgta taaaacaaaa atgggagaga   1500
gagaggtatt aaacaaatac ccccccttaga ggatactttc tgggtttgga aggtgtgctt   1560
gctgtggtac tgggtgagcg gctcatgtgt gctggctgca tggtgctggg gaggccacag   1620
ccagcccttc ctctgcacct gcctcctctg ggatgtgcat gtgtgtgtac gtgcttgtgg   1680
tcatgacgcg tgccatttag agctctcaga gcagggcaga ttgctgggct ctggtggcca   1740
gtgtctgtct gtgagggcag gaaggagagc tgcacattga gaacaaagga gggacctgag   1800
gtggagagag gcccagcacc ccaaatctct gccatcacac ggtcggggag cccatacatt   1860
ctgcaacaac cagggacttc acaggagcct tgttttcaat ttgctaacag gtgcataatc   1920
cctgtgctcc ttaagcctca tggccttcct acatttccac tttatttgtt tgtttgttta   1980
tttatttttg agacagtctc gccctgtcac ccaggctgga gtgcagtggc acgatctcag   2040
ctcactgcaa cctacgcctt ctgggttcac gtgattctct tgccttagcc tcccaagtag   2100
ctgggactac aggcacgtgc caccatgcct ggctaatttt tgtatttttt aaatagagac   2160
ggggtttcac tgtgttggcc aggctggtct cgaacacctg acctcaggtg atccattcgt   2220
cttggcctct cgaagtgctg ggattccagg cgtgagccac tgcggccagc acatttccac   2280
ttttagatcc tactccatac cacaggtttc atttaagaag aaagagctag ataaatgtgc   2340
tcttctggtt accccaccct gacagagtgc atttttacac ggctagcagg ggttgagact   2400
gcagcctggc ctgccagcca ttggaggtgt ttaaggaagg gcagataatg tgactctttg   2460
cggggtgcca tctgcttacc cattagcgag cagagggggt ttctgcgggt gaccccccagc   2520
atatttctag gttacttatg ggcagatttg taagtgacaa aactccagct gatgctggga   2580
atggggagag ggcccttgag ggactttgtg gttttgtgct tctggtttcc tggccaaccc   2640
cagggtcact tgtctggagg cccagctggg cactaatgtc tgccaccgac tatgttacag   2700
tgtataaatg attcctctat ttgggagaga tcttccaatc cagaggagcc cctcttggac   2760
tgcctgggtt aaatctgcat agcagaagtg gttgatgagt tcatctgaag aaattcaggc   2820
cccacctccc caccctgccc ctccctgctc ccttttgatg gtggcctctg ggtactcggg   2880
cagagtcctt gggacaccag cctctctggg gttctcaggc catcccgttg gggctgtcgc   2940
ccaggcctaa gtgagtcgtg tgcctctatt ggaggatggc tgttcccctg gtggttgcat   3000
ccaagtatct gtctttcttt atggaccacg aagggaagcc caccttcctg gaggcaggac   3060
cttcggccta agaaacacag gccctggtgc tatctgacct ggggtccagc gaggtgggaa   3120
tcccagtgtg tgagcgacag gccttcttct attgacttac aatattctag aaggacctac   3180
gtgtggggac acagttttcc aaactgagga aaatgttgca ataaaagaat atgttgtaag   3240
aaagacaaaa aaa                                                      3253
```

<210> SEQ ID NO 5
<211> LENGTH: 1961
<212> TYPE: DNA
<213> ORGANISM: Homo sapiens

<400> SEQUENCE: 5

```
cgcgcgtcgg cgccggcgcc aaggggcggc ctctagccac accgagtccg ccgcggcgtc     60
cagggtcggc agcaaccgca gccgagcccg agcgggtggc ggcgccatgg cgtgcgcggg    120
gctgctcacc gtgtgcctgc tccggccgcc cgcgccccag ccccagcccc agaccccgcg    180
gcacccccag ctcgcgcccg acccggggcc cgccggacac acgctcttcc aggacgtttt    240
ccgcagagca gacaagaatg atgatgggaa gctctcattt gaggaattcc agaattactt    300
```

```
tgccgatggg gttctcagcc tgggggagct gcaggaactg ttcagcggca ttgatgggca    360

tctcaccgac aatttagaaa cagaaaaact gtgtgactac ttctcagagc acctgggtgt    420

ctaccggccg gtgctggctg cattggaatc gctgaaccgt gcagtgctcg ctgccatgga    480

tgccaccaag ctggagtacg agagggcctc caaagtggac cagtttgtga cgcgcttcct    540

gctgcgggag acggtgagcc agctgcaagc ccttcagagc tcgctggagg gggcgtcaga    600

taccctggag gcccaggccc atggctggcg gtcagatgca gagagcgtgg aggcgcagag    660

caggctctgc ggcagccggc gggcaggacg ccgagccctg aggagtgtca gccggtcatc    720

cacctggtcc cccggctctt ctgacacagg gcgcagctca gaggccgaga tgcagtggcg    780

gctccaggtg aaccgcctcc aggagctcat cgaccagctc gagtgcaagg ccccccggct    840

ggaacccctg cgtgaagagg acctggccaa ggggcctgac ttgcacatcc tcatggccca    900

gaggcaggtc caggtggcag aggaaggcct gcaggacttc caccgagccc tgcgctgcta    960

tgtggacttc acaggggccc agagccattg tctgcatgtg tccgcccaga agatgctgga   1020

cggtgcctcc ttcaccctgt atgagttctg gcaggatgag gcctcctgga gaaggcacca   1080

gcagtcgcct ggcagcaagg ccttccagcg catcctcatc gaccacctgc gggccccgga   1140

caccctcacc actgtgttct tcccagcctc ctggtggata atgaataaca actgagccag   1200

acctgcacac gccgagggcc ccgggaccct gcctgcctcc ctctggagcc ttctggactg   1260

gccagcccag cgcaaagacc agggcttgtc tcctcctgga cttgggcctg gtggaagggc   1320

tctcagccca gggatcaggg actgggctgc ttgctttcta tttattattg atttatttat   1380

ccctgtattt tattgtttgt cacttcagcc tccaagctac tttggcttct gcctggctca   1440

ggagacctgg attctggtcc ctgctgtccc tgcctggctg agcgacccag ggcaggtccc   1500

gtccctgtct gggtgggcct caggccatct ggccgcctag cgagggtcct gctttcttcc   1560

tgctgtcttg ggaccaggct tctgctcctc ctcagccagc ggcagaagca gggctgatgc   1620

tcagggaccc cccaaccctc aaaccttgcc tccgaggctg ggcctgagct gggtgccccg   1680

tcgccctccc aggccactag gctctgactc ttccagcacc catggatgtg ccagaggcct   1740

ctgggttggt ttgcatgtca tttgcatatc gtttgcatgc cctcatccca cccattctca   1800

gggcagtatg ggaagcccca aggtgacctg gccaagtagc aataatttgg gtccagggtc   1860

acctattgcc cccagaggcc tctgaacccc aggctgggac cccagcacag aggcaataaa   1920

ggcagtggtc ccttccaaaa aaaaaaaaaa aaaaaaaaaa a                        1961


<210> SEQ ID NO 6
<211> LENGTH: 10650
<212> TYPE: DNA
<213> ORGANISM: Homo sapiens

<400> SEQUENCE: 6

atgcagaaag cccggggcac gcgaggcgag gatgcgggca cgagggcacc ccccagcccc     60

ggagtgcccc cgaaaagggc caaggtgggg gccggcggcg gggctcctgt ggccgtggcc    120

ggggcgccag tcttcctgcg gcccctgaag aacgcggcgg tgtgcgcggg cagcgacgtg    180

cggctgcggg tggtggtgag cgggacgccc cagcccagcc tccgctggtt ccgggatggg    240

cagctcctgc ccgcgccggc ccccgagccc agctgcctgt ggctgcggcg ctgcggggcg    300

caggacgccg gcgtgtacag ctgcatggcc cagaacgagc ggggccgggc ctcctgcgag    360

gcggtgctca cagtgctgga ggtcggagac tcagagacgg ctgaggatga catcagcgat    420
```

-continued

```
gtgcagggaa cccagcgcct ggagcttcgg gatgacgggg ccttcagcac ccccacgggg    480
ggttctgaca ccctggtggg cacctccctg gacacacccc cgacctccgt gacaggcacc    540
tcagaggagc aagtgagctg gtggggcagc gggcagacgg tcctggagca ggaagcgggc    600
agtgggggtg gcacccgccg cctcccgggc agcccaaggc aagcacaggc aaccggggcc    660
gggccacggc acctgggggt ggagccgctg gtgcgggcat ctcgagctaa tctggtgggc    720
gcaagctggg ggtcagagga tagcctttcc gtggccagtg acctgtacgg cagcgcattc    780
agcctgtaca gaggacgggc gctctctatc cacgtcagcg tccctcagag cgggttgcgc    840
agggaggagc ccgaccttca gcctcaactg gccagcgaag ccccacgccg ccctgcccag    900
ccgcctcctt ccaaatccgc gctgctcccc ccaccgtccc ctcgggtcgg gaagcggtcc    960
ccgccgggac ccccggccca gcccgcggcc acccccacgt cgccccaccg tcgcactcag   1020
gagcctgtgc tgcccgagga caccaccacc gaagagaagc gagggaagaa gtccaagtcg   1080
tccgggccct ccctggcggg caccgcggaa tcccgacccc agacgccact gagcgaggcc   1140
tcaggccgcc tgtcggcgtt gggccgatcg cctaggctgg tgcgcgccgg ctcccgcatc   1200
ctggacaagc tgcagttctt cgaggagcga cggcgcagcc tggagcgcag cgactcgccg   1260
ccggcgcccc tgcggccctg ggtgcccctg cgcaaggccc gctctctgga gcagcccaag   1320
tcggagcgcg gcgcaccgtg ggcacccccc ggggcctcgc aggaagaact gcgggcgcca   1380
ggcagcgtgg ccgagcggcg ccgcctgttc cagcagaaag cggcctcgct ggacgagcgc   1440
acgcgtcagc gcagcccggc ctcagacctc gagctgcgct tcgcccagga gctgggccgc   1500
atccgccgct ccacgtcgcg ggaggagctg gtgcgctcgc acgagtccct gcgcgccacg   1560
ctgcagcgtg ccccatcccc tcgagagccc ggcgagcccc cgctcttctc tcggccctcc   1620
acccccaaga catcgcgggc cgtgagcccc gccgccgccc agccgccctc tccgagcagc   1680
gcggagaagc cgggggacga gcctgggagg cccaggagcc gcgggccggc gggcaggaca   1740
gagccggggg aaggcccgca gcaggaggtt aggcgtcggg accaattccc gctgacccgg   1800
agcagagcca tccaggagtg caggagccct gtgccgcccc ccgccgccga tcccccagag   1860
gccaggacga aagcaccccc cggtcggaag cgggagcccc cggcgcaggc cgtgcgcttc   1920
ctgccctggg ccacgccggg cctggagggc gctgctgtac cccagacctt ggagaagaac   1980
agggcggggc ctgaggcaga gaagaggctt cgcagagggc cggaggagga cggtccctgg   2040
gggccctggg accgccgagg ggcccgcagc cagggcaaag gtcgccgggc ccggcccacc   2100
tcccctgagc tcgagtcttc ggatgactcc tacgtgtccg ctggagaaga gccccctagag  2160
gcccctgtgt ttgagatccc cctgcagaat gtggtggtgg caccaggggc agatgtgctg   2220
ctcaagtgta tcatcactgc caaccccccg ccccaagtgt cctggcacaa ggatgggtca   2280
gcgctgcgca gcgagggccg cctcctcctc cgggctgagg gtgagcggca caccctgctg   2340
ctcagggagg ccagggcagc agatgccggg agctatatgg ccaccgccac caacgagctg   2400
ggccaggcca cctgtgccgc ctcactgacc gtgagacccg gtgggtctac atcccctttc   2460
agcagcccca tcacctccga cgaggaatac ctgagccccc cagaggagtt cccagagcct   2520
ggggagacct ggccgcgaac cccccaccatg aagcccagtc ccagccagaa ccgccgttct  2580
tctgacactg gctccaaggc accccccacc ttcaaggtct cacttatgga ccagtcagta   2640
agagaaggcc aagatgtcat catgagcatc cgcgtgcagg gggagcccaa gcctgtggtc   2700
tcctggctga gaaaccgcca gcccgtgcgc ccagaccagc ggcgctttgc ggaggaggct   2760
gagggtgggc tgtgccggct gcggatcctg gctgcagagc gtggcgatgc tggtttctac   2820
```

-continued

```
acttgcaaag cggtcaatga gtatggtgct cggcagtgcg aggcccgctt ggaggtccga   2880
gcacaccctg aaagccggtc cctggccgtg ctggcccccc tgcaggacgt ggacgtgggg   2940
gccggggaga tggcgctgtt tgagtgcctg gtggcggggc ccactgacgt ggaggtggat   3000
tggctgtgcc gtggccgcct gctgcagcct gcactgctca aatgcaagat gcatttcgat   3060
ggccgcaaat gcaagctgct acttacatct gtacatgagg acgacagtgg cgtctacacc   3120
tgcaagctca gcacggccaa agatgagctg acctgcagtg cccggctgac cgtgcggccc   3180
tcgttggcac ccctgttcac acggctgctg gaagatgtgg aggtgttgga gggccgagct   3240
gcccgtttcg actgcaagat cagtggcacc ccgccccctg ttgttacctg gactcatttt   3300
ggctgcccca tggaggagag tgagaacttg cggctgcggc aggacggggg tctgcactca   3360
ctgcacattg cccatgtggg cagcgaggac gaggggctct atgcggtcag tgctgttaac   3420
acccatggcc aggcccactg ctcagcccag ctgtatgtag aagagccccg gacagccgcc   3480
tcaggcccca gctcgaagct ggagaagatg ccatccattc ccgaggagcc agagcagggt   3540
gagctggagc ggctgtccat tcctgacttc ctgcggccac tgcaggacct ggaggtggga   3600
ctggccaagg aggccatgct agagtgccag gtgaccggcc tgccctaccc caccatcagc   3660
tggttccaca atggccaccg catccagagc agcgacgacc ggcgcatgac acagtacagg   3720
gatgtccatc gcttggtgtt ccctgccgtg gggcctcagc acgccggtgt ctacaagagc   3780
gtcattgcca acaagctggg caaagctgcc tgctatgccc acctgtatgt cacagatgtg   3840
gtcccaggcc ctccagatgg cgccccgcag gtggtggctg tgacggggag gatggtcaca   3900
ctcacatgga acccccccag gagtctggac atggccatcg acccggactc cctgacgtac   3960
acagtgcagc accaggtgct gggctcggac cagtggacgg cactggtcac aggcctgcgg   4020
gagccagggt gggcagccac agggctgcgt aagggggtcc agcacatctt ccgggtcctc   4080
agcaccactg tcaagagcag cagcaagccc tcaccccctt ctgagcctgt gcagctgctg   4140
gagcacggcc caaccctgga ggaggcccct gccatgctgg acaaaccaga catcgtgtat   4200
gtggtggagg gacagcctgc cagcgtcacc gtcacattca accatgtgga ggcccaggtc   4260
gtctggagga gctgccgagg ggccctccta gaggcacggg ccggtgtgta cgagctgagc   4320
cagccagatg atgaccagta ctgtcttcgg atctgccggg tgagccgccg ggacatgggg   4380
gccctcacct gcaccgcccg aaaccgtcac ggcacacaga cctgctcggt cacattggag   4440
ctggcagagg cccctcggtt tgagtccatc atggaggacg tggaggtggg ggctggggaa   4500
actgctcgct ttgcggtggt ggtcgaggga aaaccactgc cggacatcat gtggtacaag   4560
gacgaggtgc tgctgaccga gagcagccat gtgagcttcg tgtacgagga gaatgagtgc   4620
tccctggtgg tgctcagcac gggggcccag gatggaggcg tctacacctg caccgcccag   4680
aacctggcgg gtgaggtctc ctgcaaagca gagttggctg tgcattcagc tcagacagct   4740
atggaggtcg agggggtcgg ggaggatgag gaccatcgag gaaggagact cagcgacttt   4800
tatgacatcc accaggagat cggcaggggt gctttctcct acttgcggcg catagtggag   4860
cgtagctccg gcctggagtt tgcggccaag ttcatcccca gccaggccaa gccaaaggca   4920
tcagcgcgtc gggaggcccg gctgctggcc aggctccagc acgactgtgt cctctacttc   4980
catgaggcct tcgagaggcg ccggggactg gtcattgtca ccgagctctg cacagaggag   5040
ctgctggagc gaatcgccag gaaacccacc gtgtgtgagt ctgagatccg ggcctatatg   5100
cggcaggtgc tagagggaat acactacctg caccagagcc acgtgctgca cctcgatgtc   5160
```

-continued

```
aagcctgaga acctgctggt gtgggatggt gctgcgggcg agcagcaggt gcggatctgt   5220
gactttggga atgcccagga gctgactcca ggagagcccc agtactgcca gtatggcaca   5280
cctgagtttg tagcacccga gattgtcaat cagagccccg tgtctggagt cactgacatc   5340
tggcctgtgg gtgttgttgc cttcctctgt ctgacaggaa tctccccgtt tgttggggaa   5400
aatgaccgga caacattgat gaacatccga aactacaacg tggccttcga ggagaccaca   5460
ttcctgagcc tgagcaggga ggcccggggc ttcctcatca aagtgttggt gcaggaccgg   5520
ctgagaccta ccgcagaaga gaccctagaa catccttggt tcaaaactca ggcaaagggc   5580
gcagaggtga gcacggatca cctgaagcta ttcctctccc ggcggaggtg gcagcgctcc   5640
cagatcagct acaaatgcca cctggtgctg cgccccatcc ccgagctgct gcgggccccc   5700
ccagagcggg tgtgggtgac catgcccaga aggccacccc ccagtggggg gctctcatcc   5760
tcctcggatt ctgaagagga agagctggaa gagctgccct cagtgccccg cccactgcag   5820
cccgagttct ctggctcccg ggtgtccctc acagacattc ccactgagga tgaggccctg   5880
gggaccccag agactggggc tgccacccccc atggactggc aggagcaggg aagggctccc   5940
tctcaggacc aggaggctcc cagcccagag gccctcccct ccccaggcca ggagcccgca   6000
gctggggcta gccccaggcg gggagagctc cgcaggggca gctcggctga gagcgccctg   6060
ccccgggccg ggccgcggga gctgggccgg ggcctgcaca aggcggcgtc tgtggagctg   6120
ccgcagcgcc ggagccccag cccgggagcc acccgcctgg cccggggagg cctgggtgag   6180
ggcgagtatg cccagaggct gcaggccctg cgccagcggc tgctgcgggg aggccccgag   6240
gatggcaagg tcagcggcct caggggtccc ctgctggaga gcctgggggg ccgtgctcgg   6300
gacccccgga tggcacgagc tgcctccagc gaggcagcgc cccaccacca gcccccactc   6360
gagaaccggg gcctgcaaaa gagcagcagc ttctcccagg gtgaggcgga gccccggggc   6420
cggcaccgcc gagcgggggc gcccctcgag atccccgtgg ccaggcttgg ggcccgtagg   6480
ctacaggagt ctccttccct gtctgccctc agcgaggccc agccatccag ccctgcacgg   6540
cccagcgccc ccaaacccag taccccctaag tctgcagaac cttctgccac cacacctagt   6600
gatgctccgc agccccccgc accccagcct gcccaagaca aggctccaga gcccaggcca   6660
gaaccagtcc gagcctccaa gcctgcacca cccccccagg ccctgcaaac cctagcgctg   6720
cccctcacac cctatgctca gatcattcag tccctccagc tgtcaggcca cgcccagggc   6780
ccctcgcagg gccctgccgc gccgccttca gagcccaagc cccacgctgc tgtctttgcc   6840
agggtggcct ccccacctcc gggagccccc gagaagcgcg tgccctcagc cgggggtccc   6900
ccggtgctag ccgagaaagc ccgagttccc acggtgcccc ccaggccagg cagcagtctc   6960
agtagcagca tcgaaaactt ggagtcggag gccgtgttcg aggccaagtt caagcgcagc   7020
cgcgagtcgc ccctgtcgct ggggctgcgg ctgctgagcc gttcgcgctc ggaggagcgc   7080
ggccccttcc gtggggccga ggaggaggat ggcatatacc ggcccagccc ggcggggacc   7140
ccgctggagc tggtgcgacg gcctgagcgc tcacgctcgg tgcaggacct cagggctgtc   7200
ggagagcctg gcctcgtccg ccgcctctcg ctgtcactgt cccagcggct gcggcggacc   7260
cctcccgcgc agcgccaccc ggcctgggag gcccgcggcg gggacggaga gagctcggag   7320
ggcgggagct cggcgcgggg ctccccggtg ctggcgatgc gcaggcggct gagcttcacc   7380
ctggagcggc tgtccagccg attgcagcgc agtggcagca gcgaggactc gggggcgcg   7440
tcgggccgca gcacgccgct gttcggacgg cttcgcaggg ccacgtccga gggcgagagt   7500
ctgcggcgcc ttggccttcc gcacaaccag ttggccgccc aggccggcgc caccacgcct   7560
```

-continued

```
tccgccgagt ccctgggctc cgaggccagc gccacgtcgg gctcctcagc cccaggggaa   7620
agccgaagcc ggctccgctg gggcttctct cggccgcgga aggacaaggg gttatcgcca   7680
ccaaacctct ctgccagcgt ccaggaggag ttgggtcacc agtacgtgcg cagtgagtca   7740
gacttccccc cagtcttcca catcaaactc aaggaccagg tgctgctgga gggggaggca   7800
gccaccctgc tctgcctgcc agcggcctgc cctgcaccgc acatctcctg gatgaaagac   7860
aagaagtcct tgaggtcaga gccctcagtg atcatcgtgt cctgcaaaga tgggcggcag   7920
ctgctcagca tcccccgggc gggcaagcgg cacgccggtc tctatgagtg ctcggccacc   7980
aacgtactgg gcagcatcac cagctcctgt accgtggctg tggcccgagt cccaggaaag   8040
ctagctcctc cagaggtacc ccagacctac caggacacgg cgctggtgct gtggaagccg   8100
ggagacagcc gggcaccttg cacgtatacg ctggagcggc gagtggatgg ggagtctgtg   8160
tggcaccctg tgagctcagg catccccgac tgttactaca acgtgaccca cctgccagtt   8220
ggcgtgactg tgaggttccg tgtggcctgt gccaaccgtg ctgggcaggg gcccttcagc   8280
aactcttctg agaaggtctt tgtcaggggt actcaagatt cttcagctgt gccatctgct   8340
gcccaccaag aggcccctgt cacctcaagg ccagccaggg cccggcctcc tgactctcct   8400
acctcactgg ccccacccct agctcctgct gcccccacac ccccgtcagt cactgtcagc   8460
ccctcatctc cccccacacc tcctagccag gccttgtcct cgctcaaggc tgtgggtcca   8520
ccaccccaaa cccctccacg aagacacagg ggcctgcagg ctgcccggcc agcggagccc   8580
accctaccca gtacccacgt caccccaagt gagcccaagc ctttcgtcct tgacactggg   8640
accccgatcc cagcctccac tcctcaaggg gttaaaccag tgtcttcctc tactcctgtg   8700
tatgtggtga cttcctttgt gtctgcacca ccagcccctg agcccccagc ccctgagccc   8760
cctcctgagc ctaccaaggt gactgtgcag agcctcagcc cggccaagga ggtggtcagc   8820
tcccctggga gcagtccccg aagctctccc aggcctgagg gtaccactct tcgacagggt   8880
ccccctcaga aaccctacac cttcctggag gagaaagcca ggggccgctt tggtgttgtg   8940
cgagcgtgcc gggagaatgc cacggggcga acgttcgtgg ccaagatcgt gccctatgct   9000
gccgagggca agcggcgggt cctgcaggag tacgaggtgc tgcggaccct gcaccacgag   9060
cggatcatgt ccctgcacga ggcctacatc accccctcggt acctcgtgct cattgctgag   9120
agctgtggca accgggaact cctctgtggg ctcagtgaca ggttccggta ttctgaggat   9180
gacgtggcca cttacatggt gcagctgcta caaggcctgg actacctcca cggccaccac   9240
gtgctccacc tagacatcaa gccagacaac ctgctgctgg cccctgacaa tgccctcaag   9300
attgtggact ttggcagtgc ccagccctac aacccccagg cccttaggcc ccttggccac   9360
cgcacgggca cgctggagtt catggctccg gagatggtga agggagaacc catcggctct   9420
gccacggaca tctggggagc gggtgtgctc acttacatta tgctcagtgg acgctccccg   9480
ttctatgagc cagaccccca ggaaacggag gctcggattg tgggggggccg ctttgatgcc   9540
ttccagctgt accccaatac atcccagagc gccaccctct tcttgcgaaa ggttctctct   9600
gtacatccct ggagccggcc ctccctgcag gactgcctgg cccacccatg gttgcaggac   9660
gcctacctga tgaagctgcg ccgccagacg ctcaccttca ccaccaaccg gctcaaggag   9720
ttcctgggcg agcagcggcg gcgccgggct gaggctgcca cccgccacaa ggtgctgctg   9780
cgctcctacc ctggcggccc ctagaggcac ggaccacagc caggcctcgg gcttcaactg   9840
gggttcccac caatgccacg ggacattcca gggcccacgc tgagccaggc gggcctgggg   9900
```

cttcggttac caccagcagc aacatctggc tgggctctta cctcatagac cttcaaggac 9960
agagacccca gggcctggac ctgatgccac cccaggccaa agccagagtg ggagacccat 10020
tggtcaggct cagcagggtg ggaacaggca gagggacaag aggggaatgg agaagtggag 10080
aggaaaagga atcgagggac aggaaggggg aggctctagg aaggttctgg gttgggggtc 10140
agtgcatctc agggagaacc aaggaaggtg ggcatggctg gagaggagga aaaggaagga 10200
gccccaggtg tcagggcagt aggctgggag tcagtgtggc aaagcggggg caggacacag 10260
atacagtggc aggggcccag ggctgggaca tgagagaagg cagcgaggcg gcagagggag 10320
aagagaggac tcaggtggag gtggggtggg tcagctgtca gcatccctca gaggagaaat 10380
gtggagagct ggaggccagc agtcactcac actcgctctg tcctcctgtc cagtggatac 10440
agccctgggc gctctgctgg cccaaggatg tccccactgc ccctccatgg cctctggcct 10500
tcttcccatt catatttatt tatttattga cttttatgaa gtttcccctt ccatccgatc 10560
cctactgccc atgttgtcct gaccatccct cccagccatc cagctgtctg tctgtctgcc 10620
acaaggaaat aaaaatggca agcagcataa 10650

<210> SEQ ID NO 7
<211> LENGTH: 9004
<212> TYPE: DNA
<213> ORGANISM: Homo sapiens

<400> SEQUENCE: 7
ggcggcgccg tggggccgag gtgtcgcttc ctgacggggc ggcgcggacg gacgcggccg 60
gtgccggccg ggacgccggg cccgcagcct agctcgccat ctcgctcacg ccgcccgccc 120
gcggggccgt cagcccccgc cgggccgggg ccatgcagga gagccagacc aagagcatgt 180
tcgtgtcccg ggccctggag aagatcctag ccgacaagga ggtgaagcgg ccccagcact 240
cccagctgcg cagggcctgc caggtggcgc tcgatgaaat taaagcagaa atagaaaagc 300
agaggcttgg cactgctgca ccaccaaagg caaacttcat tgaagctgac aagtattttc 360
ttccattcga gctagcttgc cagtccaagt ccccaagggt agtcagcaca tcccttgact 420
gcttgcagaa actcatcgca tacgggcaca tcactggcaa cgcccctgac agtggagccc 480
ctgggaagcg gctgatcgac agaattgttg aaaccatttg cagttgtttt cagggccctc 540
agactgatga aggggttcag ttacaaataa ttaaggctct tctgactgca gtgacttccc 600
cacacattga aattcatgag ggtactatcc tgcagacagt gagaacatgt tacaatatct 660
atttggccag caaaaatctc atcaatcaaa ccactgccaa ggctaccctt actcagatgc 720
tgaacgtcat tttcacccgc atggaaaacc aagtgttgca ggaggccaga gaactggaaa 780
aaccaatcca gtcaaaaccc cagtcccctg tgatccaagc tgcagcagta tccccaaagt 840
tcgttcgttt gaagcacagt caggcacaaa gcaaaccaac aactcccgaa aaaacagatt 900
taaccaacgg tgaacatgcc aggagtgatt ctggaaaagt aagcacagaa aatggagacg 960
cacccagaga aagaggctca tcactgtcag ggactgatga cggagcccag gaggtggtga 1020
aggacatctt ggaagatgta gtcacatctg ccattaaaga agcagcggaa aagcatggtc 1080
tgacagaacc tgagagagtt ctaggtgaac tggagtgcca ggaatgtgct attcccccag 1140
gagttgatga aaactcacag accaacggga tagccgatga caggcagtcc ttgtcgtcag 1200
cagataatct ggaatcggat gcacaaggac atcaagtggc tgccaggttc tcccacgttc 1260
tgcagaagga tgccttcctt gtgttccgct ccctgtgcaa gctgtccatg aaacccettg 1320 gtgaaggccc tccagaccca aaatcccatg agctgcgttc caaggtggtt tccctgcagc 1380

-continued

```
tgctcctctc tgtgttgcaa aatgctggcc ccgtattcag gactcacgag atgttcatca   1440
atgcaatcaa gcaatatctc tgtgtggcct tgtccaaaaa cggcgtctct tcagtgcctg   1500
atgtctttga gctctctctt gccatttttc ttactcttct ttcaaacttt aaaatgcact   1560
tgaaaatgca gatagaggtc tttttcaaag agattttcct gaacatttta gaaacatcaa   1620
caagttcttt tgagcacagg tggatggtca ttcagactct gacgaggatc tgtgcagatg   1680
cccagtgtgt tgtggatatt tatgtcaact acgactgtga tttaaatgct gctaacattt   1740
ttgagcgcct tgtaaatgat ttatccaaaa ttgctcaggg aagaagtgga catgagctgg   1800
gaatgacacc tctgcaggag ctcagcctga ggaagaaagg cctggagtgc ctcgtgtcca   1860
ttctcaagtg catggtggag tggagcaaag acctgtatgt gaatcccaac caccagacca   1920
gcctcggtca ggagaggctc acggatcagg aaatagggga tgggaaaggc cttgacatgg   1980
caagacggtg tagtgtgacg tccatggagt ccacagtgtc ctcggggacc cagacaactg   2040
ttcaggatga ccctgagcaa tttgaggtca tcaagcaaca aaaagaaatc attgaacacg   2100
gcatcgagct gttcaacaag aaacccaaga gggggatcca gtttctccag gagcagggca   2160
tgctgggaac gtcagttgaa gacatagccc aattcctgca ccaggaggag cgcctggatt   2220
ccacccaagt aggcgatttt ctgggagata gcgcaaggtt caacaaggag gtgatgtatg   2280
cctacgtgga ccaacttgac ttctgtgaaa aagaatttgt ctcagccctg cggacattcc   2340
tagaaggttt ccgcctacct ggagaagccc aaaagattga ccgattaatg gagaagtttg   2400
ccgcaagata catagaatgc aaccaagggc aaactctgtt tgctagtgct gacactgctt   2460
atgtcctagc gtattcaatt attatgctga ctacagactt gcacagtcct caggtaaaaa   2520
ataaaatgac gaaagagcag tatattaaaa tgaatcgggg tatcaatgat agtaaagatc   2580
tgccagaaga gtatctctca agcatctatg aagagataga aggcaagaaa attgcaatga   2640
aagaaacaaa agagctaacg attgcaacca aatctactaa gcagaatgta gctagtgaaa   2700
agcagcggcg gctgctgtac aacttagaga tggagcaaat ggctaaaaca gccaaagctc   2760
tgatggaggc tgtgagccat gccaaagccc cgtttaccag tgccactcac ctggaccatg   2820
tccggccaat gttcaaactg gtgtggacgc cactattggc agcctacagc atcggactcc   2880
agaactgtga tgacactgaa gtggcctcct tgtgtttgga aggcatccga tgtgcaatcc   2940
gaatcgcctg catctttgga atgcagctgg aacgagatgc ctatgttcag gctcttgctc   3000
gcttctccct actcacagcc agctccagca tcacagaaat gaagcagaaa aacatcgaca   3060
ccattaagac gcttatcaca gtggctcaca ccgatggcaa ctaccttggg aattcctggc   3120
atgagatctt gaaatgcatc agccagctgg agctcgctca gctgatagga accggtgtga   3180
agacgcgcta cctgtctgga tctgggcgtg aaagagaagg gagcctgaag ggccacacat   3240
tggcaggaga agagttcatg ggccttggcc tcggtaattt ggtgagtggc ggagtggata   3300
aaagacagat ggccagcttc caagaatcgg ttggtgagac cagctcgcag agtgtggttg   3360
tagctgtgga caggattttt actgggtcta ccagactgga tggaaatgca atagttgact   3420
ttgtccgctg gctgtgtgct gtgtccatgg atgaactggc ttcccccac catcctcgca   3480
tgttcagctt gcagaagatt gtggagatat catactacaa catgaatcgg atccgactac   3540
agtggtctcg aatatggcat gtgattggag atcacttcaa taaggttggc tgcaacccta   3600
atgaagatgt ggctatcttt gctgttgact cattaaggca actctccatg aagtttcttg   3660
agaagggtga attagccaac ttccgtttcc agaaagattt tctgaggccc tttgagcata   3720
```

ttatgaagaa aaacaggtct cccaccatcc gggacatggc gatccgctgc attgcccaga 3780
tggtgaactc ccaggcggcc aacatccgct caggttggaa gaacatcttt gccgtgttcc 3840
accaggcagc ctctgatcat gatgggaaca ttgtggagct ggccttccag accacttgcc 3900
acattgtcac aactattttc cagcaccatt ttcctgcagc catcgattcc tttcaggatg 3960
ctgtgaagtg cttatcagag ttcgcctgca acgccgcttt ccctgacacg agcatggaag 4020
cgattcggct catccgcttc tgtggcaaat acgtctctga gaggcctcgg gtgctacaag 4080
aatacacaag tgatgacatg aatgtagctc ctggtgacag agtctgggtc cgaggctggt 4140
tccccatctt attcgaactc tcctgcatca ttaatagatg caagttagat gtacgaacaa 4200
ggggactcac agtcatgttt gagatcatga agagctatgg ccacaccttt gaaaagcact 4260
ggtggcagga cctgttcaga atcgtgtttc ggatttttga caatatgaaa ctccctgagc 4320
aactgtcaga gaaatctgag tggatgacaa caacctgcaa tcacgcactt tatgctattt 4380
gtgatgtttt tacccagttt tatgaagctt tgaatgaagt tcttctttct gatgtatttg 4440
cacaattgca gtggtgtgtc aaacaagata atgaacagtt ggcgcgatca ggtacaaatt 4500
gcttagaaaa cttagtaata tccaatggag agaaattcag tcctgaagtc tgggatgaaa 4560
cctgcaactg tatgttggat attttcaaaa caaccatccc acatgttttg ctgacatgga 4620
gacctgtagg aatggaggaa gattcatcag aaaagcattt ggatgtggat ctggaccgcc 4680
agtctttaag cagcatagat aaaaatccct ctgagagggg acagagccag ctctctaacc 4740
caacagatga cagctggaag ggtagaccat acgcaaatca gaaactgttt gccagcctcc 4800
tcatcaagtg tgtggtccag ttggaattga tacagaccat tgacaacatt gtgttctacc 4860
ctgcgacgag caaaaaggag gatgcagagc acatggttgc cgcccagcaa gacacgctgg 4920
atgcagatat ccacatagag acggaggatc agggcatgta taagtacatg tcttcccagc 4980
acctcttcaa gctgttggac tgtttgcagg aatcccattc attctcaaag gccttcaact 5040
ccaattacga gcagcggact gtcctgtggc gagcaggttt taagggcaag tctaaaccca 5100
atcttctaaa acaagaaacc agcagcctgg cctgttgttt gaggatcctg tttcgaatgt 5160
atgttgatga gaaccgcagg gattcctggg aagaaataca gcagagactt ttaactgttt 5220
gcagtgaagc tcttgcctat ttcatcactg tgaattctga gagccatcgg gaggcctgga 5280
caagtctctt gttgttactt ctaactaaaa ccctcaaaat aaatgatgaa aagttcaaag 5340
cacatgcttc aatgtactac ccctacttgt gtgaaattat gcagtttgac ctgatccctg 5400
agctccgagc agttctgcgg aagttcttcc tacggatagg tgttgtgtat aagatatgga 5460
taccagaaga gccatcacag gtaccagcag cactgtcacc agtgtggtag ccctggctgc 5520
ccaggccagt gctgcagctc tgcagaatgt tcagcatgcc atttctgact ggcacatctc 5580
gtgaagtttc atagaaacaa ggagttggca tcttggatct cagaatggcc tggaaacgga 5640
tggcctctac gctgttccat cacagtctcc aactaaggct tatggtattt cattaaactg 5700
ttgcataccc agttagcaca gtaggtgggg agtctgcttc atttctatca ttccattttt 5760
ctgattaaac tgtcaaatct gtcattgcat atgccatcgt tttctagcaa aatcccatga 5820
ttggctataa acgttttgta agaagtcact ctccttgaaa atactgaaca tagctgtata 5880
ggtttgtgat tattagagaa tatgttaata aaacttcttg taacggctaa ctgccaccta 5940
aaatatgctg ggttttctgt tgtttgagtg tgttagagaa atttgaatgt ttttgtcagt 6000
tacgagtcag ccgtaattag attagtttaa ggacaggtca ggattagaga agagttgttt 6060
ttgtgttttg ttaatgtctg agtgattttt aaagtatttt acaaaaagat attgaaaatt 6120

-continued

```
tggttgaagg cagagtttag taattaagtt agaattaaga gttttgcgag gttaaaaaaa   6180
tgtgcctcgt ggatctccct gttttagtaa catggagaga aaaagtctac acgaaaaagt   6240
gaacaattta atgaagatga ttagccttcc ttgaaataag tatttgtgga tgggtgttaa   6300
attaaaattt ccagaataca ctgtccatct cacacactct gaaatctaat atatgaagta   6360
gtaatgaaaa tgaagtagta atttaaccag agttcattta tccttgaata aacctttttta   6420
ttttcacctc agaaaagtga gtgtactggc agttagtgtc actgctttgc acagtcccca   6480
ttaaaggacc ctccagagag ggacagtaac tgtgcatgag aagccgctcc cataagcctc   6540
ctcagccaga tgtcatgggt ggaactggag ctgtgtcggg gccagcacag ctgaactgtg   6600
acaatggcag gaggtggcat gtgcccagca cttccattaa tctgagccta ggagttgaat   6660
tctttggcaa ggttggattc tgaggtcctt attatgttaa tgatggtgca atactctcac   6720
ctgcagtaga actgagttct gctgcagctt gtgtaaaagt gggcagtaca caagtacgtc   6780
ccaaagcctg tgagcagtat acgtggatgc tcacccatga gaaggagcac acacgcctca   6840
ttctctgccc tcacccactg ctcacctaga gcatcgctga gcgttagaca aagtgttaca   6900
cagaatgatt aaaactttca gacttctacc tatgctcttt agtcctgtaa attgggttgt   6960
attgatgtca actctggtgc cttagaagtt agtagtttgg gaacctatct gtaaaatcag   7020
atgtttttc tttgtagaga aggatttctg gtgcttttgc ttactaagag accgatattc   7080
ttaagttgtt ttcttgtttt aacagccttg agaaatgttt ggttttggcc agcagaattc   7140
ttgtctactt ttttctttcc caaaaagtgt tttttaattt ctctaccaaa gaaaaaatga   7200
gcaggtttag gtttttacat gacttatata cattagataa aaggagctgt ataatttagc   7260
aggaagggac tatgggagaa tactttactg tgagtggaaa atgttagcac atttgactgg   7320
tttgccctgg aatccactgc acctttacac tgcaccatga aacctacact ccctggtatc   7380
atagcgcgtc atcacctcaa caagtcagtc gtctccattg atatttgtac aaaaggtata   7440
catggggaac acgtgttcat tcattaagtc catcttgcgt gcagctatat ccctgattgg   7500
ttatttttcc tttccttctg aggttctcat gtcattttct tcatcggatg tgactaaaat   7560
ttttctggtg tcttctgccc tctctttaat tttgcctctt gaggggtagc agatgtgtca   7620
gtgcatttta ttacttgctg aaacattcag gcttacattt cttattagtt tagtatttta   7680
aaagatttaa ttttctgaat gaggcatttg aattgtacca gcaatggact tttaaaaaat   7740
tggatgtaaa accattcagg gtgatttttc ttgtcagtgg acagtgacga acagagattt   7800
gaaatccctt acctccaata ataagccatt cagcctaaat tcatttttat gaataaatct   7860
cttctttctc atggtaaatg tggcttgtgc cactcaaaca ctagtgaaag ggtatgtaca   7920
accgcaacat caggccagga caccatttat ttaaccaagt aatggaggag agtgaaacat   7980
tttccaaggc cttatttctt tttcagaatg ctttaagtgt tgattatatg tgctgggtct   8040
ctagagaagt ttttatttgt tacaatactg ctgctttgag caattttgtt tctcttcatt   8100
gtctgttagg gaaatcacca gctttggcat cttaacaaca aacagtggat gggtaatttt   8160
tatttctgat acgcatcttt agagtcaaat atatcttttc cctgtactcc tcatgtacaa   8220
ccaaagaaca tacattatga aaattgtatt ataatatctg gaaacacaac attttcctct   8280
ggcaggtgac ttttgtacga aatgaaaaaa aaaaaacctg tattttttt gttgttcttt   8340
tgtgattaag gatatacatt tagtagtctt tgttattaaa ggaacctgct gataagtaca   8400
agtgtgacca tctcattcaa atgtttgttg ttatgatgca aatggatatt ggtttcaata   8460
```

-continued gaagctggat ccttaatact gcattttctg aattctgttt taatatttgt gttaaagtag 8520
acatagctga actcacatgg aatcctggag ttttgttatc agcagctttg cagtttggga 8580
aacaaagaaa ccaaagctga gtgttttaaa gaatgaacat atctggaaat ccttgctctc 8640
aaaacaaaac aatataatct atcaaaggtg ttttactcag tgttctaatt tttaaaaaat 8700
tttatctgca tatttgcatc aaatatttat gtgtaaaatg tatgttttac ctccttaaaa 8760
tgcctaaaag ttagttaata gttactttgg tttaacctat acacaatgat taagtgcatt 8820
taatattggt aatttaatga aaaccattcc ttgcccaatg gatgtataaa tttttgaaag 8880
aataagcaga attatataat atgaaatgct atgtaaagtt ttctatgtaa aaatattatg 8940
tataatacta ttaaaatatc ccatgctttg atcaggtggt acatcaataa aattttaaaa 9000
agta 9004

<210> SEQ ID NO 8
<211> LENGTH: 7230
<212> TYPE: DNA
<213> ORGANISM: Homo sapiens

<400> SEQUENCE: 8
gaacccgttt cttttccttc cccagtgcgt ctttcctgcg tcgttccggc gcggcgggag 60
cagagatctg cggccgtttg cagcttgcgg tagggaggcg tggtggtctg aagcctccga 120
gcagccgcgg ccatggcgga tgtaaccgcc cgtagtctgc aatacgagta caaggcgaac 180
tcgaatcttg tgctccaagc tgaccgttct ctcattgacc ggacccgccg ggatgaaccc 240
acaggagagg tgctgtccct tgttgggaag ctggagggca cccgtatggg agacaaggct 300
caacggacca aaccgcagat gcaggaggaa agaagagcca agcgaagaaa gcgtgatgag 360
gaccggcatg acatcaacaa gatgaagggt tatactctgc tgtcggaggg cattgatgag 420
atggtgggca tcatctacaa gcccaaaact aaagagactc gggagaccta tgaggtgcta 480
ctcagcttca tccaggctgc tcttggggac cagccacgtg atatcctttg tggggcagct 540
gatgaagttc tagctgttct aaagaatgaa aagctgcggg acaaggaaag gcgaaaggag 600
attgacctgc tgctgggtca aacagatgat accagatacc atgtgctagt gaacctgggc 660
aaaaagatca cagactatgg tggagataag gaaatccaaa atatggatga caacattgat 720
gagacatacg gtgtgaatgt gcagtttgag tctgatgagg aggaaggtga tgaagacgta 780
tacggggagg ttcgagaaga ggcatctgat gatgacatgg aaggggacga ggctgtcgtg 840
cgctgcaccc tctcggctaa tctcgtagcc tcaggtgaac tgatgagttc caagaagaag 900
gatttgcacc ctcgggatat tgatgcattt tggctgcagc ggcagctcag tcgtttctat 960
gatgatgcca tcgtgtcgca gaagaaggca gatgaagtat tggagatttt gaagacggcc 1020
agtgatgatc gggaatgtga aaatcagctg gttctgctgc ttggtttcaa cacctttgat 1080
ttcattaaag tgttgcggca gcacaggatg atgattttat actgtacctt gctggccagt 1140
gcacaaagtg aagctgaaaa ggaaaggatt atgggaaaga tggaagctga cccagagcta 1200
tccaagttcc tctaccagct tcatgaaacc gagaaggagg atctgatccg agaggaaagg 1260
tcccggagag agcgagtgcg tcagtctcga atggacacag atctggaaac catggatctc 1320
gaccagggtg gagaggcact ggctccacgg caggttctgg acttggagga cctggttttt 1380
acccaaggga gccactttat ggccaataaa cgctgtcagc ttcctgatgg atccttccgt 1440
cgccagcgta agggctatga agaggtgcat gtgcctgctc tgaagcccaa gccctttggc 1500
tcagaagaac aactgcttcc agtggaaaag ctgccaaagt atgcccaggc tgggtttgag 1560

-continued

```
ggcttcaaaa cactgaatcg gatccagagt aagctctacc gtgctgccct tgagacggat   1620
gagaatctgc tgctgtgtgc tcctactggt gctgggaaga ccaacgtggc cctgatgtgc   1680
atgctccgag agattgggaa acacataaac atggacggca ccatcaatgt ggatgacttc   1740
aagattatct acattgcccc catgcgctcc ttggtgcagg agatggtggg cagctttgga   1800
aagcgcctgg ccacttatgg catcactgtt gctgaactga ctggggacca ccagctgtgc   1860
aaagaagaga tcagtgccac tcagatcatc gtctgcaccc ccgagaagtg ggacatcatc   1920
acccgcaagg gtggtgagcg cacctacacc cagctggtgc ggctcatcat tctggatgag   1980
attcatcttc tccacgatga cagaggtcct gtcttagaag ctttagtggc cagggccatc   2040
cgaaacattg agatgaccca agaggatgtc cgactcattg gtctcagtgc caccctaccc   2100
aactatgaag atgtagccac ctttctacgt gttgaccctg ccaagggtct cttttacttt   2160
gacaacagct tccgtccagt gcctctggaa cagacatatg tgggtatcac agagaaaaaa   2220
gctatcaagc gtttccagat catgaatgaa atcgtctatg aaaaaatcat ggaacatgct   2280
ggaaaaaatc aggtgctggt gtttgtccac tcccggaagg agactggaaa gacagccagg   2340
gccatccggg acatgtgcct agaaaaggac actctgggtc tgtttctgag ggagggctca   2400
gcctccacag aagtcctgcg aacagaagct gagcagtgca agaacctaga gctgaaggat   2460
cttctgcctt atggctttgc tattcatcac gcaggcatga ccagggttga ccgaacactc   2520
gtggaggatc tttttgctga taaacatatt caggttttag tttccacagc aactctagct   2580
tggggtgtga atctccctgc acatacagtc atcatcaaag gcacccaggt gtacagtcca   2640
gagaaggggc gttggacaga actgggagca ctggacattc tgcagatgct gggacgtgcc   2700
ggaagacccc agtatgacac caagggtgaa ggcatactca tcacatctca tggggagcta   2760
cagtactacc tgtccctcct caatcaacaa cttcctattg aaagccagat ggtttcaaag   2820
cttcctgaca tgctcaatgc agaaatcgtg ctaggaaatg tccagaatgc caaggatgcg   2880
gtgaactggc tgggctatgc ctacctctat atccgaatgc tgcgatcccc aaccctctat   2940
ggcatctctc atgatgacct caagggagat cccctgctgg accagcgccg actagatctg   3000
gttcatacag ctgccctgat gctggacaag aacaatctgg tcaagtacga caagaagacg   3060
ggcaacttcc aggtgacaga actgggccgt atagccagcc actactacat caccaatgat   3120
acagtgcaga cttacaacca gctgctgaag cccaccctga gtgagattga gcttttcagg   3180
gtcttctcat tgtcctctga gttcaagaac atcacagtga gagaggagga gaagctggag   3240
ctgcagaagt tgctggagag ggtgcctatc cctgtaaagg agagcattga ggaacccagt   3300
gctaagatca acgttcttct gcaagccttc atctcacagc tgaaattgga gggctttgca   3360
ctgatggctg acatggtgta tgtcacacag tcggctggcc ggttgatgcg agcgatattt   3420
gaaattgtcc tgaaccgagg ttgggcacag cttacagaca agaccctgaa cctctgcaag   3480
atgatcgaca aacgcatgtg gcagtccatg tgtcctctgc gccagttccg gaaactccct   3540
gaggaagtag tgaagaagat tgagaagaag aatttcccct ttgagcgtct gtacgacctg   3600
aatcataatg agattgggga gcttatccgc atgccaaaga tggggaagac catccacaaa   3660
tatgtccatc tgtttcccaa gttggagttg tcagtgcacc tgcagcctat cacacgctcc   3720
accctgaagg tggagctgac catcacgcca gacttccagt gggatgaaaa ggtgcatggt   3780
tcatccgagg ctttttggat tctggtggag gatgtggaca gcgaggtgat tctgcaccat   3840
gagtattttc tcctcaaggc caagtacgcc caggacgagc acctcattac attcttcgtg   3900
```

-continued

```
cctgtctttg aaccgctgcc ccctcagtac ttcatccgag tggtgtctga ccgctggctc   3960
tcttgtgaga cccagctgcc tgtctccttc cggcacctga tcttgccgga gaagtacccc   4020
cctccaaccg aacttttgga cctgcagccc ttgcccgtgt ctgctctgag aaacagtgcc   4080
tttgagagtc tttaccaaga taaatttcct ttcttcaatc ccatccagac ccaggtgttt   4140
aacactgtat acaacagtga cgacaacgtg tttgtggggg cccccacggg cagcgggaag   4200
actatttgtg cagagtttgc catcctgcga atgctgctgc agagctcgga ggggcgctgt   4260
gtgtacatca cccccatgga ggccctggca gagcaggtat acatggactg gtacgagaag   4320
ttccaggaca ggctcaacaa gaaggtggta ctcctgacag gcgagaccag cacagacctg   4380
aagctgctgg gcaaagggaa cattatcatc agcacccctg agaagtggga catactttcc   4440
cggcgatgga agcagcgcaa gaacgtgcag aacatcaacc tcttcgtggt ggatgaggtc   4500
caccttatcg gggcgagaa tgggcctgtc ttagaagtga tctgctcccg aatgcgctac   4560
atctcctccc agattgagcg gcccattcgc attgtggcac tcagctcttc gctctccaat   4620
gccaaggatg tggcccactg gctgggctgc agtgccacct ccaccttcaa cttccatccc   4680
aatgtgcgtc ccgtcccctt ggagctgcac atccagggct tcaacatcag ccatacacaa   4740
acccgcctgc tctccatggc caagcctgtg taccatgcta tcaccaagca ctcgcccaag   4800
aagcctgtca ttgtctttgt gccgtctcgc aagcagaccc gcctcactgc cattgacatc   4860
ctcaccacct gtgcagcaga catccaacgg cagaggttct tgcactgcac cgagaaggat   4920
ctgattccgt acctggagaa gctaagtgac agcacgctca aggaaacgct gctaaatggg   4980
gtgggctacc tgcatgaggg gctcagcccc atggagcgac gcctggtgga gcagctcttc   5040
agctcagggg ctatccaggt ggtggtggct tctcggagtc tctgctgggg catgaacgtg   5100
gctgcccacc tggtaatcat catggatacc cagtactaca atggcaagat ccacgcctat   5160
gtggattacc ccatctatga cgtgcttcag atggtgggcc acgccaaccg ccctttgcag   5220
gacgatgagg ggcgctgtgt catcatgtgt cagggctcca agaaggattt cttcaagaag   5280
ttcttatatg agccattgcc agtagaatct cacctggacc actgtatgca tgaccacttc   5340
aatgctgaga tcgtcaccaa gaccattgag aacaagcagg atgctgtgga ctacctcacc   5400
tggacctttc tgtaccgccg catgacacag aaccccaatt actacaacct gcagggcatc   5460
tcccatcgtc acttgtcgga ccacttgtca gagctggtgg agcagaccct gagtgacctg   5520
gagcagtcca agtgcatcag catcgaggac gagatggacg tggcgcctct gaacctaggc   5580
atgatcgccg cctactatta catcaactac accaccattg agctcttcag catgtccctc   5640
aatgccaaga ccaaggtgcg agggcttatc gagatcatct ccaatgcagc agagtatgag   5700
aacattccca tccggcacca tgaagacaat ctcctgaggc agttggctca gaaggtcccc   5760
cacaagctga ataaccctaa gttcaatgat ccgcacgtca agaccaacct gctcctgcag   5820
gctcacttgt ctcgcatgca gctgagtgct gagttgcagt cagatacgga ggaaatcctt   5880
agtaaggcaa tccggctcat ccaggcctgc gtggatgtcc tttccagcaa tgggtggctc   5940
agccctgctc tggcagctat ggaactggcc cagatggtca cccaagccat gtggtccaag   6000
gactcatacc tgaagcagct gccacacttc acctctgagc atatcaaacg ttgcacagac   6060
aagggagtgg agagtgtttt cgacatcatg gagatggagg atgaagaacg gaacgcgttg   6120
cttcagctga ctgacagcca gattgcagat gtggctcgct tttgtaaccg ctaccctaat   6180
atcgaactat cttatgaggt ggtagataag gacagcatcc gcagtggcgg gccagttgtg   6240
gtgctggtgc agctggagcg agaggaggaa gtcacaggcc ctgtcattgc gcctctcttc   6300
```

-continued

```
ccgcagaaac gtgaagaggg ctggtgggtg gtgattggag atgccaagtc caatagcctc   6360

atctccatca agaggctgac cttgcagcag aaggccaagg tgaagttgga ctttgtggcc   6420

ccagccactg gtgcccacaa ctacactctg tacttcatga gtgacgctta catgggatgt   6480

gaccaggagt acaaattcag cgtggatgtg aaagaagctg agacagacag tgattcagat   6540

tgagtcctga ggcatttact tttgggtaaa ggagagttga gcctgaatta ggaatgtgta   6600

cattgtagga atcctggttg tggggaccag gtctgtgggc ctcaggtctg gccagccagg   6660

gctggtgctg tccccgccta cctccacttc ctttcccttg ctcactctgg atccagtgac   6720

agcaggtgtc atgggtcaag cataaatcat atatagcatt ttcaggcatg ttcctggtag   6780

ttcttttgag tctgacattc taataaaata atttgtagaa accatttgtc tttgtagtga   6840

ttccaaatta aaagttttct ttctccaacc tgagggcacg gccaaaaaga tctggttatt   6900

ttttagccag gaacgtgctt gttaatgagt atgtctggag gacagacctg ctcattaggt   6960

gtgctgtccc ctgtagcctc gtgagtcagc ccagaggagg gtacatgcga ctgtggcctg   7020

gcctcagtgg tacccacaca tcagcactac cacaagaacc aacactgagc ctcggaagct   7080

agatcacagg ttaggggttt ctctagatgg gggttctgaa atttgcagtg tctgctcctg   7140

ggaggcagca ccagaaaggg cactgaaatg tactagctgg atgtgaccca gtcttaataa   7200

acaggttttc taatccagaa aaaaaaaaaa                                     7230
```

<210> SEQ ID NO 9
<211> LENGTH: 1005
<212> TYPE: DNA
<213> ORGANISM: Homo sapiens

<400> SEQUENCE: 9

```
cagacgtccc tgcgcgtcgt cctcctcgcc ctccaggccg cccgcgccgc gccggagtcc     60

gctgtccgcc agctacccgc ttcctgccgc ccgccgctgc catgctgccc gccgcgctgc    120

tccgccgccc gggacttggc cgcctcgtcc gccacgcccg tgcctatgcc gaggccgccg    180

ccgcccccggc tgccgcctct ggccccaacc agatgtcctt caccttcgcc tctcccacgc   240

aggtgttctt caacggtgcc aacgtccggc aggtggacgt gcccacgctg accggagcct    300

tcggcatcct ggcggcccac gtgcccacgc tgcaggtcct gcggccgggg ctggtcgtgg    360

tgcatgcaga ggacggcacc acctccaaat actttgtgag cagcggttcc atcgcagtga    420

acgccgactc ttcggtgcag ttgttggccg aagaggccgt gacgctggac atgttggacc    480

tgggggcagc caaggcaaac ttggagaagg cccaggcgga gctggtgggg acagctgacg    540

aggccacgcg ggcagagatc cagatccgaa tcgaggccaa cgaggccctg gtgaaggccc    600

tggagtaggc ggtgcgtacc cggtgtcccg aggcccggcc aggggctggg cagggatgcc    660

aggtgggccc agccagctcc tggggtcccg gccacctggg gaagccgcgc ctgccaagga    720

ggccaccaga gggcagtgca ggcttctgcc tgggccccag gccctgcctg tgttgaaagc    780

tctggggact gggccaggga agctcctcct cagctttgag ctgtggctgc cacccatggg    840

gctctccttc cgcctctcaa gatcccccca gcctgacggg ccgcttacca tcccctctgc    900

cctgcagagc cagccgccaa ggttgacctc agcttcggag ccacctctgg atgaactgcc    960

cccagccccc gccccattaa agacccggaa gcctgaaaaa aaaaa                   1005
```

<210> SEQ ID NO 10
<211> LENGTH: 3631
<212> TYPE: DNA

<213> ORGANISM: Homo sapiens

<400> SEQUENCE: 10
gcggccgctg cagagattgg aatccgcctg ccgggcttgg cgaaggagaa gggaggaggc 60
aggagcgagg agggaggagg gccaagggcg ggcaggaagg cttaggctcg gcgcgtccgt 120
ccgcgcgcgg cgaagatcgc acggcccgat cgaggggcga ccgggtcggg gccgctgcac 180
gccaagggcg aaggccgatt cggccccac ttcgccccgg cggctcgccg cgcccacccg 240
ctccgcgccg agggctggag gatgcgttcc ctggggtccg gacttatgaa aatatgcatc 300
agtttaatac tgtcttggaa ttcatgagat ggaagcatag gtcaaagctg tttggagaaa 360
atcagaagta cagttttatc tagccacatc ttggaggagt cgtaagaaag cagtgggagt 420
tgaagtcatt gtcaagtgct tgcgatcttt tacaagaaaa tctcactgaa tgatagtcat 480
ttaaattggt gaagtagcaa gaccaattat taaaggtgac agtacacagg aaacattaca 540
attgaacaat gcctcagcta tacatttaca tcagattatt gggagcctat ttgttcatca 600
tttctcgtgt tcaaggacag aatctggata gtatgcttca tggcactggg atgaaatcag 660
actccgacca gaaaaagtca gaaaatggag taaccttagc accagaggat accttgcctt 720
ttttaaagtg ctattgctca gggcactgtc cagatgatgc tattaataac acatgcataa 780
ctaatggaca ttgctttgcc atcatagaag aagatgacca gggagaaacc acattagctt 840
cagggtgtat gaaatatgaa ggatctgatt ttcagtgcaa agattctcca aaagcccagc 900
tacgccggac aatagaatgt tgtcggacca atttatgtaa ccagtatttg caacccacac 960
tgccccctgt tgtcataggt ccgttttttg atggcagcat tcgatggctg gttttgctca 1020
tttctatggc tgtctgcata attgctatga tcatcttctc cagctgcttt tgttacaaac 1080
attattgcaa gagcatctca agcagacgtc gttacaatcg tgatttggaa caggatgaag 1140
catttattcc agttggagaa tcactaaaag accttattga ccagtcacaa agttctggta 1200
gtgggtctgg actaccttta ttggttcagc gaactattgc caaacagatt cagatggtcc 1260
ggcaagttgg taaaggccga tatggagaag tatggatggg caaatggcgt ggcgaaaaag 1320
tggcggtgaa agtattcttt accactgaag aagccagctg gtttcgagaa acagaaatct 1380
accaaactgt gctaatgcgc catgaaaaca tacttggttt catagcggca gacattaaag 1440
gtacaggttc ctggactcag ctctatttga ttactgatta ccatgaaaat ggatctctct 1500
atgacttcct gaaatgtgct acactggaca ccagagccct gcttaaattg gcttattcag 1560
ctgcctgtgg tctgtgccac ctgcacacag aaatttatgg cacccaagga aagcccgcaa 1620
ttgctcatcg agacctaaag agcaaaaaca tcctcatcaa gaaaaatggg agttgctgca 1680
ttgctgacct gggccttgct gttaaattca acagtgacac aaatgaagtt gatgtgccct 1740
tgaataccag ggtgggcacc aaacgctaca tggctcccga agtgctggac gaaagcctga 1800
acaaaaacca cttccagccc tacatcatgg ctgacatcta cagcttcggc ctaatcattt 1860
gggagatggc tcgtcgttgt atcacaggag ggatcgtgga agaataccaa ttgccatatt 1920
acaacatggt accgagtgat ccgtcatacg aagatatgcg tgaggttgtg tgtgtcaaac 1980
gtttgcggcc aattgtgtct aatcggtgga acagtgatga atgtctacga gcagttttga 2040
agctaatgtc agaatgctgg gcccacaatc cagcctccag actcacagca ttgagaatta 2100
agaagacgct tgccaagatg gttgaatccc aagatgtaaa aatctgatgg ttaaaccatc 2160
ggaggagaaa ctctagactg caagaactgt ttttacccat ggcatgggtg gaattagagt 2220
ggaataagga tgttaacttg gttctcagac tctttcttca ctacgtgttc acaggctgct 2280

```
aatattaaac ctttcagtac tcttattagg atacaagctg ggaacttcta aacacttcat   2340

tctttatata tggacagctt tattttaaat gtggtttttg atgccttttt ttaagtgggt   2400

ttttatgaac tgcatcaaga cttcaatcct gattagtgtc tccagtcaag ctctgggtac   2460

tgaattgcct gttcataaaa cggtgctttc tgtgaaagcc ttaagaagat aaatgagcgc   2520

agcagagatg gagaaataga ctttgccttt tacctgagac attcagttcg tttgtattct   2580

acctttgtaa aacagcctat agatgatgat gtgtttggga tactgcttat tttatgatag   2640

tttgtcctgt gtccttagtg atgtgtgtgt gtctccatgc acatgcacgc cgggattcct   2700

ctgctgccat ttgaattaga agaaaataat ttatatgcat gcacaggaag atattggtgg   2760

ccggtggttt tgtgctttaa aaatgcaata tctgaccaag attcgccaat ctcatacaag   2820

ccatttactt tgcaagtgag atagcttccc caccagcttt atttttaac atgaaagctg   2880

atgccaaggc caaaagaagt ttaaagcatc tgtaaatttg gactgttttc cttcaaccac   2940

catttttttt gtggttatta tttttgtcac ggaaagcatc ctctccaaag ttggagcttc   3000

tattgccatg aaccatgctt acaaagaaag cacttcttat tgaagtgaat tcctgcattt   3060

gatagcaatg taagtgccta taaccatgtt ctatattctt tattctcagt aacttttaaa   3120

agggaagtta tttatatttt gtgtataatg tgctttattt gcaaatcacc cactccttta   3180

caaccatact ttatatatgt acatacattc atactgtaga aaccagctca tgtgtacctc   3240

atatcccatc cttaagagaa gaaatgttat aaagtagaac taaatataaa ttttcagaat   3300

taatgcattc aaagtaatat atcaaatcca ggactttgtt aacttcaggt aaaaacttca   3360

ttagggtaat atcatctcaa ttttttcaaa tgaaaggatt ctctaattag aaatttatat   3420

gtcagagctg ttataaattt atcaactgtc aaatatgttc tggacagcta aatcatttga   3480

gatttttggt tttttgattt ctattcccta acttgtgaag acaatgaaaa atcaggcaga   3540

aatatttagt atctagtcag tatctgtagc tacactgtat aactgttctt caataaaatg   3600

gttcatattt tatagaaaaa aaaaaaaaaa a                                  3631
```

<210> SEQ ID NO 11
<211> LENGTH: 2533
<212> TYPE: DNA
<213> ORGANISM: Homo sapiens

<400> SEQUENCE: 11

```
gggatgctgt gtgggtttca agaagacgcc acgcctccgc cgccgccacg cccccgccgc     60

ctccaccgcc ggctgccgcg cccggaggag gtcgggatgt tatcacttcc gccggggctt    120

ctcactgtgt ccgggtcagc tgctgccgcc gacgccgtac cgctgcggcc gggggattgg    180

gccggggtct ccaccgccga ccgaggggag cgggctccgc tcggccctgc tttttgcgac    240

ctggccgtca gccccacgtc gccggcctgg aggggcgaag aggacgaggg ggccaaggct    300

tcctccgggg acattggctc cctggattat caagagtttg tagttgacat tgaatccagg    360

ctgaggatgg aaggtgtgga acttaaagaa gaatggcaag atgaagattt tccgatacct    420

ttaccagaag atgatagtat tgaagcagat atactagcta taactggacc agaggaccag    480

cctggctcac tagaagttaa tggaaataaa gtgagaaaga aactaatggc tccagacatt    540

agcctgacac tggatcctag tgatggctct gtattgtcag atgatttgga tgaaagtggg    600

gagattgact tagatggctt agacacaccg tcagagaata gtaatgagtt tgagtgggaa    660

gatgatcttc caaaacccaa gactactgaa gtaattagga aaggctcaat tactgaatac    720
```

```
acagcagcag aggaaaaaga agatggacga cgctggcgta tgttcaggat tggagaacag    780

gaccacaggg ttgatatgaa ggcaattgaa ccctataaaa aagttatcag ccatggggga    840

tattatgggg atggattaaa tgccattgtt gtgtttgctg tctgtttcat gcctgaaagt    900

agtcagccta actatagata cctgatggac aatcttttta aatatgttat tggcactttg    960

gagctattag tagcagaaaa ctacatgata gtttatttaa atggtgcaac aactcgaaga   1020

aaaatgccca gtctgggatg gctcaggaaa tgttatcagc aaattgatag aaggttacgg   1080

aaaaatctaa aatccctaat cattgtacat ccttcttggt ttatcagaac acttctggct   1140

gttacaagac catttattag ctcgaaattc agccaaaaaa ttagatacgt gtttaatttg   1200

gcagaactag cagaacttgt ccccatggaa tacgttggca taccagaatg cataaaacaa   1260

gttgatcaag aacttaatgg aaaacaagat gaaccgaaaa atgaacagta agtttggcat   1320

ctagtccaaa caagactgaa gaatgtgctg atggagcagt gctgtttctg cattcataat   1380

gcatttattg gcccatattt ttatgtaacc tgttacaaaa tagacttgac tttttcataa   1440

tggacttttg tattatacaa gggactgttc actgctgtac tggtttgcaa atttcttgaa   1500

tttagctctt taatagctaa ctgtattatt atcgttttat attttatatt gctaaataga   1560

gaaccacact ttatataaag tagtttttgc atttgtttat tgaatgatgc atcttcttcg   1620

gtgaaatatt tatatgcata aatggcaaag gaaagaaata atatatattt ttatgtcatt   1680

gagcaatatt ttttaatgtg tacctgtctt atggaagaaa tatgcaggta tataagacca   1740

cgattttcta aagtgcatat tagaattttt gtttttgtaa atggttaaat acatttcctg   1800

ggtaacttag gaaattaagt ttttcataag gcaacagatg gttaaactga ttgtcatgaa   1860

tacccaaaga tcatgtatat aatcgaagtg tattagtacc atcccaaggt ttttttctca   1920

tttaacatat ttgtttcata attcagcaag tacagatgca agcgcattgc acactttttc   1980

ctttctaaac ttaaagacaa gtcaaaaagc cattcttaga actagaggat ttaagagggt   2040

aggaattagg gtttgtatat atgtatatat gggacatttt atcttctggc ccaaagtcag   2100

aactttataa aaatcttgag tttgttcact aatgtgaaat aagctatgtg tccagggtat   2160

tgctcccctg agtgtatatg agtgctgagt agtattgcag agaatgtgat gagttattca   2220

ctgtcacaac tttttctata gaaaacaggg gctgcttttt aaactctcac tatgggcact   2280

ttaccaaaat acttccatat caattatttg aactcggtag ttgtttgacc tagttagatg   2340

tggtgtttat tcaagtttgt atgaaatcat gtttgacaat actgtaaatt aggttaattt   2400

tgtaagtctt agcatcatca tattgtgctg ttttggataa cacgtttgtt acaagcattt   2460

aaactgtttc atttggtagt acctttacat tgaaataaat tgtgtttgtg cctccaaaaa   2520

aaaaaaaaaa aaa                                                      2533
```

<210> SEQ ID NO 12
<211> LENGTH: 2663
<212> TYPE: DNA
<213> ORGANISM: Homo sapiens

<400> SEQUENCE: 12

```
gccccaagcc cagcctctcg ccagctggga gtcgcgcgct gcccacctcg ctgcccaggc      60

ccccgacgcc gcggcaggag ccccccaaga gcgcgggaag ccccgtggac ctggcgctcc     120

cggctcgggc gtggacgggg cgggcgccgg ggcggggcgc gcgtcctcgc gggtctgaat     180

ggaagggtcg aggtcgtcgt cggcggcgag cagatcctga agccagaact ccacccccggc    240

gcccgcgcca tgcggcggga gaggtgcggc gcccccccacc cgcgtcgccg ccatggaggt    300
```

```
gctgcggcgc tcctcggtct tcgccgccga gatcatggac gcctttgacc gctcgcccac    360
agacaaggag ctggtggccc aggccaaggc gctgggccgg gagtacgtgc acgcgcggct    420
gctgcgcgcc ggcctctcct ggagcgcgcc cgagcgtgcc gcgccggtcc cgggacgcct    480
ggctgaggtg tgcgcggtgc tgctgcgcct gggcgatgag ctggagatga tccggcccag    540
cgtctaccgc aacgtggcgc gtcagctgca catctccctg cagtctgagc ctgtggtgac    600
cgatgcgttc ctggccgtgg ctggccacat cttctctgca ggcatcacgt ggggcaaggt    660
ggtgtccctg tatgcggtgg ccgcggggct ggccgtggac tgtgtgaggc aggcccagcc    720
tgccatggtc cacgccctcg tggactgcct gggggagttc gtgcgcaaga ccctggcaac    780
ctggctgcgg agacgcggcg gatggactga tgtcctcaag tgtgtggtca gcacagaccc    840
tggcctccgc tcccactggc tggtggctgc actctgcagc ttcggccgct tcctgaaggc    900
tgccttcttc gtgctgctgc cagagagatg agctgcccac ctggcagtgg ccgcagcctg    960
gccctctggg cccaacgcag gaggccctca gcacccgaac acatcttcct cctccccacc   1020
cgagcctgga gcactctaac cctcggagac cccctaagcc ccgttcctcc gcagacccag   1080
gccctccgga aggggtgagt ggggaggggc tttcctgagc ctggagctgg gctttggggc   1140
agcctgcgac cctccccgct tgtgtccctt ctcctgtgat ctctgtgttt tcccttttct   1200
ttctggggcc aggaagtcag ggtcaactcc caggcctcag atgcaggggc ccagaacacc   1260
tgctctcacc tgagccccag gtgaaggggc ccgggaacac ctgctctcac ctgagcccca   1320
ggtgaagggg cccgggaaca cctgctctca cctgaacccc aggtgaaggg gcccggaaca   1380
cctgctctca cctgagcccc aggtgaaggg gcccggaaca cctgctctca cctgagcccc   1440
aggtgaaggg gcccgggaac acctgctctc acctgagccc caggtgaagg ggcccgggaa   1500
cacctgctct cacctgaacc ccaggtgaag gggcccagaa cacctgctct cacctgagcc   1560
ccaggtgaag gggcccggaa cacctgctct cacctgagcc ccaggtgaag gggcccggga   1620
acacctgctc tcacctgagc ccctggtgaa ggggcccgga acacttgctc tcacctgagc   1680
cccaggtgaa ggggcccgga acacctgctc tcacctgagc cccggtgaa ggggcccgga    1740
acacttgctc tcacctgagc cccaggtgaa ggggcccgga acacctcctc tcacctgagc   1800
cccaggtgaa ggggcccgga acacctcctg tcacctgagc cccaggtgaa ggggcccggg   1860
aacacctctc acctgaaccc gggggtccca tcccaggaag aagggccatc tcaggacatg   1920
agtcctcagg ggccctgcac attcaatctg aaggtgaccc tggcctggct gaagctggaa   1980
gagctgtggg gactcagcct gtaaacagag cgtaaggttc acatgctggt tgcttaatcc   2040
gtttctggag gaagagtatg acacccactt gtgatggggt ccttgtgcgg tggggaccgg   2100
ggccggcggg ctccaggcca gcacacctaa cccatggatg tggaacctac ggccgagaag   2160
gaatgttgca tgagtcggat cccagtccat tgtcagtgga gggtgagggt gaccccatct   2220
gctatttttg tgctcatcct catacaacca tttggggatg tgcctattag ggctccgtaa   2280
gaactcagat gcctgggaag cccagcccct caggtgcccc cacacacagc cttcccttga   2340
cgcctacatt tctaggcaca tgtgaggcat ctttcctgga gccccgagcc agccctgtcc   2400
ctccccagtg cagcatggca ctcaggagat acaggctgga catggggcag tcgttctggg   2460
gaggcctggc ctagcagcca cccacctgag ccctcccggc caggcttcgt gctggggtgg   2520
gccatgtgcc aggacaggag ggtcccggcg gaaagccagc cccggactca tcgtgacatt   2580
gagatcccac tggagggtag gggtggtaat aaacttctcc aaacgatcgt tgtcatttta   2640
```

gacagaaaaa aaaaaaaaaa aaa 2663

<210> SEQ ID NO 13
<211> LENGTH: 4635
<212> TYPE: DNA
<213> ORGANISM: Homo sapiens

<400> SEQUENCE: 13
attctttgga atactactgc tagaagtctg acttaagacc cagcttatgg gccacatggc 60
acccagctgc ttctgcagag aaggcaggcc actgatgggt acagcaaagt gtggtgctgc 120
tggccaagcc aaagacccgt gtaggatgac tgggcctctg ccccttgtgg gtgttgccac 180
tgtgcttgag tgcctggtga agaatgtgat gggatcacta gcatgtctgc ggagagcggc 240
cctgggacga gattgagaaa tctgccagta atgggggatg gactagaaac ttcccaaatg 300
tctacaacac aggcccaggc ccaaccccag ccagccaacg cagccagcac caaccccccg 360
cccccagaga cctccaaccc taacaagccc aagaggcaga ccaaccaact gcaatacctg 420
ctcagagtgg tgctcaagac actatggaaa caccagtttg catggccttt ccagcagcct 480
gtggatgccg tcaagctgaa cctccctgat tactataaga tcattaaaac gcctatggat 540
atgggaacaa taaagaagcg cttggaaaac aactattact ggaatgctca ggaatgtatc 600
caggacttca acactatgtt tacaaattgt tacatctaca acaagcctgg agatgacata 660
gtcttaatgg cagaagctct ggaaaagctc ttcttgcaaa aaataaatga gctacccaca 720
gaagaaaccg agatcatgat agtccaggca aaaggaagag gacgtgggag gaaagaaaca 780
gggacagcaa aacctggcgt ttccacggta ccaaacacaa ctcaagcatc gactcctccg 840
cagacccaga cccctcagcc gaatcctcct cctgtgcagg ccacgcctca ccccttccct 900
gccgtcaccc cggacctcat cgtccagacc cctgtcatga cagtggtgcc tccccagcca 960
ctgcagacgc cccgcccagt gcccccccag ccacaacccc cacccgctcc agctccccag 1020
cccgtacaga gccacccacc catcatcgcg gccaccccac agcctgtgaa gacaaagaag 1080
ggagtgaaga ggaaagcaga caccaccacc cccaccacca ttgaccccat tcacgagcca 1140
ccctcgctgc ccccggagcc caagaccacc aagctgggcc agcggcggga gagcagccgg 1200
cctgtgaaac ctccaaagaa ggacgtgccc gactctcagc agcacccagc accagagaag 1260
agcagcaagg tctcggagca gctcaagtgc tgcagcggca tcctcaagga gatgtttgcc 1320
aagaagcacg ccgcctacgc ctggcccttc tacaagcctg tggacgtgga ggcactgggc 1380
ctacacgact actgtgacat catcaagcac cccatggaca tgagcacaat caagtctaaa 1440
ctggaggccc gtgagtaccg tgatgctcag gagtttggtg ctgacgtccg attgatgttc 1500
tccaactgct ataagtacaa ccctcctgac catgaggtgg tggccatggc ccgcaagctc 1560
caggatgtgt tcgaaatgcg ctttgccaag atgccggacg agcctgagga gccagtggtg 1620
gccgtgtcct ccccggcagt gccccctccc accaaggttg tggccccgcc ctcatccagc 1680
gacagcagca gcgatagctc ctcggacagt gacagttcga ctgatgactc tgaggaggag 1740
cgagcccagc ggctggctga gctccaggag cagctcaaag ccgtgcacga gcagcttgca 1800
gccctctctc agccccagca gaacaaacca aagaaaaagg agaaagacaa gaaggaaaag 1860
aaaaaagaaa agcacaaaag gaaagaggaa gtggaagaga ataaaaaaag caaagccaag 1920
gaacctcctc ctaaaaagac gaagaaaaat aatagcagca acagcaatgt gagcaagaag 1980
gagccagcgc ccatgaagag caagcccccct cccacgtatg agtcggagga agaggacaag 2040
tgcaagccta tgtcctatga ggagaagcgg cagctcagct tggacatcaa caagctcccc 2100

```
ggcgagaagc tgggccgcgt ggtgcacatc atccagtcac gggagccctc cctgaagaat   2160
tccaaccccg acgagattga aatcgacttt gagaccctga agccgtccac actgcgtgag   2220
ctggagcgct atgtcacctc ctgtttgcgg aagaaaagga aacctcaagc tgagaaagtt   2280
gatgtgattg ccggctcctc caagatgaag ggcttctcgt cctcagagtc ggagagctcc   2340
agtgagtcca gctcctctga cagcgaagac tccgaaacag gtcctgccta atcattggac   2400
acggactctt aataaaacgg tcttcagttc cagattcctt cccagcaagc tatagcttaa   2460
gtccattttc ttccgtgaaa gggacaggac tccatcaagt tatggaattc ctcagagccc   2520
tgggcctgtc ccccggggtg gattagtcat gtccagcagc acacgcctag tcccgccttc   2580
gggaaggctg cctgcctggc cagccgccca ggcctctctg tgtaaagact gcctggctgt   2640
cctgcccagc cttcctggtt ctctggggtc ctctgggtgg gtggcatctc ctggagggtg   2700
atgacaatcc ccaacacatg cattcatgtg gtgctactct gtgtgcaaag ccagacccca   2760
agtatgtttt ctctctttgt cccatccctc tttttctggg actttggacc ctaactactt   2820
ccctcctgaa ccttgcagtg acatcagtcc aggagagctc tcgttcagtg tgcggaagaa   2880
cactctgacc tctagagctg tcctagataa ggagtgggag ctttagaggc aaggcctcta   2940
gaccctggaa ggctcagtga ggctcttccc acagcatgct tctcactggt gccctgtaag   3000
gctcgagcca ccgctgactc tgagcctttt ggagtctttc ctccttcgtc tccattgttc   3060
ccgtgcattt ccaaaagctt aagttgcctg gtgggcattt ccccagtttc tttggcctcc   3120
gtcttctcaa gtcacatagg gaaagtacct cctggaacca ggctgcagta tgcaggacct   3180
gccaggcagg cactggtgaa gggccttggg cctatcatcc ccccaacccc acctcacccc   3240
acccgcctcc tctagtgggg tgagtctggg ctggtggacc agagagggtg tcacagaccc   3300
tcagggactg ccccatggac acctctgact ggtgttaaca gtgtgaacat tttccccgtc   3360
ttcagtccct tagaatgacg acagcccctg gggttggggc aggcgagtgt ggccacatca   3420
tccaagccct cccagagaca caaataggct tttttgctct aaaaataaat accagccctt   3480
ttttggtcac aaatccagca tctcagcaga aaactgcctg acatgaaaag tcccctgagg   3540
aactgcatct gcgtttcagg ggcttttcat tttttctcct tttttaaagt gtagattgtg   3600
ggtgcttcct agaggcctgc cttcttctgg aactggaagt gggctatcac catgggcaag   3660
cccttgggtg caggctcccc acctgcctgg gaactctggc agctctcctc agctccttgg   3720
gcttgagcag ctgcaactgc cccagatttg ctgtggaagc aggggctagc cctggcctca   3780
ccagggcctc ccggggccct gcattgatgc tcaggagttc ctgggctgct cttgatcctt   3840
tctgggcatc cagcttccag ttaagctctg tttgccaaac aaactattct cagctgccct   3900
ttggcctgcg cctgatgtgt tcctgttgca gtcccgcctg cctgagacag gagcaggcag   3960
gagagccttc atgcccagat tcccacagga caattgggga gctgctggca ttgtctttct   4020
gggaagattc tgctttcttg gaccaaatgg cagcctgatt accagtgtcg ggcctgcatg   4080
ctgcccccga cacacgcacg cacgcgcaca cacgtgtgca catgggccat agccacaagc   4140
cagctctcct ccagggtcct ttcaacctcg ctgtccaggg accctgtcct tcttgcccgt   4200
ggggcttcca tctggcagag aacgttcagg gcttgttgaa cttgaaagct cattagactt   4260
aagctgtcac ctgtgcttgg tgccccagga acagccagag aggacagtgc ccactcactt   4320
cttgttggca gcctcctgtg caggaagtgc cagccgggcc tcgacgcacc agctggctgt   4380
gggtcctgag gaggggcggg aggcggccgc tcagtgcaga tggggactcc tctcctctgc   4440
```

cctgacctta ccctccatta cctccttcac tggagtgggg ctggggggtg ggtggaatca 4500
gtgttttaat cggattttta aaaaacattt tatttctttg tacaattacc atcctatgta 4560
aagatgaaat ttgtgttgag ttgaagattg tcatggaata aagatcacac cgtacttgag 4620
gccatcttca tgtaa 4635

<210> SEQ ID NO 14
<211> LENGTH: 2611
<212> TYPE: DNA
<213> ORGANISM: Homo sapiens

<400> SEQUENCE: 14
aactgagtgg ctgtgaaagg gtggggtttg ctcagactgt ccttcctctc tggactgtaa 60
gaatatgtct ccagggccag tgtctgctgc gatcgagtcc caccttccaa gtcctggcat 120
ctcaatgcat ctgggaagct acctgcatta agtcaggact gagcacacag gtgaactcca 180
gaaagaagaa gctatggccg cagtgattct ggagagcatc tttctgaagc gatcccaaca 240
gaaaaagaaa acatcacctc taaacttcaa gaagcgcctg tttctcttga ccgtgcacaa 300
actctcctac tatgagtatg actttgaacg tgggagaaga ggcagtaaga agggttcaat 360
agatgttgag aagatcactt gtgttgaaac agtggttcct gaaaaaaatc ctcctccaga 420
aagacagatt ccgagaagag gtgaagagtc cagtgaaatg gagcaaattt caatcattga 480
aaggttccct tatcccttcc aggttgtata tgatgaaggg cctctctacg tcttctcccc 540
aactgaagaa ctaaggaagc ggtggattca ccagctcaaa aacgtaatcc ggtacaacag 600
tgatctggtt cagaaatatc acccttgctt ctggatcgat gggcagtatc tctgctgctc 660
tcagacagcc aaaaatgcta tgggctgcca aattttggag aacaggaatg gaagcttaaa 720
acctgggagt tctcaccgga agacaaaaaa gcctcttccc ccaacgcctg aggaggacca 780
gatcttgaaa aagccactac cgcctgagcc agcagcagca ccagtctcca caagtgagct 840
gaaaaaggtt gtggcccttt atgattacat gccaatgaat gcaaatgatc tacagctgcg 900
gaagggtgat gaatatttta tcttggagga aagcaactta ccatggtgga gagcacgaga 960
taaaaatggg caggaaggct acattcctag taactatgtc actgaagcag aagactccat 1020
agaaatgtat gagtggtatt ccaaacacat gactcggagt caggctgagc aactgctaaa 1080
gcaagagggg aaagaaggag gtttcattgt cagagactcc agcaaagctg gcaaatatac 1140
agtgtctgtg tttgctaaat ccacagggga ccctcaaggg gtgatacgtc attatgttgt 1200
gtgttccaca cctcagagcc agtattacct ggctgagaag caccttttca gcaccatccc 1260
tgagctcatt aactaccatc agcacaactc tgcaggactc atatccaggc tcaaatatcc 1320
agtgtctcaa caaaacaaga atgcaccttc cactgcaggc ctgggatacg gatcatggga 1380
aattgatcca aaggacctga ccttcttgaa ggagctgggg actggacaat ttggggtagt 1440
gaagtatggg aaatggagag gccagtacga cgtggccatc aagatgatca aagaaggctc 1500
catgtctgaa gatgaattca ttgaagaagc caaagtcatg atgaatcttt cccatgagaa 1560
gctggtgcag ttgtatggcg tctgcaccaa gcagcgcccc atcttcatca tcactgagta 1620
catggccaat ggctgcctcc tgaactacct gagggagatg cgccaccgct tccagactca 1680
gcagctgcta gagatgtgca aggatgtctg tgaagccatg gaatacctgg agtcaaagca 1740
gttccttcac cgagacctgg cagctcgaaa ctgtttggta aacgatcaag gagttgttaa 1800
agtatctgat ttcggcctgt ccaggtatgt cctggatgat gaatacacaa gctcagtagg 1860
ctccaaattt ccagtccggt ggtccccacc ggaagtcctg atgtatagca agttcagcag 1920
caaatctgac atttgggctt ttggggtttt gatgtgggaa atttactccc tggggaagat 1980
gccatatgag agatttacta acagtgagac tgctgaacac attgcccaag gcctacgtct 2040
ctacaggcct catctggctt cagagaaggt atataccatc atgtacagtt gctggcatga 2100
gaaagcagat gagcgtccca ctttcaaaat tcttctgagc aatattctag atgtcatgga 2160
tgaagaatcc tgagctcgcc aataagcttc ttggttctac ttctcttctc cacaagcccc 2220
aatttcactt tctcagagga aatcccaagc ttaggagccc tggagccttt gtgctcccac 2280
tcaatacaaa aaggcccctc tctacatctg ggaatgcacc tcttctttga ttccctggga 2340
tagtggcttc tgagcaaagg ccaagaaatt attgtgcctg aaatttcccg agagaattaa 2400
gacagactga atttgcgatg aaaatatttt ttaggaggga ggatgtaaat agccgcacaa 2460
aggggtccaa cagctctttg agtaggcatt tggtagagct tgggggtgtg tgtgtggggg 2520
tggaccgaat ttggcaagaa tgaaatggtg tcataaagat gggaggggag ggtgttttga 2580
taaaataaaa ttactagaaa gcttgaaagt c 2611

<210> SEQ ID NO 15
<211> LENGTH: 841
<212> TYPE: DNA
<213> ORGANISM: Homo sapiens

<400> SEQUENCE: 15
cggctcgcgt gtagcggcgg cggcggcgtc tccgtgagga ggcgcgcggg gccatgacgt 60
cagcgtccac aaaggtcgga gagatcttct cggcggccgg cgccgccttc acgaagctcg 120
gggagctgac gatgcagctg catcccgtgg ccgactcttc tcctgcgggc gcgaagtgga 180
cggagacgga aatagagatg ctgagggctg ctgtgaagcg atttggggac gatcttaatc 240
acatcagctg tgtcatcaag gaacggacag tggcccagat aaaggccact gtgaaacgca 300
aggtatatga agattctggc atcccccttc cagctgagtc acccaagaaa gggcccaaga 360
aggtggcatc tggtgtcttg tcacctcctc cagctgcccc tcctcccagc agctccagtg 420
tccctgaggc cgggggtccc cccataaaga aacagaaggc tgatgtgaca ctcagtgctc 480
tgaacgactc cgatgccaac agtgacgtgg tggatattga agggctagga gaaactcctc 540
cagctaagaa actcaacttc gaccaggcct gaccctggat tctggccttc tcatgacctc 600
tgctgatcct cctctcctct cctgctgagc cttccacctc tgacctctca ctgttcatgc 660
cggacctgtg gatctcctgg gactccgagc aaggcctgca cgagagaggg ctgaaaggct 720
gctggggctg ccacctcgct attcccgcat aagcatctgc ccccaacccc tttgaccttc 780
atctgatgga catttttata cagaaaacaa taaagatttc cctctcaaaa aaaaaaaaaa 840
a 841

<210> SEQ ID NO 16
<211> LENGTH: 1732
<212> TYPE: DNA
<213> ORGANISM: Homo sapiens

<400> SEQUENCE: 16
cgcgaggcga gccgggcgcg gcggcagcag ggacgaccca ggctggagct gaggccgagc 60
tgagggcgcc cgagcccccc gccccgcccg tcctctggct ccgcagcgct cagccccggg 120
cccgcggaga catgaacgcc ccgcggcccc acgcaccccg ggcgcagcgg cccggccccg 180
cggccccgtg atgggctcct gcgtgtcgcg agacctgttc acaagtgccc acaagaactg 240

```
ccccatgccc cagggtgcgg accccttgaa cccagatctg ccctcgggcc gcactcccac    300
cgtggctcca gactgtgtca ttggcaagga caaacagatg gatttctgtt gggatccttg    360
gcagaggtgc ttccagacca ccaacggcta cctgtccgac tccagatccc gccccggcaa    420
ctacaacgtg gcagccctgg ccacctcgtc ccttgtgggg gtggtgcaga gcatcaagga    480
ccacatcaca aagcccacgg ccatggcccg aggccgcgtg gcccacctca tcgagtggaa    540
gggctggagt gcccagccgg caggctggga gctgtcccca gctgaggacg agcattactg    600
ctgcctcccg gatgagctgc gtgaggcccg ctttgctgca ggggtcgccg agcagtttgc    660
catcacagag gccacactga gcgcttggtc ctcgctggac gaagaggagc tgcaccccga    720
gaacagcccc caaggcatcg tccagctcca agatctggag agcatctacc ttcaggacag    780
ccttcccagc ggcccctcac aggatgacag ccttcaggcc ttctcctcgc ccagcccctc    840
ccctgacagc tgtccctcac ctgaggagcc ccccagcacc gctggcatcc cgcagccccc    900
cagcccagag ctgcagcatc ggcggcggct gcccggggcc caaggacccg agggtgggac    960
ccaccccccg ggctccctcc cctccatgga cagcggctcc ctctgggagg aggacgaggt   1020
gttctataac tgaggtgggg gctgtgctgg tccagcacct gctctcacca tgacctcgcc   1080
tggtgggcag cccaggcata tctggacccc ggggtccagg gcagggcatc ccttgacccc   1140
tcgggtaggc acagggtagg tgcggcaggg atggggccag tgctcatggt ggcctctctg   1200
tgcctcggtg gacctgcccc agcagtggga gccataaccc cctccccctt cattacttca   1260
ctcaggtggg caccttcccc tgcagggtgt ctgccctcag ggaactcacg gactctcaga   1320
gacaccaggg cagcctggcc cagaggagca acagccaggc cccaggaggg acagccatgg   1380
agagaactga gacccactta cagtggggtc tgggaaccct gcctgtacct ggggttcagt   1440
ccctcccaac tccctccttg tgtctgcccc ccagcaaagg tggggtgacc acttctggta   1500
gctaagcacc tgctccccgg ctctcttcac ccaggacatc tgtctctctg gagtgtctgt   1560
ctgtctgtcc ctccctctct gaacctgctt cctccgtgtc ccctgctcct cacccctggg   1620
agcccactcc ccctccttgc ggctccctcc catctcactc aaggttctct gaggacatta   1680
aagtggtgga ttcaccctgg aaaaaaaaaa aaaaaaaaaa aaaaaaaaaa aa           1732
```

<210> SEQ ID NO 17
<211> LENGTH: 2507
<212> TYPE: DNA
<213> ORGANISM: Homo sapiens

<400> SEQUENCE: 17

```
tggagcagct aatcctcaca gacctgtagg agctggagtg ggagctcaag caggattctt     60
cccgagtccc tggcatcctc agaagcttca actctggagg caatgggtcg aaaggaagaa    120
gatgactgca gttcctggaa gaaacagacc accaacatcc ggaaaacctt catttttatg    180
gaagtgctgg gatcaggagc tttctcagaa gttttcctgg tgaagcaaag actgactggg    240
aagctctttg ctctgaagtg catcaagaag tcacctgcct tccgggacag cagcctggag    300
aatgagattg ctgtgttgaa aaagatcaag catgaaaaca ttgtgaccct ggaggacatc    360
tatgagagca ccacccacta ctacctggtc atgcagcttg tttctggtgg ggagctcttt    420
gaccggatcc tggagcgggg tgtctacaca gagaaggatg ccagtctggt gatccagcag    480
gtcttgtcgg cagtgaaata cctacatgag aatggcatcg tccacagaga cttaaagccc    540
gaaaacctgc tttaccttac ccctgaagag aactctaaga tcatgatcac tgactttggt    600
ctgtccaaga tggaacagaa tggcatcatg tccactgcct gtgggacccc aggctacgtg    660
```

```
gctccagaag tgctggccca gaaaccctac agcaaggctg tggattgctg gtccatcggc    720
gtcatcacct acatattgct ctgtggatac cccccattct atgaagaaac ggagtctaag    780
cttttcgaga agatcaagga gggctactat gagtttgagt ctccattctg ggatgacatt    840
tctgagtcag ccaaggactt tatttgccac ttgcttgaga aggatccgaa cgagcggtac    900
acctgtgaga aggccttgag tcatccctgg attgacggaa acacagccct ccaccgggac    960
atctacccat cagtcagcct ccagatccag aagaactttg ctaagagcaa gtggaggcaa   1020
gccttcaacg cagcagctgt ggtgcaccac atgaggaagc tacacatgaa cctgcacagc   1080
ccgggcgtcc gcccagaggt ggagaacagg ccgcctgaaa ctcaagcctc agaaacctct   1140
agacccagct cccctgagat caccatcacc gaggcacctg tcctggacca cagtgtagca   1200
ctccctgccc tgacccaatt accctgccag catggccgcc ggcccactgc ccctggtggc   1260
aggtccctca actgcctggt caatggctcc ctccacatca gcagcagcct ggtgcccatg   1320
catcaggggt ccctggccgc cgggccctgt ggctgctgct ccagctgcct gaacattggg   1380
agcaaaggaa agtcctccta ctgctctgag cccacactcc tcaaaaaggc caacaaaaaa   1440
cagaacttca agtcggaggt catggtacca gttaaagcca gtggcagctc ccactgccgg   1500
gcagggcaga ctggagtctg tctcattatg tgattcctgg agcctgtgcc tatgtcactg   1560
caattttcag gagacatatt caactcctct gctcttccaa acctggtgtc tatccggcag   1620
agggaggaag gcagagcaag tggagcaggg cttagcagga gcagtttctg gccagaagca   1680
ccagcctgct gccagcgggg cagcccctca taggaggccc aggagggagc cccaaggcgt   1740
agaagccttg ttgaagctgt gagcaggaga agcggtgccc accagcttcc aggtctccct   1800
gacctgcctg ctctatgccc cacaccctac gtgccgtggc tctgtgcagt gtacgtagat   1860
agctctcgcc tgggtctgtg ctgtttgtcg tgaaaagctt aatgggctgg ccaggctgtg   1920
tcaccttctc caagcaaagc catatggagc atctacccag actcccactc tgcacacact   1980
cactcccacc tctcaagcct ccaacctctt ggccagattg ggctcattaa tgtcgttgcc   2040
tgcccatctg catgaatgac aggcagctcc ccatggtggt ctgcctgtga gctcttcaag   2100
ttctaatcct taactccagg attagctccc aagtgcgctg agacccagcc agcacacttc   2160
tggcccttct ccctgcctca atctaaaagc agtgccacac cctccaaagt ggaatagaaa   2220
gaagttcatg agtaagggct gcaaggaatt cttatcctgg ccacatgtcc tccgtgcaca   2280
cacccaatgg agttaacctt ggaagttgac tattttaatg tctgccagga gttctaatcc   2340
tgcctctgtt ccctttctc tccttgaaag tccagcacac cattcttgtc cttccccagt   2400
ttcctcgccc tccacccctc cagcttcatg ctcagtgttg tgcttaataa aatggacata   2460
tttttctcta aaaaaaaaaa aaaaaaaaaa aaaaaaaaaa aaaaaaa                 2507
```

<210> SEQ ID NO 18
<211> LENGTH: 5872
<212> TYPE: DNA
<213> ORGANISM: Homo sapiens

<400> SEQUENCE: 18

```
aaaggaggga gtgcgagaga tccacgaagg gacaggcttg gagtcgctag agggaggtgt     60
gggaccagcg aggagggggc ttcgccaggg agggggtgct ggcaggcgga gggagcggcg    120
ggaggaggcg ccggaggagg agacggaggc ctggggacgg cagaagaggc ttcgcctgag    180
ccgagcgctc tttctctcgc cgcgccgtct tgaagccgcg cgggctcgtg agcagcgcga    240
```

```
ggccgccaag gtgcctcgct tcgccggagc cgctgccgcc cgccggaggg aagccggcct    300
cgggcgcgca cgctcgtcgg agccccggcg cgccccgcgc ctgagcctgc tgacagcggc    360
cgctgggctc aggctgtccg ctctgggctc cgcggcctcg gccccgctgc actccacctc    420
cgccccctcg gactccctcc cctctgcttc tactcctcct gctccagtgc ggatcgtttc    480
gcaactgctt gccactcgtc ccgtgcctgg ctgtttttcc atttcccggc cccctcttct    540
tgagtacttt accccctgca tttggggaca gggactggaa aaggggcggg tggagcgtcc    600
agtggagaag aaggaagcga ggcccgcagg aggaggagga tcggcggact gtggggagga    660
gaccccacgc cacccttcct ggtcatctcc cctcccgccc cgcccctgcg cacactccct    720
cgcgggcgag ctactttcgg accaggaaag taagagcggc cctgggtgac agcgccgcgg    780
ggccagtccc ggggttagcc gcgcgtctgc tcgcttctgg tccgtcgcgc tcccagccag    840
ggcacagccc ggaccgagga tggcttcgac cacaacctgc accaggttca cggacgagta    900
tcagcttttc gaggagcttg gaaagggggc attctcagtg gtgagaagat gtatgaaaat    960
tcctactgga caagaatatg ctgccaaaat tatcaacacc aaaaagcttt ctgctaggga   1020
tcatcagaaa ctagaaagag aagctagaat ctgccgtctt ttgaagcacc ctaatattgt   1080
gcgacttcat gatagcatat cagaagaggg ctttcactac ttggtgtttg atttagttac   1140
tggaggtgaa ctgtttgaag acatagtggc aagagaatac tacagtgaag ctgatgccag   1200
tcattgtata cagcagattc tagaaagtgt taatcattgt cacctaaatg gcatagttca   1260
cagggacctg aagcctgaga atttgctttt agctagcaaa tccaagggag cagctgtgaa   1320
attggcagac tttggcttag ccatagaagt tcaaggggac cagcaggcgt ggtttggttt   1380
tgctggcaca cctggatatc tttctccaga agttttacgt aaagatcctt atggaaagcc   1440
agtggatatg tgggcatgtg gtgtcattct ctatattcta cttgtggggt atccacccct   1500
ctgggatgaa gaccaacaca gactctatca gcagatcaag gctggagctt atgattttcc   1560
atcaccagaa tgggacacgg tgactcctga agccaaagac ctcatcaata aaatgcttac   1620
tatcaaccct gccaaacgca tcacagcctc agaggcactg aagcacccat ggatctgtca   1680
acgttctact gttgcttcca tgatgcacag acaggagact gtagactgct tgaagaaatt   1740
taatgctaga agaaaactaa agggtgccat cttgacaact atgctggcta caaggaattt   1800
ctcagcagcc aagagtttgt tgaagaaacc agatggagta aaggagtcaa ctgagagttc   1860
aaatacaaca attgaggatg aagatgtgaa agcacgaaag caagagatta tcaaagtcac   1920
tgaacaactg atcgaagcta tcaacaatgg ggactttgaa gcctacacaa aaatctgtga   1980
cccaggcctt actgcttttg aacctgaagc tttgggtaat ttagtggaag ggatggattt   2040
tcaccgattc tactttgaaa atgctttgtc caaaagcaat aaaccaatcc acactattat   2100
tctaaaccct catgtacatc tggtagggga tgatgccgcc tgcatagcat atattaggct   2160
cacacagtac atggatggca gtggaatgcc aaagacaatg cagtcagaag agactcgtgt   2220
gtggcaccgc cgggatggaa agtggcagaa tgttcatttt catcgctcgg ggtcaccaac   2280
agtacccatc aagccaccct gtattccaaa tgggaaagaa aacttctcag gaggcacctc   2340
tttgtggcaa aacatctaag gcctgaaaac cattcacata tgggtcttct aaatttcaac   2400
agtgccactt ctgcattctc tgttctcaag gcacctggat ggtgaccctg ggccgtcctc   2460
tcctcctctt catgcatgtt tctgagtgca tgaagttgtg aaggtcctac atgtaatgca   2520
tatgtgatgc atcatcttat catatattcc ttcctataca ttgtttacac ttcaactacg   2580
gggatgttcc acacaaactt aaattactgt tggcaaaaca atagggggag attagacaaa   2640
```

aaaaaaaatc cacaatattc caagtacaac tcttcatcaa gtttctctgt taatgccaag 2700
atttaacaga cttaagaact attgttctct gaatgacagt tgtaagagaa atgtaaattt 2760
tttagaactc tttgctgtta atctgttttg gtttgtttgg ttttttttt tttttttaag 2820
gtaaaaaaaa aatacacctt cagtttcctg gtgtgatcct ggttaaaatg gatgattttt 2880
cattgaaagt tttgctgatt aacaattaaa gtgggatgat atgtgggcaa aatcacttat 2940
gaaagtagaa gcaagaatca gttggtttgc taccacataa agccatgctg tttttggtca 3000
aactgtgtaa actggaaaaa ttcacatcat ttctgagttt aatcacttta ggatatattc 3060
acattgtttt ggtgaatttg ctgaattgaa ttgtttttct ttctcaaatc tgtgatctct 3120
tttctttatc ctgtttcttt gttcctttcg tttgctttct tatttttctt ttgttccatt 3180
cttttcttac ttttttccct tttccttttt tggggaggct ggctagtagt gtgtgagaaa 3240
agaatagaag tgaaatttgc ataatgaatg taaaagggaa ataaaagtct tttgaaggta 3300
gctatactag cacttttgat catcttcagg gcccacaaaa atgttgtcaa gattttaaag 3360
gtttataatt ctgcttaagc tctagtttgg acttaggtat cctaactatg ttggaggtat 3420
ttgcattgtt taaagttagg ataaaagcaa gttcctcctg tgactgcaac gtcttactga 3480
ttgggacagt tgccaggagg ataccaactt gatagcagag gggggtttat gcaaacgcac 3540
tcacctccgc cttggggaat gaaagggtca cttctgcatc atcactagct agttttctag 3600
tgttagagag gcttacaaat gtttgccatt ctcataagtg ttttgaactt gatctttgtg 3660
acttgtgctt ttttagcttc tctcttgaat cagagtatca ttgtcttcct ccaaggagtt 3720
agaatttccc agtttaaaac aaaaagggaa atgtcctagg ttttctttgt gcttctcatt 3780
tttcctttgt tgattcaatt cctgtgattt ttgttctctt ccctgaagtg ctttacagtg 3840
catggaatct ccatcattgt tattttaacg atagtaattc acagtcctca gaagcctatt 3900
tttaaagcag aagcaaaaaa gaaaaacaaa ataacaaaaa caacccttcc tcttttctct 3960
catctcacct ctctgtgttg attactaatc atcttagata ttattgctag tggatgtatg 4020
gtagatgggt tgaagctttt ctgataatta ttacacaatt taaaacaaca tatatattta 4080
aaataaatat atacagtaaa tatattgagc catgttaacc tgccaatgag atctgtgaaa 4140
aaataatggc ctcatttttc tctttttaat ttcttttacc cttttgtgaa gcagctatac 4200
gtggcataca tgtatttaaa gaaaaaaaaa tagatgtaga gtgttttttt tacactttta 4260
acttagcatg tggtgttgaa gtattactgt agatcaagtt tgtcttccgc actaagatgt 4320
gaggaaattg tgatttgttc tctccaccac aaatgaatta cacatttatt atcttctatc 4380
attttgaaac actgcagttt accatgggac actgtatata tttcttgcca taatggtaaa 4440
ggactgattg atatatttaa gagttaataa atttgtgatt tctgctgaca gtgcgtccat 4500
ctttatttct tcagaagagg tactgtatgt atgcctgcat agtgctggcc agtgtcaagg 4560
gcagtgtgtc ctactctggt ctcatttagt acataacaat ttgcacttgg tgagaatggc 4620
aagttaattg ttctctgtga gcaaaacaat ggtctcttct gggaaaatgt tgctgagaac 4680
aatatagtta acaactaaga ctcctaaaag cttctctaaa ctgtaccctc caatccagcc 4740
ttcacatggc tgcttttttt tttttttttt aatacgaacc tgtccttgta acactttgat 4800
gttatcattt ctgggataca ggcaagcacc ccagctcctg ctactcccca gcttgaactt 4860
gagcatacat ggatgctcag cttcttttga tttgctaaaa acatcacact tgctcacatg 4920
cctgtttatg ctgttcatgt tgtttatgtt tcttacctag aataaatagt ctcttcccct 4980

-continued

```
acttcttttc ccgacttctt actttttcct aagattcagt gtacagcatc atgctccaca   5040

gcaaaccttc ctaggcccta ttctgggctt gccttccctc tcaaaaccta cataatagat   5100

tgtatttacc tctcctgtca accacattgt tttgaaaata tatttctatt tgtgtctcct   5160

ctactgcagt ataatgtctc catgggcaag aactgtgtat tcatcattgc attcctaaac   5220

ccaaaccaag gccaggaatg gagatatcat tgataaatag ttgttgaatt gaggccaagc   5280

ccttttgata acagaagcct caaggggtac ccagatagtc cttgttttaa tgatgggttc   5340

tctcaccact gtcttgatgc tctgagcaag ttacctcttc cctctgaccc tcagtttcca   5400

tatttgtaaa atgagaataa acataccaac ttaataaaga tattgtgagg attaatgggt   5460

acagagtgac tagaatgata tttgatagaa attaaatggt agcagtataa ctattctgat   5520

cactgacatt aatattccta ttgttattat tctttgctca cgagggtata caactcttgt   5580

tttgctgttg ggctgccctc tttatgtagg tttactgtta atgctgagga tatactcgga   5640

ctcaaatgtc tcagcagaag gctgagagac accaaatgaa gtggtcatct agctgaatgt   5700

aggaaaaatg aaatgtagta gcaaatcagt atattctaag gaaattttca aggaatatta   5760

atcttcaccc aaattttgaa tttttatgta aaaaattata atttaagggt aaacatagat   5820

gacacagctt tcgagtgatt tcattgaata aaattctact gacttctatg aa           5872
```

```
<210> SEQ ID NO 19
<211> LENGTH: 3818
<212> TYPE: DNA
<213> ORGANISM: Homo sapiens

<400> SEQUENCE: 19

ctccccggta aagtctcgcg gtgctgccgg gctcagcccc gtctcctcct cttgctccct     60

cggccgggcg gcggtgactg tgcaccgacg tcggcgcggg ctgcaccgcc gcgtccgccc    120

gcccgccagc atggccacca ccgccacctg cacccgtttc accgacgact accagctctt    180

cgaggagctt ggcaagggtg ctttctctgt ggtccgcagg tgtgtgaaga aaacctccac    240

gcaggagtac gcagcaaaaa tcatcaatac caagaagttg tctgcccggg atcaccagaa    300

actagaacgt gaggctcgga tatgtcgact tctgaaacat ccaaacatcg tgcgcctcca    360

tgacagtatt tctgaagaag ggtttcacta cctcgtgttt gaccttgtta ccggcgggga    420

gctgtttgaa gacattgtgg ccagagagta ctacagtgaa gcagatgcca gccactgtat    480

acatcagatt ctggagagtg ttaaccacat ccaccagcat gacatcgtcc acagggacct    540

gaagcctgag aacctgctgc tggcgagtaa atgcaagggt gccgccgtca agctggctga    600

ttttggccta gccatcgaag tacagggaga gcagcaggct tggtttggtt ttgctggcac    660

cccaggttac ttgtcccctg aggtcttgag gaaagatccc tatggaaaac ctgtggatat    720

ctgggcctgc ggggtcatcc tgtatatcct cctggtgggc tatcctccct tctgggatga    780

ggatcagcac aagctgtatc agcagatcaa ggctggagcc tatgatttcc catcaccaga    840

atgggacacg gtaactcctg aagccaagaa cttgatcaac cagatgctga ccataaaccc    900

agcaaagcgc atcacggctg accaggctct caagcacccg tgggtctgtc aacgatccac    960

ggtggcatcc atgatgcatc gtcaggagac tgtggagtgt ttgcgcaagt tcaatgcccg   1020

gagaaaactg aagggtgcca tcctcacgac catgcttgtc tccaggaact tctcagctgc   1080

caaaagccta ttgaacaaga agtcggatgg cggtgtcaag ccacagagca acaacaaaaa   1140

cagtctcgta agcccagccc aagagcccgc gcccttgcag acggccatgg agccacaaac   1200

cactgtggta cacaacgcta cagatgggat caagggctcc acagagagct gcaacaccac   1260
```

cacagaagat gaggacctca aagctgcccc gctccgcact gggaatggca gctcggtgcc 1320
tgaaggacgg agctcccggg acagaacagc cccctctgca ggcatgcagc cccagccttc 1380
tctctgctcc tcagccatgc gaaaacagga gatcattaag attacagaac agctgattga 1440
agccatcaac aatggggact ttgaggccta cacgaagatt tgtgatccag gcctcacttc 1500
ctttgagcct gaggcccttg gtaacctcgt ggaggggatg gatttccata agttttactt 1560
tgagaatctc ctgtccaaga acagcaagcc tatccatacc accatcctaa acccacacgt 1620
ccacgtgatt ggggaggacg cagcgtgcat cgcctacatc cgcctcaccc agtacatcga 1680
cgggcagggt cggcctcgca ccagccagtc agaagagacc cgggtctggc accgtcggga 1740
tggcaagtgg ctcaatgtcc actatcactg ctcaggggcc cctgccgcac cgctgcagtg 1800
agctcagcca caggggcttt aggagattcc agccggaggt ccaaccttcg cagccagtgg 1860
ctctggaggg cctgagtgac agcggcagtc ctgtttgttt gaggtttaaa acaattcaat 1920
tacaaaagcg gcagcagcca atgcacgccc ctgcatgcag ccctcccgcc cgcccttcgt 1980
gtctgtctct gctgtaccga ggtgtttttt acatttaaga aaaaaaaaaa agaaaaaaag 2040
attgtttaaa aaaaaaagga atccatacca tgatgcgttt taaaaccacc gacagccctt 2100
gggttggcaa gaaggcagga gtatgtatga ggtccatcct ggcatgagca gtggctcacc 2160
caccggcctt gaagaggtga gcttggcctc tctggtcccc atggacttag gggaccaggg 2220
caagaactct gacagagctt tgggggccgt gatgtgattg cagctcctga ggtggcctgc 2280
ttaccccagg tctaggaatg aacttctttg gaacttgcat aggcgcctag aatggggctg 2340
atgagaacat cgtgaccatc agacctactt gggagagaac gcagagctcc cagcctgctg 2400
tggaggcagc tgagaagtgg tggcctcagg actgagagcc cggacgttgc tgtactgtct 2460
tgtttagtgt agaagggaag agaattggtg ctgcagaagt gtacccgcca tgaagccgat 2520
gagaaacctc gtgttagtct gacatgcact cactcatcca tttctatagg atgcacaatg 2580
catgtgggcc ctaatattga ggccttatcc ctgcagctag gagggggagg ggttgttgct 2640
gctttgcttc gtgttttctt ctaacctggc aaggagagag ccaggccctg gtcagggctc 2700
ccgtgccgcc tttggcggtt ctgtttctgt gctgatctgg accatctttg tcttgccttt 2760
tcacggtagt ggtccccatg ctgaccctca tctgggcctg ggccctctgc caagtgcccc 2820
tgtgggatgg gaggagtgag gcagtgggag aagaggtggt ggtcgtttct atgcattcag 2880
gctgcctttg gggctgcctc ccttcttatt cttccttgct gcacgtccat ctcttttcct 2940
gtctttgaga ttgacctgac tgctctggca agaagaagag gtgtccttac agaggcctct 3000
ttactgacca actgaagtat agacttactg ctggacaatc tgcatgggca tcacccctcc 3060
ccgcatgtaa cccaaaagag gtgtccagag ccaaggcttc taccttcatt gtccctctct 3120
gtgctcaagg agttccattc caggaggaag agatctatac cctaagcaga tagcaaagaa 3180
gataatggag gagcaattgg tcatggcctt ggtttccctc aaaacaacgc tgcagattta 3240
tctgcacaaa catctccact tttgggggaa aggtgggtag attccagttc cctggactac 3300
cttcaggagg cacgagagct gggagaagag gcaaagctac aggtttactt gggagccagc 3360
tgagaagaga gcagactcac aggtgctggt gcttggattt agccaggctc ctccgagcac 3420
ctcatgcatg tcccagcccc tgggccctag ccctttcctg ccctgcagtc tgcagtgcca 3480
gcacgcaaat cccttcacca cagggtttcg ttttgctggc ttgaagacaa atggtcttag 3540
aattcattga gacccatagc ttcatatggc tgctccagcc ccacttctta gcattcttac 3600

-continued

```
tcctcttctg gggctaatgt cagcatctat agacaataga ctattaaaaa atcacctttt   3660

aaacaagaaa cggaaggcat ttgatgcaga atttttgcat gacaacatag aaataattta   3720

aaaatagtgt ttgttctgaa tgttggtaga cccttcatag ctttgttaca atgaaacctt   3780

gaactgaaaa tatttaataa aataaccttt aaacagtc                            3818
```

<210> SEQ ID NO 20
<211> LENGTH: 1925
<212> TYPE: DNA
<213> ORGANISM: Homo sapiens

<400> SEQUENCE: 20

```
aagatggccg cagtcggcaa ggagagacgt cgctgagggg cttgcctgaa gcgaggggat     60

tctaacattt tcagagaacc ttttggaaag aacaagccta cttcaataaa tgaaggagaa    120

taaagaaaat tcaagccctt cagtaacttc agcaaacctg gaccacacaa agccatgttg    180

gtactgggat aagaaagact tggctcatac accctcacaa cttgaaggac ttgatccagc    240

caccgaggcc cggtaccgcc gagagggcgc tcggttcatc tttgatgtgg gcacacgttt    300

ggggctacac tatgataccc tggcaactgg aataatttat tttcatcgct tctatatgtt    360

tcattccttc aagcaattcc caagatatgt gacaggagcc tgttgcctct ttctggctgg    420

gaaagtagaa gaaacaccaa aaaaatgtaa agatatcatc aaaacagctc gtagtttatt    480

aaatgatgta caatttggcc agtttggaga tgacccaaag gaggaagtaa tggttctgga    540

gagaatctta ctgcagacca tcaagtttga tttacaggta gaacatccat accagttcct    600

actaaaatat gcaaagcaac tcaaaggtga taaaaacaaa attcaaaagt tggttcaaat    660

ggcatggaca tttgtaaatg acagtctctg caccaccttg tcactgcagt gggaaccaga    720

gatcatagca gtagcagtga tgtatctcgc aggacgtttg tgcaaatttg aaatacaaga    780

atggacctcc aaacccatgt ataggagatg gtgggagcag tttgttcaag atgtcccggt    840

cgacgttttg gaagacatct gccaccaaat cctggatctt tactcacaag gaaaacaaca    900

gatgcctcat cacacccccc atcagctgca acagccccca tctcttcagc ctacaccaca    960

agtgccgcaa gtacagcagt cacagccgtc tcaaagctcc gaaccatccc agccccagca   1020

gaaggacccc ctcatcctcc tccagggttg ggcctgccgc cagccagcta cccacctcct   1080

gccgtccccc ctggaggaca gcctcctgtg cccccgccca ttcccccacc cggcatgcct   1140

ccagttgggg ggctggggcg ggcagcctgg atgagataac gtgagccttt tttccctctt   1200

tgttttttta acaagatttt ctaatcgact tgcagagtag ttgaagtggg taagcagcag   1260

ggtaccttgt ataatgcacg acagttgcag tatgggaaga atggaccggg cccctgggat   1320

aaaatcagag tggtcctcac acctagagga cggggacaac cagctttcag agtagcctca   1380

tcagtgccct tgcagtctga ctgtgtacac ttggttcagc taatgtctga gagtcctgca   1440

ctgggttact ttatactagt gaggacgtta accagccata ttggctcaat aaatagcttc   1500

ggtaaggagt taatttcctt ctagaaatca gtgcctattt ttcctggaaa ctcaatttta   1560

aatagtccaa ttccatctga agccaagctg ttgtcatttt cattcggtga cattctctcc   1620

catgacaccc agaaggggca gaagaaccac atttttcatt tatagatgtt tgcatccttt   1680

gtattaaaat tatttgaag gggttgcctc attggatggc tttttttttc ctccagggag   1740

aaggggagaa atgtacttgg aaattaatgt atgtttacat ctctttgcaa attcctgtac   1800

atagagatat attttttaag tgtgaatgta acaacatact gtgaattcca tcttggttac   1860

aaatgagact ccttcagtca gttatccaaa taaaagcagt tctgaaacta aaaaaaaaaa   1920
```

aaaaa 1925

<210> SEQ ID NO 21
<211> LENGTH: 4134
<212> TYPE: DNA
<213> ORGANISM: Homo sapiens

<400> SEQUENCE: 21
aggcctccct cgccagcggg gtgtggctcc cctccaaaga cggtcggctg acaggctcca 60
cagagctcca ctcacgctca gccctggacg gacaggcagt ccaacggaac agaaacatcc 120
ctcagcccac aggcacgatc tgttcctcct gggaagatgc agaggctcat gatgctcctc 180
gccacatcgg gcgcctgcct gggcctgctg gcagtggcag cagtggcagc agcaggtgct 240
aaccctgccc aacgggacac ccacagcctg ctgcccaccc accggcgcca aaagagagat 300
tggatttgga accagatgca cattgatgaa gagaaaaaca cctcacttcc ccatcatgta 360
ggcaagatca agtcaagcgt gagtcgcaag aatgccaagt acctgctcaa aggagaatat 420
gtgggcaagg tcttccgggt cgatgcagag acaggagacg tgttcgccat tgagaggctg 480
gaccgggaga atatctcaga gtaccacctc actgctgtca ttgtggacaa ggacactggc 540
gaaaacctgg agactccttc cagcttcacc atcaaagttc atgacgtgaa cgacaactgg 600
cctgtgttca cgcatcggtt gttcaatgcg tccgtgcctg agtcgtcggc tgtggggacc 660
tcagtcatct ctgtgacagc agtggatgca gacgacccca ctgtgggaga ccacgcctct 720
gtcatgtacc aaatcctgaa ggggaaagag tattttgcca tcgataattc tggacgtatt 780
atcacaataa cgaaaagctt ggaccgagag aagcaggcca ggtatgagat cgtggtggaa 840
gcgcgagatg cccagggcct ccggggggac tcgggcacgg ccaccgtgct ggtcactctg 900
caagacatca atgacaactt ccccttcttc acccagacca agtacacatt tgtcgtgcct 960
gaagacaccc gtgtgggcac ctctgtgggc tctctgtttg ttgaggaccc agatgagccc 1020
cagaaccgga tgaccaagta cagcatcttg cggggcgact accaggacgc tttcaccatt 1080
gagacaaacc ccgcccacaa cgagggcatc atcaagccca tgaagcctct ggattatgaa 1140
tacatccagc aatacagctt catcgtcgag gccacagacc ccaccatcga cctccgatac 1200
atgagccctc ccgcgggaaa cagagcccag gtcattatca acatcacaga tgtggacgag 1260
ccccccattt tccagcagcc tttctaccac ttccagctga aggaaaacca gaagaagcct 1320
ctgattggca cagtgctggc catggaccct gatgcggcta ggcatagcat tggatactcc 1380
atccgcagga ccagtgacaa gggccagttc ttccgagtca caaaaaaggg ggacatttac 1440
aatgagaaag aactggacag agaagtctac ccctggtata acctgactgt ggaggccaaa 1500
gaactggatt ccactggaac ccccacagga aaagaatcca ttgtgcaagt ccacattgaa 1560
gttttggatg agaatgacaa tgccccggag tttgccaagc cctaccagcc caaagtgtgt 1620
gagaacgctg tccatggcca gctggtcctg cagatctccg caatagacaa ggacataaca 1680
ccacgaaacg tgaagttcaa attcatcttg aatactgaga acaactttac cctcacggat 1740
aatcacgata acacggccaa catcacagtc aagtatgggc agtttgaccg ggagcatacc 1800
aaggtccact tcctacccgt ggtcatctca gacaatggga tgccaagtcg cacgggcacc 1860
agcacgctga ccgtggccgt gtgcaagtgc aacgagcagg gcgagttcac cttctgcgag 1920
gatatggccg cccaggtggg cgtgagcatc caggcagtgg tagccatctt actctgcatc 1980
ctcaccatca cagtgatcac cctgctcatc ttcctgcggc ggcggctccg gaagcaggcc 2040

-continued

```
cgcgcgcacg gcaagagcgt gccggagatc cacgagcagc tggtcaccta cgacgaggag   2100
ggcggcggcg agatggacac caccagctac gatgtgtcgg tgctcaactc ggtgcgccgc   2160
ggcggggcca agcccccgcg gcccgcgctg gacgcccggc cttccctcta tgcgcaggtg   2220
cagaagccac cgaggcacgc gcctggggca cacggagggc ccggggagat ggcagccatg   2280
atcgaggtga agaaggacga ggcggaccac gacggcgacg gcccccccta cgacacgctg   2340
cacatctacg gctacgaggg ctccgagtcc atagccgagt ccctcagctc cctgggcacc   2400
gactcatccg actctgacgt ggattacgac ttccttaacg actggggacc caggtttaag   2460
atgctggctg agctgtacgg ctcggacccc cgggaggagc tgctgtatta ggcggccgag   2520
gtcactctgg gcctggggac ccaaaccccc tgcagcccag gccagtcaga cgccaggcac   2580
cacagcctcc aaaaatggca gtgactcccc agcccagcac cccttcctcg tgggtcccag   2640
agacctcatc agccttggga tagcaaactc caggttcctg aaatatccag gaatatatgt   2700
cagtgatgac tattctcaaa tgctggcaaa tccaggctgg tgttctgtct gggctcagac   2760
atccacataa ccctgtcacc cacagaccgc cgtctaactc aaagacttcc tctggctccc   2820
caaggctgca aagcaaaaca gactgtgttt aactgctgca gggtcttttt ctagggtccc   2880
tgaacgccct ggtaaggctg gtgaggtcct ggtgcctatc tgcctggagg caaaggcctg   2940
gacagcttga cttgtggggc aggattctct gcagcccatt cccaagggag actgaccatc   3000
atgccctctc tcgggagccc tagccctgct ccaactccat actccactcc aagtgcccca   3060
ccactcccca acccctctcc aggcctgtca agagggagga aggggcccca tggcagctcc   3120
tgaccttggg tcctgaagtg acctcactgg cctgccatgc cagtaactgt gctgtactga   3180
gcactgaacc acattcaggg aaatggctta ttaaactttg aagcaactgt gaattcattc   3240
tggaggggca gtggagatca ggagtgacag atcacagggt gagggccacc tccacaccca   3300
ccccctctgg agaaggcctg gaagagctga gaccttgctt tgagactcct cagcacccct   3360
ccagttttgc ctgagaaggg gcagatgttc ccggagcaga agacgtctcc ccttctctgc   3420
ctcacctggt cgccaatcca tgctctcttt cttttctctg tctactcctt atcccttggt   3480
ttagaggaac ccaagatgtg gcctttagca aaactggaca atgtccaaac ccactcatga   3540
ctgcatgacg gagccgagcc atgtgtcttt acacctcgct gttgtcacat ctcagggaac   3600
tgaccctcag gcacaccttg cagaaggcaa ggccctgccc tgcccaacct ctgtggtcac   3660
ccatgcatct tccactggaa cgtttcactg caaacacacc ttggagaagt ggcatcagtc   3720
aacagagagg ggcagggaag gagacaccaa gctcaccctt cgtcatggac cgaggttccc   3780
actctgggca aagcccctca cactgcaagg gattgtagat aacactgact tgtttgtttt   3840
aaccaataac tagcttctta taatgatttt tttactaatg atacttacaa gtttctagct   3900
ctcacagaca tatagaataa gggtttttgc ataataagca ggttgttatt taggttaaca   3960
atattaattc aggtttttta gttggaaaaa caattcctgt aaccttctat tttctataat   4020
tgtagtaatt gctctacaga taatgtctat atattggcca aactggtgca tgacaagtac   4080
tgtatttttt tatacctaaa taaagaaaaa tctttagcct gggcaacaaa aaaa         4134
```

<210> SEQ ID NO 22
<211> LENGTH: 2325
<212> TYPE: DNA
<213> ORGANISM: Homo sapiens

<400> SEQUENCE: 22

```
gcgggaagca ggggcggggc ctctggtggc ggtcgggaac tcggtgggag gcggcaacat     60
```

```
tgtttcaagt tggccaaatt gacaagagcg agaggtatac tgcgttccat cccgacccgg    120
ggccacggta ctgggccctg tttccccctc ctcggccccc gagagccagg gtccgccttc    180
tgcagggttc ccaggccccc gctccagggc cgggctgacc cgactcgctg gcgcttcatg    240
gagaacttcc aaaaggtgga aaagatcgga gagggcacgt acggagttgt gtacaaagcc    300
agaaacaagt tgacgggaga ggtggtggcg cttaagaaaa tccgcctgga cactgagact    360
gagggtgtgc ccagtactgc catccgagag atctctctgc ttaaggagct taaccatcct    420
aatattgtca agctgctgga tgtcattcac acagaaaata aactctacct ggtttttgaa    480
tttctgcacc aagatctcaa gaaattcatg gatgcctctg ctctcactgg cattcctctt    540
cccctcatca agagctatct gttccagctg ctccagggcc tagctttctg ccattctcat    600
cgggtcctcc accgagacct taaacctcag aatctgctta ttaacacaga gggggccatc    660
aagctagcag actttggact agccagagct tttggagtcc ctgttcgtac ttacacccat    720
gaggtggtga ccctgtggta ccgagctcct gaaatcctcc tgggctgcaa atattattcc    780
acagctgtgg acatctggag cctgggctgc atctttgctg agatggtgac tcgccgggcc    840
ctattccctg gagattctga gattgaccag ctcttccgga tctttcggac tctggggacc    900
ccagatgagg tggtgtggcc aggagttact tctatgcctg attacaagcc aagtttcccc    960
aagtgggccc ggcaagattt tagtaaagtt gtacctcccc tggatgaaga tggacggagc   1020
ttgttatcgc aaatgctgca ctacgaccct aacaagcgga tttcggccaa ggcagccctg   1080
gctcaccctt tcttccagga tgtgaccaag ccagtacccc atcttcgact ctgatagcct   1140
tcttgaagcc cccagcccta atctcaccct ctcctccagt gtgggcttga ccaggcttgg   1200
ccttgggcta tttggactca ggtgggccct ctgaacttgc cttaaacact caccttctag   1260
tcttggccag ccaactctgg gaatacaggg gtgaaagggg ggaaccagtg aaaatgaaag   1320
gaagtttcag tattagatgc acttaagtta gcctccacca ccctttcccc cttctcttag   1380
ttattgctga agagggttgg tataaaaata attttaaaaa agccttccta cacgttagat   1440
ttgccgtacc aatctctgaa tgccccataa ttattatttc cagtgtttgg gatgaccagg   1500
atcccaagcc tcctgctgcc acaatgttta taaaggccaa atgatagcgg gggctaagtt   1560
ggtgcttttg agaaccaagt aaaacaaaac cactgggagg agtctatttt aaagaattcg   1620
gttgaaaaaa tagatccaat cagtttatac cctagttagt gttttgcctc acctaatagg   1680
ctgggagact gaagactcag cccgggtggg gctgcagaaa aatgattggc cccagtcccc   1740
ttgtttgtcc cttctacagg catgaggaat ctgggaggcc ctgagacagg gattgtgctt   1800
cattccaatc tattgcttca ccatggcctt atgaggcagg tgagagatgt ttgaattttt   1860
ctcttccttt tagtattctt agttgttcag ttgccaagga tccctgatcc catttcctc    1920
tgacgtccac ctcctacccc ataggagtta gaagttaggg tttaggcatc attttgagaa   1980
tgctgacact tttcagggc tgtgattgag tgagggcatg ggtaaaaata tttctttaaa    2040
agaaggatga acaattatat ttatatttca ggttatatcc aatagtagag ttggcttttt   2100
ttttttttt ttggtcatag tgggtggatt tgttgccatg tgcaccttgg ggttttgtaa    2160
tgacagtgct aaaaaaaaaa agcatttttt ttttatgatt tgtctctgtc acccttgtcc   2220
ttgagtgctc ttgctattaa cgttatttgt aatttagttt gtagctcatt aaaaaaatgt   2280
gcctagtttt ataaaaaaaa aaaaaaaaaa caaaaaaaaa aaaaa                   2325
```

<210> SEQ ID NO 23

<211> LENGTH: 3837
<212> TYPE: DNA
<213> ORGANISM: Homo sapiens

<400> SEQUENCE: 23
agaagaagga gcaggagcag atgctaaagg aagagaggaa acgcgagttg gaggagaagg 60
tcaaggcagt ggaagatcga gcgaagagga gaaagctcag ggaagaaagg gcatggctgc 120
tggctcaagg aaaggagctc cctccagaac tttcccatct ggaccccaat tcccccatga 180
gagaggaaaa aaagactaaa gacctctttg agttggatga tgatttcact gctatgtata 240
aagttctaga cgtggtaaag gctcacaagg attcctggcc cttcttggaa cctgtggatg 300
aatcttatgc ccctaactat tatcagatta ttaaggcccc catggatatt tccagcatgg 360
agaagaaact gaatggaggt ttatactgta ccaaggagga atttgtaaat gacatgaaga 420
ccatgttcag gaattgtcga aagtataatg gggaaagtag tgagtatacc aagatgtctg 480
ataatttaga gaggtgtttc catcgggcaa tgatgaaaca ttttcctgga gaagatggag 540
acacagatga agaattttgg attcgagagg atgaaaagcg ggagaaaaga cggagtcggg 600
ctgggcgaag tggtgggagc catgtttgga cccgctccag ggacccagaa gggtccagca 660
ggaaacagca gcccatggag aatggaggaa agtcgttgcc ccccacacgc cgagcgccct 720
cttctgggga cgatcagagc agcagctcca cacagccccc gcgggaggtg ggcacttcca 780
atggccgagg tttttctcat cccctgcatt gtggtgggac acccagccag gcaccctttt 840
taaaccagat gaggccagca gtaccaggaa catttggccc tctgcgagga tcagatcctg 900
ccaccttgta tggctcctct ggagtcctgg agccacaccc cggggagcct gtgcagcagc 960
gtcagccttt caccatgcag cctccagttg gaattaacag cctccgagga cccaggctag 1020
gcacaccaga ggagaagcaa atgtgcgggg ggctgacaca cctttctaac atgggcccac 1080
accctggatc cttgcagctt gggcagataa gtggcccaag tcaggatgga agcatgtatg 1140
ctccagctca gttccagcca ggattcattc ctccccggca tggggggggct ccagcccggc 1200 caccagactt tcctgaaagc tcagaaattc ctcccagcca tatgtatcga tcgtacaagt 1260
acctgaatcg agtacactct gccgtctgga atgggaacca tggtgctacg aaccaaggac 1320
ccttgggccc agatgagaag ccccacctgg ggccaggacc ctctcaccag cctcgcactc 1380
tcggtcacgt gatggattcc cgagtcatga gaccacctgt ccccccccaac cagtggactg 1440 aacaatcagg cttcctacct catggagttc cttcctcagg gtacatgcga ccgccctgca 1500
agtctgccgg acatcggtta cagccacctc cagtgccagc acccagttct ttgtttggag 1560
cacctgccca ggctcttcgg ggggtgcagg gaggggactc catgatggac agcccagaga 1620
tgattgcgat gcagcagctc tcctcccgcg tctgcccccc aggtgtgcct taccaccccc 1680
accagcctgc acacccccgt ttacctggcc cttttccgca ggtagctcac ccaatgtcag 1740
tcactgtgtc agcccccaag cctgccctgg gcaaccctgg gagggcaccg gagaacagtg 1800
aagcacaaga gcctgagaat gaccaagcag agccgttgcc tggccttgaa gagaaaccac 1860
caggtgttgg tacttcagag gggtctacc tcacacaact acctcacccc acacctcccc 1920
tgcagactga ctgcaccagg cagagctcac cacaagaaag ggaaacagtg ggcccggagc 1980
tcaaaagcag ctcctccgaa tctgcggaca actgtaaagc aatgaagggc aagaatccct 2040
ggccctcgga tagcagctac cccggcccag ccgcccaagg gtgcgtgaga gacctctcca 2100
cggtggcaga caggggcgct ctatccgaga acggagtcat tggggaagca tctccttgtg 2160
gatcggaggg gaagggcctt ggtagcagtg gttccgaaaa gctgctctgc cccagaggca 2220

```
gaacgttgca ggaaaccatg ccatgcacgg gacagaacgc agcgacaccg cccagcacag   2280
accccggttt gacgggaggc actgtgagcc agtttccccc gctgtatatg cctggcctag   2340
agtacccgaa ttcagctgcc cattaccaca tcagtccagg cctgcagggt gtgggccctg   2400
tgatgggagg gaagtcccca gcatcccatc cccagcattt tcccccaagg ggctttcagt   2460
ctaaccaccc acattctgga ggctttcccc ggtatcgccc cccacaagga atgaggtatt   2520
cctaccaccc accgccacag ccttcctacc accactatca gcgaactcct tactatgcct   2580
gtccacagag cttttctgac tggcagagac ctctccatcc ccagggaagc ccaagcggac   2640
ccccagccag tcagcctccc ccaccaaggt ccctcttctc agataagaat gccatggcca   2700
gtctgcaagg ctgtgagaca ctgaatgctg ccttaacttc tccaacccgt atggatgcag   2760
tggctgctaa agtcccaaat gacgggcaga atcctggtcc agaggaagag aagctggatg   2820
aatctatgga gaggccagag agtcccaaag aatttttaga cctggacaac cataacgcag   2880
ctaccaagcg gcagagctcg ttgtcagcca gcgagtatct ctatggaact cctccgcctc   2940
tgagttcagg aatgggattt ggttcatctg catttccacc ccacagtgtg atgctgcaga   3000
cggggcctcc ctatacccct cagcggccgg ccagtcactt tcagcccagg gcttactctt   3060
cccctgtggc tgccctccca cctcaccacc caggggccac ccagcccaac ggcctctctc   3120
aggagggtcc catctatcgc tgccaggaag aaggcctggg tcactttcaa gctgtgatga   3180
tggaacaaat tggcactaga agtggaataa gaggaccttt ccaggaaatg tacagaccat   3240
caggaatgca gatgcacccg gtccagtcgc aggcctcgtt cccaaagacc cccacagcag   3300
caacatcaca ggaggaggtg ccgcctcata agcctccaac acttcccctg gatcagagct   3360
agtccaagga ggaaatgagc cccaagcaat ggaaagctgc acacgaagac tggaatgtgg   3420
agaactgggg agtgccctgt cagctctatt cccatcacct gctccacccc ttcacggcga   3480
cccactcgtg ccatacttga gctggagcca gtcacgggcc ctaaaaggac actccttaga   3540
tgactgacac acagattgca aaggtcctcg gccagggatc tcttgcacag ctgatgtaga   3600
cagtcaggca aaactaatga acgtggagtt aatgatgact tttccaaatc ctgagacact   3660
tttcagggaa aatcacttta aacttggggg agggggtata ctcaagaatg gagtggtgct   3720
tttaaacttt gatgagcagc taaactcagg tatatatttg ggaagggac tactcttagt   3780
attaatggtt ttggagctgg gtccagttta cagaattttc atgttgcctt ttaaaat      3837
```

<210> SEQ ID NO 24
<211> LENGTH: 5773
<212> TYPE: DNA
<213> ORGANISM: Homo sapiens

<400> SEQUENCE: 24

```
aaagatcgct gtgcagtcag ccttaaacac tgactgcacc cctcccagat ttcttttaca     60
ttaactaaaa agtcttatca cacaatctca taaaatttat gtaatttcat ttaattttag    120
ccacaaatca tcaaaatgac gaggattttg acagctttca aagtggtgag gacactgaag    180
actggttttg gctttaccaa tgtgactgca caccaaaaat ggaaattttc aagacctggc    240
atcaggctcc tttctgtcaa ggcacagaca gcacacattg tcctggaaga tggaactaag    300
atgaaaggtt actcctttgg ccatccatcc tctgttgctg gtgaagtggt ttttaatact    360
ggcctgggag ggtacccaga agctattact gaccctgcct acaaaggaca gattctcaca    420
atggccaacc ctattattgg gaatggtgga gctcctgata ctactgctct ggatgaactg    480
```

-continued ggacttagca aatatttgga gtctaatgga atcaaggttt caggtttgct ggtgctggat 540
tatagtaaag actacaacca ctggctggct accaagagtt tagggcaatg gctacaggaa 600
gaaaaggttc ctgcaattta tggagtggac acaagaatgc tgactaaaat aattcgggat 660
aagggtacca tgcttgggaa gattgaattt gaaggtcagc ctgtggattt tgtggatcca 720
aataaacaga atttgattgc tgaggtttca accaaggatg tcaaagtgta cggcaaagga 780
aaccccacaa aagtggtagc tgtagactgt gggattaaaa acaatgtaat ccgcctgcta 840
gtaaagcgag gagctgaagt gcacttagtt ccctggaacc atgatttcac caagatggag 900
tatgatggga ttttgatcgc gggaggaccg gggaacccag ctcttgcaga accactaatt 960
cagaatgtca gaaagatttt ggagagtgat cgcaaggagc cattgtttgg aatcagtaca 1020
ggaaacttaa taacaggatt ggctgctggt gccaaaacct acaagatgtc catggccaac 1080
agagggcaga atcagcctgt tttgaatatc acaaacaaac aggctttcat tactgctcag 1140
aatcatggct atgccttgga caacaccctc cctgctggct ggaaaccact tttgtgaat 1200 gtcaacgatc aaacaaatga ggggattatg catgagagca aacccttctt cgctgtgcag 1260
ttccacccag aggtcacccc ggggccaata gacactgagt acctgtttga ttcctttttc 1320
tcactgataa agaaaggaaa agctaccacc attacatcag tcttaccgaa gccagcacta 1380
gttgcatctc gggttgaggt ttccaaagtc cttattctag gatcaggagg tctgtccatt 1440
ggtcaggctg gagaatttga ttactcagga tctcaagctg taaaagccat gaaggaagaa 1500
aatgtcaaaa ctgttctgat gaacccaaac attgcatcag tccagaccaa tgaggtgggc 1560
ttaaagcaag cggatactgt ctactttctt cccatcaccc ctcagtttgt cacagaggtc 1620
atcaaggcag aacagccaga tgggttaatt ctgggcatgg gtggccagac agctctgaac 1680
tgtggagtgg aactattcaa gagaggtgtg ctcaaggaat atggtgtgaa agtcctggga 1740
acttcagttg agtccattat ggctacggaa gacaggcagc tgttttcaga taaactaaat 1800
gagatcaatg aaaagattgc tccaagtttt gcagtggaat cgattgagga tgcactgaag 1860
gcagcagaca ccattggcta cccagtgatg atccgttccg cctatgcact gggtgggtta 1920
ggctcaggca tctgtcccaa cagagagact ttgatggacc tcagcacaaa ggcctttgct 1980
atgaccaacc aaattctggt ggagaagtca gtgacaggtt ggaaagaaat agaatatgaa 2040
gtggttcgag atgctgatga caattgtgtc actgtctgta acatggaaaa tgttgatgcc 2100
atgggtgttc acacaggtga ctcagttgtt gtggctcctg cccagacact ctccaatgcc 2160
gagtttcaga tgttgagacg tacttcaatc aatgttgttc gccacttggg cattgtgggt 2220
gaatgcaaca ttcagtttgc ccttcatcct acctcaatgg aatactgcat cattgaagtg 2280
aatgccagac tgtcccgaag ctctgctctg gcctcaaaag ccactggcta cccattggca 2340
ttcattgctg caaagattgc cctaggaatc ccacttccag aaattaagaa cgtcgtatcc 2400
gggaagacat cagcctgttt tgaacctagc ctggattaca tggtcaccaa gattccccgc 2460
tgggatcttg accgttttca tggaacatct agccgaattg gtagctctat gaaaagtgta 2520
ggagaggtca tggctattgg tcgtaccttt gaggagagtt tccagaaagc tttacggatg 2580
tgccacccat ctatagaagg tttcactccc cgtctcccaa tgaacaaaga atggccatct 2640
aatttagatc ttagaaaaga gttgtctgaa ccaagcagca cgcgtatcta tgccattgcc 2700
aaggccattg atgacaacat gtcccttgat gagattgaga agctcacata cattgacaag 2760
tggtttttgt ataagatgcg tgatatttta aacatggaaa agacactgaa aggcctcaac 2820
agtgagtcca tgacagaaga aaccctgaaa agggcaaagg agattgggtt ctcagataag 2880

-continued

```
cagatttcaa aatgccttgg gctcactgag gcccagacaa gggagctgag gttaaagaaa   2940
aacatccacc cttgggttaa acagattgat acactggctg cagaataccc atcagtaaca   3000
aactatctct atgttaccta caatggtcag gagcatgatg tcaattttga tgaccatgga   3060
atgatggtgc taggctgtgg tccatatcac attggcagca gtgtggaatt tgattggtgt   3120
gctgtctcta gtatccgcac actgcgtcaa cttggcaaga agacggtggt ggtgaattgc   3180
aatcctgaga ctgtgagcac agactttgat gagtgtgaca aactgtactt tgaagagttg   3240
tccttggaga gaatcctaga catctaccat caggaggcat gtggtggctg catcatatca   3300
gttggaggcc agattccaaa caacctggca gttcctctat acaagaatgg tgtcaagatc   3360
atgggcacaa gcccccctgca gatcgacagg gctgaggatc gctccatctt ctcagctgtc   3420
ttggatgagc tgaaggtggc tcaggcacct tggaaagctg ttaatacttt gaatgaagca   3480
ctggaatttg caaagtctgt ggactacccc tgcttgttga ggccttccta tgttttgagt   3540
gggtctgcta tgaatgtggt attctctgag gatgagatga aaaaattcct agaagaggcg   3600
actagagttt ctcaggagca cccagtggtg ctgacaaaat ttgttgaagg ggcccgagaa   3660
gtagaaatgg acgctgttgg caaagatgga agggttatct ctcatgccat ctctgaacat   3720
gttgaagatg caggtgtcca ctcgggagat gccactctga tgctgcccac acaaaccatc   3780
agccaagggg ccattgaaaa ggtgaaggat gctacccgga agattgcaaa ggcttttgcc   3840
atctctggtc cattcaacgt ccaatttctt gtcaaaggaa atgatgtctt ggtgattgag   3900
tgtaacttga gagcttctcg atccttcccc tttgtttcca agactcttgg ggttgacttc   3960
attgatgtgg ccaccaaggt gatgattgga gagaatgttg atgagaaaca tcttccaaca   4020
ttggaccatc ccataattcc tgctgactat gttgcaatta aggctcccat gttttcctgg   4080
ccccggttga gggatgctga ccccattctg agatgtgaga tggcttccac tggagaggtg   4140
gcttgctttg gtgaaggtat tcatacagcc ttcctaaagg caatgctttc cacaggattt   4200
aagatacccc agaaaggcat cctgataggc atccagcaat cattccggcc aagattcctt   4260
ggtgtggctg aacaattaca caatgaaggt ttcaagctgt ttgccacgga agccacatca   4320
gactggctca acgccaacaa tgtccctgcc accccagtgg catggccgtc tcaagaagga   4380
cagaatccca gcctctcttc catcagaaaa ttgattagag atggcagcat tgacctagtg   4440
attaaccttc ccaacaacaa cactaaattt gtccatgata attatgtgat tcggaggaca   4500
gctgttgata gtggaatccc tctcctcact aattttcagg tgaccaaact tttgctgaa   4560
gctgtgcaga aatctcgcaa ggtggactcc aagagtcttt tccactacag gcagtacagt   4620
gctggaaaag cagcatagag atgcagacac cccagcccca ttattaaatc aacctgagcc   4680
acatgttatc taaaggaact gattcacaac tttctcagag atgaatattg ataactaaac   4740
ttcatttcag tttactttgt tatgccttaa tattctgtgt cttttgcaat taaattgtca   4800
gtcacttctt caaaacctta cagtccttcc taagttactc ttcatgagat ttcatccatt   4860
tactaatact gtatttttgg tggactaggc ttgcctatgt gcttatgtgt agctttttac   4920
tttttatggt gctgattaat ggtgatcaag gtaggaaaag ttgctgttct attttctgaa   4980
ctctttctat actttaagat actctatttt taaaacacta tctgcaaact caggacactt   5040
taacagggca gaatactcta aaaacttgat aaaattaaat atagatttaa tttatgaacc   5100
ttccatcatg atgtttgtgt attgcttctt tttggatcct cattctcacc catttggcta   5160
atccaggaat attgttatcc cttcccatta tattgaagtt gagaaatgtg acagaggcat   5220
```

-continued

```
ttagagtatg gacttttctt ttctttttct ttttcttttt ttctttttga gatggagtca   5280

cactctccag gctggagtgc agtggcacaa tctcggctca ctgcaatttc cgtctcccaa   5340

gttcaagcga ttctcctgct ttagactatg gatttcttta aggaatactg gtttgcagtt   5400

ttgttttctg gactatatca gcagatggta gacagtgttt atgtagatgt gttgttgttt   5460

ttatcattgg attttaactt ggcccgagtg aaataatcag atttttgtca ttcacactct   5520

cccccagttt tggaataact tggaagtaag gttcattccc ttaagacgat ggattctgtt   5580

gaactatggg gtcccacact gcactattaa ttccacccac tgtaagggca aggacaccat   5640

tccttctaca tataagaaaa aagtctctcc ccaagggcag cctttgttac ttttaaatat   5700

tttctgttat tacaagtgct ctaattgtga acttttaaat aaaatactat taagaggtaa   5760

aaaaaaaaaa aaa                                                      5773
```

<210> SEQ ID NO 25
<211> LENGTH: 1201
<212> TYPE: DNA
<213> ORGANISM: Homo sapiens

<400> SEQUENCE: 25

```
gccattaaca aagatggtgc ttatggggca ggttccctaa cagtcaggat tccggttgca     60

gtttttctcc cccgccccaa agatacgtgg ttgcagacgg agaaatggag gccagagaca    120

aacaagtact ccgctcactt cgcctggagc tgggtgcaga ggtattggtg gagggactgg    180

ttcttcagta cctctaccag gaaggaatct tgacggaaaa ccatattcaa gaaatcaatg    240

ctcaaaccac aggcctccgg aaaacaatgc tcctgctgga tatcctacct tccaggggcc    300

ctaaagcatt tgatacattc ctagattccc tacaggagtt tccctgggtc agggagaagc    360

tgaagaaggc aagggaagag gccatgaccg acctgcctgc aggtgacaga ttgactggga    420

tcccctcgca catcctcaac agctccccat cagaccggca gattaaccag ctggcccaga    480

ggctgggccc tgagtgggag cccatggtgc tgtctctggg actgtcccag acggatatct    540

accgctgtaa ggccaaccac ccccacaacg tgcagtcgca ggtggtggag gccttcatcc    600

gttggcggca gcgcttcggg aagcaggcca ccttccagag cctgcacaac gggctgcggg    660

ctgtggaggt ggacccctcg ctgctcctgc acatgttgga gtgatggtgc ctccagcaac    720

cgctggggag tgtgtccctg agtcatgtgg gctgaatcct gactttcact cagagcaggt    780

ggtttttttgt gtaggtttgt tttttatttt tgatgatctt cagatggaag gagaaaacag    840

ggtttccact agacattact tgaaaggcca gattactcag cagatctccc atgttggctc    900

aacaattctt tgtttttaat tgcttgaaga ttgcattgtt gtaattgttc agtttttaaa    960

tgtgtaatgg cattttaata gactagtaaa tcacagtggt tcaaaatata tatccatata   1020

tatatatatc catatatata tctcatgtca tcacattaca ggcaggtgtc tcatatgtaa   1080

aacatttacc tgaatgttgt ctgaggactg aactgtggac tttactattc ataatgataa   1140

aataataaaa tgcgaattac tatatataat gtgcctcact catgagaaaa aaaaaaaaaa   1200

a                                                                   1201
```

<210> SEQ ID NO 26
<211> LENGTH: 8310
<212> TYPE: DNA
<213> ORGANISM: Homo sapiens

<400> SEQUENCE: 26

```
aagtgccgtt tcggtttaat ctagtgtgtg actgggtctg tgtgagggag agagtgtgtg     60
```

```
tggtgtggag gtgaaacgga ggcaagaaag ggggctacct caggagcgag ggacaaaggg    120
ggcgtgaggc acctaggccg cggcaccccg gcgacaggaa gccgtcctga accgggctac    180
cgggtagggg aagggcccgc gtagtcctcg cagggcccca gagctggagt cggctccaca    240
gccccgggcc gtcggcttct cacttcctgg acctccccgg cgcccgggcc tgaggactgg    300
ctcggcggag ggagaagagg aaacagactt gagcagctcc ccgttgtctc gcaactccac    360
tgccgaggaa ctctcatttc ttccctcgct ccttcacccc ccacctcatg tagaagggtg    420
ctgaggcgtc gggagggagg aggagcctgg gctaccgtcc ctgccctccc cacccccttc    480
ccggggcgct ttggtgggcg tggagttggg gttggggggg tgggtggggg ttgctttttg    540
gagtgctggg gaactttttt cccttcttca ggtcagggga aagggaatgc ccaattcaga    600
gagacatggg ggcaagaagg acgggagtgg aggagcttct ggaactttgc agccgtcatc    660
gggaggcggc agctctaaca gcagagagcg tcaccgcttg gtatcgaagc acaagcggca    720
taagtccaaa cactccaaag acatggggtt ggtgaccccc gaagcagcat ccctgggcac    780
agttatcaaa cctttggtgg agtatgatga tatcagctct gattccgaca ccttctccga    840
tgacatggcc ttcaaactag accgaaggga gaacgacgaa cgtcgtggat cagatcggag    900
cgaccgcctg cacaaacatc gtcaccacca gcacaggcgt tcccgggact tactaaaagc    960
taaacagacc gaaaaagaaa aaagccaaga agtctccagc aagtcgggat cgatgaagga   1020
ccggatatcg ggaagttcaa agcgttcgaa tgaggagact gatgactatg ggaaggcgca   1080
ggtagccaaa agcagcagca aggaatccag gtcatccaag ctccacaagg agaagaccag   1140
gaaagaacgg gagctgaagt ctgggcacaa agaccggagt aaaagtcatc gaaaaaggga   1200
aacacccaaa agttacaaaa cagtggacag cccaaaacgg agatccagga gcccccacag   1260
gaagtggtct gacagctcca aacaagatga tagcccctcg ggagcttctt atggccaaga   1320
ttatgacctt agtccctcac gatctcatac ctcgagcaat tatgactcct acaagaaaag   1380
tcctggaagt acctcgagaa ggcagtcggt cagtcccccct tacaaggagc cttcggccta   1440
ccagtccagc acccggtcac cgagccccta cagtaggcga cagagatctg tcagtcccta   1500
tagcaggaga cggtcgtcca gctacgaaag aagtggctct tacagcgggc gatcgcccag   1560
tccctatggt cgaaggcggt ccagcagccc tttcctgagc aagcggtctc tgagtcggag   1620
tccactcccc agtaggaaat ccatgaagtc cagaagtaga agtcctgcat attcaagaca   1680
ttcatcttct catagtaaaa agaagagatc cagttcacgc agtcgtcatt ccagtatctc   1740
acctgtcagg cttccactta attccagtct gggagctgaa ctcagtagga aaaagaagga   1800
aagagcagct gctgctgctg cagcaaagat ggatggaaag gagtccaagg gttcacctgt   1860
atttttgcct agaaaagaga acagttcagt agaggctaag gattcaggtt tggagtctaa   1920
aaagttaccc agaagtgtaa aattggaaaa atctgcccca gatactgaac tggtgaatgt   1980
aacacatcta aacacagagg taaaaaattc ttcagataca gggaaagtaa agttggatga   2040
gaactccgag aagcatcttg ttaaagattt gaaagcacag ggaacaagag actctaaacc   2100
catagcactg aaagaggaga ttgttactcc aaaggagaca gaaacatcag aaaaggagac   2160
ccctccacct cttcccacaa ttgcttctcc cccacccccct ctaccaacta ctacccctcc   2220
acctcagaca ccccctttgc cacctttgcc tccaatacca gctcttccac agcaaccacc   2280
tctgcctcct tctcagccag catttagtca ggttcctgct tccagtactt caactttgcc   2340
cccttctact cactcaaaga catctgctgt gtcctctcag gcaaattctc agccccctgt   2400
```

-continued

```
acaggtttct gtgaagactc aagtatctgt aacagctgct attccacacc tgaaaacttc   2460
aacgttgcct cctttgcccc tcccaccctt attacctgga gatgatgaca tggatagtcc   2520
aaaagaaact cttccttcaa aacctgtgaa gaaagagaag gaacagagga cacgtcactt   2580
actcacagac cttcctctcc ctccagagct ccctggtgga gatctgtctc ccccagactc   2640
tccagaacca aaggcaatca caccacctca gcaaccatat aaaaagagac caaaaatttg   2700
ttgtcctcgt tatggagaaa gaagacaaac agaaagcgac tgggggaaac gctgtgtgga   2760
caagtttgac attattggga ttattggaga aggaacctat ggccaagtat ataaagccaa   2820
ggacaaagac acaggagaac tagtggctct gaagaaggtg agactagaca atgagaaaga   2880
gggcttccca atcacagcca ttcgtgaaat caaaatcctt cgtcagttaa tccaccgaag   2940
tgttgttaac atgaaggaaa ttgtcacaga taaacaagat gcactggatt tcaagaagga   3000
caaaggtgcc ttttaccttg tatttgagta tatggaccat gacttaatgg gactgctaga   3060
atctggtttg gtgcactttt ctgaggacca tatcaagtcg ttcatgaaac agctaatgga   3120
aggattggaa tactgtcaca aaaagaattt cctgcatcgg gatattaagt gttctaacat   3180
tttgctgaat aacagtgggc aaatcaaact agcagatttt ggacttgctc ggctctataa   3240
ctctgaagag agtcgccctt acacaaacaa agtcattact ttgtggtacc gacctccaga   3300
actactgcta ggagaggaac gttacacacc agccatagat gtttggagct gtggatgtat   3360
tcttggggaa ctattcacaa agaagcctat ttttcaagcc aatctggaac tggctcagct   3420
agaactgatc agccgacttt gtggtagccc ttgtccagct gtgtggcctg atgttatcaa   3480
actgccctac ttcaacacca tgaaaccgaa gaagcaatat cgaaggcgtc tacgagaaga   3540
attctctttc attccttctg cagcacttga tttattggac cacatgctga cactagatcc   3600
tagtaagcgg tgcacagctg aacagaccct acagagcgac ttccttaaag atgtcgaact   3660
cagcaaaatg gctcctccag acctccccca ctggcaggat tgccatgagt tgtggagtaa   3720
gaaacggcga cgtcagcgac aaagtggtgt tgtagtcgaa gagccacctc catccaaaac   3780
ttctcgaaaa gaaactacct cagggacaag tactgagcct gtgaagaaca gcagcccagc   3840
accacctcag cctgctcctg gcaaggtgga gtctggggct ggggatgcaa taggccttgc   3900
tgacatcaca caacagctga atcaaagtga attggcagtg ttattaaacc tgctgcagag   3960
ccaaaccgac ctgagcatcc ctcaaatggc acagctgctt aacatccact ccaacccaga   4020
gatgcagcag cagctggaag ccctgaacca atccatcagt gccctgacgg aagctacttc   4080
ccagcagcag gactcagaga ccatggcccc agaggagtct ttgaaggaag caccctctgc   4140
cccagtgatc ctgccttcag cagaacagac gacccttgaa gcttcaagca caccagctga   4200
catgcagaat atattggcag ttctcttgag tcagctgatg aaaacccaag agccagcagg   4260
cagtctggag gaaaacaaca gtgacaagaa cagtgggcca caggggcccc gaagaactcc   4320
cacaatgcca caggaggagg cagcagcatg tcctcctcac attcttccac cagagaagag   4380
gcccccctgag ccccccggac ctccaccgcc gccacctcca ccccctctgg ttgaaggcga   4440
tctttccagc gccccccagg agttgaaccc agccgtgaca gccgccttgc tgcaactttt   4500
atcccagcct gaagcagagc ctcctggcca cctgccacat gagcaccagg ccttgagacc   4560
aatggagtac tccacccgac cccgtccaaa caggacttat ggaaacactg atgggcctga   4620
aacagggttc agtgccattg acactgatga acgaaactct ggtccagcct tgacagaatc   4680
cttggtccag accctggtga agaacaggac cttctcaggc tctctgagcc accttgggga   4740
gtccagcagt taccagggca cagggtcagt gcagtttcca ggggaccagg acctccgttt   4800
```

```
tgccagggtc cccttagcgt tacacccggt ggtcgggcaa ccattcctga aggctgaggg   4860
aagcagcaat tctgtggtac atgcagagac caaattgcaa aactatgggg agctggggcc   4920
aggaaccact ggggccagca gctcaggagc aggccttcac tggggggggcc caactcagtc   4980
ttctgcttat ggaaaactct atcgggggcc tacaagagtc ccaccaagag gggaagaggg   5040
gagaggagtt ccttactaac ccagagactt cagtgtcctg aaagattcct ttcctatcca   5100
tccttccatc cagttctctg aatctttaat gaaatcattt gccagagcga ggtaatcatc   5160
tgcatttggc tactgcaaag ctgtccgttg tattccttgc tcacttgcta ctagcaggcg   5220
acttacgaaa taatgatgtt ggcaccagtt ccccctggat gggctatagc cagaacattt   5280
acttcaactc taccttagta gatacaagta gagaatatgg agaggatcat tacattgaaa   5340
agtaaatgtt ttattagttc attgcctgca cttactgatc ggaagagaga aagaacagtt   5400
tcagtattga gatggctcag gagaggctct ttgattttta aagttttggg gtgggggatt   5460
gtgtgtggtt tctttctttt gaattttaat ttaggtgttt tgggtttttt tcctttaaag   5520
agaatagtgt tcacaaaatt tgagctgctc tttggctttt gctataaggg aaacagagtg   5580
gcctggctga tttgaataaa tgtttctttc ctctccacca tctcacattt tgcttttaag   5640
tgaacacttt ttccccattg agcatcttga acatactttt tttccaaata aattactcat   5700
ccttaaagtt tactccactt tgacaaaaga tacgcccttc tccctgcaca taaagcaggt   5760
tgtagaacgt ggcattcttg ggcaagtagg tagactttac ccagtctctt tcctttttg    5820
ctgatgtgtg ctctctctct ctctttctct ctctctctct ctctctctct ctctctctct   5880
ctctctgtct cgcttgctcg ctctcgctgt ttctctctct ttgaggcatt tgtttggaaa   5940
aaatcgttga gatgcccaag aacctgggat aattctttac ttttttgaa ataaaggaaa    6000
ggaaattcag actcttacat tgttctctgt aactcttcaa ttctaaaatg ttttgttttt   6060
taaaccatgt tctgatgggg aagttgattt gtaagtgtgg acagcttgga cattgctgct   6120
gagctgtggt tagagatgat gcctccattc ctagagggct aataacagca tttagcatat   6180
tgtttacaca tatattttta tgtcaaaaaa aaaacaaaaa cctttcaaac agagcattgt   6240
gatattgtca aagagaaaaa caaatcctga agatacatgg aaatgtaacc tagtttaggg   6300
tgggtatttt tctgaagata catcaatacc tgaccttttt taaaaaaata attttaaaac   6360
agcatactgt gaggaagaac agtattgaca tacccacatc ccagcatgtg taccctgcca   6420
gttcttttag ggatttttcc tccaaagaga tttggatttg gttttggtaa aaggggttaa   6480
attgtgcttc caggcaagaa ctttgcctta tcataaacag gaaatgaaaa agggaagggc   6540
tgtcaggatg ggataatttg ggaggcttct cattctggct tctatttcta tgtgagtacc   6600
agcatataga gtgttttaaa aacagataca tgtcatataa tttatctgca cagacttaga   6660
ccttcaggaa acataggtta agccccccttt tacaaagaaa aagtaaacat acttcagcat  6720
cttggagggt agttttcaaa actcaagttt catgtttcaa tgccaagttc ttattttaaa   6780
aaataaaatc tacttataag agaaaggtgc attacttaaa aaaaaaaaac tttaaagaaa   6840
tgaaagaaga accctcttca gatacttact tgaagactgt tttcccctgt taatgagata   6900
tagctagata tcggtgtgtg tatttcttta ttattctctg gtttttgatc tggccttgcc   6960
tccagggcca aacactgatt tagaaagaga gccttctagc tattttggca ttgatggctt   7020
tttataccag tgtgtccagt tagatttact aggcttactg acatgctatt ggtaaatcgc   7080
attaaagttc atctgaacct tctgtctgtt gacttcttag tcctcagaca tgggcctttg   7140
```

tgttttagaa tatttgaatt tgagttattg ggccccactc cctgtttttt attaaagaac 7200
gtgagcctgg gatactttca gaagtatctg ttcaatgaaa aaaagttggt ttcccatcaa 7260
atatgaataa aattctctat atatttcatt gtattttggt tatcagcagt catcaataat 7320
gtttttccct cccctctccc acctcttatt tttaattatg ccaaatatcc taaataatat 7380
acttaagcct ccattccctc atccctacta gggaaggggg tgagtgtatg tgtgagtgta 7440
tgtgtatgta tgatcccatc tcacccccac ccccattttg ggagtctttt aaaatgaaaa 7500
caaagtttgg tagttttgac tatttctaaa agcagaggag aaaaaaaaac ttatttaaat 7560
atcctggaat ctgtatggag gaagaaaagg tatttgttaa tttttcagtt acgttatcta 7620
taaacatgat ggaagtaaag gtttggcaga atttcacctt gactatttga aaattacaga 7680
cccaattaat tccattcaaa agtggttttc gttttgtttt aattattgta caatgagaga 7740
tattgtctat taaatacatt attttgaaca gatgagaaat ctgattctgt tcatgagtgg 7800
gaggcaaaac tggtttgacc gtgatcattt ttgtggtttt gaaaacaaat atacttgacc 7860
cagtttcctt agttttttct tcaactgtcc ataggaacga taagtatttg aaagcaacat 7920
caaatctata cgtttaaagc agggcagtta gcacaaattt gcaagtagaa cttctattag 7980
cttatgccat agacatcacc caaccacttg tatgtgtgtg tgtatatata atatgcatat 8040
atagttaccg tgctaaaatg gttaccagca ggttttgaga gagaatgctg catcagaaaa 8100
gtgtcagttg ccacctcatt ctccctgatt taggttcctg acactgattc ctttctctct 8160
cgtttttgac ccccattggg tgtatcttgt ctatgtacag atattttgta atatattaaa 8220
tttttttctt tcagtttata aaaatggaaa gtggagattg gaaaattaaa tatttcctgt 8280
tactatacca aaaaaaaaaa aaaaaaaaaa 8310

<210> SEQ ID NO 27
<211> LENGTH: 2670
<212> TYPE: DNA
<213> ORGANISM: Homo sapiens

<400> SEQUENCE: 27
ggttgggatc tgaggggtcc tctctgtgcc catcacagtt tgagcttcag ggaaaagaag 60
aagaggtctt tgcccttcgt tttccacgg gaggagaatc aagagtgagc catggagcta 120
cgtgtgggga acaagtaccg cctgggacgg aagatcggga gcgggtcctt cggagatatc 180
tacctgggtg ccaacatcgc ctctggtgag gaagtcgcca tcaagctgga gtgtgtgaag 240
acaaagcacc cccagctgca catcgagagc aagttctaca agatgatgca gggtggcgtg 300
gggatcccgt ccatcaagtg gtgcggagct gagggcgact acaacgtgat ggtcatggag 360
ctgctggggc ctagcctcga ggacctgttc aacttctgtt cccgcaaatt cagcctcaag 420
acggtgctgc tcttggccga ccagatgatc agccgcatcg agtatatcca ctccaagaac 480
ttcatccacc gggacgtcaa gcccgacaac ttcctcatgg ggctggggaa gaagggcaac 540
ctggtctaca tcatcgactt cggcctggcc aagaagtacc gggacgcccg cacccaccag 600
cacattccct accgggaaaa caagaacctg accggcacgg cccgctacgc ttccatcaac 660
acgcacctgg gcattgagca aagccgtcga gatgacctgg agagcctggg ctacgtgctc 720
atgtacttca acctgggctc cctgccctgg caggggctca aagcagccac caagcgccag 780
aagtatgaac ggatcagcga gaagaagatg tcaacgccca tcgaggtcct ctgcaaaggc 840
tatccctccg aattctcaac atacctcaac ttctgccgct ccctgcggtt tgacgacaag 900
cccgactact cttacctacg tcagctcttc cgcaacctct tccaccggca gggcttctcc 960

-continued

```
tatgactacg tctttgactg gaacatgctg aaattcggtg cagcccggaa tcccgaggat   1020

gtggaccggg agcggcgaga acacgaacgc gaggagagga tggggcagct acgggggtcc   1080

gcgacccgag ccctgccccc tggcccaccc acgggggcca ctgccaaccg gctccgcagt   1140

gccgccgagc ccgtggcttc cacgccagcc tcccgcatcc agccggctgg caatacttct   1200

cccagagcga tctcgcgggt cgaccgggag aggaaggtga gtatgaggct gcacaggggt   1260

gcgcccgcca acgtctcctc ctcagacctc actgggcggc aagaggtctc ccggatccca   1320

gcctcacaga caagtgtgcc atttgaccat ctcgggaagt gaggagagcc cccattggac   1380

cagtgtttgc ttagtgtctt cactgtattt tctttaaaaa aaaaaaaaaa aaaaaaaagg   1440

caaaaataaa ccactcaaaa gaacaacaaa aaaacccagc acaaaaccga cgatggagtt   1500

tgtttctttg atttctttgc caatggcaag aagatgagat gccctcagca ctgaggattc   1560

ttgcccccctt gtggtgcccg ctgcccccaa ccttcaggct gccagatgct cccctgacaa   1620

caccaggcta caggagccag acgccagggc ctgcccggcc tcctgttcct gcccccaccc   1680

accacctgcc tggagaggaa cgggtcgggt ccgtgtcgga gaagtgacag gtcccagagc   1740

caaagccggc cctcaagcat catcagggag tggtgtagtc agttgaaggc agttcccacc   1800

gagttttccg agcctcagaa tccaggagat acgcacagcc ccacccactc tgagatgaca   1860

gtggctgact tcccgtgctg ggcttttcca ttgtcccccct ggcctccagg ctcctcctct   1920

gcctctccat ggagtgggtg gggaggtggt gggggccggc gtcccctgcg tgtgtgtgtg   1980

tgtgtgtgtg tgtggatgta ttgacctgtg tttcccaaga cagcaggtgc cacggcccgc   2040

cccgcctgcc agcccgaatt cccgttctcc tgtgtctact aacaaggaca tgggggtggg   2100

cggtgacctc cgcatccctc agagctcaga gggtcctcgc tgccaccggt ccccccctag   2160

cccgtcatca gccggtggca gctccatctt ccattcctgg ttttagggca gaatccatgg   2220

agactgcttc cagaaggcat ctggctctga gttataaatt acttccctgg tcctgacagt   2280

cacctggggt ccccccctctc cctggttcca cctttctgag gaggagcctg gagtcagggc   2340

tgggttttgg attaacccat ccttcctagt taacaccttt ttgtttttat tttattttat   2400

ttttgtttgt tttctccgtg tgtgtgtttt cctaatttat ttacctctgt ttccccttttt   2460

tcctttttttt ttttaattaa agagcaaagc tttttattac tttgtaattt aaaaaaactga   2520

aaaaaaaaaa actgaagaac tttgggggga attttgtact tttttcctgt gtaaatattg   2580

gactttttttg agctttatcg tggttgttaa tttgaagtaa taaagtagaa aagataaagt   2640

gaaaaaaaaa aaaaaaaaaa aaaaaaaaaa                                     2670
```

<210> SEQ ID NO 28
<211> LENGTH: 3217
<212> TYPE: DNA
<213> ORGANISM: Homo sapiens

<400> SEQUENCE: 28

```
tccctcgccc ggaggcagag atgcgctggc gcatcaccgc caggagccca cagtgaaaga     60

ccatcggatg gaaggcgacg cccagaactc caggagaccg ctgtgggagg acgcgaggcc    120

aggtgacgaa taggccaggc gtgagttccc aaacagcctc ctccccttca agagagtaag    180

cttgggccac aggctgggac ggaagcagag gggcagacac gccaccaccc gcccggcctc    240

gaacctacgg cggcacagtt cagcggaggc ggcccagcgg tcctgtcccg cgcctgcgca    300

ctccaggccc cgccccgccc cgcgccctcc aggcccggcc cgccctccaa cctctgcgtg    360
```

-continued

```
cgcacagcct agagcccgcc tccgtgaaag actgccgggc gcatgcggtc ggggttgttc    420
actggctgtc cggggctccg cgcgcgtcgc cggcccagct ctgtcgctga cgggaggatc    480
tgaagccggc cgcaggtcaa agagtaaaat gaagtacatt ctggttactg gtggtgttat    540
atcaggaatt ggaaaaggaa tcattgccag cagtgtgggc acaatactca agtcatgtgg    600
tttacatgta acttcaatca aaattgaccc ctacattaac attgatgcag gaacattctc    660
tccttatgag catggtgagg tttttgtgct ggatgatggt ggggaagtag accttgacct    720
gggtaactat gagcggttcc ttgacatccg cctcaccaag gacaataatc tgaccactgg    780
aaagatatac cagtatgtca ttaacaagga acggaaagga gattacttgg ggaaaactgt    840
ccaagttgtc cctcatatca cagatgcaat ccaggagtgg gtgatgagac aggcgttaat    900
acctgtagat gaagatggcc tggaacctca agtgtgtgtt attgagcttg gtggaaccgt    960
gggggacata gaaagcatgc cctttattga ggccttccgt cagttccaat tcaaggtcaa   1020
aagagagaac ttttgtaaca tccacgtcag tctagttccc cagccaagtt caacagggga   1080
acagaagact aaacctaccc agaatagtgt tcgggaactt agaggacttg ggctttcccc   1140
agatctggtt gtatgcaggt gctcaaatcc acttgacaca tcagtgaagg agaaaatatc   1200
aatgttctgc catgttgagc ctgaacaagt gatctgtgtc cacgatgtct catccatcta   1260
ccgagtcccc ttgttgttag aggagcaagg ggttgtagat tattttcttc gaagacttga   1320
ccttcctatt gagaggcagc caagaaaaat gctgatgaaa tggaaagaga tggctgacag   1380
atatgatcgc ttgctggaga cctgctctat tgcccttgtg ggcaaataca cgaagttctc   1440
agactcctat gcctctgtca ttaaggctct ggagcattct gcactggcca tcaaccacaa   1500
attggaaatc aagtacatag attctgcgga cttggagccc atcacctcgc aagaagagcc   1560
cgtgcgctac cacgaagctt ggcagaagct ctgtagtgct catggagtgc tggttccagg   1620
aggatttggt gttcgaggaa cagaaggaaa aatccaagca attgcctggg ctcggaatca   1680
gaaaaagcct tttttgggcg tgtgcttagg gatgcagttg gcagtggttg aattctcaag   1740
aaacgtgctg ggatggcaag atgccaattc tacagagttt gaccctacga ccagtcatcc   1800
cgtggtcgta gacatgccag aacacaaccc agggcagatg ggcggaacca tgaggctggg   1860
caagaggaga accctgttcc agaccaagaa ctcagtcatg aggaaactct atggagacgc   1920
agactacttg gaagagaggc accgccaccg atttgaggtg aatccagtct ggaaaaagtg   1980
tttggaagaa caaggcttga agtttgttgg ccaagatgtt gaaggagaga gaatggaaat   2040
tgtggagtta gaagatcatc cctttttgt tggggttcag taccaccctg agttcctgtc   2100
caggcctatc aagccctccc caccatactt tggcctcctc ctggcctctg tggggcggct   2160
ctcacattac ctccagaaag gctgcaggct ctcacccagg gacacctata gtgacaggag   2220
tggaagcagc tcccctgact ctgaaatcac cgaactgaag tttccatcaa taaatcatga   2280
ctgatcttgt agcggatgat tcttcaagag acccttcaaa cttgggtaga gtttacagct   2340
ctgactttac actcggcttt ggagactttc tttaaattat gtttttatta agattatttt   2400
attatgcgga aaggtatttg ggaaacttgt cacttgcatg tcccatcacg tgtactggct   2460
cctctgtggt gtctgcctgt tgcgtgacac tctccttgca gttcttgagt tgcggcagaa   2520
catcgcgatg ggaaccgatg gtgggtgggg ctgcagagtg ccccatcggt caccttgttt   2580
ctcaactacc tcgcatcatt gcagatgcta gcgcgttgcc tgtcgctttc ccttggatac   2640
ctagaccgtt ataaagtgtg ccacatggac ttaccgagca tggagagagg attttagcta   2700
ggatttgaac acttggtgct gggaacctca gggtattgct tgccactaag ccatgaaacc   2760
```

```
agagacaaaa tctctatact gccctgagtt ggggggaatt ctcagtgcca actgtggctg   2820

gtcctcattc aaagggacgg tcagtttggt gtcaacatga aacaccaaga tgtctgtctc   2880

tgaagcgtga ttttaaaatc cccatgcctg tggctgcgct tcctatttct agggctggga   2940

aacactcctt gcatcaaggg gtcacttaca gaacaaagaa tcttttgggg gaaacttcct   3000

ctaaaaccct ctcatatata gacagctttg actggagggt ccatttttct tccaggatgg   3060

tgttactgca gttgaaaggg caatatgaag ttactttctt aatgtgacct agcaataggc   3120

atagctacgt ggcactatat tctggccaga ctcgatgtgt actctaactt aagaaataaa   3180

tcagtaaggc agaacaagaa aaaaaaaaaa aaaaaaa                            3217
```

```
<210> SEQ ID NO 29
<211> LENGTH: 2141
<212> TYPE: DNA
<213> ORGANISM: Homo sapiens

<400> SEQUENCE: 29

gcgcacgccg gccgcgccca cgtgaccggt ccgggtgcaa acacgcgggt cagctgatcc     60

ggcccaactg cggcgtcatc ccggctataa gcgcacggcc tcggcgaccc tctccgaccc    120

ggccgccgcc gccatgcagc cctccagcct tctgccgctc gccctctgcc tgctggctgc    180

acccgcctcc gcgctcgtca ggatcccgct gcacaagttc acgtccatcc gccggaccat    240

gtcggaggtt gggggctctg tggaggacct gattgccaaa ggccccgtct caaagtactc    300

ccaggcggtg ccagccgtga ccgaggggcc cattcccgag gtgctcaaga actacatgga    360

cgcccagtac tacggggaga ttggcatcgg gacgcccccc cagtgcttca cagtcgtctt    420

cgacacgggc tcctccaacc tgtgggtccc ctccatccac tgcaaactgc tggacatcgc    480

ttgctggatc caccacaagt acaacagcga caagtccagc acctacgtga agaatggtac    540

ctcgtttgac atccactatg gctcgggcag cctctccggg tacctgagcc aggacactgt    600

gtcggtgccc tgccagtcag cgtcgtcagc ctctgccctg ggcggtgtca aagtggagag    660

gcaggtcttt ggggaggcca ccaagcagcc aggcatcacc ttcatcgcag ccaagttcga    720

tggcatcctg ggcatggcct acccccgcat ctccgtcaac aacgtgctgc ccgtcttcga    780

caacctgatg cagcagaagc tggtggacca gaacatcttc tccttctacc tgagcaggga    840

cccagatgcg cagcctgggg gtgagctgat gctgggtggc acagactcca agtattacaa    900

gggttctctg tcctacctga atgtcacccg caaggcctac tggcaggtcc acctggacca    960

ggtggaggtg gccagcgggc tgaccctgtg caaggagggc tgtgaggcca ttgtggacac   1020

aggcacttcc ctcatggtgg gcccggtgga tgaggtgcgc gagctgcaga aggccatcgg   1080

ggccgtgccg ctgattcagg gcgagtacat gatcccctgt gagaaggtgt ccaccctgcc   1140

cgcgatcaca ctgaagctgg gaggcaaagg ctacaagctg tccccagagg actacacgct   1200

caaggtgtcg caggccggga agaccctctg cctgagcggc ttcatgggca tggacatccc   1260

gccacccagc gggccactct ggatcctggg cgacgtcttc atcggccgct actacactgt   1320

gtttgaccgt gacaacaaca gggtgggctt cgccgaggct gcccgcctct agttcccaag   1380

gcgtccgcgc gccagcacag aaacagagga gagtcccaga gcaggaggcc cctggcccag   1440

cggcccctcc cacacacacc cacacactcg cccgcccact gtcctgggcg ccctggaagc   1500

cggcggccca agcccgactt gctgttttgt tctgtggttt tcccctccct gggttcagaa   1560

atgctgcctg cctgtctgtc tctccatctg tttggtgggg gtagagctga tccagagcac   1620
```

-continued

```
agatctgttt cgtgcattgg aagaccccac ccaagcttgg cagccgagct cgtgtatcct   1680

ggggctccct tcatctccag ggagtcccct ccccggccct accagcgccc gctgggctga   1740

gcccctaccc cacaccaggc cgtcctcccg ggccctccct tggaaacctg ccctgcctga   1800

gggcccctct gcccagcttg ggcccagctg ggctctgcca ccctacctgt tcagtgtccc   1860

gggcccgttg aggatgaggc cgctagaggc ctgaggatga gctggaagga gtgagagggg   1920

acaaaaccca ccttgttgga gcctgcaggg tggtgctggg actgagccag tcccaggggc   1980

atgtattggc ctggaggtgg ggttgggatt gggggctggt gccagccttc ctctgcagct   2040

gacctctgtt gtcctcccct tgggcggctg agagccccag ctgacatgga aatacagttg   2100

ttggcctccg gcctcccctc tgtaaaaaaa aaaaaaaaaa a                       2141
```

<210> SEQ ID NO 30
<211> LENGTH: 2964
<212> TYPE: DNA
<213> ORGANISM: Homo sapiens

<400> SEQUENCE: 30

```
ggaaagagtg gtggcaggtg aagtcggaga cgacagagga actggtttcc tccgccccgc     60

aaggcacaca gcctgccgac gccccattaa tacatgtgga aggggaaaga gactgaatgg    120

aggaatgaat acaacttgat ccaggtcgtg cttcggaagc ggtcacttta cctgtgaacc    180

tctctgcctg acaaacgggc aatgtacgga atcaaccacc aagatggcgg cgcccgtgaa    240

gaatccgcaa ttaggtcgcc gtcatatgtc gcctaggaac gtacggaatt cgacccacgt    300

acggaatcgg attccaagat gacggcatct atgaggaagt cacgcagtag gtgcagccat    360

gttgcctgta cgtcgaggcc gtacaagcag ccgccgtacg gactctactg acaaggtggc    420

ggcgccctcg ggaaagccac attagagcgc ggccatgttc ccggcgaaca tatggattcg    480

gccaccatac ggatacgata agcaagatgg cggcgcctga ggggtcttgg gggctctagg    540

ccggccacct actggtttgc agcggagacg acgcatgggg cctgcgcaat aggagtacgc    600

tgcctgggag gcgtgactag aagcggaagt agttgtgggc gcctttgcaa ccgcctggga    660

cgccgccgag tggtctgtgc aggttcgcgg gtcgctggcg gggtcgtga gggagtgcgc    720

cgggagcgga gatatggagg gagatggttc agacccagag cctccagatg ccggggagga    780

cagcaagtcc gagaatgggg agaatgcgcc catctactgc atctgccgca aaccggacat    840

caactgcttc atgatcgggt gtgacaactg caatgagtgg ttccatgggg actgcatccg    900

gatcactgag aagatggcca aggccatccg ggagtggtac tgtcgggagt gcagagagaa    960

agaccccaag ctagagattc gctatcggca caagaagtca cgggagcggg atggcaatga   1020

gcgggacagc agtgagcccc gggatgaggg tggagggcgc aagaggcctg tccctgatcc   1080

agacctgcag cgccgggcag ggtcagggac aggggttggg gccatgcttg ctcggggctc   1140

tgcttcgccc cacaaatcct ctccgcagcc cttggtggcc acacccagcc agcatcacca   1200

gcagcagcag cagcagatca aacggtcagc ccgcatgtgt ggtgagtgtg aggcatgtcg   1260

gcgcactgag gactgtggtc actgtgattt ctgtcgggac atgaagaagt tcgggggccc   1320

caacaagatc cggcagaagt gccggctgcg ccagtgccag ctgcgggccc gggaatcgta   1380

caagtacttc ccttcctcgc tctcaccagt gacgccctca gagtccctgc caaggccccg   1440

ccggccactg cccacccaac agcagccaca gccatcacag aagttagggc gcatccgtga   1500

agatgagggg gcagtggcgt catcaacagt caaggagcct cctgaggcta cagccacacc   1560

tgagccactc tcagatgagg acctacctct ggatcctgac ctgtatcagg acttctgtgc   1620
```

```
aggggccttt gatgaccatg gcctgccctg gatgagcgac acagaagagt ccccattcct   1680
ggaccccgcg ctgcggaaga gggcagtgaa agtgaagcat gtgaagcgtc gggagaagaa   1740
gtctgagaag aagaaggagg agcgatacaa gcggcatcgg cagaagcaga agcacaagga   1800
taaatggaaa cacccagaga gggctgatgc caaggaccct gcgtcactgc cccagtgcct   1860
ggggcccggc tgtgtgcgcc ccgcccagcc cagctccaag tattgctcag atgactgtgg   1920
catgaagctg gcagccaacc gcatctacga gatcctcccc cagcgcatcc agcagtggca   1980
gcagagccct tgcattgctg aagagcacgg caagaagctg ctcgaacgca ttcgccgaga   2040
gcagcagagt gcccgcactc gccttcagga aatggaacgc cgattccatg agcttgaggc   2100
catcattcta cgtgccaagc agcaggctgt gcgcgaggat gaggagagca acgagggtga   2160
cagtgatgac acagacctgc agatcttctg tgtttcctgt gggcacccca tcaacccacg   2220
tgttgccttg cgccacatgg agcgctgcta cgccaagtat gagagccaga cgtcctttgg   2280
gtccatgtac cccacacgca ttgaaggggc cacacgactc ttctgtgatg tgtataatcc   2340
tcagagcaaa acatactgta agcggctcca ggtgctgtgc cccgagcact cacgggaccc   2400
caaagtgcca gctgacgagg tatgcgggtg ccccccttgta cgtgatgtct ttgagctcac   2460
gggtgacttc tgccgcctgc ccaagcgcca gtgcaatcgc cattactgct gggagaagct   2520
gcggcgtgcg gaagtggact tggagcgcgt gcgtgtgtgg tacaagctgg acgagctgtt   2580
tgagcaggag cgcaatgtgc gcacagccat gacaaaccgc gcgggattgc tggccctgat   2640
gctgcaccag acgatccagc acgatcccct cactaccgac ctgcgctcca gtgccgaccg   2700
ctgagcctcc tggcccggac cccttacacc ctgcattcca gatgggggag ccgcccggtg   2760
cccgtgtgtc cgttcctcca ctcatctgtt tctccggttc tccctgtgcc catccaccgg   2820
ttgaccgccc atctgccttt atcagaggga ctgtccccgt cgacatgttc agtgcctggt   2880
ggggctgcgg agtccactca tccttgcctc ctctccctgg gttttgttaa taaaattttg   2940
aagaaaccaa ggaaaaaaaa aaaa                                           2964
```

<210> SEQ ID NO 31
<211> LENGTH: 1870
<212> TYPE: DNA
<213> ORGANISM: Homo sapiens

<400> SEQUENCE: 31

```
ctccgagacg ggtggggccg gagctccaag ctggtttgaa caagccctgg gcatgtttgg     60
cgggaagttg gcttagctcg gctacctgtg gccccgcagt tttgtagtcc ccgccttgtt    120
tctccccaga ggcctctcaa tcctccctcc atgatcttcg catagagcac agtacccctt    180
cacacggagg acgcgatggc tcccaagaaa cgcccagaaa cccagaagac ctccgagatt    240
gtattacgcc ccaggaacaa gaggagcagg agtcccctgg agctggagcc cgaggccaag    300
aagctctgtg cgaagggctc cggtcctagc agaagatgtg actcagactg cctctgggtg    360
gggctggctg gcccacagat cctgccacca tgccgcagca tcgtcaggac cctccaccag    420
cataagctgg gcagagcttc ctggccatct gtccagcagg ggctccagca gtccttttg     480
cacactctgg attcttaccg gatattacaa aaggctgccc cctttgacag gagggctaca    540
tccttggcgt ggcacccaac tcaccccagc accgtggctg tgggttccaa agggggagat    600
atcatgctct ggaattttgg catcaaggac aaacccacct tcatcaaagg gattggagct    660
ggagggagca tcactgggct gaagtttaac cctctcaata ccaaccagtt ttacgcctcc    720
```

-continued

```
tcaatggagg gaacaactag gctgcaagac tttaaaggca acattctacg agtttttgcc    780

agctcagaca ccatcaacat ctggttttgt agcctggatg tgtctgctag tagccgaatg    840

gtggtcacag gagacaacgt ggggaacgtg atcctgctga acatggacgg caaagagctt    900

tggaatctca gaatgcacaa aaagaaagtg acgcatgtgg ccctgaaccc atgctgtgat    960

tggttcctgg ccacagcctc cgtagatcaa acagtgaaaa tttgggacct gcgccaggtt   1020

agagggaaag ccagcttcct ctactcgctg ccgcacaggc atcctgtcaa cgcagcttgt   1080

ttcagtcccg atggagcccg gctcctgacc acggaccaga agagcgagat ccgagtttac   1140

tctgcttccc agtgggactg ccccctgggc ctgatcccgc accctcaccg tcacttccag   1200

cacctcacac ccatcaaggc agcctggcat cctcgctaca acctcattgt tgtgggccga   1260

tacccagatc ctaatttcaa aagttgtacc ccttatgaat tgaggacgat cgacgtgttc   1320

gatggaaact cagggaagat gatgtgtcag ctctatgacc cagaatcttc tggcatcagt   1380

tcgcttaatg aattcaatcc catgggggac acgctggcct ctgcaatggg ttaccacatt   1440

ctcatctgga gccaggagga agccaggaca cggaagtgag agacactaaa gaaggtgtgg   1500

gccagacaag gccttggagc ccacacatgg gatcaagtcc tgcaagcaga ggtggcgatt   1560

tgttaaaggg ccaaaagtat ccaaggttag ggttggagca ggggtgctgg gacctggggc   1620

actgtgggac tgggacactt ttatgttaat gctctggact tgcctccaga gactgctcca   1680

gagttggtga cacagctgtc ccaagggccc ctctgtatct agcctggaac caaggttatc   1740

ttggaactaa atgacttttc tcctctcagt gggtggtagc agagggatca agcagttatt   1800

tgatttgtgc tcacttttga tatggccaat aaaaccatac cgactgagaa aaaaaaaaaa   1860

aaaaaaaaaa                                                          1870


<210> SEQ ID NO 32
<211> LENGTH: 5335
<212> TYPE: DNA
<213> ORGANISM: Homo sapiens

<400> SEQUENCE: 32

gcttctctcc atcttgtgat tcctttttcc tcctgaaccc tccagtgggg gtgcgagttt     60

gtctttatca ccccccatcc caccgccttc ttttcttctc gctctcctac ccctccccag    120

cttggtgggc gcctctttcc tttctcgccc cctttcattt ttatttattc atatttattt    180

ggcgcccgct ctctctctgt ccctttgcct gcctccctcc ctccggatcc ccgctctctc    240

cccggagtgg cgcgtcgggg gctccgccgc tggccaggcg tgatgttgca cgtggagatg    300

ttgacgctgg tgtttctggt gctctggatg tgtgtgttca gccaggaccc gggctccaag    360

gccgtcgccg accgctacgc tgtctactgg aacagcagca accccagatt ccagaggggt    420

gactaccata ttgatgtctg tatcaatgac tacctggatg ttttctgccc tcactatgag    480

gactccgtcc cagaagataa gactgagcgc tatgtcctct acatggtgaa ctttgatggc    540

tacagtgcct gcgaccacac ttccaaaggg ttcaagagat gggaatgtaa ccggcctcac    600

tctccaaatg gaccgctgaa gttctctgaa aaattccagc tcttcactcc cttttctcta    660

ggatttgaat tcaggccagg ccgagaatat ttctacatct cctctgcaat cccagataat    720

ggaagaaggt cctgtctaaa gctcaaagtc tttgtgagac caacaaatag ctgtatgaaa    780

actataggtg ttcatgatcg tgttttcgat gttaacgaca aagtagaaaa ttcattagaa    840

ccagcagatg acaccgtaca tgagtcagcc gagccatccc gcggcgagaa cgcggcacaa    900

acaccaagga tacccagccg cctttttggca atcctactgt tcctcctggc gatgcttttg    960
```

acattatagc acagtctcct cccatcactt gtcacagaaa acatcagggt cttggaacac 1020
cagagatcca cctaactgct catcctaaga agggacttgt tattgggttt tggcagatgt 1080
cagatttttg ttttcttttct ttcagcctga attctaagca acaacttcag gttgggggcc 1140
taaacttgtt cctgcctccc tcaccccacc ccgccccacc cccagccctg gcccttggct 1200
tctctcaccc ctcccaaatt aaatggactc cagatgaaaa tgccaaattg tcatagtgac 1260
accagtggtt cgtcagctcc tgtgcattct cctctaagaa ctcacctccg ttagcgcact 1320
gtgtcagcgg gctatggaca aggaagaata gtggcagatg cagccagcgc tggctagggc 1380
tgggagggtt ttgctctcct atgcaatatt tatgccttct cattcagaac tgtaagatga 1440
tcgcgcaggg catcatgtca ccatgtcagg tccggagggg aggtattaag aatagatacg 1500
atattacacc atttcctata ggagtatgta aatgaacagg cttctaaaag gttgagacac 1560
tggttttttt ttttaatatg actgtcttaa agcattcttg acagcaaaac ttgtgctctc 1620
taaaagaagc cttttttttt tttctaggag gcaggttggg tgtggaatgc taatacagag 1680
caggtgtgaa aacagagaaa actacaggtt tgctgggggt gtgtatgtgt gagtgcctct 1740
aatttttttg gtgactgggc agtgcacacc agatattttt tctttgaata cagatcacca 1800
tggtgctaca actttttttt tttttttttt tttttttttt ttttttttta agaaactcaa 1860
agaggcattt ttatgaataa agtgaccttc cccaaggctg acaagccagg gttgatgagt 1920
gcatagtgga atagctttgg atactcctct gggggatgac atgtaccaag gagaggaccg 1980
cagtggccag aggagacatg atttggcttt gctggagcgc cagtgtgctg tggcctttcc 2040
ccgcctccca ccctagtacc cacgttttgc tccacactcc ttgaccgcag gggctcggac 2100
acaaacccct gtcaccagga gagtcagtca gcactacttg ggagggctaa agggaaattt 2160
ggaaataaaa ttccaaagtt tggagtaaaa aaattcaagt gttgatttta tattctttcc 2220
ctttctgaca cagcctaaag cgtaggggga acatgtgttt atctgtggga gataaacaag 2280
atggagtccc aaagacttta acaaaatatt tttttaaaaa tccactagaa tagaaaatac 2340
attatttaga tatactttat gctgagagtg agtatatatg cttgtcctat ttaaacttgt 2400
gagaaaaagt ggtatccctt gatacattta gaaatatggg ggctatcttg tttcattgtg 2460
ggggtggggc agaaggagaa taaatgcagg atgaccctgt tgaaggaatc ttagcatggc 2520
caacagggga cgtttccagt cgattaccag gaaatgcaag ccttggggtt tctactggtg 2580
gtggggctgt catgaacttt aaaatccaaa gcctagacaa ggaaaagtgt tagaccaatt 2640
gaaaagcaat ccagcccttt tttttttttt ttttttggct ttgcacgaca tgtcaacaga 2700
aaccatgcct ttcaatataa gaaataaatg tgatgatcat gtaaaatgtg aaaaattgaa 2760
agcattccag caaaataaga attttttata tatttgtttt ttaagatgta tatgttaaaa 2820
aaagagaagg tcgcattatg gacagacttc gtgaatggga atttgcttag aattgtgagt 2880
agttctgaat tagaaaagta tgtgaaggaa aggcagctgt aaacgtattg tgccctggag 2940
agttgtacac atgttgaaat gtaatctggg cttacctgat ccatttggag tggatgtcac 3000
tgccgagtct gttctcacat ggaaccatgt gtgtggggtt gccagcctca cagatacaat 3060
caatcctatt cccctctgac ataaggaact cctctggagt ggcagagtct tatcacagaa 3120
ggcagccacc atttcaccaa aacaaaagtt cacggcattc aattcctttt tcctttagct 3180
atttatatat gcagtactct cagtcatatg cagaaatact tttttttttt taattaatag 3240
ttacaggctt gttggtccag tgggatttgg gtagggggag aaagatacct tctaaaatgg 3300
atcaatagaa ccaaaataat acagcatgtt ctataaccac aaggaaatca aatgatcctg 3360
tcatgattcc agttagtcat aactatgtta gcagtgctaa atgcatttta gaaatggtga 3420
cttctgtggt tttcctagca tttgtctcta acaaatggtg aaataattac tcatggccct 3480
ctctgccatt gtctttcatt ttttcacagt gaaattagac ccctttactt caccattctg 3540
ccactgcaaa ttaagtataa agaaaatagc aagagtgtcc acaccagtag acagtaagct 3600
tctctacctg taagtgatga aatcatagct aatgcacttg ccatggagtt ttcaagatga 3660
ttggtgtcag acagttttca ctttgtttaa aaagtgttgg tggccttttg tggtggtgtt 3720
acaatcctct gggggcttag gaggatgttg atgcaacttt tagaagcttt taatttcaaa 3780
aacaactcaa aaatctgaag gacagtcata gctgccactc agccccagtt agtcaaaccc 3840
cagtgacctt tgcccctggt tgccaagggc tttgcaacat caagcaggga aataaggatc 3900
tgtctgttta gtggataccg tgtatccttt aatagaccag gtaacagttc gtgttagttt 3960
agactattgt tttgtactgt actttcttgg gtggcagagg aaagaaaagt aaaacattaa 4020
aaaaaaaaaa aaaactgcgt tctttaaatt ctgtattatt agcaacctct gttgtacata 4080
gtgtttgata ataaagtatt aatttgattc ttatgtcttt tgtaagtgag aacaatagac 4140
tttcaggata caaaacatgc attgaggctt tgaaacatcc aatgtgtacc atggctgaaa 4200
aaaagagtca caagtggctg agacactgct ccatacagga ctcatgtgtg gtcattgccc 4260
acccaatctt atgactccat catcttggga cctggaacaa catgactttt ttgatcgata 4320
ttttgtcctc ggtgttttca aggtctgatg ttggagccct gtggcccacc ctcccttctc 4380
caccagcatg ttggtttgaa aaggataggg aatttagaaa cagttctgta ctttggtttg 4440
gtttggtttt ctgtttgtga ttgttttcat ggactgtttt attttttccc aggaagagtc 4500
tttatcaata tcatgtgcag ctcactcatg gaaatggttg caaaccaatc agtgtaggaa 4560
gcttaaatgg ggctgtttcc ctctctgtgt cgttgtgaaa ggaagagtca cacagtacct 4620
gtggattttc agggactctg tttttctccg gtgccttagc aacggcagca gccatttgta 4680
ttattttcaa ataattagaa aaacagtttt caactcctcc tttccattca ttgctctcag 4740
agttgtggtc actgactttt cttttgaaaa ccgcctccac caacaccccc gtttgcctac 4800
accacccccc ttttacttag tatgtttatt ttttgtgtgt ctcttgcctt cctcccacgt 4860
tttatttccc ctcagagctg tgaatgggca ggtctgtctc tggtttggca tcactgagtt 4920
tttcccatgc attggcccca gggctgctag gatgtgagac aaatctccct acaatgggct 4980
tgctcccatt gtctgtacag tttaatagat gctggcatgt cggaggttac ccatgagtca 5040
aaatccgctc tccatgctta ctcttgacac cccattgaag ccactcattg tgtgtgcgtc 5100
tgggtgtgaa gtccagctcc gtgtggtcct gtgcttgtac tgccctgctt tgcagttcct 5160
ttgcacttac tcatcgagtg ctgttttgaa atgctgacat tatataaacg taaaagaaaa 5220
tgtaaaaaaa aaaaacccac acacaaacaa acccatacga tctgtatttg tatatacacg 5280
tgtccgtaca agtataacta aataaaaatt aaagattttc atcattttaa ttgga 5335

<210> SEQ ID NO 33
<211> LENGTH: 2109
<212> TYPE: DNA
<213> ORGANISM: Homo sapiens

<400> SEQUENCE: 33
aaagtaccag ctggcgcctt ttaagagata caggtctgtg aagcaggcag gttgctcagc 60
tgcccccgga gcggttcctc cacctgaggc agactccacg tcggctggca tgagccggcg 120

```
cccctgcagc tgcgccctac ggccaccccg ctgctcctgc agcgccagcc ccagcgcagt    180

gacagccgcc gggcgccctc gaccctcgga tagttgtaaa gaagaaagtt ctaccctttc    240

tgtcaaaatg aagtgtgatt ttaattgtaa ccatgttcat tccggactta aactggtaaa    300

acctgatgac attggaagac tagtttccta cacccctgca tatttggaag gttcctgtaa    360

agactgcatt aaagactatg aaaggctgtc atgtattggg tcaccgattg tgagccctag    420

gattgtacaa cttgaaactg aaagcaagcg cttgcataac aaggaaaatc aacatgtgca    480

acagacactt aatagtacaa atgaaataga agcactagag accagtagac tttatgaaga    540

cagtggctat tcctcatttt ctctacaaag tggcctcagt gaacatgaag aaggtagcct    600

cctggaggag aatttcggtg acagtctaca atcctgcctg ctacaaatac aaagcccaga    660

ccaatatccc aacaaaaact tgctgccagt tcttcatttt gaaaaagtgg tttgttcaac    720

attaaaaaag aatgcaaaac gaaatcctaa agtagatcgg gagatgctga aggaaattat    780

agccagagga aattttagac tgcagaatat aattggcaga aaaatgggcc tagaatgtgt    840

agatattctc agcgaactct ttcgaagggg actcagacat gtcttagcaa ctattttagc    900

acaactcagt gacatggact taatcaatgt gtctaaagtg agcacaactt ggaagaagat    960

cctagaagat gataaggggg cattccagtt gtacagtaaa gcaatacaaa gagttaccga   1020

aaacaacaat aaattttcac ctcatgcttc aaccagagaa tatgttatgt tcagaacccc   1080

actggcttct gttcagaaat cagcagccca gacttctctc aaaaaagatg ctcaaaccaa   1140

gttatccaat caaggtgatc agaaaggttc tacttatagt cgacacaatg aattctctga   1200

ggttgccaag acattgaaaa agaacgaaag cctcaaagcc tgtattcgct gtaattcacc   1260

tgcaaaatat gattgctatt tacaacgggc aacctgcaaa cgagaaggct gtggatttga   1320

ttattgtacg aagtgtctct gtaattatca tactactaaa gactgttcag atggcaagct   1380

cctcaaagcc agttgtaaaa taggtcccct gcctggtaca aagaaaaagca aaaagaattt  1440

acgaagattg tgatctctta ttaaatcaat tgttactgat catgaatgtt agttagaaaa   1500

tgttaggttt taacttaaaa aaaattgtat tgtgattttc aattttatgt tgaaatcggt   1560

gtagtatcct gaggtttttt tccccccaga agataaagag gatagacaac ctcttaaaat   1620

atttttacaa tttaatgaga aaaagtttaa aattctcaat acaaatcaaa caatttaaat   1680

attttaagaa aaaaggaaaa gtagatagtg atactgaggg taaaaaaaaa ttgattcaat   1740

tttatggtaa aggaaaccca tgcaatttta cctagacagt cttaaatatg tctggttttc   1800

catctgttag catttcagac attttatgtt cctcttactc aattgatacc aacagaaata   1860

tcaacttctg gagtctatta aatgtgttgt cacctttcta aagctttttt tcattgtgtg   1920

tatttcccaa gaaagtatcc tttgtaaaaa cttgcttgtt ttccttattt ctgaaatctg   1980

ttttaatatt tttgtataca tgtaaatatt tctgtatttt ttatatgtca aagaatatgt   2040

ctcttgtatg tacatataaa aataaatttt gctcaataaa attgtaagct taaaaaaaaa   2100

aaaaaaaaa                                                           2109
```

<210> SEQ ID NO 34
<211> LENGTH: 3618
<212> TYPE: DNA
<213> ORGANISM: Homo sapiens

<400> SEQUENCE: 34

```
cccagactcc agccctggac cgcgcatccc gagcccagcg cccagacaga gtgtccccac     60
```

-continued

```
accctcctct gagacgccat gttcaactcg atgaccccac caccaatcag tagctatggc    120
gagccctgct gtctccggcc cctccccagt caggggggccc ccagtgtggg gacagaagga    180
ctgtctggcc cgcccttctg ccaccaagct aacctcatgt ccggccccca cagttatggg    240
ccagccagag agaccaacag ctgcaccgag ggcccactct tttcttctcc ccggagtgca    300
gtcaagttga ccaagaagcg ggcactgtcc atctcacctc tgtcggatgc cagcctggac    360
ctgcagacgg ttatccgcac ctcacccagc tccctcgtag ctttcatcaa ctcgcgatgc    420
acatctccag gaggctccta cggtcatctc tccattggca ccatgagccc atctctggga    480
ttcccagccc agatgaatca ccaaaaaggg ccctcgcctt cctttggggt ccagccttgt    540
ggtccccatg actctgcccg ggtgggatg atcccacatc ctcagtcccg gggacccttc    600
ccaacttgcc agctgaagtc tgagctggac atgctggttg gcaagtgccg ggaggaaccc    660
ttggaaggtg atatgtccag ccccaactcc acaggcatac aggatcccct gttggggatg    720
ctggatgggc gggaggacct cgagagagag gagaagcgtg agcctgaatc tgtgtatgaa    780
actgactgcc gttgggatgg ctgcagccag gaatttgact cccaagagca gctggtgcac    840
cacatcaaca gcgagcacat ccacggggag cggaaggagt tcgtgtgcca ctgggggggc    900
tgctccaggg agctgaggcc cttcaaagcc cagtacatgc tggtggttca catgcgcaga    960
cacactggcg agaagccaca caagtgcacg tttgaagggt gccggaagtc atactcacgc   1020
ctcgaaaacc tgaagacgca cctgcggtca cacacgggtg agaagccata catgtgtgag   1080
cacgagggct gcagtaaagc cttcagcaat gccagtgacc gagccaagca ccagaatcgg   1140
acccattcca atgagaagcc gtatgtatgt aagctccctg gctgcaccaa acgctataca   1200
gatcctagct cgctgcgaaa acatgtcaag acagtgcatg gtcctgacgc ccatgtgacc   1260
aaacggcacc gtggggatgg ccccctgcct cgggcaccat ccatttctac agtggagccc   1320
aagagggagc gggaaggagg tcccatcagg gaggaaagca gactgactgt gccagagggt   1380
gccatgaagc cacagccaag ccctggggcc cagtcatcct gcagcagtga ccactccccg   1440
gcagggagtg cagccaatac agacagtggt gtggaaatga ctggcaatgc agggggcagc   1500
actgaagacc tctccagctt ggacgaggga ccttgcattg ctggcactgg tctgtccact   1560
cttcgccgcc ttgagaacct caggctggac cagctacatc aactccggcc aatagggacc   1620
cggggtctca aactgcccag cttgtcccac accggtacca ctgtgtcccg ccgcgtgggc   1680
cccccagtct ctcttgaacg ccgcagcagc agctccagca gcatcagctc tgcctatact   1740
gtcagccgcc gctcctccct ggcctctcct ttccccccctg gctccccacc agagaatgga   1800
gcatcctccc tgcctggcct tatgcctgcc cagcactacc tgcttcgggc aagatatgct   1860
tcagccagag gggtggtac ttcgcccact gcagcatcca gcctggatcg gataggtggt   1920
cttcccatgc ctccttggag aagccgagcc gagtatccag gatacaaccc caatgcaggg   1980
gtcacccgga gggccagtga cccagcccag gctgctgacc gtcctgctcc agctagagtc   2040
cagaggttca agagcctggg ctgtgtccat accccaccca ctgtggcagg gggaggacag   2100
aactttgatc cttacctccc aacctctgtc tactcaccac agcccccccag catcactgag   2160
aatgctgcca tggatgctag agggctacag gaagagccag aagttgggac ctccatggtg   2220
ggcagtggtc tgaaccccta tatggacttc ccacctactg atactctggg atatgggga   2280
cctgaagggg cagcagctga gccttatgga gcgaggggtc caggctctct gcctcttggg   2340
cctggtccac ccaccaacta tggccccaac ccctgtcccc agcaggcctc atatcctgac   2400
cccacccaag aaacatgggg tgagttccct tcccactctg ggctgtaccc aggccccaag   2460
```

gctctaggtg gaacctacag ccagtgtcct cgacttgaac attatggaca agtgcaagtc 2520
aagccagaac aggggtgccc agtggggtct gactccacag gactggcacc ctgcctcaat 2580
gcccacccca gtgaggggcc cccacatcca cagcctctct tttcccatta cccccagccc 2640
tctcctcccc aatatctcca gtcaggcccc tatacccagc cacccccctga ttatcttcct 2700 tcagaaccca ggccttgcct ggactttgat tcccccaccc attccacagg gcagctcaag 2760
gctcagcttg tgtgtaatta tgttcaatct caacaggagc tactgtggga gggtgggggc 2820
agggaagatg cccccgccca ggaaccttcc taccagagtc ccaagtttct ggggggttcc 2880
caggttagcc caagccgtgc taaagctcca gtgaacacat atggacctgg ctttggaccc 2940
aacttgccca atcacaagtc aggttcctat cccacccctt caccatgcca tgaaaatttt 3000
gtagtggggg caaatagggc ttcacatagg gcagcagcac cacctcgact tctgcccccca 3060 ttgcccactt gctatgggcc tctcaaagtg ggaggcacaa accccagctg tggtcatcct 3120
gaggtgggca ggctaggagg gggtcctgcc ttgtaccctc ctcccgaagg acaggtatgt 3180
aaccccctgg actctcttga tcttgacaac actcagctgg actttgtggc tattctggat 3240
gagccccagg ggctgagtcc tcctccttcc catgatcagc ggggcagctc tggacatacc 3300
ccacctccct ctgggccccc caacatggct gtgggcaaca tgagtgtctt actgagatcc 3360
ctacctgggg aaacagaatt cctcaactct agtgcctaaa gagtagggaa tctcatccat 3420
cacagatcgc atttcctaag ggtttctat ccttccagaa aaattggggg agctgcagtc 3480
ccatgcacaa gatgccccag ggatgggagg tatgggctgg gggctatgta tagtctgtat 3540
acgttttgag gagaaatttg ataatgacac tgtttcctga taataaagga actgcatcag 3600
aaaaaaaaaa aaaaaaaa 3618

<210> SEQ ID NO 35
<211> LENGTH: 5843
<212> TYPE: DNA
<213> ORGANISM: Homo sapiens

<400> SEQUENCE: 35
ttggttgctg gtccacttac aaacactttt catatttgta tgtctttcca atggttatcc 60
tgttttgttc atttcaggca tatggccctg atcagattaa ctgacatgat gtatatgcaa 120
agccttttga gttcttcaga aaaataaatt atcttattca agactgattg cttataagga 180
acttattata gctaatatag taggcacaat tttttttttg taattctcct agatgagtca 240
gaacttagtt ttgacgtagg taaaaatttt atggtcacaa atctcaggtg tgagaaaatc 300
tctttccttg atactctata taaatagagg atataaatat ttcaagtctg gaagtagtga 360
gagaagctgg taattctgga catatagtga cagtcaaaaa ggagctcagg tacaggactg 420
gtctaagctg ctcaagattc aggagacagc cagtacacag agaagctgag gagatacata 480
agatatatct aaaacattta tctaaccttc tgtggtaaca agctccttaa aggggctgga 540
tgatgttgtg ttcacttttt atcaccagca aaggctaaga taatgtatat agtaaatatt 600
tagtaactat ttattaaata aataaatatt taagacagaa taaacaagta taataaatga 660
accaataaga atgcaccatc taagtcaaaa tagccacttt tatccttaac attgtacctg 720
ctttggctgc tgcagaagca aacttgttgg cattagacaa atcaagctgg tgatttaata 780
aattccaatg taagtcttac cagtattgat gaataactat ccagcactca ccatgaaagt 840
taaagaaaca acacagaaaa agttcctaag tggtcccaat ttgaaatgat cagataacct 900

```
ataaaagaac atattcatat tatactaaca taaacacata taaatgcact tacagcagtt    960
acacagtatt ctcttcaata actagtttcc ttatgcatta atgtgtaata acagcaacta   1020
caatatttag ataattataa aaaccaaggc aataatttaa aaactgatta accgttttac   1080
tctaacttaa gcatggattg gatcagtaag attgattaat aaatttgaat gcagtcagtt   1140
ggattgattc taatttaaag ttttaatttg ttgtagaata attttaagtg aatatatttg   1200
tccagtgttc gagtgctcaa cagtgtgttt gaaaaggaaa acaaagaaat gtttttgaga   1260
aatgtgttaa ttccttaaga caatggattt taattggatc tagttgtttt catttttctt   1320
cattatcatt atacatctgt atgttggaca gaacactaac actaaatagt ttttagaaaa   1380
atttttaaa gttatttaaa tcataatatc atgactgact tttaaattca aaattaggct   1440
gtgactatcc ttcttcactt aggaagagtg ttgtgaaagc cagaccatct gctgaggtgc   1500
tacagttaca tgtggccctc agaatgcatt tggcctgctc tgttttagca ctctgttgga   1560
ttaccaatac acaaaacaag ttaaccttga tctttcacat taagtatctc agggacaaaa   1620
tttgacatac gtctaaacct gtgacgtttc catctaaaga aggcagaaat aaaacaggac   1680
tttagattcg gttacaataa aatatcagat gcaccagaga cacaaggctt gaagctctgt   1740
cctgggaaaa tatggcaaac agtgcctctc ctgaacagaa tcaaaatcac tgttcagcca   1800
tcaacaacag catcccactg atgcagggca acctccccac tctgaccttg tctggaaaga   1860
tccgagtgac ggttactttc ttcctttttc tgctctctgc gacctttaat gcttctttct   1920
tgttgaaact tcagaagtgg acacagaaga aagagaaagg gaaaaagctc tcaagaatga   1980
agctgctctt aaaacatctg accttagcca acctgttgga gactctgatt gtcatgccac   2040
tggatgggat gtggaacatt acagtccaat ggtatgctgg agagttactc tgcaaagttc   2100
tcagttatct aaagcttttc tccatgtatg ccccagcctt catgatggtg gtgatcagcc   2160
tggaccgctc cctggctatc acgaggcccc tagctttgaa aagcaacagc aaagtcggac   2220
agtccatggt tggcctggcc tggatcctca gtagtgtctt tgcaggacca cagttataca   2280
tcttcaggat gattcatcta gcagacagct ctggacagac aaaagtttc tctcaatgtg   2340
taacacactg cagtttttca caatggtggc atcaagcatt ttataacttt ttcaccttca   2400
gctgcctctt catcatccct cttttcatca tgctgatctg caatgcaaaa atcatcttca   2460
ccctgacacg ggtccttcat caggaccccc acgaactaca actgaatcag tccaagaaca   2520
atataccaag agcacggctg aagactctaa aaatgacggt tgcatttgcc acttcattta   2580
ctgtctgctg gactccctac tatgtcctag gaatttggta ttggtttgat cctgaaatgt   2640
taaacaggtt gtcagaccca gtaaatcact tcttctttct ctttgccttt ttaaacccat   2700
gctttgatcc acttatctat ggatattttt ctctgtgatt gatagactac acaagaagtc   2760
atatgaagaa gggtaaggta atgaatctct ccatctggga atgattaaca caaatgttgg   2820
agcatgttta catacaaaca aagtaggatt tacacttaag ttatcattct tttagaaact   2880
cagtcttcag agcctcaatt attaaggaaa agtcttcagg aaaaatacta aaatattttc   2940
tcttcctcat aagcttctaa attaatctct gccttttctg acctcatata acacattatg   3000
taggtttctt atcactttct ctttgcataa taatgtacta atatttaaaa taccttcagc   3060
ctaaggcaca aggatgccaa aaaaacaaag gtgagaaacc acaacacagg tctaaactca   3120
gcatgctttg gtgagttttt ctccaaaagg ggcatattag caattagagt tgtatgctat   3180
ataatacata gagcacagag ccctttgccc ataatatcaa ctttccctcc tatagttaaa   3240
aagaaaaaaa atgaatctat ttttctcttt ggcttcaaaa gcattctgac atttggagga   3300
```

gtcagtaacc aatcccacca accactccag caacctgaca agactatgag tagttctcct 3360
tcatcctatt tatgtggtac aggttgtgaa gtatctctat ataaagggaa attttagagg 3420
ggttaggatt tggacagggg tttagaacat tcctctaagc tatctagtct gtggagtttg 3480
tggcaattaa ttgccataaa ataacaatgt ttccaaatgc aactaagaaa atactcatag 3540
tgagtacgct ctatgcatag tatgacttct attttaatgt gaagaatttt ttgtctctct 3600
cctgatctta ctaaatccat atttcataaa taactgagaa taattaaaac aaaattaagc 3660
aaatgcacaa gcaaaaagat gcttgataca caaaaggaac tctggagaga aaactacagc 3720
ttcagtctgt acagatcaaa gaagacagaa catgtcaggg gaaggaggga aagatcttga 3780
tgcagggttt cttaacctgc agtctatgca caacactata tttccatgta atgtttttat 3840
ttcagcccta tttgtattat tttgtgcatt taaaaaacac aatcttaagg ggatagacta 3900
gactgccaca gcagcccatg gcacaactaa cacctactga tattcacatt aaatagtatg 3960
gtttccaaaa tatgtctgca caacaagacc tctttatgta attcaggctt gtgtctacct 4020
cttccatgaa aaatggaaag ggatgaaaat aatgggagta taatacccat ttaatgtgaa 4080
aaacataaga gtcttaaaag aaattaagcc atttaacatt ttttaaatag gtaagatacc 4140
attatattta tatgagctat gtactgccac aaaaaaagat gaaatgtaat ttctaaatac 4200
tccaggtgtg tggtattatg gaaagcaaat tgccaactaa tggcacgtcc tttctttctt 4260
tgattttctc ctctcatact tcagttttat agtgttgtgt tgttgttttt ttcatatcct 4320
accttacttt ccaattctgt ctcaattgaa ctccctctgt ctactcactc tttcattcat 4380
agcttctttt ccattaaact catacccttta attaaccaat tcatggccca gttctacagt 4440
tgaattggac aaggctaaaa ttctgtagtg tgctaaaatg ctcaagttgg cacataaacc 4500
cattccaaga ttttatagtt cttgtagata acacagggat gtagataagt tgaaacaaaa 4560
ccagtgtcct ctaagtctct atcatatact tattcctaaa ctgataattc ttacttctgg 4620
atttaaaatc aaaaataaca cacttgtaca gatacaatct aagggcttta tcacacacgt 4680
gttaacgaat gtatctcagc ttggttcttc ttgtgtgctc attatggatc tctctgtctt 4740
aggaattgcc tcaggcattt ttttttttta cacattaact aaagggctat tcgaaatctt 4800
gactcagggg ttcttaacct acatttcatg caaaaaaatat atatatttca atgtattttt 4860
tattttagtc ctatttgtat tattttatgc atttaaaaac acagtcctga gagggatgga 4920
ccagactgcc acagcagctc atagcacaaa aaaaggttaa gaagtcctag ttgactttgt 4980
atatatataa agaaatctat tacaataaaa atataacata atctattcat ctatttatat 5040
gcaaacataa aaatgtaaat attgaaacaa gattgcttca atatgcttat tgttttcaaa 5100
ccaacaaact ctcttaaggt tcaatatgta ataaaaaaca taacacaaat aattattcta 5160
tatgaatatt atggttcata aattataatg tataatctat acattataat gtaatatata 5220
aactaaaatt tatggcacaa aagataaata tggctttgaa attaaagata ttccactcaa 5280
cagacaatat ttcatatttg atattacaat catttatttt atgtcctatt ataataaaag 5340
gtgaggactc cttgtaaaaa aggaaatgtt ccacagagtc aatctaatat atcagatatt 5400
ggagattcta tcttggtttc tcttccttta cttagcctat aaaactagtt aaaaatggaa 5460
tttcttttag caattcagtt tagtacagga gtgacattaa ctaatgacaa taaattaaac 5520
aaagcctaca ttagttcaat ttaagcctat tcaacagaaa tatagaaata tagtagctaa 5580
aaaaatactc tggggaaggt accacaaaca ttatctacca gggaacatag cataaattag 5640

```
tctgaaattt cctgagagtg actttgtctt agaacttagg tggtagtcat gaagagataa   5700

tgtttttagg cagttaaaat acttctagaa ctccatctat tttacctgtg gtccactttc   5760

ctacattgaa ccaatgcctt gggcttctct aattactata cattgtgctc atatgaataa   5820

aagaaatttt aaaagaaaaa aaa                                           5843


<210> SEQ ID NO 36
<211> LENGTH: 2100
<212> TYPE: DNA
<213> ORGANISM: Homo sapiens

<400> SEQUENCE: 36

acaggccaca ggccaagggc agcagtcagg cctgctctgt ctgtgaacgc tcccggcttg     60

gcctcggctg atgggccctc acgcctgaag cgggcaggaa gctccgggat ggatttcggg    120

tctttggaga ccgtggtggc caactctgcc ttcatcgccg cccgaggcag ctttgacggc    180

agcagctccc aaccctcccg ggacaagaag tacctggcca agctcaagct gcccccgctg    240

tccaagtgtg agtccctccg cgacagcctc agcctggagt ttgagagtgt gtgcttggag    300

cagcccatcg gcaagaagct ctttcagcag ttcctacaat cggcagagaa gcacctgccg    360

gccctggagc tctggaaaga catcgaggac tatgacacgg cagacaatga cctccagcca    420

cagaaggccc agaccatcct ggcccagtac ctggaccccc aggccaaact cttctgcagc    480

ttcctggatg aggggatagt ggcgaagttt aaggaggggc ctgtggagat ccaggacggg    540

ctcttccagc ccctgctgca ggccaccctg gcacacctgg gccaagcccc cttccaggag    600

tacctgggca gcctgtactt cctgaggttc ctgcagtgga agtggctgga agcccagccc    660

atgggggagg actggttcct ggacttcagg gtcctgggga aagggggctt cggggaggtg    720

tcggcctgcc agatgaaggc gaccggcaag ctgtatgcct gcaagaagct gaacaagaag    780

cggctgaaga agaggaaggg ctaccagggt gctatggtgg agaagaagat tctgatgaaa    840

gtacacagca ggttcatcgt gtctctggcc tatgcgtttg aaaccaaagc cgacctctgt    900

ctggtgatga ccatcatgaa cggaggtgac atcaggtacc acatctacaa cgtgaatgag    960

gagaaccctg gcttcccgga gccgcgcgcc ctcttctaca cggcgcagat catctgcggc   1020

ctggagcacc tgcaccagag gcggatcgtc taccgcgacc tcaagcccga gaacgtgctg   1080

ctggacaatg acggcaatgt ccggatctct gaccttgggc tggccgtgga gctgctggac   1140

ggacagagca agaccaaggg ctacgcaggg accccaggtt tcatggcccc cgagctcctg   1200

cagggcgagg agtacgactt ctccgtggac tactttgccc tgggggtcac cctgtatgag   1260

atgattgcgg ccagaggacc cttccgagcc cgtggagaga aggtggagaa caaggagctg   1320

aagcaccgga tcatctcaga gcccgtgaag taccctgata agttcagcca ggccagcaag   1380

gacttctgcg aggcgctgct ggagaaggac ccggagaagc gcctggggtt cagagatgag   1440

acctgcgaca agctccgtgc ccaccccctc ttcaaggacc ttaactggag gcagctggag   1500

gctgggatgc tgatgccccc tttcatccca gactccaaaa ctgtctacgc aaaggatatt   1560

caggacgtgg gtgccttttc caccgtcaaa ggtgtggcct ttgacaaaac agacacagaa   1620

ttctttcagg aatttgccac tggcaactgc ccatcccct ggcaggagga gatgatcgag    1680

acgggcatct ttggcgagct gaacgtgtgg cgctcggacg gtcagatgcc ggacgacatg   1740

aagggcatct ccgggggctc cagctcctcg tccaagtcag ggatgtgtct ggtttcctag   1800

gtgacgcccc agagtccacg tggaggaaaa ggacccatac ggctcgatgg gggccgcctg   1860

cctccgtggt gccagcctgg ggtctgctag caaggggaca cgtggttccc tccacccagg   1920
```

tccccatcac gccatctcct tgcggcccaa ggaggagaaa gccacgtcgg cctgagccgc 1980
cagatgcaca tgctggtgcc gtgagccccc gactgcatat ttcacgtctt ttgctccatc 2040
tcactgagaa gacataagat gctctccaga gggagtaagc caaaaatcta caaactctta 2100

<210> SEQ ID NO 37
<211> LENGTH: 2797
<212> TYPE: DNA
<213> ORGANISM: Homo sapiens

<400> SEQUENCE: 37
gtttgcgttt gaacctcttg gcgggtgccg gccatggcgg cttcgctccc gggacctggg 60
agccggcttt tccgcacata tggggctgcg gacggcagga gacagcggcg gccgggccgg 120
gaagccgcgc agtggttccc gccgcaggac cggaggcgtt tcttcaacag cagcggcagc 180
agcgacgcca gcatcggcga cccctcgcag tccgacgatc ctgacgatcc cgacgacccc 240
gacttccccg gcagcccggt gaggcggcgg cggaggcgtc ccggcggccg agtgcccaag 300
gaccggccca gcctgaccgt gaccccaaag cgctggaagc tgcgagctcg cccaagccta 360
accgtgaccc caagacgcct ggggctgcga gctcggcccc cgcagaagtg cagcacaccc 420
tgcggcccgc tccgacttcc gcccttcccc agccgcgact ccggccgcct cagcccggac 480
ctcagcgtgt gcggccagcc cagggacggc gacgagctgg gcatcagtgc ctccctgttc 540
agctctctgg cctcgccctg ccccgggtcc ccaacgccaa gggacagtgt catctcgatc 600
ggcacctccg cctgtctggt tgcagcctca gccgtcccga gcggcctcca cctcccagaa 660
gtctccctgg accgagcatc tctcccctgc tcccaggagg aagcgacagg aggagccaag 720
gacaccagga tggtccacca aacccgcgcc agcctcaggt cagttctctt tggccttatg 780
aactcaggaa cccctgagga ttctgagttt cgggcagatg ggaagaatat gagagagtcc 840
tgctgtaaaa ggaaactggt ggtgggaaat ggaccagagg gtccaggtct gtcaagcaca 900
ggcaagagga gggccacagg ccaggactct tgtcaagaga gagggcttca agaggccgtc 960
cggagagagc atcaggaggc cagtgttccc aagggccgca ttgtgccaag gggaatagac 1020
aggctggaga gaactagatc aagccggaag agcaaacatc aggaggcaac ggaaacctct 1080
ctcctccatt cccaccgctt taaaaagggc caaaagctgg gaaaagattc gttccccacc 1140
caggacctga ctcctttaca gaatgtctgc ttttggacca aaaccagggc ttccttcagt 1200
ttccacaaga agaaaattgt gactgatgtg tcagaggtct gcagcatcta taccactgcc 1260
acttctctct ctggatccct cctatcagaa tgttcaaacc ggcctgtcat gaacagaaca 1320
agtggtgctc cgtcctcttg gcactcctcc tctatgtatt tgctaagccc cttaaacact 1380
ctaagtattt caaacaaaaa ggcatctgat gctgaaaagg tttatgggga atgcagtcag 1440
aagggtcctg tccccttag ccattgcctt cccacagaaa aactgcaacg ctgtgagaag 1500
attggggaag gggtgtttgg cgaagtgttt caaacaattg ctgatcacac acccgtagcc 1560
ataaaaatca ttgctattga aggaccagat ttagtcaatg gatcccatca gaaaaccttt 1620
gaggaaatcc tgccagagat catcatctcc aaagagttga gcctcttatc cggtgaagtg 1680
tgcaaccgca cagaaggctt tatcgggctg aactcagtgc actgtgtcca gggatcttac 1740
cctcccttgc tcctcaaagc ctgggatcac tataattcaa ccaaaggctc tgcaaatgac 1800
cggcctgatt tttttaaaga cgaccagctc ttcattgtgc tggaatttga gtttggaggg 1860
attgacttag agcaaatgcg aaccaagttg tcttccttgg ctactgcaaa gagcattcta 1920
caccagctca cagcctccct cgcagtggca gaggcatcac tgcgctttga gcaccgagac 1980
ttacactggg ggaacgtgct cttaaagaaa accagcctca aaaaactcca ctacaccctc 2040
aatgggaaga gcagcactat ccccagctgt gggttgcaag tgagcatcat tgactacacc 2100
ctgtcgcgct tggaacggga tgggattgtg gttttctgtg acgtttccat ggatgaggac 2160
ctgtttaccg gtgacggtga ctaccagttt gacatctaca ggctcatgaa gaaggagaat 2220
aacaaccgct ggggtgaata tcacccttat agtaatgtgc tctggttaca ttacctgaca 2280
gacaagatgc tgaaacaaat gaccttcaag actaaatgta acactcctgc catgaagcaa 2340
attaagagaa aaatccagga gttccacagg acaatgctga acttcagctc tgccactgac 2400
ttgctctgcc agcacagtct gtttaagtaa gctaaatgta tcttactgcc ccgaaatgag 2460
aggagactgg tcttgaagcc tctggtgctg tttcaacctc catccccaca ggagggtgga 2520
actcccattc tcacaggttt ccagtcagct tttcaaacaa gaattttgtt tccaaatgga 2580
aactgaaata tttgttgaaa tgtttaaatt tgctgataac aaatgttctg aaagaagtaa 2640
actagccggg cacagtggcg tgcgcctgta gtcccagcta ctcgggaggc tgaggcagga 2700
ggatcgcttg agcccaagag ttcatatcta gcctggtcaa catagcaaga cccctgtctc 2760
tattttttta aataaataaa ctacatgtga aaacaaa 2797

<210> SEQ ID NO 38
<211> LENGTH: 1708
<212> TYPE: DNA
<213> ORGANISM: Homo sapiens

<400> SEQUENCE: 38
ctcttctgaa ttctccattc tgggctcttg cctgtgaaat ctttctttgc tttccccatc 60
ttttcctcgc attttttcac catctttccc tcaatctcca ggagccaatg cgagactttg 120
gctccgatta agcgacggcc cgagactcgg ggtgcgcgag gaggatcgac agagtggtga 180
tggagagcac cccttcaagg ggactgaacc gagtacacct acaatgcagg aatctgcagg 240
aattcttagg gggcctgagc cctggggtat tggaccgatt gtatgggcac cctgccacat 300
gtctggctgt cttcagggag ctcccatcct tggctaagaa ctgggtgatg cggatgctct 360
ttctggagca gcctttgcca caggctgctg tagctctgtg ggtaaagaag gaattcagca 420
aggctcagga ggaaagtaca gggctgctga gcggcctccg gatctggcac acacagctgc 480
tcccaggcgg gctccagggc ctcatcctca accccatttt ccgccagaac ctccgcattg 540
cccttctggg tggggggaag gcctggtctg atgacacaag tcagctggga ccagacaagc 600
atgcccggga cgttccctcc cttgacaagt acgccgagga gcgatgggag gtggtcttgc 660
acttcatggt gggctccccc agtgcagctg tcagccagga cttggctcag ctcctcagcc 720
aggctgggct catgaagagt actgaacctg gagagccgcc ctgcattact tccgctggct 780
tccagttcct gttgctggac accccggctc agctctggta ctttatgttg cagtatttgc 840
agacagccca gagccggggc atggacctgg tagagattct ctccttcctc ttccagctca 900
gcttctctac tctgggcaag gattactctg tggaaggtat gagtgattct ctgttgaact 960
tcctgcaaca tctgcgtgag tttgggcttg ttttccagag gaagaggaaa tctcggcgtt 1020
actaccccac acgcctggcc atcaatctct catcaggtgt ctctggagct gggggcactg 1080
tgcatcagcc aggtttcatt gtcgtggaaa ccaattaccg actgtatgcc tacacggagt 1140
cggagctgca gattgccctc attgccctct tctctgagat gctctatcgg ttccccaaca 1200
tggtggtggc gcaggtgacc cgggagagtg tgcagcaggc aatcgccagt ggcatcacag 1260

```
cccagcagat aatccatttc ctaaggacaa gagcccaccc agtgatgctc aaacagacac   1320
ctgtgctgcc ccccaccatc accgaccaga tccggctctg ggagctggaa agggacagac   1380
tccggttcac tgagggtgtc ctgtataacc agttcctgtc gcaagtggac tttgagctgc   1440
tgctggccca cgcgcgggag ctgggcgtgc tcgtgttcga gaactcggcc aagcggctca   1500
tggtggtgac cccggccggg cacagcgacg tcaagcgctt ttggaagcgg cagaaacata   1560
gctcctgaga gcgcgggact tggacacgga cctcggcggg cgggactggg cggggcgggg   1620
catcagaact caggtgtttt ttatttacgc gtcagggctt ttcttgttta ataaagttat   1680
gatagctaaa aaaaaaaaaa aaaaaaaa                                      1708
```

<210> SEQ ID NO 39
<211> LENGTH: 2168
<212> TYPE: DNA
<213> ORGANISM: Homo sapiens

<400> SEQUENCE: 39

```
ggagttagcc tcgctcaggg cgcggctaag gcgcccagat ggcctgcggg cgccaccacg     60
tccctggtcc cagctcggga gcacatcaga ggcttagagg cgagtgggaa gggactcaga    120
cagtgcagga cgagaaacgc ccgcggcacc aaagcccctc agagcgtcgc ccccgcctct    180
agttctagaa agtcagtttc ccggcactgg caccccggaa cctcaggggc tgccgagctg    240
ggggggcgct caagctgcga ggatccgggc tgcccgcgag acgaggagcg ggcgcccagg    300
atggggtgca tgaagtccaa gttcctccag gtcggaggca atacattctc aaaaactgaa    360
accagcgcca gcccacactg tcctgtgtac gtgccggatc ccacatccac catcaagccg    420
gggcctaata gccacaacag caacacacca ggaatcaggg aggcaggctc tgaggacatc    480
atcgtggttg ccctgtatga ttacgaggcc attcaccacg aagacctcag cttccagaag    540
ggggaccaga tggtggtcct agaggaatcc ggggagtggt ggaaggctcg atccctggcc    600
acccggaagg agggctacat cccaagcaac tatgtcgccc gcgttgactc tctggagaca    660
gaggagtggt ttttcaaggg catcagccgg aaggacgcag agcgccaact gctggctccc    720
ggcaacatgc tgggctcctt catgatccgg gatagcgaga ccactaaagg aagctactct    780
ttgtccgtgc gagactacga ccctcggcag ggagataccg tgaaacatta caagatccgg    840
accctggaca acgggggctt ctacatatcc ccccgaagca ccttcagcac tctgcaggag    900
ctggtggacc actacaagaa ggggaacgac gggctctgcc agaaactgtc ggtgccctgc    960
atgtcttcca agccccagaa gccttgggag aaagatgcct gggagatccc tcgggaatcc   1020
ctcaagctgg agaagaaact tggagctggg cagtttgggg aagtctggat ggccacctac   1080
aacaagcaca ccaaggtggc agtgaagacg atgaagccag ggagcatgtc ggtggaggcc   1140
ttcctggcag aggccaacgt gatgaaaact ctgcagcatg acaagctggt caaacttcat   1200
gcggtggtca ccaaggagcc catctacatc atcacggagt tcatggccaa aggaagcttg   1260
ctggactttc tgaaaagtga tgagggcagc aagcagccat tgccaaaact cattgacttc   1320
tcagcccaga ttgcagaagg catggccttc atcgagcaga ggaactacat ccaccgagac   1380
ctccgagctg ccaacatctt ggtctctgca tccctggtgt gtaagattgc tgactttggc   1440
ctggcccggg tcattgagga caacgagtac acggctcggg aaggggccaa gttccccatc   1500
aagtggacag ctcctgaagc catcaacttt ggctccttca ccatcaagtc agacgtctgg   1560
tcctttggta tcctgctgat ggagatcgtc acctacggcc ggatccctta cccagggatg   1620
```

tcaaaccctg aagtgatccg agctctggag cgtggatacc ggatgcctcg cccagagaac 1680
tgcccagagg agctctacaa catcatgatg cgctgctgga aaaaccgtcc ggaggagcgg 1740
ccgaccttcg aatacatcca gagtgtgctg gatgacttct acacggccac agagagccag 1800
taccaacagc agccatgata gggaggacca gggcagggcc agggggtgcc caggtggtgg 1860
ctgcaaggtg gctccagcac catccgccag ggcccacacc cccttcctac tcccagacac 1920
ccaccctcgc ttcagccaca gtttcctcat ctgtccagtg ggtaggttgg actggaaaat 1980
ctctttttga ctcttgcaat ccacaatctg acattctcag gaagcccca agttgatatt 2040 tctatttcct ggaatggttg gattttagtt acagctgtga tttggaaggg aaactttcaa 2100
aatagtgaaa tgaatattta aataaaagat ataaatgcca aagtctttac caaaaaaaaa 2160
aaaaaaaa 2168

<210> SEQ ID NO 40
<211> LENGTH: 3628
<212> TYPE: DNA
<213> ORGANISM: Homo sapiens

<400> SEQUENCE: 40
aaaggcgggg aagggcgtgg tgggaagctc tgtccgcggt cgcgccagct gttccccggg 60
cagggtcgcc tctaggtgct cacctccgcc acttcgccat ggcgggtcct ggcccgggcg 120
cggtgctgga gtccccccgg cagctgctgg gccgcgtgcg cttcttggca gaggcagcgc 180
ggagcctccg cgccgggcgg ccgctgccag cagcgctggc tttcgtgccg cgagaggtgc 240
tctacaagct ttacaaggac ccagcgggac cgtcgcgcgt gcttctgccg gtgtgggagg 300
cagagggcct ggggctgcgt gtgggcgccg caggcccagc ccccggtacc ggctccgggc 360
ccctccgcgc cgcccgcgac agcattgagc tccggcgcgg cgcctgcgtg cgcaccacgg 420
gcgaggagct gtgcaatggc cacgggctct gggtgaagct gacaaaggag cagctggcag 480
agcacctggg cgactgcggg ctgcaggaag gctggctgct ggtgtgccgc ccggcggagg 540
gcggagcccg cctggtaccc atcgacactc ccaaccacct ccagcggcag cagcagctct 600
ttggcgtgga ttatcggccg gtgctcaggt gggaacaggt ggtggacctg acatactcac 660
atcgcctggg atcgagacct cagccggcag aggcatacgc agaagctgta caaaggctac 720
tctatgtacc cccgacatgg acctacgagt gcgacgagga cctgatccac ttcttgtatg 780
accacctggg caaggaggat gagaacctgg gtagcgtgaa gcagtatgtg gagagcatag 840
acgtttcctc ctacacggag gagttcaacg tgtcctgcct gacagacagc aatgccgata 900
cctactggga gagcgatggg tcccagtgcc aacactgggt acggcttact atgaagaagg 960
gcaccattgt caagaagctg ctactcacag tggataccac agatgacaac tttatgccaa 1020
agcgggtggt ggtctatggg ggtgaagggg acaacctgaa gaagctgagt gacgtgagca 1080
ttgacgagac cctcatcggg gatgtctgtg tcctggagga catgaccgtc cacctcccga 1140
tcatcgagat ccgcatcgtg gagtgccgag atgatgggat tgatgttcgt ctccgagggg 1200
tcaagatcaa gtcatctaga cagcgggaac tagggttgaa tgcagacctg ttccagccaa 1260
ctagtctggt gcgatatcca cgcctagaag gcaccgaccc tgaagtactg taccgcagag 1320
ctgtcctcct gcagagattc atcaagatcc tcgatagtgt cctgcaccac ctggtacctg 1380
cctgggacca cacactgggc accttcagtg agattaagca agtgaagcag ttcctactgc 1440
tgtcccgcca gcggccaggc ctggtggctc agtgcctgcg tgactctgag agcagcaagc 1500
ccagcttcat gccacgccta tacatcaacc gccgtcttgc catggaacac cgtgcctgcc 1560

```
cctctcgaga ccctgcctgc aagaatgcag tcttcaccca ggtatatgaa ggcctcaagc   1620
cctctgacaa atatgaaaag cccctggact acaggtggcc catgcgctat gaccagtggt   1680
gggagtgtaa atttattgca gaaggcatca ttgaccaagg gggtggtttc cgggacagcc   1740
tggcagatat gtcagaagag ctgtgcccta gctcagcgga tacccccgtg cccctgccct   1800
tctttgtacg cacagccaac cagggcaatg gcactggtga ggctcgggac atgtatgtac   1860
ccaacccctc ctgccgagac tttgccaagt atgaatggat cggacagctg atgggggctg   1920
cccttcgggg taaggagttc ctggtcctgg ccctgcctgg ttttgtgtgg aagcagcttt   1980
ctggtgagga ggtgagctgg agcaaggact tcccagctgt ggactctgtg ctggtgaagc   2040
tcctggaagt gatggaagga atggacaagg agacgtttga gttcaagttt gggaaggaac   2100
taacattcac cactgtactg agtgaccaac aggtggtgga gctgatccct gggggtgcag   2160
gcatcgtcgt gggatatggg gaccgttctc gtttcatcca actggtccag aaggcacggc   2220
tagaggagag caaggagcag gtggcagcta tgcaggcagg tctgctgaag gtggtaccac   2280
aggctgtgct ggacttgctg acctggcaag agttggagaa gaaagtgtgt ggggatccag   2340
aggtcactgt ggatgctctg cgcaagctca cccggtttga ggacttcgag ccatctgact   2400
cgcgggtgca gtatttctgg gaggcactga acaacttcac caacgaggac cggagccgct   2460
tcctgcgctt tgtcacgggc cgcagtcgcc tgccagcacg gatctacatc tacccagaca   2520
agctgggcta cgagaccaca gacgcgctgc ccgagtcttc cacttgctcc agcaccctct   2580
tcctgccaca ctatgccagt gccaaggtat gcgaggagaa gctccgctat gcggcctaca   2640
actgcgtggc catcgacact gacatgagcc cttgggagga gtgaggcgtg ccgccggctg   2700
tgggaccagc aagactgcac gtgtccctct tggccttgcc cagggcgaag acaccttccc   2760
tgccctggtt tggctgacgt gctcagcaaa accccatgtg ccctgctcct gtgtgcagtt   2820
ggggtagggg cagctggcat ggtcaggtaa cactagtggc ccagccccgc agacccacaa   2880
gccctacccg tgctggggct tgcttcccga ggtatttcac ctcttaagag ggaatcttcc   2940
acaagcccag cacaagctgc caggcctgag ctacttgaag gggccatct  aggtccccaa   3000
cccatggact ttgcctccat tttcagctcc gcctttttc  tcctattttc tctctggctt   3060
tcttcagcca tgactcacaa ctaaaaacat aaaacactgg aggttagtgg aggcccctcc   3120
ccaagcaggg agcctgggat gggcagggag tgatagccaa actccttggt cacctgctcc   3180
aagaaggaag cagtagctga gcacctgccc tcacattctg ctcttttccc ctctccctcc   3240
ataccagaga tgtggtgagc tctgttcttc taccaaccca gtctcaacac acaaagtgcc   3300
accaccttcc ctgactcaga acccacatcc actcaatgtg aactctacta ccacgacctc   3360
cccatattcc tcacttctcc atcacctcca gcctgactcc ctgtctgccc tttcaccccc   3420
aagattttgc acaggttaag gccagttatg gcctttttga aatctgtaat agctcccctt   3480
tccccaactc taaagcctag accttaaacc tgttcctaga gctatgcaca cccctgcccc   3540
agtttaccgt tcctccctca gggcctccgt gacactccat gaaaagaagt tcttgcatac   3600
cggaaagttg aataaatgga tgaattca                                      3628
```

<210> SEQ ID NO 41
<211> LENGTH: 3729
<212> TYPE: DNA
<213> ORGANISM: Homo sapiens

<400> SEQUENCE: 41

-continued

```
ggtcctaccc ggaagcgcgc ccgggctcct gcaggcgggg cgctgtgcgc gccgcgatcc     60
ggtacgtggg cctccgggct gtcccctctg ggggcggcga tcctccctcc ggagcccccc    120
ttcaaccctc ccggaagtga ggaccaggga tgctgtgctg ctctcccatg agccagtcac    180
cgagtcggtc tgctgcagcc ctttctgaac ctctggccgt ctggatgctc cactgtgctt    240
gccaagatga agtgcgtctt ggtggccact gagggcgcag aggtcctctt ctactggaca    300
gatcaggagt ttgaagagag tctccggctg aagttcgggc agtcagagaa tgaggaagaa    360
gagctccctg ccctggagga ccagctcagc accctcctag ccccggtcat catctcctcc    420
atgacgatgc tggagaagct ctcggacacc tacacctgct tctccacgga aaatggcaac    480
ttcctgtatg tccttcacct gtttggagaa tgcctgttca ttgccatcaa tggtgaccac    540
accgagagcg agggggacct gcggcggaag ctgtatgtgc tcaagtacct gtttgaagtg    600
cactttgggc tggtgactgt ggacggtcat cttatccgaa aggagctgcg gcccccagac    660
ctggcgcagc gtgtccagct gtgggagcac ttccagagcc tgctgtggac ctacagccgc    720
ctgcgggagc aggagcagtg cttcgccgtg gaggccctgg agcgactgat tcacccccag    780
ctctgtgagc tgtgcataga ggcgctggag cggcacgtca tccaggctgt caacaccagc    840
cccgagcggg gaggcgagga ggccctgcat gccttcctgc tcgtgcactc caagctgctg    900
gcattctact ctagccacag tgccagctcc ctgcgcccgg ccgacctgct tgccctcatc    960
ctcctggttc aggacctcta ccccagcgag agcacagcag aggacgacat tcagccttcc   1020
ccgcggaggg cccggagcag ccagaacatc cccgtgcagc aggcctggag ccctcactcc   1080
acgggcccaa ctgggggggag ctctgcagag acggagacag acagcttctc cctccctgag   1140
gagtacttca caccagctcc ttcccctggc gatcagagct caggtagcac catctggctg   1200
gaggggggca cccccccat ggatgccctt cagatagcag aggacaccct ccaaacactg   1260
gttccccact gccctgtgcc ttccggcccc agaaggatct tcctggatgc caacgtgaag   1320
gaaagctact gccccctagt gccccacacc atgtactgcc tgcccctgtg gcagggcatc   1380
aacctggtgc tcctgaccag gagccccagc gcgcccctgg ccctggttct gtcccagctg   1440
atggatggct tctccatgct ggagaagaag ctgaaggaag ggccggagcc cggggcctcc   1500
ctgcgctccc agcccctcgt gggagacctg cgccagagga tggacaagtt tgtcaagaat   1560
cgaggggcac aggagattca gagcacctgg ctggagttta aggccaaggc tttctccaaa   1620
agtgagcccg gatcctcctg ggagctgctc caggcatgtg ggaagctgaa gcggcagctc   1680
tgcgccatct accggctgaa ctttctgacc acagccccca gcaggggagg cccacacctg   1740
ccccagcacc tgcaggacca agtgcagagg ctcatgcggg agaagctgac ggactggaag   1800
gacttcttgc tggtgaagag caggaggaac atcaccatgg tgtcctacct agaagacttc   1860
ccaggcttgg tgcacttcat ctatgtggac cgcaccactg ggcagatggt ggcgccttcc   1920
ctcaactgca gtcaaaagac ctcgtcggag ttgggcaagg ggccgctggc tgcctttgtc   1980
aaaactaagg tctggtctct gatccagctg gcgcgcagat acctgcagaa gggctacacc   2040
acgctgctgt tccaggaggg ggatttctac tgctcctact tcctgtggtt cgagaatgac   2100
atggggtaca aactccagat gatcgaggtg cccgtcctct ccgacgactc agtgcctatc   2160
ggcatgctgg gaggagacta ctacaggaag ctcctgcgct actacagcaa gaaccgccca   2220
accgaggctg tcaggtgcta cgagctgctg gccctgcacc tgtctgtcat ccccactgac   2280
ctgctggtgc agcaggccgg ccagctggcc cggcgcctct gggaggcctc ccgtatcccc   2340
ctgctctagg ccaaggtggc cgcagtctgc ctttgcatcc tgtcctccag ccacccttgc   2400
```

```
ttgccactgt tccccatgac gagagcctcc tgtctgcagt ggccatcctg aggatagggc   2460
agagtgccca gggtggcccc agggcttcta aaaccccacc tagaccaccc tccatgtcag   2520
gtactgagca aggccccaga tccttctctc tggaggaaga gggaagccca ggggtcctgt   2580
ttgtaaaaca acggtggcaa cagctcctct tccagagctg cctctgcctt tatcctggga   2640
gatggggagg aagccccatc tctgctgttc cctgcgtgga ggaagcccac ccagcaagct   2700
ctctcctacc ccaggtaaaa ggtgctcctt tgcctgggtt tgaattccag cgctgccact   2760
tcctctctgc acctcctggc aagtttcttc tattccccac gtttaaagcg atggcacctc   2820
cgtcccaggg tggtgtgagg attacccagt gtggtaggtg ctcaataaat gttggtcatt   2880
gttatcactg aagcccaaca tgctagtgct tctagaccct tctgtcagtg ctgataagcc   2940
cttgctaagt cccagcccct tcatgcttgg ctggcgtctg ccctagggct ggggttctca   3000
agcccctggc cctggcccag agatttggat tcccttggcg gccgtggagc ccagcctttg   3060
atgtctttca aagcttctgt ggtgcgccct ggattgagaa ccaccacccg aggggtacag   3120
cccctctctt ccaaccgaga agttcctgtc ccagaatgga cccagggaca agagaccctg   3180
agagccctgg gactgggagt gtctgctcct ctgaggccag gaggccggtg ctgggccaga   3240
gaggacggcg tggcgaaagt cagcgtccac tgcagcacag gatcagatgg ccgtgtgctg   3300
tgcatgcagg agcctcgcct tctgtgtctt tagtcttgag ccaaaatttg ctcaaagact   3360
gatctcttcc ttgcagggaa cagctttggg gctgggggaa ctagaaccca catgttggtc   3420
taaaccctga gaaggtggca gtgaggaagt atcccctcag gtgactggat ctgtgttcct   3480
ccttaacatc atctgatgga atggcaatga aaagcgtgga ttgtggaaaa tacagaaaaa   3540
cataaaggaa aaaactccaa tcccctgagc ccaccactgt tcaggacccc tgcttttgtc   3600
acctactatt tccctttagt ttttagcagc ggctggatgt gatatgtcta gtttaaccag   3660
tcccttgat ctttctatat aataaataac acaggagtga acatcctgaa tcagaaaaaa   3720
aaaaaaaaa                                                           3729
```

<210> SEQ ID NO 42
<211> LENGTH: 2710
<212> TYPE: DNA
<213> ORGANISM: Homo sapiens

<400> SEQUENCE: 42

```
gctcatcttc ctaccagaaa tcggcaagtc actgaccctc gtcccgcccc cgccattccc     60
cgcctcctcc tgtcccgcag tcggcgtcca gcggctctgc ttgttcgtgt gtgtgtcgtt    120
gcaggcctta ttcatgggct caccgctgag gttcgacggg cgggtggtac tggtcaccgg    180
cgcgggggca ggattgggcc gagcctatgc cctggctttt gcagaaagag gagcgttagt    240
tgttgtgaat gatttgggag gggacttcaa aggagttggt aaaggctcct tagctgctga    300
taaggttgtt gaagaaataa gaaggagagg tggaaaagca gtggccaact atgattcagt    360
ggaagaagga gagaaggttg tgaagacagc cctggatgct tttggaagaa tagatgttgt    420
ggtcaacaat gctggaattc tgagggatcg ttcctttgct aggataagtg atgaagactg    480
ggatataatc cacagagttc atttgcgggg ttcattccaa gtgacacggg cagcatggga    540
acacatgaag aaacagaagt atggaaggat tattatgact tcatcagctt caggaatata    600
tggcaacttt ggccaggcca attatagtgc tgcaaagttg ggtcttctgg gccttgcaaa    660
ttctcttgca attgaaggca ggaaaagcaa cattcattgt aacaccattg ctcctaatgc    720
```

gggatcacgg atgactcaga cagttatgcc tgaagatctt gtggaagccc tgaagccaga 780
gtatgtggca cctcttgtcc tttggctttg tcacgagagt tgtgaggaga atggtggctt 840
gtttgaggtt ggagcaggat ggattggaaa attacgctgg gagcggactc ttggagctat 900
tgtaagacaa aagaatcacc caatgactcc tgaggcagtc aaggctaact ggaagaagat 960
ctgtgacttt gagaatgcca gcaagcctca gagtatccaa gaatcaactg gcagtataat 1020
tgaagttctg agtaaaatag attcagaagg aggagtttca gcaaatcata ctagtcgtgc 1080
aacgtctaca gcaacatcag gatttgctgg agctattggc cagaaactcc ctccattttc 1140
ttatgcttat acggaactgg aagctattat gtatgccctt ggagtgggag cgtcaatcaa 1200
ggatccaaaa gatttgaaat ttatttatga aggaagttct gatttctcct gtttgcccac 1260
cttcggagtt atcataggtc agaaatctat gatgggtgga ggattagcag aaattcctgg 1320
actttcaatc aactttgcaa aggttcttca tggagagcag tacttagagt tatataaacc 1380
acttcccaga gcaggaaaat taaaatgtga agcagttgtt gctgatgtcc tagataaagg 1440
atccggtgta gtgattatta tggatgtcta ttcttattct gagaaggaac ttatatgcca 1500
caatcagttc tctctctttc ttgttggctc tggaggcttt ggtggaaaac ggacatcaga 1560
caaagtcaag gtagctgtag ccatacctaa tagacctcct gatgctgtac ttacagatac 1620
cacctctctt aatcaggctg ctttgtaccg cctcagtgga gactggaatc ccttacacat 1680
tgatcctaac tttgctagtc tagcaggttt tgacaagccc atattacatg gattatgtac 1740
atttggattt tctgccaggc gtgtgttaca gcagtttgca gataatgatg tgtcaagatt 1800
caaggcaatt aaggctcgtt ttgcaaaacc agtatatcca ggacaaactc tacaaactga 1860
gatgtggaag gaaggaaaca gaattcattt tcaaaccaag gtccaagaaa ctggagacat 1920
tgtcatttca aatgcatatg tggatcttgc accaacatct ggtacttcag ctaagacacc 1980
ctctgagggc gggaagcttc agagtacctt tgtatttgag gaaataggac gccgcctaaa 2040
ggatattggg cctgaggtgg tgaagaaagt aaatgctgta tttgagtggc atataaccaa 2100
aggcggaaat attggggcta agtggactat tgacctgaaa agtggttctg gaaaagtgta 2160
ccaaggccct gcaaaaggtg ctgctgatac aacaatcata ctttcagatg aagatttcat 2220
ggaggtggtc ctgggcaagc ttgaccctca gaaggcattc tttagtggca ggctgaaggc 2280
cagagggaac atcatgctga gccagaaact tcagatgatt cttaaagact acgccaagct 2340
ctgaagggca cactacacta ttaataaaaa tggaatcatt aaatactctc ttcacccaaa 2400
tatgcttgat tattctgcaa aagtgattag aactaagatg caggggaaat tgcttaacat 2460
tttcagatat cagataactg cagattttca ttttctacta atttttcatg tatcattatt 2520
tttacaagga actatatata agctagcaca taattatcct tctgttctta gatctgtatc 2580
ttcataataa aaaattttgc ccaagtcctg tttccttaga atttgtgata gcattgataa 2640
gttgaaagga aaattaaatc aataaaggcc tttgatacct ttgttaaaaa aaaaaaaaaa 2700
aaaaaaaaaa 2710

<210> SEQ ID NO 43
<211> LENGTH: 888
<212> TYPE: DNA
<213> ORGANISM: Homo sapiens

<400> SEQUENCE: 43
gcatggcggc caccaggtgc ctgcgctggg gcctgagccg agccggagtc tggctgctcc 60
caccgcccgc acggtgccca cgccgggcgc tgcacaagca gaaagacggc actgagttca 120
agagcatcta cagcctggac aagctctacc ccgaatctca gggctcggac accgcctgga 180
gggtcccgaa tggtgcaaag caagccgaca gtgacatccc tctagatcgc ttgacaatat 240
cttattgtcg gagtagtggt cctggggggc agaatgtgaa caaagtgaat tccaaggcag 300
aagtcaggtt ccatttggca actgccgagt ggatcgcgga gcccgtgcgg cagaagatag 360
ccatcacgca taaaaacaag atcaacaggt taggagagtt gatccttacc tctgagagca 420
gccgctatca gttccggaat ctggcagatt gcctgcagaa aattcgagac atgatcactg 480
aggccagcca gacaccgaag gagccaacaa aagaagatgt taaacttcat agaatcagga 540
tagaaaacat gaatcgggaa aggctgagac aaaagagaat tcattctgct gtaaagacaa 600
gcaggagggt cgacatggac tgaaatcacc ctctgcagct gggagggctc ttctgggcgt 660
ccgggcagct gcagctgaga ggactttcac accataagga gatttctgtt tttctttttg 720
gctgttaatg cttgtctata acattggagc catcacaaga atgttcattt ggaatgaagg 780
ctgcaggcac tggttgcaga cgtctttata ggcagtcacc atgttgtcaa accttaataa 840
tgcacctcat gtattagtca caataaaaat cagaactcaa aaaaaaaa 888

<210> SEQ ID NO 44
<211> LENGTH: 9093
<212> TYPE: DNA
<213> ORGANISM: Homo sapiens

<400> SEQUENCE: 44
cgagcccagt cgagccgcgc tcacctcggg ctcccgctcc gtctccacct ccgcctttgc 60
cctggcggcg cgaccccgtc ccgggcgcgg cccccagcag tcgcgcgccg ttagcctcgc 120
gcccgccgcg cagtccgggc ccggcgcgat gggggccgcc gccggccgga gcccccacct 180
ggggcccgcg cccgcccgcc gcccgcagcg ctctctgctc ctgctgcagc tgctgctgct 240
cgtcgctgcc ccggggtcca cgcaggccca ggccgccccg ttccccgagc tgtgcagtta 300
tacatgggaa gctgttgata ccaaaaataa tgtactttat aaaatcaaca tctgtggaag 360
tgtggatatt gtccagtgcg ggccatcaag tgctgtttgt atgcacgact tgaagacacg 420
cacttatcat tcagtgggtg actctgtttt gagaagtgca accagatctc tcctggaatt 480
caacacaaca gtgagctgtg accagcaagg cacaaatcac agagtccaga gcagcattgc 540
cttcctgtgt gggaaaaccc tgggaactcc tgaatttgta actgcaacag aatgtgtgca 600
ctactttgag tggaggacca ctgcagcctg caagaaagac atatttaaag caaataagga 660
ggtgccatgc tatgtgtttg atgaagagtt gaggaagcat gatctcaatc ctctgatcaa 720
gcttagtggt gcctacttgg tggatgactc cgatccggac acttctctat tcatcaatgt 780
ttgtagagac atagacacac tacgagaccc aggttcacag ctgcgggcct gtcccccccgg 840 cactgccgcc tgcctggtaa gaggacacca ggcgtttgat gttggccagc cccgggacgg 900
actgaagctg gtgcgcaagg acaggcttgt cctgagttac gtgagggaag aggcaggaaa 960
gctagacttt tgtgatggtc acagccctgc ggtgactatt acatttgttt gcccgtcgga 1020
gcggagagag ggcaccattc ccaaactcac agctaaatcc aactgccgct atgaaattga 1080
gtggattact gagtatgcct gccacagaga ttacctggaa agtaaaactt gttctctgag 1140
cggcgagcag caggatgtct ccatagacct cacaccactt gcccagagcg gaggttcatc 1200
ctatatttca gatggaaaag aatatttgtt ttatttgaat gtctgtggag aaactgaaat 1260
acagttctgt aataaaaaac aagctgcagt ttgccaagtg aaaaagagcg atacctctca 1320
agtcaaagca gcaggaagat accacaatca gaccctccga tattcggatg gagacctcac 1380
cttgatatat tttggaggtg atgaatgcag ctcagggttt cagcggatga gcgtcataaa 1440
ctttgagtgc aataaaaccg caggtaacga tgggaaagga actcctgtat tcacagggga 1500
ggttgactgc acctacttct tcacatggga cacggaatac gcctgtgtta aggagaagga 1560
agacctcctc tgcggtgcca ccgacgggaa gaagcgctat gacctgtccg cgctggtccg 1620
ccatgcagaa ccagagcaga attgggaagc tgtggatggc agtcagacgg aaacagagaa 1680
gaagcatttt ttcattaata tttgtcacag agtgctgcag gaaggcaagg cacgagggtg 1740
tcccgaggac gcggcagtgt gtgcagtgga taaaaatgga agtaaaaatc tgggaaaatt 1800
tatttcctct cccatgaaag agaaaggaaa cattcaactc tcttattcag atggtgatga 1860
ttgtggtcat ggcaagaaaa ttaaaactaa tatcacactt gtatgcaagc caggtgatct 1920
ggaaagtgca ccagtgttga gaacttctgg ggaaggcggt tgcttttatg agtttgagtg 1980
gcacacagct gcggcctgtg tgctgtctaa gacagaaggg gagaactgca cggtctttga 2040
ctcccaggca gggttttctt ttgacttatc acctctcaca aagaaaaatg gtgcctataa 2100
agttgagaca aagaagtatg acttttatat aaatgtgtgt ggcccggtgt ctgtgagccc 2160
ctgtcagcca gactcaggag cctgccaggt ggcaaaaagt gatgagaaga cttggaactt 2220
gggtctgagt aatgcgaagc tttcatatta tgatgggatg atccaactga actacagagg 2280
cggcacaccc tataacaatg aaagacacac accgagagct acgctcatca cctttctctg 2340
tgatcgagac gcgggagtgg gcttccctga atatcaggaa gaggataact ccacctacaa 2400
cttccggtgg tacaccagct atgcctgccc ggaggagccc ctggaatgcg tagtgaccga 2460
cccctccacg ctggagcagt acgacctctc cagtctggca aaatctgaag gtggccttgg 2520
aggaaactgg tatgccatgg acaactcagg ggaacatgtc acgtggagga aatactacat 2580
taacgtgtgt cggcctctga atccagtgcc gggctgcaac cgatatgcat cggcttgcca 2640
gatgaagtat gaaaaagatc agggctcctt cactgaagtg gtttccatca gtaacttggg 2700
aatggcaaag accggcccgg tggttgagga cagcggcagc ctccttctgg aatacgtgaa 2760
tgggtcggcc tgcaccacca gcgatggcag acagaccaca tataccacga ggatccatct 2820
cgtctgctcc aggggcaggc tgaacagcca ccccatcttt tctctcaact gggagtgtgt 2880
ggtcagtttc ctgtggaaca cagaggctgc ctgtcccatt cagacaacga cggatacaga 2940
ccaggcttgc tctataaggg atcccaacag tggatttgtg tttaatctta atccgctaaa 3000
cagttcgcaa ggatataacg tctctggcat tgggaagatt tttatgttta atgtctgcgg 3060
cacaatgcct gtctgtggga ccatcctggg aaaacctgct tctggctgtg aggcagaaac 3120
ccaaactgaa gagctcaaga attggaagcc agcaaggcca gtcggaattg agaaaagcct 3180
ccagctgtcc acagagggct tcatcactct gacctacaaa gggcctctct ctgccaaagg 3240
taccgctgat gcttttatcg tccgctttgt ttgcaatgat gatgtttact cagggcccct 3300
caaattcctg catcaagata tcgactctgg gcaagggatc cgaaacactt actttgagtt 3360
tgaaaccgcg ttggcctgtg ttccttctcc agtggactgc caagtcaccg acctggctgg 3420
aaatgagtac gacctgactg gcctaagcac agtcaggaaa ccttggacgg ctgttgacac 3480
ctctgtcgat gggagaaaga ggactttcta tttgagcgtt tgcaatcctc tcccttacat 3540
tcctggatgc cagggcagcg cagtggggtc ttgcttagtg tcagaaggca atagctggaa 3600
tctgggtgtg gtgcagatga gtccccaagc cgcggcgaat ggatctttga gcatcatgta 3660
tgtcaacggt gacaagtgtg ggaaccagcg cttctccacc aggatcacgt ttgagtgtgc 3720
tcagatatcg ggctcaccag catttcagct tcaggatggt tgtgagtacg tgtttatctg 3780
gagaactgtg gaagcctgtc ccgttgtcag agtggaaggg gacaactgtg aggtgaaaga 3840
cccaaggcat ggcaacttgt atgacctgaa gcccctgggc ctcaacgaca ccatcgtgag 3900
cgctggcgaa tacacttatt acttccgggt ctgtgggaag ctttcctcag acgtctgccc 3960
cacaagtgac aagtccaagg tggtctcctc atgtcaggaa aagcgggaac cgcagggatt 4020
tcacaaagtg gcaggtctcc tgactcagaa gctaacttat gaaaatggct tgttaaaaat 4080
gaacttcacg gggggggaca cttgccataa ggtttatcag cgctccacag ccatcttctt 4140
ctactgtgac cgcggcaccc agcggccagt atttctaaag gagacttcag attgttccta 4200
cttgtttgag tggcgaacgc agtatgcctg cccacctttc gatctgactg aatgttcatt 4260
caaagatggg gctggcaact ccttcgacct ctcgtccctg tcaaggtaca gtgacaactg 4320
ggaagccatc actgggacgg gggacccgga gcactacctc atcaatgtct gcaagtctct 4380
ggccccgcag gctggcactg agccgtgccc tccagaagca gccgcgtgtc tgctgggtgg 4440
ctccaagccc gtgaacctcg gcagggtaag ggacggacct cagtggagag atggcataat 4500
tgtcctgaaa tacgttgatg gcgacttatg tccagatggg attcggaaaa agtcaaccac 4560
catccgattc acctgcagcg agagccaagt gaactccagg cccatgttca tcagcgccgt 4620
ggaggactgt gagtacacct ttgcctggcc cacagccaca gcctgtccca tgaagagcaa 4680
cgagcatgat gactgccagg tcaccaaccc aagcacagga cacctgtttg atctgagctc 4740
cttaagtggc agggcgggat tcacagctgc ttacagcgag aaggggttgg tttacatgag 4800
catctgtggg gagaatgaaa actgccctcc tggcgtgggg gcctgctttg gacagaccag 4860
gattagcgtg ggcaaggcca acaagaggct gagatacgtg gaccaggtcc tgcagctggt 4920
gtacaaggat gggtcccctt gtccctccaa atccggcctg agctataaga gtgtgatcag 4980
tttcgtgtgc aggcctgagg ccgggccaac caataggccc atgctcatct ccctggacaa 5040
gcagacatgc actctcttct tctcctggca cacgccgctg gcctgcgagc aagcgaccga 5100
atgttccgtg aggaatggaa gctctattgt tgacttgtct ccccttattc atcgcactgg 5160
tggttatgag gcttatgatg agagtgagga tgatgcctcc gataccaacc ctgatttcta 5220
catcaatatt tgtcagccac taaatcccat gcacggagtg ccctgtcctg ccggagccgc 5280
tgtgtgcaaa gttcctattg atggtccccc catagatatc ggccgggtag caggaccacc 5340
aatactcaat ccaatagcaa atgagattta cttgaatttt gaaagcagta ctccttgctt 5400
agcggacaag catttcaact acacctcgct catcgcgttt cactgtaaga gaggtgtgag 5460
catgggaacg cctaagctgt taaggaccag cgagtgcgac tttgtgttcg aatgggagac 5520
tcctgtcgtc tgtcctgatg aagtgaggat ggatggctgt accctgacag atgagcagct 5580
cctctacagc ttcaacttgt ccagcctttc cacgagcacc tttaaggtga ctcgcgactc 5640
gcgcacctac agcgttgggg tgtgcacctt tgcagtcggg ccagaacaag gaggctgtaa 5700
ggacggagga gtctgtctgc tctcaggcac caagggggca tcctttggac ggctgcaatc 5760
aatgaaactg gattacaggc accaggatga agcggtcgtt ttaagttacg tgaatggtga 5820
tcgttgccct ccagaaaccg atgacggcgt cccctgtgtc ttccccttca tattcaatgg 5880
gaagagctac gaggagtgca tcatagagag cagggcgaag ctgtggtgta gcacaactgc 5940
ggactacgac agagaccacg agtggggctt ctgcagacac tcaaacagct accggacatc 6000
cagcatcata tttaagtgtg atgaagatga ggacattggg aggccacaag tcttcagtga 6060

-continued

```
agtgcgtggg tgtgatgtga catttgagtg gaaaacaaaa gttgtctgcc ctccaaagaa   6120
gttggagtgc aaattcgtcc agaaacacaa aacctacgac ctgcggctgc tctcctctct   6180
caccgggtcc tggtccctgg tccacaacgg agtctcgtac tatataaatc tgtgccagaa   6240
aatatataaa gggcccctgg gctgctctga aagggccagc atttgcagaa ggaccacaac   6300
tggtgacgtc caggtcctgg gactcgttca cacgcagaag ctgggtgtca taggtgacaa   6360
agttgttgtc acgtactcca aaggttatcc gtgtggtgga aataagaccg catcctccgt   6420
gatagaattg acctgtacaa agacggtggg cagacctgca ttcaagaggt ttgatatcga   6480
cagctgcact tactacttca gctgggactc ccgggctgcc tgcgccgtga agcctcagga   6540
ggtgcagatg gtgaatggga ccatcaccaa ccctataaat ggcaagagct tcagcctcgg   6600
agatatttat tttaagctgt tcagagcctc tggggacatg aggaccaatg gggacaacta   6660
cctgtatgag atccaacttt cctccatcac aagctccaga aacccggcgt gctctggagc   6720
caacatatgc caggtgaagc ccaacgatca gcacttcagt cggaaagttg gaacctctga   6780
caagaccaag tactaccttc aagacggcga tctcgatgtc gtgtttgcct cttcctctaa   6840
gtgcggaaag gataagacca agtctgtttc ttccaccatc ttcttccact gtgaccctct   6900
ggtggaggac gggatccccg agttcagtca cgagactgcc gactgccagt acctcttctc   6960
ttggtacacc tcagccgtgt gtcctctggg ggtgggcttt gacagcgaga atcccgggga   7020
cgacgggcag atgcacaagg ggctgtcaga acggagccag gcagtcggcg cggtgctcag   7080
cctgctgctg gtggcgctca cctgctgcct gctggccctg ttgctctaca agaaggagag   7140
gagggaaaca gtgataagta agctgaccac ttgctgtagg agaagttcca acgtgtccta   7200
caaatactca aaggtgaata aggaagaaga gacagatgag aatgaaacag agtggctgat   7260
ggaagagatc cagctgcctc ctccacggca gggaaaggaa gggcaggaga acggccatat   7320
taccaccaag tcagtgaaag ccctcagctc cctgcatggg gatgaccagg acagtgagga   7380
tgaggttctg accatcccag aggtgaaagt tcactcgggc aggggagctg gggcagagag   7440
ctcccaccca gtgagaaacg cacagagcaa tgcccttcag gagcgtgagg acgatagggt   7500
ggggctggtc aggggtgaga aggcgaggaa agggaagtcc agctctgcac agcagaagac   7560
agtgagctcc accaagctgg tgtccttcca tgacgacagc gacgaggacc tcttacacat   7620
ctgactccgc agtgcctgca ggggagcacg gagccgcggg acagccaagc acctccaacc   7680
aaataagact tccactcgat gatgcttcta taattttgcc tttaacagaa actttcaaaa   7740
gggaagagtt tttgtgatgg gggagagggt gaaggaggtc aggccccact ccttcctgat   7800
tgtttacagt cattggaata aggcatggct cagatcggcc acagggcggt accttgtgcc   7860
cagggttttg ccccaagtcc tcatttaaaa gcataaggcc ggacgcatct caaaacagag   7920
ggctgcattc gaagaaaccc ttgctgcttt agtcccgata gggtatttga ccccgatata   7980
ttttagcatt ttaattctct cccccctattt attgactttg acaattactc aggtttgaga   8040
aaaaggaaaa aaaaacagcc accgtttctt cctgccagca ggggtgtgat gtaccagttt   8100
gtccatcttg agatggtgag gctgtcagtg tatggggcag cttccggcgg gatgttgaac   8160
tggtcattaa tgtgtcccct gagttggagc tcattctgtc tcttttctct tttgctttct   8220
gtttcttaag ggcacacaca cgtgcgtgcg agcacacaca cacatacgtg cacagggtcc   8280
ccgagtgcct aggttttgga gagtttgcct gttctatgcc tttagtcagg aatggctgca   8340
cctttttgca tgatatcttc aagcctgggc gtacagagca catttgtcag tatttttgcc   8400
ggctggtgaa ttcaaacaac ctgcccaaag attgatttgt gtgtttgtgt gtgtgtgtgt   8460
```

gtgtgtgtgt gtgtgtgtga gtggagttga ggtgtcagag aaaatgaatt ttttccagat 8520
ttggggtata ggtctcatct cttcaggttc tcatgatacc acctttactg tgcttatttt 8580
tttaagaaaa aagtgttgat caaccattcg acctataaga agccttaatt tgcacagtgt 8640
gtgacttaca gaaactgcat gaaaaatcat gggccagagc ctcggcccta gcattgcact 8700
tggcctcatg ctggagggag gctgggcggg tacagcgcgg aggaggaggg aggccaggcg 8760
ggcatggcgt ggaggaggag ggaggccggg cggtcacagc atggaggagg agggaggcgc 8820
tgctggtgtt cttattctgg cggcagcgcc tttcctgcca tgtttagtga atgacttttc 8880
tcgcattgta gaattgtata tagactctgg tgttctattg ctgagaagca aaccgccctg 8940
cagcatccct cagcctgtac cggtttggct ggcttgtttg atttcaacat gagtgtattt 9000
tttaaaattg atttttctct tcattttttt ttcaatcaac tttactgtaa tataaagtat 9060
tcaacaattt caataaaaga taaattatta aaa 9093

<210> SEQ ID NO 45
<211> LENGTH: 7014
<212> TYPE: DNA
<213> ORGANISM: Homo sapiens

<400> SEQUENCE: 45
cggggaccgc gacgagcccg ggtcgccgtt ggcagcagca gcagcaacac cagcagcagc 60
agcagccccg gcggcggcgc ggaccccgag cgcccgggcg caccccggct tcccggagcg 120
cgacgcggcg gcagcagccc cggtgcggcc gcgcgcgcct taggctcggc cccgcggctc 180
ggggaccccg actcccggcc cagcgagcgc gtcccccggc gccgcccgag agcccgagga 240
ggcagcggcc gcaggcagcc ggggaggggg gcggccaccg cccgcgccgg gcatcctcag 300
gagccccaga gcgcggaggg cgcggcgccg ccgagcggtg ctggccccgg cgggcctccc 360
cggaccttcc ccaccgcctg ggcccgaggg acgcgtgatc gggcgggcgg ccgggcgcaa 420
gggtgggagg gagccgcccc cgcccgcgcc ccctccgccc ctcgccccaa cccctgggcg 480
ccgggcccgg gccgcgcggc ctgaagcgcc cgcgatggcg agcccgccgc ggcacgggcc 540
gcccgggccg gcgagcggag acggccccaa cctcaacaac aacaacaaca acaacaacca 600
cagcgtgcgc aagtgcggct acctgcgcaa gcagaagcat ggccacaagc gcttcttcgt 660
gctgcgcgga cccggcgcgg gcggcgacga ggcgacggcg ggcggggggt cggcgccgca 720
accgccgcgg ctcgagtact acgagagcga gaaaaagtgg cggagcaagg caggcgcgcc 780
gaaacgggtg atcgctctcg actgctgcct gaacatcaac aagcgcgccg acgccaagca 840
caagtacctg atcgccctct acaccaagga cgagtacttc gccgtggccg ccgagaacga 900
gcaggagcag gagggctggt accgcgcgct caccgacctg gtcagcgagg gccgcgcggc 960
cgccggagac gcgccccccg ccgccgcgcc cgccgcgtcc tgcagcgcct ccctgcccgg 1020
cgccctgggc ggctctgccg gcgccgccgg ggccgaggac agctacgggc tggtggctcc 1080
cgccacggcc gcctaccgtg aggtgtggca ggtgaacctg aagcccaagg gtctgggcca 1140
gagcaagaac ctgacggggg tgtaccgtct gtgcctgtct gcgcgcacca tcggcttcgt 1200
gaagctcaac tgcgagcagc cgtcggtgac gctgcagctc atgaacatcc gccgctgcgg 1260
ccactcggac agcttcttct tcatcgaggt gggccgctcg gccgtcacag gccccggcga 1320
gctgtggatg caggcggacg actcggtggt ggcgcagaac atccacgaga ccatcctgga 1380
ggccatgaag gcgctcaagg agctcttcga gttccggccg cgcagtaaga gccaatcgtc 1440

-continued

```
ggggtcgtcg gccacgcacc ccatcagcgt ccccggcgcg cgccgccacc accacctggt   1500
caacctgccc cccagccaga cgggcctggt gcgccgctcg cgcaccgaca gcctggccgc   1560
caccccgccg gcggccaagt gcagctcgtg ccgggtgcgc accgccagcg agggcgacgg   1620
cggcgcggcg gcgggagcgg cggccgcggg cgccaggccg gtgtcggtgg ctgggagccc   1680
cctgagcccc gggccggtgc gcgcgcccct gagccgctcg cacaccctga gcggcggctg   1740
cggcggccgc gggagcaagg tggcgctgct gccggcaggg ggcgcgctgc aacacagccg   1800
ctccatgtcc atgcccgtgg cgcactcgcc gcccgccgcc accagccccg gctccctgtc   1860
gtccagcagc ggccacggct cgggctccta cccgccgccg cccggcccgc acccgcctct   1920
gccgcatccg ctgcaccacg gccccggcca gcggccctcc agcggcagcg cctccgcctc   1980
gggctccccc agcgaccccg gcttcatgtc cctggacgag tacggctcca gcccaggcga   2040
cctgcgcgcc ttctgcagcc accgaagcaa cacgcccgag tccatcgcgg agacgccccc   2100
ggcccgagac ggcggcggcg gcggtgagtt ctacgggtac atgaccatgg acaggcccct   2160
gagccactgt ggccgctcct accgccgggt ctcgggggac gcggcccagg acctggaccg   2220
agggctgcgc aagaggacct actccctgac cacgccagcc cggcagcggc cggtgcccca   2280
gccctcctct gcctcgctgg atgaatacac cctgatgcgg gccaccttct cgggcagcgc   2340
gggccgcctc tgcccgtcct gccccgcgtc ctctcccaag gtggcctacc acccctaccc   2400
agaggactac ggagacatcg agatcggctc ccacaggagc tccagcagca acctgggggc   2460
agacgacggc tacatgccca tgacgcccgg cgcggccctc gcgggcagtg ggagcggcag   2520
ctgcaggagc gacgactaca tgcccatgag ccccgccagc gtgtccgccc ccaagcagat   2580
cttgcagccc agggccgccg ccgccgccgc cgccgccgtg ccttctgcgg ggcctgcggg   2640
gccagcaccc acctctgcgg cgggcaggac attcccggcg agcgggggcg gctacaaggc   2700
cagctcgccc gccgagagct cccccgagga cagtgggtac atgcgcatgt ggtgcggttc   2760
caagctgtcc atggagcatg cagatggcaa gctgctgccc aacggggact acctcaacgt   2820
gtcccccagc gacgcggtca ccacgggcac cccgcccgac ttcttctccg cagccctgca   2880
ccccggcggg gagccgctca ggggcgttcc cggctgctgc tacagctcct tgccccgctc   2940
ctacaaggcc ccctacacct gtggcgggga cagcgaccag tacgtgctca tgagctcccc   3000
cgtggggcgc atcctggagg aggagcgtct ggagcctcag gccacgccag ggcccagcca   3060
ggcggccagc gccttcgggg ccggccccac gcagcccccct caccctgtag tgccttcgcc   3120
cgtgcggcct agcggcggcc gcccggaggg cttcttgggc cagcgcggcc gggcggtgag   3180
gcccacgcgc ctgtccctgg aggggctgcc cagcctgccc agcatgcacg agtacccact   3240
gccaccggag cccaagagcc ccggcgagta catcaacatc gactttggcg agcccggggc   3300
ccgcctgtcg ccgcccgcgc ctcccctgct ggcgtcggcg gcctcgtcct cctcgctctt   3360
gtccgccagc agcccggcct cgtcgctggg ctcaggcacc ccgggcacca gcagcgacag   3420
ccggcagcgg tctccgctct ccgactacat gaacctcgac ttcagctccc ccaagtctcc   3480
taagccgggc gccccgagcg gccaccccgt gggctccttg gacggcctcc tgtcccccga   3540
ggcctcctcc ccgtatccgc cgttgccccc gcgtccgtcc gcgtccccgt cgtcgtctct   3600
gcagccgccg ccaccgccgc cggccccggg ggagctgtac cgcctgcccc ccgcctcggc   3660
cgttgccacc gcccagggcc cgggcgccgc ctcatcgttg tcctcggaca ccggggacaa   3720
tggtgactac accgagatgg cttttggtgt ggccgccacc ccgccgcaac ctatcgcggc   3780
ccccccgaag ccagaagctg cccgcgtggc cagcccgacg tcgggcgtga agaggctgag   3840
```

-continued

```
cctcatggag caggtgtcgg gagtcgaggc cttcctgcag gccagccagc cccggaccc   3900
ccaccgcggc gccaaggtca tccgcgcaga cccgcagggg ggccgccgcc gccacagttc   3960
cgagaccttc tcctccacca cgacggtcac ccccgtgtcc ccgtccttcg cccacaaccc   4020
caagcgccac aactcggcct ccgtggaaaa tgtctctctc aggaaaagca gcgagggcgg   4080
cgtgggtgtc ggccctggag ggggcgacga gccgcccacc tccccacgac agttgcagcc   4140
ggcgcccccct ttggcaccgc agggccggcc gtggaccccg ggtcagcccg gggcttggt   4200
cggttgtcct gggagcggtg gatcgcccat gcgcagagag acctctgccg gcttccagaa   4260
tggtctcaac tacatcgcca tcgacgtgag ggaggagccc gggctgccac cccagccgca   4320
gccgccgccg ccgccgcttc ctcagccggg agacaagagc tcctggggcc ggacccgaag   4380
cctcgggggt ctcatcagcg ctgtgggcgt cggcagcacc ggcggcgggt gcggggggcc   4440
gggtcccggt gccctgcccc ctgccaacac ctacgccagc attgacttct tgtcccacca   4500
cttgaaggag gccaccatcg tgaaagagtg aagatctgtc tggctttatc accaggatgt   4560
cacatgtcag agagtatcat taaaagaaga cgctcagcac tgtttcagcc cgaagctgct   4620
tgcagttttc ttttggatct gagcaatgac tgtgtttgga aacatctgtg gactctgtta   4680
gatgaggcac caacaaggca aggtcacctg cctctttccc ttgttcccgg atggggcatt   4740
catcattgtg ctgtttgcgt tttgttttgt tttgttttaa caaaattagc tgaagaagtt   4800
attctcaaga aaattggatg ttttcattgg ccttcttaaa ttgtggccag tgtcttttaa   4860
tttcttcttc ttttcctttt ggcaaagcag atataaccct cagcatgcta ggagagtgca   4920
cccgtaccta tggaagtggt aaaatctggt atttactggc ttacactcaa aacgaccaca   4980
gtcctacctc agttcaaggt aaagccggat ttccgtggcg ggggtcccac aggacctcct   5040
gtagtagccc ctgcgctgtg tgtctggagc gcggtcctcg gccttattga aatggtccaa   5100
gtagacagct gcttgttgga ttccagtgca ggtacctgcg atgtttacgt ccacaccgag   5160
cccagtgtgg gactgacatt tctcaatgga agtgaaattt gggattggac tttgaagacg   5220
gattactaaa taataattat tatatgtaac tgaagcaacc tacttttgaa aatcaactgt   5280
attgggtagt gggaggtggg agggaagggc tttgggaagg ggatgaatat ctctttttac   5340
ctttaacaga cttgtttaat cttctcgatg tagatgttta tgtaggtact tcacattgca   5400
aacgcctttt attctattta caagctcaga tgtctctgct ctcctgaatc ttgggcatgc   5460
ctttctgtaa ccaaaaatcc ctgtaggcgt gctagcaatt ccagggtggt ccgggtttgg   5520
cagatttgat ttttaaaaaa cgtattatct ttaataaaat gttattatgt caaccagtga   5580
ggctgccctg aacaaaaaaa acaaaaagaa aaaaaaaaaa ggaaagaaag aaactgataa   5640
aaagaggcat tccagcccct atgttattga tggaaaaaga aaaagaagaa aagcaatctc   5700
gcagtacatg ttacttgtcg aaaaaattcc ggacaagact acccttgttt tatgttttca   5760
gtattctgaa aataccagtg tgtggcagtt ctcgcagatg ttacctaaaa ctgctgaact   5820
tgaccggcag aatgttctgc cgttttctgc tccctcgaca cttgattgga gggctgtcga   5880
cctctcctcc cgtgggggct tccccagtgc ctatcttctc tgatagtcat ggagaggtta   5940
cactaattca ttggagatgt aagttgttgg ttttgttttg ttttgttttt agaaaaatat   6000
atataaatat ataatagata tctatcgcta tagaataatg cattaataaa atgaggcttt   6060
tttagaggaa gaccaaaaaa ttcaatgtct taaaaatata tttaatggca atgcaaaagt   6120
cttcctgctt ccgtgctgaa ctttagaaca gaggattgta ttgcaagaca aagttgaatg   6180
```

taaagtgatc tccctgaaca tttttaaggt tttacttttc tgaaattata catcacagca 6240
gtgcataggc catataatgt tagctggaag gtcaatttca gtgtatgata tactttatta 6300
agatgtataa aaatcctgaa gtttttattt agttttggga ataggcatca atgggtggta 6360
tttgctttgt aactcccccc aggtacgata gggactgaat atggaccctg ctgaaagcag 6420
tgtattgacg catatttaac tcgccctcta tccgtagagt agtcatgaca ctatacagat 6480
ggttcgtgtt catactgcag cttaaaacaa gcaaaataca cagatgataa tatgctaaat 6540
tttcctctat cctgtacatt tcacaaaaag gcatatgcaa tatttacatt tttaatttag 6600
tttacagaat ggaaccaaaa tgtataaatg ttatgtttgc taaaacttca caatgtatat 6660
tgggtctttg tacattttgc ctgacttacc ttaaatttaa aatatttttt gctatataaa 6720
ctttaacagt tattaaacag tgttttcttt ttgggtacgt attgtttctg gatatcaaga 6780
tgttaaatat atttcttgct attgtgatat gacaagagac ttaacttatc ttgctctgtc 6840
ttccactgta cacgctgtat ataggggtca atgtgatgct gctggagacg agaataaact 6900
ggactagaat agtgcattgt atttagtctg tattgatcat ggatgccctc cttaatagcc 6960
atatgcaata aaataaagta cattatttat gaaatgaaaa aaaaaaaaaa aaaa 7014

<210> SEQ ID NO 46
<211> LENGTH: 3392
<212> TYPE: DNA
<213> ORGANISM: Homo sapiens

<400> SEQUENCE: 46
gcggagccag cccctcccct acccggagca gcccgctggg gccgtcccga gcggcgacac 60
actaggagtc ccggccggcc agccagggca gccgcggtcc cgggactcgg ccgtgagtgc 120
tgcgggacgg atggtggcgg cggggcgcgg gccagcgcgg gcgccgtgag ccggagctgc 180
gcgcggggca tgcggctgcg gccccccggcc ctcggccccc gcgctccggc cccagccccg 240
gccgccggcc cccgcggagt gcagcgaccg cgccgccgct gagggaggcg ccccaccatg 300
ccgcgggccc cggcgccgct gtacgcctgc ctcctggggc tctgcgcgct cctgccccgg 360
ctcgcaggtc tcaacatatg cactagtgga agtgccacct catgtgaaga atgtctgcta 420
atccacccaa aatgtgcctg gtgctccaaa gaggacttcg gaagcccacg gtccatcacc 480
tctcggtgtg atctgagggc aaaccttgtc aaaaatggct gtggaggtga gatagagagc 540
ccagccagca gcttccatgt cctgaggagc ctgcccctca gcagcaaggg ttcgggctct 600
gcaggctggg acgtcattca gatgacacca caggagattg ccgtgaacct ccggcccggt 660
gacaagacca ccttccagct acaggttcgc caggtggagg actatcctgt ggacctgtac 720
tacctgatgg acctctccct gtccatgaag gatgacttgg acaatatccg gagcctgggc 780
accaaactcg cggaggagat gaggaagctc accagcaact tccggttggg atttgggtct 840
tttgttgata aggacatctc tcctttctcc tacacggcac cgaggtacca gaccaatccg 900
tgcattggtt acaagttgtt tccaaattgc gtcccctcct ttgggttccg ccatctgctg 960
cctctcacag acagagtgga cagcttcaat gaggaagttc ggaaacagag ggtgtcccgg 1020
aaccgagatg cccctgaggg gggctttgat gcagtactcc aggcagccgt ctgcaaggag 1080
aagattggct ggcgaaagga tgcactgcat ttgctggtgt tcacaacaga tgatgtgccc 1140
cacatcgcat tggatggaaa attgggaggc ctggtgcagc cacacgatgg ccagtgccac 1200
ctgaacgagg ccaacgagta cactgcatcc aaccagatgg actatccatc ccttgccttg 1260
cttggagaga aattggcaga gaacaacatc aacctcatct ttgcagtgac aaaaaaccat 1320

```
tatatgctgt acaagaattt tacagccctg atacctggaa caacggtgga gattttagat   1380
ggagactcca aaaatattat tcaactgatt attaatgcat acaatagtat ccggtctaaa   1440
gtggagttgt cagtctggga tcagcctgag gatcttaatc tcttctttac tgctacctgc   1500
caagatgggg tatcctatcc tggtcagagg aagtgtgagg gtctgaagat tggggacacg   1560
gcatcttttg aagtatcatt ggaggcccga agctgtccca gcagacacac ggagcatgtg   1620
tttgccctgc ggccggtggg attccgggac agcctggagg tgggggtcac ctacaactgc   1680
acgtgcggct gcagcgtggg gctggaaccc aacagtgcca ggtgcaacgg gagcgggacc   1740
tatgtctgcg gcctgtgtga gtgcagcccc ggctacctgg gcaccaggtg cgagtgccag   1800
gatggggaga accagagcgt gtaccagaac ctgtgccggg aggcagaggg caagccactg   1860
tgcagcgggc gtggggactg cagctgcaac cagtgctcct gcttcgagag cgagttcggc   1920
aagatctatg ggcctttctg tgagtgcgac aacttctcct gtgccaggaa caagggagtc   1980
ctctgctcag gccatggcga gtgtcactgc ggggaatgca agtgccatgc aggttacatc   2040
ggggacaact gtaactgctc gacagacatc agcacatgcc ggggcagaga tggccagatc   2100
tgcagcgagc gtgggcactg tctctgtggg cagtgccaat gcacggagcc gggggccttt   2160
ggggagatgt gtgagaagtg ccccacctgc ccggatgcat gcagcaccaa gagagattgc   2220
gtcgagtgcc tgctgctcca ctctgggaaa cctgacaacc agacctgcca cagcctatgc   2280
agggatgagg tgatcacatg ggtggacacc atcgtgaaag atgaccagga ggctgtgcta   2340
tgtttctaca aaaccgccaa ggactgcgtc atgatgttca cctatgtgga gctccccagt   2400
gggaagtcca acctgaccgt cctcagggag ccagagtgtg gaaacacccc caacgccatg   2460
accatcctcc tggctgtggt cggtagcatc ctccttgttg ggcttgcact cctggctatc   2520
tggaagctgc ttgtcaccat ccacgaccgg agggagtttg caaagtttca gagcgagcga   2580
tccagggccc gctatgaaat ggcttcaaat ccattataca gaaagcctat ctccacgcac   2640
actgtggact tcaccttcaa caagttcaac aaatcctaca atggcactgt ggactgatgt   2700
ttccttctcc gaggggctgg agcggggatc tgatgaaaag gtcagactga aacgccttgc   2760
acggctgctc ggcttgatca cagctcccta ggtaggcacc acagagaaga ccttctagtg   2820
agcctgggcc aggagcccac agtgcctgta caggaaggtg cctggccatg tcacctggct   2880
gctaggccag agccatgcca ggctgcgtcc ctccgagctt gggataaagc aaggggacct   2940
tggcactctc agctttccct gccacatcca gcttgttgtc ccaatgaaat actgagatgc   3000
tgggctgtct ctcccttcca ggaatgctgg gcccccagcc tggccagaca agacgactgt   3060
caggaagggt cggagtctgt aaaaccagca tacagtttgg ctttttttcac attgatcatt   3120
tttatatgaa ataaaaagat cctgcattta tggtgtagtt ctgagtcctg agacttttcc   3180
gcgtgatggc tatgccttgc acacaggtgt tggtgatggg gctgttgaga tgcctgttga   3240
aggtacatcg tttgcaaatg tcagtttcct ctcctgtccg tgtttgttta gtacttttat   3300
aatgaaaaga aacaagattg tttgggattg gaagtaaaga ttaaaaccaa aagaatttgt   3360
gtttgtctga taaaaaaaaa aaaaaaaaaa aa                                 3392
```

<210> SEQ ID NO 47
<211> LENGTH: 3463
<212> TYPE: DNA
<213> ORGANISM: Homo sapiens

<400> SEQUENCE: 47

-continued

```
aatgaaacga agcgctgagg aaagtggctt gggtttgaat attgtggttg agtctgaagc     60
gctgggaggc ggacattaaa gtgaagtggt tgcggtaacc tggcctgggc ctgaagtgag    120
tgagaggcac atgaagagaa gtattcaagt atttatacag ataggaatca agataatcaa    180
caatgtctgt cactgaggaa gacctgtgcc accatatgaa agtagtagtt cgtgtacgtc    240
cggaaaacac taaagaaaaa gcagctggat ttcataaagt ggttcatgtt gtggataaac    300
atatcctagt ttttgatccc aaacaagaag aagtcagttt tttccatgga aagaaaacta    360
caaatcaaaa tgttataaag aaacaaaata aggatcttaa atttgtattt gatgctgttt    420
ttgatgaaac gtcaactcag tcagaagttt ttgaacacac tactaagcca attcttcgta    480
gtttttttgaa tggatataat tgcacagtac ttgcctatgg tgccactggt gctgggaaga    540
cccacactat gctaggatca gctgatgaac ctggagtgat gtatctaaca atgttacacc    600
tttacaaatg catggatgag attaaagaag agaaaatatg tagtactgca gtttcatatc    660
tggaggtata taatgaacag attcgtgatc tcttagtaaa ttcagggcca cttgctgtcc    720
gggaagatac ccaaaaaggg gtggtcgttc atggacttac tttacaccag cccaaatcct    780
cagaagaaat tttacattta ttggataatg gaaacaaaaa caggacacaa catcccactg    840
atatgaatgc cacatcttct cgttctcatg ctgttttcca aatttacttg cgacaacaag    900
acaaaaacagc aagtatcaat caaaatgtcc gtattgccaa gatgtcactc attgacctgg    960
caggatctga gcgagcaagt acttccggtg ctaaggggac ccgatttgta gaaggcacaa   1020
atattaatag atcactttta gctcttggga atgtcatcaa tgccttagca gattcaaaga   1080
gaaagaatca gcatatccct tacagaaata gtaagcttac tcgcttgtta aaggattctc   1140
ttggaggaaa ctgtcaaact ataatgatag ctgctgttag tccttcctct gtattctacg   1200
atgacacata taacactctt aagtatgcta accgggcaaa ggacattaaa tcttctttga   1260
agagcaatgt tcttaatgtc aataatcata taactcaata tgtaaagatc tgtaatgagc   1320
agaaggcaga gattttattg ttaaaagaaa aactaaaagc ctatgaagaa cagaaagcct   1380
tcactaatga aaatgaccaa gcaaagttaa tgatttcaaa ccctcaggaa aaagaaatcg   1440
aaaggtttca agaaatcctg aactgcttgt tccagaatcg agaagaaatt agacaagaat   1500
atctgaagtt ggaaatgtta cttaaagaaa atgaacttaa atcattctac caacaacagt   1560
gccataaaca aatagaaatg atgtgttctg aagacaaagt agaaaaggcc actggaaaac   1620
gagatcatag acttgcaatg ttgaaaactc gtcgctccta cctggagaaa aggagggagg   1680
aggaattgaa gcaatttgat gagaatacta attggctcca tcgtgtcgaa aaagaaatgg   1740
gactcttaag tcaaaacggt catattccaa aggaactcaa gaaagatctt cattgtcacc   1800
atttgcacct ccagaacaaa gatttgaaag cacaaattag acatatgatg gatctagctt   1860
gtcttcagga acagcaacac aggcagactg aagcagtatt gaatgcttta cttccaaccc   1920
taagaaaaca atattgcaca ttaaaagaag ccggcctgtc aaatgctgct tttgaatctg   1980
acttcaaaga gatcgaacat ttggtagaga ggaaaaaagt ggtagtttgg gctgaccaaa   2040
ctgccgaaca accaaagcaa aacgatctac cagggatttc tgttcttatg acctttccac   2100
aacttggacc agttcagcct attccttgtt gctcatcttc aggtggaact aatctggtta   2160
agattcctac agaaaaaaga actcggagaa aactaatgcc atctcccttg aaaggacagc   2220
atactctaaa gtctccacca tctcaaagtg tgcagctcaa tgattctctt agcaaagaac   2280
ttcagcctat tgtatataca ccagaagact gtagaaaagc ttttcaaaat ccgtctacag   2340
taaccttaat gaaaccatca tcatttacta caagttttca ggctatcagc tcaaacataa   2400
```

acagtgataa ttgtctgaaa atgttgtgtg aagtagctat ccctcataat agaagaaaag 2460
aatgtggaca ggaggacttg gactctacat ttactatatg tgaagacatc aagagctcga 2520
agtgtaaatt acccgaacaa gaatcactac caaatgataa caaagacatt ttacaacggc 2580
ttgatccttc ttcattctca actaagcatt ctatgcctgt accaagcatg gtgccatcct 2640
acatggcaat gactactgct gccaaaagga aacggaaatt aacaagttct acatcaaaca 2700
gttcgttaac tgcagacgta aattctggat ttgccaaacg tgttcgacaa gataattcaa 2760
gtgagaagca cttacaagaa aacaaaccaa caatggaaca taaaagaaac atctgtaaaa 2820
taaatccaag catggttaga aaatttggaa gaaatatttc aaaaggaaat ctaagataaa 2880
tcacttcaaa accaagcaaa atgaagttga tcaaatctgc ttttcaaagt ttatcaatac 2940
cctttcaaaa atatatttaa aatctttgaa agaagaccca tcttaaagct aagtttaccc 3000
aagtactttc agcaagcaga aaaatgaaac tctttgtttt cttcttttgt gttctaaaaa 3060
aataaaattt caaaagaaaa ggttgtcttt taagtttttt aaatatttgt tgccttttaa 3120
aatccctgag tgtaagttac catggtggca gcttagtttt actatgccac aacaagttga 3180
ctaggacatt ttagtaaatg gtagtgagtt aaattatctt tattattttt taaaaataag 3240
aatttagaag tggtaaaatt atggcccaag atgtatttgg ttctctatta tgttttgata 3300
cattatttta atcatatata tgactttcct tttcaaaaat actttaatgt acaagtgtaa 3360
atatatgtgc ccataaaatc attgtaaata ttatttagtc atcacaaata aaatattgtc 3420
ccttgctact tgatatatta aagatgtaga ttttaaagtg ttt 3463

<210> SEQ ID NO 48
<211> LENGTH: 7533
<212> TYPE: DNA
<213> ORGANISM: Homo sapiens

<400> SEQUENCE: 48
gcgacgctca cgaacgatca gagctgcggg cgacgcaacg aagcccggag gccgcaggct 60
gcgcgctccc tcgcagcagc cgggcgggca aaagccccca gtcctcggcc cccgcgcaag 120
cgacgccggg aaatgcccac atccgggaaa cctgcagcgg agtgcggcgg cggcgacact 180
gagtggaagg caaaatggcg gcggcggcgg cggtggcctg gtgttaaggg gagagccagg 240
tcctcacgac ccctgggacg ggccgcgctg gcccgcggca gcccccccgt tcgtctcccc 300
gctctgcccc accagggata cttggggttg ctgggacgga ctctggccgc ctcagcgtcc 360
gccctcaggc ccgtggccgc tgtccaggag ctctgctctc ccctccagag ttaattattt 420
atattgtaaa gaattttaac agtcctgggg acttccttga aggatcattt tcacttttgc 480
tcagaagaaa gctctggatc tatcaaataa agaagtcctt cgtgtgggct acatatatag 540
atgttttcat gaagaggagt gaaaagccag aaggatatag acaaatgagg cctaagacct 600
ttcctgccag taactatact gtcagtagcc ggcaaatgtt acaagaaatt cgggaatccc 660
ttaggaattt atctaaacca tctgatgctg ctaaggctga gcataacatg agtaaaatgt 720
caaccgaaga tcctcgacaa gtcagaaatc cacccaaatt tgggacgcat cataaagcct 780
tgcaggaaat tcgaaactct ctgcttccat ttgcaaatga aacaaattct tctcggagta 840
cttcagaagt taatccacaa atgcttcaag acttgcaagc tgctggattt gatgaggata 900
tggttataca agctcttcag aaaactaaca acagaagtat agaagcagca attgaattca 960
ttagtaaaat gagttaccaa gatcctcgac gagagcagat ggctgcagca gctgccagac 1020

-continued

```
ctattaatgc cagcatgaaa ccagggaatg tgcagcaatc agttaaccgc aaacagagct   1080
ggaaaggttc taaagaatcc ttagttcctc agaggcatgg cccgccacta ggagaaagtg   1140
tggcctatca ttctgagagt cccaactcac agacagatgt aggaagacct ttgtctggat   1200
ctggtatatc agcatttgtt caagctcacc ctagcaacgg acagagagtg aaccccccac   1260
caccacctca agtaaggagt gttactcctc caccacctcc aagaggccag actccccctc   1320
caagaggtac aactccacct ccccccttcat gggaaccaaa ctctcaaaca aagcgctatt   1380
ctggaaacat ggaatacgta atctcccgaa tctctcctgt cccacctggg gcatggcaag   1440
agggctatcc tccaccacct ctcaacactt cccccatgaa tcctcctaat caaggacaga   1500
gaggcattag ttctgttcct gttggcagac aaccaatcat catgcagagt tctagcaaat   1560
ttaactttcc atcagggaga cctggaatgc agaatggtac tggacaaact gatttcatga   1620
tacaccaaaa tgttgtccct gctggcactg tgaatcggca gccaccacct ccatatcctc   1680
tgacagcagc taatggacaa agcccttctg ctttacaaac agggggatct gctgctcctt   1740
cgtcatatac aaatggaagt attcctcagt ctatgatggt gccaaacaga aatagtcata   1800
acatggaact atataacatt agtgtacctg gactgcaaac aaattggcct cagtcatctt   1860
ctgctccagc ccagtcatcc ccgagcagtg ggcatgaaat ccctacatgg caacctaaca   1920
taccagtgag gtcaaattct tttaataacc cattaggaaa tagagcaagt cactctgcta   1980
attctcagcc ttctgctaca acagtcactg caattacacc agctcctatt caacagcctg   2040
tgaaaagtat gcgtgtatta aaaccagagc tacagactgc tttagcacct acacaccctt   2100
cttggatacc acagccaatt caaactgttc aacccagtcc ttttcctgag ggaaccgctt   2160
caaatgtgac tgtgatgcca cctgttgctg aagctccaaa ctatcaagga ccaccaccac   2220
cctacccaaa acatctgctg caccaaaacc catctgttcc tccatacgag tcaatcagta   2280
agcctagcaa agaggatcag ccaagcttgc ccaaggaaga tgagagtgaa aagagttatg   2340
aaaatgttga tagtggggat aaagaaaaga aacagattac aacttcacct attactgtta   2400
ggaaaaacaa gaaagatgaa gagcgaaggg aatctcgtat tcaaagttat tctcctcaag   2460
catttaaatt ctttatggag caacatgtag aaaatgtact caaatctcat cagcagcgtc   2520
tacatcgtaa aaaacaatta gagaatgaaa tgatgcgggt tggattatct caagatgccc   2580
aggatcaaat gagaaagatg ctttgccaaa aagaatctaa ttacatccgt cttaaaaggg   2640
ctaaaatgga caagtctatg tttgtgaaga taaagacact aggaatagga gcatttggtg   2700
aagtctgtct agcaagaaaa gtagatacta aggctttgta tgcaacaaaa actcttcgaa   2760
agaaagatgt tcttcttcga aatcaagtcg ctcatgttaa ggctgagaga gatatcctgg   2820
ctgaagctga caatgaatgg gtagttcgtc tatattattc attccaagat aaggacaatt   2880
tatactttgt aatggactac attcctgggg gtgatatgat gagcctatta attagaatgg   2940
gcatctttcc agaaagtctg gcacgattct acatagcaga acttacctgt gcagttgaaa   3000
gtgttcataa aatgggtttt attcatagag atattaaacc tgataatatt ttgattgatc   3060
gtgatggtca tattaaattg actgactttg gcctctgcac tggcttcaga tggacacacg   3120
attctaagta ctatcagagt ggtgaccatc cacggcaaga tagcatggat ttcagtaatg   3180
aatgggggga tccctcaagc tgtcgatgtg gagacagact gaagccatta gagcggagag   3240
ctgcacgcca gcaccagcga tgtctagcac attctttggt tgggactccc aattatattg   3300
cacctgaagt gttgctacga acaggataca cacagttgtg tgattggtgg agtgttggtg   3360
ttattctttt tgaaatgttg gtgggacaac ctcctttctt ggcacaaaca ccattagaaa   3420
```

cacaaatgaa ggttatcaac tggcaaacat ctcttcacat tccaccacaa gctaaactca 3480
gtcctgaagc ttctgatctt attattaaac tttgccgagg acccgaagat cgcttaggca 3540
agaatggtgc tgatgaaata aaagctcatc cattttttaa aacaattgac ttctccagtg 3600
acctgagaca gcagtctgct tcatacattc ctaaaatcac acacccaaca gatacatcaa 3660
attttgatcc tgttgatcct gataaattat ggagtgatga taacgaggaa gaaaatgtaa 3720
atgacactct caatggatgg tataaaaatg gaaagcatcc tgaacatgca ttctatgaat 3780
ttaccttccg aaggtttttt gatgacaatg gctacccata taattatccg aagcctattg 3840
aatatgaata cattaattca caaggctcag agcagcagtc ggatgaagat gatcaaaaca 3900
caggctcaga gattaaaaat cgcgatctag tatatgttta acacactagt aaataaatgt 3960
aatgaggatt tgtaaaaggg cctgaaatgc gaggtgtttt gaggttctga gagtaaaatt 4020
atgcaaatat gacagagcta tatatgtgtg ctctgtgtac aatattttat tttcctaaat 4080
tatgggaaat ccttttaaaa tgttaattta ttccagccgt ttaaatcagt atttagaaaa 4140
aaattgttat aaggaaagta aattatgaac tgaatattat agtcagttct tggtacttaa 4200
agtacttaaa ataagtagtg ctttgtttaa aaggagaaac ctggtatcta tttgtatata 4260
tgctaaataa ttttaaaata caagagtttt tgaaattttt ttgaaagaca gttttagttt 4320
tatcttgctt taaccaaata tgaaacatac cccctatttt acagagctct tttttcccct 4380
cataaccttg tttttggtag aaaataagct agagaaatta agccatcgtg ttggtgagtg 4440
ttcctaggct aatgataatc tgtataattc acatcctgaa actaaggaat acagggttga 4500
aaaaatatta atatgtttgt cagaaggaaa aataatgcat ttatcttccc ccccaccccc 4560
cgccccatgg aatatttaat ctatttaatc ttcttgcatt tatttctcaa gaattactgg 4620
ctttaaaaga agccaaagca ctactagctt tttttccata ttggtatttt tgatgctgct 4680
tccaatttta aaagggaaca aagctgccat aaatcgaaat gttcaatact aaaagctaaa 4740
atatttctca ccatcctaag cagataatta ttttaatttt catatacttt tcctgtatag 4800
taactatttt gattatatca tcaatgttac ctgtttcctc tttcagaaca gtgctgcata 4860
tacagattgt tattggcaaa ggaaaatctg gctatctggc aatattttac ctaagcgcag 4920
attaattggt gaaaaaatta actcttaaga tggccattaa taattaggaa agtttacaga 4980
gtggtcttag tagaaaattc aagtcctcct aatttattta aggttcaata atgcgttcaa 5040
catgcctgtt atgtataacg cttaggttct aaggaagatt aaggtttcat accaaaatac 5100
atgtagctta tcttttagga aggggaaaaa ggctccattt tgaccatagt aaaatttgtg 5160
ttgtgtttta tttccttttc ttaagctcca ctgataaggg attgttttta tcaaaagtta 5220
ctatttgtag attggaggca taattttagt gattttcata cttttagctt tcttcgcata 5280
aaagctaatt gaaaccgtat atgtagtaaa attaaaggca gagctgttgc agttgaattg 5340
gagagttagg gcaaagaaca cttattagcc cacacttccc acctttctac aggtggtcct 5400
ttcagagctc agcctgaaaa cccactactg tgttatcgtg cgtcttttgg ggttagtggt 5460
tcttttgaga atctgaagga agctgtggac tcttcctaga aaaaaaaacc acacatacac 5520
atacaatgtt gcatgcagtt tcaagggatt ttggacatat tgaaacctat cacaggctgt 5580
aggttatgga cctctgtgcc atgagaaaat tgatacatta aactaagaac tttgttttta 5640
acttaccaat cactactcag cacatcttat ataagctgat aatttgtgat ggaaaaggtc 5700
tgtagcatgt gatataaggt gaccttatga atgcctctct tgctggtaca ttaagttgtt 5760
ttaatatatc atttggaggg gactgaaatg ttaggctcat tacaagcttg atacagaaat 5820
atttctgaag gatttctaat cagaattgta aaacaatgtg ctatcatgaa atcgcagtct 5880
tcacctcatg gttcatggaa catttggtta gtcccataaa atcctatgca aaacaaagta 5940
gttcaagaat ttttaggtgg gtagtcacat ttataaggta ttcctcttac tctttgggct 6000
ttttcagtct gatttattta aattttcatt tagttgtttt acttttggac taaggtgcaa 6060
tacagtagaa gataactttg ttacatttat gttgtaggaa aactaaggtg ctgtctcctc 6120
ccccttccct tcccacaaaa tctgtattcc ccctattgct gaaatgtaac agacactaca 6180
aattttgtat tcttttttg ttttttgttt tgagacaggg tctcactctg tcacccaggc 6240
tggagggcag tggcgcttca cagctcactg catcctcaac cttgggggct cacgcagtcc 6300
tcccgcctca gcctcccaag tagctgggca tgcgccacca agcccagcta atttttgtat 6360
ctttagtaga gatggggttt cgccatgttg cccaggttgg tgtggaattc ctgggctcca 6420
gttatatgcc cacctcagcc tcccaaagtg ctgggattac agacgtgacc caccgcgcct 6480
ggcgcaaata tgtattcttt taaaatttcc tctgatacta taagcttttt gcatttatct 6540
gaagcagtat acatgccttt ggtatcagca attttaacag tttggatata cttatcagct 6600
atcttattcc aaaactacat ctacttcttc cagtatagaa tctggtgctt cctgaccaaa 6660
aagatgagaa aaacaatgtt aaaaatatag atgctttcca ttgaaatgga gtgaaaacat 6720
tggttctata tgtttcttt taaaataatt ttcttattaa aaacttgctg tctttattat 6780
acttaccctt tttatgcata tcaatagtat ttataagatg tgttctataa ttatgtaatt 6840
gtagatactg ttatgcattg tccagtgaca tcataaggca ggccctactg ctgtatcttt 6900
tctaccttct tatttgtaat agaaactata gaatgtatga ctaaaaagtc actttgagat 6960
tgactttttt aaaaagttat taccttctgc tgttgcaaag tgcaaaactg tgagtggaat 7020
tgttttattc tgacttaatg tgttagaaat tagagaatac agtgggagga tttttagaca 7080
ttgctgctgc tgttacccaa ggtattttag ataaaaaatt tttaataaac atccctttgg 7140
tatttaaagt ggaacattta gcctgttcat tttaatctaa agcaaaaagt aatttgggtc 7200
aaaatattgg tatatttgta aagcgcctta atatatccct ttgtggaagg cactacacag 7260
tttactttta tattgtattg tgtatataag tattttgtat taaaattgaa tcagtggcaa 7320
cattaaagtt ttataaaatc atgctttgtt agaaaaagaa ttacagcttt gcaatataac 7380
taattgtttc gcataattct gaatgtaata gatatgaata atcagcctgt gtttttaatg 7440
aacttatttg tattttccca atcattttct ctagtgtaat gtttgctggg ataataaaaa 7500
aaattcaaat ctttcaaaaa aaaaaaaaaa aaa 7533

<210> SEQ ID NO 49
<211> LENGTH: 3701
<212> TYPE: DNA
<213> ORGANISM: Homo sapiens

<400> SEQUENCE: 49
taggcggtgc atcccgttcg cgcctggggc tgtggtcttc ccgcgcctga ggcggcggcg 60
gcaggagctg aggggagttg tagggaactg aggggagctg ctgtgtcccc cgcctcctcc 120
tccccatttc cgcgctcccg ggaccatgtc cgcgctggcg ggtgaagatg tctggaggtg 180
tccaggctgt ggggaccaca ttgctccaag ccagatatgg tacaggactg tcaacgaaac 240
ctggcacggc tcttgcttcc ggtgttcaga atgccaggat tccctcacca actggtacta 300
tgagaaggat gggaagctct actgccccaa ggactactgg gggaagtttg gggagttctg 360

```
tcatgggtgc tccctgctga tgacagggcc ttttatggtg gctggggagt tcaagtacca    420
cccagagtgc tttgcctgta tgagctgcaa ggtgatcatt gaggatgggg atgcatatgc    480
actggtgcag catgccaccc tctactgtgg gaagtgccac aatgaggtgg tgctggcacc    540
catgtttgag agactctcca cagagtctgt tcaggagcag ctgccctact ctgtcacgct    600
catctccatg ccggccacca ctgaaggcag gcggggcttc tccgtgtccg tggagagtgc    660
ctgctccaac tacgccacca ctgtgcaagt gaaagaggtc aaccggatgc acatcagtcc    720
caacaatcga aacgccatcc accctgggga ccgcatcctg gagatcaatg ggaccccgt    780
ccgcacactt cgagtggagg aggtggagga tgcaattagc cagacgagcc agacacttca    840
gctgttgatt gaacatgacc ccgtctccca acgcctggac cagctgcggc tggaggcccg    900
gctcgctcct cacatgcaga atgccggaca cccccacgcc ctcagcaccc tggacaccaa    960
ggagaatctg gaggggacac tgaggagacg ttccctaagg cgcagtaaca gtatctccaa   1020
gtcccctggc cccagctccc caaaggagcc cctgctgttc agccgtgaca tcagccgctc   1080
agaatccctt cgttgttcca gcagctattc acagcagatc ttccggccct gtgacctaat   1140
ccatggggag gtcctgggga agggcttctt tgggcaggct atcaaggtga cacacaaagc   1200
cacgggcaaa gtgatggtca tgaaagagtt aattcgatgt gatgaggaga cccagaaaac   1260
ttttctgact gaggtgaaag tgatgcgcag cctggaccac cccaatgtgc tcaagttcat   1320
tggtgtgctg tacaaggata agaagctgaa cctcctgaca gagtacattg agggggcac   1380
actgaaggac tttctgcgca gtatggatcc gttcccctgg cagcagaagg tcaggtttgc   1440
caaaggaatc gcctccggaa tggcctattt gcactctatg tgcatcatcc accgggatct   1500
gaactcgcac aactgcctca tcaagttgga caagactgtg gtggtggcag actttgggct   1560
gtcacggctc atagtggaag agaggaaaag ggcccccatg gagaaggcca ccaccaagaa   1620
acgcaccttg cgcaagaacg accgcaagaa gcgctacacg gtggtgggaa acccctactg   1680
gatggcccct gagatgctga acggaaagag ctatgatgag acggtggata tcttctcctt   1740
tgggatcgtt ctctgtgaga tcattgggca ggtgtatgca gatcctgact gccttccccg   1800
aacactggac tttggcctca acgtgaagct tttctgggag aagtttgttc ccacagattg   1860
tcccccggcc ttcttcccgc tggccgccat ctgctgcaga ctggagcctg agagcagacc   1920
agcattctcg aaattggagg actcctttga ggccctctcc ctgtacctgg gggagctggg   1980
catcccgctg cctgcagagc tggaggagtt ggaccacact gtgagcatgc agtacggcct   2040
gacccgggac tcacctccct agccctggcc cagccccctg caggggggtg ttctacagcc   2100
agcattgccc ctctgtgccc cattcctgct gtgagcaggg ccgtccgggc ttcctgtgga   2160
ttggcggaat gtttagaagc agaacaagcc attcctatta cctccccagg aggcaagtgg   2220
gcgcagcacc agggaaatgt atctccacag gttctggggc ctagttactg tctgtaaatc   2280
caatacttgc ctgaaagctg tgaagaagaa aaaaacccct ggcctttggg ccaggaggaa   2340
tctgttactc gaatccaccc aggaactccc tggcagtgga ttgtgggagg ctcttgctta   2400
cactaatcag cgtgacctgg acctgctggg caggatccca gggtgaacct gcctgtgaac   2460
tctgaagtca ctagtccagc tgggtgcagg aggacttcaa gtgtgtggac gaaagaaaga   2520
ctgatggctc aaagggtgtg aaaaagtcag tgatgctccc cctttctact ccagatcctg   2580
tccttcctgg agcaaggttg agggagtagg ttttgaagag tcccttaata tgtggtggaa   2640
caggccagga gttagagaaa gggctggctt ctgtttacct gctcactggc tctagccagc   2700
```

```
ccagggacca catcaatgtg agaggaagcc tccacctcat gttttcaaac ttaatactgg   2760
agactggctg agaacttacg gacaacatcc tttctgtctg aaacaaacag tcacaagcaa   2820
aggaagaggc tgggggacta gaaagaggcc ctgccctcta gaaagctcag atcttggctt   2880
ctgttactca tactcgggtg ggctccttag tcagatgcct aaaacatttt gcctaaagct   2940
cgatgggttc tggaggacag tgtggcttgt cacaggccta gagtctgagg gaggggagtg   3000
ggagtctcag caatctcttg gtcttggctt catggcaacc actgctcacc cttcaacatg   3060
cctggtttag gcagcagctt gggctgggaa gaggtggtgg cagagtctca aagctgagat   3120
gctgagagag atagctccct gagctgggcc atctgacttc tacctcccat gtttgctctc   3180
ccaactcatt agctcctggg cagcatcctc ctgagccaca tgtgcaggta ctggaaaacc   3240
tccatcttgg ctcccagagc tctaggaact cttcatcaca actagatttg cctcttctaa   3300
gtgtctatga gcttgcacca tatttaataa attgggaatg ggtttggggt attaatgcaa   3360
tgtgtggtgg ttgtattgga gcagggggaa ttgataaagg agagtggttg ctgttaatat   3420
tatcttatct attgggtggt atgtgaaata ttgtacatag acctgatgag ttgtgggacc   3480
agatgtcatc tctggtcaga gtttacttgc tatatagact gtacttatgt gtgaagtttg   3540
caagcttgct ttagggctga gccctggact cccagcagca gcacagttca gcattgtgtg   3600
gctggttgtt tcctggctgt ccccagcaag tgtaggagtg gtgggcctga actgggccat   3660
tgatcagact aaataaatta agcagttaac ataactggca a                       3701
```

<210> SEQ ID NO 50
<211> LENGTH: 2191
<212> TYPE: DNA
<213> ORGANISM: Homo sapiens

<400> SEQUENCE: 50

```
atgaagcccc tctacagtgg ctgctgcagg tgctggctgg accccgctgg gccccttctc     60
accccacatc ccattgattg attagtcagg cagggcagtg aggacacctc acagatgggg    120
aaactgaagc ccagggaggt actcaagatg tgcccagtgc gggctgagat aaggccctgg    180
agtccacctc caggctgggt ctgtcctgct ctgctccctg cagggctggt gggcctcctt    240
ccccctttg actaacggcc tggcttggag agagggggct cccggcatgg gtgatggcag    300
aggctggcac ccttgtggcc agggcctgat ggctcatggg agtgcagggg acattgatgt    360
caagggatag ccagacgcct caccttctct ccattctatg ggagtgcagg ggacattgat    420
gtcaagggat agccagacgc ctcaccttct ctccattcta ggaaaatcca agaggaagaa    480
ggatctacgg atatcctgca tgtccaagcc acccgcaccc aaccccacac ccccccggaa    540
cctggactcc cggaccttca tcaccattgg agacagaaac tttgaggtgg aggctgatga    600
cttggtgacc atctcagaac tgggccgtgg agcctatggg gtggtagaga aggtgcggca    660
cgcccagagc ggcaccatca tggccgtgaa gcggatccgg gccaccgtga actcacagga    720
gcagaagcgg ctgctcatgg acctggacat caacatgcgc acggtcgact gtttctacac    780
tgtcaccttc tacggggcac tattcagaga gggagacgtg tggatctgca tggagctcat    840
ggacacatcc ttggacaagt tctaccggaa ggtgctggat aaaaacatga caattccaga    900
ggacatcctt ggggagattg ctgtgtctat cgtgcgggcc ctggagcatc tgcacagcaa    960
gctgtcggtg atccacagag atgtgaagcc ctccaatgtc cttatcaaca aggagggcca   1020
tgtgaagatg tgtgactttg gcatcagtgg ctacttggtg gactctgtgg ccaagacgat   1080
ggatgccggc tgcaagccct acatggcccc tgagaggatc aacccagagc tgaaccagaa   1140
```

-continued

```
gggctacaat gtcaagtccg acgtctggag cctgggcatc accatgattg agatggccat   1200
cctgcggttc ccttacgagt cctgggggac cccgttccag cagctgaagc aggtggtgga   1260
ggagccgtcc ccccagctcc cagccgaccg tttctccccc gagtttgtgg acttcactgc   1320
tcagtgcctg aggaagaacc ccgcagagcg tatgagctac ctggagctga tggagcaccc   1380
cttcttcacc ttgcacaaaa ccaagaagac ggacattgct gccttcgtga aggagatcct   1440
gggagaagac tcatagggc tgggcctcgg accccactcc ggccctccag agccccacag   1500
ccccatctgc gggggcagtg ctcacccaca ccataagcta ctgccatcct ggcccagggc   1560
atctgggagg aaccgagggg gctgctccca cctggctctg tggcgagcca tttgtcccaa   1620
gtgccaaaga agcagaccat tggggctccc agccaggccc ttgtcggccc caccagtgcc   1680
tctccctgct gctcctagga cccgtctcca gctgctgaga tcctggactg agggggcctg   1740
gatgcccccct gtggatgctg ctgcccctgc acagcaggct gccagtgcct gggtggatgg   1800
gccaccgcct tgcccagcct ggatgccatc caagttgtat attttttaa tctctcgact   1860
gaatggactt tgcacacttt ggcccagggt ggccacacct ctatcccggc tttggtgcgg   1920
ggtacacaag aggggatgag ttgtgtgaat accccaagac tcccatgagg gagatgccat   1980
gagccgccca aggccttccc ctggcactgg caaacagggc ctctgcggag cacactggct   2040
cacccagtcc tgcccgccac cgttatcggt gtcattcacc tttcgtgttt tttttaattt   2100
atcctctgtt gatttttctt tttgctttat gggtttggct tgtttttctt gcatggtttg   2160
gagctgatcg cttctccccc accccctagg g                                 2191
```

<210> SEQ ID NO 51
<211> LENGTH: 3386
<212> TYPE: DNA
<213> ORGANISM: Homo sapiens

<400> SEQUENCE: 51

```
gcggtgtttg tctgccggac tgacgggcgg ccgggcggtg cgcggcggcg gtggcggcgg     60
ggaagatggc ggcgtcctcc ctggaacaga agctgtcccg cctggaagca aagctgaagc    120
aggagaaccg ggaggcccgg cggaggatcg acctcaacct ggatatcagc ccccagcggc    180
ccaggcccac cctgcagctc ccgctggcca acgatggggg cagccgctcg ccatcctcag    240
agagctcccc gcagcacccc acgccccccg cccggccccg ccacatgctg gggctcccgt    300
caaccctgtt cacaccccgc agcatggaga gcattgagat tgaccagaag ctgcaggaga    360
tcatgaagca gacgggctac ctgaccatcg gggccagcg ctaccaggca gaaatcaacg    420
acctggagaa cttgggcgag atgggcagcg gcacctgcgg ccaggtgtgg aagatgcgct    480
tccggaagac cggccacgtc attgccgtta agcaaatgcg gcgctccggg aacaaggagg    540
agaacaagcg catcctcatg gacctggatg tggtgctgaa gagccacgac tgcccctaca    600
tcgtgcagtg ctttgggacg ttcatcacca acacggacgt cttcatcgcc atggagctca    660
tgggcacctg cgctgagaag ctcaagaagc ggatgcaggg ccccatcccc gagcgcattc    720
tgggcaagat gacagtggcg attgtgaagg cgctgtacta cctgaaggag aagcacggtg    780
tcatccaccg cgacgtcaag ccctccaaca tcctgctgga cgagcggggc cagatcaagc    840
tctgcgactt cggcatcagc ggccgcctgg tggactccaa agccaagacg cggagcgccg    900
gctgtgccgc ctacatggca cccgagcgca ttgacccccc agaccccacc aagccggact    960
atgacatccg ggccgacgta tggagcctgg gcatctcgtt ggtggagctg gcaacaggac   1020
```

-continued

```
agtttcccta caagaactgc aagacggact ttgaggtcct caccaaagtc ctacaggaag   1080
agcccccgct tctgcccgga cacatgggct tctcggggga cttccagtcc ttcgtcaaag   1140
actgccttac taaagatcac aggaagagac caaagtataa taagctactt gaacacagct   1200
tcatcaagcg ctacgagacg ctggaggtgg acgtggcgtc ctggttcaag gatgtcatgg   1260
cgaagactga gtcaccgcgg actagcggcg tcctgagcca gccccacctg cccttcttca   1320
ggtagctgct tggcggcggc cagccccaca gggggccagg ggcatggcca caggcccccc   1380
tccccacttg gccacccagc tgcctgccag gggagacctg ggacctggac ggccacctag   1440
gactgaggac agagagtggg gggtgcccac ccaccccccc cgcccgggc ctaccaagcc   1500
cccgcccttc ccaccccggg gtcagccggc cgtgtgcgtc ccccgacaga cactgtgaac   1560
ggaagacagc aggccgcgat cagagtcgct gttcattcag ccgcagcctc tgggccgggg   1620
cggcccccag gggccaggag agagccctgg agtcccgcag ccaccatgca cgctcccagc   1680
gtgctgtgtc cttcgccact cccacgcgcc cgttcctctt ccgtcgccct ctgtcccctg   1740
ctctacctct ctgtccttgt ctggctctcc cgtcaccctc cctgcctctg tctctcttct   1800
ggcctgagcc tgggcccagc cacctcctga cgggtcccct gggtctgcat aggtctccca   1860
tggcgcaatg agtcagtggc cccagccag gcagtgtggg cattgccact gcggctggac   1920
ggggctgcgc gctcgcgctc tctctctctc tctctctctc tctttgatct caggggggtcc   1980
tttttggagt ttattgtatt ttattgtact tggtggggtg tttggggtgg gggcggagga   2040
gagcttgttc tcgtggggtt gtcggtacct tcagaaactt ttaccaaagt cacgattagc   2100
tgcttgtggt ggggccccaa ccgccctcgg gcactgggga gctgggctgg ggctgctgct   2160
ctggggtctc cgggggccac agcttggggt gagttgaaga cctcagggga tgtggagggg   2220
tctgcggggc cctggccgca caggatggcc ttcagggaag gtggtcttgg ggcatggtgc   2280
agagcaggtg accggaggga atcggtgacg gagcggggcc aagggagggg tccggaggga   2340
gtcagggatg gagggcagag ggagtggatg tgggggtttg aggacgtgtg acaagctcca   2400
gcaggggtgg gggccgggct gagggtgggg gtgcgaggtg gtcactccca tcgtgcccct   2460
ggccgtccct ccactcaccc acacctggcc cagtccacgt tgaggtccag gactgggaag   2520
gaccgggtga gtgcaccggg gacccaggcc aggtgccccc cggagcctgc tggggtggcc   2580
agagcaggag gggggtgttt tcctttttgt gggtgttgca tgcaaatcaa gtggacaaga   2640
aaaaataaca aaacaaaaaa caagaaaaaa aaaacacaaa accccgtaaa atcacaaaga   2700
aaatccaaca ccaaaggcgc agaagccggc tggccgtggt gggggcagcg taggcgtagc   2760
atccctctcc tctcacttag cctgttgact cttgttatta tcatgatatt cacaaaacgc   2820
cgcatgttta aaaagtcata gatgtcatct tctctctgcc cccagggagg aaagccacct   2880
tctcttgccc cttggcccct ttgtcagggg ccaggggtct gccgggtggg ggtgccaaca   2940
ggcctggccc tttcctcccc tgcatccagc catgggggcc tctgcgattg ccggaaggtt   3000
gcatggctgg tcccagggcc agcacaggcc cgaggccggg ctgcctggtt ttatttttat   3060
ttaactttat tttctgtttt atgagtgtgt gtccgcccac ccccaccccc ttcagtgtta   3120
agtggggagc cctgggggag tctctcctgc ctcccagcct ctcccaagac ctccccccctc   3180
gtcaccagcc atccctctgg accaggcaga gggcggaccg ggtgggcagg ggcctgaggg   3240
tggctcgggc cagcccacca gccaatggac ccctcctcag gccgccagtg tcgccctgcc   3300
ccttttttaaa acaaaatgcc ctcgtttgta aacccttaga cgcttgagaa taaacccctt   3360
ccttttcttc caaaaaaaaa aaaaaa                                         3386
```

<210> SEQ ID NO 52
<211> LENGTH: 9945
<212> TYPE: DNA
<213> ORGANISM: Homo sapiens

<400> SEQUENCE: 52
accagattcc ttctaaaaga aggaaggcca tgtctgcctg aagcctattg gctgggccta 60
ctctggaccc gcccctcttt tttttttcat gacacacacc acagcgaagt ctgtgcggaa 120
tcctaaacca gcccaattta catccattca tgaatctgtg acgtcagcaa gcctttgggc 180
tcctttgcgg tgggctggag gattgtgtgg gtggaatccc cctccccttt atttttccaa 240
ttctgcaagg cttttaaaat tcaccttaca tcttttcaaa gcaagaaaat ggaacagcat 300
gtgtaggaat tcttcgttgt tgttttggag ccctctctta agtcagaact ctgtcccaaa 360
aatcttctga gtgtcatctc aggactttgg ttatactcat ggcacgatgg ccaactttca 420
ggagcacctg agctgctcct cttctccaca cttacccttc agtgaaagca aaaccttcaa 480
tggactacaa gatgagctca cagctatggg gaaccaccct tctcccaagc tgctcgagga 540
ccagcaggaa aaggggatgg tacgaacaga gctaatcgag agcgtgcaca gccccgtcac 600
cacaacagtg ttgacgagcg taagtgagga ttccagggac cagtttgaga acagcgttct 660
tcagctaagg gaacacgatg aatcagagac ggcggtgtct caggggaaca gcaacacggt 720
ggacggagag agcacaagcg gaactgaaga cataaagatt cagttcagca ggtcaggcag 780
tggcagtggt gggtttcttg aaggactatt tggatgctta aggcctgtat ggaatatcat 840
tgggaaggca tattccactg attacaaatt gcagcagcaa gatacttggg aagtgccatt 900
tgaggagatc tcagagctgc agtggctggg tagtggagcc caaggagcgg tcttcttggg 960
caagttccgg gcggaagagg tggccatcaa gaaagtgaga gaacagaatg agacggatat 1020
caagcatttg aggaagttga agcaccctaa catcatcgca ttcaagggtg tttgtactca 1080
ggccccatgt tattgtatta tcatggaata ctgtgcccat ggacaactct acgaggtctt 1140
acgagctggc aggaagatca cacctcgatt gctagtagac tggtccacag gaattgcaag 1200
tggaatgaat tatttgcacc tccataaaat tattcatcgt gatctcaaat cacctaatgt 1260
tttagtgacc cacacagatg cggtaaaaat ttcagatttt ggtacatcta aggaactcag 1320
tgacaaaagt accaagatgt catttgctgg cacggtcgca tggatggcgc cagaggtgat 1380
acggaatgaa cctgtctctg aaaaagttga tatatggtct tttggagtgg tgctttggga 1440
gctgctgaca ggagagatcc cttacaaaga tgtagattct tcagccatta tctggggtgt 1500
tggaagcaac agcctccacc ttccagttcc ttccacttgc cctgatggat tcaaaatcct 1560
tatgaaacag acgtggcaga gtaaacctcg aaaccgacct tcttttcggc agacactcat 1620
gcatttagac attgcctctg cagatgtact tgccacccca caagaaactt acttcaagtc 1680
tcaggctgaa tggagagaag aagtgaaaaa acattttgag aagatcaaaa gtgaaggaac 1740
ttgtatacac cggttagatg aagaactgat tcgaaggcgc agagaagagc tcaggcatgc 1800
gctggatatt cgtgaacact atgagcggaa gcttgagcgg gcgaataatt tatacatgga 1860
attgagtgcc atcatgctgc agctagaaat gcgggagaag gagctcatta agcgtgagca 1920
agcagtggaa aagaagtatc ctgggaccta caaacgacac cctgttcgtc ctatcatcca 1980
tcccaatgcc atggagaaac tcatgaaaag gaaaggagtg cctcacaaat ctgggatgca 2040
gaccaaacgg ccagacttgt tgagatcaga agggatcccc accacagaag tggctcccac 2100

-continued

```
tgcatcccct ttgtccggaa gtcccaaaat gtccacttct agcagcaaga gccgatatcg   2160
aagcaaacca cgccaccgcc gagggaatag cagaggcagc catagtgact ttgccgcaat   2220
cttgaaaaac cagccagccc aggaaaattc accccatccc acttacctgc accaagctca   2280
atcccaatac ccttctcttc atcaccataa ttctctgcag cagcaatacc agcagccccc   2340
tcctgccatg tcccagagtc accatcccag actcaatatg cacggacagg acatagcaac   2400
ctgcgccaac aacctgaggt atttcggccc agcagcagcc ctgcggagcc cactcagcaa   2460
ccatgctcag agacagctgc ccggctcgag ccctgacctc atctccacag ccatggctgc   2520
agactgctgg agaagttctg agcctgacaa gggccaagct ggtccctggg gctgttgcca   2580
ggctgacgct tatgacccct gccttcagtg caggccagaa cagtatgggt ccttagacat   2640
accctctgct gagccagtgg ggaggagccc tgacctttcc aagtcaccag cacataatcc   2700
tctcttggaa aacgcccaga gttctgagaa aacggaagaa aatgaattca gcggctgtag   2760
gtctgagtca tccctcggca cctctcatct cggcacccct ccagcgctac ctcgaaaaac   2820
aaggcctctg cagaagagtg gagatgactc ctcagaagag gaagaagggg aagtagatag   2880
tgaagttgaa tttccacgaa gacagaggcc ccatcgctgt atcagcagct gccagtcata   2940
ttcaaccttt agctctgaga atttctctgt gtctgatgga gaagagggaa ataccagtga   3000
ccactcaaac agtcctgatg agttagctga taaacttgaa gaccgcttgg cagagaagct   3060
agacgacctg ctgtcccaga cgccagagat tcccattgac atatcctcac actcggatgg   3120
gctctctgac aaggagtgtg ccgtgcgccg tgtgaagact cagatgtctc tgggcaagct   3180
gtgtgtggag gaacgtggct atgagaaccc catgcagttt gaagaatcgg actgtgactc   3240
ttcagatggg gagtgttctg atgccacagt taggaccaat aaacactaca gctctgctac   3300
ctggtaatga aggaatacac atcctgaaga tctcgtgact atactggcat ttcagatcca   3360
ccccaccccc agactcatcc cactctctcc cagcattttg tctgggaaga gagactaccc   3420
catctttacc accccctaga aatgagctgc aataacagga acatgagact tcgcaaatct   3480
ctggaaaata atatccaaat gaaattaagt ctcactgaac atttcaatca agaatggcag   3540
ggatctattt tattgaatat tctagctact gtaacattga tatttatttt tgtttgacat   3600
tttaacactt tgtactgcaa agagtgaact atatatgaga tagagagaca ataatttctt   3660
gcaaaaaaaa aaagagataa aagaaagaac agaaaaaaag aaataagtgg aatttaagag   3720
caacatcctt gggaatttgt ggggccggga ggtattattg ctgcttgaac aggggaccag   3780
gtcttttggc cataagtgac taaagaagag ccagagcaag acattgaaca ttttagaaca   3840
caaagaacag caaaagaaaa gcaattccag gcaacttgtg aacagaccat attcacttca   3900
accagcttgt ccaggtggct tacggaaatg acctagaaaa gtctggtgac cagatacttg   3960
cacccaatgt cttcaagggc atgtgcttcc tctaggaggg aaaaacagac aaacaaacaa   4020
acaaacaaac ctgtgtatgt ggaagctggt ttcattttta aatgtttaag cagcagttgg   4080
tagtgaggtt tacagatagt gtcaaatctt gtttttggca aatacgtccc tttttagtgc   4140
tgtcactgtc attaccttgg caaatgtgct accttgaccc aacgtgttga tctttcatac   4200
tcaagtgcca tttccttgta gctcatttcc tttctgcctg ctgaccactt cctgtaggaa   4260
caaaggttgg ggggcagtac tgaggaggag aaaagggtga gagaggaaga acatctacag   4320
tggtgttagg aaaacgaacg tggaatttat aaaactccat tctcaggatc actcagttca   4380
gctacgagga gaagatggaa ccacccctct ctggagccag gttgcttgtc tacttgagtc   4440
atattgattc aagcaggaga acagactttg aaggcagcta ggatgtatgt gtgtctatac   4500
```

-continued

```
aatgtctgag cccaaaccat ccctttgttt ttattcaata actcattcta tcttagaagt   4560
tctttttttt tttttttttt ttgacagagt tttgctcttt ttgcccaggc tagagtgcaa   4620
tggcacaatc tcagttcact gcaacctcca tctcccaggt tcaagcgatt ctcctgcctc   4680
agcctcccga gtagctggga ttacaggcgc ccgcaaccac gcctggctaa ttttgtattt   4740
ttagtagaca cggggtttca ccatgttggc caggcttgtc tcaaactcct gacctcaggt   4800
gatccgcctg cctcggcctc ccaaagtgct gggattacag gcatcagcca ctgtgcccgg   4860
cctatcttag aagtcttaat gactggctac cactgtcaga ataaaagcaa aaacaagcag   4920
cttgcaaaag gcaactcctc tcccagcaca atagcatttt tgttcaatgc tacttgtaaa   4980
atatctttta cttcactcca aatcaatgca gttttaaata actggatttg aacatttgtg   5040
gaaagaacaa gggatgctga gcagggatag gaaggatttt tacattgcca aaagcatgag   5100
gtcctgcctg tctccagggt catgggctct gaaaagcatt ccaaggtact tcatggtgcc   5160
ttggccttaa ggaaaaattt ttttagaatt ttatgtacaa ataggtgttg acctagtacc   5220
tgtccctgtc tccaagacag attaccgtca aacaacctct ctagattcac tggactcttt   5280
gacactgcat catgttggac gttaggaaat acttgcacag acagctgtta aaccatttcc   5340
aatgcacatg aaaatgttgc cgctcctctg ggttttactg attgcatcag ccaaaaagga   5400
aaggcaggag ggaatttaga gttccttttg cttgtttgat ccatttgttt acactttatg   5460
ttgatacatt gatttaaaat gtagtgtctg tgatttatag ctcttaggat gaaggaaaat   5520
gtttaattta tacaaagagc agtattgttt gcattaattt attccatttt gtaaaaattc   5580
tgtagctgga ctacatgaaa gatcttaagt tatggcatta ttatcattgt tattttattt   5640
tataatatta tcattctcat tttctgtcga tcagaaggtg tgatttatga tgtggcacaa   5700
tggttgtgtt tattgctaac caggaattat tatggatttt atgattttaa tgaaggaatg   5760
aaaatggaat tcccatttgg gagctccctg gtattgatct tagctgtgtt ccctaatttt   5820
ctgtgtacaa caatcatctg aggacgcatg ttctgccctg aagcccaatg gatacattgt   5880
gattttgact tgatcatgaa agctcctggg tgggccgatg acccccagga tgtcaaatag   5940
tggatggaca tatagttaaa aagctgtaaa ctttctaaag tttcttagga aataaattca   6000
tgggactata ttagaaataa aaagagaatg atttaatgtc ctgagaggaa cagacctaga   6060
gggtttccgc acagggctca tggattcgtt tcaagaattg acaacatagt ttgcaatctc   6120
cttcctgcca gacccctttg ttctcccacc tttattctcc tagtggagag tagcagggag   6180
actaaaaaaa gaaatggtat acagtagtcc cctcttaccc atggcttcat tttcatggtt   6240
tcagttacgc tcaacagcag tccaaaaaata tttgatggaa cattccagaa ataaacaatt   6300
cataaatttt aattgcacag cattctgagg agcatgatga gatcttgccc cttgctgccc   6360
tggaggtgat cctccctctg tccagcatat tcatgctgct catccattag tcacttagta   6420
gcagtctcgg tgatcagatc gactgtctcg gttatcagat gactgtatcg cagtgcttgt   6480
gttcaagtac ccctatttaa ttaataatag ccccaaaggg caagagtgct gtgcctaatt   6540
tacaaattaa attttatcat agatatgtaa gtatagaaaa aaaaacatag tatatatagg   6600
gtttggtact atcagagttt ttaggcatcc actgggggtc ttggaatgta tcccccagaa   6660
ataagggagg actaccgtat atacatgtag ggcatgacat aaaatgccta actgtgatgt   6720
catcctagaa caagactaaa gaactttaag aaggaggcct ggtcacttag aggaccaacg   6780
actggaaaaa aattcttgaa aggctatatt ttccatcctc ttgacttcag atctcactgt   6840
```

-continued

```
actgtaaatc tctctggttc attattcctt ggaacagaga tgctacaact ctatgtcttc   6900
tttctatcca acataaaaca ctggcagttt tgtccaattc ttgcccacct ttagtggcaa   6960
cagagaaaca tgagggtcag cttttatctt acatctttca gtgatggtct tcctagaaaa   7020
cctacccctg atacctcgta attttgatca gttttttttg aattctcatc ttgattatct   7080
gttatgctat tgtcatcata caccttatgt ggattaactg ttatgagtat gttagggtag   7140
tacgtagtgg ctgaatctca gtcattcatt gtatagtcga gagttgaata aagtccatat   7200
tgaacacatt tttttaagta gaattgacta gaggtttcag aggagaataa ggtccttagt   7260
ggaggttaaa aagggaaata ccttctctag cccagcctgg tccttcgctg cctgccttgt   7320
gataaccggg aaaatcttga attgatgtat gtttctttga gaacgactcc acagtcatct   7380
gaagagtgtt gaatcaagag ctcagggaag ttatgagcta attcttcagt cctgacaagt   7440
gtgttacaac agtgcttcca ggaacctcac aagactgtga tttcaagctg cttcattgat   7500
ggaaagtttc accatcttgg gatgaatgtc catgttccgt tagcgtctgt ttttaactga   7560
ctgcaagatg atgagtttta atttgggttg cagatgagca tttggttctg attttcatct   7620
atttcaagat catatcctct ggataacagt tccttttaaa attgctttgc agaggggctg   7680
agaagcctgc atctactttg aaattataat ggaccttacc accacttaag tttagacctg   7740
tttgcaagat ggtggggagc tcctactgag aaagatgaag atgctagctc tattgtaaac   7800
tggcgtcttc atctagctac ttgaagttga gatactatat tttaaaatgt tggcatcaaa   7860
caaatctatc cttctagaag taaagacatt ttgagtagga tttagtaagt actggacatc   7920
tcctgtagag cttcatcatg ctaaattatt cccctctcct tttctaaata atagatgtgc   7980
ttgggtttgg gatttacctg gcaccaaccc agactttttt tggggggggg tgagggcgca   8040
ggatctcact ctgtcaccag gttggagtac agtggcatga ttatggctca ctgcagcctc   8100
aacctcctgg gctcaagtga tcctcccacc tcagcctcct gagtagctgg gaccacaggt   8160
gtgtgccacc atgcacaaca attttttttt ttttttgta gagatgggcg tctccctgtg   8220
ttgcccaggc tggtatcgaa ctctgggctc tagcgatcct cctgctttgg cctcccaaag   8280
tactgggatt acaaacgtga gctgccatgc ccagcctcca gactatttta aatgccctct   8340
cccactgtgg aacattggca tcctttaaga ataaatgcat ccttttgat caaatgattt   8400
actctttttt tcttcaatgt cctcatgtct caattttttt ttccttttct taaaacagtc   8460
ccacttgaac ttcctggaac tgaattctcc agaacataat atttataatc catagaattc   8520
ctgccctgct ctgcagtaga gtgtgctatg ttttgtttc ccactgagcc agaagccgaa   8580
atattatact accacttacc accatctacc acctccaaga ccaagaccaa cattatgtat   8640
tgagcatcgt atctttccta ctgagcctag acacagcctc agaacctctc aacatagcac   8700
ttggagcaac aattgccgct tgattggaat tgccatttga gcttgagtta gccccaatgg   8760
cagaacgaca ggctcgcact agtgtccacc tgtggctgtc aggggcggta ccacagaaag   8820
gggaaaggcc acttgcctct acccactgcc cttttggaca acaattccaa ttgaaggaac   8880
accaatcact gatggatccc attccaaaat gtctcttcat tcacatcatt taattctgtt   8940
gaatgaatat gttcctccct caccttttat aaacagaaaa ttaatataag tcccagttac   9000
ttgcttctta gactctgtga gactcatgta ccaaaacaat gtgacattct tttcgagact   9060
ttgacttgta cggtcagtat gaatttagtg cctttccagg cagcaaaatg tttcttcttt   9120
gctgatttca taggacaaat atcctagcat actcacacca ccagtgtccc accctcacag   9180
actggcacat tagaatcata ttaatctgct tgtttgcatg ttacaactga tactgcaaaa   9240
```

gcctattcaa gtcggactga actaggctaa gcagaggacc cttgtggaac ctggagcatt 9300
tctcagggac aggtggctaa agaggggagc tctaaaatca ctgctctgag aaacaggagg 9360
tgggttaagg cttttgttaa ctgtcatgtg gccagggtac gatggcagga cttcacagag 9420
cagagcccta agcagatggc aaggccactg taaggaagct cccggcagca tcccaggtct 9480
gctctccaga gccacttcac agcactcagg gatcgctggc tcccggccct aggctgctgt 9540
ccagtgacca ggtggacagg gtcctccagt gactgcaggc caagggaacc ccagccagca 9600
tgtgcaagct attaggaaga tgtcccatct tgcccatatc accccagtgg ctcttcacct 9660
tcagagtgac cacttcccag actctggaag tgggaagacc ctctttgacg ctttattaca 9720
gtaatttgag ctcctatcga cttggagcga atgaatttct cttttgtggt taggtctcca 9780
aatgaacctc cttacctggc tcccctctgg tctcctgtac tgtcagtccc cagctcccag 9840
tgttgttttc tgatgccggc tccctctctg tattgaacgg caatgggaac aagaatgact 9900
atcaaagcaa acaaatgcat ggaattaaac aaaaagtgta cttca 9945

<210> SEQ ID NO 53
<211> LENGTH: 2163
<212> TYPE: DNA
<213> ORGANISM: Homo sapiens

<400> SEQUENCE: 53
gggccggcgg cggcggcggc gcgcggagga gaccgcagtg cggccggcgc taggacccgc 60
gggggcctcc caggccgcgg cgcctcccgc tttcccccac tccccgaccc ttcttcgccc 120
ccaaaatgag gaaacggagc aactcgctcc aagttgtgca gccgggaccg cctcggggtg 180
tgcagccggc tcgcggaggc cctcctgggg gcgggcgcgg ggcgcggctc gggggcgccc 240
cctgagcaga aaacaggaag aaccaggctc ggtccagtgg cacccagctc cctacctcct 300
gtgccagccg actggcctgt ggcaggccat tcccagcgtc cccgactgtg accacttgct 360
cagtgtgcct ctcacctgcc tcagtttccc tctgggggcg atggcggggc gaggctctct 420
ggtttcctgg cgggcatttc acggctgtga ttctgctgag gaacttcccc gggtgagccc 480
ccgcttcctc cgagcctggc accccccctcc cgtctcagcc aggatgccaa cgaggcgctg 540
ggccccgggc acccagtgta tcaccaaatg cgagcacacc cgccccaagc caggggagct 600
ggccttccgc aagggcgacg tggtcaccat cctggaggcc tgcgagaaca agagctggta 660
ccgcgtcaag caccacacca gtggacagga ggggctgctg gcagctgggg cgctgcggga 720
gcgggaggcc ctctccgcag accccaagct cagcctcatg ccgtggttcc acgggaagat 780
ctcgggccag gaggctgtcc agcagctgca gcctcccgag gatgggctgt tcctggtgcg 840
ggagtccgcg cgccaccccg gcgactacgt cctgtgcgtg agctttggcc gcgacgtcat 900
ccactaccgc gtgctgcacc gcgacggcca cctcacaatc gatgaggccg tgttcttctg 960
caacctcatg gacatggtgg agcattacag caaggacaag ggcgctatct gcaccaagct 1020
ggtgagacca aagcggaaac acgggaccaa gtcggccgag gaggagctgg ccagggcggg 1080
ctggttactg aacctgcagc atttgacatt gggagcacag atcggagagg gagagtttgg 1140
agctgtcctg cagggtgagt acctggggca aaaggtggcc gtgaagaata tcaagtgtga 1200
tgtgacagcc caggccttcc tggacgagac ggccgtcatg acgaagatgc aacacgagaa 1260
cctggtgcgt ctcctgggcg tgatcctgca ccaggggctg tacattgtca tggagcacgt 1320
gagcaagggc aacctggtga actttctgcg gacccggggt cgagccctcg tgaacaccgc 1380

-continued tcagctcctg cagttttctc tgcacgtggc cgagggcatg gagtacctgg agagcaagaa 1440
gcttgtgcac cgcgacctgg ccgcccgcaa catcctggtc tcagaggacc tggtggccaa 1500
ggtcagcgac tttggcctgg ccaaagccga gcggaagggg ctagactcaa gccggctgcc 1560
cgtcaagtgg acggcgcccg aggctctcaa acacgggaag ttcaccagca agtcggatgt 1620
ctggagtttt ggggtgctgc tctgggaggt cttctcatat ggacgggctc cgtaccctaa 1680
aatgtcactg aaagaggtgt cggaggccgt ggagaagggg taccgcatgg aacccccga 1740 gggctgtcca ggccccgtgc acgtcctcat gagcagctgc tgggaggcag agcccgcccg 1800
ccggccaccc ttccgcaaac tggccgagaa gctggcccgg gagctacgca gtgcaggtgc 1860
cccagcctcc gtctcagggc aggacgccga cggctccacc tcgccccgaa gccaggagcc 1920
ctgaccccac ccggtggggc ccttggcccc agaggaccga gagagtggag agtgcggcgt 1980
gggggcactg accaggccca aggagggtcc aggcgggcaa gtcatcctcc tggtgcccac 2040
agcaggggct ggcccacgta gggggctctg ggcggcccgt ggacacccca gacctgcgaa 2100
ggatgatcgc ccgataaaga cggattctaa ggactctaaa aaaaaaaaaa aaaaaaaaaa 2160
aaa 2163

<210> SEQ ID NO 54
<211> LENGTH: 4107
<212> TYPE: DNA
<213> ORGANISM: Homo sapiens

<400> SEQUENCE: 54
gcgcaaccct ccggaagctg ccgcccttt cccttttat gggaatactt tttttaaaaa 60
aaaagagttc gctggcgcca ccccgtagga ctggccgccc taaaaccgtg ataaaggagc 120
tgctcgccac ttctcacttc cgcttccttc cagtaaggag tcggggtctt ccccagtttt 180
ctcagccagg cggcggcggc gactggcaat gtttggcctc aaaagaaacg cggtaatcgg 240
actcaacctc tactgtgggg gggccggctt gggggccggc agcggcggcg ccacccgccc 300
gggagggcga cttttggcta cggagaagga ggcctcggcc cggcgagaga tagggggagg 360
ggaggccggc gcggtgattg gcggaagcgc cggcgcaagc cccccgtcca ccctcacgcc 420
agactcccgg agggtcgcgc ggccgccgcc cattggcgcc gaggtccccg acgtcaccgc 480
gacccccgcg aggctgcttt tcttcgcgcc cacccgccgc gcggcgccgc ttgaggagat 540
ggaagccccg gccgctgacg ccatcatgtc gcccgaagag gagctggacg ggtacgagcc 600
ggagcctctc gggaagcggc cggctgtcct gccgctgctg gagttggtcg gggaatctgg 660
taataacacc agtacggacg ggtcactacc ctcgacgccg ccgccagcag aggaggagga 720
ggacgagttg taccggcagt cgctggagat tatctctcgg taccttcggg agcaggccac 780
cggcgccaag gacacaaagc caatgggcag gtctggggcc accagcagga aggcgctgga 840
gaccttacga cgggttgggg atggcgtgca gcgcaaccac gagacggcct tccaaggcat 900
gcttcggaaa ctggacatca aaaacgaaga cgatgtgaaa tcgttgtctc gagtgatgat 960
ccatgttttc agcgacggcg taacaaactg ggcaggatt gtgactctca tttcttttgg 1020
tgcctttgtg gctaaacact tgaagaccat aaaccaagaa agctgcatcg aaccattagc 1080
agaaagtatc acagacgttc tcgtaaggac aaaacgggac tggctagtta aacaaagagg 1140
ctgggatggg tttgtggagt tcttccatgt agaggaccta gaaggtggca tcaggaatgt 1200
gctgctggct tttgcaggtg ttgctggagt aggagctggt ttggcatatc taataagata 1260
gccttactgt aagtgcaata gttgactttt aaccaaccac caccaccacc aaaaccagtt 1320

```
tatgcagttg gactccaagc tgtaacttcc tagagttgca ccctagcaac ctagccagaa   1380
aagcaagtgg caagaggatt atggctaaca agaataaata catgggaaga gtgctcccca   1440
ttgattgaag agtcactgtc tgaaagaagc aaagttcagt ttcagcaaca aacaaacttt   1500
gtttgggaag ctatggagga ggacttttag atttagtgaa gatggtaggg tggaaagact   1560
taatttcctt gttgagaaca ggaaagtggc cagtagccag gcaagtcata gaattgatta   1620
cccgccgaat tcattaattt actgtagtgt taagagaagc actaagaatg ccagtgacct   1680
gtgtaaaagt tacaagtaat agaactatga ctgtaagcct cagtactgta caagggaagc   1740
ttttcctctc tctaattagc tttcccagta tacttcttag aaagtccaag tgttcaggac   1800
ttttatacct gttatacttt ggcttggttt ccatgattct tactttatta gcctagttta   1860
tcaccaataa tacttgacgg aaggctcagt aattagttat gaatatggat atcctcaatt   1920
cttaagacag cttgtaaatg tatttgtaaa aattgtatat atttttacag aaagtctatt   1980
tctttgaaac gaaggaagta tcgaatttac attagttttt ttcataccct tttgaacttt   2040
gcaacttccg taattaggaa cctgtttctt acagcttttc tatgctaaac tttgttctgt   2100
tcagttctag agtgtataca gaacgaattg atgtgtaact gtatgcagac tggttgtagt   2160
ggaacaaatc tgataactat gcaggtttaa attttcttat ctgattttgg taagtattcc   2220
ttagataggt ttttctttga aaacctggga ttgagaggtt gatgaatgga aattctttca   2280
cttcattata tgcaagtttt caataattag gtctaagtgg agttttaagg ttactgatga   2340
cttacaaata atgggctctg attgggcaat actcatttga gttccttcca tttgacctaa   2400
tttaactggt gaaatttaaa gtgaattcat gggctcatct ttaaagcttt tactaaaaga   2460
ttttcagctg aatggaactc attagctgtg tgcatataaa aagatcacat caggtggatg   2520
gagagacatt tgatcccttg tttgcttaat aaattataaa atgatggctt ggaaaagcag   2580
gctagtctaa ccatggtgct attattaggc ttgcttgtta cacacacagg tctaagccta   2640
gtatgtcaat aaagcaaata cttactgttt tgtttctatt aatgattccc aaaccttgtt   2700
gcaagttttt gcattggcat ctttggattt cagtcttgat gtttgttcta tcagacttaa   2760
ccttttattt cctgtccttc cttgaaattg ctgattgttc tgctccctct acagatattt   2820
atatcaattc ctacagcttt cccctgccat ccctgaactc tttctagccc ttttagattt   2880
tggcactgtg aaacccctgc tggaaacctg agtgaccctc cctccccacc aagagtccac   2940
agacctttca tctttcacga acttgatcct gttagcaggt ggtaatacca tgggtgctgt   3000
gacactaaca gtcattgaga ggtgggagga agtccctttt ccttggactg gtatcttttc   3060
aactattgtt ttatcctgtc tttgggggca atgtgtcaaa agtcccctca ggaattttca   3120
gaggaaagaa cattttatga ggctttctct aaagtttcct ttgtatagga gtatgctcac   3180
ttaaatttac agaaagaggt gagctgtgtt aaacctcaga gtttaaaagc tactgataaa   3240
ctgaagaaag tgtctatatt ggaactaggg tcatttgaaa gcttcagtct cggaacatga   3300
cctttagtct gtggactcca tttaaaaata ggtatgaata agatgactaa gaatgtaatg   3360
gggaagaact gccctgcctg cccatctcag agccataagg tcatctttgc tagagctatt   3420
tttacctatg tatttatcgt tcttgatcat aagccgctta tttatatcat gtatctctaa   3480
ggacctaaaa gcactttatg tagtttttaa ttaatcttaa gatctggtta cggtaactaa   3540
aaaagcctgt ctgccaaatc cagtggaaac aagtgcatag atgtgaattg gtttttaggg   3600
gccccacttc ccaattcatt aggtatgact gtggaaatac agacaaggat cttagttgat   3660
```

```
atttgggct tggggcagtg agggcttagg acaccccaag tggtttggga aaggaggagg   3720

ggagtggtgg gtttataggg ggaggaggag gcaggtggtc taagtgctga ctggctacgt   3780

agttcgggca aatcctccaa aagggaaagg gaggatttgc ttagaaggat ggcgctccca   3840

gtgactactt tttgacttct gtttgtctta cgcttctctc agggaaaaac atgcagtcct   3900

ctagtgtttc atgtacattc tgtggggggt gaacaccttg gttctggtta aacagctgta   3960

cttttgatag ctgtgccagg aagggttagg accaactaca aattaatgtt ggttgtcaaa   4020

tgtagtgtgt ttccctaact ttctgttttt cctgagaaaa aaaaataaat cttttattca   4080

aatacaggga aaaaaaaaaa aaaaaaa                                       4107
```

<210> SEQ ID NO 55
<211> LENGTH: 4102
<212> TYPE: DNA
<213> ORGANISM: Homo sapiens

<400> SEQUENCE: 55

```
ttgaagacgt ggatggcggg aattctcgct tctggcctgg gtgagctaga agggagaagc     60

aaggacattg gagtccctat caccggttgc ctagacaact tcatgggaag gcccttggga    120

atctgagatg gagcaggcga accctttacg tccagatggc gagtccaaag gaggtgtttt    180

agctcacttg gaaaggctag agacccaagt gagcagatcc cgtaaacagt ctgaagagct    240

gcagagcgtg caggcccagg aaggtgctct tggaaccaag attcataaac taaggcgtct    300

gcgagatgag ctgagggctg tggtgcggca ccggcgagcc agcgtgaaag catgtattgc    360

caatgtagaa cccaaccaaa cagtggagat caatgagcaa gaagcattgg aagagaaatt    420

ggaaaatgtg aaagccattc tgcaggcata tcattttaca ggcctcagtg gtaaactgac    480

cagccgagga gtttgtgtct gcatcagtac tgcttttgag gggaacctat tggattccta    540

ttttgtggac cttgtcatac agaaaccact ccggatacat caccattcag tcccagtctt    600

cattcccctg gaagagatag ctgcaaaata tttacagacc aacatccagc acttcctgtt    660

cagtctctgc gagtacctga atgcttactc tgggaggaag taccaggcag accggcttca    720

gagtgacttt gcagccctcc tgactgggcc cttgcagaga aacccactgt gtaacttgct    780

gtcatttact tacaaactgg atccaggggg tcagtccttc ccgttctgtg ctagattgct    840

gtataaggac ctcacagcaa ctcttcccac tgacgtcacc gtgacatgtc aaggagtgga    900

agtattatcc acttcatggg aggagcaacg agcatctcat gaaactctgt tctgtacgaa    960

gcccttgcat caagtgtttg cctcatttac aagaaaagga gaaaagttgg atatgagtct   1020

ggtctcctaa tagattgttt tcactgcact gggagcacat cagagaaata aatccccccct   1080

cccctgccag gtgaaaggaa atattgcact ttctgttctc atgactaagg ggacaggagt   1140

tccagaagaa cctttcaaga tgatcaggaa caccaggacg agggccgtct cacctcactc   1200

ggaccacatg gagacctccc ttcaaaatgg gagccatgtc ctgccccacc aagccctgtc   1260

tgaagtggag cttccccgcc tgtgctccct ccacagtccc ggaaagccca gcggcaaagg   1320

cagctttgtc ccagctctgc caccctcctg ctcacagtgg tcagggcccc tcaggggcaa   1380

ggacggcagg gattggaacg agggctctgg aaggactgtt cagccctatg cctaagaccc   1440

ctatgctggg gacactacag gcacacacag gaatagcagg gccaccctca gagctcacac   1500

atccacgaac aaatgaaggc tgaggaggtt tctaaaccta aagtccatga gtgtgcactt   1560

caatccagga aggtcgggac ttccttcagt ttcaaaaaat aaattctccc ttccggtttg   1620

gactgttgca ggctcgaggc cattcaggag ttgtccacca cctggtgggg cagtgtgaca   1680
```

```
gaggggccat tggggaaggt ggctagctta tcccgcccct tcaagaagaa ggtcagcagc   1740
tccccccttcc ccttcacaaa gatggggcct cgcctcacaa agcggaagcc gtactctcgg   1800
aggatgactt gggtttcttc taccacctgg agagggaggg ggagcaagaa cgtggcgtta   1860
cggggggagc ctagactgag ggcgggtggg ggctttgggt ggttggagcc gagcactgat   1920
ccatgggtcc caagcagtac gggacactcc ccaaacctcc cagggccaag cccttccacc   1980
cgtggcgagc agcgggtggg aaggagaacc ctggagtgac tggctggggg cctcctctca   2040
tccagagact tctctcctag gatggccatg gtcacctggg tggcagcact gttacctgga   2100
aactgccact gcctgctctt ctgtcccttt gcccctttcg tggagctttt ctgccagacg   2160
ccactgagac agatcacaag gtattagaag gttcataccc aaaggtaggc catatgcatc   2220
tagaacttca gcccagattt tgtggatggg tggaagtgtt tcttcctgtg ctgaggctag   2280
ctattgcaga gattcttttc cacttgcccc acgtctctgc ctctggactt actgttcagg   2340
gccagggtgg gaggcagggg cacgtgggaa agcactgttc cggttttgtt ctcatgccga   2400
gtctgagcac gtgccagctg tgccactgga catacctgaa tgttgcccat gacccccgtg   2460
gactccatcc tgctggctac attgactgta ttgccccaga tgtcgtagtg tggtttccgg   2520
gctccgatga ccccagccag aaccccgcct ttgttcatgc ctagggtaga ggcataaagt   2580
tcagcacagc cacaggccac accttgttat gggcctcaga agccatctcc tctccagacc   2640
tgtaccacaa agctcctaat gtaacacatc attgtcctca ttcaacttgg ctgtatgcta   2700
ttggagggtg gaaatcacat ctcctgttta tccgtgtgct tgttaggtgt cagccgccac   2760
ccccccccca tatgcagatt tactcggcat ggtagtggcc agcttctaac acagctggta   2820
tttcaagtct cctgggacct cactcaggaa tgataccccc tcagtagaag cagcaggtga   2880
tcttaactcc tttcaaagag caggcctgtc tgggaagcca tgtcctcagc aggcacagca   2940
acccctctgg aaatggatca caaactcact tctcagccag gcaggccaag cttctattgt   3000
aacagtaggc acagtatagt cggatcatca catcagctgg gtttttggtt tagtcatcta   3060
gagtcgtctg gactaaaggt ctttcaggtc tccttgccct gtgagtgcgt gaacctcccc   3120
acccgaattg cctcagttgt cctgagcctc atgtctctcc tggtggtggg ccaggcccct   3180
gcatgggaag ggagcctgct gcggggcagg ccagctgggg gtgctcacct atgcgcagca   3240
tgaagttatt gaaggactgg ttgttgatgt tggtgagcgt atccttcatg gccagcgcga   3300
agtcggccag gtcagccagg tgctgccagc gctctctctc ggacttgtct tcctgtgcca   3360
ggggaccgtg gagaaagtgt caggggccgc tcactgcagc agcctgctct gctgccttcc   3420
ctggcagtgt tctgggggtg gattccctac acctagatgt tcaaggcctt acttttcctc   3480
ccacaaagga gtcgcagcca cgctagctct gacttgccac tgtgacaaag ttcacgtagc   3540
aggtctaggc aaagactggg caattgagca gaggagacgg acctgtgagt ctgaccacga   3600
ggcggacccc ttcaccttgg ctgggcctgg tcctggtcct taggttttgt caggttgtcc   3660
ttgtttggat ccctcaacta ggtgataagc actggagggg gatgacccgc cttggacgtg   3720
tttctttaac ctcatccata taatagggcc gtgggatggt tgtagaggta aagcaggatg   3780
atggtgtttt aagaccagag cttgggacca gggctcctac acctaatttt ctctcctggt   3840
agctgaacaa aggtctaaat tagcttaaca aaagaacagg ctgccgtcag ccagagttct   3900
gaaggccatg ctttcagttt cccttgttga caattgctct ccagttccta tgaaagcaca   3960
gagccttagg gggcctggcc acagaacaca accatcttag gcctgagctg tgaacagcag   4020
```

ggggttgtgt gtctgttctg tttctctgct tgccgaactt tctcaataaa ccctatttct 4080
tatttataaa aaaaaaaaaa aa 4102

<210> SEQ ID NO 56
<211> LENGTH: 7998
<212> TYPE: DNA
<213> ORGANISM: Homo sapiens

<400> SEQUENCE: 56
aggagtctgt cagctacgga ggacaatgac cttgcagaca ccaccgcctg agtgagaacc 60
aggggtctgt gcctctcctc attccccgct cttgcccttg tcaagcctgc accagcatgt 120
caggaacctc caaggagagt ctggggcatg gggggctgcc agggttgggc aagacctgct 180
taacaaccat ggacacaaag ctgaacatgc tgaacgagaa ggtggaccag ctcctgcact 240
tccaagaaga tgtcacagag aagttgcaga gcatgtgccg agacatgggc cacctggagc 300
ggggcctgca caggctggag gcctcccggg caccgggccc gggcggggct gatggggttc 360
cccacattga cacccaggct gggtggcccg aggtcctgga gctggtgagg gccatgcagc 420
aggatgcggc ccagcacggt gccaggctgg aggccctctt caggatggtg gctgcggtgg 480
acagggccat cgctttggtg ggggccacgt tccagaaatc aaaggtggcg gatttcctca 540
tgcaggggcg tgtgccctgg aggagaggca gcccaggtga cagccctgag gagaataaag 600
agcgagtgga agaagaggga ggaaaaccaa agcatgtgct gagcaccagt ggggtgcagt 660
ctgatgccag ggagcctggg gaagagagcc agaaggcgga cgtgctggag gggacagcgg 720
agaggctgcc ccccatcaga gcgtcagggc tgggagctga ccccgcccag gcagtggtct 780
caccgggcca gggagatggt gttcctggcc cagcccaggc attccctggc cacctgcccc 840
tgcccacaaa ggtggaagcc aaggctcctg agacacccag cgagaacctc aggactggcc 900
tggaattggc tccagcaccc ggcagggtca atgtggtctc ccccgagcctg gaggttgcac 960 caggtgcagg acaaggagca tcgtccagca ggcctgaccc tgagccctta gaggaaggca 1020
cgaggctgac tccagggcct ggccctcagt gcccagggcc tccagggctg ccagcccagg 1080
ccagggcaac ccacagtggt ggagaaacac ctccaaggat ctccatccac atacaagaga 1140
tggatactcc tggggagatg ctgatgacag gcaggggcag ccttggaccc accctcacca 1200
cagaggctcc agcagctgcc cagccaggca agcagggccc acctgggacc gggcgctgcc 1260
tccaagcccc tgggactgag cccggagaac agacccctga aggagccaga gagctctccc 1320
cgctgcagga gagcagcagc cccgggggag tgaaggcaga ggaggagcaa agggctgggg 1380
ccgagcctgg cacgagacca agcttggcca ggagtgacga caatgaccac gaggttgggg 1440
ccctgggcct gcagcagggc aaaagcccag gggcgggaaa ccctgagcct gagcaggact 1500
gtgcagccag ggctccggtg agagctgaag cagtaaggag gatgccccca ggcgccgagg 1560
ctggcagcgt ggttctggat gacagtccgg ccccaccagc tccttttgaa caccgggtag 1620
tgagcgtcaa ggagacctcc atctctgcgg gttacgaggt gtgccagcac gaagtcttgg 1680
gagggggtcg gtttggccag gtccacaggt gcacagagaa gtccacaggc ctcccactgg 1740
ctgccaagat catcaaagtg aagagcgcca aggaccggga ggacgtgaag aacgagatca 1800
acatcatgaa ccagctcagc cacgtgaacc tgatccagct ctatgacgcc ttcgagagca 1860
agcacagctg caccccttgtc atggagtacg tggacggggg tgagctcttc gaccggatca 1920
cagatgagaa gtaccacctg actgagctgg atgtggtcct gttcaccagg cagatctgtg 1980
agggtgtgca ttacctgcac cagcactaca tcctgcacct ggacctcaag ccggagaaca 2040

```
tattgtgcgt caatcagaca ggacatcaaa ttaagatcat tgactttggg ctggccagaa   2100
ggtacaagcc tcgagagaag ctgaaggtga acttcggcac tcctgagttc ctggccccag   2160
aagtcgtcaa ttatgagttt gtctcattcc ccacagacat gtggagtgtg ggagtcatca   2220
cctacatgct actcagtggc ttgtccccat ttctagggga aacagatgca gagaccatga   2280
atttcattgt aaactgtagc tgggattttg atgctgacac ctttgaaggg ctctcggagg   2340
aggccaagga ctttgtttcc cggttgctgg tcaaagagaa gagctgcaga atgagtgcca   2400
cacagtgcct gaaacacgag tggctgaata atttgcctgc caaagcttca agatccaaaa   2460
ctcgtctcaa atcccaacta ctgctgcaga aatacatagc tcaaagaaaa tggaagaaac   2520
atttctatgt ggtgactgct gccaacaggt taaggaaatt tccaacttct ccctaatctt   2580
caactctgct gctccaatgg gtccagaaat tactgaggcc agtggtgaag tgaagagatg   2640
actcaaacat ttaaataatt tggctttttg gtattattga ttccacttat tttgtaaaaa   2700
tggttatggc tgctgccttc cttgtggatg aaaagtggct gtaaagaagc ttcctaagaa   2760
cgtttttttc tgccttgtaa gatcactacg tgtgaaatgc tctgagtacc tttcaaatat   2820
acctactttt ggtggtaagt gtagggatgc tttaggtagg tactttgcat ctgtcgaatt   2880
taaattctaa actcacactg attaaggaac tcagtagact actttgcagg ggccatgtta   2940
ttcagtgtta tctcctccag tacaaagaat tcctagaatt ttgatttgct caggtgtgag   3000
ctgacatttt attgtactac cccattcttg tgttaagcca tgtggattta ggacagtgat   3060
cttcaaactt gctttaactt atgctccctt ttgagaatca gcatcacttg aaatgtcaaa   3120
atatgtcaac tctcatagcc aaatcaaaga agtgatcatt ttgactgtgc tttttaaatc   3180
tccacacacc tccacctctc tcctaattct gcctgtctta acccctctgt cttagttata   3240
aatttctggt cttgtaagtc tggaagctga taggcaattt atgaaagaga taagaatgta   3300
atgaggttcc gctttctgag aaacacagaa atgatacatc ctgagacata aaggaaagct   3360
gctcttctgc tgcctcaggc tgtagcactc tcaatgttgt cactctacac atacactttc   3420
tatatacatg tacagttgac ccttgaacag ggtttgaatt gcagtcaact taaatgtgga   3480
ttttctttca cctttgtcac ccctgagaca gcaacaccat gctctcctct tcatcccact   3540
ctgcagccta ctcaacagga agatgatgaa gatgaacacc tttatgatga tccactttca   3600
cttaatgaat agtaaacata tgttttcctc cttatgattt tagtaacttt tctctagctt   3660
actttattgt aagaatacag tatataagct gggtgtggtg gctcatgccc ataatcccag   3720
cactttggga ggctgaggca ggcagatcac ttgaggtcag gagttcaaga ccagcctggc   3780
caacacagtg aaaccccatc tctactaaaa atacaaaaat tagtggggcg tggtggcgga   3840
tgcctgtaat gtcagctact ctggaggctg aggcaggaga actgcttgaa cctgggaggt   3900
ggagtttgca gtgagccaag attgcaccac tgcactccag cctaggcaac agagcaagac   3960
tccgtctcaa aaaaaaaaaa aaaaaagaat acagtatatg tatatataca cacacacaaa   4020
cacacacaca cacgaacaca tatgtgtgta tgggtattaa ctgactgttt atattattga   4080
tagggcttcc agtcaacatt aggctattag tagttaagtt tttggggaga caaaagttat   4140
actcagattt tctactgcaa gggggtaggc actcctaacc ctcacattgt tcaagggtcc   4200
actgtacatt taaacacttt tctatatgca ttagagtagc cctgtcatcc cttcactgaa   4260
atcatactgt tctcaacatg gcaagcaact aacacttttt tttttttttg agacagggtc   4320
tcactctgtt gcccaggctg cagtgcagtg gtgtgatctt ggctcactgt agcctccgcc   4380
```

-continued tcctgggctc aggcgatcat gagtacctgg gaccataggt gcccgctact acacccagct 4440
aatttttgta tttttagtgg agatagggtt ttgccatgtt gcccaacctg gtcttgagct 4500
caagcgatcc acctgcccca gcctcccaaa gtgctgggat tataggtgtg agccaccaca 4560
cccagcttca actaacacat ttacgaactt gtatacatgt atatttagat actttaccaa 4620
cttgtaaaat ggttaaagga gtactttatt atgaaaaaat atacaatctt taaaatttcc 4680
ttacttctac atgatttttg tgctattccc attttttcc tcaggtgagc agctttagtt 4740 ttttatttt tttgagagag tcttcctctg tcacccaggc tggagtgcac tggtgtgttc 4800
ttggctcact gcaacctctg cctcccgggt tcaagtgatc ttgtgcctca gcctcccagg 4860
tagctgggat tacaggcgtg tgctgccacg cccagctaat tttgtattt ttggtagaga 4920 tggggttttg ccatgttggc caggctggtc tcgaactcct gacctcagat gatccacctg 4980
tcttggcctc ccaaagagct gggaatatag gcatgagcca ctgtgcttgg cctcaggtga 5040
gcagctttag tcaatgttgt gaattttaga ttttaattag acatgcaaca gtttcactac 5100
ctttcaggat ttttgtcctg taacagaggc tcttgctttt tgacagagag gtaggcaggt 5160
ggagaggtta tcctgctgct gcagttctca agttgttaag tttcctctgg aaggctaacc 5220
cttgttggga actaacagtt tcaataccag caagtctagg cctgctccaa gttggtcagc 5280
tgaagaatga acatcagaag acacagctgc tgaaagttgt cctttgatga gacagtgata 5340
gtgatttggt aaaatgtctt attttttaaa tgtcagttat ctttctttaa aaggttttt 5400 gagggcagcc tccagaagga gctagagagt atattttata gttctattgt ggttcatacc 5460
ctgttttcga cttaagattc tggagaatgc tatgaaacat ctccccagaa aaagacagtt 5520
aattaccata tctagagcag cactgcccaa caaaaatata gtacaggcta tacacataat 5580
taaaacattt ctagtagctt ctctaacaaa acccattgaa agccaatttt aataatttat 5640
ataacttagt gtatcaaaaa tatttcaata tgtaatcaac ataaaattga gatactttac 5700
cagctactag ggaggctgag gccagagaat cacttgaacc caggggtgg aggttgcagt 5760 gagccaagat cacaccattg aactccagcc tgggcaacaa gagcaaaact ccgtctcaaa 5820
aaaaaagaga tattttatat tctttttctc atactaagtc tcaaaaatct ggtatatttt 5880
acacttaaaa acacatgtca aggctaggca tggtggctca catctgtaat cccagcactt 5940
tgggaggcca aggtgggcag attgctggcc aacatggtaa aacccatct ctaaaaatat 6000 aaaaattagc tgggcgtggt ggcgcatacc tgtaatccca gctacttggg aggctaaggc 6060
acaagaatca cttaaacagg aggcaggggt tgcagtgagc tgagatcaca ccactgcact 6120
ccagcctggg tggcagagca aaactttgtc cccacccctg acaaaaaaca aacaaacaaa 6180
caaaacaaaa aaaaacctgt caattcagat gctaggtttt catcagacgt acttaatctg 6240
tatttagatt tcttaaaact tactgtggaa aatgtattta catactcaag ttgtttgaaa 6300
cataactcac tgttttccaa taactgaagt atccactttt acatgtatta aaattaaata 6360
aaattagaaa ttcagttctg cagttgcact agccacattt taagtgttta atagccacac 6420
gtggttagtg gcatctatat tggacagggc agatctagag agaatcctgt atctaacaat 6480 tttaatttt ttcccttat gctgttattc cttacctaga gaaacaattt ccctccaaag 6540
ttcctttgag ggtctgttt aggccaggcc aacacaagtg acctatgtgg attttagcat 6600
cctttttttg aaatttgagg ttttatgaag cttgagtttt tctggatatt tttagtaatt 6660
tgctggtgtg tacttagctc aaatacttga ttgcaactgt gttgggtcaa ctatttctaa 6720
tgggactttt ccatttgcat gtacagtcac tggaaactgc tgggcagaga aactctaaaa 6780
ggtagttggg gcacactttt tccacctgtc agattggtga agaattggtg aggctgtggg 6840
gaaaatggca ttctcccact tttgatggat atgtatccaa ataaaagtca ttcccatgct 6900
ttctttcatc cagaaatttt atttctagaa atttatccct ccgtacttga acaattgtat 6960
agagatttat tcaaaatgat gtttactata gcactgttgc taatggccca gtaaaaacaa 7020
ccaacacatg cctattagtt tggttttagt taaatgaatt ttgccacatc catgtagtgg 7080
aatacctcac agctgttata gatagatcta gatatactga aagccatttt ttcttaaatt 7140
atagaatgta tatatggtat catcccattt gtgaagagac atatgcttat atgtgcatta 7200
aaaaaccgta ggatatgcaa gaaacttaac agtggagtgt gaaaagtggg tgattgggag 7260
agggggaatt ccacttttca tttatctttc tgaacctttt gaatcttttt tttttttttt 7320
tttacaatga gcatgtattc cttttttttt ttttctttcc aagatggagt ctcactctgt 7380
tgccaggctg gagtgcagtg gcgcaatctt ggcttactgc aacatccacc tcccgagttc 7440
aagtgatttc tcctgcctca gcctcccaag tagctgggac tacaggcatg cgccaccacg 7500
cccagctaat ttttgtgttt ttagtagaga tgggctttca ccatgctggc caggatggtc 7560
tcgatctctt gacctcgtga tctgcccacc tcggcctccc aaagtgctgg gattacaggt 7620
gtgagccact gcgcctggcc cgcatgtatt acatttataa ttaaaaattc acaactcaat 7680
gtcaagtgtg aaccttgtgt tgaccctgat ttgagcaagc aataaaaaga tatttttgag 7740
acatttagat tatgaatttc acatttgatg atagttacta ttaattttgt gaggtgtgat 7800
attggcaatg tggttagatg acttcagaga aaaaggaagg tatagttaag caagtatggc 7860
aacatctaat aacttgggtc taggtgatgt gtatgggttt cattatactg tcctctttac 7920
tgttgtatgt atttgaaaac attcatgaca aaaaaacttt ttaatcagtt aaataaacca 7980
tgaagaacgg ttaaagaa 7998

<210> SEQ ID NO 57
<211> LENGTH: 7852
<212> TYPE: DNA
<213> ORGANISM: Homo sapiens

<400> SEQUENCE: 57
ggcgctgagc gagctcggag cccgcgctgt gcgcctgcgg ccggggcgcc ccgccgagcg 60
ccggtgcccc ggctcccggg ccgccttcgc cgcgcgggaa ggattcttca aaattaacag 120
aaaccaattc gggccagctg aagagaaaaa ataaaggtgg ctcccggctg cctctgctgc 180
agttcagagc aacttcagga gcttcccagc cgagagcttc aggacgcctt tcctgtccca 240
ctggcccagt tgccacaaca aacaacagag aagacggtga ccatgggggga tgtgaagctg 300 gttgcctcgt cacacatttc caaaacctcc ctcagtgtgg atccctcaag agttgactcc 360
atgcccctga cagaggcccc tgctttcatt ttgccccctc ggaacctctg catcaaagaa 420
ggagccaccg ccaagttcga agggcgggtc cggggttacc cagagcccca ggtgacatgg 480
cacagaaacg ggcaacccat caccagcggg ggccgcttcc tgctggattg cggcatccgg 540
gggactttca gccttgtgat tcatgctgtc catgaggagg acaggggaaa gtatacctgt 600
gaagccacca atggcagtgg tgctcgccag gtgacagtgg agttgacagt agaaggaagt 660
tttgcgaagc agcttggtca gcctgttgtt tccaaaacct taggggatag attttcagct 720
ccagcagtgg agacccgtcc tagcatctgg ggggagtgcc caccaaagtt tgctaccaag 780
ctgggccgag ttgtggtcaa agaaggacag atgggacgat tctcctgcaa gatcactggc 840

-continued

```
cggccccaac cgcaggtcac ctggctcaag ggaaatgttc cactgcagcc gagtgcccgt    900
gtgtctgtgt ctgagaagaa cggcatgcag gttctggaaa tccatggagt caaccaagat    960
gacgtgggag tgtacacgtg cctggtggtg aacgggtcgg ggaaggcctc gatgtcagct   1020
gaactttcca tccaaggttt ggacagtgcc aataggtcat ttgtgagaga aacaaaagcc   1080
accaattcag atgtcaggaa agaggtgacc aatgtaatct caaaggagtc gaagctggac   1140
agtctggagg ctgcagccaa aagcaagaac tgctccagcc cccagagagg tggctcccca   1200
ccctgggctg caaacagcca gcctcagccc ccaagggagt ccaagctgga gtcatgcaag   1260
gactcgccca gaacggcccc gcagaccccg gtccttcaga agacttccag ctccatcacc   1320
ctgcaggccg caagagttca gccggaacca agagcaccag gcctgggggt cctatcacct   1380
tctggagaag agaggaagag gccagctcct ccccgtccag ccaccttccc caccaggcag   1440
cctggcctgg ggagccaaga tgttgtgagc aaggctgcta acaggagaat ccccatggag   1500
ggccagaggg attcagcatt ccccaaattt gagagcaagc cccaaagcca ggaggtcaag   1560
gaaaatcaaa ctgtcaagtt cagatgtgaa gtttccggga ttccaaagcc tgaagtggcc   1620
tggttcctgg aaggcacccc cgtgaggaga caggaaggca gcattgaggt ttatgaagat   1680
gctggctccc attacctctg cctgctgaaa gcccggacca gggacagtgg gacatacagc   1740
tgcactgctt ccaacgccca aggccagctg tcctgtagct ggaccctcca agtggaaagg   1800
cttgccgtga tggaggtggc cccctccttc tccagtgtcc tgaaggactg cgctgttatt   1860
gagggccagg attttgtgct gcagtgctcc gtacggggga ccccagtgcc ccggatcact   1920
tggctgctga atgggcagcc catccagtac gctcgctcca cctgcgaggc cggcgtggct   1980
gagctccaca tccaggatgc cctgccggag gaccatggca cctacacctg cctagctgag   2040
aatgccttgg ggcaggtgtc ctgcagcgcc tgggtcaccg tccatgaaaa gaagagtagc   2100
aggaagagtg agtaccttct gcctgtggct cccagcaagc ccactgcacc catcttcctg   2160
cagggcctct ctgatctcaa agtcatggat ggaagccagg tcactatgac tgtccaagtg   2220
tcagggaatc caccccctga agtcatctgg ctgcacaatg ggaatgagat ccaagagtca   2280
gaggacttcc actttgaaca gagaggaact cagcacagcc tttgtatcca ggaagtgttc   2340
ccggaggaca cgggcacgta cacctgcgag gcctggaaca gcgctggaga ggtccgcacc   2400
caggccgtgc tcacggtaca agagcctcac gatggcaccc agccctggtt catcagtaag   2460
cctcgctcag tgacagcctc cctgggccag agtgtcctca tctcctgcgc catagctggt   2520
gaccccttttc ctaccgtgca ctggctcaga gatggcaaag ccctctgcaa agacactggc   2580
cacttcgagg tgcttcagaa tgaggacgtg ttcaccctgg ttctaaagaa ggtgcagccc   2640
tggcatgccg gccagtatga gatcctgctc aagaaccggg ttggcgaatg cagttgccag   2700
gtgtcactga tgctacagaa cagctctgcc agagcccttc cacgggggag ggagcctgcc   2760
agctgcgagg acctctgtgg tggaggagtt ggtgctgatg gtggtggtag tgaccgctat   2820
gggtccctga ggcctggctg gccagcaaga gggcagggtt ggctagagga ggaagacggc   2880
gaggacgtgc gaggggtgct gaagaggcgc gtggagacga ggcagcacac tgaggaggcg   2940
atccgccagc aggaggtgga gcagctggac ttccgagacc tcctggggaa gaaggtgagt   3000
acaaagaccc tatcggaaga cgacctgaag gagatcccag ccgagcagat ggatttccgt   3060
gccaacctgc agcggcaagt gaagccaaag actgtgtctg aggaagagag gaaggtgcac   3120
agcccccagc aggtcgattt tcgctctgtc ctggccaaga aggggacttc caagaccccc   3180
gtgcctgaga aggtgccacc gccaaaacct gccaccccgg attttcgctc agtgctgggt   3240
```

ggcaagaaga aattaccagc agagaatggc agcagcagtg ccgagaccct gaatgccaag 3300
gcagtggaga gttccaagcc cctgagcaat gcacagcctt cagggccctt gaaacccgtg 3360
ggcaacgcca agcctgctga gaccctgaag ccaatgggca acgccaagcc tgccgagacc 3420
ctgaagccca tgggcaatgc caagcctgat gagaacctga aatccgctag caaagaagaa 3480
ctcaagaaag acgttaagaa tgatgtgaac tgcaagagag gccatgcagg gaccacagat 3540
aatgaaaaga gatcagagag ccaggggaca gccccagcct tcaagcagaa gctgcaagat 3600
gttcatgtgg cagagggcaa gaagctgctg ctccagtgcc aggtgtcttc tgaccccccca 3660 gccaccatca tctggacgct gaacggaaag accctcaaga ccaccaagtt catcatcctc 3720
tcccaggaag gctcactctg ctccgtctcc atcgagaagg cactgcctga ggacagaggc 3780
ttatacaagt gtgtagccaa gaatgacgct ggccaggcgg agtgctcctg ccaagtcacc 3840
gtggatgatg ctccagccag tgagaacacc aaggccccag agatgaaatc ccggaggccc 3900
aagagctctc ttcctcccgt gctaggaact gagagtgatg cgactgtgaa aaagaaacct 3960
gcccccaaga cacctccgaa ggcagcaatg ccccctcaga tcatccagtt ccctgaggac 4020
cagaaggtac gcgcaggaga gtcagtggag ctgtttggca aagtgacagg cactcagccc 4080
atcacctgta cctggatgaa gttccgaaag cagatccagg aaagcgagca catgaaggtg 4140
gagaacagcg agaatggcag caagctcacc atcctggccg cgcgccagga gcactgcggc 4200
tgctacacac tgctggtgga gaacaagctg ggcagcaggc aggcccaggt caacctcact 4260
gtcgtggata agccagaccc cccagctggc acaccttgtg cctctgacat tcggagctcc 4320
tcactgaccc tgtcctggta tggctcctca tatgatgggg gcagtgctgt acagtcctac 4380
agcatcgaga tctgggactc agccaacaag acgtggaagg aactagccac atgccgcagc 4440
acctctttca acgtccagga cctgctgcct gaccacgaat ataagttccg tgtacgtgca 4500
atcaacgtgt atggaaccag tgagccaagc caggagtctg aactcacaac ggtaggagag 4560
aaacctgaag agccgaagga tgaagtggag gtgtcagatg atgatgagaa ggagcccgag 4620
gttgattacc ggacagtgac aatcaatact gaacaaaaag tatctgactt ctacgacatt 4680
gaggagagat taggatctgg gaaatttgga caggtctttc gacttgtaga aaagaaaact 4740
cgaaaagtct gggcagggaa gttcttcaag gcatattcag caaaagagaa agagaatatc 4800
cggcaggaga ttagcatcat gaactgcctc caccacccta agctggtcca gtgtgtggat 4860
gcctttgaag aaaaggccaa catcgtcatg gtcctggaga tcgtgtcagg aggggagctg 4920
tttgagcgca tcattgacga ggactttgag ctgacggagc gtgagtgcat caagtacatg 4980
cggcagatct cggagggagt ggagtacatc cacaagcagg gcatcgtgca cctggacctc 5040
aagccggaga acatcatgtg tgtcaacaag acgggcacca ggatcaagct catcgacttt 5100
ggtctggcca ggaggctgga gaatgcgggg tctctgaagg tcctctttgg caccccagaa 5160
tttgtggctc ctgaagtgat caactatgag cccatcggct acgccacaga catgtggagc 5220
atcggggtca tctgctacat cctagtcagt ggcctttccc ccttcatggg agacaacgat 5280
aacgaaacct tggccaacgt tacctcagcc acctgggact tcgacgacga ggcattcgat 5340
gagatctccg acgatgccaa ggatttcatc agcaatctgc tgaagaaaga tatgaaaaac 5400
cgcctggact gcacgcagtg ccttcagcat ccatggctaa tgaaagatac caagaacatg 5460
gaggccaaga aactctccaa ggaccggatg aagaagtaca tggcaagaag gaaatggcag 5520
aaaacgggca atgctgtgag agccattgga agactgtcct ctatggcaat gatctcaggg 5580

-continued

```
ctcagtggca ggaaatcctc aacagggtca ccaaccagcc cgctcaatgc agaaaaacta   5640
gaatctgaag aagatgtgtc ccaagctttc cttgaggctg ttgctgagga aaagcctcat   5700
gtaaaaccct atttctctaa gaccattcgc gatttagaag ttgtggaggg aagtgctgct   5760
agatttgact gcaagattga aggataccca gaccccgagg ttgtctggtt caaagatgac   5820
cagtcaatca gggagtcccg ccacttccag atagactacg atgaggacgg gaactgctct   5880
ttaattatta gtgatgtttg cggggatgac gatgccaagt acacctgcaa ggctgtcaac   5940
agtcttggag aagccacctg cacagcagag ctcattgtgg aaacgatgga ggaaggtgaa   6000
ggggaagggg aagaggaaga agagtgaaac aaagccagag aaaagcagtt tctaagtcat   6060
attaaaagga ctatttctct aaaactcaaa aaaaaaaaaa aaactcaaga tagtaaaagc   6120
acctagtgtg atagattatc ggttaggtca tttgtgggtt gattcttcag aaacagcagt   6180
tgatacctag cagcgttatt gatgggcatt aatctatgtt agttggcacc ttaagatact   6240
agtgcagcta gatttcattt agggaaatca ccagtaactt gactgaccaa ttgattttag   6300
agagaaagta accaaaccaa atatttatct gggcaaagtc ataaattctc cacttgaatg   6360
cgctcatgaa aaataaggcc aaaacaagag ttctgggcca cagctcagcc cagagggttc   6420
ctggggatgg gaggcctctc tctccccacc ccctgactct agagaactgg gttttctccc   6480
agtactccag caattcattt ctgaaagcag ttgagccact ttattccaaa gtacactgca   6540
gatgttcaaa ctctccattt ctctttcccc ttccacctgc cagttttgct gactctcaac   6600
ttgtcatgag tgtaagcatt aaggacatta tgcttcttcg attctgaaga caggtccctg   6660
ctcatggatg actctggctt ccttaggaaa atatttttct tccaaaatca gtaggaaatc   6720
taaacttatc cctctttgc agatgtctag cagcttcaga catttggtta agaacccatg    6780
ggaaaaaaaa aatccttgct aatgtggttt cctttgtaaa ccaggattct tatttgtgct   6840
gttatagaat atcagctctg aacgtgtggt aaagattttt gtgtttgaat ataggagaaa   6900
tcagtttgct gaaaagttag tcttaattat ctattggcca cgatgaaaca gatttcaact   6960
gataaagagc tggagaactc catgtacttt ggaatctcct ccaagatagc cagagtttaa   7020
tacatcttca ttctcaacac tctccaaaga acttgaccta ccttatgggt tccatatttt   7080
tcttcttaaa tgtgcatcaa tcatgccttg cccccaacct ttaaatatat tcttagacct   7140
ggtaaatgca ctcagacttg cgtctttagg aatttttaac tttctttcac tacattggca   7200
cttaaatttt ttctttataa agctttttga aggtcataaa caaagaccat aattgatgat   7260
agacctaata catttcctct gtgtgtgtgt gtaacattcc aaatactttt tttttctttt   7320
ccactgtttg taaggtgcaa caatttaata tttttaaggg actttttaag agttccttaa   7380
gaaccaattt aaaattactt cagtgcaatc ctacacagta tcaacattag aattttgata   7440
ttagtcttat gttatcttcc attctatttt tatctgcttt ttgctgctag tttcaaactg   7500
ccagtatttt tccttttgct tttaaaatag ttacaatatt tttcatgata gccacagtat   7560
tgccacagtt tattataata aagggttttt atttgattta gcgcattcaa agcttttttc   7620
tatcactttt gtgttcagaa tataaccttt gtgtgcgtgt atgttgtgtg tgtgcatgtg   7680
tggcgtatat gtgtgttaca ggttaatgcc ttcttggaat tgtgttaatg ttctcttggt   7740
ttattatgcc atcagaatgg taaatgagaa cactacaact gtagtcagct cacaattttt   7800
aaataaagga taccacagtg catgctgttt gttcaaaaaa aaaaaaaaaa aa           7852
```

<210> SEQ ID NO 58
<211> LENGTH: 6230

<212> TYPE: DNA
<213> ORGANISM: Homo sapiens

<400> SEQUENCE: 58
ctagatcgaa agtcctttgg taatgatgtg tcatacattc tagtcatcaa agacaccatt 60
ttctgggcct gaagtgttct gctggttttt ggaggaatga gaatccaatc tctcataagc 120
cggattcaga aaataggtca tcgatgaaac atctgtatgg attatttcac tataatccta 180
tgatgcttgg acttgaatca cttccagatc ccacagacac ctgggaaatt atagagacca 240
ttggtaaagg cacctatggc aaagtctaca aggtaactaa caagagagat gggagcctgg 300
ctgcagtgaa aattctggat ccagtcagtg atatggatga agaaattgag gcagaataca 360
acattttgca gttccttcct aatcatccca atgttgtaaa gttttatggg atgttttaca 420
aagcggatca ctgtgtaggg ggacagctgt ggctggtcct ggagctgtgt aatgggggct 480
cagtcactga gcttgtcaaa ggtctactca gatgtggcca gcggttggat gaagcaatga 540
tctcatacat cttgtacggg gccctcttgg gccttcagca tttgcacaac aaccgaatca 600
tccaccgtga tgtgaagggg aataacattc ttctgacaac agaaggagga gttaagctcg 660
ttgactttgg tgtttcagct caactcacca gtacacgtct gcggagaaac acatctgttg 720
gcaccccgtt ctggatggcc cctgaggtca ttgcctgtga gcagcagtat gactcttcct 780
atgacgctcg ctgtgacgtc tggtccttgg ggatcacagc tattgaactg ggggatggag 840
accctcccct ctttgacatg catcctgtga aaacactctt taagattcca agaaatcctc 900
cacctacttt acttcatcca gaaaaatggt gtgaagaatt caaccacttt atttcacagt 960
gtcttattaa ggattttgaa aggcgacctt ccgtcacaca tctccttgac cacccattta 1020
ttaaaggagt acatggaaaa gttctgtttc tgcaaaaaca gctggccaag gttctccaag 1080
accagaagca tcaaaatcct gttgctaaaa ccaggcatga gaggatgcat accagaagac 1140
cttatcatgt ggaagatgct gaaaaatact gccttgagga tgatttggtc aacctagagg 1200
ttctggatga ggatacaatt atccatcagt tgcagaaacg ttatgcagac ttgctaattt 1260
acacatatgt tggagacatc ttaattgcct taaacccctt ccagaatcta agcatatact 1320
ctccacagtt ttccagactt tatcatgggg tgaaacgcgc ctccaatccc ccccacatat 1380
ttgcatcagc agatgctgct taccagtgca tggttactct cagcaaagac cagtgcattg 1440
tcatcagcgg agagagtggc tctgggaaga cagaaagcgc ccacctgatt gttcagcatt 1500
tgactttctt gggaaaggcc aataatcaga ccttgagaga gaaaattcta caagtcaact 1560
ccctggtgga agcctttggg aactcatgca ctgccatcaa tgacaactcg agccgttttg 1620
gaaaatatct ggaaatgatg tttacaccaa ctggagttgt gatgggggca agaatctctg 1680
aatatctcct ggaaaaatcc agagttataa aacaggcagc gagagagaaa aattttcata 1740
tattttacta tatttatgct ggtcttcatc accaaaagaa gctttctgat ttcagacttc 1800
ctgaggaaaa acctcctagg tacatagctg atgaaactgg aagggtgatg cacgacataa 1860
cttccaagga gtcttacaga agacaattcg aagcaattca gcattgcttc aggattatag 1920
ggttcacgga caaagaggtg cactcagtgt acagaatttt ggctgggatt ttgaatattg 1980
ggaacattga gttcgcagct atttcctctc aacatcagac tgataaaagt gaggtgccca 2040
atgctgaagc tttgcaaaat gctgcctctg ttctgtgcat tagccctgaa gagctccagg 2100
aggccctcac ctcccactgt gtggtcaccc ggggcgagac catcatccgt gccaacactg 2160
tagacagggc tgcggacgtt cgagacgcca tgtccaaagc cctgtatggg aggctcttca 2220

-continued

```
gctggattgt gaatcgcatt aatacactcc tgcagccaga cgaaaacata tgtagtgcag   2280
gaggtggaat gaatgtgggg atcttggata tctttggatt cgagaatttt cagagaaatt   2340
catttgagca gctctgcata aacatcgcca atgagcaaat ccagtactat ttcaatcagc   2400
atgtttttgc tcttgagcag atggaatatc agaatgaagg cattgatgct gtacccgtgg   2460
aatatgagga caaccgcccg ctcttggaca tgttcctcca gaaacccctg ggactgcttg   2520
cacttttgga tgaggaaagt cggtttcccc aagcaactga ccagaccctg gttgataaat   2580
ttgaagataa tctacgatgc aaatacttct ggaggcccaa aggagtggaa ctgtgctttg   2640
gcattcagca ttatgctgga aaggtattat atgatgcttc tggggttctt gagaaaaata   2700
gagacactct ccctgccgat gtggttgtgg tcctgagaac gtcagaaaac aagcttcttc   2760
agcagctctt ctcaatccct ctgaccaaaa caggtaattt ggcccagaca agagctagga   2820
taacagtggc ctcaagttct ttgcctccac atttcagtgc tgggaaagcc aaggtggaca   2880
ctctggaggt gatacggcat ccggaagaaa ccaccaacat gaagaggcaa actgtggctt   2940
cttacttccg gtattctctg atggacctgc tctccaaaat ggtggttgga cagccccact   3000
ttgtgcgctg cattaaaccc aatgatgacc gagaggccct gcagttctct cgagagaggg   3060
tgctggccca gctccgctcc acagggattc tggagacagt cagcatccgc cgccagggct   3120
attcccaccg catccttttt gaagaatttg tgaaaaggta ttattacttg gcattcacag   3180
cacatcaaac acctcttgct agcaaagaga gctgtgtggc tatcttggaa aagtccagat   3240
tagatcactg ggtactggga aaaacaaagg tttttctcaa atattaccat gttgagcaat   3300
taaatttgct gcttcgagaa gtcataggca gagtggttgt gctgcaggca tataccaagg   3360
ggtggcttgg agccaggaga tacaaaaggg tcagagagaa gagagagaag ggagccattg   3420
ccatccagtc agcctggaga ggatatgatg ctcggaggaa atttaagaaa ataagcaaca   3480
gaaggaatga gtctgctgct cataatcaag caggggacac ttcaaaccaa agcagtgggc   3540
cacattcccc cgtcgcagca ggtacgaggg gaagtgccga ggttcaagac tgcagcgagc   3600
ctggtgacca taaagttctc aggggctctg tacatcgtag gagccattca caagcagaat   3660
ccaacaatgg ccgtacacag acttcaagca actctcctgc tgtcacagag aaaaatgggc   3720
attcacaagc ccagagttct ccaaaagggt gcgatatctt cgcaggacat gcaaacaagc   3780
actcggtttc tgggactgat ttgctgtctt ctcggatatg ccatcctgct ccagatcagc   3840
aaggattgag tctctgggga gcccctcaaa agcctggttc agaaaatggt cttgcacaga   3900
agcatcgaac acctcgccga cgatgtcagc agcccaaaat gctgagtagc cctgaggaca   3960
ccatgtacta taaccagtta aatggaactc tagaatatca agggagcaag aggaagccaa   4020
gaaaacttgg ccaaatcaaa gtacttgatg gggaagatga atattacaaa tctctgtcac   4080
cagtggactg tatccctgag gagaacaact cagcccaccc ttcctttttt tcttcatcct   4140
caaaaggaga ctcttttgct caacattaaa ttgtgcttcc taaccctaaa tctgtccaga   4200
gtaggaacat tcatggtaat cgactgtctg tcattgcgta agaaagcact gatatggggt   4260
cagcttcttt ggacatatgg tccatgcctg aaccttactg aaccacttgc agattccaaa   4320
acatcttatc ctatcctcta ccactctccc acatgtgttg tgcagcctga gctgggcgct   4380
gccttccttt ctcatcccat ggggccctgt gggacactga gaacaccttt acaatagttt   4440
aaacagtcat tcatgccccc agtgtctagg aagataacag ccagtctcac cccagtctaa   4500
tcatggaccc tgataatatt gcttgatttt tcctatcaag ttacttttca atccattcag   4560
aatctgcccc agtggagacc caggagttcc tttcctgcac tcttctccat cctcccacct   4620
```

```
ttgctgggct tttctatcac tcccacctcc cccagagtca gggctccatt gctgagtgcc   4680

ccatcctgga ggattggccc caagatctcc tagaacagga taattgcctg tgtttaggca   4740

gataggccta aatctttcag attctttcta caaggcaaat aacccctctc ttgttaatta   4800

tgatgctgag aaagcctctg tctctttatt tcaccttgcc aagacaccca cactactttg   4860

gtgatgaaaa gaaaggaatg agagggaaag tttggacctg tcactttggt gacagggaaa   4920

gtccaggtca ctttattctg taactctcca ttcactggtc aaataactcc atgaggctat   4980

cagtggctac agtggaagga cctgatcttg tccatctttg tgtgcacaga gcctagcaca   5040

gggcttggta gagggtatat ctagtgaatg gagaatacat ggagaaactt aactaagtta   5100

cacaagcata tctgacagga atgttacctt caattgtatg ttacatatga ttagtcactt   5160

ttcatacact ataacctctg atttttcact caagtttggg ctgattatat tgtaatgatg   5220

ttagataata ctcaacatga ttcagtatga caaacttttt tgagcaccta ctttatataa   5280

aacatgacaa attgcagtgt gatgtaatca aaaacaaaga agccctataa gaccatttct   5340

ctagaacaga tgttcttaat atttttctta ctctaaaata tgtggtagat agtatgcaag   5400

aaaagccggg tgcggtggct caggcctgta atcccagcac tttgggaggc caagatgggc   5460

ggatcatgaa gtcaggagtt cgagaccagc ctgaccaaca tggtgaaacc ccgtctctac   5520

taaaaaaaat aatgataata caaaaattag cccagcatgg tggtgcatac ctgtaatccc   5580

agctactcag gaggctgacg caggagaatc acttgaaccc gggaagcaaa ggttgcagtc   5640

agctgagagc gcaccactgc actccagcct gggcgacagg gcaagactct gtctcaaaaa   5700

aaaaaaaaaa aaaaaaaaaa agagatagta tgcaagaaga cacctaaatt ttgagagaaa   5760

taaccttgaa gaaaatcttg ttatcagagt tttgaaaggg agcacattaa taggcctttt   5820

atgaagataa ataatgaaat gaggtattta aagatctcag aaattgtaat tttacaagta   5880

aaataaatat agccaatttt tcaatagctg aacttcaccc aaaaggtaat gtttataagt   5940

agagcagaaa aaatgcagat aaattttatt ttattgttta aaaaataatg tgtagaatat   6000

ataaattttt tatgttactg ttaatatacg agtgcttttg gaagtttcac ttttgtcact   6060

gattgtctac ttttggtttg ataatatgag ctgcttttca aattgttgaa tggaaatgtt   6120

cataactccc tgcttgtccg tgcacaatgt aattctaaac ctggcttgtt tctcatttaa   6180

atatatctat aaataaactt aaaaagaaaa caaaaaaaaa aaaaaaaaaa              6230
```

<210> SEQ ID NO 59
<211> LENGTH: 1896
<212> TYPE: DNA
<213> ORGANISM: Homo sapiens

<400> SEQUENCE: 59

```
ctctttctcg cctcagggcc tttgtactgg cggttccttc cgccggacac gtcgggtttc     60

ctcgtttttg cggactggcg ctttctgatt tcagagactc tccgcaacag aaccatctca    120

agtgggtcta cctcctcgcc ttttttttgtt gttgttgttg cttggctgcg cttctgacag    180

ggcaggccgt gatgatgttt gtttatgagt taggtctgac tgttcgttgg tgcttaagat    240

ccccaccggg tccctagggc ctgtgcgtac cgcgcacctg tgcacgtcct gcgcgcagct    300

gcaggcgact ccgctctggc tcgtcgctgc tgtttcctgc tgggggtgcc gaccctgtcc    360

cacgctagct gggtgacttc ccccaaccgc agagacagcg gcgacccggg gcctcagacc    420

tgcccccgca tctcgccggc gccaggcagt gggaagtcag gttcttccgc cacctcccag    480
```

```
ccaggactct gccaccctcc ctcaggatgc ctgagggccc cgagctgcac ctggccagcc    540

agtttgtgaa tgaggcctgc agggcgctgg tgttcggcgg ctgcgtggag aagtcctctg    600

tcagccgcaa ccctgaggtg ccctttgaga gcagtgccta ccgcatctca gcttcagccc    660

gcggcaagga gctgcgcctg atactgagcc ctctgcctgg ggcccagccc caacaggagc    720

cactggccct ggtcttccgc ttcggcatgt ccggctcttt tcagctggtg ccccgcgagg    780

agctgccacg ccatgcccac ctgcgctttt acacggcccc gcctggcccc cggctcgccc    840

tatgtttcgt ggacatccgc cggttcggcc gctgggacct tgggggaaag tggcagccgg    900

gccgcgggcc ctgtgtcttg caggagtacc agcagttcag ggagaatgtg ctacgaaacc    960

tagcggataa ggcctttgac cggcccatct gcgaggccct cctggaccag aggttcttca   1020

atggcattgg caactatctg cgggcagaga tcctgtaccg gctgaagatc ccccccttg   1080

agaaggcccg ctcggtcctg gaggccctgc agcagcacag gccgagcccg gagctgaccc   1140

tgagccagaa gataaggacc aagctgcaga atccagacct gctggagcta tgtcactcag   1200

tgcccaagga agtggtccag ttgggggca aaggctacgg gtcagagagc ggggaggagg   1260

actttgctgc ctttcgagcc tggctgcgct gctatggcat gccaggcatg agctccctgc   1320

aggaccggca tggccgtacc atctggttcc agggggatcc tggaccgttg gcacccaaag   1380

ggcgcaagtc ccgcaaaaag aaatccaagg ccacacagct gagtcctgag gacagagtgg   1440

aggacgcttt gcctccaagc aaggcccctt ccaggacacg aagggcaaag agagaccttc   1500

ctaagaggac tgcaacccag cggcctgagg ggaccagcct ccagcaggac ccagaagctc   1560

ccacagtgcc caagaagggg aggaggaagg ggcgacaggc agcctctggc cactgcagac   1620

cccggaaggt caaggctgac atcccatcct tggaaccaga ggggacctca gcctcttagc   1680

aggaggctct ccttgcttgc actcaccctt tcttattgtc ttgccctgca tctgggggtc   1740

tgaatttttg ggagcaggca atatctgaag gtgcaaacag gccctacggc tgttccctgc   1800

acaactctca tggttttaat tgtaccccat cttccacatc tttaaagctc atgtgaaaaa   1860

tgctgcattt ttaataaact gatacatttg aacttc                              1896
```

<210> SEQ ID NO 60
<211> LENGTH: 2161
<212> TYPE: DNA
<213> ORGANISM: Homo sapiens

<400> SEQUENCE: 60

```
gcgacggtta aacggggccc aaggcagggg tggcgggtca gtgctgctcg gggcttctc     60

catccaggtc cctggagttc ctggtccctg gagctccgca cttggcggcg caacctgcgt    120

gaggcagcgc gactctggcg actggccggc catgccttcc cgggctgagg actatgaagt    180

gttgtacacc attggcacag gctcctacgg ccgctgccag aagatccgga ggaagagtga    240

tggcaagata ttagtttgga aagaacttga ctatggctcc atgacagaag ctgagaaaca    300

gatgcttgtt tctgaagtga atttgcttcg tgaactgaaa catccaaaca tcgttcgtta    360

ctatgatcgg attattgacc ggaccaatac aacactgtac attgtaatgg aatattgtga    420

aggaggggat ctggctagtg taattacaaa gggaaccaag gaaaggcaat acttagatga    480

agagtttgtt cttcgagtga tgactcagtt gactctggcc ctgaaggaat gccacagacg    540

aagtgatggt ggtcataccg tattgcatcg ggatctgaaa ccagccaatg ttttcctgga    600

tggcaagcaa aacgtcaagc ttggagactt tgggctagct agaatattaa accatgacac    660

gagttttgca aaaacatttg ttggcacacc ttattacatg tctcctgaac aaatgaatcg    720
```

```
catgtcctac aatgagaaat cagatatctg gtcattgggc tgcttgctgt atgagttatg    780

tgcattaatg cctccattta cagcttttag ccagaaagaa ctcgctggga aaatcagaga    840

aggcaaattc aggcgaattc cataccgtta ctctgatgaa ttgaatgaaa ttattacgag    900

gatgttaaac ttaaaggatt accatcgacc ttctgttgaa gaaattcttg agaacccttt    960

aatagcagat ttggttgcag acgagcaaag aagaaatctt gagagaagag ggcgacaatt   1020

aggagagcca gaaaaatcgc aggattccag ccctgtattg agtgagctga aactgaagga   1080

aattcagtta caggagcgag agcgagctct caaagcaaga gaagaaagat tggagcagaa   1140

agaacaggag ctttgtgttc gtgagagact agcagaggac aaactggcta gagcagaaaa   1200

tctgttgaag aactacagct tgctaaagga acggaagttc ctgtctctgg caagtaatcc   1260

agaacttctt aatcttccat cctcagtaat taagaagaaa gttcatttca gtggggaaag   1320

taaagagaac atcatgagga gtgagaattc tgagagtcag ctcacatcta agtccaagtg   1380

caaggacctg aagaaaaggc ttcacgctgc ccagctgcgg gctcaagccc tgtcagatat   1440

tgagaaaaat taccaactga aaagcagaca gatcctgggc atgcgctagc caggtagaga   1500

gacacagagc tgtgtacagg atgtaatatt accaaccttt aaagactgat attcaaatgc   1560

tgtagtgttg aatacttggt tccatgagcc atgcctttct gtatagtaca catgatattt   1620

cggaattggt tttactgttc ttcagcaact attgtacaaa atgttcacat ttaatttttc   1680

tttcttcttt taagaacata ttataaaaag aatactttct tggttgggct tttaatcctg   1740

tgtgtgatta ctagtaggaa catgagatgt gacattctaa atcttgggag aaaaaataat   1800

gttaggaaaa aaatatttat gcaggaagag tagcactcac tgaatagttt taaatgactg   1860

agtggtatgc ttacaattgt catgtctaga tttaaatttt aagtctgaga ttttaaatgt   1920

ttttgagctt agaaaaccca gttagatgca atttggtcat taataccatg acatcttgct   1980

tataaatatt ccattgctct gtagttcaaa tctgttagct ttgtgaaaat tcatcactgt   2040

gatgtttgta ttcttttttt ttttctgttt aacagaatat gagctgtctg tcatttacct   2100

acttctttcc cactaaataa aagaattctt cagtttccct gtaaaaaaaa aaaaaaaaaa   2160

a                                                                   2161
```

<210> SEQ ID NO 61
<211> LENGTH: 1139
<212> TYPE: DNA
<213> ORGANISM: Homo sapiens

<400> SEQUENCE: 61

```
gggcggggcc tcggcgtggt aggcgcgctg cgtaaagagg cctgcagtcc cgcggcgcgg     60

ggcaggttcc gggctgctta ggttggcacc ggtccgtggt ccccgggggc gcagtcgcag    120

cgctcccgcc ctccaggcgt cagcgagtgc gcggtccagt gcggccggaa cctggcgcaa    180

ctcctagagc ggtccttggg gagacgcggg tcccagtcct gcggctccta ctggggagtg    240

cgctggtcgg aagattgctg gactcgctga agagagacta cgcaggaaag ccccagccac    300

ccatcaaatc agagagaagg aatccacctt cttacgctat ggcaggtaag aaagtactca    360

ttgtctatgc acaccaggaa cccaagtctt tcaacggatc cttgaagaat gtggctgtag    420

atgaactgag caggcagggc tgcaccgtca cagtgtctga tttgtatgcc atgaaccttg    480

agccgagggc cacagacaaa gatatcactg gtactctttc taatcctgag gttttcaatt    540

atggagtgga aacccacgaa gcctacaagc aaaggtctct ggctagcgac atcactgatg    600
```

-continued agcagaaaaa ggttcgggag gctgacctag tgatatttca gttcccgctg tactggttca 660
gcgtgccagc catcctgaag ggctggatgg atagggtgct gtgccagggc tttgcctttg 720
acatcccagg attctacgat tccggtttgc tccagggtaa actagcgctc ctttccgtaa 780
ccacgggagg cacggccgag atgtacacga agacaggagt caatggagat tctcgatact 840
tcctgtggcc actccagcat ggcacattac acttctgtgg atttaaagtc cttgcccctc 900
agatcagctt tgctcctgaa attgcatccg aagaagaaag aaaggggatg gtggctgcgt 960
ggtcccagag gctgcagacc atctggaagg aagagcccat cccctgcaca gcccactggc 1020
acttcgggca ataactctgt ggcacgtggg catcacgtaa gcagcacact aggaggccca 1080
ggcgcaggca aagagaagat ggtgctgtca tgaaataaaa ttacaacata gctacctgg 1139

<210> SEQ ID NO 62
<211> LENGTH: 1939
<212> TYPE: DNA
<213> ORGANISM: Homo sapiens

<400> SEQUENCE: 62
aggaaggagg ggtggcctga cccctcggca gtccctcccc tcagcctttc cccaaattgc 60
tacttctctg gggctccagg tcctgcttgt gctcagctcc agctcactgg ctggccaccg 120
agacttctgg acaggaaact gcaccatcct cttctcccag caaggggggct ccagagactg 180 cccacccagg aagtctggtg gcctggggat ttggacagtg ccttggtaat gaccagggct 240
ccaggaagag atgtccttgt ggctgggggc ccctgtgcct gacattcctc ctgactctgc 300
ggtggagctg tggaagccag gcgcacagga tgcaagcagc caggcccagg gaggcagcag 360
ctgcatcctc agagaggaag ccaggatgcc ccactctgct gggggtactg caggggtggg 420
gctggaggct gcagagccca cagccctgct caccagggca gagccccctt cagaacccac 480
agagatccgt ccacaaaagc ggaaaaaggg gccagccccc aaaatgctgg ggaacgagct 540
atgcagcgtg tgtggggaca aggcctcggg cttccactac aatgttctga gctgcgaggg 600
ctgcaaggga ttcttccgcc gcagcgtcat caagggagcg cactacatct gccacagtgg 660
cggccactgc cccatggaca cctacatgcg tcgcaagtgc caggagtgtc ggcttcgcaa 720
atgccgtcag gctggcatgc gggaggagtg tgtcctgtca gaagaacaga tccgcctgaa 780
gaaactgaag cggcaagagg aggaacaggc tcatgccaca tccttgcccc ccagggcttc 840
ctcacccccc caaatcctgc cccagctcag cccggaacaa ctgggcatga tcgagaagct 900
cgtcgctgcc cagcaacagt gtaaccggcg ctccttttct gaccggcttc gagtcacgcc 960
ttggcccatg gcaccagatc cccatagccg ggaggcccgt cagcagcgct ttgcccactt 1020
cactgagctg gccatcgtct ctgtgcagga gatagttgac tttgctaaac agctacccgg 1080
cttcctgcag ctcagccggg aggaccagat tgccctgctg aagacctctg cgatcgaggt 1140
gatgcttctg gagacatctc ggaggtacaa ccctgggagt gagagtatca ccttcctcaa 1200
ggatttcagt tataaccggg aagactttgc caaagcaggg ctgcaagtgg aattcatcaa 1260
ccccatcttc gagttctcca gggccatgaa tgagctgcaa ctcaatgatg ccgagtttgc 1320
cttgctcatt gctatcagca tcttctctgc agaccggccc aacgtgcagg accagctcca 1380
ggtagagagg ctgcagcaca catatgtgga agccctgcat gcctacgtct ccatccacca 1440
tccccatgac cgactgatgt tcccacggat gctaatgaaa ctggtgagcc tccggaccct 1500
gagcagcgtc cactcagagc aagtgtttgc actgcgtctg caggacaaaa agctcccacc 1560
gctgctctct gagatctggg atgtgcacga atgactgttc tgtccccata ttttctgttt 1620

```
tcttggccgg atggctgagg cctggtggct gcctcctaga agtggaacag actgagaagg   1680
gcaaacattc ctgggagctg ggcaaggaga tcctcccgtg gcattaaaag agagtcaaag   1740
ggttgcgagt tttgtggcta ctgagcagtg gagccctcgc taacactgtg ctgtgtctga   1800
agatcatgct gaccccacaa acggatgggc ctgggggcca ctttgcacag ggttctccag   1860
agccctgccc atcctgcctc caccacttcc tgtttttccc acagggcccc aagaaaaatt   1920
ctccactgtc aaaaaaaaa                                                1939
```

<210> SEQ ID NO 63
<211> LENGTH: 2663
<212> TYPE: DNA
<213> ORGANISM: Homo sapiens

<400> SEQUENCE: 63

```
tgcagctggg agcgcacaga cggctgcccc gcctgagcga ggcgggcgcc gccgcgatgc     60
tgcgaggcgg acggcgcggg cagcttggct ggcacagctg ggctgcgggg ccgggcagcc    120
tgctggcttg gctgatactg gcatctgcgg gcgccgcacc ctgccccgat gcctgctgcc    180
cccacggctc ctcgggactg cgatgcaccc gggatggggc cctggatagc ctccaccacc    240
tgcccggcgc agagaacctg actgagctct acatcgagaa ccagcagcat ctgcagcatc    300
tggagctccg tgatctgagg ggcctggggg agctgagaaa cctcaccatc gtgaagagtg    360
gtctccgttt cgtggcgcca gatgccttcc atttcactcc tcggctcagt cgcctgaatc    420
tctccttcaa cgctctggag tctctctcct ggaaaactgt gcagggcctc tccttacagg    480
aactggtcct gtcggggaac cctctgcact gttcttgtgc cctgcgctgg ctacagcgct    540
gggaggagga gggactgggc ggagtgcctg aacagaagct gcagtgtcat gggcaagggc    600
ccctggccca catgcccaat gccagctgtg gtgtgcccac gctgaaggtc caggtgccca    660
atgcctcggt ggatgtgggg gacgacgtgc tgctgcggtg ccaggtggag gggcggggcc    720
tggagcaggc cggctggatc ctcacagagc tggagcagtc agccacggtg atgaaatctg    780
gggtctgcc atccctgggg ctgaccctgg ccaatgtcac cagtgacctc aacaggaaga     840
acgtgacgtg ctgggcagag aacgatgtgg gccgggcaga ggtctctgtt caggtcaacg    900
tctccttccc ggccagtgtg cagctgcaca cggcggtgga gatgcaccac tggtgcatcc    960
ccttctctgt ggatgggcag ccggcaccgt ctctgcgctg gctcttcaat ggctccgtgc   1020
tcaatgagac cagcttcatc ttcactgagt tcctggagcc ggcagccaat gagaccgtgc   1080
ggcacgggtg tctgcgcctc aaccagccca cccacgtcaa caacggcaac tacacgctgc   1140
tggctgccaa ccccttcggc caggcctccg cctccatcat ggctgccttc atggacaacc   1200
ctttcgagtt caaccccgag gaccccatcc ctgtctcctt ctcgccggtg gacactaaca   1260
gcacatctgg agacccggtg gagaagaagg acgaaacacc ttttggggtc tcggtggctg   1320
tgggcctggc cgtctttgcc tgcctcttcc tttctacgct gctccttgtg ctcaacaaat   1380
gtggacggag aaacaagttt gggatcaacc gcccggctgt gctggctcca gaggatgggc   1440
tggccatgtc cctgcatttc atgacattgg gtggcagctc cctgtccccc accgagggca   1500
aaggctctgg gctccaaggc cacatcatcg agaacccaca atacttcagt gatgcctgtg   1560
ttcaccacat caagcgccgg gacatcgtgc tcaagtggga gctgggggag ggcgcctttg   1620
ggaaggtctt ccttgctgag tgccacaacc tcctgcctga gcaggacaag atgctggtgg   1680
ctgtcaaggc actgaaggag gcgtccgaga gtgctcggca ggacttccag cgtgaggctg   1740
```

-continued agctgctcac catgctgcag caccagcaca tcgtgcgctt cttcggcgtc tgcaccgagg 1800 gccgcccccct gctcatggtc tttgagtata tgcggcacgg ggacctcaac cgcttcctcc 1860
gatcccatgg acctgatgcc aagctgctgg ctggtgggga ggatgtggct ccaggccccc 1920
tgggtctggg gcagctgctg gccgtggcta gccaggtcgc tgcggggatg gtgtacctgg 1980
cgggtctgca ttttgtgcac cgggacctgg ccacacgcaa ctgtctagtg ggccagggac 2040
tggtggtcaa gattggtgat tttggcatga gcagggatat ctacagcacc gactattacc 2100
gtgtgggagg ccgcaccatg ctgcccattc gctggatgcc gcccgagagc atcctgtacc 2160
gtaagttcac caccgagagc gacgtgtgga gcttcggcgt ggtgctctgg gagatcttca 2220
cctacggcaa gcagccctgg taccagctct ccaacacgga ggcaatcgac tgcatcacgc 2280
agggacgtga gttggagcgg ccacgtgcct gcccaccaga ggtctacgcc atcatgcggg 2340
gctgctggca gcgggagccc cagcaacgcc acagcatcaa ggatgtgcac gcccggctgc 2400
aagccctggc ccaggcacct cctgtctacc tggatgtcct gggctagggg gccggcccag 2460
gggctgggag tggttagccg gaatactggg gcctgccctc agcatccccc atagctccca 2520
gcagccccag ggtgatctca aagtatctaa ttcaccctca gcatgtggga agggacaggt 2580
gggggctggg agtagaggat gttcctgctt ctctaggcaa ggtcccgtca tagcaattat 2640
atttattatc ccttgaaaaa aaa 2663

<210> SEQ ID NO 64
<211> LENGTH: 3961
<212> TYPE: DNA
<213> ORGANISM: Homo sapiens

<400> SEQUENCE: 64
gtgtgtgtga gtgcgagagt gtgtaagcca gtgtgtgtgc cgtccccctg ctggggacag 60
cagctgggtc cagcagagag ctggctgggg gcttgacagg agtttatcct aactgatgct 120
gggtgggcgc aggccctgag atgggcgtca gggagagggg acgccagaca cacggcctga 180
gcagggtgag gagcagctgc cagccccggc aggcccaggc cctgtctggg tgcacaggac 240
agagacacag caagatgccc agggagtgcc gcttcctggg ctagagacaa gcaccagcct 300
gcagtggaga acgcaggacc ccgctgccca gaaggagcag ccacggcctg cggaggactg 360
gcccagcaag gtcccaggtc ttccctctcc tcagcgccta agagagaggc ccagtgcggg 420
tgaggagtcg cgaggaagag gcggaaggcg ccggaaggca ccatgttccg caagaaaaag 480
aagaaacgcc ctgagatctc agcgccacag aacttccagc accgtgtcca cacctccttc 540
gaccccaaag aaggcaagtt tgtgggcctc cccccacaat ggcagaacat cctggacaca 600
ctgcggcgcc ccaagcccgt ggtggaccct tcgcgaatca cacgggtgca gctccagccc 660
atgaagacag tggtgcgggg cagcgcgatg cctgtggatg gctacatctc ggggctgctc 720
aacgacatcc agaagttgtc agtcatcagc tccaacaccc tgcgtggccg cagccccacc 780
agccggcggc gggcacagtc cctggggctg ctgggggatg agcactgggc caccgaccca 840
gacatgtacc tccagagccc ccagtctgag cgcactgacc cccacggcct ctacctcagc 900
tgcaacgggg gcacaccagc aggccacaag cagatgccgt ggcccgagcc acagagccca 960
cgggtcctgc ccaatgggct ggctgcaaag gcacagtccc tgggccccgc cgagtttcag 1020
ggtgcctcgc agcgctgtct gcagctgggt gcctgcctgc agagctcccc accaggagcc 1080
tcgcccccca cgggcaccaa taggcatgga atgaaggctg ccaagcatgg ctctgaggag 1140
gcccggccac agtcctgcct ggtgggctca gccacaggca ggccaggtgg ggaaggcagc 1200
cctagcccta agacccggga gagcagcctg aagcgcaggc tattccgaag catgttcctg 1260
tccactgctg ccacagcccc tccaagcagc agcaagccag gccctccacc acagagcaag 1320
cccaactcct ctttccgacc gccgcagaaa gacaaccccc caagcctggt ggccaaggcc 1380
cagtccttgc cctcggacca gccggtgggg accttcagcc ctctgaccac ttcggatacc 1440
agcagccccc agaagtccct ccgcacagcc ccggccacag gccagcttcc aggccggtct 1500
tccccagcgg gatccccccg cacctggcac gcccagatca gcaccagcaa cctgtacctg 1560
ccccaggacc ccacggttgc caagggtgcc ctggctggtg aggacacagg tgttgtgaca 1620
catgagcagt tcaaggctgc gctcaggatg gtggtggacc agggtgaccc ccggctgctg 1680
ctggacagct acgtgaagat tggcgagggc tccaccggca tcgtctgctt ggcccgggag 1740
aagcactcgg gccgccaggt ggccgtcaag atgatggacc tcaggaagca gcagcgcagg 1800
gagctgctct tcaacgaggt ggtgatcatg cgggactacc agcacttcaa cgtggtggag 1860
atgtacaaga gctacctggt gggcgaggag ctgtgggtgc tcatggagtt cctgcaggga 1920
ggagccctca cagacatcgt ctcccaagtc aggctgaatg aggagcagat tgccactgtg 1980
tgtgaggctg tgctgcaggc cctggcctac ctgcatgctc agggtgtcat ccaccgggac 2040
atcaagagtg actccatcct gctgaccctc gatggcaggg tgaagctctc ggacttcgga 2100
ttctgtgctc agatcagcaa agacgtccct aagaggaagt ccctggtggg aacccccctac 2160 tggatggctc ctgaagtgat ctccaggtct ttgtatgcca ctgaggtgga tatctggtct 2220
ctgggcatca tggtgattga gatggtagat ggggagccac cgtacttcag tgactcccca 2280
gtgcaagcca tgaagaggct ccgggacagc cccccaccca agctgaaaaa ctctcacaag 2340
gtctccccag tgctgcgaga cttcctggag cggatgctgg tgcgggaccc ccaagagaga 2400
gccacagccc aggagctcct agaccacccc ttcctgctgc agacagggct acctgagtgc 2460
ctggtgcccc tgatccagct ctaccgaaag cagacctcca cctgctgagc ccacccccaag 2520 tatgcctgcc acctacgccc acaggcaggg cacactgggc agccagcctg ccggcaggac 2580
ttgcctgcct cctcctctca gtattctctc caaagattga aatgtgaagc cccagcccca 2640
ccctctgccc ttcagcctac tgggccaggc cggacctgcc ccctcagtgt ctctccctcc 2700
cgagtcccca gatggagacc cctttctaca ggatgacccc ttgatatttg cacagggata 2760
tttctaagaa acgcagaggc cagcgttcct ggcctctgca gccaacacag tagaaaaggc 2820
tgctgtggtt ttttaaaggc agttgtccac tagtgtccta ggccactgca gagggcagac 2880
tgctggtctc cacagatacc tgctgttctc agctccagct tcaaacctcg agtctcgaga 2940
gggccacggg gtggttttta tgaccggaat cccgcttcct ccctcacgtc tgatgtcctg 3000
aaggtgcagt cccacctgta cagcccctcc ccgcccagaa ctgtgaatgg cctgctccag 3060
gccatggctg gggggcaggga gtgaggggac aatttctgag tgaaagagaa agaatggggt 3120
cggtggtgaa ggtgctctca ctttacagaa tggagagaac atcgtgtgtg tgtgtgtgtg 3180
tgtgtgtgtg tgtgtgtgtg tgtaagggga ggaaagccac cttgacagcc caggtccctc 3240
caggtcaccc acagccagtt tcaggaaggc tgcccctctc tcccactaag ttctggcctg 3300
aagggacctg ctttcttggc ctggcttcca cctctccact cctgtgtcta cctggccagt 3360
ggagtggtcc atgctaagtc taacactcct gggagctcag gaggcttctg agcttctcct 3420
gtactgtgca tcgtgagggc cagagacagg aatgtaagga ttggcaactg tgttaccttt 3480
caagtttatc tcaataacca ggtcatcagg gacccattgt tctcttcaga accctatctg 3540

-continued ggagagaagg cgaaccacct ccgggtttcc atcatgtcaa ggtcacaggc atccatgtgt 3600
gcaaaccatc tgccccagct gcctccacag actgctgtct ccttgtcctc ctcggccctg 3660
ccccacttca gggctgctgt gagatggaat tccaggaaag aacttcaggt gtctggaccc 3720
tttctatcta gataatattt ttagattctt ctgctcccta gtgacctacc tgggggcaaa 3780
gaaattgcaa ggactttttt ttaagggtca gagttttcaa aacaaaagca tcttccctag 3840
aaatttttgt gaattgtttg cacttgtgcc tgttttaaat taaattgagt gttcaaagcc 3900
aaaaaaaaaa aaaaaaaaaa aaaaaaaaaa aaaaaaaaaa aaaaaaaaaa aaaaaaaaaa 3960
a 3961

<210> SEQ ID NO 65
<211> LENGTH: 1899
<212> TYPE: DNA
<213> ORGANISM: Homo sapiens

<400> SEQUENCE: 65
agcgcgcgac tttttgaaag ccaggagggt tcgaattgca acggcagctg ccgggcgtat 60
gtgttggtgc tagaggcagc tgcagggtct cgctgggggc cgctcgggac caattttgaa 120
gaggtacttg gccacgactt attttcacct ccgacctttc cttccaggcg gtgagactct 180
ggactgagag tggctttcac aatggaaggg atcagtaatt tcaagacacc aagcaaatta 240
tcagaaaaaa agaaatctgt attatgttca actccaacta taaatatccc ggcctctccg 300
tttatgcaga agcttggctt tggtactggg gtaaatgtgt acctaatgaa aagatctcca 360
agaggtttgt ctcattctcc ttgggctgta aaaaagatta atcctatatg taatgatcat 420
tatcgaagtg tgtatcaaaa gagactaatg gatgaagcta agattttgaa aagccttcat 480
catccaaaca ttgttggtta tcgtgctttt actgaagcca atgatggcag tctgtgtctt 540
gctatggaat atggaggtga aaagtctcta aatgacttaa tagaagaacg atataaagcc 600
agccaagatc cttttccagc agccataatt ttaaaagttg ctttgaatat ggcaagaggg 660
ttaaagtatc tgcaccaaga aaagaaactg cttcatggag acataaagtc ttcaaatgtt 720
gtaattaaag gcgattttga aacaattaaa atctgtgatg taggagtctc tctaccactg 780
gatgaaaata tgactgtgac tgaccctgag gcttgttaca ttggcacaga gccatggaaa 840
cccaaagaag ctgtggagga gaatggtgtt attactgaca aggcagacat atttgccttt 900
ggccttactt tgtgggaaat gatgacttta tcgattccac acattaatct ttcaaatgat 960
gatgatgatg aagataaaac ttttgatgaa agtgattttg atgatgaagc atactatgca 1020
gcgttgggaa ctaggccacc tattaatatg gaagaactgg atgaatcata ccagaaagta 1080
attgaactct tctctgtatg cactaatgaa gaccctaaag atcgtccttc tgctgcacac 1140
attgttgaag ctctggaaac agatgtctag tgatcatctc agctgaagtg tggcttgcgt 1200
aaataactgt ttattccaaa atatttacat agttactatc agtagttatt agactctaaa 1260
attggcatat ttgaggacca tagtttcttg ttaacatatg gataactatt tctaatatga 1320
aatatgctta tattggctat aagcacttgg aattgtactg ggttttctgt aaagttttag 1380
aaactagcta cataagtact ttgatactgc tcatgctgac ttaaaacact agcagtaaaa 1440
cgctgtaaac tgtaacatta aattgaatga ccattacttt tattaatgat ctttcttaaa 1500
tattctatat tttaatggat ctactgacat tagcactttg tacagtacaa aataaagtct 1560
acatttgttt aaaacactga accttttgct gatgtgttta tcaaatgata actggaagct 1620
gaggagaata tgcctcaaaa agagtagctc cttggatact tcagactctg gttacagatt 1680
gtcttgatct cttggatctc ctcagatctt tggtttttgc tttaatttat taaatgtatt 1740
ttccatactg agtttaaaat ttattaattt gtaccttaag catttcccag ctgtgtaaaa 1800
acaataaaac tcaaatagga tgataaagaa taaaggacac tttgggtacc agaaaaaaaa 1860
aaaaaaaaaa aaaaaaaaaa aaaaaaaaaa aaaaaaaaa 1899

<210> SEQ ID NO 66
<211> LENGTH: 1025
<212> TYPE: DNA
<213> ORGANISM: Homo sapiens

<400> SEQUENCE: 66
cggggtggga ttccaaccca gaagcgggca tttggagccc tcatgcttca ccctagctcc 60
ctgaaacaag cacggaggat ggctctgagc agcgaggaaa gtgctggaag caagcaggcc 120
gagcgcgtcc ctggctgggg acgttaatca ttaccggagg gcggcccgag cgcggccccg 180
ccccgggacg gcagcctgcg cgcccggccg ccgcctgccc tctccgctgg ccacctgctg 240
ccgcccgcgc catggctggc aaagcacaca ggctgagcgc tgaggagagg gaccagctgc 300
tgccaaacct gagggctgtg gggtggaatg agctggaagg ccgtgatgcc atcttcaagc 360
agtttcattt caaagacttc aacagggcct ttgggttcat gacaagagtg gccctgcagg 420
ctgagaaact ggaccaccat cctgaatggt ttaacgtgta caacaaggtc cacatcacgc 480
tgagcaccca tgagtgtgcc ggcctttcag aacgggacat aaacctggcc agcttcatcg 540
aacaagtagc agtgtccatg acatagaccc tgcccttcct ctttgaattc ttccggggga 600
aggggtgact gaactgggag tccagggagg gagctgagga gcccttaccc tcccaccact 660
cccctcccaa gacccagccg ccgccgttga gggctgagtc cttgctgtgg gatgtgccag 720
tgtccccacc aacaccagga atttagacct tttccctgca ccactctctt catcctgggg 780
gctctgttac actaatttga ataaactctc ccctttcttt gcaacttccc agcaacaata 840
atgattttct tgccaggccg tctcttgctc cctaattcat ttcccaggaa gctgtgatac 900
agggtgaaat aaagtcttgt cttagaaacc aggaccctaa accccacact atgtaataga 960
aacacatgtg tttttatgtc tcaaataaaa ctattatatc acttggaaaa aaaaaaaaaa 1020
aaaaa 1025

<210> SEQ ID NO 67
<211> LENGTH: 4576
<212> TYPE: DNA
<213> ORGANISM: Homo sapiens

<400> SEQUENCE: 67
gatccccgcc cctgctgccc gccacgtccc tcacgtacca ctcggcagag gcgcggggaa 60
acctggcgta ctggctgtgg cttctctagc gggactcggc atgaggctgg cgcggctgct 120
tcgcggagcc gccttggccg gcccgggccc ggggctgcgc gccgccggct tcagccgcag 180
cttcagctcg gactcgggct ccagcccggc gtccgagcgc ggcgttccgg gccaggtgga 240
cttctacgcg cgcttctcgc cgtccccgct ctccatgaag cagttcctgg acttcggatc 300
agtgaatgct tgtgaaaaga cctcatttat gtttctgcgg caagagttgc ctgtcagact 360
ggcaaatata atgaaagaaa taagtctcct tccagataat cttctcagga caccatccgt 420
tcaattggta caaagctggt atatccagag tcttcaggag cttcttgatt ttaaggacaa 480
aagtgctgag gatgctaaag ctatttatga ctttacagat actgtgatac ggatcagaaa 540

-continued

```
ccgacacaat gatgtcattc ccacaatggc ccagggtgtg attgaataca aggagagctt    600
tggggtggat cctgtcacca gccagaatgt tcagtacttt ttggatcgat tctacatgag    660
tcgcatttca attagaatgt tactcaatca gcactcttta ttgtttggtg gaaaaggcaa    720
aggaagtcca tctcatcgaa aacacattgg aagcataaat ccaaactgca atgtacttga    780
agttattaaa gatggctatg aaaatgctag gcgtctgtgt gatttgtatt atattaactc    840
tcccgaacta gaacttgaag aactaaatgc aaaatcacca ggacagccaa tacaagtggt    900
ttatgtacca tcccatctct atcacatggt gtttgaactt ttcaagaatg caatgagagc    960
cactatggaa caccatgcca acagaggtgt ttacccccct attcaagttc atgtcacgct   1020
gggtaatgag gatttgactg tgaagatgag tgaccgagga ggtggcgttc ctttgaggaa   1080
aattgacaga cttttcaact acatgtattc aactgcacca agacctcgtg ttgagacctc   1140
ccgcgcagtg cctctggctg gttttggtta tggattgccc atatcacgtc tttacgcaca   1200
atacttccaa ggagacctga agctgtattc cctagagggt tacgggacag atgcagttat   1260
ctacattaag gctctgtcaa cagactcaat agaaagactc ccagtgtata acaaagctgc   1320
ctggaagcat tacaacacca accacgaggc tgatgactgg tgcgtcccca gcagagaacc   1380
caaagacatg acgacgttcc gcagtgccta gacacacttg ggacatcgga aaatccaaat   1440
gtggcttttg tattaaattt ggaaggtatg gtgttcagaa ctatattata ccaagtactt   1500
tatttatcgt tttcacaaaa ctatttgagt agaataaatg gaaactgaat tccatttgtg   1560
cccgttaaac ctcctaaagg atgaaattgc acctatttta cacttatatt ttcacagtta   1620
attgaacata tttttaaaca actgtagttt tgggcaactt ttcactttgt ggtagacttc   1680
agaagtgtgg aaatcttcgg gtttctatag gaaactagtt tttttttttt aagaaatact   1740
ttcatttatg tttgctagaa acattttcta aatgatagtg attagctggt tagccatctt   1800
cctgttattt ggaggagttc tgccatcttt tattcggtag tgacagctgt aatatggtct   1860
tcatgtttat cagtgacttg actacaagta aagcagaaaa cagttggcct gtaatcacag   1920
aaccagccac ccttcggcgt ctacatgcat tgtcttagct ctgaggttaa tttaccattt   1980
ttaaatttta ttgtaaagaa gtgtaatgac tagctctctg tggatctatg ccaaaatcat   2040
gggccatctt ttctaagtgt acttctgatt aatgcaaggg gaaattttta tactgaaaac   2100
aaacaaacaa actagcagct actaaaatag agaagaaatt gagggcaaag taatatgtct   2160
ccaaaactga actgattgct tgttgagatt acctagaaag cttttggaaa aaaatagagc   2220
ttttctgcat cctactccag atacactgaa tcggaatccc tagggctaga gcctagaaat   2280
ctcacttttt aaaatgcttc caaggtaagt ctgatgccta ccctaggttg ggaaccactc   2340
tttcaaagta aacagtgatg acacagcatt tgctaaagta acatctgtag gttttggttt   2400
ccacctattt aaagtcagat ttatagactc gaggagacag aaactgaatc ccacacctgg   2460
tgcaattaga agcataatta gaagcagaag aacaaaatgc cacgtaacca aagcatcaga   2520
gccatcattg cacgtgtctt tttttctttt ttctttttt tttttcaaga cagggtctcg   2580
ctcttttgcc caggatggag tacagtggca tggtcaaggc tcactgcagc ttcaatcttc   2640
tgggctcaag taatccttcc acctcagcct cccatatagc tggaactaca gttgtgcact   2700
accacaccca gctaattttt tgatttcttg tggagatgag gtctcagtat gttcccaggc   2760
tagtgttgaa ctcctgagct caagaaatcc tcctgcctga gtctctgaaa gtgctgggat   2820
tacaggcgtg agccaccaca catggcctat tgcacaagtc ttgacaaaca acatatattt   2880
tctaaaacta tccagatttc attatcaggg aaaagtttgc ttaggtttat tacagcagtc   2940
```

cttggcattt gtatggtaat ttgtacttta caaatacttt gatatattat aactctattg 3000
gtctttgaaa caaagcgata cagtgtaggt ggtatcattc tctttctcac tcagtgtggc 3060
ccagagttgc tcagaattgg agcagagcct gagacgtatc tgcagatcct gtcatcagct 3120
ggcaagtcca ggagactgtg tcatttagag actgtgttgt tagttatccc tcaacatctt 3180
ctaaggtggc aggaaataat attggaaata acattttaaa gtaaaaattt taaagtttaa 3240
agaagagttt tgccacttaa acaggggagc tttgtctgga aaatacactg agttgaaaca 3300
cttcatcctt ggaaggatta tataagatga acagttgtga taaatgtgta gattagaggg 3360
atgtgaatgg gcagttagtc cagtgccctc atttaagagg ccaagatcct gattcagagg 3420
aggcatcctt tgcccagagc tgcttagcta atctgaccaa atgttgggaa aaatgtctca 3480
cctaacccac tattccttaa ttatggattt tgtgaaaaac aatagaacat gttaatgagt 3540
aatttatatt agttcgatgt attacaattt tttagcttta aattacagtt ttcttataat 3600
gttgaaatgt tttagaatcc tttgaatcta agtatttgtt tcctaaatga aacatttgta 3660
caacatttga tgtttttact tatgaaatat tctcctcccc caagaaaatt taaacttttt 3720
ctctctattt aaaagctaag aaatgtttta aaggaaaaat gaaattatct tcctttagct 3780
tatttttaag gtaaaacagc tttttactct gttattgtgg taatggacag aatattacat 3840
acaaaaatat tctgggagag ctttttccta gttggtttta aatcattgtg ccacctgaaa 3900
ggtttttaga ttttatagga gctaatttgt ccaccagcat taatgtaaca cagtgtagtt 3960
atgaaaatat attgaaggac aggaagtgga cacgaagtga tttttgtaac ctgagcagtt 4020
aatgaatgtg ccaacatttt ctaggaaggg acagcaagaa tattctgctc tgtagttaaa 4080
atactggctg gcttttgatg tcttcatgct taattgtgat cactttcttg cactgtgatg 4140
tttttacgtg aatatgttga agtagaagtc taccatatta ttttataaaa tgttttctgt 4200
atggcaataa actgaaaaca tggatcaacc cttcttttga aaataaactg agtcaattta 4260
gccttttaaa aatatagtca tctcttttaa atagaatcct cttccaccat caaggctcaa 4320
cattttgtaa gcatccaaaa aattggtaat tagggggctt gcactaaatt tcactatctt 4380
cagtagagag gaactgtttg gaacttagat ttccaatgtg tatattctaa tggagaaagc 4440
aagaggtaga gtttgtatgt ttgacttacc ttagattttt attttccata catactgcaa 4500
atgattgact tgttgcataa atgaagatct tctgttgtgt gcttttcaaa cactgtaaat 4560
aaatttgaaa tttgaa 4576

<210> SEQ ID NO 68
<211> LENGTH: 2312
<212> TYPE: DNA
<213> ORGANISM: Homo sapiens

<400> SEQUENCE: 68
agacagcgtg gggtggggag ggtcctcggg gtccttggca gggcacgtgc gggaggaagt 60
ggagctccct gtacgcgcgg ccctagtcgg ctcctcaacg tggagcgatg ggaggccttg 120
agaagaagaa gtatgaacga ggctcggcca ccaactacat cacccggaac aaagcccgga 180
agaagctcca gctgagcttg gctgacttta ggcggctgtg cattctgaag ggcatttatc 240
cccatgaacc caaacacaag aagaaggtta acaagggttc tacagcagcc cgaacgtttt 300
accttatcaa agacatcagg tttctcctcc acgaacccat tgtcaacaag ttccgtgaat 360
acaaggtgtt cgtccggaag ctccggaagg cttatgggaa gagcgagtgg aacactgtag 420

```
agcgtttaaa ggacaataag cccaactaca aactcgacca catcatcaag gaacggtatc    480

ccacgttcat cgatgccctg cgggacctgg acgatgccct ctccatgtgc ttcctgtttt    540

ccaccttccc gcggactggc aagtgccacg tgcagaccat tcagctgtgc cgccggctca    600

ctgtggagtt catgcactac attatcgctg cccgtgccct gcgcaaggtc ttcctgtcca    660

tcaaaggcat ttactaccag gccgaggtac tggggcagcc catcgtgtgg atcactccct    720

atgccttctc ccatgaccac ccgacagacg tggactacag ggtcatggcc accttcaccg    780

agttctacac cacgctgctg ggctttgtca acttccgcct ttaccagttg ctcaacctcc    840

actatccccc gaagctcgag ggtcaggccc aagcagaggc aaaggccggt gagggcacct    900

acgcgttgga ctccgagagt tgtatggaga aactggcagc cctcagtgcc agcctggccc    960

gcgtggtggt gcctgccaca gaggaggagg ccgaggtgga tgagtttccc accgatgggg   1020

agatgtcagc gcaggaggaa gaccgcagga aggagctgga ggcgcaggag aagcacaaga   1080

agctttttga gggcctgaag ttcttcctga accgagaggt gccccgtgag gccctggcct   1140

tcatcatcag gagttttggt ggggaagtgt cctgggacaa atctttgtgc attggggcca   1200

cctatgacgt cacagactcc cgcatcaccc atcagattgt cgaccggcct gggcagcaga   1260

cctcagtcat tggcaggtgc tacgtgcagc cccagtgggt gtttgactca gtgaacgcca   1320

ggctccttct ccccgtggca gagtacttct ctggggtgca gctgccccca cacctttcac   1380

cctttgtgac cgagaaggaa ggagattacg ttccacctga gaagctgaag ctgctggctc   1440

tgcagcgggg agaggaccca ggaaacctga atgagtcaga agaggaggag gaagaggacg   1500

acaacaacga aggtgatggt gatgaagagg gagaaaatga ggaggaggag gaagatgcag   1560

aggctggttc agaaaaggag gaagaggccc ggctggcagc cctggaagag cagaggatgg   1620

aggggaagaa gcccagggtg atggcaggca ccttgaagct ggaggataag cagcggctgg   1680

cccaggagga ggagagtgag gccaagcgcc tggccattat gatgatgaag aagcgggaga   1740

agtacctgta ccagaagatc atgtttggca agaggcgaaa aatccgagag gccaacaagc   1800

tggcggagaa gcggaaagcc cacgatgagg cggtgaggtc tgagaagaag gccaagaagg   1860

caaggccgga gtgagtgcct gcggcccctc acagggctga ggccagcccc tagcagctgg   1920

atgtggcaga ggcaggccag aggacctaag tgtgatggac cagagtcact tctcctcctc   1980

ctttctccag ccagccctga cccctcatgc tctctggctg ggccagtggg cagccctcgc   2040

ttcccttgga tggagctgcc ctgctggtgc ctggtcagag aagaggcctc tgtgcccagc   2100

ctgattctct gctcccagga gccagtgaca tgaggtgcag aggcccaccc agccccctac   2160

ctactgcccc cattcatcct ggctttccac agccccctcc cacacagttg gacccgtgat   2220

tctcagggtg ctgtgatggg gtgagggtag ggggagcatt tgttattaaa tgactggact   2280

tttgtgccaa ttgcaaaaaa aaaaaaaaaa aa                                 2312
```

<210> SEQ ID NO 69
<211> LENGTH: 4123
<212> TYPE: DNA
<213> ORGANISM: Homo sapiens

<400> SEQUENCE: 69

```
agattactat ggaatcggta gggtcctgac cgctggggaa gcaggaaagc gtatcctggg     60

aagaaaggct tggcttggac tccggagaag aatactacat cgagacctgc tggggaattt    120

tattttattt tattattttt ttggtcttgg ttgtactgag ggaggaagaa gaggttgtgt    180

ggcccggtcg aacttgtggc agcctgaagg ccccctcagg cggcgccgcg ggcagccccg    240
```

-continued cagccggggc ctggtgcagc ctccgcggcc gctgtcaggg aagcgcaggc ggccaatgga 300
acccgggagc ggtcgctgct gctgaggcgg cagtgtcggc agtccaaccg cgactgcccg 360
caccccctcc gcgggggtcc cccagaggat caactaaacc ttgaactaag aagaaaaatg 420
tgttgtgagc agggggagcc tcagctgcct caggccgttc aggacagaag ggtgtttctg 480
aaggccggag caagttttga agaagtccct atcagattac acttggttga ctactccgga 540
gcagccacta agagggatga acaggcctgc gtggaaattg aatgagattc ttggaagctc 600
gaagtctggc tgtggccatg ggagatacag tagtggagcc tgccccccttg aagccaactt 660
ctgagcccac ttctggccca ccagggaata atgggggtc cctgctaagt gtcatcacgg 720
agggggtcgg ggaactatca gtgattgacc ctgaggtggc ccagaaggcc tgccaggagg 780
tgttggagaa agtcaagctt ttgcatggag gcgtggcagt ctctagcaga ggcaccccac 840
tggagttggt caatggggat ggtgtggaca gtgagatccg ttgcctagat gatccacctg 900
cccagatcag ggaggaggaa gatgagatgg gggccgctgt ggcctcaggc acagccaaag 960
gagcaagaag acggcggcag aacaactcag ctaaacagtc ttggctgctg aggctgtttg 1020
agtcaaaact gtttgacatc tccatggcca tttcatacct gtataactcc aaggagcctg 1080
gagtacaagc ctacattggc aaccggctct tctgctttcg caacgaggac gtggacttct 1140
atctgcccca gttgcttaac atgtacatcc acatggatga ggacgtgggt gatgccatta 1200
agccctacat agtccaccgt tgccgccaga gcattaactt ttccctccag tgtgccctgt 1260
tgcttggggc ctattcttca gacatgcaca tttccactca acgacactcc cgtgggacca 1320
agctacggaa gctgatcctc tcagatgagc taaagccagc tcacaggaag agggagctgc 1380
cctccttgag cccggcccct gacacagggc tgtctccctc caaaaggact caccagcgct 1440
ctaagtcaga tgccactgcc agcataagtc tcagcagcaa cctgaaacga acagccagca 1500
accctaaagt ggagaatgag gatgaggagc tctcctccag caccgagagt attgataatt 1560
cattcagttc ccctgttcga ctggctcctg agagagaatt catcaagtcc ctgatggcga 1620
tcggcaagcg gctggccacg ctccccacca aagagcagaa aacacagagg ctgatctcag 1680
agctctccct gctcaaccat aagctccctg cccgagtctg gctgcccact gctggctttg 1740
accaccacgt ggtccgtgta ccccacacac aggctgttgt cctcaactcc aaggacaagg 1800
ctccctacct gatttatgtg gaagtccttg aatgtgaaaa ctttgacacc accagtgtcc 1860
ctgcccggat ccccgagaac cgaattcgga gtacgaggtc cgtagaaaac ttgcccgaat 1920
gtggtattac ccatgagcag cgagctggca gcttcagcac tgtgcccaac tatgacaacg 1980
atgatgaggc ctggtcggtg gatgacatag gcgagctgca agtggagctc cccgaagtgc 2040
ataccaacag ctgtgacaac atctcccagt tctctgtgga cagcatcacc agccaggaga 2100
gcaaggagcc tgtgttcatt gcagcagggg acatccgccg gcgcctttcg gaacagctgg 2160
ctcatacccc gacagccttc aaacgagacc cagaagatcc ttctgcagtt gctctcaaag 2220
agccctggca ggagaaagta cggcggatca gagagggctc cccctacggc catctcccca 2280
attggcggct cctgtcagtc attgtcaagt gtggggatga ccttcggcaa gagcttctgg 2340
cctttcaggt gttgaagcaa ctgcagtcca tttgggaaca ggagcgagtg ccccttttgga 2400
tcaagccata caagattctt gtgatttcgg ctgatagtgg catgattgaa ccagtggtca 2460
atgctgtgtc catccatcag gtgaagaaac agtcacagct ctccttgctc gattacttcc 2520
tacaggagca cggcagttac accactgagg cattcctcag tgcacagcgc aattttgtgc 2580

```
aaagttgtgc tgggtactgc ttggtctgct acctgctgca agtcaaggac agacacaatg   2640
ggaatatcct tttggacgca gaaggccaca tcatccacat cgactttggc ttcatcctct   2700
ccagctcacc ccgaaatctg ggctttgaga cgtcagcctt taagctgacc acagagtttg   2760
tggatgtgat gggcggcctg gatggcgaca tgttcaacta ctataagatg ctgatgctgc   2820
aagggctgat tgccgctcgg aaacacatgg acaaggtggt gcagatcgtg gagatcatgc   2880
agcaaggttc tcagcttcct tgcttccatg gctccagcac cattcgaaac ctcaaagaga   2940
ggttccacat gagcatgact gaggagcagc tgcagctgct ggtggagcag atggtggatg   3000
gcagtatgcg gtctatcacc accaaactct atgacggctt ccagtacctc accaacggca   3060
tcatgtgaca cgctcctcag cccaggagtg gtggggggtc cagggcaccc tccctagagg   3120
gcccttgtct gagaaacccc aaaccaggaa accccaccta cccaaccatc cacccaaggg   3180
aaatggaagg caagaaacac gaaggatcat gtggtaactg cgagagcttg ctgaggggtg   3240
ggagagccag ctgtggggtc cagacttgtt ggggcttccc tgcccctcct ggtctgtgtc   3300
agtattacca ccagactgac tccaggactc actgccctcc agaaaacaga ggtgacaaat   3360
gtgagggaca ctggggcctt tcttctcctt gtaggggtct ctcagaggtt ctttccacag   3420
gccatcctct tattccgttc tggggcccag gaagtgggga agagtaggtt ctcggtactt   3480
aggacttgat cctgtggttg gccactggcc atgctgctgc ccagctctac cctcccaggg   3540
gacctacccc tcccagggac cgacccctgg cccaagctcc ccttgctggc gggcgctgcg   3600
tgggccctgc acttgctgag gttccccatc atgggcaagg aagggaattc ccacagccct   3660
ccagtgtact gagggtactg gcctagccat gtggaattcc ctaccctgac tccttcccca   3720
aacccaggga aaagagctct caattttta tttttaattt ttgtttgaaa taaagtcctt   3780
agttagccac ttgtgtcatt tccaggtttt ctgggggagt gcagggggag atgggtgatg   3840
aggtatgaac ggatgcctca gtgtccaaga tacaaaaggc actacataga agtttgcttt   3900
ttccctgcct gtcttggtca ctaccacctc ttccctgaga agggcgggcc ttccatgttc   3960
tctcacccgc ttcaactcca cattgtccaa gtcacagaaa aagagaggcc tgaatggaga   4020
ttcgaccaca aacagtttta atggtctggt tttctcccta gttccccaac tgtttgttag   4080
tattattatt actacaagaa taaaggattc ctgagagcct gtc                    4123
```

<210> SEQ ID NO 70
<211> LENGTH: 3097
<212> TYPE: DNA
<213> ORGANISM: Homo sapiens

<400> SEQUENCE: 70

```
acgcggcggc ctggccaggc gaggcgggag ccgagcaggc cggagcgggc cgcgcgccgg     60
ggagggtcgc gccgcgcccg ccccctcccc gccacgcccg gggcgcacgc gcgctcctct    120
ggccgcccct ccctccgcgc ggggacccct ggcgggcggc aggaggacat ggccagcgac    180
gccgtgcaga gtgagcctcg cagctggtcc ctgctagagc agctgggcct ggccggggca    240
gacctggcgg cccccggggt acagcagcag ctggagctgg agcgggagcg gctgcggcgg    300
gaaatccgca aggagctgaa gctgaaggag ggtgctgaga acctgcggcg ggccaccact    360
gacctgggcc gcagcctggg ccccgtagag ctgctgctgc ggggctcctc gcgccgcctc    420
gacctgctgc accagcagct gcaggagctg cacgcccacg tggtgcttcc cgacccggcg    480
gccacccacg atggccccca gtcccctggt gcgggtggcc ccacctgctc ggccaccaac    540
ctgagccgcg tggcgggcct ggagaagcag ttggccattg agctgaaggt gaagcagggg    600
```

-continued

```
gcggagaaca tgatccagac ctacagcaat ggcagcacca aggaccggaa gctgctgctg    660
acagcccagc agatgttgca ggacagtaag accaagattg acatcatccg catgcaactc    720
cgccgggcgc tgcaggccgg ccagctggag aaccaggcag ccccggatga cacccaaggg    780
agtcctgacc tgggggctgt ggagctgcgc atcgaagagc tgcggcacca cttccgagtg    840
gagcacgcgg tggccgaggg tgccaagaac gtactgcgcc tgctcagcgc tgccaaggcc    900
ccggaccgca aggcagtcag cgaggcccag gagaaattga cagaatccaa ccagaagctg    960
gggctgctgc gggaggctct ggagcggaga cttggggagc tgcccgccga ccaccccaag   1020
gggcggctgc tgcgagaaga gctcgctgcg gcctcctccg ctgccttcag cacccgcctg   1080
gccgggccct ttcccgccac gcactacagc accctgtgca agcccgcgcc gctcacaggg   1140
accctggagg tacgagtggt gggctgcaga gacctcccag agaccatccc gtggaaccct   1200
acccccctcaa tggggggacc tgggacccca gacagccgcc ccccttcct gagccgccca   1260
gcccggggcc tttacagccg aagcggaagc ctcagtggcc ggagcagcct caaagcagaa   1320
gccgagaaca ccagtgaagt cagcactgtg cttaagctgg ataacacagt ggtggggcag   1380
acgtcttgga agccatgtgg ccccaatgcc tgggaccaga gcttcactct ggagctggaa   1440
agggcacggg aactggagtt ggctgtgttc tggcgggacc agcggggcct gtgtgccctc   1500
aaattcctga agttggagga tttcttggac aatgagaggc atgaggtgca gctggacatg   1560
gaaccccagg gctgcctggt ggctgaggtc accttccgca accctgtcat tgagaggatt   1620
cctcggctcc gacggcagaa gaaaattttc tccaagcagc aagggaaggc gttccagcgt   1680
gctaggcaga tgaacatcga tgtcgccacg tgggtgcggc tgctccggag gctcatcccc   1740
aatgccacgg gcacaggcac ctttagccct ggggcttctc caggatccga ggcccggacc   1800
acgggtgaca tatcggtgga gaagctgaac ctcggcactg actcggacag ctcacctcag   1860
aagagctcgc gggatcctcc ttccagccca tcgagcctga gctcccccat ccaggaatcc   1920
actgctcccg agctgccttc ggagacccag gagaccccag gccccgccct gtgcagccct   1980
ctgaggaagt cacctctgac cctcgaagat ttcaagttcc tggcggtgct gggccggggt   2040
cattttggga aggtgctcct ctccgaattc cggcccagtg gggagctgtt cgccatcaag   2100
gctctgaaga aaggggacat tgtggcccga gacgaggtgg agagcctgat gtgtgagaag   2160
cggatattgg cggcagtgac cagtgcggga cacccccttcc tggtgaacct cttcggctgt   2220
ttccagacac cggagcacgt gtgcttcgtg atggagtact cggccggtgg ggacctgatg   2280
ctgcacatcc acagcgacgt gttctctgag ccccgtgcca tcttttattc cgcctgcgtg   2340
gtgctgggcc tacagtttct tcacgaacac aagatcgtct acagggacct gaagttggac   2400
aatttgctcc tggacaccga gggctacgtc aagatcgcag actttggcct ctgcaaggag   2460
gggatgggct atggggaccg gaccagcaca ttctgtggga ccccggagtt cctggcccct   2520
gaggtgctga cggacacgtc gtacacgcga gctgtggact ggtggggact gggtgtgctg   2580
ctctacgaga tgctggttgg cgagtcccca ttcccagggg atgatgagga ggaggtcttc   2640
gacagcatcg tcaacgacga ggttcgctac cccccgcttcc tgtcggccga agccatcggc   2700
atcatgagaa ggctgcttcg gaggaaccca gagcggaggc tgggatctag cgagagagat   2760
gcagaagatg tgaagaaaca gcccttcttc aggactctgg gctgggaagc cctgttggcc   2820
cggcgcctgc caccgccctt tgtgcccacg ctgtccggcc gcaccgacgt cagcaacttc   2880
gacgaggagt tcaccgggga ggcccccaca ctgagcccgc cccgcgacgc gcggcccctc   2940
```

acagccgcgg agcaggcagc cttcctggac ttcgacttcg tggccggggg ctgctagccc 3000
cctcccctgc ccctgcccct gcccctgccc gagagctctt agtttttaaa aaggcctttg 3060
ggatttgccg gatccttgca aaaaaaaaaa aaaaaaa 3097

<210> SEQ ID NO 71
<211> LENGTH: 5455
<212> TYPE: DNA
<213> ORGANISM: Homo sapiens

<400> SEQUENCE: 71
gggagattcg ggaccatggc acctgtgcac ggcgacgact ctctgtcaga ttcagggagt 60
tttgtatctt ctcgagcccg gcgagaaaaa aaatcaaaga aggggcgcca agaagcccta 120
gaaagactga aaaaggctaa agctggtgag aagtataaat atgaagtcga ggacttcaca 180
ggtgtttatg aagaagttga tgaagaacag tattcgaagc tggttcaggc acgccaggat 240
gatgactgga ttgtggatga tgatggtatt ggctatgtgg aagatggccg agagattttt 300
gatgatgacc ttgaagatga tgcccttgat gctgatgaga aaggaaaaga tggtaaagca 360
cgcaataaag acaagaggaa tgtaaagaag ctcgcagtga caaaaccgaa caacattaag 420
tcaatgttca ttgcttgtgc tggaaagaaa actgcagata aagctgtaga cttgtccaag 480
gatggtctgc taggtgacat tctacaggat cttaacactg agacacctca aataactcca 540
ccacctgtaa tgatactgaa gaagaaaaga tccattggag cttcaccgaa tcctttctct 600
gtgcacaccg ccacggcagt tccttcagga aaaattgctt cccctgtctc cagaaaggag 660
cctccattaa ctcctgttcc tcttaaacgt gctgaatttg ctggcgatga tgtacaggtc 720
gagagtacag aagaagagca ggagtcaggg gcaatggagt ttgaagatgg tgactttgat 780
gagcccatgg aagttgaaga ggtggacctg gagcctatgg ctgccaaggc ttgggacaaa 840
gagagtgagc cagcagagga agtgaaacaa gaggcggatt ctgggaaagg gaccgtgtcc 900
tacttaggaa gttttctccc ggatgtctct tgttgggaca ttgatcaaga aggtgatagc 960
agtttctcag tgcaagaagt tcaagtggat tccagtcacc tcccattggt aaaaggggca 1020
gatgaggaac aagtattcca cttttattgg ttggatgctt atgaggatca gtacaaccaa 1080
ccaggtgtgg tatttctgtt tgggaaagtt tggattgaat cagccgagac ccatgtgagc 1140
tgttgtgtca tggtgaaaaa tatcgagcga acgctttact tccttccccg tgaaatgaaa 1200
attgatctaa atacggggaa agaaacagga actccaattt caatgaagga tgtttatgag 1260
gaatttgatg agaaaatagc aacaaaatat aaaattatga agttcaagtc taagccagtg 1320
gaaaagaact atgcttttga gatacctgat gttccagaaa aatctgagta cttggaagtt 1380
aaatactcgg ctgaaatgcc acagcttcct caagatttga aaggagaaac tttttctcat 1440
gtatttggga ccaacacatc tagcctggaa ctgttcttga tgaacagaaa gatcaaagga 1500
ccttgttggc ttgaagtaaa aagtccacag ctcttgaatc agccagtcag ttggtgtaaa 1560
gttgaggcaa tggctttgaa accagacctg gtgaatgtaa ttaaggatgt cagtccacca 1620
ccgcttgtcg tgatggcttt cagcatgaag acaatgcaga atgcaaagaa ccatcaaaat 1680
gagattattg ctatggcagc tttggtccat cacagttttg cattggataa agcagcccca 1740
aagcctccct ttcagtcaca cttctgtgtt gtgtctaaac caaaggactg tatttttcca 1800
tatgctttca aagaagtcat tgagaaaaag aatgtgaagg ttgaggttgc tgcaacagaa 1860
agaacactgc taggtttttt ccttgcaaaa gttcacaaaa ttgatcctga tatcattgtg 1920
ggtcataata tttatgggtt tgaactggaa gtactactgc agagaattaa tgtgtgcaaa 1980

```
gctcctcact ggtccaagat aggtcgactg aagcgatcca acatgccaaa gcttgggggc   2040
cggagtggat ttggtgaaag aaatgctacc tgtggtcgaa tgatctgtga tgtggaaatt   2100
tcagcaaagg aattgattcg ttgtaaaagc taccatctgt ctgaacttgt tcagcagatt   2160
ctaaaaactg aaagggttgt aatcccaatg gaaaatatac aaaatatgta cagtgaatct   2220
tctcaactgt tatacctgtt ggaacacacc tggaaagatg ccaagttcat tttgcagatc   2280
atgtgtgagc taaatgttct tccattagca ttgcagatca ctaacatcgc tgggaacatt   2340
atgtccagga cgctgatggg tggacgatcc gagcgtaacg agttcttgtt gcttcatgca   2400
ttttacgaaa acaactatat tgtgcctgac aagcagattt tcagaaagcc tcagcaaaaa   2460
ctgggagatg aagatgaaga aattgatgga gataccaata aatacaagaa aggacgtaag   2520
aaagcagctt atgctggagg cttggttttg gaccccaaag ttggttttta tgataagttc   2580
attttgcttc tggacttcaa cagtctatat ccttccatca ttcaggaatt taacatttgt   2640
tttacaacag tacaaagagt tgcttcagag gcacagaaag ttacagagga tggagaacaa   2700
gaacagatcc ctgagttgcc agatccaagc ttagaaatgg gcattttgcc cagagagatc   2760
cggaaactgg tagaacggag aaaacaagtc aaacagctaa tgaaacagca agacttaaat   2820
ccagacctta ttcttcagta tgacattcga cagaaggctt tgaagctcac agcgaacagt   2880
atgtatggtt gcctgggatt ttcctatagc agattttacg ccaaaccact ggctgccttg   2940
gtgacataca aaggaaggga gattttgatg catacgaaag agatggtaca aaagatgaat   3000
cttgaagtta tttatggaga tacagattca attatgataa acaccaatag caccaatctg   3060
gaagaagtat ttaagttggg aaacaaggta aaaagtgaag tgaataagtt gtacaaactg   3120
cttgaaatag acattgatgg ggttttcaag tctctgctac tgctgaaaaa aaagaagtac   3180
gctgctctgg ttgttgagcc aacgtcggat gggaattatg tcaccaaaca ggagctcaaa   3240
ggattagata tagttagaag agattggtgt gatcttgcta aagacactgg aaactttgtg   3300
attggccaga ttctttctga tcaaagccgg gacactatag tggaaaacat tcagaagagg   3360
ctgatagaaa ttggagaaaa tgtgctaaat ggcagtgtcc cagtgagcca gtttgaaatt   3420
aacaaggcat tgacaaagga tccccaggat taccctgata aaaaaagcct acctcatgta   3480
catgttgccc tctggataaa ttctcaagga ggcagaaagg tgaaagctgg agatactgtg   3540
tcatatgtca tctgtcagga tggatcaaac ctcactgcaa gtcagagggc ctatgcgcct   3600
gagcagctgc agaaacagga taatctaacc attgacaccc agtactacct ggcccagcag   3660
atccacccag tcgtggctcg gatctgtgaa ccaatagacg gaattgatgc tgtcctcatt   3720
gcaacgtggt tgggacttga ccccacccaa tttagagttc atcattatca taaagatgaa   3780
gagaatgatg ctctacttgg tggcccagca cagctcactg atgaagagaa atacagggac   3840
tgtgaaagat tcaaatgtcc atgccctaca tgtggaactg agaatattta tgataatgtc   3900
tttgatggtt cgggaacaga tatggagccc agcttgtatc gttgcagtaa catcgattgt   3960
aaggcttcac ctctgacctt tacagtacaa ctgagcaaca aattgatcat ggacattaga   4020
cgtttcatta aaaagtacta tgatggctgg ttgatatgtg aagagccaac ctgtcgcaat   4080
cgaactcgtc accttcccct tcaattctcc cgaactgggc ctctttgccc agcctgcatg   4140
aaagctacac ttcaaccaga gtattctgac aagtccctgt acacccagct gtgcttttac   4200
cggtacattt ttgatgcgga gtgtgcactg gagaaactta ctaccgatca tgagaaagat   4260
aaattgaaga agcaattttt tacccccaaa gttctgcagg actacagaaa actcaagaac   4320
```

acagcagagc aattcttgtc ccgaagtggc tactccgaag tgaatctgag caaactcttc 4380
gctggttgtg ccgtgaaatc ctaagggaat cccaggagta accaaggagg gggtagttga 4440
aaaatcccag cttcctctgt gcctccactc tggccctaaa tgctcctcca gcatctgttt 4500
ctcccttggg actgtgtctc atgtttgtgt gaatgtagac caggaaaggg ggctgcaaaa 4560
atgttgagtc taatgttcgt aagcatcata gaaattcctg tcttcatatt aagatgtact 4620
gctttaaaac acaactccag agcccctccc caagctcccc tccccaagct cctgaagacc 4680
cggtttctga gggagggaaa ttgctacttg gattgagagt agctggaatg taagtgaccc 4740
caggctttgc ctcagggcct ttagcctatg tccccccccac ataaagagag cttctcagag 4800
cctgactgaa gagctgacgt tttgcttttt catatgccaa ttaaacccgg tctaaatcca 4860
aatgcttctc cagccatcca ggagtggctg tccttttcag tcttgtcttt tatataggta 4920
gctgaggggg aagatttaga agccttgcac tcactaaata gattaaacag agcaggcttg 4980
tttgttgaat tgctccaaag tccaacagac acacactgag caggtgtttt acactcacat 5040 tcccttttttg ccccttaaat agaaagtgca ggtaaaggtt tatacaacaa gaaagcacat 5100
tgaaaataat ttgatactct aacaatccat taacatgtgt aggggttacg gtgaggatca 5160
ctgtgttgta ttcagaaaaa cggggagagg gatgcttaat tggccctggc gcttgctatt 5220
tttttctcat ttcttcacaa taggaccgtc tttggcagca gcaaaatgta tttcagtatg 5280
gcagtctttc ctctcttaca ttattggtaa gattatacta acaaaatgtt tccccttgta 5340
caattatgct gtgtttttaa aaaacattga cctgtgtgtt tttataaaag aaaaagtatg 5400
ttgtgccttc ttcttaagaa taaagttttc taaagggaaa aaaaaaaaaa aaaaa 5455

<210> SEQ ID NO 72
<211> LENGTH: 8412
<212> TYPE: DNA
<213> ORGANISM: Homo sapiens

<400> SEQUENCE: 72
agccgcgtca acggcccttc gcagcgggcg cgctgtcaga cctcagtctg gcggctgcat 60
tgctgggcgc gccgctctcg tctgatccct gctggggacg gttgcccggg caggatcctt 120
tacgatccct tctcggtttc tccgtcgtca cagggaataa atctcgctcg aaactcactg 180
gaccgctcct agaaaggcga aaagatattc aggagccctt ccattttcct tccagtaggc 240
accgaaccca gcattttcgg caaccgctgc tggcagtttt gccaggtgtt tgttaccttg 300
aaaaatggct actggacagg atcgagtggt tgctctcgtg gacatggact gtttttttgt 360
tcaagtggag cagcggcaaa atcctcattt gaggaataaa ccttgtgcag ttgtacagta 420
caaatcatgg aagggtggtg gaataattgc agtgagttat gaagctcgtg catttggagt 480
cactagaagt atgtgggcag atgatgctaa gaagttatgt ccagatcttc tactggcaca 540
agttcgtgag tcccgtggga aagctaacct caccaagtac cgggaagcca gtgttgaagt 600
gatggagata atgtctcgtt ttgctgtgat tgaacgtgcc agcattgatg aggcttacgt 660
agatctgacc agtgctgtac aagagagact acaaaagcta caaggtcagc ctatctcggc 720
agacttgttg ccaagcactt acattgaagg gttgccccaa ggccctacaa cggcagaaga 780
gactgttcag aaagagggga tgcgaaaaca aggcttattt caatggctcg attctcttca 840
gattgataac ctcacctctc cagacctgca gctcaccgtg ggagcagtga ttgtggagga 900
aatgagagca gccatagaga gggagactgg ttttcagtgt tcagctggaa tttcacacaa 960
taaggtcctg gcaaaactgg cctgtggact aaacaagccc aaccgccaaa ccctggtttc 1020

```
acatgggtca gtcccacagc tcttcagcca aatgcccatt cgcaaaatcc gtagtcttgg   1080
aggaaagcta ggggcctctg tcattgagat cctagggata gaatacatgg gtgaactgac   1140
ccagttcact gaatcccagc tccagagtca ttttggggag aagaatgggt cttggctata   1200
tgccatgtgc cgagggattg aacatgatcc agttaaaccc aggcaactac ccaaaaccat   1260
tggctgtagt aagaacttcc caggaaaaac agctcttgct actcgggaac aggtacaatg   1320
gtggctgttg caattagccc aggaactaga ggagagactg actaaagacc gaaatgataa   1380
tgacagggta gccacccagc tggttgtgag cattcgtgta caaggagaca aacgcctcag   1440
cagcctgcgc cgctgctgtg cccttacccg ctatgatgct cacaagatga gccatgatgc   1500
atttactgtc atcaagaact gtaatacttc tggaatccag acagaatggt ctcctcctct   1560
cacaatgctt ttcctctgtg ctacaaaatt ttctgcctct gccccttcat cttctacaga   1620
catcaccagc ttcttgagca gtgacccaag ttctctgcca aaggtgccag ttaccagctc   1680
agaagctaag acccagggaa gtggcccagc ggtgacagcc actaagaaag caaccacgtc   1740
tctggaatca ttcttccaaa aagctgcaga aaggcagaaa gttaaagaag cttcgctttc   1800
atctcttact gctcccactc aggctcccat gagcaattca ccatccaagc cctcattacc   1860
ttttcaaacc agtcaaagta caggaactga gcccttcttt aagcagaaaa gtctgcttct   1920
aaagcagaaa cagcttaata attcttcagt ttcttccccc caacaaaacc catggtccaa   1980
ctgtaaagca ttaccaaact ctttaccaac agagtatcca gggtgtgtcc ctgtttgtga   2040
aggggtgtcg aagctagaag aatcctctaa agcaactcct gcagagatgg atttggccca   2100
caacagccaa agcatgcacg cctcttcagc ttccaaatct gtgctggagg tgactcagaa   2160
agcaacccca aatccaagtc ttctagctgc tgaggaccaa gtgccctgtg agaagtgtgg   2220
ctccctggta ccggtatggg atatgccaga acacatggac tatcattttg cattggagtt   2280
gcagaaatcc tttttgcagc cccactcttc aaacccccag gttgtttctg ccgtatctca   2340
tcaaggcaaa agaaatccca agagcccttt ggcctgcact aataaacgcc ccaggcctga   2400
gggcatgcaa acattggaat cattttttaa gccattaaca cattagtgct gccctcaggc   2460
ttgcctgtag gatttaatat tttttatctt tacagatctt tatctttaat attttatctt   2520
tacagatttc cctgagaaag ggaattatga aatttttaat acaaaaaata atccatttag   2580
gtgctgagtt acggtcccat ctcttcacag gcatggattc taatcccact gctgacagag   2640
atgtaaaaat tcatcctacc agagttttta atctttagca tttagggagg cagtgtcata   2700
aagtaaaaag tgtgtgggcc ttggagtcta agagacgtgg ttgcaaactt agctctggtt   2760
attgcaatga gggccttgaa caagtcattt tcttcacatt ctcatctgta aaatggagat   2820
aataccttac agattattgc agattaataa caatgtattc aaattatgta actcggccgg   2880
gtacaatggc tcacgcctgt aatcctaaca ctttgggagg ccgaggcaga cagatcacct   2940
gaggtcagga gtttgagacc agcctggcca acatggcaaa accatctcta ctaaaaatag   3000
aaaaattagc caggcacgtt ccaggcacct gtgatcccag ctacttagag gctgaggcag   3060
aagaattgct ttaaccttgg aggcggaggt tgcattgagc tgagatcatg ctagtgcgct   3120
ccagcctggg caacagagcg agacttcatc tcagaaaata aaaaataggg gccaggcaca   3180
gtggctcata cctgtaatgc cagcactttg ggaggccaag gcgggcagat cacgaggtca   3240
ggagtttcag accaatatgg tgaaacccca tctctactaa aattacaaaa aaaattatcc   3300
aggcgtggtg gtgcacgcct gtaatcccag ctactcagga ggctaaggca ggagaatcac   3360
```

-continued

```
ttgaacccag gaggcagagg ttggagtgag ctgagatcgc gccaccgcac tccagcctgg   3420
gcaacagagc gagactccat ctcaaacaaa aacaagaaca aaaacaaaca taaagttggc   3480
acagaaaagg gaccaagttt aaaaaagggt tttaaatgta atgagacttg catagttaaa   3540
aaaaaaaaag ggattatttt tatttttatt ttttattttt gagacggagt ctccctctgt   3600
cgtcaggcta gaatgcagtg gtgcgttctc agctcaccgc aacctccgtc tcctgggttc   3660
aagcaattct cctgcctcag cctcccaagt agctgggact acaggcacgt gctaccacac   3720
tcagctaatt tttgtatttt taatagagat gaggtttcac catgttggcc aggatggtct   3780
cgattgcttg acctcatgat ccgcctgcct cgacctccca aagttgctgg gattacagat   3840
gttagccacc gatcctggcc cccccaaaaa aaggatttta agaaaaactt ctcttggccg   3900
ggcgcagtgg ctcacgcctg caatcccagc actttgggag gccgaggcgg gcggatcaca   3960
aggtcaggag atcgagacca cggtgaaacc ccgtctctac taaaaaatac aaaaaaaaat   4020
tagccgggtg cggtggcagg cgcctgtagt cccagctact cgggaggctg aggcaggaga   4080
atggtgtgaa cccgggaggc ggagcttgca gtgagccgag agcgcgccac tgcactccag   4140
cctgggtgac agagcgagac tccgtctcaa aaaaaaaaaa aaaagaaaaa cttctcttta   4200
ggctgggtgc ggttcctcat gcctataatc ccagcattta gggaggctga ggtgagtgga   4260
ttgcaggagc tcaggagttc gagaccagcc tgggcaaggt ggcaaaaccc cgtctctact   4320
aaaaaaaatt agctgggctt ggtggcaggc gcctgtaatc ccaggtactc gggagactga   4380
ggcaggagaa ttgcttgaac ctggaaggtg gaggttgcag tgagttgaga tcacaccaat   4440
gcactccagc cagggtgaga gtgagagact gtctcaaaaa aaaaaaaaac aaaagaaaaa   4500
cttctctcta gctctgtgac gggcagttca gataatacct tcaccagatt tacctgtttt   4560
cagctgaaga atgtgagatg aagccttgaa accctaaaag tgatatggta actagggcag   4620
gtctttctgt acataaaagt gacttaataa acagtgaatt tcatacaggt aaaccctatt   4680
ataccctcag ttctaaccat tggcctatct cttgcgtttt gttctaatgt agaattagat   4740
tgctacttga ctagttcagg aactctgttt agatctgata agtcataatc aaatcttgcc   4800
aggcgtggtg gtttatgcct gttatcccag cactttggga ggccaaggca ggtggaccac   4860
gtgaagtcag gagttcaaga caagcatggc caacatggcg aaaccctgta tctactaaaa   4920
atacaaaaat tagccgggca tggtggtggg tgcgtgtaat cccagctagt tgggaggctg   4980
aggcaggaga atcacttgaa cctgggaggc agaggttgca gtgagccgag atttccactg   5040
cattccagcc tgggcgatag agtaactctg tctcaaaaaa acccactaga tcatctctag   5100
aacattgcta ctcccaagta tgatttgagg aacagcagcc tcagtatcac cagggaactt   5160
attagaaata gtctcagcct caccactatt cccacttaat tgtaatctga tattaacaag   5220
atttcccaat gtgggtcagg tgtggtggct catgcctgta atcccacact ttgggaggcc   5280
aaggtgggcg gatcacttga ggctgggagt ttgagaccag gctggccaac atggggaaaa   5340
cccatctcta caaaaaataa caaaaattag gtgtgtgtgg tgacgcatgc gtgtaatccc   5400
agctacttag gaggctgagg caggagaatc acttgaatct gggaggcaga ggttgtagtg   5460
agctgagatt gtgccactgc actccagtct gggcaacaga gtgacactgt ttaaaaaaaa   5520
aaaaattccc aatgtgggcc gggtgcagtg gctcatgcct gtaatcccag cactttggga   5580
ggctgaggtg ggtgtatcac gaggtcaaga gatcaaggcc atcctggcca acatggtgaa   5640
accccgtctc tactgaaaat acaactgggc gtggtggtgc acgcctgtag tcccagctac   5700
ttgggaggct gaggcagaag aattgcttga cctgggaggc ggagcttgca gtgagcccag   5760
```

atcgtgccac tgcactgcac cctggcgaca cagcaagact gtctcaaaaa aaaaaaaatt 5820
cccaatgtgt atcttaaagt ttgagaaatg ctgatctaaa agatactaat gaccaggtgt 5880
gtagaggaca ttttcttaag cccttaagta caaatttaag aggtaagtgc ttcagccatt 5940
agggttactg gcttgttcat ctttcccact gagtgtaaat atttagctta gggtttaaaa 6000
tttgttatgt agctttttgc acttgtccat gtttatacta ctgtattatt attatttttt 6060
tttgagatgg agtctcgctg tgtagccagg ctggagtgca gtggtgcaat cttggctcac 6120
tgcaacctcc gtctctcggg ttcaagcaat tctcctgcct cagcttcccg aatagctgag 6180
actacaagcg tgcaccacca tgcccagcta atttttgtat ttttagtaga gacaggtttt 6240
caccatgttg gccaggctgg tctctatcta gacctcgtga tccatccgcc tcggcctccc 6300
aaagtgctgg gattataggc atgagccacc acgcccagcc tatagtactg tattcttatt 6360
ctccactctt gtgtgtgaaa agtcagctct tttggctttt ctgttatggg gaaacttgaa 6420
ttacacaggg aacccaactg aagaaaatga actgaagtag gtggcgctgg gtgaagtggg 6480
cccagagaat ggtgtacaca tccctcccat acatataccc aaacttctat ttttttatgt 6540
gacggagttt ctctcatcgc cccggctgga atgcaatggc acgatctcgg ctcactgcaa 6600
cctccgcctc ccgggttcaa gcgattctcc tgcatcagcc tcctgagtag ctgggattat 6660
aggcatgcac catcacgcct ggctaatttt tgtattttta gtagagatgg ggtttcgcca 6720
cgttggccag gctggtcttg aactcttgat ctcaagtgat ccacccgccc tggcctccca 6780
aagtgctggg attacaggcc tgagccacca ggccagcccc aacttctact ttttatttta 6840
tttataaatt gggggggggg ttctatattt agtttgaaga ggtggggaag atttgaaaac 6900
cactagattt accaggaaat ttttttcttc aaaaatattt tctgctttta tgatacttga 6960
atatctaata aaagacaata tttagccagt cacggtggct gatgcttgta atcctaacac 7020
tttgggaggc tgaggtgggt ggactactgg agccctggag ttcaaaaccg gcctaagcca 7080
catggcaaaa cagtctttac aaaaaataca aagatggtgg cttatgcctg tagtcgtacc 7140
tactcaggag gctgaggttg ggaggatcac ctgaatctgg gagtttgggg ctgcaataag 7200
ccatgattgt gccgctgcac tccagcctgg gtgacagtct gagaccctgt ctcaaaaaaa 7260
aaaaaaaaaa aaaaaaaaaa aaagactaca ttcactgtat acgtggcctt ttccccctaa 7320
ctagctatgt agcttcttaa aggcaaagat tcttcatagt gctttgcaca tgataggtgc 7380
tgatactcat tggatgaatg tatatagtga agaattttag atctgattac cacaattggg 7440
atcataaaca tgtataaact ccttgggagt ctgccttata tactttttat cccccctaaat 7500 gttccattaa tgttgcagag aggctcacta gttcctggag atgtcttatt aagtactgaa 7560
atgtgatttt ccaaaatttt ctttacaata caggcaaaag ataagtaaat tgtggacaaa 7620
gctttcatct ctatcagcag ctatagagag gaagtaaaca gcttagcccc taatacagga 7680
ggaagttgtt caactacagg cttgttagta gcaagttaaa ccagttacat tttataaaac 7740
agcctgagtg gtagggaagc tatcacttta atactctaga ggcagaatgc cacataggac 7800
tttgggtcac atatttcttt tccagggtct cctcaaaatg cagtttctat ttacagttga 7860
ctttggcccc tatttaccca taaaatgtca aaatcaagta gtatgaacat ggaaacagga 7920
gcagggacta aggtttggtc aagtggccct cattgttcca agagtaattt aggctatgta 7980
aacttgaaaa atatgggacc agattacctt ttgtctctaa attctactct tctttaagta 8040
gctggcactg tatctctgcc agggcacaga agtgggctcc ttactattct gaccactagc 8100
aagtggccaa ctcttcaaat acagggtagc tacctatttc acgtgaaagg cctcagtatt 8160
ctgctcactt gaactacgga aaataggcca caatacttgg ttacaatact ggaactctga 8220
acctatgtgg aggagagaaa aacaatggtg aacgagatac cagctgggct ctttccacat 8280
tcagggctca gcagtgttgg ggtttcactt gtctctaatc ctgaagaggt atctagccct 8340
ggaaggaagc tgagcctgta gctaacgcat aagcacagtg tattcaataa aacattttta 8400
ttctgtacaa ta 8412

<210> SEQ ID NO 73
<211> LENGTH: 2866
<212> TYPE: DNA
<213> ORGANISM: Homo sapiens

<400> SEQUENCE: 73
ggattcggcg caggcgcagt ccgcgcgggt tctcgcgcgg agaaggggtg cgagcggcgg 60
cggcggcgga ggctgccatg gacgacgagg aggagacgta ccggctctgg aaaatccgca 120
agaccatcat gcagctgtgc cacgaccgtg gctatctggt gacccaggac gagcttgacc 180
agaccctgga ggagttcaaa gcccaatttg gggacaagcc gagtgagggg cggccgcggc 240
gcacggacct caccgtgctg gtggcccaca acgatgaccc caccgaccag atgtttgtgt 300
tctttccaga ggagcccaag gtgggcatca agaccatcaa ggtgtactgc cagcgcatgc 360
aggaggagaa catcacacgg gctctcatcg tggtgcagca gggcatgaca ccctccgcca 420
agcagtccct ggtcgacatg gcccccaagt acatcctgga gcagtttctg cagcaggagc 480
tgctcatcaa catcacggag cacgagctag tccctgagca cgtcgtcatg accaaggagg 540
aggtgacaga gctgctggcc cgatataagc tccgagagaa ccagctgccc aggatccagg 600
cgggggaccc tgtggcgcgc tactttggga taaagcgtgg gcaggtggtg aagatcatcc 660
ggcccagtga gacggctggc aggtacatca cctaccggct ggtgcagtag ctaccgcctg 720
acagccccta gaggcggaca cacagcgacc cccatccctg caggacaaac gcccctgccc 780
tgccagaatc cggcccccac agctctcacg gctgctgctc ctctggactc cccaaggcag 840
gtggcctcca cccacgttct cccgtcctgg ggtgaggctt cctgtggccc agcccgcccc 900
attcacctgt ggatttgtgc gagatgcagc ctcagaagga acaaggcccc cagagggagg 960
tcacctgggg gcagctggtg ccgggtcttc acccagacca cgctgggtcc cctctgttgg 1020
gggtttgggg tccgggtctc ccaccagcca ctgcttcctc ctgggccctc ggccttccac 1080
ccctcgtctt ccctccctcg ggggccctga tgcgtggcgg cccccgcccg gcctcggctc 1140
tttactccat tcacagccat gcacgcgctc aagccaccag ggtgcgagat gccagctctg 1200
gagttctcgg ttgttgtagg aggttgggtg ttttcaaatg gtaaagatgt tttgagcaaa 1260
taaatttgct tgatacagaa accaggccga ctaacaaggt ttccagcagg tggccttgcc 1320
tcaccccaag cacacgaggt cagcctggca ggtgtgccct cctcgcgctg gcttcagggg 1380
tcagtgtctc cccaggccct cgccctgccc tcccacttcg tgctcctggg taaggcgtga 1440
gcgtgtctgt ctcttccctt cccgtgaggg tgtggagttg ttctctggct tgtgcagctg 1500
tggtttgcgg ccagttcctc ttacagacgt ttgggatctg gctctacttc cccgtttgct 1560
tactgtctga tttcagaagg cctcgcctgc ccaagtttaa cctagccacg tggttctctc 1620
acagtagctt tattaagatg taattcaccc tcgggcggtc ggtggtctgt aacgcgccca 1680
ctgttctgtg cagcagggtc cccagatccc caggccgcgg actgtgtgtg tgatggggac 1740
agtgcttccc cttctctcca aatgtacttt tttcaaaatt gtcttggcca aagcaagcca 1800

```
gacccaaagg gacaaacact gatgtcactc ctaggaggtc actagagtcg tcagagactg   1860

gaagtaggat gggggttccc gggactgggg agttgggtgg ggatgggggt tcccagggct   1920

ggggaggagg gaggggacag agtgtgtcat gtgcacagtt ttagtttggg aagatgagaa   1980

aattctggag gtggccgggc gcggtggctc acgcctgtaa tcccagcact ttgggaggcc   2040

gaggtgggcg gatcacctga ggtcgggagt tcgagaccag cctgaccaac atggcaaaat   2100

cccatcactg caaaaaatac aaaaattacc tgggcgtggt ggtgcatgcc tgtaatccca   2160

gctacttggg agctaaggca ggagaatcac ttgaacccag gaagtggagg atcgcttgag   2220

ctcaggagtt aaaagaccag cccgggcaac acagagaaac cccccacctc tacaaaaaac   2280

tttaagatta cctgggcaca gtggctcaca cctgtaatcc caacactttg ggaggctgag   2340

gcgggaggat catttgagcc caggaggccg aggctgcagt gagctacgat tgtgctcctg   2400

tactccagcc tgggccacag ggtcacaccc tgtctcaaaa aaaaaaaaaa atgcagttcc   2460

acaggcgcat gggccacgtt tccagtgctt ggtggccatg tggggctgac gtgcgaaacc   2520

ttagagccgg gggatacgtc cgtcatcgag aacgttttcc tggactgccc tgggctgcag   2580

gtggacgtga cgaggtcatt cgatgcctga ccgtctgcac agcctgtggt gaagaccacc   2640

cgggctccca cctcgcgggg ccccgtggcg gggggttccc ttcctcacac atccctcccc   2700

tagggggagg cccagggcca cgccacgggg ctctctctgt cccctccctg gccccttctt   2760

ctaagcttgc agctgccaca gaaaatcttc taagcttgca gctgccacag aaaacacccg   2820

attaaaaact ttttatttca gcaaaataaa cgtgcctgtg aaagaa                  2866
```

<210> SEQ ID NO 74
<211> LENGTH: 885
<212> TYPE: DNA
<213> ORGANISM: Homo sapiens

<400> SEQUENCE: 74

```
ggcccgggaa aggaccagaa caggcggcga agactgaagc ccggaggtag gagtggcaag     60

agctcgccca gtccgcgaag ggtaaactcg cgcatgcgca ctggccttca accaagccaa    120

gcgccttggc ttctgtcctg gatgctcagt gttttgcggt ttacgatgcg catcgttttc    180

ccggctctgg caccagatcc atactattct gtaaactgag gcggcgatgc ccaaaaattg    240

gaagcaatta ctctaagata tcaaaagatt gaagcaagcc atgaaacctc tgcgcggaga    300

gagccgagcc cgaggcggcg gggagccagc acgtgtgcgc agctccgccc tcttttggcg    360

aagcacctag gcctggcccc tcccgcgacc tgtagcgcgg cggagcaagc gcggaaggct    420

gggagggctg cgcgggctgc gcgtcgccat ggagcccgac gggacttacg agccgggctt    480

cgtgggtatt cgcttctgcc aggaatgtaa caacatgctg taccccaagg aagacaagga    540

gaaccgcatt ctgctctacg cgtgccggaa ctgtgattac cagcaggagg ccgacaacag    600

ctgcatctat gtcaacaaga tcacgcacga agtggacgaa ctgacccaga ttatcgccga    660

cgtgtcccag gaccccacgt tgccgcggac cgaggaccac ccgtgccaaa agtgcggcca    720

caaggaggct gtgttcttcc agtcacacag tgcgcgggcc gaggacgcca tgcgccttta    780

ctacgtgtgc acagccccac actgcggcca ccgctggacc gagtgacctc ctctctcccc    840

cgagtgtaat aaacaccaga ttccatgcgt gaaaaaaaaa aaaaa                   885
```

<210> SEQ ID NO 75
<211> LENGTH: 3207
<212> TYPE: DNA

<213> ORGANISM: Homo sapiens

<400> SEQUENCE: 75

```
gattgcgcac ccgcgacttc agcccgaggg gcggggattt tcttggagcg acgggacgcg     60
acgccaatcg cgacgaggct tcgccccgtg gcgcggtttg aaattttgcg ggctcaacg     120
gctcgcggag cggctacgcg gagtgacatc gccggtgttt gcgggtggtt gttgctctcg    180
gggccgtgtg gagtaggtct ggacctggac tcacggctgc ttggagcgtc cgccatgagg    240
agaagtgagg tgctggcgga ggagtccata gtatgtctgc agaaagccct aaatcacctt    300
cgggaaatat gggagctaat tgggattcca gaggaccagc ggttacaaag aactgaggtg    360
gtaaagaagc atatcaagga actcctggat atgatgattg ctgaagagga aagcctgaag    420
gaaagactca tcaaaagcat atccgtctgt cagaaagagc tgaacactct gtgcagcgag    480
ttacatgttg agccatttca ggaagaagga gagacgacca tcttgcaact agaaaaagat    540
ttgcgcaccc aagtggaatt gatgcgaaaa cagaaaaagg agagaaaaca ggaactgaag    600
ctacttcaag agcaagatca agaactgtgc gaaattcttt gtatgcccca ctatgatatt    660
gacagtgcct cagtgcccag cttagaagag ctgaaccagt tcaggcaaca tgtgacaact    720
ttgagggaaa caaaggcttc taggcgtgag gagtttgtca gtataaagag acagatcata    780
ctgtgtatgg aagaattaga ccacacccca gacacaagct ttgaaagaga tgtggtgtgt    840
gaagacgaag atgccttttg tttgtctttg gagaatattg caacactaca aaagttgcta    900
cggcagctgg aaatgcagaa atcacaaaat gaagcagtgt gtgaggggct gcgtactcaa    960
atccgagagc tctgggacag gttgcaaata cctgaagaag aaagagaagc tgtggccacc   1020
attatgtctg ggtcaaaggc caaggtccgg aaagcgctgc aattagaagt ggatcggttg   1080
gaagaactga aaatgcaaaa catgaagaaa gtgattgagg caattcgagt ggagctggtt   1140
cagtactggg accagtgctt ttatagccag gagcagagac aagcttttgc ccctttctgt   1200
gctgaggact acacagaaag tctgctccag ctccacgatg ctgagattgt gcggttaaaa   1260
aactactatg aagttcacaa ggaactcttt gaaggtgtcc agaagtggga agaaacctgg   1320
aggcttttct tagagtttga gagaaaagct tcagatccaa atcgatttac aaaccgagga   1380
ggaaatcttc taaaagaaga aaaacaacga gccaagctcc agaaaatgct gcccaagctg   1440
gaagaagagt tgaaggcacg aattgaattg tgggaacagg aacattcaaa ggcatttatg   1500
gtgaatgggc agaaattcat ggagtatgtg gcagaacaat gggagatgca tcgattggag   1560
aaagagagag ccaagcagga aagacaactg aagaacaaaa aacagacaga gacagagatg   1620
ctgtatggca gcgctcctcg aacacctagc aagcggcgag gactggctcc caatacaccg   1680
ggcaaagcac gtaagctgaa cactaccacc atgtccaatg ctacggccaa tagtagcatt   1740
cggcctatct ttggagggac agtctaccac tcccccgtgt ctcgacttcc tccttctggc   1800
agcaagccag tcgctgcttc cacctgttca gggaagaaaa caccccgtac tggcaggcat   1860
ggagccaaca aggagaacct ggagctcaac ggcagcatcc tgagtggtgg gtaccctggc   1920
tcggcccccc tccagcgcaa cttcagcatt aattctgttg ccagcaccta ttctgagttt   1980
gcgaaggatc cgtccctctc tgacagttcc actgttgggc ttcagcgaga actttcaaag   2040
gcttccaaat ctgatgctac ttctggaatc ctcaattcaa ccaacatcca gtcctgagaa   2100
gccctgatca gtcaaccagc tgtggcttcc tgtgcctaga ctggacctaa ttatatgggg   2160
gtgactttag tttttcttca gcttaggcgt gcttgaaacc ttggccaggt tccatgacca   2220
tgggcctaac ttaaagatgt gaatgagtgt tacagttgaa agcccatcat aggtttagtg   2280
```

gtcctaggag acttggtttt gacttatata catgaaaagt ttatggcaag aagtgcaaat 2340
tttagcatat ggggcctgac ttctctacca cataattcta cttgctgaag catgatcaaa 2400
gcttgtttta tttcaccact gtaggaaaat gattgactat gcccatccct gggggtaatt 2460
ttggcatgta tacctgtaac tagtaattaa catctttttt gtttaggcat gttcaattaa 2520
tgctgtagct atcatagctt tgctcttacc tgaagccttg tccccaccac acaggacagc 2580
cttcctcctg aagagaatgt ctttgtgtgt ccgaagttga gatggcctgc cctactgcca 2640
aagaggtgac aggaaggctg ggagcagctt tgttaaattg tgttcagttc tgttacacag 2700
tgcattgccc tttgttgggg gtatgcatgt atgaacacac atgcttgtcg gaacgctttc 2760
tcggcgtttg tcccttggct ctcatctccc ccattcctgt gcctactttg cctgagttct 2820
tctacccccg cagttgccag ccacattggg agtctgtttg ttccaatggg ttgagctgtc 2880
tttgtcgtgg agatctggaa ctttgcacat gtcactactg gggaggtgtt cctgctctag 2940
cttccacgat gaggcgccct ctttacctat cctctcaatc actactcttc ttgaagcact 3000
attatttatt cttccgctgt ctgcctgcag cagtactact gtcaacatag tgtaaatggt 3060
tctcaaaagc ttaccagtgt ggacttggtg ttagccacgc tgtttactca tacagtacgt 3120
gtcctgtttt taaaatatac aattattctt aaaaataaat taaaatctgt atacttacat 3180
ttcaaaaaga aaaaaaaaaa aaaaaaa 3207

<210> SEQ ID NO 76
<211> LENGTH: 2846
<212> TYPE: DNA
<213> ORGANISM: Homo sapiens

<400> SEQUENCE: 76
gtaatcagtc caaaaaccag cgtgccaaag cgtttcccca gggctctgtc cggactctga 60
agcactgcat aaaggggtct gtctgagccc aatttacttc cggtggggaa gggaaaggga 120
agacaccacc ggaagcaagg aaggtgctgt gtaatcatta aggagcggag gcttttggag 180
ctgctaaaat gccggattac ctcggtgccg atcagcggaa gaccaaagag gatgagaagg 240
acgacaagcc catccgagct ctggatgagg gggatattgc cttgttgaaa acttatggtc 300
agagcactta ctctaggcag atcaagcaag ttgaagatga cattcagcaa cttctcaaga 360
aaattaatga gctcactggt attaaagaat ctgacactgg cctggcccca ccagcactct 420
gggatttggc tgcagataag cagacactcc agagtgaaca gcctttacag gttgccaggt 480
gtacaaagat aatcaatgct gattcggagg acccaaaata cattatcaac gtaaagcagt 540
ttgccaagtt tgtggtggac cttagtgatc aggtggcacc tactgacatt gaagaaggga 600
tgagagtggg cgtggataga aataaatatc aaattcacat tccattgcct cctaagattg 660
acccaacagt taccatgatg caggtggaag agaaacctga tgtcacatac agtgatgttg 720
gtggctgtaa ggaacagatt gagaaactgc gagaagtagt tgaaacccca ttacttcatc 780
cagagaggtt tgtgaacctt ggcattgagc ctcccaaggg cgtgctgctc tttggtccac 840
ccggtacagg caagacactc tgtgcgcggg cagttgctaa tcggactgat gcgtgcttca 900
ttcgagttat tggatctgag cttgtacaga aatacgtcgg tgagggggct cgaatggttc 960
gtgaactctt tgaaatggcc agaacaaaaa aagcctgcct tatcttcttt gatgaaattg 1020
atgctattgg aggggctcgt tttgatgatg gtgctggagg tgacaatgaa gtgcagagaa 1080
caatgttgga actgatcaat cagcttgatg gttttgatcc tcgaggcaat attaaagtgc 1140

```
tgatggccac taacagacct gatactttgg atccagcact gatgaggcca gggagattgg   1200

atagaaaaat tgaatttagc ttgcccgatc tagagggtcg gacccacata tttaagattc   1260

acgctcgttc aatgagtgtt gaaagagata tcagatttga actgttagca cgactgtgtc   1320

caaatagcac tggtgctgag attagaagcg tctgcacaga ggctggtatg tttgccatca   1380

gagcacggcg aaaaattgct accgagaagg atttcttgga agctgtaaat aaggtcatta   1440

agtcttatgc caaattcagt gctactcctc gttacatgac atacaactga accctgaagg   1500

ctttcaagtg aaaactttaa attggaatcc taaccttata tagacttgtt aataaccaat   1560

tcataaacaa ataaatggct tcaaaattgt atgctttttt ccatatctct tcttgtaata   1620

taataaaagg tgatttctaa tgttattagg cagaaaagct tgttagaata tattttgact   1680

attttttga cccacacccg tttaaggatt tcacatcata caaagcgctt gcttagatgg   1740

cttctatcct aggcatatgc tggccgggtg ctctacatat aaattctcat tgtatcctcc   1800

catctgtcca ctgaggaaga ttatcaaatg gatcttcatc caatggatgc ataaactttc   1860

ctacttactt gtagtggcaa agctggcttt caagtacaag tttgttggct ccattaccta   1920

tgctcctatt atccgcttct gtcccgcaac aaagtagctc acttaggcgt atgaccacat   1980

gcattatgat agtttcccac caccatattg aataataaaa gctttggcca aagctttttt   2040

aaagtaggag aaacattgga tgtatatgtt ttgcattgcc atttgatttc aaattaatca   2100

ggaagaatta gtgattttaa tgagcagtaa agtggtgcaa taaagcagaa agaaaaatgt   2160

tcagccagaa gtgaaagact agtaaaaaaa gaaaaaaaaa tatttgtaca tatgatctaa   2220

tttagaaagt ccagaattgg cttcatacag aaaagtgatt actttcattt tacaaattac   2280

tttaaaattt tggtaaagtt tctgttaggc ttctggtcta cagtgaggta ttttaaaaat   2340

aaaggttata ttagaatcct caacatctct ttaaaattac ctcctgtgta accaccacca   2400

aatcctatct tctaccacaa ttaccccttc ccccaatgcc aagaccaaag cacaataatg   2460

aatattttta ttgaagttcg atattcataa ataagttgca aaataagagt tggatatatt   2520

tttaattcac aatagaaaaa gttgacaaca tagaaaatgc tgctttgcac tgaaatactt   2580

aaaattatga aagttttcaa gtaaagaaat taaagccttt tataaaatcc aaccaacatt   2640

cttgattttt catttttatg aacttgatca gaaaaattca tctttttaa ccctgcccta   2700

atttttcttg aggaattaaa tagagcaaac tattttcagg ttatgcttac aataaaatat   2760

acttaagaaa atgactgaag atgtatgttt ttgaatgttt tgattaaata aatgtacaca   2820

tttagaacac aaaaaaaaaa aaaaaa                                         2846
```

<210> SEQ ID NO 77
<211> LENGTH: 3925
<212> TYPE: DNA
<213> ORGANISM: Homo sapiens

<400> SEQUENCE: 77

```
agcggggctg cgcgaagtca tcgctgttcc agacagcgat gactcgagag cggtgggggt     60

ggcggcgcga tcggccgggc tgtaaccgtc gtctgtccgg gagcggctgg agcggcagcg    120

gcggccgggc acggcgcgag gtgacgccac agggcagcgg cggcagcgga ggcagcggcg    180

gcagcaggag acgcagcggc ggccgcagca gcagcagcaa gacggactcg tggagacgcg    240

ccgccgccgc cgccgccggg ccgggccggg tgtcgcgcgc cgaggctggg ggggagtcgt    300

cgccgccgcc gccaccgcta ccgccgccgc cgccgccgcc gaggtgactg aggagagagg    360

cgcctcctcg ctcccgccac cgccggactt caatgcccag tccccagctc gccagcgttt    420
```

```
ttcgttggaa tatacgttgc acatttatgg cgattctgag tgtgagggca gacttctgcc    480
aggctcagca cagcattttc gctgacaagt gagcttggag gttctatgtg ccataattaa    540
cattgccttg aagactcctg gacaccgaga ctggcctcag aaatagttgg cttttttttt    600
tttttaattg caagcatatt tcttttaatg actccagtaa aattaagcat caagtaaaca    660
agtggaaagt gacctacact tttaacttgt ctcactagtg cctaaatgta gtaaaggctg    720
cttaagtttt gtatgtagtt ggatttttttg gagtccgaat atttccatct gcagaaattg    780
aggcccaaat tgaatttgga ttcaagtgga ttctaaatac tttgcttatc ttgaagagag    840
aagcttcata aggaataaac aagttgaata gagaaaacac tgattgataa taggcatttt    900
agtggtcttt ttaatgtttt ctgctgtgaa acatttcaag atttattgat tttttttttt    960
cactttcccc atcacactca cacgcacgct cacacttttt atttgccata atgaaccgtc   1020
cagcccctgt ggagatctcc tatgagaaca tgcgttttct gataactcac aaccctacca   1080
atgctactct caacaagttc acagaggaac ttaagaagta tggagtgacg actttggttc   1140
gagtttgtga tgctacatat gataaagctc cagttgaaaa agaaggaatc cacgttctag   1200
attggccatt tgatgatgga gctccacccc ctaatcagat agtagatgat tggttaaacc   1260
tgttaaaaac caaatttcgt gaagagccag gttgctgtgt tgcagtgcat tgtgttgcag   1320
gattgggaag ggcacctgtg ctggttgcac ttgctttgat tgaatgtgga atgaagtacg   1380
aagatgcagt tcagtttata agacaaaaaa gaaggggagc gttcaattcc aaacagctgc   1440
tttatttgga gaaataccga cctaagatgc gattacgctt cagagatacc aatgggcatt   1500
gctgtgttca gtagaaggaa atgtaaacga aggctgactt gattgtgcca tttagaggga   1560
actcttggta cctggaaatg tgaatctgga atattacctg tgtcatcaaa gtagtgatgg   1620
attcagtact cctcaaccac tctcctaatg attggaacaa aagcaaacaa aaaagaaatc   1680
tctctataaa atgaataaaa tgtttaagaa aagagaaaga gaaaaggaat taattcagtg   1740
aaggatgatt ttgctcctag ttttggagtt tgaatttctg ccaggattga attattttga   1800
aatctcctgt ctttttaaac tttttcaaaa taggtctcta aggaaaacca gcagaacatt   1860
aggcctgtgc aaaaccatct gtttggggag cacactcttc cattatgctt ggcacataga   1920
tctccctgtg gtgggatttt ttttttccct ttttttgtgg gggagggttg gtggtatatt   1980
tttcccctct tttttccttc ctctcctaca tctccctttt cccccgatcc aagttgtaga   2040
tggaatagaa gcccttgttg ctgtagatgt gcgtgcagtc tggcagcctt aagcccacct   2100
gggcactttt agataaaaaa aaaaaaaaac aaaaaacaac accaaaaaaa cagcagtgat   2160
atatatattc caggtggttt ttagtcttta ctgatgaaag ggtgttcatg ttagtttctt   2220
caaaacccta tctaatacta ggcaaagtag ccaagagcct tttgttttgt ttttattttg   2280
ataaattagt ggagaaatgg cattttaaga ggagtctctt ctcaacttac ctgagagtcg   2340
aattcttctc ttccctaacc aatgaagcta agtggttatc ccagaaactt gtcttctaaa   2400
agggaggact ccaggccatc aataaagatg tccaggcagt gagcgtactt tttacaccct   2460
gtagaattgt gggctgtagc gttactctga ttttctgtct agtatcagag aatgctggta   2520
gcttaaaatt tttattttag gacttgtact ctgaattttc aggaaccgtc aaaggagcag   2580
cagcaaattc acatattttc gacttgagaa atgcttgtgg tatgtgtttt ccaaactgcc   2640
ccctatatgt aaagttcagt ttaaccactg attgccttgt tattactagg tttttttgaga   2700
ttaaaaaaaa aaaatccctg gtttaaaacc aacaatgatg cctagtgagt atgtgtccac   2760
```

```
aggccataac agggtagaag agagacatcg tgcaacccaa tgagtagtga agggactgtg   2820
ttgcttgtga agcggtgtag tagcattttt gcagattctt ggctgggttt agtgtactga   2880
tctagaaaag ctgtttttct gctcctttgt ggaaggcagt tatgatcagg ctgcatggac   2940
aaagcaggta gaggggcacc atcaggggct cttgcactat tttcacctct aaatattacg   3000
tactcagtag tgccctgctt ctagggctct gaatacgggc ttaaagtcat cttgtcctgc   3060
tggaatttgc tgtgcagagc cataagcctc ccattttgtt agcgtcagct aggccaatag   3120
gaacagaccg ggaccttgtc tcacactgat gatacctcac atgttgaccg gctatgtgaa   3180
ctgcctattt cctatgctgg agttttgatt tttaactaaa cgcaaatctg tagattctct   3240
cctctcccat cccagaaaac aaaacaaaat aatgcttttc gaaattgttt ctaggacttt   3300
aaaacataat ggtatatcca aaattcttta tttcagaatg caacaataga ttccattaat   3360
atagactcaa gatcaaaaca gcatacctgc taagctaaga tagatggtgt tgattccact   3420
gggttttgat caatacaata acaaaccttt ttcctttgac atactctgaa ttttgttgtt   3480
tggggggagg gggtgtgtgt gtgtgtgtgt gtgtgtgtgt gtattgtgtg tgtgtgtgtg   3540
tgcacgcgca gtgtccatca gtatcagtgc ctgcctgagt taggaaaatt acattcctgg   3600
ttctgtattg aggagaagga tgtataaagc aacatgaaac attagccctc cttttatttt   3660
aaagactaat gttaattgtt cttaaaactg gatttttttt ccttaaagca attttttttct   3720
tttcgattta atgaagtatt gctagctgaa gccagtttga catagagaga tgtcagattg   3780
atttgaaagg tgtgcagcct gatttaaaac caaaccctga accctttttaa agaacaataa   3840
aacatatttt acacgctcaa aaaaaaaaaa aaaaaaaaaa aaaaaaaaaa aaaaaaaaaa   3900
aaaaaaaaaa aaaaaaaaaa aaaaa                                         3925
```

<210> SEQ ID NO 78
<211> LENGTH: 3956
<212> TYPE: DNA
<213> ORGANISM: Homo sapiens

<400> SEQUENCE: 78

```
ggctgaggca gccgcgcagg tcgcagggcc agcgtccgcg aggacggccc ggctgggcgg     60
ccccgagctc tgtggcgctg tggaggagcg ggagcgcggc cgagaaagcg gggcgccgag    120
ggggtcggcg gccttcggga aatttccgcc gacccttcgc tcccggctct aaaagttcct    180
gatttcctat ttccttttaa atcccgagtg gctgttagct cttcgcctgc actttttctt    240
ccccaggaga taagggggag tgtgaggaac ggagcgaata atataaaaaa ggatttcctc    300
ccggaagaga gcggcagttc ggagagattt ttcttaagga agcagaagcg gcgtttgcgg    360
ccgctgcagg cgccgggccc tgccggccac actatgcgcg agccggcccc gggctgctga    420
ggcgcgggga cgcggaagcg gaggccgagc gcgccgggct cccgcgctcg cgagcgagtt    480
ttgtccgccc ggcggcggtg gcggggggat ggagcccgcg accgcgcccc ggcccgacat    540
ggcgccggag ctgaccccgg aggaggagca ggctaccaag cagtttctcg aagagattaa    600
caagtggaca gttcagtaca atgtttcccc gctgtcttgg aatgtggctg tcaagttcct    660
catggcaagg aagtttgatg tgctccgtgc catagaattg ttccactcct acagagaaac    720
tcgaaggaag gaaggcattg taaagctgaa acctcatgag gaacctcttc gttctgagat    780
cctcagtgga aaattcacca tcttaaatgt tcgggaccca acaggagcct ccattgccct    840
ctttactgcc aggttgcatc atccccacaa gtcagtccaa catgtggtac ttcaggctct    900
gttttacttg ctagacagag ctgtggatag ctttgaaact cagaggaatg gactggtgtt    960
```

```
tatctatgac atgtgtggtt ctaattatgc caactttgag ctggatcttg gcaagaaagt   1020
cctaaacctg ctgaagggag catttccagc tcgtttgaag aaggtgctga ttgtgggggc   1080
acccatatgg ttccgagtgc cctattccat catcagtctc ctcctgaagg acaaagtccg   1140
ggagaggatt caaatattaa agacatctga ggtcacgcag catctgccca gggagtgtct   1200
tccagaaaac ctgggtgggt acgtcaaaat tgatctcgcc acttggaatt tccagttcct   1260
accccaggtg aacggccacc cagatccctt cgatgagatc atcctgttct ccctccctcc   1320
tgccttagac tgggactcag tacatgttcc aggtccccat gctatgacca tccaagagtt   1380
ggtggactat gttaatgcca ggcaaaagca aggaatctat gaggaatatg aagacattcg   1440
tcgtgagaac cctgttggca ctttccactg ttccatgtct ccaggaaacc tagagaaaaa   1500
ccgttatggg gatgtaccct gcctggacca aactagagtg aagctaacaa agcgaagtgg   1560
ccatactcag acagattaca tcaatgccag tttcatggat ggctacaagc agaagaatgc   1620
ttacattggc acacaaggtc ctttggagaa tacctatcgt gatttctggc tcatggtatg   1680
ggagcaaaaa gtcttggtga ttgtcatgac cacccgcttt gaggaaggcg gcaggagaaa   1740
gtgtggccag tactggcctt tagaaaaaga ctctcggatc cgatttggct tcctcacagt   1800
gaccaatcta ggcgtggaga acatgaatca ttataagaaa acaacgctag aaattcacaa   1860
cacagaggaa cggcagaaac gccaggtgac ccacttccag ttcttgagct ggccagacta   1920
tggtgtccct tcctcagcag cttccctcat tgacttcttg agagtggtca gaaaccagca   1980
gagtctggct gtgagcaaca tgggagcacg ctccaaaggg cagtgccctg agccacccat   2040
tgtggtccat tgcagtgcag gcattggcag gacaggtacc ttctgctcac tggacatctg   2100
cctggcacag ctggaggagc ttggcaccct taatgtgttc cagacggtgt cacgcatgag   2160
gacccagagg gccttcagca tccagacccc tgagcagtac tatttttgct acaaggccat   2220
cctggagttc gcagagaagg agggcatggt atcctctggc caaaacctgc tggccgtgga   2280
gagtcagtaa ctctcctacg aacctcctac ctgttggcca gccttcctta aactaccctg   2340
gacaccgctg agcctatagg ttgccatcag ttacgctgaa gccatggatc aacttctttc   2400
ttgtgtctcc cagcacacgt gtgcacgcaa ggcagccttt ccctttggct agataaatgt   2460
ggtgaaattg ccactagaaa gggccagtag caatgtgttc ttaattccta gcatctgcta   2520
tcaaactgtg ccttattaaa accaaattgt ggctattgat tttgctaggg tccccgaggg   2580
taagtgggga aggaacctcc ctcctccttt ctcccgccat tctttttctg aggtctcctg   2640
tctcccactc cttccctttc ctaggatttt atggggaggt ttgatgagca tttgcctttc   2700
tccccagaga gcttgaccaa gttacatatt ctagagatcg tcctgagtgc caagcacgtt   2760
tataagtagg gcgtgtattc cagtcctttc tgtcattctg tgtgtgtgtg tgtgtgcact   2820
tatgtgtatg ggtccatatg tacgtgtgta tataatatat attgtatgtg ataatatgat   2880
cgtattctat aaatacatat acacacgata ctcctttcca gaagttcctg ggctccgtg    2940
ttgcagttca ggactccttg cttcttggac cctactattt atcctggact agcttgggtt   3000
ggtgatcatg tctcctcttg tcaggctaca gagtggtgga agaggacaca cacacatctc   3060
ctccatgttc ctgccacagg gccccttcct taagtaatga cttatctcct tccagttgcc   3120
acctgttgga gccaagaatg tattagtttg tggtgacact gggttagctc agcatggatt   3180
tcccttatcc gatgattttt ctacatttac ttggccaatt tggggaacag acctccactg   3240
tgattccata ctctctcttt gctttcacta tcccagggat gggaggcgga gggtagagat   3300
```

-continued

```
gaactcactg agcagccaga gccaaatgca atcggtacga atcttagaag gaaggagggg   3360
gagcccaggt atgagaaaga aaaaaccact aagaaaatac ctccctggga ggatgagctg   3420
gggccctttt tcttttgctg gatggttcct ttatgcagct tggccctgtc taccgagatg   3480
cccatctctt cctgcctgct agcctgctag accctcaaac tgggtgggtt ctgtgtcaat   3540
aaaaagcttc accccctggc tgagtgaggt ggtcccctgc aatcactgtt tgtcccctac   3600
ccacccaacc tgtccctgcc tgctcccagc ccactcatcc ttatgtgcta gggataaatc   3660
aagagtcctc agcactccac attcccaaaa aatcccagga actcctaaac cttcccctgt   3720
gacagaagat gaggttggca gctgatcaga cctcaataat tttatactgt aataagctct   3780
ttgaatgtgt atattattat tttttacaat catttcattt tgtatttaat atcaatggac   3840
tgagtctgat tcagaaaata attgtaatgt tcatattcaa tatcttacag tgatacagtt   3900
ttgtatttac atataaatat accgacatga tcaaaaccaa aaaaaaaaaa aaaaaa       3956
```

```
<210> SEQ ID NO 79
<211> LENGTH: 3773
<212> TYPE: DNA
<213> ORGANISM: Homo sapiens

<400> SEQUENCE: 79
```

```
aggcgcacag gtaccatttt gaccgtaaac atcctgccga tttgaaccga ggatttgggc     60
ggcaggaaga gccgcggcgt aacggcagcc atcttgtttg tttgagtgaa tcggaaagga    120
ggcgccggct gtggcggcgg cgggagctgc tcggaagcta cacctcgcaa gggctccccc    180
ctttccccac cccctccccc gaccctttc  ccctccccgg gccacccagc ccgcccaact    240
cccagcggag agcaaggttt tcttctgttt tcatagccag ccagaacaat gttctacgca    300
cattttgttc tcagtaaaag agggcctctg gccaaaattt ggctagcggc ccattgggat    360
aagaagctaa ccaaagccca tgtgttcgag tgtaatttag agagcagcgt ggagagtatc    420
atctcaccaa aggtgaaaat ggcattacgg acatcaggac atctcttact gggagtagtt    480
cgaatctatc acaggaaagc caaatacctt cttgcagact gtaatgaagc attcattaag    540
ataaagatgg cttttcggcc aggtgtggtt gacctgcctg aggaaaatcg ggaagcagct    600
tataatgcca ttactttacc tgaagaattt catgactttg atcagccact gcctgactta    660
gatgacatcg atgtggccca gcagttcagc ttgaatcaga gtagagtgga agagataacc    720
atgagagaag aagttgggaa catcagtatt ttacaagaaa atgattttgg tgattttgga    780
atggatgatc gtgagataat gagagaaggc agtgcttttg aggatgacga catgttagta    840
agcactacta cttctaacct cctattagag tctgaacaga gcaccagcaa tctgaatgag    900
aaaattaacc atttagaata tgaagatcaa tataaggatg ataattttgg agaaggaaat    960
gatggtggaa tattagatga caaacttatt agtaataatg atggcggtat ctttgatgat   1020
ccccctgccc tctctgaggc aggggtgatg ttgccagagc agcctgcaca tgacgatatg   1080
gatgaggatg ataatgtatc aatgggtggg cctgatagtc ctgattcagt ggatcccgtt   1140
gaaccaatgc caaccatgac tgatcaaaca acacttgttc caaatgagga agaagcattt   1200
gcattggagc ctattgatat aactgttaaa gaaacaaaag ccaagaggaa gaggaagcta   1260
attgttgaca gtgtcaaaga gttggatagc aagacaatta gagcccaact tagtgattat   1320
tcagatattg ttactacttt ggatctggca ccgcccacca agaaattgat gatgtggaaa   1380
gagacaggag gagtagaaaa actgttttct ttacctgctc agcctttgtg gaataacaga   1440
ctactgaagc tctttacacg ctgtcttaca ccgcttgtac cagaagacct tagaaaaagg   1500
```

-continued

```
aggaaaggag gagaggcaga taatttggat gaattcctca aagaatttga aaatccagag   1560
gttcctagag aggaccagca acagcagcat cagcagcgtg atgttatcga tgagcccatt   1620
attgaagagc caagccgcct ccaggagtca gtgatggagg ccagcagaac aaacatagat   1680
gagtcagcta tgcctccacc accacctcag ggagttaagc gaaaagctgg acaaattgac   1740
ccagagcctg tgatgcctcc tcagcaggta gagcagatgg aaataccacc tgtagagctt   1800
cccccagaag aacctccaaa tatctgtcag ctaataccag agttagaact tctgccagaa   1860
aaagagaagg agaaagagaa ggaaaaagaa gatgatgaag aggaagagga tgaagatgca   1920
tcagggggcg atcaagatca ggaagaaaga agatggaaca aaaggactca gcagatgctt   1980
catggtcttc agcgtgctct tgctaaaact ggagctgaat ctatcagttt gcttgagtta   2040
tgtcgaaata cgaacagaaa acaagctgcc gcaaagttct acagcttctt ggttcttaaa   2100
aagcagcaag ctattgagct gacacaggaa gaaccgtaca gtgacatcat cgcaacacct   2160
ggaccaaggt tccatattat ataaggagct agaagcatta tagctagtgt ttgattcact   2220
agtgcttaca aattgccccc atgtgtaggg gacacagaac cctttgagaa aacttagatt   2280
tttgtctgta caaagtcttt gccttttttcc ttcttcattt ttttccagta cattaaattt   2340
gtcaatttca tctttgaggg aaactgatta gatgggttgt gtttgtgttc tgatggagaa   2400
aacagcaccc caaggactca gaagatgatt ttaacagttc agaacagatg tgtgcaatat   2460
tggtgcatgt aataatgttg agtggcagtc aaaagtcatg atttttatct tagttcttca   2520
ttactgcatt gaaaaggaaa acctgtctga gaaaatgcct gacagtttaa tttaaaacta   2580
tggtgtaagt ctttgacaag aaaaaaaaac aaacaaacac ttctttccat cagtaacact   2640
ggcaatcttc ctgttaacca ctctccttag ggatggtatc tgaaacaaca atggtcaccc   2700
tcttgagatt cgttttaagt gtaattccat aatgagcaga ggtgtacgcg aaattgtgtt   2760
atgactgata gccttcagct acaaaaagat aggactgacc tggtttaaag tgttctattt   2820
tgtaaatcat tccatttgag tctttctgat gaacttggct atactgaaat ctgttatttt   2880
agtgaggctc caaaatgagc aaagctaggc ctgattagag tagagtgact attaaaaaac   2940
ataactttct aggagctata aatcaaagtt ttaaaaagat gtttggatat atttgagtat   3000
tccgatcatg aaaacagaaa ttgccctgcc tactacaagg acagactgat gggaaattat   3060
gcacctggtc aacttagctt ttaagcagac gatgctgtaa aaactaacgg cttctctgat   3120
atttattgta agttttagta ctgatctcct tttccagtgc tgcacactcc tggtttggaa   3180
ctttaatagc gttgcaacga aatcctatat ccagtttcct gtaatttaat tgaagaaaaa   3240
tacatccaaa taaagacttt attattaaca gaccagatag catcagaaat catgtgactg   3300
ttatgattat cagaatgtct taacttttta gggcaaagtt aacactgaaa gttctagctt   3360
aagtgttgaa acttttgtgg gaaaaaaaaa tcacttttga aactcagact tcagtgtata   3420
cccaataatt taaaattatg tgaaatgttt taaatttgtg aactcgtaat tactgtttta   3480
atgattcagt ttcttcagag tggtaattgt ataaaattgc tattgcagct ttacattcaa   3540
tatgatgtgc ctgtaaacca aggagttttc cccgtttgta aaaagacatt gtagataatt   3600
gaatgtttga ttttagaaag gtcattagtt tcttgttaca cattttgtta gtctggtttt   3660
tgttgcttat cgggtttaat attgttcttg aaaatagttg atgctatgtt atgtataact   3720
tttctaataa aagttgtgtt ataagctgta aaaaaaaaaa aaaaaaaaaa aaa          3773
```

<210> SEQ ID NO 80

<211> LENGTH: 6414
<212> TYPE: DNA
<213> ORGANISM: Homo sapiens

<400> SEQUENCE: 80
gtgcgtgtgt ccctgtccgc gctgctgaaa cgggctcttc gagggatcgg cgtcacatga 60
ctccgcctgc ccctcgccag cgcgcagatc gccagtccct cagtttgccc ggcaccggag 120
gagggtcggg cggcatcttc cgggtactgg ggctctgcgg agcggagaag aggttccagc 180
ggggaatggt atatctggat tcaagaagcc gcggctcggc gccagatcct ggagtgtaga 240
tatttggggg gaggggagag ctagagggag cgagcgagcg agcgccagag agaggcagcg 300
cgcagcgcgc acggacgggg ggctgctgcg cggagaagat gtaagcgcgt ggggtctcgc 360
tggcctctga gcaccatgca gaaggggatc cggctgaatg atggccacgt cgcgtccctg 420
ggactgctgg cgcgcaagga cggcacgcgc aaaggctacc tgagcaagcg gagttcggac 480
aacacaaaat ggcaaaccaa gtggttcgcg ctgctgcaga acctgctctt ctacttcgag 540
agcgactcga gctcgcggcc ctcggggctt tacctgctgg agggctgcgt ctgcgaccgc 600
gcgccctccc ccaagccggc gctgtcggcc aaggagccgc tggagaaaca gcattacttc 660
acggtgaact tcagccatga gaaccagaaa gccttggagc tgaggacaga ggacgcaaaa 720
gattgtgacg aatgggtggc agccattgca catgccagct acaggaccct cgccacagag 780
catgaggcat taatgcagaa atacctgcac ctgctgcaga tcgtggagac agagaagacc 840
gtggccaagc agcttcggca gcagatcgag gatggggaga tcgagatcga gcggctgaag 900
gcagagatca catccctgct caaggacaat gagcgcatcc agtccaccca gactgtcgcc 960
cccaacgatg aagacagcga catcaagaaa attaagaagg tgcagagctt cctgcggggc 1020
tggctgtgcc ggcggaagtg gaagaccatc atccaggact acatccggtc accccatgct 1080
gacagcatgc gcaagaggaa ccaggtggtg ttcagcatgc tggaggctga ggctgagtac 1140
gtgcagcagc tgcacatcct tgtcaacaat ttcctgcgcc cgctgcggat ggccgccagc 1200
tccaagaagc ctcccatcac acacgacgac gtcagcagca tcttcctgaa cagcgaaacc 1260
atcatgtttt tacatcagat cttttaccaa ggcctgaagg cccgcatctc cagctggccc 1320
acgctggtcc tggctgacct atttgacatc ctgctgccca tgctcaacat ctaccaagag 1380
ttcgtccgca accaccagta cagcctgcag atcctggccc actgcaagca gaaccgtgac 1440
ttcgacaagc tgctgaagca ctacgaggcc aagcctgact gcgaggagag gacgctggag 1500
accttcctca cctaccccat gttccagatc cccaggtaca tcctgaccct ccatgagctc 1560
ctggcccaca cgcctcatga gcacgttgag cgcaacagcc tggactacgc caagtccaaa 1620
ctggaggagc tgtccagaat aatgcacgat gaagtaagtg agacggagaa catccggaaa 1680
aacctggcca tcgagcgcat gatcatcgaa ggctgtgaga tcctcctgga caccagccag 1740
acctttgtga gacaaggttc cctcattcag gtgcccatgt ctgaaaaggg caagatcacc 1800
agggggcgcc tggggtctct ctccctaaag aaagagggcg agcgacagtg cttcctgttt 1860
tctaagcatc tgattatctg taccagaggc tctggaggga agcttcactt gaccaagaat 1920
ggagtcatat ccctcattga ctgcacttta ttggaggagc cagaaagcac ggaggaggaa 1980
gccaaaggat ccggccaaga catagatcac ttggatttta aaatcggggt ggagccaaag 2040
gattccccgc cctttacagt catcctagtg gcctcgtcca gacaggagaa ggcagcgtgg 2100
accagtgaca tcagccagtg tgtggataac atccgatgca atgggctcat gatgaacgca 2160
tttgaagaaa attccaaggt cactgtgccg cagatgatca agaggaccag ggaggggacc 2220

-continued

```
agggaagcag aaatgagcag gtccgacgcc tccttatatt gtgatgatgt tgacattcgc   2280
ttcagcaaaa ccatgaactc ctgcaaagtg ctgcagatcc gctacgccag tgtggagcgg   2340
ctgctggaga ggctgacgga cctgcgcttc ctgagcatcg acttcctcaa caccttcctg   2400
cactcctacc gcgtcttcac caccgccatc gtggtcctgg acaagctcat taccatctac   2460
aagaagccta tcagtgccat tcctgccagg tggctgaggt cgctggagct cctgtttgcc   2520
agtggccaga acaataagct cctgtacggt gaaccccccca agtccccgcg cgccacccgc   2580
aagttctcct cgccgccacc tctgtccatc accaagacat cgtcaccgag ccgccggcgg   2640
aagctctccc tgaacatccc catcatcact ggcggcaagg ccctggacct ggccgccctc   2700
agctgcaact ccaatggcta caccagcatg tactcggcca tgtcaccctt cagcaaggcc   2760
acgctggaca ccagcaagct ctatgtgtcc agcagcttca ccaacaagat tccagatgag   2820
ggcgatacga cccctgagaa gcccgaagac ccttcagcgc tcagcaagca gagctcagaa   2880
gtctccatga gagaggagtc agatattgat caaaaccaga gtgatgatgg tgatactgaa   2940
acatcaccaa ctaaatctcc aacaacaccc aaatcagtca aaaacaaaaa ttcttcagag   3000
ttcccactct tttcctataa caatggagtc gtcatgacct cctgtcgtga actggacaat   3060
aaccgcagtg ccttgtcggc cgcctctgcc tttgccatag caaccgccgg ggccaacgag   3120
ggcaccccaa acaaggagaa gtaccggagg atgtccttag ccagtgcagg gtttccccca   3180
gaccagagga atggagacaa ggagtttgtg atccgcagag cagccaccaa tcgtgtcttg   3240
aacgtgctcc gccactgggt gtccaagcac tctcaggact ttgagaccaa cgatgagctc   3300
aaatgcaagg tgatcggctt cctggaagaa gtcatgcacg acccggagct cctgacccag   3360
gagcggaagg ctgcagccaa catcatcagg actctgaccc aggaggaccc aggtgacaac   3420
cagatcacgc tggaggagat cacgcagatg gctgaaggcg tgaaggctga gccctttgaa   3480
aaccactcag ccctggagat cgcggagcag ctgaccctgc tagatcacct cgtcttcaag   3540
aagattcctt atgaggagtt cttcggacaa ggatggatga aactggaaaa gaatgaaagg   3600
acccccttata tcatgaaaac cactaagcac ttcaatgaca tcagtaactt gattgcttca   3660
gaaatcatcc gcaatgagga catcaacgcc agggtgagcg ccatcgagaa gtgggtggcc   3720
gtagctgaca tatgccgctg cctccacaac tacaatgccg tactggagat cacctcgtcc   3780
atgaaccgca gtgcaatctt ccggctcaaa aagacgtggc tcaaagtctc taagcagact   3840
aaagctttga ttgataagct ccaaaagctt gtgtcatctg agggcagatt taagaatctc   3900
agagaagctc tgaaaaattg tgacccaccc tgtgtccctt acctggggat gtacctcacc   3960
gacctggcct tcatcgagga ggggacgccc aattacacgg aagacggcct ggtcaacttc   4020
tccaagatga ggatgatatc ccatattatc cgagagattc gccagtttca acaaactgcc   4080
tacaaaatag agcaccaagc aaaggtaacg caatatttac tggaccaatc ttttgtaatg   4140
gatgaagaaa gcctctacga gtcttctctc cgaatagaac caaaactccc cacctgaagc   4200
tgagcccagc ccagacccag ctgctcccgg ggacatgtgc tagatgatac tgtacatatt   4260
cgtttggttt cactggattt tcttcttcag tatgtgcttc tccaagaata caaatcgtcc   4320
ttgttcttag attcctgtag aaccggaata tgaatttctg caccgtttca gacttcgccc   4380
acccatccct cccctcgtct cctgcagtgc ctgtttcttt taaacagctg tactcttggt   4440
ccctcttccc tagactcctc actcttctca gaggggaaac agcacccttg catacaagaa   4500
tcttagactc cagtcctgct tccgtccctc cccagcccag gctcctgggt tgaggtggcc   4560
```

acccaggcat cctcccagca tgttccatgt agttgttata actgggtggg gggtgggggg 4620
cggcgggagg gggaaaccat accctgaagt ccagtcattg acaaatcttc ccgctgatgg 4680
tgatgtcaat ttccaaagca gcttctccag ccaaaatcgc aggtctcaaa actccccatg 4740
tgtctcccag taacctggac ggaagggagt cctctctgct cagaaccaca cccctcgtac 4800
caatgctgcc atctcgttca ggccccacgt cgctccttgc tctaggatta acaccagata 4860
gcatgaatag cagtctcaat acaactggat gaggccctag acttcccgag gaaatggagt 4920
cacaaacacc aagccacgtc gactcttgcc gaccactggc ccagcatcca ctgaaagtcg 4980
ggaacacaaa aatgtcactt ttcctcttta agctgcctaa cggtcactac aagcttacat 5040
tgagatgctc taagtctgta taccttgtga taattagtac cacactgtag aattaggaaa 5100
tcaataacca agtgttttta ttgcatatac tgtagtcctg tctaaatgcc ttctagcagg 5160
aatatagtaa tgtagtgctt attctgtgaa tattaccatg tattttttac actgtacagt 5220
atagaaaaca caggttaact ccgaagtggc aggcatgctc cactacaaca gacagacaac 5280
ttttgctgta agcaatacct agtggtatga gaattctatt tcaagtccta aaatatttca 5340
acttacagct tgtttggaaa aaaatttcca tttttgtaaa aatatatgtt tcctgattac 5400
ctcttgctaa taaatctatt ctatctcagg gtgaacagcg agttttgatg ggtttcattc 5460
gttcagtcaa ggaatatttg atgagcactt gctccttacc cagcccagcc tgggaccgga 5520
gatccagagt gtcaaggaca ccatacctgc tttttaggca ccaacagttt ggtggggaag 5580
actgtttcag ttgcctattg caccaagaac aagccactcc aaaacataat ggcttaaaac 5640
catttttgtt acctttcaca gttctatggg ttgactgggt ccagctgtca gttcttattt 5700
ggagtctctc atgaagtttc agtcactcag caactgggac tggagtcatc tgaaggctca 5760
actggaccgg gtggtgctct agttggtgca ccaagatggc gctgtcacat ggctggatgt 5820
tgatgtctgc tgggctgcac tggggctgtt catgggagca tccacacgtg gcctctctgt 5880
gtggcttggg ctcctcacag tccggaagct gggttccaag agcgactgtt ccagcagcct 5940
caggcagaag ctacaaggct gcccagatgc catcctgccc agatgtgtcc tcactgtcac 6000
ccaggaaggg aagccccgga acaccaccct cagtcacagg catggggccc actgcaaggc 6060
acaacccact ccagagctcc caaggccgcc tcccctggga cctgcagcca gctggctcca 6120
taactgcttt tccgtttcct ccaggcattt tcatcctagc cctactttgt gctgggatct 6180
gagggggata gcaagcggag aaagaaggga tctagaggga gaagattcta gatccttctt 6240
ttgactgcca gctgattttg attgccagct ttacctgctt catgagctca gccaagtcac 6300
ttaacctctc agagcttcac tgttctcatc tgaaaaatgg ggatgaaaat ggtatctcat 6360
tacagagtag aattaaatga attattataa ttaaaaaaaa aaaaaaaaaa aaaa 6414

<210> SEQ ID NO 81
<211> LENGTH: 1554
<212> TYPE: DNA
<213> ORGANISM: Homo sapiens

<400> SEQUENCE: 81
ggggaggggg cagtgtcctc cgagccagga caggcatgtt gttgggactg gcggccatgg 60
agctgaaggt gtgggtggat ggcatccagc gtgtggtctg tggggtctca gagcagacca 120
cctgccagga agtggtcatc gcactagccc aagcaatagg ccagactggc cgctttgtgc 180
ttgtgcagcg gcttcgggag aaggagcggc agttgctgcc acaagagtgt ccagtgggcg 240
cccaggccac ctgcggacag tttgccagcg atgtccagtt tgtcctgagg cgcacagggc 300

```
ccagcctagc tgggaggccc tcctcagaca gctgtccacc cccggaacgc tgcctaattc     360
gtgccagcct ccctgtaaag ccacgggctg cgctgggctg tgagccccgc aaaacactga     420
cccccgagcc agcccccagc ctctcacgcc ctgggcctgc ggcccctgtg acacccacac     480
caggctgctg cacagacctg cggggcctgg agctcagggt gcagaggaat gctgaggagc     540
tgggccatga ggccttctgg gagcaagagc tgcgccggga gcaggcccgg gagcgagagg     600
gacaggcacg cctgcaggca ctaagtgcgg ccactgctga gcatgccgcc cggctgcagg     660
ccctggacgc tcaggcccgt gccctggagg ctgagctgca gctggcagcg gaggcccctg     720
ggcccccctc acctatggca tctgccactg agcgcctgca ccaggacctg gctgttcagg     780
agcggcagag tgcggaggtg cagggcagcc tggctctggt gagccgggcc ctggaggcag     840
cagagcgagc cttgcaggct caggctcagg agctggagga gctgaaccga gagctccgtc     900
agtgcaacct gcagcagttc atccagcaga ccggggctgc gctgccaccg cccccacggc     960
ctgacagggg ccctcctggc actcagggcc ctctgcctcc agccagagag gagtccctcc    1020
tgggcgctcc ctctgagtcc catgctggtg cccagcctag gccccgaggt ggcccccatg    1080
acgcagaact cctggaggta gcagcagctc ctgccccaga gtggtgtcct ctggcagccc    1140
agccccaggc tctgtgacag cctagtgagg gctgcaagac catcctgccc ggaccacaga    1200
aggagagttg gcggtcacag agggctcctc tgccaggcag tgggaagccc tgggtttggc    1260
ctcaggagct gggggtgcag tgggggactg ccctagtcct tgccaggtcg ccagcaccct    1320
ggagaagcat ggggcgtagc cagctcggaa cttgccaggc cccaaaggcc acgactgcct    1380
gttggggaca ggagatgcat ggacagtgtg ctcaagctgt gggcatgtgc ttgcctgcgg    1440
gagaggtcct tcactgtgtg tacacagcaa gagcatgtgt gtgccacttc ccctacccca    1500
acgtgaaaac ctcaataaac tgcccgaagc agcttgaaaa aaaaaaaaaa aaaa          1554
```

<210> SEQ ID NO 82
<211> LENGTH: 4751
<212> TYPE: DNA
<213> ORGANISM: Homo sapiens

<400> SEQUENCE: 82

```
agagccaccg cggagcgcgc gcggggttgg ttgccgcgag cgtgggggag cgtggaccgc      60
ggcgctgctc agcggtgggg ctgccttccc ccggccctcc tccctggtcc ctggcgaggg     120
cactggcggc ggcggggccg gggtccgcaa ggccggagaa ggccgccggg cccgggcatg     180
gtggtctggg gcaacgcgga agaagctcca ccatgaggcg aggtggatgg aggaagcgag     240
ctgaaaatga tggctgggaa acatggggtg ggtatatggc tgccaaggtc cagaaattgg     300
aggaacagtt tcgatcagat gctgctatgc agaaggatgg gacttcatct acaattttta     360
gtggagttgc catctatgtt aatggataca cagatccttc cgctgaggaa ttgagaaaac     420
taatgatgtt gcatggaggt caataccatg tatattattc cagatctaaa acaacacata     480
ttattgccac aaatcttccc aatgccaaaa ttaaagaatt aaagggggaa aaagtaattc     540
gaccagaatg gattgtggaa agcatcaaag ctggacgact cctctcctac attccatatc     600
agctgtacac caagcagtcc agtgtgcaga aaggtctcag ctttaatcct gtatgcagac     660
ctgaggatcc tctgccaggt ccaagcaata tagccaaaca gctcaacaac agggtaaatc     720
acatcgttaa gaagattgaa acggaaaatg aagtcaaagt caatggcatg aacagttgga     780
atgaagaaga tgaaaataat gattttagtt ttgtggatct ggagcagacc tctccgggaa     840
```

-continued

```
ggaaacagaa tggaattccg catcccagag ggagcactgc catttttaat ggacacactc    900
ctagctctaa tggtgcctta aagacacagg attgcttggt gcccatggtc aacagtgttg    960
ccagcaggct ttctccagcc ttttcccagg aggaggataa ggctgagaag agcagcactg   1020
atttcagaga ctgcactctg cagcagttgc agcaaagcac cagaaacaca gatgctttgc   1080
ggaatccaca cagaactaat tctttctcat tatcaccttt gcacagtaac actaaaatca   1140
atggtgctca ccactccact gttcaggggc cttcaagcac aaaaagcact tcttcagtat   1200
ctacgtttag caaggcagca ccttcagtgc catccaaacc ttcagactgc aattttattt   1260
caaacttcta ttctcattca agactgcatc acatatcaat gtggaagtgt gaattgactg   1320
agtttgtcaa taccctacaa agacaaagta atggtatctt tccaggaagg gaaaagttaa   1380
aaaaaatgaa aacaggcagg tctgcacttg ttgtaactga cacaggagat atgtcagtat   1440
tgaattctcc cagacatcag agctgtataa tgcatgttga tatggattgc ttctttgtat   1500
cagtgggtat acgaaataga ccagatctca aaggaaaacc agtggctgtt acaagtaaca   1560
gaggcacagg aagggcacct ttacgtcctg gcgctaaccc ccagctggag tggcagtatt   1620
accagaataa aatcctgaaa ggcaaagcag cagatatacc agattcatca ttgtgggaga   1680
atccagattc tgcgcaagca aatggaattg attctgtttt gtcaagggct gaaattgcat   1740
cttgtagtta tgaggccagg caacttggca ttaagaacgg aatgtttttt gggcatgcta   1800
aacaactatg tcctaatctt caagctgttc catacgattt tcatgcatat aaggaagtcg   1860
cacaaacatt gtatgaaaca ttggcaagct acactcataa cattgaagct gtcagttgtg   1920
atgaagcgct ggtagacatt accgaaatcc ttgcagagac caaacttact cctgatgaat   1980
ttgcaaatgc tgttcgtatg gaaatcaaag accagacgaa atgtgctgcc tctgttggaa   2040
ttggttctaa tattctcctg gctagaatgg caactagaaa agcaaaacca gatgggcagt   2100
accacctaaa accagaagaa gtagatgatt ttatcagagg ccagctagtg accaatctac   2160
caggagttgg acattcaatg gaatctaagt tggcatcttt gggaattaaa acttgtggag   2220
acttgcagta tatgaccatg gcaaaactcc aaaaagaatt tggtcccaaa acaggtcaga   2280
tgctttatag gttctgccgt ggcttggatg atagaccagt tcgaactgaa aaggaaagaa   2340
aatctgtttc agctgagatc aactatggaa taaggtttac tcagccaaaa gaggcagaag   2400
cttttcttct gagtctttca gaagaaattc aaagaagact agaagccact ggcatgaagg   2460
gtaaacgtct aactctcaaa atcatggtac gaaagcctgg ggctcctgta gaaactgcaa   2520
aatttggagg ccatggaatt tgtgataaca ttgccaggac tgtaactctt gaccaggcaa   2580
cagataatgc aaaaataatt ggaaaggcga tgctaaacat gtttcataca atgaaactaa   2640
atatatcaga tatgagaggg gttgggattc acgtgaatca gttggttcca actaatctga   2700
acccttccac atgtcccagt cgcccatcag ttcagtcaag ccactttcct agtgggtcat   2760
actctgtccg tgatgtcttc caagttcaga aagctaagaa atccaccgaa gaggagcaca   2820
aagaagtatt tcgggctgct gtggatctgg aaatatcatc tgcttctaga acttgcactt   2880
tcttgccacc ttttcctgca catctgccga ccagtcctga tactaacaag gctgagtctt   2940
cagggaaatg gaatggtcta catactcctg tcagtgtgca gtcgagactt aacctgagta   3000
tagaggtccc gtcaccttcc cagctggatc agtctgtttt agaagcactt ccacctgatc   3060
tccgggaaca agtagagcaa gtctgtgctg tccagcaagc agagtcacat ggcgacaaaa   3120
agaaagaacc agtaaatggc tgtaatacag gaattttgcc acaaccagtt gggacagtct   3180
tgttgcaaat accagaacct caagaatcga acagtgacgc aggaataaat ttaatagccc   3240
```

ttccagcatt ttcacaggtg gaccctgagg tatttgctgc ccttcctgct gaacttcaga 3300
gggagctgaa agcagcgtat gatcaaagac aaaggcaggg cgagaacagc actcaccagc 3360
agtcagccag cgcatctgtg ccaaagaatc ctttacttca tctaaaggca gcagtgaaag 3420
aaaagaaaag aaacaagaag aaaaaaacca ttggttcacc aaaaaggatt cagagtcctt 3480
tgaataacaa gctgcttaac agtcctgcaa aaactctgcc aggggcctgt ggcagtcccc 3540
agaagttaat tgatgggttt ctaaaacatg aaggacctcc tgcagagaaa cccctggaag 3600
aactctctgc ttctacttca ggtgtgccag gcctttctag tttgcagtct gacccagctg 3660
gctgtgtgag acctccagca cccaatctag ctggagctgt tgaattcaat gatgtgaaga 3720
ccttgctcag agaatggata actacaattt cagatccaat ggaagaagac attctccaag 3780
ttgtgaaata ctgtactgat ctaatagaag aaaaagattt ggaaaaactg gatctagtta 3840
taaaatacat gaaaaggctg atgcagcaat cggtggaatc ggtttggaat atggcatttg 3900
actttattct tgacaatgtc caggtggttt tacaacaaac ttatggaagc acattaaaag 3960
ttacataaat attaccagag agcctgatgc tctctgatag ctgtgccata agtgcttgtg 4020
aggtatttgc aaagtgcatg atagtaatgc tcggagtttt tataatttta aatttctttt 4080
aaagcaagtg ttttgtacat ttcttttcaa aaagtgccaa atttgtcagt attgcatgta 4140
aataattgtg ttaattattt tactgtagca tagattctat ttacaaaatg tttgtttata 4200
aagttttatg gatttttaca gtgaagtgtt tacagttgtt taataaagaa ctgtatgtat 4260
attttgtaca ggctcctttt tgtgaatcct taaaaactca actctaggaa gcaactactg 4320
tttattatac taaaaggctg aaaaacctcc aggccagact gctaagctct gaaattcctg 4380
agaggtctca gaccgggatt ctacttgttc caagaaaggg taaagcttct aaaccatctt 4440
attcttgtct ccaagcatga acacaggagc atgttaagaa aatctttact acttcttcca 4500
tgcggagaaa tctacatatt ttgaattaga aacaccctca cacccacttg aagatttttt 4560
tcctgggaac attatgtccc gtagatcaga ggtggtgttg tctttttgct tctactggcc 4620
attgagaaac tttgatgata aaaaagaacg gtatagattt ttcaaacgta tataaaatat 4680
ttttatgtta tatgttatgc cataacttta aaataaaaat agtttaaaat tctaaaaaaa 4740
aaaaaaaaaa a 4751

<210> SEQ ID NO 83
<211> LENGTH: 2667
<212> TYPE: DNA
<213> ORGANISM: Homo sapiens

<400> SEQUENCE: 83
ctctccgccc cgccccggct cgggcggccg gaggacccgg agctaaggcg cccgaacccg 60
cggcggcggt ggggacgatg tggttctttg cccgggaccc ggtccgggac tttccgttcg 120
agctcatccc ggagccccca gagggcggcc tgcccgggcc ctgggccctg caccgcggcc 180
gcaagaaggc cacaggcagc cccgtgtcca tcttcgtcta tgatgtgaag cctggcgcgg 240
aagagcagac ccaggtggcc aaagctgcct tcaagcgctt caaaactcta cggcacccca 300
acatcctggc ttacatcgat ggactggaga cagaaaaatg cctccacgtc gtgacagagg 360
ctgtgacccc gttgggaata tacctcaagg cgagagtgga ggctggtggc ctgaaggagc 420
tggagatctc ctgggggcta caccagatcg tgaaagccct cagcttcctg gtcaacgact 480
gcagcctcat ccacaacaat gtctgcatgg ccgccgtgtt cgtggaccga gctggcgagt 540

```
ggaagcttgg gggcctggac tacatgtatt cggcccaggg caacggtggg ggacctcccc    600
gcaaggggat ccccgagctt gagcagtatg accccccgga gttggctgac agcagtggca    660
gagtggtcag agagaagtgg tcagcagaca tgtggcgctt gggctgcctc atttgggaag    720
tcttcaatgg gcccctacct cgggcagcag ccctacgcaa ccctgggaag atccccaaaa    780
cgctggtgcc ccattactgt gagctggtgg gagcaaaccc caaggtgcgt cccaacccag    840
cccgcttcct gcagaactgc cgggcacctg gtggcttcat gagcaaccgc tttgtagaaa    900
ccaacctctt cctggaggag attcagatca aagagccagc cgagaagcaa aaattcttcc    960
aggagctgag caagagcctg gacgcattcc ctgaggattt ctgtcggcac aaggtgctgc   1020
cccagctgct gaccgccttc gagttcggca atgctggggc cgttgtcctc acgcccctct   1080
tcaaggtggg caagttcctg agcgctgagg agtatcagca gaagatcatc cctgtggtgg   1140
tcaagatgtt ctcatccact gaccgggcca tgcgcatccg cctcctgcag cagatggagc   1200
agttcatcca gtaccttgac gagccaacag tcaacaccca gatcttcccc cacgtcgtac   1260
atggcttcct ggacaccaac cctgccatcc gggagcagac ggtcaagtcc atgctgctcc   1320
tggccccaaa gctgaacgag gccaacctca atgtggagct gatgaagcac tttgcacggc   1380
tacaggccaa ggatgaacag ggccccatcc gctgcaacac cacagtctgc ctgggcaaaa   1440
tcggctccta cctcagtgct agcaccagac acagggtcct tacctctgcc ttcagccgag   1500
ccactaggga cccgtttgca ccgtcccggg ttgcgggtgt cctgggcttt gctgccaccc   1560
acaacctcta ctcaatgaac gactgtgccc agaagatcct gcctgtgctc tgcggtctca   1620
ctgtagatcc tgagaaatcc gtgcgagacc aggccttcaa ggccattcgg agcttcctgt   1680
ccaaattgga gtctgtgtcg gaggacccga cccagctgga ggaagtggag aaggatgtcc   1740
atgcagcctc cagccctggc atgggaggag ccgcagctag ctgggcaggc tgggccgtga   1800
ccggggtctc ctcactcacc tccaagctga tccgttcgca cccaaccact gccccaacag   1860
aaaccaacat tccccaaaga cccacgcctg aaggagttcc tgccccagcc cccacccctg   1920
ttcctgccac ccctacaacc tcaggccact gggagacgca ggaggaggac aaggacacag   1980
cagaggacag cagcactgct gacagatggg acgacgaaga ctggggcagc ctggagcagg   2040
aggccgagtc tgtgctggcc cagcaggacg actggagcac cgggggccaa gtgagccgtg   2100
ctagtcaggt cagcaactcc gaccacaaat cctccaaatc ccccagagtcc gactggagca   2160
gctgggaagc tgagggctcc tgggaacagg gctggcagga gccaagctcc caggagccac   2220
ctcctgacgg tacacggctg gccagcgagt ataactgggg tggcccagag tccagcgaca   2280
agggcgaccc cttcgctacc ctgtctgcac gtcccagcac ccagccgagg ccagactctt   2340
ggggtgagga caactgggag ggcctcgaga ctgacagtcg acaggtcaag gctgagctgg   2400
cccggaagaa gcgcgaggag cggcggcggg agatggaggc caaacgcgcc gagaggaagg   2460
tggccaaggg ccccatgaag ctgggagccc ggaagctgga ctgaaccgtg gcggtggccc   2520
ttcccggctg cggagagccc gccccacaga tgtatttatt gtacaaacca tgtgagcccg   2580
gccggcccag ccaggccatc tcacgtgtac ataatcagag ccacaataaa ttctatttca   2640
caccccttga aaaaaaaaaa aaaaaaa                                       2667
```

<210> SEQ ID NO 84
<211> LENGTH: 2615
<212> TYPE: DNA
<213> ORGANISM: Homo sapiens

<400> SEQUENCE: 84

```
actcgccgca gcctgcgcgc cttctccagt ccgcggtgcc atggcccccg cccgtctgtt     60
cgcgctgctg ctgttcttcg taggcggagt cgccgagtcg atccgagaga ctgaggtcat    120
cgacccccag gacctcctag aaggccgata cttctccgga gccctaccag acgatgagga    180
tgtagtgggg cccgggcagg aatctgatga ctttgagctg tctggctctg gagatctgga    240
tgacttggaa gactccatga tcggccctga agttgtccat cccttggtgc ctctagataa    300
ccatatccct gagagggcag ggtctgggag ccaagtcccc accgaaccca agaaactaga    360
ggagaatgag gttatcccca agagaatctc acccgttgaa gagagtgagg atgtgtccaa    420
caaggtgtca atgtccagca ctgtgcaggg cagcaacatc tttgagagaa cggaggtcct    480
ggcagctctg attgtgggtg gcatcgtggg catcctcttt gccgtcttcc tgatcctact    540
gctcatgtac cgtatgaaga agaaggatga aggcagctat gacctgggca agaaacccat    600
ctacaagaaa gcccccacca atgagttcta cgcgtgaagc ttgcttgtgg gcactggctt    660
ggactttagc ggggagggaa gccaggggat tttgaagggt ggacattagg gtagggtgag    720
gtcaacctaa tactgacttg tcagtatctc cagctctgat acctttgaa gtgttcagaa    780
gagacattgt cttctactgt tctgccaggt tcttcttgag ctttgggcct cagttgccct    840
ggcagaaaaa tggattcaac ttggcctttc tgaaggcaag actgggattg gatcacttct    900
taaacttcca gttaagaatc taggtccgcc ctcaagccca tactgaccat gcctcatcca    960
gagctcctct gaagccaggg ggctaacgga tgttgtgtgg agtcctggct ggaggtcctc   1020
ccccagtggc cttcctccct tcctttcaca gccggtctct ctgccaggaa atgggggaag   1080
gaactagaac cacctgcacc ttgagatgtt tctgtaaatg ggtacttgtg atcacactac   1140
gggaatctct gtggtatata cctggggcca ttctaggctc tttcaagtga cttttggaaa   1200
tcaacctttt ttatttgggg gggaggatgg ggaaaagagc tgagagttta tgctgaaatg   1260
gatttataga atatttgtaa atctattttt agtgtttgtt cgttttttta actgttcatt   1320
cctttgtgca gagtgtatat ctctgcctgg gcaagagtgt ggaggtgccg aggtgtcttc   1380
attctctcgc acatttccac agcacctgct aagtttgtat ttaatggttt ttgtttttgt   1440
ttttgtttgt ttcttgaaaa tgagagaaga gccggagaga tgatttttat taattttttt   1500
ttttttttt tttttttact atttatagct ttagataggg cctcccttcc cctcttcttt   1560
ctttgttctc tttcattaaa ccccttcccc agtttttttt ttatacttta aaccccgctc   1620
ctcatggcct tggccctttc tgaagctgct tcctcttata aaatagcttt tgccgaaaca   1680
tagttttttt ttagcagatc ccaaaatata atgaagggga tggtgggata tttgtgtctg   1740
tgttcttata atatattatt attcttcctt ggttctagaa aaatagataa atatattttt   1800
ttcaggaaat agtgtggtgt ttccagtttg atgttgctgg gtggttgagt gagtgaattt   1860
tcatgtggct gggtgggttt ttgccttttt ctcttgccct gttcctggtg ccttctgatg   1920
gggctggaat agttgaggtg gatggttcta ccctttctgc cttctgtttg ggacccagct   1980
ggtgttcttt ggtttgcttt cttcaggctc tagggctgtg ctatccaata cagtaaccac   2040
atgcggctgt ttaaagttaa gccaattaaa atcacataag attaaaaatt ccttcctcag   2100
ttgcactaac cacgtttcta gaggcgtcac tgtatgtagt tcatggctac tgtactgaca   2160
gcgagagcat gtccatctgt tggacagcac tattctagag aactaaactg gcttaacgag   2220
tcacagcctc agctgtgctg ggacgaccct tgtctccctg ggtagggggg ggggaatggg   2280
ggagggctga tgaggcccca gctggggcct gttgtctggg accctccctc tcctgagagg   2340
```

```
ggaggcctgg tggcttagcc tgggcaggtc gtgtctcctc ctgaccccag tggctgcggt   2400

gaggggaacc accctccctt gctgcaccag tggccattag ctcccgtcac cactgcaacc   2460

cagggtccca gctggctggg tcctcttctg cccccagtgc ccttcccctt gggctgtgtt   2520

ggagtgagca cctcctctgt aggcacctct cacactgttg tctgttactg atttttttttg   2580

ataaaaagat aataaaacct ggtactttct aaaaa                              2615
```

<210> SEQ ID NO 85
<211> LENGTH: 4766
<212> TYPE: DNA
<213> ORGANISM: Homo sapiens

<400> SEQUENCE: 85

```
ttttttttt ttttttttt tttttcgcaa tttccactcg cggggagcag gaaacccggc     60

gcagccgggc gcattgggcc gcgatgcaac agcagcagca ggagtcgccc cggggcagca    120

gcggcagcag cagcagaggc agcagcgggc ggcgctgagc cgccgccgcc gccactgagg    180

aagaagccgg cccagccgcc gccgcgtccg gaccctcgcg cctggatccc agcgccccga    240

tcccggcgcc ccaaccccca cgcccgcctc cgccaacttt cacgctgcct cggcggcccg    300

gcccggctcg acgccaatgg tggaggccat agtggagttt gactaccagg cccagcacga    360

tgatgagctg acgatcagcg tgggtgaaat catcaccaac atcaggaagg aggatggagg    420

ctggtgggag ggacagatca acggcaggag aggtttgttc cctgacaact ttgtaagaga    480

aataaagaaa gagatgaaga aagaccctct caccaacaaa gctccagaaa agcccctgca    540

cgaagtgccc agtggaaact ctttgctgtc ttctgaaacg attttaagaa ccaataagag    600

aggcgagcga cggaggcgcc ggtgccaggt ggcattcagc tacctgcccc agaatgacga    660

tgaacttgag ctgaaagttg gcgacatcat agaggtggta ggagaggtag aggaaggatg    720

gtgggaaggt gttctcaacg ggaagactgg aatgtttcct tccaacttca tcaaggagct    780

gtcaggggag tcggatgagc ttggcatttc ccaggatgag cagctatcca agtcaagttt    840

aagggaaacc acaggctccg agagtgatgg gggtgactca agcagcacca agtctgaagg    900

tgccaacggg acagtggcaa ctgcagcaat ccagcccaag aaagttaagg gagtgggctt    960

tggagacatt ttcaaagaca agccaatcaa actaagacca aggtcaattg aagtagaaaa   1020

tgactttctg ccggtagaaa agactattgg gaagaagtta cctgcaacta cagcaactcc   1080

agactcatca aaaacagaaa tggacagcag gacaaagagc aaggattact gcaaagtaat   1140

atttccatat gaggcacaga atgatgatga attgacaatc aaagaaggag atatagtcac   1200

tctcatcaat aaggactgca tcgacgtagg ctggtgggaa ggagagctga acggcagacg   1260

aggcgtgttc cccgataact tcgtgaagtt acttccaccg gactttgaaa aggaagggaa   1320

tagacccaag aagccaccgc ctccatccgc tcctgtcatc aaacaagggg caggcaccac   1380

tgagagaaaa catgaaatta aaaagatacc tcctgaaaga ccagaaatgc ttccaaacag   1440

aacagaagaa aaagaaagac cagagagaga gccaaaactg gatttacaga agccctccgt   1500

tcctgccata ccgccaaaaa agcctcggcc acctaagacc aattctctca gcagacctgg   1560

cgcactgccc ccgagaaggc cggagagacc ggtgggtccg ctgacacaca ccaggggtga   1620

cagtccaaag attgacttgg ccggcagttc gctatctggc atcctggaca aagatctctc   1680

ggaccgcagc aatgacattg acttagaagg ttttgactcc gtggtatcat ctactgagaa   1740

actcagtcat ccgaccacaa gcagaccaaa agctacaggg aggcggcctc cgtcccagtc   1800

cctcacatct tcatcccttt caagccctga tatcttcgac tccccaagtc ccgaagagga   1860
```

-continued

```
taaggaggaa cacatttcac ttgcgcacag aggagtggac gcgtcaaaga aaacttccaa   1920
gactgttacc atatcccaag tgtctgacaa caaagcatcc ctgccgccca agccggggac   1980
catggcagca ggtggcggtg ggccagcccc tctgtcctca gcggcgccct ccccccctgtc   2040
atcctctttg ggaacagctg gacacagagc caactccccg tctctgttcg gcacggaagg   2100
aaaaccaaag atggagcctg cggccagcag ccaggcggcc gtggaggagc taaggacaca   2160
ggtccgcgag ctgaggagca tcatcgagac catgaaggac cagcagaaac gagagattaa   2220
acagttattg tctgagttgg atgaagagaa gaaaatccgg cttcggttgc agatggaagt   2280
gaacgacata aagaaagctc tacaatcaaa atgaatactt gatcaatgaa atgtcacatt   2340
attcatcctg agtccgagac tcaaattttc tgccccagcc aaaataatct tgtgccaaaa   2400
gattaaaggt ttgcctcaaa atgtccctgt ttgaaagatt agcacaaaag tcttgatagc   2460
acaacacaaa ttccatccaa gaggagaatc ttccccaggg tttagtcctg gggctggcac   2520
tcgttgtgac ttacacagag caaaattgtg ctaaaggctt ttctactctg agatctcaat   2580
gcgaaatgaa aactcaggca gtttagtcca tagtggtact attttgatga tattttccat   2640
taataaaatg taatttcaga ttattcgttt acaagcttta taattttatg attttttaat   2700
cgtgttttgt cacagacttc cctagtgttt gtactacacg tagtcagaag cgagtgtcct   2760
tttcttttgc ttcaggctaa gagctgcctc gctctttgtc cccccattag gattctatta   2820
catatgcaat tgtaggttca acctgtccct ttccctgcca gcaaacccca ccaccctaag   2880
agaaatttta gcttatatat gacggtatat ttacaaaaag agaaagagaa aatctggtat   2940
ttgcaatgat ctgtgccttc tttttaccac cctcttgatt ggagcttttg tgatgcagct   3000
accatgattc aaaaaaatta aaaattaaaa aaaaaaaatc tgccacttat ccaagtccac   3060
tagaggccac tgtcttcaaa gcttctctca ccctagccaa aggtcctaag aggagacagc   3120
tgtgaagttg ggcgtgctct gtggtaccag ctgtgacttt tctatttctc ctagttttag   3180
gttgttcatg aaactagaaa tgtcatcctg cttgattttt catcagccaa gttaaacccc   3240
tgctttctgt cctttgcacc ttttgcgtga acagaatatg cattattaaa gcaaaaataa   3300
ataaaagtaa aatgcaaatg aaaacaaggg agggaaagtt gtattatttc ctgcactggg   3360
ttacccgtgt gtgttatcgt ttaaactgta ttcacataat gtcatttgcc ttgctcactt   3420
gtaacccctt cctcaggtcc aagagaatgg gaggagggtc atgttgaagt gtagccactg   3480
gaactttctt gcatttatgg agttgctttt tctttcccaa ggaaactgat gtttgcctgt   3540
ccgctttatc tttgtagtac atgaacagtt cagccttaga ctatgtaact gttttctcat   3600
ccttagctga aaatgagggg cctactgtat tgcgagactg ttcaggggta ggggtggagg   3660
gggtggtccc ttaatggccc ctgaagatgt tggatgtgtt tctcaaaagc tgctttgtct   3720
ctttcctgag tttaatagtg aaactactaa acattaatag atttgcacag ccacaaagaa   3780
tgagagttga taataccgaa gaagtgatgc aaaaacaaaa aatcacatta ctgatcattg   3840
atagtattac aaataaatgt ctcttccttt ctcttcctcc cttcctcccc ctgccttcct   3900
cttaacctat gtgctcatcc ttgctacttg aggctgttat ttccctccga gtatttaagg   3960
agcccaaaca ccttggtctt cctgggtggg ggcataatta agggaaggga gtgtataagg   4020
aaggaaacct catacccctcc attcccatcc ctggatatat tgccttttca gcagcctcgg   4080
gttcagtgtg cttggggtca ggagtgccag gttcccaaga gcagcgtaaa acatccctgt   4140
acccccttgac agttataagc atttctgcgt taaacttgaa gattccagag attccccacg   4200
```

-continued

```
acctaatgat ctaagaatgc agattggatt ctttgatgtt caaatttctc atttacttat   4260

gaaaatccct aattatatag ttttatataa tgtgtataca gagtaggatt gttgatgaaa   4320

ttgagcggtt ggaacaccct catggaacac tggcaacatg gaatgtagag agctgatgtc   4380

ttccccctca tagaggccat tggcttcctt tgtataagga gagggagaag tgattctgga   4440

aggagaagtt ggtatgtcta gcttcattgc ggcccctcgg gctacccagc aagaggattc   4500

tgcatcaagg aactggacga gccgctaccc aaactgccac catctttact ctttacaaaa   4560

tggacccatc gagaatgttg aaaagcttgg aagtatcact tttgaaaaaa aaaaaaatta   4620

ttttgcattc agcatggact cgaccaggca tctatggaga ttattttttt gcttcatttt   4680

ataaagttgt atttagaaaa gtcttaagta ttgtgctttg taaagaagat gattaaaatg   4740

aaattttgtg agaatagttt tgttca                                        4766


<210> SEQ ID NO 86
<211> LENGTH: 4611
<212> TYPE: DNA
<213> ORGANISM: Homo sapiens

<400> SEQUENCE: 86

ccccgtctgc gtccgcgttc gcggctcccg tttgcatcat ctccagccgg cggctgctcc     60

agggaggctg ggcgcgatcc tctccgcccg cggctccaac ccgcactctg cgcctctcct    120

cgcctttctc gcacctgctc ctgcgccagg cccggagacc cccggggcgg cttcccagaa    180

cctgcggagc acaactggcc gaccgaccca ttcattggga accccgtctt ttgccagagc    240

ccacgtcccc tgccacctct agctcggagc ggcgtgtagc gccatggaga agagcaacga    300

gaccaacggc taccttgaca gcgctcaggc ggggcctgcg gccgggcccg gagctccggg    360

gaccgcggcg ggacgcgcac ggcgttgcgc gggcttcctg cggcgccaag cgctggtgct    420

gctcaccgtg tccggggtgc tggcgggcgc gggcctgggc gcggcgttgc gcgggctcag    480

cctgagccgc acgcaggtca cctacctggc cttccccggc gagatgctgc tccgcatgct    540

gcgcatgatc atcctgccgc tggtggtctg cagcctggtg tcgggcgccg cctcgctcga    600

tgccagctgc ctcgggcgtc tgggcggcat cgctgtcgcc tactttggcc tcaccacact    660

gagtgcctcg gcgctcgccg tggccttggc gttcatcatc aagccaggat ccggtgcgca    720

gacccttcag tccagcgacc tggggctgga ggactcgggg cctcctcctg tccccaaaga    780

gacggtggac tctttcctcg acctggccag aaacctgttt ccctccaatc ttgtggttgc    840

agctttccgt acgtatgcaa ccgattataa agtcgtgacc cagaacagca gctctggaaa    900

tgtaacccat gaaaagatcc ccataggcac tgagatagaa gggatgaaca ttttaggatt    960

ggtcctgttt gctctggtgt taggagtggc cttaaagaaa ctaggctccg aaggagaaga   1020

cctcatccgt ttcttcaatt ccctcaacga ggcgacgatg gtgctggtgt cctggattat   1080

gtggtacgta cctgtgggca tcatgttcct tgttggaagc aagatcgtgg aaatgaaaga   1140

catcatcgtg ctggtgacca gcctggggaa atacatcttc gcatctatat tgggccatgt   1200

tattcatgga ggaattgttc tgccacttat ttattttgtt ttcacacgaa aaaacccatt   1260

cagattcctc ctgggcctcc tcgccccatt tgcgacagca tttgctacct gctccagctc   1320

agcgaccctt ccctctatga tgaagtgcat tgaagagaac aatggtgtgg acaagaggat   1380

cagcaggttt attctcccca tcggggccac cgtgaacatg gacggagcag ccatcttcca   1440

gtgtgtggcc gcggtgttca ttgcgcaact caacaacgta gagctcaacg caggacagat   1500

tttcaccatt ctagtgactg ccacagcgtc cagtgttgga gcagcaggcg tgccagctgg   1560
```

```
aggggtcctc accattgcca ttatcctgga ggccattggg ctgcctactc atgacctgcc   1620
tctgatcctg gctgtggact ggattgtgga ccggaccacc acggtggtga atgtggaagg   1680
ggatgccctg ggtgcaggca ttctccacca cctgaatcag aaggcaacaa agaaaggcga   1740
gcaggaactt gctgaggtga aagtggaagc catccccaac tgcaagtctg aggaggagac   1800
atcgcccctg gtgacacacc agaaccccgc tggccccgtg gccagtgccc cagaactgga   1860
atccaaggag tcggttctgt gatggggctg ggctttgggc ttgcctgcca gcagtgatgt   1920
cccaccctgt tcacccagcc gccagtcatg gacacagggc actgcccttg ccaactttta   1980
ccctcccaag caatgctttg gcccagtcgc tggcctgagg cttacctctc ggcactggca   2040
ttgggctccc cagccggaac tggttaccaa ggacaaggac actctgacat tcggcttgat   2100
ccatgtccag gtgcaactgt gtgtacacca gggatctgtt tggaaacaac cccttgagct   2160
gccaggctca agaaatcatg gactcacagg gtcctgtgtg gttacatctt ggaaaaaatg   2220
cagatgtatt tcactctccc cggtcagctc tgcatcaggt gttttctgag caaaccaagg   2280
gggtttatag tcatctgtcg cattgcctcg agttgcagta attgaaaaaa tgctcaaatt   2340
cttagccatg gctggccttt gctgagctgg gactcaggtg tttaaagagt ttgtgctata   2400
gctaggtgtg gatagcttct gatccctggg ttctgggaga ctgcaggtgc cgcacattgt   2460
caagttagaa atactccagg tgggtgttag cactgtggtg gtctctggtc cacagcctta   2520
ggtaaacaac ttagattctg aggtcaaaga aaaaaggaga gggaatgcag ccttgtgggg   2580
gagaagcggg gcagagggtt ctctaatcta atcaggacag gacaggtttc acatacaatt   2640
gtcccagttc gcatcccagc cctggggcac ttttctgctt ccttccagag gcctgggcct   2700
ctgataacac tttggctttt tctccattca cgctgatttg gcaaaaggcc agagatgggc   2760
ctccttccct ggggaggtgt gatgtagtta tcacattcag gacccttgtt gatttatcat   2820
ctattatttg aattcaactg gacactctgt aaaatgctgc actgcagcaa aaacaaaacc   2880
accaccaccc cagagaaaac catgtactaa ttggagtggg gtacccccat tcacaggttc   2940
ccaggtcccc tggctttggc tgatttcaaa atatagagcc ctttcttgcc agtacatcca   3000
agtttaaaat tatcagcgaa atggtccatg tttttccaat tacctgctga cacggttcta   3060
agctaagtga aggggaagat ctgagagcgt gctgtttgtg gctgttgatg catattcgtg   3120
atgtaacagg tcctggggcc tcactttacc ccatttgtaa aatggggcta atgtcacctg   3180
cctcttacct acctcagagg gatttggtga agcaaactgt taatcttcga aaacgaccat   3240
ttcacttctt ggatatcaag tgctaaccca gtatgttctt cttttttatg taagggacag   3300
ctttctccac agagtccttt ctgctggtga ggacagcatt tctgagcagg gctttgttct   3360
ctatgtgcat taggactttt atcatgccct tgttctgtgt gtagttactt gacagcatca   3420
aatgccgcct cttcctaatg tccttcaagt tttcatgaac tagcaacccc accttccacc   3480
atggttctgg gcgcctgatt ttgctgtgac tcccagaccc agccactgtt tctgccaccc   3540
tgtaacaggc cattaaagct ccccagtgtt cagcctcctt cactcccttg ttttccctgt   3600
tgctatgtgt cacctgggcc ctacagacag gggcacacgc ttatggatgt gtgtaccatt   3660
gagatgagaa tgggtagatg gaacggagac catcaagcca caccccctc ttaaaactgg    3720
ggacatgagc ctgagcagaa agggtgaaga agagccatgg gacacagagt tgacccagcc   3780
agggggaaag cccagctctc tttaaaccag ctaagccatt ccagtctcct gtgaagccaa   3840
aagggaccag gaaccgtgca aaggaaactg gaaacttttc cccgctgggt agagcatgtt   3900
```

-continued

```
gctgatactc ttctgttttc aagggaaaca atcacattgt ttgattccaa atggtaaatg   3960

aacactcact attcttcagg cttcagtaaa tcttttttc ttccttcata tatatataca   4020

caacacacac acacatatgt atatctatac acacatgtgt gttgtgtata tgcatgtgtg   4080

tgtgtgcgtg tgtgtatagt tttagctcca agccaagcaa gtttgtgttt ggatagaggg   4140

gaacttaact attaactaca agttgtatgt ctgtggtatc ttgattttcc catttctaaa   4200

gatgaatttc acaaagccat aaagcgtgaa attagagctg gacttaagac tcattggccg   4260

accatcctgt gtcctggcct ggccctgcag taagaagcgt gtctgggtct ggagaagggt   4320

gcttccgaga gtgtgcaggt ggcccttccc cttggaggcg agaagagaga atgtgctgtc   4380

tatcttcctg gttttcagtc cacagagtcg gtagaccagg ggttacgtga ctggggaaaa   4440

tctcacatct ccttgtctga aaacatttcc cctgctgttc tctttctaac atgttgtggt   4500

aaatctgttc agatactgct catctgactg ttttgtacat gtgacaattg ccttaaaacc   4560

tagcacagtc ctcagaaatg aataccgtgt ttccactgga aaaaaaaaaa a            4611
```

<210> SEQ ID NO 87
<211> LENGTH: 2686
<212> TYPE: DNA
<213> ORGANISM: Homo sapiens

<400> SEQUENCE: 87

```
aacctgaagc tctcagagct tccctgtctt catctatcag cccagggaga ggaatcagtg     60

gttttccaaa agctgtacct ctttccataa atacaaggat gaagggctga gatgatggca    120

gttagaatta tattgagaaa tggtagcggg atctgagaaa gcaaggccat gagttgaaag    180

cagagagaag gcggttcgag tggagccctg atgaagttca tgctcatggt tgcccagcca    240

ttaacacggg ctcatcacat ctgtttccag attgcttcta gaacttagct accctcgttc    300

tataagatgg aatgaaaatg cgtactacat acagatcatg aaaagacgca aagaaaatgc    360

atcttcacat tgcagttcag aatcacgccg gcctcattct accgctgctc tctcctggat    420

ctcggccacg gatcttttgc tcgcgaaagt tcctccgtct agctgcacac aacgctgctg    480

caggaaaccg aggtaaggga tttgccgaga cttagctcca ccacactccc cgaggccccg    540

cccctcctct ctggccctcc cctaggccca ggtgtctcgc gttgcacgtg cagttgttgt    600

ggttctacgt cacgtggtcc cggaagttca agacagaccc gcctcaaaca tggcggcgcc    660

cagcgcgcga ggacgtgatc cgcttctgct ccggcttgga ttgtagcctt gacgaggtct    720

gagcgaccat ggaccggccg gggttcgtgg cagcgctggt ggctggtggg gtagcaggtg    780

tttctgttga cttgatatta tttcctctgg ataccattaa aaccaggctg cagagtcccc    840

aaggatttag taaggctggt ggttttcatg gaatatatgc tggcgttcct tctgctgcta    900

ttggatcctt tcctaatgct gctgcatttt ttatcaccta tgaatatgtg aagtggtttt    960

tgcatgctga ttcatcttca tatttgacac ctatgaaaca tatgttggct gcctctgctg   1020

gagaagtggt tgcctgcctg attcgagttc catctgaagt ggttaagcag agggcacagg   1080

tatctgcttc tacaagaaca tttcagattt tctctaacat cttatatgaa gagggtatcc   1140

aagggttgta tcgaggctat aaaagcacag ttttaagaga gattcctttt tctttggtcc   1200

agtttccctt atgggagtcc ttaaaagccc tctggtcctg gaggcaggat catgtggtgg   1260

attcttggca gtcagcagtc tgtggagctt ttgcaggtgg atttgccgct gcagtcacca   1320

cccctctaga cgtggcaaag acaagaatta cgctggcaaa ggctggctcc agcactgctg   1380

atgggaatgt gctctctgtc ctgcatgggg tctggcggtc acaggggctg gcaggattat   1440
```

```
ttgcaggtgt cttccctcga atggcagcca tcagtctggg aggtttcatc tttctggggg   1500
cttatgaccg aacgcacagc ttgctgttgg aagttggcag aaagagtcct tgaagcagag   1560
acaagcctca cctccacttc tgtcaagaga ggggcctgca gtgcaaaccc tcttccgctg   1620
agcagctgtc tgaactatag gccccagtgc tgaagaccag ttgtgctaag ataccggcat   1680
ggagattgtg ccatccgtgg tataggctgg ctggtatgaa gtcattggcc tgtatgccag   1740
agagctaaga gaagaaaacg gggtctgtgg cggtactctg aacaatttcc tcagaacctc   1800
ttaataaata agtttggtaa tgctgaggcc aggcctttta gagctttcat ttgatctgta   1860
tctgatcttt catttcctgc cacctgatgg tggattcagc agaaggcaag atggttataa   1920
ttctaaaaga atagcttgtt tgtttgtttg ggaaaaggag acttggggaa gagttgtgta   1980
tgtgggtgtt tctcccccta gttaattcct gttgtgtaag ggtaggcttt gttgaaaaag   2040
aaagaaagat tgaactacag gtgcatagca agcactcttt ctgggtaact aggctgctgg   2100
ttttaattac cctcagattt cacccataaa aacgcacaat tgtattattt tacagagatg   2160
tgtccagcgc cccctgtggt gtgtgagaga aagcagctgc aactcaagtg actaggtggg   2220
cccagctggc ttcgtgcagg agggcacggt gggtgagcca ttctcgccat tctcatgtca   2280
gactgaaagg agggcctggg ccagctttga aaaggcagga tgaaatggaa aggtcaccac   2340
acttagggat tttagacctt gactaacaag ctccaggtgt agaaaaattc aaaacaaaat   2400
gtcaggaatc tagcagtgtt gtctgccctg gagcaaacaa acagtatgtg attttgcttc   2460
gcctattttt tttttctttt ttgggggaag ataattaaag gcagaatgac tgcgtttgta   2520
aaagaaggac caccaactat actgacattt ataaatgaac ctttattaaa gacacttcaa   2580
tgccatttgt tagacacttc aatattttac atggttttca atgtacactg taccaaaatt   2640
tctataaata aataactttg tacataaaag taaaaaaaaa aaaaaa                  2686
```

<210> SEQ ID NO 88
<211> LENGTH: 3909
<212> TYPE: DNA
<213> ORGANISM: Homo sapiens

<400> SEQUENCE: 88

```
gagcgagagt gtgtcgagtg agtgtgcgtc tgtgtgtccc ggcgagggtg cgcgctcggc     60
gccgggagcg cggccagccg agtccggagg catcgggagg tcgagagccg ccgggacccc    120
agctctgcgt tcactgcccc gtccggagct ggacttcggg gccggggccg gggccgtgcg    180
ccggggacag gcagggccgg gtcgcgggcc gcgcgtcccc caggccggag atctgcgagt    240
gaagagggac gagggaaaag aaacaaagcc acagacgcaa cttgagactc ccgcatccca    300
aaagaagcac cagatcagca aaaaaagaag atgggccccc cgagcctcgt gctgtgcttg    360
ctgtccgcaa ctgtgttctc cctgctgggt ggaagctcgg ccttcctgtc gcaccaccgc    420
ctgaaaggca ggtttcagag ggaccgcagg aacatccgcc ccaacatcat cctggtgctg    480
acggacgacc aggatgtgga gctgggttcc atgcaggtga tgaacaagac ccggcgcatc    540
atggagcagg gcggggcgca cttcatcaac gccttcgtga ccacacccat gtgctgcccc    600
tcacgctcct ccatcctcac tggcaagtac gtccacaacc acaacaccta caccaacaat    660
gagaactgct cctcgccctc ctggcaggca cagcacgaga gccgcacctt tgccgtgtac    720
ctcaatagca ctggctaccg gacagctttc ttcgggaagt atcttaatga atacaacggc    780
tcctacgtgc cacccggctg gaaggagtgg gtcggactcc ttaaaaactc ccgcttttat    840
```

-continued

```
aactacacgc tgtgtcggaa cggggtgaaa gagaagcacg gctccgacta ctccaaggat    900
tacctcacag acctcatcac caatgacagc gtgagcttct tccgcacgtc caagaagatg    960
tacccgcaca ggccagtcct catggtcatc agccatgcag ccccccacgg ccctgaggat   1020
tcagccccac aatattcacg cctcttccca aacgcatctc agcacatcac gccgagctac   1080
aactacgcgc ccaacccgga caaacactgg atcatgcgct acacggggcc catgaagccc   1140
atccacatgg aattcaccaa catgctccag cggaagcgct tgcagaccct catgtcggtg   1200
gacgactcca tggagacgat ttacaacatg ctggttgaga cgggcgagct ggacaacacg   1260
tacatcgtat acaccgccga ccacggttac cacatcggcc agtttggcct ggtgaaaggg   1320
aaatccatgc catatgagtt tgacatcagg gtcccgttct acgtgagggg ccccaacgtg   1380
gaagccggct gtctgaatcc ccacatcgtc ctcaacattg acctggcccc caccatcctg   1440
gacattgcag gcctggacat acctgcggat atggacggga aatccatcct caagctgctg   1500
gacacggagc ggccggtgaa tcggtttcac ttgaaaaaga agatgagggt ctggcgggac   1560
tccttcttgg tggagagagg caagctgcta cacaagagag acaatgacaa ggtggacgcc   1620
caggaggaga actttctgcc caagtaccag cgtgtgaagg acctgtgtca gcgtgctgag   1680
taccagacgg cgtgtgagca gctgggacag aagtggcagt gtgtggagga cgccacgggg   1740
aagctgaagc tgcataagtg caagggcccc atgcggctgg gcggcagcag agccctctcc   1800
aacctcgtgc ccaagtacta cgggcagggc agcgaggcct gcacctgtga cagcggggac   1860
tacaagctca gcctggccgg acgccggaaa aaactcttca agaagaagta caaggccagc   1920
tatgtccgca gtcgctccat ccgctcagtg gccatcgagg tggacggcag ggtgtaccac   1980
gtaggcctgg gtgatgccgc ccagccccga aacctcacca agcggcactg gccaggggcc   2040
cctgaggacc aagatgacaa ggatggtggg gacttcagtg gcactggagg ccttcccgac   2100
tactcagccg ccaaccccat taaagtgaca catcggtgct acatcctaga gaacgacaca   2160
gtccagtgtg acctggacct gtacaagtcc ctgcaggcct ggaaagacca caagctgcac   2220
atcgaccacg agattgaaac cctgcagaac aaaattaaga acctgaggga agtccgaggt   2280
cacctgaaga aaaagcggcc agaagaatgt gactgtcaca aaatcagcta ccacacccag   2340
cacaaaggcc gcctcaagca cagaggctcc agtctgcatc ctttcaggaa gggcctgcaa   2400
gagaaggaca aggtgtggct gttgcgggag cagaagcgca agaagaaact ccgcaagctg   2460
ctcaagcgcc tgcagaacaa cgacacgtgc agcatgccag gcctcacgtg cttcacccac   2520
gacaaccagc actggcagac ggcgcctttc tggacactgg ggcctttctg tgcctgcacc   2580
agcgccaaca ataacacgta ctggtgcatg aggaccatca atgagactca caatttcctc   2640
ttctgtgaat ttgcaactgg cttcctagag tactttgatc tcaacacaga cccctaccag   2700
ctgatgaatg cagtgaacac actggacagg gatgtcctca accagctaca cgtacagctc   2760
atggagctga ggagctgcaa gggttacaag cagtgtaacc cccggactcg aaacatggac   2820
ctgggactta aagatggagg aagctatgag caatacaggc agtttcagcg tcgaaagtgg   2880
ccagaaatga agagaccttc ttccaaatca ctgggacaac tgtgggaagg ctgggaaggt   2940
taagaaacaa cagaggtgga cctccaaaaa catagaggca tcacctgact gcacaggcaa   3000
tgaaaaacca tgtgggtgat ttccagcaga cctgtggtat tggccaggag gcctgagaaa   3060
gcaagcacgc actctcagtc aacatgacag attctggagg ataaccagca ggagcagaga   3120
taacttcagg aagtccattt ttgcccctgc ttttgctttg gattatacct caccagctgc   3180
acaaaatgca tttttcgta tcaaaaagtc accactaacc ctcccccaga agctcacaaa   3240
```

```
ggaaaacgga gagagcgagc gagagagatt tccttggaaa tttctcccaa gggcgaaagt   3300

cattggaatt tttaaatcat aggggaaaag cagtcctgtt ctaaatcctc ttattctttt   3360

ggtttgtcac aaagaaggaa ctaagaagca ggacagaggc aacgtggaga ggctgaaaac   3420

agtgcagaga cgtttgacaa tgagtcagta gcacaaaaga gatgacattt acctagcact   3480

ataaaccctg gttgcctctg aagaaactgc cttcattgta tatatgtgac tatttacatg   3540

taatcaacat gggaactttt aggggaacct aataagaaat cccaattttc aggagtggtg   3600

gtgtcaataa acgctctgtg gccagtgtaa aagaaaatcc ctcgcagttg tggacatttc   3660

tgttcctgtc cagataccat ttctcctagt atttctttgt tatgtcccag aactgatgtt   3720

tttttttaa ggtactgaaa agaaatgaag ttgatgtatg tcccaagttt tgatgaaact   3780

gtatttgtaa aaaaaatttt gtagtttaag tattgtcata cagtgttcaa aaccccagcc   3840

aatgaccagc agttggtatg aagaaccttt gacattttgt aaaaggccat ttcttgggaa   3900

aaaaaaaaa                                                            3909
```

```
<210> SEQ ID NO 89
<211> LENGTH: 1075
<212> TYPE: DNA
<213> ORGANISM: Homo sapiens

<400> SEQUENCE: 89

gcattcccca cacaacaccc acactcagcc actgcgggcg aggagggcac aaggccaggt     60

tcccaagagc tcaggaacat ggagctgatc caggacatct ctcgcccgcc actggagtac    120

gtgaaggggg tcccgctcat caagtacttt gcagaggcac tggggcccct gcagagcttc    180

caggcccggc ctgatgacct gctcatcagc acctacccca agtccggcac cacctgggtg    240

agccagattc tggacatgat ctaccagggc ggtgacctgg aaaagtgtca ccgagctccc    300

atcttcatgc gggtgccctt ccttgagttc aaagtcccag ggattccctc agggatggag    360

actctgaaaa acacaccagc cccacgactc ctgaagacac acctgcccct ggctctgctc    420

ccccagactc tgttggatca gaaggtcaag gtggtctatg ttgcccgcaa cgcaaaggat    480

gtggcggttt cctactacca cttctaccac atggccaaag tgtaccctca ccctgggacc    540

tgggaaagct tcctggagaa gttcatggct ggagaagtgt cctatgggtc ctggtaccag    600

cacgtgcaag agtggtggga gctgagccgc acccaccctg ttctctacct cttctatgaa    660

gacatgaagg agaaccccaa aagggagatt caaaagatcc tggagtttgt ggggcgctcc    720

ctgccagagg agactgtgga cctcatggtt gagcacacgt cgttcaagga gatgaagaag    780

aaccctatga ccaactacac caccgtccgc cgggagttca tggaccacag catctccccc    840

ttcatgagga aaggcatggc tggggactgg aagaccacct tcaccgtggc gcagaatgag    900

cgcttcgatg cggactatgc ggagaagatg gcaggctgca gcctcagctt ccgctctgag    960

ctgtgagagg ggttcctgga gtcactgcag agggagtgtg cgaatcaagc ctgaccaaga   1020

ggctccagaa taaagtatga tttgtgttca aaaaaaaaaa aaaaaaaaaa aaaaa        1075
```

```
<210> SEQ ID NO 90
<211> LENGTH: 2745
<212> TYPE: DNA
<213> ORGANISM: Homo sapiens

<400> SEQUENCE: 90

ctcgcgaggc cggctaggcc cgaatgtcgt tagccgtggg gaaagatggc ggaaaattta     60
```

-continued

```
aaaggctgca gcgtgtgttg caagtcttct tggaatcagc tgcaggacct gtgccgcctg    120
gccaagctct cctgccctgc cctcggtatc tctaagagga acctctatga ctttgaagtc    180
gagtacctgt gcgattacaa gaagatccgc gaacaggaat attacctggt gaaatggcgt    240
ggatatccag actcagagag cacctgggag ccacggcaga atctcaagtg tgtgcgtatc    300
ctcaagcagt tccacaagga cttagaaagg gagctgctcc ggcggcacca ccggtcaaag    360
accccccggc acctggaccc aagcttggcc aactacctgg tgcagaaggc caagcagagg    420
cgggcgctcc gtcgctggga gcaggagctc aatgccaagc gcagccatct gggacgcatc    480
actgtagaga atgaggtgga cctggacggc cctccgcggg ccttcgtgta catcaatgag    540
taccgtgttg gtgagggcat caccctcaac caggtggctg tgggctgcga gtgccaggac    600
tgtctgtggg cacccactgg aggctgctgc ccgggggcgt cactgcacaa gtttgcctac    660
aatgaccagg gccaggtgcg gcttcgagcc gggctgccca tctacgagtg caactcccgc    720
tgccgctgcg gctatgactg cccaaatcgt gtggtacaga agggtatccg atatgacctc    780
tgcatcttcc gcacggatga tgggcgtggc tggggcgtcc gcaccctgga gaagattcgc    840
aagaacagct tcgtcatgga gtacgtggga gagatcatta cctcagagga ggcagagcgg    900
cggggccaga tctacgaccg tcagggcgcc acctacctct ttgacctgga ctacgtggag    960
gacgtgtaca ccgtggatgc cgcctactat ggcaacatct cccactttgt caaccacagt   1020
tgtgacccca acctgcaggt gtacaacgtc ttcatagaca accttgacga gcggctgccc   1080
cgcatcgctt tctttgccac aagaaccatc cgggcaggcg aggagctcac ctttgattac   1140
aacatgcaag tggaccccgt ggacatggag agcacccgca tggactccaa ctttggcctg   1200
gctgggctcc ctggctcccc taagaagcgg gtccgtattg aatgcaagtg tgggactgag   1260
tcctgccgca aatacctctt ctagccctta gaagtctgag gccagactga ctgagggggc   1320
ctgaagctac atgcacctcc cccactgctg ccctcctgtc gagaatgact gccagggcct   1380
cgcctgcctc cacctgcccc cacctgctcc tacctgctct acgttcaggg ctgtggccgt   1440
ggtgaggacc gactccagga gtcccctttc cctgtcccag ccccatctgt gggttgcact   1500
tacaaacccc cacccacctt cagaaatagt ttttcaacat caagactctc tgtcgttggg   1560
attcatggcc tattaaggag gtccaagggg tgagtcccaa cccagcccca gaatatattt   1620
gtttttgcac ctgcttctgc ctggagattg aggggtctgc tgcaggcctc ctccctgctg   1680
ccccaaaggt atggggaagc aaccccagag caggcagaca tcagaggcca gagtgcctag   1740
cccgacatga agctggttcc ccaaccacag aaactttgta ctagtgaaag aaagggggtc   1800
cctgggctac gggctgaggc tggtttctgc tcgtgcttac agtgctgggt agtgttggcc   1860
ctaagagctg tagggtctct tcttcagggc tgcatatctg agaagtggat gcccacatgc   1920
cactggaagg gaagtgggtg tccatgggcc actgagcagt gagaggaagg cagtgcagag   1980
ctggccagcc ctggaggtag gctgggacca agctctgcct tcacagtgca gtgaaggtac   2040
ctagggctct tgggagctct gcggttgcta ggggccctga cctggggtgt catgaccgct   2100
gacaccactc agagctggaa ccaagatcta gatagtccgt agatagcact taggacaaga   2160
atgtgcattg atggggtggt gatgaggtgc caggcactgg gtagagcacc tggtccacgt   2220
ggattgtctc agggaagcct tgaaaaccac ggaggtggat gccaggaaag ggcccatgtg   2280
gcagaaggca aagtacaggc caagaattgg gggtggggga gatggcttcc ccactatggg   2340
atgacgaggc gagagggaag cccttgctgc ctgccattcc cagaccccag ccctttgtgc   2400
tcaccctggt tccactggtc tcaaaagtca cctgcctaca aatgtacaaa aggcgaaggt   2460
```

tctgatggct gccttgctcc ttgctccccc acccccctgtg aggacttctc taggaagtcc 2520
ttcctgacta cctgtgccca gagtgcccct acatgagact gtatgccctg ctatcagatg 2580
ccagatctat gtgtctgtct gtgtgtccat cccgccgacc ccccagacta acctccaggc 2640
atggactgaa tctggttctc ctcttgtaca cccctcaacc ctatgcagcc tggagtgggc 2700
atcaataaaa tgaactgtcg actgaacaaa aaaaaaaaaa aaaaa 2745

<210> SEQ ID NO 91
<211> LENGTH: 4000
<212> TYPE: DNA
<213> ORGANISM: Homo sapiens

<400> SEQUENCE: 91
aaaggcagaa tgagtcctcc cacccccctac cctgccaccc ctcccaccca agccacctca 60
tttcctcttc ctccccagca ccgacccaca ctgaccaaca caggctgagc agtcaggccc 120
acagcatctg accccaggcc cagctcgtcc tggctggcct gggtcggcct ctggagtatg 180
gtctggcggg tgcccccttt cttgctcccc atcctcttct tggcttctca tgtgggcgcg 240
gcggtggacc tgacgctgct ggccaacctg cggctcacgg acccccagcg cttcttcctg 300
acttgcgtgt ctggggaggc cggggcgggg aggggctcgg acgcctgggg cccgcccctg 360
ctgctggaga aggacgaccg tatcgtgcgc accccgcccg ggccacccct gcgcctggcg 420
cgcaacggtt cgcaccaggt cacgcttcgc ggcttctcca agccctcgga cctcgtgggc 480
gtcttctcct gcgtgggcgg tgctggggcg cggcgcacgc gcgtcatcta cgtgcacaac 540
agccctggag cccacctgct tccagacaag gtcacacaca ctgtgaacaa aggtgacacc 600
gctgtacttt ctgcacgtgt gcacaaggag aagcagacag acgtgatctg gaagagcaac 660
ggatcctact tctacaccct ggactggcat gaagcccagg atgggcggtt cctgctgcag 720
ctcccaaatg tgcagccacc atcgagcggc atctacagtg ccacttacct ggaagccagc 780
cccctgggca gcgccttctt tcggctcatc gtgcggggtt gtggggctgg gcgctggggg 840
ccaggctgta ccaaggagtg cccaggttgc ctacatggag gtgtctgcca cgaccatgac 900
ggcgaatgtg tatgcccccc tggcttcact ggcacccgct gtgaacaggc ctgcagagag 960
ggccgttttg ggcagagctg ccaggagcag tgcccaggca tatcaggctg ccggggcctc 1020
accttctgcc tcccagaccc ctatggctgc tcttgtggat ctggctggag aggaagccag 1080
tgccaagaag cttgtgcccc tggtcatttt ggggctgatt gccgactcca gtgccagtgt 1140
cagaatggtg gcacttgtga ccggttcagt ggttgtgtct gcccctctgg gtggcatgga 1200
gtgcactgtg agaagtcaga ccggatcccc cagatcctca acatggcctc agaactggag 1260
ttcaacttag agacgatgcc ccggatcaac tgtgcagctg cagggaaccc cttccccgtg 1320
cggggcagca tagagctacg caagccagac ggcactgtgc tcctgtccac caaggccatt 1380
gtggagccag agaagaccac agctgagttc gaggtgcccc gcttggttct tgcggacagt 1440
gggttctggg agtgccgtgt gtccacatct ggcggccaag acagccggcg cttcaaggtc 1500
aatgtgaaag tgccccccgt gcccctggct gcacctcggc tcctgaccaa gcagagccgc 1560
cagcttgtgg tctccccgct ggtctcgttc tctggggatg gacccatctc cactgtccgc 1620
ctgcactacc ggccccagga cagtaccatg gactggtcga ccattgtggt ggaccccagt 1680
gagaacgtga cgttaatgaa cctgaggcca aagacaggat acagtgttcg tgtgcagctg 1740
agccggccag gggaaggagg agaggggggcc tgggggcctc ccaccctcat gaccacagac 1800

-continued

```
tgtcctgagc ctttgttgca gccgtggttg gagggctggc atgtggaagg cactgaccgg   1860
ctgcgagtga gctggtcctt gcccttggtg cccgggccac tggtgggcga cggtttcctg   1920
ctgcgcctgt gggacgggac acgggggcag gagcggcggg agaacgtctc atccccccag   1980
gcccgcactg ccctcctgac gggactcacg cctggcaccc actaccagct ggatgtgcag   2040
ctctaccact gcaccctcct gggcccggcc tcgcccccctg cacacgtgct tctgcccccc  2100
agtgggcctc cagccccccg acacctccac gcccaggccc tctcagactc cgagatccag   2160
ctgacatgga agcacccgga ggctctgcct gggccaatat ccaagtacgt tgtggaggtg   2220
caggtggctg gggtgcaggg agacccactg tggatagacg tggacaggcc tgaggagaca   2280
agcaccatca tccgtggcct caacgccagc acgcgctacc tcttccgcat gcgggccagc   2340
attcaggggc tcggggactg gagcaacaca gtagaagagt ccaccctggg caacgggctg   2400
caggctgagg gcccagtcca agagagccgg gcagctgaag agggcctgga tcagcagctg   2460
atcctggcgg tggtgggctc cgtgtctgcc acctgcctca ccatcctggc tgccctttta   2520
accctggtgt gcatccgcag aagctgcctg catcggagac gcaccttcac ctaccagtca   2580
ggctcgggcg aggagaccat cctgcagttc agctcaggga ccttgacact tacccggcgg   2640
ccaaaactgc agcccgagcc cctgagctac ccagtgctag agtgggagga catcaccttt   2700
gaggacctca tcggggaggg gaacttcggc caggtcatcc gggccatgat caagaaggac   2760
gggctgaaga tgaacgcagc catcaaaatg ctgaaagagt atgcctctga aaatgaccat   2820
cgtgactttg cgggagaact ggaagttctg tgcaaattgg ggcatcaccc caacatcatc   2880
aacctcctgg gggcctgtaa gaaccgaggt tacttgtata tcgctattga atatgccccc   2940
tacgggaacc tgctagattt tctgcggaaa agccgggtcc tagagactga cccagctttt   3000
gctcgagagc atgggacagc ctctaccctt agctcccggc agctgctgcg tttcgccagt   3060
gatgcggcca atggcatgca gtacctgagt gagaagcagt tcatccacag ggacctggct   3120
gcccggaatg tgctggtcgg agagaaccta gcctccaaga ttgcagactt cggcctttct   3180
cggggagagg aggtttatgt gaagaagacg atggggcgtc tccctgtgcg ctggatggcc   3240
attgagtccc tgaactacag tgtctatacc accaagagtg atgtctggtc ctttggagtc   3300
cttctttggg agatagtgag ccttggaggt acaccctact gtggcatgac ctgtgccgag   3360
ctctatgaaa agctgcccca gggctaccgc atggagcagc ctcgaaactg tgacgatgaa   3420
gtgtacgagc tgatgcgtca gtgctggcgg gaccgtccct atgagcgacc cccctttgcc   3480
cagattgcgc tacagctagg ccgcatgctg gaagccagga aggcctatgt gaacatgtcg   3540
ctgtttgaga acttcactta cgcgggcatt gatgccacag ctgaggaggc ctgagctgcc   3600
atccagccag aacgtggctc tgctggccgg agcaaactct gctgtctaac ctgtgaccag   3660
tctgaccctt acagcctctg acttaagctg cctcaaggaa ttttttttaac ttaagggaga  3720
aaaaaaggga tctggggatg gggtgggctt aggggaactg ggttcccatg ctttgtaggt   3780
gtctcatagc tatcctgggc atccttcttt ctagttcagc tgccccacag gtgtgtttcc   3840
catcccactg ctcccccaac acaaaccccc actccagctc cttcgcttaa gccagcactc   3900
acaccactaa catgccctgt tcagctactc ccactcccgg cctgtcattc agaaaaaaat   3960
aaatgttcta ataagctcca ttaaaaaaaa aaaaaaaaaa                         4000
```

<210> SEQ ID NO 92
<211> LENGTH: 3658
<212> TYPE: DNA
<213> ORGANISM: Homo sapiens

<400> SEQUENCE: 92
aaggaggagt gcactggccg ggatcggtgc agcgctcaca ctcactcaca gtcactctct 60
ctgagcgcgt ctcgctcgct ctcatacacg cccggagccc aggagcgctc aggatcccga 120
gcgccgcgaa aaagttcccc cggcttttgc tggagactca tcgttttggg aagtgcattt 180
gcttcgtggc tccgccgagc ctgctgaatc ctgtcctcgc ggcacgggac cccgggatcg 240
ctgaccgctg ccgccgccgc ctctgcctcc cggactatcg gcagcctcgg caacaatagt 300
ggcggccgcc cccagcgagg ctccgggagc ccttgcctgc gggggtccgg ggactcgagc 360
cggcctccgc ctcccggacg cacagccagc gtggtccccg cgtgcaacgc gagcgccggg 420
gagtggctcc tgctttgccc ctcgtggggg ccgagccaag accagtctgc aaactccatc 480
ccgccggctg gaagaagtcg cggagccggc accaaacccg cagcgtcttc ccgcgcggat 540
cccgggactt aaaaagccgg ggccaccccg gcccaggacg ggatgcgggt cggtccggtg 600
cgctctgcca tgagcggcgc ctcgcagccc cgcggcccgg ccctgctctt cccagccacc 660
cgaggcgtcc cggccaaacg cctgctggac gccgacgacg cggcggctgt ggcggccaag 720
tgcccgcgcc tctccgagtg ctccagcccc ccggactacc tcagcccccc cggctcgccc 780
tgcagcccgc agcccccgcc tgccgctccg ggggccggcg gaggctccgg gagcgcgccg 840
gggcccagcc gcatcgccga ctacctgctg ctgcccctag ccgagcgcga gcatgtgtcc 900
cgggcgctgt gcatccacac tggacgcgag ctgcgctgca aggtgtttcc cattaaacac 960
taccaggaca aaatcaggcc ttacatccag ctgccatcgc acagcaacat tactggcatt 1020
gtggaagtga tccttgggga aaccaaggcc tatgtcttct ttgagaagga ctttggggac 1080
atgcactcct atgtgcgaag ccggaagagg ctgcgggaag aggaagccgc ccggctcttc 1140
aagcagattg tctccgccgt cgcccactgc caccagtcag ccatcgtgct gggggacctg 1200
aagcttagga agttcgtctt ctccacggag gagagaaccc agcttagact agaaagtcta 1260
gaagacacac acataatgaa gggggaagat gatgctttgt cagacaaaca tggctgccca 1320
gcctacgtga gccctgagat cctcaacacc actgggacct actccggaaa ggctgcggac 1380
gtttggagcc tgggggtgat gctctacacc cttctggttg gacgataccc cttccatgac 1440
tcagacccca gtgccctttt ctccaaaatt cggcgtggac agttctgcat tcctgagcac 1500
atttcccccca aagccaggtg cctcattcgc agcctcttga gacgggagcc ctccgagaga 1560
ctcactgccc ccgagatcct actgcacccc tggtttgagt ccgtcttgga acccgggtac 1620
atcgactcag aaataggaac ttcagaccag attgttccag agtaccagga ggacagtgac 1680
attagttcct tcttctgcta atccccaaaa cctcagaaac ctcataattc ttaacacctg 1740
gcatttccat ttctaaagat ggacaggccc tttggcgtgg taccaaccag ataatgactg 1800
catcaggatg aaagctgctg aactcggcat ggcgcctcct cttctctgtt gggatgagtg 1860
actttattga tttgagcagc atatgctgtg attggctgcc ctgcaaattt gtttccctta 1920
aggaaccctc accaactatc tctgctggat ttgggagttc cgcatctttt gtggagggca 1980
gagtatggac atcttacacc cggtggtcaa gtgtgtaata aacttgagca ttcgaatggg 2040
agaaaaagca aatcgcacaa tgacatattt tgagtaataa ccgtattttt cacagggtga 2100
caaattgggc caataaatct gccatctttg aactcatctt tggtggctag actgctacgg 2160
cagcttctct gatgggaaag ttccttttt ggcttaacac tcaccctttc ttcacactca 2220
catttaccaa tgactctgct ccgtttttgg agcagactgt tttaagttgc tcaggagcct 2280
gatggaacca tgaaccgaga ctcttctctg tttcctgcca agacctcatc tgcactaatg 2340
ccttctccct gaccttgaca cttcccccctt tagctataaa agcacttacc agccgaacgt 2400
ggaacagtat cacaaaagat tccatctccc aacgatttca gaactctgag ctcagagaga 2460
ctccagattt taaaaaataa tttgagtgct tggaaactat tagcttttta agttccttcc 2520
aaatatgtta gtacctaccc tttacttttt ccccaagacc atctcagggt ggagcattct 2580
gtctaagaga agaaagataa ggaggctccc acccacctct cccaagagca gacattaaac 2640
atctttgtgc tttgaagaga gtgaattttg gatagtcttg tgattctcag actaacttcc 2700
agaattatac tttaacccct cccagatatg gtccgccttt ggcattgtgt gtacatctgc 2760
agttttgcat ggtgggttgt taatatttca aatgtgtggt ttatgaatac gtctgtataa 2820
tcggcttctg gagtgaaaca gcaaacccca aatcttcaaa gttggaagga actttaaaaa 2880
tcatccggtc caatctcttt cctctttctg ccacctccca aggcagaaat cccctcttca 2940
gcttcttttg taggtgggaa tccagcctct gttagatatg tccagagatg gaaactcact 3000
cccctacaaa agatggagct taatggagaa attgcaactt tcattaaaaa acaaattcag 3060
atgaaatatc agtaactgtc ttggacagtg ctgaaatcag gtggttaaac gggtaaacaa 3120
aatatactgt attttgagaa atggcacaaa aacaggcagt catctttaag ggctatgcct 3180
aggcaaacta ctaacatgca ttgtgagaat gccgtgtata cctcacgtac tgtgtacttt 3240
gtacatatat tttacctttt atacctatgt tcgattttgt tttgttttgt tttgttctgg 3300
ctttgaggct tgttttgttg tctgtgtctg tctgaataac ctgcgtgtct aaaaccacgt 3360
gaaatgtgaa tgattattgg caatattacc ttgacagaat catgggactt tgagaagagg 3420
gaggacagag gcctctgtcg cactaacgct ctcgtggttg ctcgactgtt gtatctgtga 3480
tacattatcc gactaaggac tctgggctgg cagggccttc tgccgggaaa gctagaaaca 3540
ctaggttctt cctgtacata cgtgtatata tgtgaacagt gagatggccg tttctgactt 3600
gtagagaaat tttaataaac ctggtttcgt aaaaaaaaaa aaaaaaaaaa aaaaaaaa 3658

<210> SEQ ID NO 93
<211> LENGTH: 2408
<212> TYPE: DNA
<213> ORGANISM: Homo sapiens

<400> SEQUENCE: 93
cgggtcagga ggtggtgcgc ctcgcgcggc agattcgaag ctagggcggg gcccgcgggc 60
tgaggcagcg gctgtggcgg cgacgctggg cgtgaggtgg cggcggccgc gccctggttg 120
ggtccccact gctctcgggg gcgccatgga cgaggccgtg ggcgacctga agcaggcgct 180
tccctgtgtg gccgagtcgc caacggtcca cgtggaggtg catcagcgcg gcagcagcac 240
tgcaaagaaa gaagacataa acctgagtgt tagaaagcta ctcaacagac ataatattgt 300
gtttggtgat tacacatgga ctgagtttga tgaacctttt ttgaccagaa atgtgcagtc 360
tgtgtctatt attgacacag aattaaaggt taaagactca cagcccatcg atttgagtgc 420
atgcactgtt gcacttcaca ttttccagct gaatgaagat ggccccagca gtgaaaatct 480
ggaggaagag acagaaaaca taattgcagc aaatcactgg gttctacctg cagctgaatt 540
ccatgggctt tgggacagct tggtatacga tgtggaagtc aaatcccatc tcctcgatta 600
tgtgatgaca actttactgt tttcagacaa gaacgtcaac agcaacctca tcacctggaa 660
ccgggtggtg ctgctccacg gtcctcctgg cactggaaaa acatccctgt gtaaagcgtt 720
agcccagaaa ttgacaatta gactttcaag caggtaccga tatggccaat taattgaaat 780
aaacagccac agcctctttt ctaagtggtt ttcggaaagt ggcaagctgg taaccaagat 840
gtttcagaag attcaggatt tgattgatga taaagacgcc ctggtgttcg tgctgattga 900
tgaggtggag agtctcacag ccgcccgaaa tgcctgcagg gcgggcaccg agccatcaga 960
tgccatccgc gtggtcaatg ctgtcttgac ccaaattgat cagattaaaa ggcattccaa 1020
tgttgtgatt ctgaccactt ctaacatcac cgagaagatc gacgtggcct tcgtggacag 1080
ggctgacatc aagcagtaca ttgggccacc ctctgcagca gccatcttca aaatctacct 1140
ctcttgtttg gaagaactga tgaagtgtca gatcatatac cctcgccagc agctgctgac 1200
cctccgagag ctagagatga ttggcttcat tgaaaacaac gtgtcaaaat tgagccttct 1260
tttgaatgac atttcaagga agagcgaggg cctcagcggc cgggtcctga gaaaactccc 1320
ctttctggct catgcgctgt atgtccaggc ccccaccgtc accatagagg ggttcctcca 1380
ggccctgtct ctggcagtgg acaagcagtt tgaagagaga aagaagcttg cagcttacat 1440
ctgatcctgg gcttccccat ctggtgcttt tcccatggag aacacacaac cagtaagtga 1500
ggttgcccca cacagccgtc tcccagggaa tcccttctgc aaaccaaacg ttacttagac 1560
tgcaagctag aaagccacca aggccaggct ttgttaaaag aagtgtattc tatttatgtt 1620
gttttaaaat gcatactgag agacaaacat cttgtcattt tcactgtttg taaaagataa 1680
ttcagattgt ttgtctcctt gtgaagaacc atcgaaacct gtttgttccc agcccacccc 1740
cagtggatgg gatgcataat gccagcaagt tttgtttaac agcaaaaaag gaagattaat 1800
gcaggtgtta tagaagccag aagagaaact gtgtcaccct aaagaagcat ataatcatag 1860
cattaaaaat gcacacatta ctccaggtgg aaggtggcaa ttgctttctg atatcagctc 1920
gtttgattta gtgcaaaaat gttttcaaga ctatttaatg gatgtaaaaa agcctatttc 1980
tacattatac caactgagaa aaaaatggtc ggtaaagtgt tctttcataa taaataatca 2040
gacatggtcc catttgcagg aaaagtgcag actctgagtg ttccagggaa acacatgctg 2100
gacatccctt gtaacccggt atgggcgccc ctgcattgct gggatgtttc tgcccacggt 2160
tttgtttgtg caataacgtt atcacatttc taatgaggat tcacattaat ataatataaa 2220
ataaataggt cagttactgg tctctttctc cgaatgttat gttttgcttt tatctcacag 2280
taaaataaat ataattaatg gtttgcatgt gaaattcact tttgaaagaa catgttacct 2340
taccttttgt tttagaagtt ttcaagtatt aaaatatttt ttagaatttt aaaaaaaaaa 2400
aaaaaaaa 2408

<210> SEQ ID NO 94
<211> LENGTH: 12608
<212> TYPE: DNA
<213> ORGANISM: Homo sapiens

<400> SEQUENCE: 94
cgcgccgggg cctggtgctc ggtcggcggg tgctgccgct ttaagcgggg gcgggactgc 60
gcgcggccga gcggttgcga cgagggctcg gctgggggtc gccggggtcg cgggccgggc 120
ctgcaggagc cgggccgccg aggtcggggc tggttgaact catggacctg atacttttct 180
cttgagaagc aaaccagccc aaaagaaaaa tggcgtttgt tgcaacacag ggggccacgg 240
tggttgacca gaccactttg atgaaaaagt accttcagtt tgtggcagct ctcacagatg 300
tgaatacacc tgatgaaaca aagttgaaaa tgatgcaaga agttagtgaa aattttgaga 360
atgtcacgtc atctcctcag tattctacat tcctagaaca tatcatccct cgattcctta 420

-continued

```
catttctcca agatggagaa gttcagtttc ttcaggagaa accagcacag caactgcgga    480
agctcgtact tgaaataatt catagaatac caaccaacga acatcttcgt cctcacacaa    540
aaaatgtttt gtctgtgatg tttcgctttt tagagacgga aatgaagaa aatgttctta     600
tttgtctaag aataattatt gagctacaca aacagttcag gccaccgatc acacaagaaa    660
ttcatcattt tctggatttt gtgaaacaga tttacaagga gcttccaaaa gtagtgaacc    720
gctactttga gaaccctcaa gtgatccccg agaacacagt gcctccccca gaaatggttg    780
gtatgataac aacgattgct gtgaaagtca acccggagcg tgaggacagt gagactcgaa    840
cacattccat cattccgagg ggatcacttt ctctgaaagt gttggcagaa ttgcccatta    900
ttgttgtttt aatgtatcag ctctacaaac tgaacatcca caatgttgtt gctgagtttg    960
tgcccttgat catgaacacc attgccattc aggtgtctgc acaagcgagg caacataagc   1020
tttacaacaa ggagttgtat gctgacttca ttgctgctca gattaaaaca ttgtcatttt   1080
tagcttacat tatcaggatt taccaggagt tggtgactaa gtattctcag cagatggtga   1140
aaggaatgct ccagttactt tcaaattgtc cagcagagac tgcacacctc agaaaggagc   1200
ttctgattgc tgccaaacac atcctcacca cagagctgag aaaccagttc attccttgca   1260
tggacaagct gtttgatgaa tccatactaa ttggctcagg atatactgcc agagagactc   1320
taaggcccct cgcctacagc acgctggccg acctcgtgca ccatgtccgc cagcacctgc   1380
ccctcagcga cctctccctc gccgtccagc tcttcgccaa gaacatcgac gatgagtccc   1440
tgcccagcag catccagacc atgtcctgca agctcctgct gaacctggtg gactgcatcc   1500
gttccaagag cgagcaggag agtggcaatg ggagagacgt cctgatgcgg atgctggagg   1560
ttttcgttct caaattccac acaattgctc ggtaccagct ctctgccatt tttaagaagt   1620
gtaagcctca gtcagaactt ggagccgtgg aagcagctct gcctggggtg cccactgccc   1680
ctgcagctcc tggccctgct ccctccccag cccctgtccc tgccccacct ccaccccccgc   1740
ccccaccccc acctgccacc cctgtgaccc cggcccccgt gcctcccttc gagaagcaag   1800
gagaaaagga caaggaagac aagcagacat tccaagtcac agactgtcga agtttggtca   1860
aaaccttggt gtgtggtgtc aagacaatca cgtggggcat aacatcatgc aaagcacctg   1920
gtgaagctca gttcattccc aacaagcagt tacaacccaa agagacacag atttacatca   1980
aacttgtgaa atatgcaatg caagctttag atatttatca ggtccagata gcaggaaatg   2040
gacagacata catccgtgtg gccaactgcc agactgtgag aatgaaagag gagaaggagg   2100
tattggagca tttcgctggt gtgttcacaa tgatgaaccc cttaacgttc aaagaaatct   2160
tccaaactac ggtcccttat atggtggaga gaatctcaaa aaattatgct cttcagattg   2220
ttgccaattc cttcttggca aatcctacta cctctgctct gtttgctacg attctggtgg   2280
aatatctcct tgatcgcctg ccagaaatgg gctccaacgt ggagctctcc aacctgtacc   2340
tcaagctgtt caagctggtc tttggctctg tctccctctt tgcagctgaa aatgaacaaa   2400
tgctgaagcc tcacttgcac aagattgtga acagctctat ggagctcgcg cagactgcca   2460
aggaacccta caactacttc ttgctgctac gggcgctgtt tcgctctatt ggtggaggta   2520
gccacgatct cttgtatcag gagttcttgc ctctccttcc aaacctcctg caagggctga   2580
acatgcttca gagtggcctg cacaagcagc acatgaagga cctctttgtg gagctgtgtc   2640
tcaccgtccc tgtgcggctg agctcgcttt tgccgtacct gcccatgctt atggatccct   2700
tggtgtctgc actcaatggg tctcagacat tggtcagcca aggcctcagg acgctggagc   2760
tgtgtgtgga caacctgcag cccgacttcc tctacgacca catccagccg gtgcgcgcag   2820
```

-continued

```
agctcatgca ggctctgtgg cgcaccttac gcaaccctgc tgacagcatc tcccacgtgg   2880
cctaccgtgt gctcggtaag tttggcggca gtaacaggaa gatgctgaag gagtcgcaga   2940
agctgcacta cgttgtgacc gaggttcagg gccccagcat cactgtggag ttttccgact   3000
gcaaagcttc tctccagctc cccatggaga aggccattga aactgctctg gactgcctga   3060
aaagcgccaa cactgagccc tactaccgga ggcaggcgtg ggaagtgatc aaatgcttcc   3120
tggtggccat gatgagcctg gaggacaaca agcacgcact ctaccagctc ctggcacacc   3180
ccaactttac agaaaagacc atccccaatg ttatcatctc acatcgctac aaagcccagg   3240
acactccagc ccggaagact tttgagcagg ccctgacagg cgccttcatg tctgctgtca   3300
ttaaggacct gcggcccagc gccctgccct ttgtcgccag cttgatccgc cactatacga   3360
tggtggcagt cgcccagcag tgtggccctt tcttgctgcc ttgctaccag gtgggcagcc   3420
agcccagcac agccatgttt cacagtgaag aaaatggctc gaaaggaatg gatcctttgg   3480
ttctcattga tgcaattgct atttgtatgg catatgaaga aaaggagctt tgcaaaatcg   3540
gggaggtggc cctagctgtg atatttgatg ttgcaagtat catcctgggc tccaaggaga   3600
gggcctgcca gctgcccctg ttttcttaca tcgtggagcg cctgtgtgca tgttgttatg   3660
aacaggcgtg gtatgcaaag ctgggggggtg tggtgtctat taagtttctc atggagcggc   3720
tgcctctcac ttgggttctc cagaaccagc agacattcct gaaagcactt ctctttgtca   3780
tgatggactt aactggagag gtttccaatg gggcagtcgc tatggcaaag accacgctgg   3840
agcagcttct gatgcggtgc gcaacgcctt taaaagacga ggagagagcc gaagagatcg   3900
tggccgccca ggaaaagtct ttccaccatg tgacacacga cttggttcga gaagtcacct   3960
ctccaaactc cactgtgagg aagcaggcca tgcattcgct gcaggtgttg gcccaggtca   4020
ctgggaagag tgtcacggtg atcatggaac cccacaaaga ggtcctgcag gatatggtcc   4080
cccctaagaa gcacctgctc cgacaccagc ctgccaacgc acagattggc ctgatggagg   4140
ggaacacgtt ctgtaccacg ttgcagccca ggctcttcac aatggacctt aacgtggtgg   4200
agcataaggt gttctacaca gagctgttga atttgtgtga ggctgaagat tcagctttaa   4260
caaagctgcc ctgttataaa agccttccgt cactcgtacc tttacgaatt gcggcattaa   4320
atgcacttgc tgcctgcaat taccttcctc agtccaggga gaaaatcatc gctgcactct   4380
tcaaagccct gaattccacc aatagtgagc tccaagaggc cggagaagcc tgtatgagaa   4440
agtttttaga aggtgctacc atagaagtcg atcaaatcca cacacatatg cgacctttgc   4500
tgatgatgct gggagattac cggagcttga cgctgaatgt tgtgaatcgc ctgacttcgg   4560
tcacgaggct cttcccaaat tccttcaatg ataaattttg tgatcagatg atgcaacatc   4620
tgcgcaagtg gatggaagtg gtggtgatca cccacaaagg gggccagagg agcgacggaa   4680
acgaaatgaa gatttgctca gcaattataa acctttttca tctgatcccg gctgctcctc   4740
agacactggt gaagcctttg ctagaggttg tcatgaaaac ggagcgggcg atgctgatcg   4800
aggcggggag tccattccga gagcccctga tcaagttcct gactcgacat ccctcgcaga   4860
cagtggagct gttcatgatg gaagccacac tgaacgatcc ccagtggagc agaatgttta   4920
tgagtttttt aaaacacaaa gacgccagac ctctgcggga tgtgctggct gccaacccca   4980
acaggttcat caccctgctg ctgccggggg gtgcccagac ggctgtgcgc cccggttcgc   5040
ccagcaccag caccatgcgc ctggacctcc agttccaggc catcaagatc ataagcatta   5100
tagtgaaaaa cgatgactcc tggctggcca gccagcactc tctggtgagc cagttgcgac   5160
```

-continued

```
gtgtgtgggt gagtgagaac ttccaagaga ggcaccgcaa ggagaacatg gcagccacca   5220
actggaagga gcccaagctg ctggcctact gcctgctgaa ctactgcaaa aggaattacg   5280
gagatataga attgctgttc cagctgctcc gagcctttac tggtcgtttt ctctgcaaca   5340
tgacattctt aaaagagtat atggaggaag agattcccaa aaattacagc atcgctcaga   5400
aacgtgccct gttctttcgc tttgtagact tcaacgaccc caacttcgga gatgaattaa   5460
aagctaaagt tctgcagcat atcttgaatc ctgctttctt gtacagcttt gagaaggggg   5520
aaggagagca gctcttggga cctcccaatc cagaaggaga taacccagaa agcatcacca   5580
gtgtgtttat taccaaggtc ctggaccccg agaagcaggc ggacatgctg gactcgctgc   5640
ggatctacct gctgcagtac gccacgctgc tggtggagca cgccccccac cacatccatg   5700
acaacaacaa gaaccgcaac agcaagctgc gccgcctcat gaccttcgcc tggccctgcc   5760
tgctctccaa ggcctgcgtg gacccagcct gcaagtacag cggacacttg ctcctggcgc   5820
acattatcgc caaattcgcc atacacaaga agatcgtcct gcaggttttt catagtctcc   5880
tcaaggctca cgcaatggaa gctcgagcga tcgtcagaca ggcgatggcc attctgaccc   5940
cggcggtgcc ggccaggatg gaggacgggc accagatgct gacccactgg acccggaaga   6000
tcattgtgga ggaggggcac accgtcccgc agctggtcca cattctgcac ctgatagtgc   6060
aacacttcaa ggtgtactac ccggtacggc accacttggt gcagcacatg gtgagcgcca   6120
tgcagaggct gggcttcacg cccagtgtca ccatcgagca gaggcggctg gccgtggacc   6180
tgtctgaagt cgtcatcaag tgggagctgc agaggatcaa ggaccagcag ccggattcag   6240
atatggaccc aaattccagt ggagaaggag tcaattctgt ctcatcctcc attaagagag   6300
gcctgtccgt ggattctgcc caggaagtga aacgctttag gacggccacc ggagccatca   6360
gtgcagtctt tgggaggagc cagtcgctac ctggagcaga ctctctcctc gccaagccca   6420
ttgacaagca gcacacagac actgtggtga acttccttat ccgcgtggcc tgtcaggtta   6480
atgacaacac caacacagcg gggtcccctg gggaggtgct ctctcgccgg tgtgtgaacc   6540
ttctgaagac tgcgttgcgg ccagacatgt ggcccaagtc cgaactcaag ctgcagtggt   6600
tcgacaagct gctgatgact gtggagcagc caaaccaagt gaactatggg aatatctgca   6660
cgggcctaga agtgctgagc ttcctgctaa ctgtcctcca gtccccagcc atcctcagta   6720
gcttcaaacc tctgcagcgt ggaattgccg cctgcatgac atgtggaaac accaaggtgt   6780
tgcgagccgt ccacagcctt ctctcgcgcc tgatgagcat ttcccaaca gagccgagta   6840
cttccagtgt ggcctccaaa tatgaagagc tggagtgcct ctacgcagcc gtcggaaagg   6900
tcatctatga agggctcacc aactacgaga aggccaccaa tgccaatccc tcccagctct   6960
tcgggaccct tatgatcctc aagtctgcct gcagcaacaa ccccagctac atagacaggc   7020
tgatctccgt ctttatgcgc tccctgcaga agatggtccg ggagcattta aaccctcagg   7080
cagcgtcagg aagcaccgaa gccacctcag gtacaagcga gctggtgatg ctgagtctgg   7140
agctggtgaa gacgcgcctg gcagtgatga gcatggagat gcggaagaac ttcatccagg   7200
ccatcctgac atccctcatc gaaaaatcac cagatgccaa aatcctccgg gctgtggtca   7260
aaatcgtgga agaatgggtc aagaataact ccccaatggc agccaatcag acacctacac   7320
tccgggagaa gtccattttg cttgtgaaga tgatgactta catagaaaaa cgctttccgg   7380
aagaccttga attaaatgcc cagtttttag atcttgttaa ctatgtctac agggatgaga   7440
ccctctctgg cagcgagctg acggcgaaac ttgagcctgc ctttctctct gggctgcgct   7500
gtgcccagcc actcatcagg gcaaagtttt tcgaggtttt tgacaactcc atgaaacgtc   7560
```

```
gtgtctacga gcgcttgctc tatgtgacct gttcgcagaa ctgggaagcc atggggaacc   7620
acttctggat caagcagtgc attgagctgc ttctggccgt gtgtgagaag agcaccccca   7680
ttggcaccag ctgccaagga gccatgctcc cgtccatcac caacgtcatc aacctggccg   7740
atagccacga ccgtgccgcc ttcgccatgg tcacacatgt caagcaggag ccccgggagc   7800
gggagaacag cgagtccaaa gaggaggatg tagagataga catcgaacta gctcctgggg   7860
atcagaccag cacgcccaaa accaaagaac tttcagaaaa ggacattgga aaccagctgc   7920
acatgctaac caacaggcac gacaagtttc tggacactct ccgagaggtg aagactggag   7980
cgctgctcag cgctttcgtt cagctgtgcc acatttccac gacgctggca gagaagacgt   8040
gggtccagct tttccccaga ttgtggaaga tcctctctga cagacagcag catgcactcg   8100
cgggtgagat aagtccattt ctgtgcagcg gcagtcacca ggtgcagcgg gactgccagc   8160
ccagcgcgct gaactgcttt gtggaagcca tgtcccagtg cgtgccgcca atccccatcc   8220
gaccctgcgt cctgaagtac ctggggaaga cacacaacct ctggttccgg tccacgctga   8280
tgttggagca ccaggctttt gaaaagggtc tgagtcttca gattaagccg aagcaaacaa   8340
cggagtttta tgagcaggag agcatcaccc cgccgcagca ggagatactg gattcccttg   8400
cggagcttta ctccctgtta caagaggaag atatgtgggc tggtctgtgg cagaagcggt   8460
gcaagtactc ggagacagcg actgcgattg cttacgagca gcacgggttc tttgagcagg   8520
cacaagaatc ctatgaaaag gcaatggata aagccaaaaa agaacatgag aggagtaacg   8580
cctcccctgc tattttccct gaataccagc tctgggaaga ccactggatt cgatgctcca   8640
aggaattgaa ccagtgggaa gccctgacgg agtacggtca gtccaaaggc cacatcaacc   8700
cctacctcgt cctggagtgc gcctggcggg tgtccaactg gactgccatg aaggaggcgc   8760
tggtgcaggt ggaagtgagc tgtccgaagg agatggcctg gaaggtgaac atgtaccgcg   8820
gatacctggc catctgccac cccgaggagc agcagctcag cttcatcgag cgcctggtgg   8880
agatggccag cagcctggcc atccgcgagt ggcggcggct gccccacgta gtgtcccacg   8940
tgcacacgcc tctcctacag gcagcccagc aaatcatcga actccaggaa gctgcacaaa   9000
tcaacgcagg cttacagcca accaacctgg gaaggaacaa cagcctgcac gacatgaaga   9060
cggtggtgaa gacctggagg aaccgactgc ccatcgtgtc tgacgacttg tcccactgga   9120
gcagcatctt catgtggagg cagcatcatt accaggcgat tgtaactgcc tatgagaata   9180
gctctcagca tgatcccagt tcaaataacg ctatgcttgg ggttcatgca tcagcttcag   9240
cgatcatcca gtatggaaaa atcgcccgga aacaaggact ggtcaatgta gctctggata   9300
tattaagtcg gattcatact attccaactg ttcctatcgt ggattgcttc cagaagattc   9360
gacagcaagt taaatgctac ctccagctgg caggcgtcat gggcaaaaac gagtgcatgc   9420
agggccttga agttattgaa tctacaaatt taaaatactt cacaaaagag atgacagccg   9480
aattttatgc actgaaggga atgttcttgg ctcagatcaa caagtccgag gaggcaaaca   9540
aagccttctc tgcagctgtg cagatgcacg atgtgctggt gaaagcctgg gccatgtggg   9600
gcgactacct ggagaacatc tttgtgaagg agcggcagct gcacctgggc gtgtctgcca   9660
tcacctgcta cctgcacgcc tgccggcatc agaacgagag caaatcgagg aaatacttag   9720
ccaaggtgct gtggcttttg agttttgatg atgacaaaaa cactttggca gatgccgtcg   9780
acaagtactg cattggtgtg ccacccatcc agtggctggc ctggatccca cagctgctca   9840
cctgcctggt tggctcggag ggaaagctgc tcttgaacct cattagccag gttggacgcg   9900
```

-continued

```
tgtatcccca agcggtctac tttcccatcc ggaccctgta cctgaccctg aaaatagaac   9960
agcgggaacg ctacaagagc gatccagggc ccataagagc aacagcaccc atgtggcgct  10020
gcagccgaat catgcacatg cagcgagagc tccaccccac ccttctgtct tccctggaag  10080
gcatcgtcga tcagatggtc tggttcagag aaaattggca tgaagaggtt ctcaggcagc  10140
tccaacaggg cctggcgaaa tgttactccg tggcgtttga gaaaagtgga gcggtgtccg  10200
atgctaaaat cacccccac actctcaatt ttgtgaagaa gttggtgagc acgtttgggg  10260
tgggcctgga gaatgtgtcc aacgtctcga ccatgttctc cagcgcagcc tctgagtctc  10320
tggcccggcg ggcgcaggcc actgcacaag accctgtctt tcagaagctg aaaggccagt  10380
tcacgacgga ttttgacttc agcgttccag gatccatgaa gcttcataat cttatttcta  10440
agttgaaaaa gtggatcaaa atcttggagg ccaagaccaa gcaactcccc aaattcttcc  10500
tcatagagga aaagtgccgg ttcttgagca atttctcggc acagacagct gaagtggaaa  10560
ttcctgggga gtttctgatg ccaaagccaa cgcattatta catcaagatt gcacggttca  10620
tgccccgggt agagattgtg cagaagcaca acaccgcagc ccggcggctg tacatccggg  10680
gacacaatgg caagatctac ccatacctcg tcatgaacga cgcctgcctc acagagtcac  10740
ggcgagagga gcgtgtgttg cagctgctgc gtctgctgaa cccctgtttg gagaagagaa  10800
aggagaccac caagaggcac ttgtttttca cagtgccccg ggttgtggca gtttccccac  10860
agatgcgcct cgtggaggac aacccctctt cactttccct tgtggagatc tacaagcagc  10920
gctgcgccaa gaagggcatc gagcatgaca accccatctc ccgttactat gaccggctgg  10980
ctacggtgca ggcgcgggga acccaagcca gccaccaggt cctccgcgac atcctcaagg  11040
aggttcagag taacatggtg ccgcgcagca tgctcaagga gtgggcgctg cacaccttcc  11100
ccaatgccac ggactactgg acgttccgga agatgttcac catccagctg gctctgatag  11160
gcttcgcgga attcgtcctg catttaaata gactcaaccc cgagatgtta cagatcgctc  11220
aggacactgg caaactgaat gttgcctact ttcgatttga cataaacgac gcgactggag  11280
acctggatgc caaccgtcct gtcccatttc gactcacgcc caacatttct gagtttctga  11340
ccaccatcgg ggtctccggc ccgttgacag cgtccatgat tgcggtcgcc cggtgcttcg  11400
cccagccaaa ctttaaggtg gatggcattc tgaaaacggt tctccgggac gagatcattg  11460
cttggcacaa aaaaacacaa gaggacacgt cctctcctct ctcggccgcc gggcagccag  11520
agaacatgga cagccagcaa ctggtgtccc tggttcagaa agccgtcacc gccatcatga  11580
cccgcctgca caacctcgcc cagttcgaag gcggggaaag caaggtgaac accctggtgg  11640
ccgcggcaaa cagcctggac aatctgtgcc gcatggaccc cgcctggcac ccctggctgt  11700
gactgtggcc gccacggcca cccggaatgt gaagggcgct ccgggctctg agcccgcagc  11760
ttttacgact tctccctgcc tcgttcctta tattcacaga agccccatag tttcactggg  11820
ttgcggttat tttcctggta gtttgcgtgt aagaaaggga gaatatagtt ttagaggaag  11880
ctgaactatg acgatgctgg gcgaagcggt tggaaatggc agagctgaaa cttattccaa  11940
gctttcaaaa taatctttta agaagccagg attctccggt ctggaatttc tgagtgagtc  12000
cttttttat ggtgtcctcc ctctgtgaat gtacaggcgg aactgtacga acagctccct  12060
tccatccatt tttaactctt tcggaaataa cacctcacag cagcttcgtg cttttgtaca  12120
gacctttgta acaagtgtac agaaaactca ttttgtttga gaaacaggag ttgatgaacc  12180
catcatgctg gtttttctct gagcacaaag ttttaggctg tacacagcca gccttgggaa  12240
tctcgttgag cgttcggcgt ggatccacgg ggccaggcca ccctgcggga gcgccacacg  12300
```

```
catccacttc ggattcagtg ggtgaagaca gaactctgag agtctgcagg cggctcctgt  12360
gctttttatt tctggctctt cggatgtctt ctagacattt actatcactg cacctgaaga  12420
aaaaatcact tttaccttcc taatttaaaa agacaaaaca gaaatgtacg ttccttcgct  12480
agctttagtc tttctgttcc catttttata aatctgagca ttgataatgt tctatctaaa  12540
tttgtacagt gtgatttttt tttttagaat aaatatttta taaaagggtt aaaaaaaaaa  12600
aaaaaaaa                                                           12608
```

<210> SEQ ID NO 95
<211> LENGTH: 2914
<212> TYPE: DNA
<213> ORGANISM: Homo sapiens

<400> SEQUENCE: 95

```
gatttcagtt gaaagatgtg tttttgtgag tagagcaccg cagaagaact gaagactgtt     60
gtgtgctccc cgcagaaggg gctaccatga tcctttcctc ctataacacc atccagtcgg    120
ttttctgttg ctgctgttgc tgttcagtgc agaagcgaca aatgagaaca cagataagcc    180
tgagcacaga tgaagagctt ccagaaaaat acacccagcg tcgcaggccg tggctcagcc    240
aattgtcaaa taagaagcaa tccaacacgg gccgtgtgca gccgtcaaaa cgaaagccac    300
tgcctcccct cccaccctct gaggttgctg aagagaagat ccaagtcaag gcactttatg    360
atttctgcc cagagaaccc tgtaatttag ccttaaggag agcagaagaa tacctgatac     420
tggagaaata caatcctcac tggtggaagg caagagaccg tttggggaat gaaggcttaa    480
tcccaagcaa ctatgtgact gaaaacaaaa taactaattt agaaatatat gagtggtacc    540
atagaaacat taccagaaat caggcagaac atctattgag acaagagtct aaagaaggtg    600
catttattgt cagagattca agacatttag gatcctacac aatttccgta tttatgggag    660
ctagaagaag tacggaggct gccataaaac attatcagat aaaaaagaat gactcaggac    720
agtggtatgt ggctgaaaga cacgcctttc aatcaatccc tgagttaatc tggtatcacc    780
agcacaatgc agccggtctc atgactcgtc tccgatatcc agttgggctg atgggcagtt    840
gtttaccagc cacagctggg tttagctacg aaaagtggga gatagatcca tctgagttgg    900
cttttataaa ggagattgga agcggtcagt ttggagtggt ccatttaggt gaatggcggt    960
cacatatcca ggtagctatc aaggccatca atgaaggctc catgtctgaa gaggatttca   1020
ttgaagaggc caaagtgatg atgaaattat ctcattcaaa gctagtgcaa ctttatggag   1080
tctgtataca gcggaagccc ctttacattg tgacagagtt catggaaaat ggctgcctgc   1140
ttaactatct cagggagaat aaaggaaagc ttaggaagga aatgctactg agtgtatgcc   1200
aggatatatg tgaaggaatg gaatatctgg agaggaatgg ctatattcat agggatttgg   1260
cggcaaggaa ttgtttggtc agttcaacat gcatagtaaa aatttcagac tttggaatga   1320
caaggtacgt tttggatgat gagtatgtca gttcttttgg agccaagttc ccaatcaagt   1380
ggtcccctcc tgaagttttt cttttcaata agtacagcag taaatctgat gtctggtcat   1440
ttggagtttt aatgtgggaa gtttttacag aaggaaaaat gccttttgaa aataagtcaa   1500
atttgcaagt cgtggaagct atttctgaag gcttcaggct atatcgccct cacctggcac   1560
caatgtccat atatgaagtc atgtacagct gctggcatga gaaacctgaa ggccgcccta   1620
catttgccga gctgctgcgg gctgtcacag agattgcgga aacctggtga ccggaaacag   1680
aatgccaacc caaagagtca tcttgcaaaa ctgtcattta ttgtgaatat cttcaccata   1740
```

tggggtcact tatggtgaat atctttcttc agagttgctg actcttgaaa acagtgcaaa 1800
gatcacagtt tttaaaagtt ttaaaaattt aagaatattc acacaatcgt ttttctatgt 1860
gtgagaggga tttgcacact cttatttttc tgtaaaatat ttcacatccc aaatgtgaag 1920
aagtgaaaaa gacttcgcag cagtcttcat tgtggtgctc ttcatgatca tagccccagg 1980
aacccttgag gttcttcttc acaaggctga gagtgcttcc ttcttgaaga cgagtgacat 2040
tcatcacttc agtgatccat gcatagaata tgaaaataaa ttcttccaac tcatgggata 2100
aaggggactc ccttgaagaa tttcatgttt ttgggctgta tagctcttta cagaaaatgc 2160
acctttataa atcacatgaa tgttagtatt ctggaaatgt cttttgttaa tataatcttc 2220
ccatgttatt taacaaattg tttttgcaca tatctgatta tattgaaagc agtttttttgc 2280 attcgagttt taaacactgt tataaaatgt agccaaagct cacctttgaa cagatcccgg 2340
tgacattcta tttccaggaa aatccggaac ctgattttag ttctgtgatt ttacactttt 2400
tacatgtgag attggacagt ttcagaggcc ttattttgtc atactaagtg tctcctgtaa 2460
ttttcaggaa gatgatttgt tctttccaga agaggagaca aaagcaagat agccaaatgt 2520
gacatcaagc tccattgttt cggaaatcca ggattttgaa ttcgagatga aacaaccagc 2580
aatcacagtt aaatcttaac tttgcctgca ctctttgtag gaatgatcag aaatttatct 2640
ttatcattct gagtgcttca ggagtacaat aggaagaaag atactggaga aagcactaat 2700
gtaatcacca tgaagtctga caacaggagc ccattatttg cgtactgtcc caccctgtat 2760
catggttctc tgggaacaag ctttatgatt ctcattagag tttatttgtt gattgtcagt 2820
agttgcgact tttaaattat atttccccca ctcaaagaat ggtatcttta tatatcaatg 2880
acattcaata aatgtgtatt atttctaatg agaa 2914

<210> SEQ ID NO 96
<211> LENGTH: 2871
<212> TYPE: DNA
<213> ORGANISM: Homo sapiens

<400> SEQUENCE: 96
gcccgcgcca gggtcctcgg agctgctctg gctgcgcgcg gagcgggctc cggagggaag 60
tcccgagaca aagggaagcg ccgccgccgc cgccccgctc ggtcctccac ctgtccgcta 120
cgctcgccgg ggctgcggcc gcccgaggga ctttgaacat gtcggggatc gccctcagca 180
gactcgccca ggagaggaaa gcatggagga aagaccaccc atttggtttc gtggctgtcc 240
caacaaaaaa tcccgatggc acgatgaacc tcatgaactg ggagtgcgcc attccaggaa 300
agaaagggac tccgtgggaa ggaggcttgt ttaaactacg gatgcttttc aaagatgatt 360
atccatcttc gccaccaaaa tgtaaattcg aaccaccatt atttcacccg aatgtgtacc 420
cttcggggac agtgtgcctg tccatcttag aggaggacaa ggactggagg ccagccatca 480
caatcaaaca gatcctatta ggaatacagg aacttctaaa tgaaccaaat atccaagacc 540
cagctcaagc agaggcctac acgatttact gccaaaacag agtggagtac gagaaaaggg 600
tccgagcaca agccaagaag tttgcgccct cataagcagc gaccttgtgg catcgtcaaa 660
aggaagggat tggtttggca agaacttgtt tacaacattt ttgcaaatct aaagttgctc 720
catacaatga ctagtcacct ggggggggttg ggcgggcgcc atcttccatt gccgccgcgg 780
gtgtgcggtc tcgattcgct gaattgcccg tttccataca gggtctcttc cttcggtctt 840
ttgtattttt gattgttatg taaaactcgc ttttatttta atattgatgt cagtatttca 900
actgctgtaa aattataaac ttttatactt gggtaagtcc cccaggggcg agttcctcgc 960
tctgggatgc aggcatgctt ctcaccgtgc agagctgcac ttggcctcag ctggctgtat 1020
ggaaatgcac cctccctcct gccgctcctc tctagaacct tctagaacct gggctgtgct 1080
gcttttgagc ctcagacccc aggtcagcat ctcggttctg cgccacttcc tttgtgttta 1140
tatggcgttt tgtctgtgtt gctgtttaga gtaaataaac tgtttatata aaggttttgg 1200
ttgcattatt atcattgaaa gtgagaggag gcggcctccc agtgcccggc cctccccacc 1260
cacctgcagc cccaccgcgg gccaggacca ggctctccat ctgcttcgga tgcacgcagg 1320
ctgtgaggct ctgtcttgcc ctggatcttt gtaaacaggg ctgtgtacaa agtgctgctg 1380
aggtttctgt gctccccgca tctgcgggct gtagagcgct gggcagctaa gatctgcata 1440
ggtcgggatt ggcatcgaga ccctggcaac tgcaccggtg ccagctgtct tgggggccac 1500
aaggccaggt ccagaccagg gctgggggct gcctgaggac tcctatccgg gcagcctgct 1560
ggcgggggtt cccctcttca gtggccaggt cacagggatg gagctgcgct gtgcataggg 1620
tgccacctca ggtgtctgtc ccttgtgtcc tcaggaggca gccttgctac cacccgtggc 1680
aaacgccagg tgctttttct gggagagccc acagccgtgg ccctccaggg cttccccgac 1740
ccttagcgcc aggtagaggg ccctgggcag cctgtgtctg gaattcttcg tcctgaggcc 1800
acctgagtgt ggtctgtcct ggggaggctg tgcgcctcag cagccgtcct gacgctgagc 1860
cctctgcaaa ggttgggccg gccaggcctc ttggggctgc ctgagccact gcaggaagtg 1920
gcctggctgg gaagttgggt gccggtcacc tcccagcagg aaggcacagt ggacagagat 1980
gggaagccct gggggacaca gcccggtgct cccagccctc caacctctgg ctcccaaccc 2040
agtctcccca tcctagcgag cttggccctc ctcagtttcg tttcaagcct tggggctgga 2100
gctggccctg ctgccctggc accccccggt ggctggagct gggtccccgt ggcccaagtg 2160
cagggtccca agagggcagg gcggggctcc ccaaaggagc aaagaatgca gggagggcgg 2220
tccagggccc tgggaagggg agctcggcac cctccaggtc cgtgtgggac tccagccgct 2280
gttggctggg aatcgaagtt agaggtgact tccaaaggcc ccccgagccg gcagtgcccc 2340
ccaccacccc tccagcgact ctgcggtgcc agtgccttgt tggcttttcc ggctacgcac 2400
cctgcagtca ctgagctctc ggtctgacgt ctgatgtttg tggtttgttt ataacacggg 2460
gccttacctg gggaattcag ctggtttgaa tatttgtagc ccgctcccag aatgtcttat 2520
tttgtaatga ctgaactaca tttagtaata gttacacatg tatatggtta atacatatgg 2580
aaattcaata tattttgtag ttaacgtatt ctgaagtaac ggatgtttct cgccaatcgt 2640
agtgacttca gctaacgaaa tgttcttttg tagtaccacg gtcctcggcc taacgaagga 2700
cgtgaacctt gtaagaggag agctctgaaa cgcggtcacc tttgtttagt ggaagggaaa 2760
gtgtgttccc ggcatgaggt gcctcggaat tagtaaagaa ttgtgggcaa tggattaacc 2820
actgtatcta agaatccacc attaaagcat ttgcacagac aaaaaaaaaa a 2871

<210> SEQ ID NO 97
<211> LENGTH: 1892
<212> TYPE: DNA
<213> ORGANISM: Homo sapiens

<400> SEQUENCE: 97
cgtgagcatg gtgaagagaa gacggagccc cgcgctggga gaggaacgct tcagtccgag 60
ttccattctg cacccaaggc tcccettggt cctcctggga accagggtgc cccttagtgg 120
tggtggccca ggagaacccg accaaggcag gagcgccccc tcctggaaga gcctcgcttc 180

```
aacgcatcat cattcccggc cggcagcagg ggcgacgcca gcaaggcctg cgactcagag    240
ccagcttggc ccgttcgccc cgccccttcc cggtgtccgc cccgcccctt tcccggtgtc    300
cgccccgcct ccttcccggt gtccgccccg ccccttccc tgtgtccgcc ccgccccctt     360
ccctgtgtcc gccctgcccg cttcactgtg gtcctgcctc tgggtggtgc cggggcgggg    420
ggtgggagcc cggggcccgc gcaggcggag atgtcgccca atgggaaggg tcggtcggga    480
agggggtggg cgcaggcggg tgggcgggaa gaacgctgga ggttgattgg cggtcttgcc    540
ggccagtgaa gccagggcat gggcggggcg cggctcggag cgcgaaacat ggcggggcag    600
gacgctggct gcggccgtgg cggcgacgac tactcagagg acgagggcga cagcagcgtg    660
tccagggcgg ctgtggaggt gttcgggaag ctgaaggacc taaactgccc cttcctcgag    720
ggtctgtata tcacagagcc aaagacaatt caggaactgc tgtgcagccc ctcagagtac    780
cgcttggaga tcctagagtg gatgtgtacc cgggtctggc cctcactgca ggacaggttc    840
agctcactga aaggggtccc aacagaggtg aagatccaag aaatgacgaa gctgggccac    900
gagctgatgc tgtgtgcgcc agatgaccag gagctcctca agggctgtgc ctgcgcccag    960
aagcagctac acttcatgga ccagttgctc gataccatcc ggagcctgac cattgggtgc   1020
tccagttgct cgagcctgat ggagcacttc gaggacacca gggagaagaa cgaggccttg   1080
ctgggggagc tcttctctag cccccacctg cagatgctcc tgaatccaga gtgcgacccg   1140
tggcccctgg acatgcagcc cctcctcaac aagcagagtg atgactggca gtgggccagt   1200
gcctctgcca agtccgagga ggaggagaag ctggcggagc ttgccaggca gctgcaggag   1260
agtgctgcca agttgcacgc gcttagaacg gagtactttg cacagcatga gcaaggggct   1320
gctgcgggcg cagccgacat cagcacccta gaccagaagc tgcgtctggt cacttccgac   1380
ttccaccagc taatcttggc ttttctccaa gtctacgacg acgagctggg cgagtgctgc   1440
cagcgcccag gccctgacct ccacccgtgc ggccccatca tccaggccac gcaccagaat   1500
ctgacttcct acagccaact gctgcaagtg gtcatggcag ttgctgacac ctctgcgaag   1560
gccgtggaga ccgtgaagaa gcagcaaggc gagcagatct gctggggtgg cagcagctcc   1620
gtcatgagtc tagctaccaa gatgaatgaa ctaatggaga aatagaaagt cttcagtgat   1680
ggcctacgcc aaagcacagg atggggcggg caggaagccc tctcccaaga tcgagttggc   1740
cgaggatgga tgattgtggc agcagaagcc gttgcagccc cacgttgtgc tctaggcagg   1800
gacctttggc ccctttgggg agggagagac agacgggcgg tttgacttgg acacaaagaa   1860
agccttggtt tctaagcaaa aaaaaaaaaa aa                                1892
```

<210> SEQ ID NO 98
<211> LENGTH: 3374
<212> TYPE: DNA
<213> ORGANISM: Homo sapiens

<400> SEQUENCE: 98

```
ctgagactgg acctgaggag acctcagcct cggtgctcgg gccgccccgc ctctgccgga     60
aagtccgcgc cgccgctgcc gccaccgtcc gcagcccgag cgccccggag ccgcaggccg    120
ccgccgcgca gagacgccgc ggctgcgact aggcgcgccc agccgcacgt ggcggacccg    180
cccccaggcc cgcagtgtcc tggaccccgc aggcctccgc tctcctgtcc tcggccccgt    240
ccccagggcc gcgatgagct tcctgagccg acagcagccg ccgccacccc gccgcgccgg    300
ggcggcctgc accttgcggc agaagctgat cttctcgccc tgcagcgact gtgaggagga    360
ggaagaagag gaggaggagg agggcagcgg ccacagcacc ggggaggact cggcctttca    420
```

```
agagcccgac tcgccgctgc cgcccgcgcg gagccccacg gagcccgggc ccgagcgccg    480
ccgctcgccc gggccggccc ccggcagccc cggcgagctg gaggaggacc tgttgctgcc    540
cggcgcctgc ccgggcgcgg acgaggcggg cggtggggcg gagggcgact cgtgggagga    600
ggagggcttc ggctcctcgt cgccggtcaa gtcgccggcg gccccctact tcctgggtag    660
ctctttctcg ccggtgcgct gcggcggccc aggagatgcg tcgccgcggg gttgcggggc    720
gcgccgggcg ggcgaaggcc gccgctcgcc gcggccggac cacccgggca ccccgccaca    780
caagaccttc cgcaagctgc gactcttcga caccccgcac acgcccaaga gtttgctctc    840
caaagctcgg ggaattgatt ccagctctgt taaactccgg ggtagttctc tcttcatgga    900
tacagaaaaa tcaggaaaaa gggaatttga tgtgcgacag actcctcaag tgaatattaa    960
tcctttact ccggattctt tgttgcttca ttcctcagga cagtgtcgtc gtagaaagag   1020
aacgtattgg aatgattcct gtggtgaaga catggaagcc agtgattatg agcttgaaga   1080
tgaaacaaga cctgctaaga gaattacaat tactgaaagc aatatgaagt cccggtatac   1140
aacagaattt catgagctag agaaaatcgg ctctggagaa tttggttctg tatttaagtg   1200
tgtgaagagg ctggatggat gcatttatgc cattaagcga tcaaaaaagc cattggcggg   1260
ctctgttgat gagcagaacg ctttgagaga agtatatgct catgcagtgc ttggacagca   1320
ttctcatgta gttcgatatt tctctgcgtg ggcagaagat gatcatatgc ttatacagaa   1380
tgaatattgt aatggtggaa gtttagctga tgctataagt gaaaactaca gaatcatgag   1440
ttactttaaa gaagcagagt tgaaggatct ccttttgcaa gttggccgag gcttgaggta   1500
tattcattca atgtctttgg ttcacatgga tataaaacct agtaatattt tcatatctcg   1560
aacctcaatc ccaaatgctg cctctgaaga aggagacgaa gatgattggg catccaacaa   1620
agttatgttt aaaataggtg atcttgggca tgtaacaagg atctccagtc cacaagttga   1680
agagggcgat agtcgttttc ttgcaaatga agttttacag gagaattata cccatctacc   1740
aaaagcagat atttttgcgc ttgccctcac agtggtatgt gctgctggtg ctgaacctct   1800
tccgagaaat ggagatcaat ggcatgaaat cagacagggt agattacctc ggataccaca   1860
agtgctttcc caagaattta cagagttgct aaaagttatg attcatccag atccagagag   1920
aagaccttca gcaatggcac tggtaaagca ttcagtattg ctgtccgctt ctagaaagag   1980
tgcagaacaa ttacgaatag aattgaatgc cgaaaagttc aaaaattcac ttttacaaaa   2040
agaactcaag aaagcacaga tggcaaaagc tgcagctgag gaaagagcac tcttcactga   2100
ccggatggcc actaggtcca ccacccagag taatagaaca tctcgactta ttggaaagaa   2160
aatgaaccgc tctgtcagcc ttactatata ctgagctact cctttcccac ctccccctga   2220
acactgtgac aagaggaagc taggttgaaa tcactgatag aatccagttt gcaattactt   2280
tctcgattgg tgtcagtagt tttactgatt aggactttta ttgtgaatta cagttgaaag   2340
ctgtattttg atgattgcta tgtcaggctt tcatctaatc ttaccagtct gtcttctgta   2400
ggatgtgtca ctgttggatg ttacaccagc ctttccaggg ttaaccactg tggtggtgtg   2460
ctgcttatag tttgctgttg cattgtaata aaaggtgtct ttccctgtag tgacctgtaa   2520
aaagtactca agggctttat tacagacata ccctcccttt gaaaagggac atgctaaaag   2580
actcattact actcagcctt caatgtacct gtgtgtccat cttatatttc ttttttttt   2640
aattgtgaat tagacttgta tatcccactg ggagcacttt gtaggcattg catgaaccat   2700
gggatgatga ttctgtggag gtattgcctt gtgaatttgc tgctatttta gttttgtctt   2760
```

tgctgtaaac ttgtagcatt aaacaatcat tgttgttaat aggtcttctt tttgaaacaa 2820
ttatgtgaaa tgtatagctg cttttgatga aaagcagcta tttgcctttt tttttttttc 2880
ctttgaactt tgaagctagt gcattggaaa aatgcaccct ttccctcctt tggaatgctg 2940
tattaatgta gtataataat tactggtttt gtaacttgtt ctggtaatgt ccttcccgga 3000
ctctttttaa atgtctcccc ctaagtttta tacttgattg tattattagt ctgtttttaa 3060
atgttttgcc cggtttttct cttcaatatt tgtgtatata aaccgatctt cgtgatactg 3120
tacatagctg tttgaaatgc cagaatgact tctgacattc caagtttttc acaaaatata 3180
ttttatctgt gattagccat ttgactaata atactggcta acagatgttg aaaaaaattg 3240
tctgtttgtt ttctcattaa ttttggtcta aaacatgttt gcacttgtct ttgacttgtg 3300
ttttattaac attgattggc atattaaaag tcactctgag cttaccttaa ttgtctaaaa 3360
aaaaaaaaaa aaaa 3374

<210> SEQ ID NO 99
<211> LENGTH: 2108
<212> TYPE: DNA
<213> ORGANISM: Homo sapiens

<400> SEQUENCE: 99
aatttctttt caatattagc ttattcccaa attggctaat gggtattttt aaagccatgc 60
taaattaaag gaattcaatt ttctcactag tatttggtaa cacatgggag actatgtgtc 120
atatccagaa gagttctgta catgaactgc atttaattgc tccgagagtc actggagctt 180
tctttaatca gaatggaaat caggataagc tgaggtctta tagattggtg gtacttaagg 240
cagaaaatta acaccgtgtt ttgtagctgt tagttggtag agggaaattc aggctaccgt 300
cgcgaaacct gcaggttaag ttattttctc ctccctgctt ctgtaggttc acagcgttcc 360
cttctgatag agctttttgt ctgtgttgta aagctctttg gctgagatgg atgacaaaga 420
tattgacaaa gaactaaggc agaaattaaa cttttcctat tgtgaggaga ctgagattga 480
agggcagaag aaagtagaag aaagcaggga ggcttcgagc caaaccccag agaagggtga 540
agtgcaggat tcagaggcaa agggtacacc accttggact cccccttagca acgtgcatga 600 gctcgacaca tcttcggaaa aagacaaaga aagtccagat cagattttga ggactccagt 660
gtcacaccct ctcaaatgtc ctgagacacc agcccaacca gacagcagga gcaagctgct 720
gcccagtgac agcccctcta ctcccaaaac catgctgagc cggttggtga tttctccaac 780
agggaagctt ccttccagag gccctaagca tttgaagctc acacctgctc ccctcaagga 840
tgagatgacc tcattggctc tggtcaatat taatcccttc actccagagt cctataaaaa 900
attatttctt caatctggtg gcaagaggaa aataagagga gatcttgagg aagctggtcc 960
agaggaaggc aagggagggc tgcctgccaa gagatgtgtt ttacgagaaa ccaacatggc 1020
ttcccgctat gaaaaagaat tcttggaggt tgaaaaaatt ggggttggcg aatttggtac 1080
agtctacaag tgcattaaga ggctggatgg atgtgtttat gcaataaagc gctctatgaa 1140
aacttttaca gaattatcaa atgagaattc ggctttgcat gaagtttatg ctcacgcggt 1200
gcttgggcat cacccccatg tggtacgtta ctattcctca tgggcagaag atgaccacat 1260
gatcattcag aatgaatact gcaatggtgg gagtttgcaa gctgctatat ctgaaaacac 1320
taagtctggc aatcattttg aagagccaaa actcaaggac atccttctac agatttccct 1380
tggccttaat tacatccaca actctagcat ggtacacctg gacatcaaac ctagtaatat 1440
attcatttgt cacaaggtgc aaagtgaatc ctctggagtc atagaagaag ttgaaaatga 1500
agctgattgg tttctctctg ccaatgtgat gtataaaatt ggtgacctgg gccacgcaac 1560
atcaataaac aaacccaaag tggaagaagg agatagtcgc ttcctggcta atgagatttt 1620
gcaagaggat taccggcacc ttcccaaagc agacatattt gccttgggat taacaattgc 1680
agtggctgca ggagcagagt cattgcccac caatggtgct gcatggcacc atatccgcaa 1740
gggtaacttt ccggacgttc ctcaggagct ctcagaaagc ttttccagtc tgctcaagaa 1800
catgatccaa cctgatgccg aacagagacc ttctgcagca gctctggcca gaaatacagt 1860
tctccggcct tccctgggaa aaacagaaga gctccaacag cagctgaatt tggaaaagtt 1920
caagactgcc acactggaaa gggaactgag agaagcccag caggcccagt caccccaggg 1980
atatacccat tatggtgaca ctggggtctc tgggacccac acaggatcaa gaagcacaaa 2040
acgcctggtg ggaggaaaga gtgcaaggtc ttcaagcttt acctcaggag agcgtgagcc 2100
tctgcatt 2108

<210> SEQ ID NO 100
<211> LENGTH: 10461
<212> TYPE: DNA
<213> ORGANISM: Homo sapiens

<400> SEQUENCE: 100
ccggcccttc gcctctgggc gatgggcgac ctgtgaggcc ggtccccatc gctgggggcg 60
cgtgtgggag gaggcggccg cccgagtgac cgggagccgg gccgcggcct tccctcgccc 120
gcctcggccc ctcccactcc tctgccccgg ggccgccacc gcccgggcgt cggacctggt 180
cccgtgctcg cggtgccgcc gccctctggg cctagcccgc ccagctcggc gagcggcggc 240
agtgggagcc gcgtccgccg catccgcctc gactcggtgc cggcccctgg ccctcccctc 300
atgactgcgg cgcctctgct gccaccgccc gcccggccgc cgctcgccgc aggatggatg 360
cggaccgtgc ggcgctaacc cccgtggctc agctcccgaa tcgcccgcct tcgagccctc 420
ctcgtgagcc gcagcagcct cggtgccagc ccccgccgca gctgggccca gcggtccgcc 480
tgtccctcgt tgcggcttgt cggtgctgag tgaggcgtcg tccgggtcgg cgcgaacccg 540
cccggccgcg gttccctgca gacctctgcg cgggcggctc ggcccttcac gcccttttcg 600
ttcacgaatc cgagcccgct cgcctctctc cagcgaaccg accatgtctg gcggcgccgc 660
agagaagcag agcagcactc ccggttccct gttcctctcg ccgccggctc ctgcccccaa 720
gaatggctcc agctccgatt cctccgtggg ggagaaactg ggagccgcgg ccgccgacgc 780
tgtgaccggc aggaccgagg agtacaggcg ccgccgccac actatggaca aggacagccg 840
tggggcggcc gcgaccacta ccaccactga gcaccgcttc ttccgccgga gcgtcatctg 900
tgactccaat gccactgcac tggagcttcc cggccttcct ctttccctgc cccagcccag 960
catccccgcg gctgtcccgc agagtgctcc accggagccc caccgggaag agaccgtgac 1020
cgccaccgcc acttcccagg tagcccagca gcctccagcc gctgccgccc ctggggaaca 1080
ggccgtcgcg ggccctgccc cctcgactgt ccccagcagt accagcaaag accgcccagt 1140
gtcccagcct agccttgtgg ggagcaaaga ggagccgccg ccggcgagaa gtggcagcgg 1200
cggcggcagc gccaaggagc cacaggagga acggagccag cagcaggatg atatcgaaga 1260
gctggagacc aaggccgtgg gaatgtctaa cgatggccgc tttctcaagt ttgacatcga 1320
aatcggcaga ggctccttta agacggtcta caaaggtctg gacactgaaa ccaccgtgga 1380
agtcgcctgg tgtgaactgc aggatcgaaa attaacaaag tctgagaggc agagatttaa 1440
agaagaagct gaaatgttaa aaggtcttca gcatcccaat attgttagat tttatgattc 1500
ctgggaatcc acagtaaaag gaaagaagtg cattgttttg gtgactgaac ttatgacgtc 1560
tggaacactt aaaacgtatc tgaaaaggtt taaagtgatg aagatcaaag ttctaagaag 1620
ctggtgccgt cagatcctta aaggtcttca gtttcttcat actcgaactc cacctatcat 1680
tcaccgcgat cttaaatgtg acaacatctt tatcaccggc cctactggct cagtcaagat 1740
tggagacctc ggtctggcaa ccctgaagcg ggcttctttt gccaagagtg tgataggtac 1800
cccagagttc atggcccctg agatgtatga ggagaaatat gatgaatccg ttgacgttta 1860
tgcttttggg atgtgcatgc ttgagatggc tacatctgaa tatccttact cggagtgcca 1920
aaatgctgca cagatctacc gtcgcgtgac cagtggggtg aagccagcca gttttgacaa 1980
agtagcaatt cctgaagtga aggaaattat tgaaggatgc atacgacaaa acaaagatga 2040
aagatattcc atcaaagacc ttttgaacca tgccttcttc caagaggaaa caggagtacg 2100
ggtagaatta gcagaagaag atgatggaga aaaaatagcc ataaaattat ggctacgtat 2160
tgaagatatt aagaaattaa agggaaaata caaagataat gaagctattg agtttttcttt 2220
tgatttagag agagatgtcc cagaagatgt tgcacaagaa atggtagagt ctgggtatgt 2280
ctgtgaaggt gatcacaaga ccatggctaa agctatcaaa gacagagtat cattaattaa 2340
gaggaaacga gagcagcggc agttggtacg ggaggagcaa gaaaaaaaaa agcaggaaga 2400
gagcagtctc aaacagcagg tagaacaatc cagtgcttcc cagacaggaa tcaagcagct 2460
cccttctgct agcaccggca tacctactgc ttctaccact tcagcttcag tttctacaca 2520
agtagaacct gaagaacctg aggcagatca acatcaacaa ctacagtacc agcaacccag 2580
tatatctgtg ttatctgatg ggacggttga cagtggtcag ggatcctctg tcttcacaga 2640
atctcgagtg agcagccaac agacagtttc atatggttcc caacatgaac aggcacattc 2700
tacaggcaca gtcccagggc atataccttc tactgtccaa gcacagtctc agccccatgg 2760
ggtatatcca ccctcaagtg tggcacaggg gcagagccag ggtcagccat cctcaagtag 2820
cttaacaggg gtttcatctt cccaacccat acaacatcct cagcagcagc agggaataca 2880
gcagacagcc cctcctcaac agacagtgca gtattcactt tcacagacat caacctccag 2940
tgaggccact actgcacagc cagtgagtca gcctcaagct ccacaagtct tgcctcaagt 3000
atcagctgga aaacagcttc cagtttccca gccagtacca actatccaag gcgaacctca 3060
gatcccagtt gcgacacaac cctcggttgt tccagtccac tctggtgctc atttccttcc 3120
agtgggacag ccgctcccta ctcccttgct ccctcagtac cctgtctctc agattcccat 3180
atcaactcct catgtgtcta cggctcagac aggtttctca tcccttccca tcacaatggc 3240
agctggcatt actcagcctc tgctcacgtt ggcttcatct gctacaacag ctgcgatccc 3300
gggggtatca actgtggttc ctagtcagct tccaaccctt ctgcagcctg tgactcagct 3360
gccaagtcag gttcacccac agctcctaca accagcagtt cagtccatgg gaataccagc 3420
taaccttgga caagctgctg aggttccact ttcctctgga gatgttctgt accagggctt 3480
cccacctcga ctgccaccac agtacccagg agattcaaat attgctccct cttccaacgt 3540
ggcttctgtt tgcatccatt ctacagtcct atcccctccc atgccgacag aagtactggc 3600
tacacctggg tactttccca cagtggtgca gccttatgtg gaatcaaatc ttttagttcc 3660
tatgggtggt gtaggaggac aggttcaagt gtcccagcca ggagggagtt tagcacaagc 3720
ccccactaca tcctcccagc aagcagtttt ggagagtact cagggagtct ctcaggttgc 3780
tcctgcagag ccagttgcag tagcacagac ccaagctacc cagccgacca ctttggcttc 3840

```
ctctgtagac agtgcacatt cagatgttgc ttcaggtatg agtgatggca atgagaacgt   3900
cccatcttcc agtggaaggc atgaaggaag aactacaaaa cggcattacc gaaaatctgt   3960
aaggagtcgc tctcgacatg aaaaaacttc acgcccaaaa ttaagaattt tgaatgtttc   4020
aaataaagga gaccgagtag tagaatgtca attagagact cataatagga aaatggttac   4080
attcaaattt gacctagatg gtgacaaccc cgaggagata gcaacaatta tggtgaacaa   4140
tgactttatt ctagcaatag agagagagtc gtttgtggat caagtgcgag aaattattga   4200
aaaagctgat gaaatgctca gtgaggatgt cagtgtggaa ccagagggtg atcagggatt   4260
ggagagtcta caaggaaagg atgactatgg cttttcaggt tctcagaaat tggaaggaga   4320
gttcaaacaa ccaattcctg cgtcttccat gccacagcaa ataggcattc ctaccagttc   4380
tttaactcaa gttgttcatt ctgcgggaag gcggtttata gtgagtcctg tgccagaaag   4440
ccgattacga gaatcaaaag ttttccccag tgaaataaca gatacagttg ctgcctctac   4500
agctcagagc cctggaatga acttgtctca ctctgcatca tcccttagtc tacaacaggc   4560
cttttctgaa cttagacgtg cccaaatgac agaaggaccc aacacagcac ctccaaactt   4620
tagtcataca ggaccaacat ttccagtagt acctcctttc ttaagtagca ttgctggagt   4680
cccaaccaca gcagcagcca cagcaccagt ccctgcaaca agcagccctc ctaatgacat   4740
ttccacatca gtaattcagt ctgaggttac agtgcccact gaagagggga ttgctggagt   4800
tgccaccagc acaggtgtgg taacttcagg tggtctcccc ataccacctg tgtctgaatc   4860
accagtactt tccagcgtag tttcaagtat cacaatacct gcagttgtct caatatctac   4920
tacatccccg tcacttcaag tccccacatc cacatctgag atcgttgttt ctagtacagc   4980
actgtatcct tcagtaacag tttcagcaac ttcagcctct gcagggggca gtactgctac   5040
cccaggtcct aagcctccag ctgtagtatc tcagcaggca gcaggcagca ctactgtggg   5100
agccacatta acatcagttt ctaccaccac ttcattccca agcacagctt cacagctgtg   5160
cattcagctt agcagcagta cttctactcc tactttagct gaaaccgtgg tagttagcgc   5220
acactcacta gataagacat ctcatagcag tacaactgga ttggctttct ccctctctgc   5280
accatcttcc tcttcctctc ctggagcagg agtgtctagt tatatttctc agcctggtgg   5340
gctgcatcct ttggtcattc catcagtgat agcttctact cctattcttc cccaagcagc   5400
aggacctact tctacacctt tattacccca agtacctagt atcccacccct tggtacagcc   5460
tgttgccaat gtgcctgctg tacagcagac actaattcat agtcagcctc aaccagcttt   5520
gcttcccaac cagccccata ctcattgtcc tgaagtagat tctgatacac aacccaaagc   5580
tcctggaatt gatgacataa agactctaga agaaaagctg cggtctctgt tcagtgaaca   5640
cagctcatct ggagctcagc atgcctctgt ctcactggag acctcactag tcatagagag   5700
cactgtcaca ccaggcatcc caactactgc tgttgcacca agcaaactcc tgacttctac   5760
cacaagtact tgcttaccac caaccaattt accactagga acagttgctt tgccagttac   5820
accagtggtc acacctgggc aagtttctac cccagtcagc actactacat caggagtgaa   5880
acctggaact gctccctcca agccacctct aactaaggct ccggtgctgc cagtgggtac   5940
tgaacttcca gcaggtactc tacccagcga gcagctgcca ccttttccag gaccttctct   6000
aacccagtcc cagcaacctc tagaggatct tgatgctcaa ttgagaagaa cacttagtcc   6060
agagatgatc acagtgactt ctgcggttgg tcctgtgtcc atggcggctc caacagcaat   6120
cacagaagca ggaacacagc ctcagaaggg tgtttctcaa gtcaaagaag gccctgtcct   6180
```

-continued

```
agcaactagt tcaggagctg gtgtttttaa gatgggacga tttcaggttt ctgttgcagc   6240
agacggtgcc cagaaagagg gtaaaaataa gtcagaagat gcaaagtctg ttcattttga   6300
atccagcacc tcagagtcct cagtgctatc aagtagtagt ccagagagta ccttggtgaa   6360
accagagccg aatggcataa ccatccctgg tatctcttca gatgtgccag agagtgccca   6420
caaaactact gcctcagagg caaagtcaga cactgggcag cctaccaagg ttggacgttt   6480
tcaggtgaca actacagcaa acaaagtggg tcgtttctct gtatcaaaaa ctgaggacaa   6540
gatcactgac acaaagaaag aaggaccagt ggcatctcct ccttttatgg atttggaaca   6600
agctgttctt cctgctgtga taccaaagaa agagaagcct gaactgtcag agccttcaca   6660
tctaaatggg ccgtcttctg acccggaggc cgctttttta agtagggatg tggatgatgg   6720
ttccggtagt ccacactcgc cccatcagct gagctcaaag agccttccta gccagaatct   6780
aagtcaaagc cttagtaatt catttaactc ctcttacatg agtagcgaca atgagtcaga   6840
tatcgaagat gaagacttaa agttagagct gcgacgacta cgagataaac atctcaaaga   6900
gattcaggac ctgcagagtc gccagaagca tgaaattgaa tctttgtata ccaaactggg   6960
caaggtgccc cctgctgtta ttattccccc agctgctccc ctttcaggga gaagacgacg   7020
acccactaaa agcaaaggca gcaaatctag tcgaagcagt tccttgggga ataaaagccc   7080
ccagctttca ggtaacctgt ctggtcagag tgcagcttca gtcttgcacc cccagcagac   7140
cctccaccct cctggcaaca tcccagagtc cgggcagaat cagctgttac agccccttaa   7200
gccatctccc tccagtgaca acctctattc agccttcacc agtgatggtg ccatttcagt   7260
accaagcctt tctgctccag gtcaaggaac cagcagcaca aacactgttg ggcaacagt    7320
gaacagccaa gccgcccaag ctcagcctcc tgccatgacg tccagcagga agggcacatt   7380
cacagatgac ttgcacaagt tggtagacaa ttgggcccga gatgccatga atctctcagg   7440
caggagagga agcaaagggc acatgaatta cgagggccct ggaatggcaa ggaagttctc   7500
tgcacctggg caactgtgca tctccatgac ctcgaacctg ggtggctctg cccccatctc   7560
tgcagcatca gctacctctc taggtcactt caccaagtct atgtgccccc cacagcagta   7620
tggctttcca gctaccccat ttggcgctca atggagtggg acgggtggcc cagcaccaca   7680
gccacttggc cagttccaac ctgtgggaac tgcctccttg cagaatttca acatcagcaa   7740
tttgcagaaa tccatcagca accccccagg ctccaacctg cggaccactt agacctagag   7800
acattaactg aatagatctg gggcaggag atggaatgct gagggggtgg gtgggggtgg    7860
gaagtagcct atatactaac tactagtgct gcatttaact ggttatttct tgccagaggg   7920
gaatgttttt aatactgcat tgagccctca gaatggagag tctcccccgc tccagttatt   7980
ggaatgggag aggaaggaaa gaacagcttt tttgtcaagg ggcagcttca gaccatgctt   8040
tcctgtttat ctatactcag taatgaggat gagggctagg aaagtcttgt tcataaggaa   8100
gctggagaac tcaatgtaaa atcaaaccca tctgtaattt cgagtgggtg gagctcttgc   8160
ttttggtaca tgccctgaat ccctcactcc ctcaagaatc cgaaccacag gacaaaaacc   8220
acctactggg ctctctccta ccctgccctc ctcccttttt tttacccctc tcttttttat   8280
tttttctttg ctctttagaa cccagtgaaa aataccaggg tactggggtg caactctttc   8340
ttatgatagg tcattagtgc tttaagcaaa agatattagc agctttgact gcagcattag   8400
caattaggaa aaaaaaaaaa ttaagttccc tgcggacatg taactttgcc atcagttttg   8460
atgtggaaac actgtgatat ataaaatgtt gttggacaac agtagtttta agagtaaaat   8520
atgaaacgtt taaaaagttc caaaaaaagc tagctctgtc ctttacttat tgagacactt   8580
```

taacttttttc ctttgtattt ccattgtatt agataaataa atgtgaatgt aaaattgtat 8640
aaattactgt acttgaatac ttctgtttcc cagtgttgct tgctggacat tttagtgcct 8700
tggacttcta ttgcttctgc cattagcatc aacttaccag accccagatc aataaagggc 8760
atgtggaagg aaatcgtagg tccatgtgac cccagcagtc cagcagtggt tatgccaaag 8820
ggaaattgaa aaagtatttt tttaagtcat tcaacaactt tgtctagagc aggtgtaaga 8880
tgagtagggt gggaagttag gttggcatca gtggttaaaa acagaaagtt ctgtttcggg 8940
aatagtgagg agggggtgtt gtaacaaaat tggacaactt aaaagaatgg tgtgtgctgg 9000
gtgaaagaca aagactaaag aatgaggaaa caaacgtgat gcctggccag tgactgtcat 9060
ataaaccttt cttatttgag ctaggcttga acagacgtga cctagaagaa actgaacata 9120
aagagaaggg ggtgggggc tagttttcaa gttggggaac ctgatagtga aaagtcacag 9180
atggagaaaa ttgctctcag aaaaactgtt tggattgctt tcctcttgtt gcacatgtac 9240
catgcatttc tcagcttggg gtactacatt ttgtggaaag ttaatctatc tatctttcca 9300
catctgaatt aatcattcta ggaaagaata cttattccta ctcatttcct tttatgatgtc 9360 caaatggttg caggatcata atctattgtg ccacctttat ttctagaagt acaactaata 9420
tgttcacatt ttcaaataaa taatactccc cgtaagtaat aactgcaacc aatcagtgtt 9480
attcagtgct atgcctcctt gtaatgggta gttattaatt attttcagag ctttccggaa 9540
atactgtcct aactggctat gtttaggatc tttgttatct ctgaagacaa agaaagaagc 9600
taggactctt aattttgggg tgcttcttga ctcttagttg ggaaactgaa aatatttcca 9660
accttttacc cacgtcaatg gcatattctg ggaatcacca ccaccaccac cactaccaca 9720
gaaagaggct ggaggctcct gtaccctgtt cattccttaa gggccctgct tcccttagta 9780
agtaagtaag ttggtctacg gccctaaata tgcaaatgag agctgaaggt ttttaaaagg 9840
tagaaaggaa aagggcaagg gcttccaccc ctgctttaaa atgatttatt tattctctgc 9900
ttgtatttct tgtggagaga gtaaggatag aaccaacaag gggctgagta gctgagaaag 9960
gggccaccca agagtgaaac atactttata ccagaggagc agtggagcct catgcagcac 10020
attatcattt gttatttggg tttaataata attttgacat cttttcactc atacacaaaa 10080
aaagtcagaa ctggtgttat ttactgttga tttcatcctc ctgtgtatga aataacaagc 10140
ctagaggaat gaactagtgc tactgaactg tttaaattat ttttgtgtta atagtacact 10200
ttgagtatct ttttccacat taaaaacttt ctgaattata aatgttttcc ttacattatt 10260
taacaatgta cactgttaaa aataaaaata aaaattcaaa ctttgggggt ttctcagcag 10320
ccgttaattg tacattttgc actaactctg ggtgttgcgc ttcttgtaag attgcgcttt 10380
gtgcttcagt ttgttacctt tgtagactta tttaatgaaa ccattcaaat aaaccaaact 10440
tgcttttgtt gaaaaaaaaa a 10461

<210> SEQ ID NO 101
<211> LENGTH: 1712
<212> TYPE: DNA
<213> ORGANISM: Homo sapiens

<400> SEQUENCE: 101
ttgggtacag tgcaagatgc ttgggtgatg ggtgcactga aatcaccact aaagaactag 60
tttcccaaaa actattgaaa aaaaaagtgg cagctaaatt aggccctaaa gaatggttag 120
gattttcaca tgtaaagatt acaggccggg catggtgtct cacgcctgcc attttagcac 180
tttgggaagc caaggcagga ggactgcttg agcccagaag ttcgagacca gcttgggcaa 240

-continued

```
catggcaaaa cttcgtctct acaaaaaata caaagaatta gtcaggcgtg gtagtgtgca    300
cctgtagttc cagctactca ggaggctgag gtgggaggat cacctgagcc ccaggaggtc    360
aaggctgcag tgagctgaaa tcacgccact atactctagc ctgagcaaca gagggagacc    420
ctatctcgaa aaacaacaac aacaaacatt acagatggag gtaactgtac agaagtatgg    480
aggttgaaag aaagcactat gtctaaagca gggtttctca atctcagcac cgctaccatt    540
ttgggcctga taattctgtt gtggggggaa gggggggttt gcctgcacat ttctgtacac    600
tgtaggaggt tcagcagtat acctggcctc tacccactag atgtcaagca gtagccccca    660
ggttgtaacc accaaaaaag tctgtagaca ttgtcagatg tcccctggtg agtggcggta    720
cagggcaata tctcctctga ctgagaacct ctggcctttc taggaaagaa attaaaatat    780
atttgttgtc atgtcaaaag aagtgtaaag aggctactac ttgctctatg tataatgcaa    840
aggataccta gtcaagttct ttcttggagg aaataactat cagaaagcca cagcagtaca    900
tgattttatg aatgaaatca atgtctctat gactcttctg agggaagcta aaacaattct    960
tattctggaa aaccctgtat agtcaagaga gttaagcaaa acacacaaca cattacaagc   1020
ttttatgtaa aagtaatttt accttgtctt gctgtgtatt cattgtcttc aattaacctt   1080
gctaaaccaa agtctgctat tttgcacaca agattttctc ctacaagaat attagcagcc   1140
cgaagatctc ggtgaatata gttcattctt tcaatatatg ccataccatc agcaatcttg   1200
gaaagagaaa aacaaaaaac acaagacata cgatacaaag ggaagcagag agaagacaat   1260
tatggttaat atcaaattgt gtcactgaaa atcatattat tttagaagga gatgatggta   1320
acagggtata gtctagaaga taacaggaaa accagaaaac ataataaaaa tgcaggctaa   1380
attcagattt caaaaatcta acactggctg ggtgcggtgg cccacaccta taatcccatt   1440
aatttgggag gccgaggcag gtggatcact tgaggtcatg agttcgagat cagcctggcc   1500
aacacggtga aaccctgtct ctattaaaaa tacaaaaatt agccgggcct ggtggcaggt   1560
gcctgtaatc ccagctacag gggaggctga ggcaggagaa tcatttgaac ctgggaggtg   1620
gaggttgcag tgagctgaga ttgtaccact gcactccagc ctgggcaaca gattgagact   1680
gtgtctcaaa gcaaaaaaaa aaaaaaaaaa aa                                 1712
```